United States Patent
Thede et al.

(10) Patent No.: US 10,130,633 B2
(45) Date of Patent: Nov. 20, 2018

(54) COMPOUNDS

(71) Applicant: BAYER PHARMA AKTIENGESELLSCHAFT, Berlin (DE)

(72) Inventors: Kai Thede, Berlin (DE); William Scott, Guilford, CT (US); Eckhard Bender, Langenfeld (DE); Stefan Golz, Mülheim an der Ruhr (DE); Andrea Hägebarth, Berlin (DE); Philip Lienau, Berlin (DE); Florian Puehler, Wellesley, MA (US); Daniel Basting, Köln (DE); Dirk Schneider, Wuppertal (DE); Manfred Möwes, Berlin (DE); Anja Richter, Berlin (DE); Ludwig Zorn, Berlin (DE); Ningshu Liu, Berlin (DE); Ursula Mönning, Woltersdorf (DE); Franziska Siegel, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/778,568

(22) PCT Filed: Mar. 17, 2014

(86) PCT No.: PCT/EP2014/055300
§ 371 (c)(1),
(2) Date: Sep. 18, 2015

(87) PCT Pub. No.: WO2014/147021
PCT Pub. Date: Sep. 25, 2014

(65) Prior Publication Data
US 2016/0263122 A1 Sep. 15, 2016

Related U.S. Application Data

(60) Provisional application No. 61/803,549, filed on Mar. 20, 2013, provisional application No. 61/871,369, filed on Aug. 29, 2013, provisional application No. 61/938,779, filed on Feb. 12, 2014.

(51) Int. Cl.
*A61K 31/5377* (2006.01)
*A61K 31/5386* (2006.01)
*A61K 31/4439* (2006.01)
*A61K 31/496* (2006.01)
(Continued)

(52) U.S. Cl.
CPC ........ *A61K 31/5377* (2013.01); *A61K 31/433* (2013.01); *A61K 31/4418* (2013.01);
(Continued)

(58) Field of Classification Search
CPC ............ A61K 31/5377; A61K 31/5386; A61K 31/4439; A61K 31/496; A61K 31/433;
(Continued)

(56) References Cited

U.S. PATENT DOCUMENTS 5,011,472 A   4/1991   Aebischer et al.
5,023,252 A   6/1991   Hseih
(Continued)

FOREIGN PATENT DOCUMENTS

JP   2010138079   6/2010
WO   WO-199828282   7/1998
(Continued)

OTHER PUBLICATIONS

CAS Printout of Registry No. 1302360-51-5, May 29, 2011.*
Al-Chaqmaqchi, H.A.M. et al. (Jul. 2013). "Activation of Wnt/β-Catenin Pathway in Monocytes Derived from Chronic Kidney Disease Patients," *Plos One* 8(7): 1-8.
(Continued)

Primary Examiner — Brenda L Coleman
(74) Attorney, Agent, or Firm — Morrison & Foerster LLP

(57) ABSTRACT

The present invention relates to substituted N-(phenyl-heteroaryl)-3-acetylamino-benzamides and N-[3-(acetylamino)phenyl]-phenyl-heteroaryl-carboxamides of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease such as cancer, wherein i.a.: $L_A$ represents an optionally substituted methylene or ethylene group; $L^B$ represents —N(H)—C(=O)— or —C(=O)—N(H)—; $R^1$ represents an optionally substituted 5- to 8-membered heterocycloalkyl, 4- to 10-membered heterocycloalkenyl, aryl, heteroaryl or —N(R7)(Ci-C6-alkyl) group; $R^2$ represents an optionally substituted 5- or 6-membered heteroaryl group; $R^3$ represents an optionally substituted phenyl group.

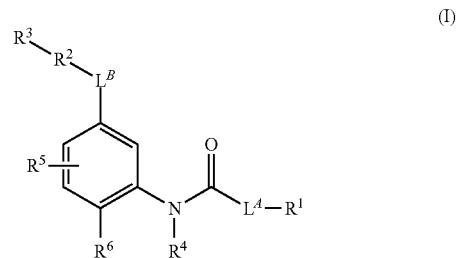

(I)

17 Claims, No Drawings
Specification includes a Sequence Listing.

(51) Int. Cl.

| | |
|---|---|
| *A61K 31/433* | (2006.01) |
| *A61K 31/4418* | (2006.01) |
| *A61K 31/4995* | (2006.01) |
| *A61K 31/551* | (2006.01) |
| *A61K 31/553* | (2006.01) |
| *A61K 45/06* | (2006.01) |
| *C07C 205/45* | (2006.01) |
| *C07C 233/54* | (2006.01) |
| *C07C 233/15* | (2006.01) |
| *C07C 205/59* | (2006.01) |
| *C07C 317/44* | (2006.01) |
| *C07C 229/64* | (2006.01) |
| *C07C 255/56* | (2006.01) |
| *C07D 213/75* | (2006.01) |
| *C07D 295/15* | (2006.01) |
| *C07D 213/82* | (2006.01) |
| *C07D 333/38* | (2006.01) |
| *C07D 285/135* | (2006.01) |
| *C07D 295/155* | (2006.01) |
| *C07D 213/76* | (2006.01) |
| *C07D 213/73* | (2006.01) |
| *C07D 277/56* | (2006.01) |
| *C07D 231/14* | (2006.01) |
| *C07D 401/12* | (2006.01) |
| *C07D 417/12* | (2006.01) |
| *C07D 263/34* | (2006.01) |
| *C07D 487/08* | (2006.01) |
| *C07D 271/06* | (2006.01) |
| *C07D 271/07* | (2006.01) |
| *C07D 271/113* | (2006.01) |
| *C07D 207/34* | (2006.01) |
| *C07D 498/08* | (2006.01) |
| *C07D 277/46* | (2006.01) |

(52) U.S. Cl.
CPC ........ *A61K 31/4439* (2013.01); *A61K 31/496* (2013.01); *A61K 31/4995* (2013.01); *A61K 31/5386* (2013.01); *A61K 31/551* (2013.01); *A61K 31/553* (2013.01); *A61K 45/06* (2013.01); *C07C 205/45* (2013.01); *C07C 205/59* (2013.01); *C07C 229/64* (2013.01); *C07C 233/15* (2013.01); *C07C 233/54* (2013.01); *C07C 255/56* (2013.01); *C07C 317/44* (2013.01); *C07D 207/34* (2013.01); *C07D 213/73* (2013.01); *C07D 213/75* (2013.01); *C07D 213/76* (2013.01); *C07D 213/82* (2013.01); *C07D 231/14* (2013.01); *C07D 263/34* (2013.01); *C07D 271/06* (2013.01); *C07D 271/07* (2013.01); *C07D 271/113* (2013.01); *C07D 277/46* (2013.01); *C07D 277/56* (2013.01); *C07D 285/135* (2013.01); *C07D 295/15* (2013.01); *C07D 295/155* (2013.01); *C07D 333/38* (2013.01); *C07D 401/12* (2013.01); *C07D 417/12* (2013.01); *C07D 487/08* (2013.01); *C07D 498/08* (2013.01)

(58) Field of Classification Search
CPC ............ A61K 31/4418; A61K 31/4995; A61K 31/551; A61K 31/553; A61K 45/06; C07C 205/45; C07C 233/54; C07C 233/15; C07C 205/59; C07C 317/44; C07C 229/64; C07C 255/56; C07D 213/75; C07D 295/15; C07D 213/82; C07D 333/38; C07D 285/135; C07D 295/155; C07D 213/76; C07D 213/73; C07D 277/56

See application file for complete search history.

(56) References Cited

U.S. PATENT DOCUMENTS

| | | |
|---|---|---|
| 2006/0217380 A1 | 9/2006 | Chaffee et al. |
| 2008/0075714 A1 | 3/2008 | Lee et al. |
| 2011/0189097 A1 | 8/2011 | Agalliu et al. |
| 2012/0322717 A9 | 12/2012 | Liu et al. |
| 2016/0052898 A1 | 2/2016 | Thede et al. |
| 2017/0107212 A1 | 4/2017 | Thede et al. |
| 2017/0114070 A1 | 4/2017 | Thede et al. |

FOREIGN PATENT DOCUMENTS

| | | |
|---|---|---|
| WO | WO-200007991 | 2/2000 |
| WO | WO-200055120 | 9/2000 |
| WO | WO-2004006906 | 1/2004 |
| WO | WO-2004022536 | 3/2004 |
| WO | WO-2005084368 | 9/2005 |
| WO | WO-2008071397 | 6/2008 |
| WO | WO-2008075064 | 6/2008 |
| WO | WO-2010014948 | 2/2010 |
| WO | WO-2010101964 | 9/2010 |
| WO | WO-2011035321 | 3/2011 |
| WO | WO-2011099832 | 8/2011 |
| WO | WO-2012088712 | 7/2012 |
| WO | WO-2012140274 | 10/2012 |
| WO | WO-2013093508 | 6/2013 |
| WO | WO-2014147182 | 9/2014 |
| WO | WO-2015140195 | 9/2015 |
| WO | WO-2015140196 | 9/2015 |
| WO | WO-2016131794 | 8/2016 |
| WO | WO-2016131808 | 8/2016 |
| WO | WO-2016131810 | 8/2016 |

OTHER PUBLICATIONS

Askevold, E.T. et al. (2014). "The cardiokine secreted Frizzled-related protein 3, a modulator of Wnt signalling, in clinical and experimental heart failure," *Journal of Internal Medicine* doi:10.1111/joim.12175: 1-10.

Bafico, A. et al. (Nov. 2004). "An autocrine mechanism for constitutive Wnt pathway activation in human cancer cells," *Cancer Cell* 6: 497-506.

Blankesteijn, W.M. et al. (May 1997). "A homologue of *Drosophila* tissue polarity gene frizzled is expressed in migrating myofibroblasts in the infarcted rat heart," *Nature Medicine* 3(5): 541-544.

Boyden, L.M. et al (May 16, 2002). "High Bone Density due to a mutation in LDL-receptor-related protein 5," *The New England Journal of Medicine* 346(2): 1513-1521.

Dawson, K. et al. (2013). "Role of the Wnt-Frizzled system in cardiac pathophysiology: a rapidly developing, poorly understood area with enormous potential," *The Journal of Physiology* 591(6): 1409-1432.

de Oliveira, R.B. et al. (2013). "Disturbances of Wnt/b-catenin pathway and energy metabolism in early CKD: effect of phosphate binders," *Nephrol Dial Transplant* 28(10): 2510-2517.

Gong Y, et al. (Nov. 16, 2001). "LDL receptor-related protein 5 (LRP5) affects bone accrual and eye development," *Cell* 107:513-523.

Hagenmueller, M. et al. (2013). "Dapper-1 induces myocardial remodeling through activation of canonical Wnt signaling in cardiomyocytes," *Hypertension* 61(6):1177-1183.

He, T.C. et al. (Sep. 4, 1998). "Identification of c-MYC as a Target of the APC Pathway," *Science* 281:1509-1512.

Huang, H.C. et al. (2004). "The Frizzled family: receptors for multiple signal transduction pathways," *Genome Biology* 5 (7): 234.1-234.8.

International Search Report dated Jun. 1, 2015 for PCT Application No. PCT/EP2014/055300 filed on Mar. 17, 2014, 9 pages.

(56) References Cited

OTHER PUBLICATIONS

Kanazawa A, et al. (Nov. 2004). "Association of the gene encoding wingless-type mammary tumor virus integration-site family member 5B (Wnt5B) with type 2 diabetes," *Am J Hum Genet* 75(5):832-843.

Kuhl et al. "The Wnt/Ca$^2$ pathway, a new vertebrate Wnt signaling pathway takes shape," *Trends Genet*. 16(7): 279-283, 2000.

Lee, J. et al (2010). "Synthesis of aminoquinazoline derivatives and their antiproliferative activities against melanoma cell line," *Bioorganic & Medicinal Chemistry Letters* V20(19): 5722-5725.

McMahon, A.P. (1992). "The Wnt family of developmental regulators," *Trends Genet*. 8(7): 236-242.

Molenaar, M. et al. (1996). "XT cf-3 Transcription Factor Mediates β-Catenin-Induced Axis Formation in Xeopus Embryos," *Cell* 86(3): 391-399.

Morin, P.J. et al. (Mar. 21, 1997). "Activation of β-Catenin-Tcf Signaling in Colon Cancer by Mutations in β-Catenin or APC," *Science* 275: 1787-1790.

Najdi, J. et al. (2011). "Wnt signaling and colon carcinogensis: Beyond APC," *Journal of Carcinogenesis* 10(1): 5.

Nguyen, D.X. et al. (Jul. 10, 2009) "WNT/TCF Signaling through LEF1 and HOXB9 Mediates Lung Adenocarcinoma Metastasis," *Cell* 138: 51-62.

Polakis, P. (2012). "Drugging Wnt signaling in cancer," *The EMBO Journal* 31: 2737-2746.

Reya, T. et al. (Apr. 14, 2005). "Wnt signaling in stem cells and cancer," *Nature* 434: 843-850.

Sun, A. et al (2006). "Nonpeptide Inhibitors of Measles Virus Entry," *Journal of Medicinal Chemistry* 49(17): 5080-5092.

Tamai, K. et al. (Jan. 16, 2004). "A Mechanism for Wnt Coreceptor Activation," *Molecular Cell* 13: 149-156.

Tsaousi, A. et al. (Feb. 18, 2011). "Wnt4/β-Catenin Signaling Induces VSMC Proliferation and Is Associated With Intimal Thickening," *Circulation Research* 108: 427-436.

Vermeulen, L. et al. (May 2010). "Wnt activity defines colon cancer stem cells and is regulated by the microenvironment," *Nature Cell Biology* 12(5): 468-476 with Supplementary Information, 1-8.

Yee, D.S. et al. (2010). "The Wnt inhibitory factor 1 restoration in prostate cancer cells was associated with reduced tumor growth, decreased capacity of cell migration and invasion and a reversal of epithelial to mesenchymal transition," *Molecular Cancer* 9:162-176.

\* cited by examiner

COMPOUNDS

CROSS REFERENCE TO RELATED APPLICATIONS

This application is a National Phase application under 35 U.S.C. § 371 of International Application Serial No. PCT/EP2014/055300, filed Mar. on 17, 2014, which claims priority benefit of U.S. Provisional Application Ser. No. 61/938,779, filed on Feb. 12, 2014, U.S. Provisional Application Ser. No. 61/871,369, filed on Aug. 29, 2013, and U.S. Provisional Application Ser. No. 61/803,549, filed on Mar. 20, 2013, the disclosures of each of which are hereby incorporated by reference in their entireties.

The present invention relates to substituted N-(phenyl-heteroaryl)-3-acetylamino-benzamides and N-[3-(acetylamino)phenyl]-phenyl-heteroaryl-carboxamides of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyper-proliferative disorder, as a sole agent or in combination with other active ingredients.

BACKGROUND OF THE INVENTION

The Wnt signaling pathways are a group of signal transduction pathways made of proteins that pass signals from outside of a cell through cell surface receptors to the inside of the cell.

Wnt proteins are secreted glycoproteins with a molecular weight in the range of 39-46 kD, whereby in total 19 different members of the Wnt protein family are known (McMahon et al., Trends Genet. 8, 1992, 236-242). They are the ligands of so-called Frizzled receptors, which form a family of seven-transmembrane spanning receptors comprising 10 distinct subtypes. A certain Wnt ligand can thereby activate several different Frizzled receptor subtypes and vice versa a particular Frizzled receptor can be activated by different Wnt protein subtypes (Huang et al., Genome Biol. 5, 2004, 234.1-234.8).

Binding of a Wnt to its receptor can activate two different signaling cascades, one is called the non-canonical pathway, which involves CamK II and PKC (Kuhl et al., Trends Genet. 16 (7), 2000, 279-283). The other, the so-called canonical pathway (Tamai et al., Mol. Cell 13, 2004, 149-156) regulates the concentration of the transcription factor β-catenin.

In the case of non-stimulated canonical Wnt signaling, β-catenin is captured by a destruction complex consisting of adenomatous polyposis coli (APC), glycogen synthase kinase 3-β (GSK-3β), Axin-1 or -2 and Casein Kinase 1α. Captured β-catenin is then phosphorylated, ubiquitinated and subsequently degraded by the proteasome.

However, when a canonical Wnt activates the membrane complex of a Frizzled receptor and its Lipoprotein 5 or 6 (LRP 5/6) co-receptor, this leads to the recruitment of disheveled (Dvl) by the receptors and subsequent phosphorylation of LRP 5/6, followed by binding of Axin-1 or Axin-2 to the membrane complex as well. The deprivation of Axin from the β-catenin destruction complex leads to the disassembly of the latter and β-catenin can reach the nucleus, where it together with TCF and LEF transcription factors and other transcriptional coregulators like Pygopus, BCL9/Legless, CDK8 module of Mediator and TRRAP initiates transcription of genes with promoters containing TCF elements (Najdi, J. Carcinogenesis 2011; 10:5).

The Wnt signaling cascade can be constitutively activated by mutations in genes involved in this pathway. This is especially well documented for mutations of the APC and axin genes, and also for mutations of the β-catenin phosphorylation sites, all of which are important for the development of colorectal and hepatocellular carcinomas (Polakis, EMBO J., 31, 2012, 2737-2746).

The Wnt signaling cascade has important physiological roles in embryonal development and tissue homeostasis the latter especially for hair follicles, bones and the gastrointestinal tract. Deregulation of the Wnt pathway can activate in a cell and tissue specific manner a number of genes known to be important in carcinogenesis. Among them are c-myc, cyclin D1, Axin-2 and metalloproteases (He et al., Science 281, 1998, 1509-1512).

Deregulated Wnt activity can drive cancer formation, increased Wnt signaling can thereby be caused through autocrine Wnt signaling, as shown for different breast, ovarian, prostate and lung carcinomas as well as for various cancer cell lines (Bafico, Cancer Cell 6, 2004, 497-506; Yee, Mol. Cancer 9, 2010, 162-176; Nguyen, Cell 138, 2009, 51-62).

For cancer stem cells (CSCs) it was shown that they have increased Wnt signaling activity and that its inhibition can reduce the formation of metastases (Vermeulen et al., Nature Cell Biol. 12 (5), 2010, 468-476; Polakis, EMBO J. 31, 2012, 2737-2746; Reya, Nature, 434, 2005, 843-850).

Furthermore, there is a lot of evidence supporting an important role of Wnt signaling in cardiovascular diseases. One aspect thereby is heart failure and cardiac hypertrophy where deletion of Dapper-1, an activator of the canonical β-catenin Wnt pathway has been shown to reduce functional impairment and hypertrophy (Hagenmueller, M. et al.: *Dapper-1 induces myocardial remodeling through activation of canonical wnt signaling in cardiomyocytes*; Hypertension, 61 (6), 2013, 1177-1183).

Additional support for a role of Wnt signaling in heart failure comes from animal experimental models and clinical studies with patients, in which it was shown, that the level of secreted frizzled related protein 3 (sFRP3) is associated with the progression of heart failure (Askevold, E. T. et al.: *The cardiokine secreted Frizzled-related protein 3, a modulator of Wnt signaling in clinical and experimental heart failure*; J. Intern Med., 2014 (doi:10.1111/joim.12175)). For cardiac remodeling and infarct healing the expression of Fzd2 receptors on myofibroblasts migrating into the infarct area has been demonstrated (Blankesteijn, W. M. et al.: *A homologue of Drosophila tissue polarity gene frizzled is expressed in migrating myofibroblasts in the infracted rat heart*; Nat. Med. 3, 1997, 541-544). The manifold effects of Wnt signaling in heart failure, fibrosis and arrhythmias have been recently reviewed by Dawson et al. (Dawson, K. et al.: *Role of the Wnt-Frizzled system in cardiac pathophysiology: a rapidly developing, poorly understood area with enormous potential*; J. Physiol. 591 (6), 2013, 1409-1432).

For the vasculature, effects of Wnt signaling could be shown as well, mainly in respect to restenosis via enhancement of vascular smooth muscle cell proliferation (Tsaousi, A. et al.: *Wnt4/b-catenin signaling induces VSMC proliferation and is associated with initmal thickening*; Circ. Res. 108, 2011, 427-436).

Besides the effects on heart and vasculature, dysregulated Wnt signaling is also an important component in chronic kidney disease as could be shown for upregulated Wnt activity in immune cells from corresponding patients (Al- Chaqmaqchi, H. A. et al.: *Activation of Wnt/b-catenin pathway in monocytes derived from chronic kidney disease patients*; PLoS One, 8 (7), 2013, doi: 10.1371) and altered levels of secreted Wnt inhibitor in patient sera (de Oliveira, R. B. et al.: *Disturbances of Wnt/b-catenin pathway and energy metabolism in early CKD: effect of phosphate binders*; Nephrol. Dial. Transplant. (2013) 28 (10): 2510-2517).

In adults, mis-regulation of the Wnt pathway also leads to a variety of abnormalities and degenerative diseases. An LRP mutation has been identified that causes increased bone density at defined locations such as the jaw and palate (Boyden L M et al.: *High bone density due to a mutation in LDL-receptor-related protein 5*; N Engl J Med. 2002 May 16; 346(20):1513-21, Gong Y, et al.: *LDL receptor-related protein 5 (LRP5) affects bone accrual and eye development*; Cell 2001; 107:513-23). The mutation is a single amino-acid substitution that makes LRP5 insensitive to Dkk-mediated Wnt pathway inhibition, indicating that the phenotype results from overactive Wnt signaling in the bone. Recent reports have suggested that Wnt signaling is an important regulator for adipogenesis or insulin secretion and might be involved in the pathogenesis of type 2 diabetes. It has been shown that expression of the Wnt5B gene was detectable in several tissues, including adipose, pancreas, and liver. Subsequent in vitro experiments identified the fact that expression of the Wnt5b gene was increased at an early phase of adipocyte differentiation in mouse 3T3-L1 cells. Furthermore, overexpression of the Wnt5b gene in preadipocytes resulted in the promotion of adipogenesis and the enhancement of adipocytokine-gene expression. These results indicate that the Wnt5B gene may contribute to conferring susceptibility to type 2 diabetes and may be involved in the pathogenesis of this disease through the regulation of adipocyte function (Kanazawa A, et al.: *Association of the gene encoding wingless-type mammary tumor virus integration-site family member 5B (Wnt5B) with type 2 diabetes*; Am J Hum Genet. 2004 November; 75(5):832-43)

Accordingly, identification of methods and compounds that modulate the Wnt-dependent cellular responses may offer an avenue for regulating physiological functions and therapeutic treatment of diseases associated with aberrant activity of the pathways.

Inhibitors of the Wnt signalling pathway are disclosed e.g. in US2008-0075714(A1), US2011-0189097(A1), US2012-0322717(A9), WO2010/014948(A1), WO2012/088712 (A1), WO2012/140274(A2,A3) and WO2013/093508(A2).

WO 2005/084368(A2) discloses heteroalkyl-substituted biphenyl-4-carboxylic acid arylamide analogues and the use of such compounds for treating conditions related to capsaicin receptor activation, for identifying other agents that bind to capsaicin receptor, and as probes for the detection and localization of capsaicin receptors. The structural scope of the compounds claimed in claim 1 is huge, whereas the structural space spanned by the few examples is much smaller. There is no specific example which is covered by the formula (I) as described and defined herein.

WO 2000/55120(A1) and WO 2000/07991 (A1) disclose amide derivatives and their use for the treatment of cytokine mediated diseases. The few specific examples disclosed in WO 2000/55120(A1) and WO 2000/07991 (A1) are not covered by the formula (I) as described and defined herein.

WO 1998/28282 (A2) discloses oxygen or sulfur containing heteroaromatics as factor Xa inhibitors. The specific examples disclosed in WO 1998/28282 (A2) are not covered by the formula (I) as described and defined herein.

WO 2011/035321 (A1) discloses methods of treating Wnt/Frizzled-related diseases, comprising administering niclosamide compounds. According to the specification of WO 2011/035321 (A1) libraries of FDA-approved drugs were examined for their utility as Frizzled internalization modulators, employing a primary imaged-based GFP-fluorescence assay that used Frizzled1 endocytosis as the readout. It was discovered that the antihelminthic niclosamide, a drug used for the treatment of tapeworms, promotes Frizzled1 internalization (endocytosis), down regulates Disheveled-2 protein, and inhibits Wnt3A-stimulated β-catenin stabilization and LEF/TCF reporter activity. The specific examples disclosed in WO 2011/035321 (A1) are not covered by the formula (I) as described and defined herein. Additionally, WO 2011/035321 (A1) does neither teach nor suggest the compounds of formula (I) as described and defined herein. The same is true for the related publication WO 2004/006906 (A2) which discloses a method for treating a patient having a cancer or other neoplasm by administering to the patient a niclosamide.

JP 2010-138079 (A) relates to amide derivatives exhibiting insecticidal effects. The specific examples disclosed in JP 2010-138079 (A) are not covered by the formula (I) as described and defined herein.

WO 2004/022536 (A1) relates to heterocyclic compounds that inhibit phosphodiesterase type 4 (PDE 4) and their use for treating inflammatory conditions, diseases of the central nervous system and insulin resistant diabetes. The specific examples disclosed in WO 2004/022536 (A1) are not covered by the formula (I) as described and defined herein.

SUMMARY OF THE INVENTION

The present invention relates to compounds of general formula (I):

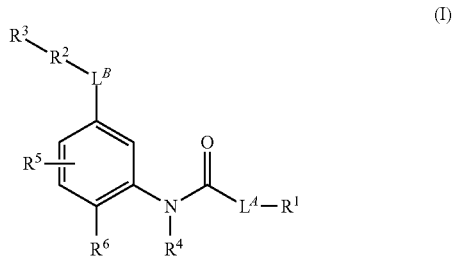

in which:

$L^A$ represents a methylene or ethylene group, said methylene or ethylene group being optionally substituted, one or more times, identically or differently, with a substituent selected from:

hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-, 3- to 10-membered heterocycloalkyl-;

or, when two substituents are present at the same carbon atom, the two substituents, together with the carbon atom they are attached to, may form a $C_3$-$C_6$-cycloalkyl- or 3- to 6-membered heterocycloalkyl-ring; wherein said ring is optionally substituted one or more times, identically or differently, with a substituent selected from: halo-, hydroxy-, cyano-, $C_1$-$C_3$-alkyl-, $C_1$-$C_3$-alkoxy-;

$L^B$ represents —N(H)—C(=O)— or —C(=O)—N(H)—;

R¹ represents a group selected from:
  5- to 8-membered heterocycloalkyl-, 4- to 10-membered heterocycloalkenyl-, aryl-, heteroaryl-, and —N(R⁷)—(C₁-C₆-alkyl);
  wherein said 5- to 8-membered heterocycloalkyl-, 4- to 10-membered heterocycloalkenyl-, aryl-, heteroaryl-, and —N(R⁷)—(C₁-C₆-alkyl) group is optionally substituted, one or more times, identically or differently, with a substituent selected from: halo-, hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-;
R² represents a group selected from:

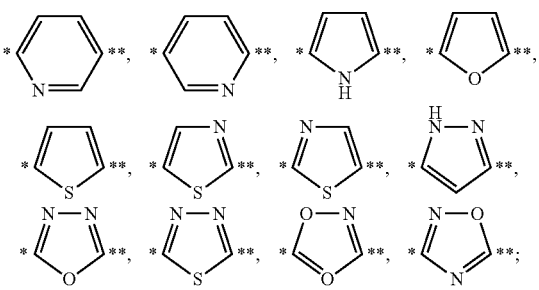

wherein "*" indicates the point of attachment to R³, and "**" indicates the point of attachment to $L^B$; wherein said group is optionally substituted, one or more times, identically or differently, with a $C_1$-$C_3$-alkyl- group;
R³ represents a phenyl-group,
  said phenyl-group being optionally substituted, one or more times, identically or differently, with a substituent selected from:
  halo-, hydroxy-, —N(R⁹)(R¹⁰), —N(H)C(=O)R⁹, cyano-, nitro-, $C_1$-$C_3$-alkyl-, $C_1$-$C_3$-alkoxy-, halo-$C_1$-$C_3$-alkyl-, hydroxy-$C_1$-$C_3$-alkyl-, amino-$C_1$-$C_3$-alkyl-, halo-$C_1$-$C_3$-alkoxy-;
R⁴ represents a hydrogen atom or a $C_1$-$C_3$-alkyl- group;
R⁵ represents a hydrogen atom or a halogen atom or a group selected from:
  cyano-, $C_1$-$C_3$-alkyl-, $C_1$-$C_3$-alkoxy-;
R⁶ represents a group selected from:
  $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkoxy-, halo-, hydroxy-, cyano-, aryl-,
  heteroaryl-, —N(R⁹)(R¹⁰), —C(=O)—O—C₁-C₄-alkyl, —C(=O)—N(R⁹)(R¹⁰), R⁹—S—, R⁹—S(=O)—, R⁹—S(=O)₂—;
  said $C_1$-$C_6$-alkyl-, $C_2$-$C_6$-alkenyl-, $C_2$-$C_6$-alkynyl-, aryl-, heteroaryl-, and $C_1$-$C_6$-alkoxy- group being optionally substituted, one or more times, identically or differently, with a substituent selected from: halo-, cyano-, nitro-, hydroxy-, $C_1$-$C_3$-alkyl-, $C_1$-$C_3$-alkoxy-, halo-$C_1$-$C_3$-alkoxy-, hydroxy-$C_1$-$C_3$-alkoxy-, $C_1$-$C_3$-alkoxy-$C_2$-$C_3$-alkoxy-,
  $C_3$-$C_7$-cycloalkyl-, $C_4$-$C_7$-cycloalkenyl-,
  3- to 10-membered heterocycloalkyl-, 4- to 10-membered heterocycloalkenyl-,
  aryl-, heteroaryl-, —C(=O)R⁹, —C(=O)O—(C₁-C₄-alkyl), —OC(=O)—R⁹, —N(H)C(=O)R⁹, —N(R¹⁰)C(=O)R⁹,
  —N(H)C(=O)NR¹⁰R⁹, —N(R¹¹)C(=O)NR¹⁰R⁹, —N(H)R⁹, —NR¹⁰R⁹,
  —C(=O)N(H)R⁹, —C(=O)NR¹⁰R⁹, R⁹—S—, R⁹—S(=O)—, R⁹—S(=O)₂—,
  —N(H)S(=O)R⁹, —N(R¹⁰)S(=O)R⁹, —S(=O)N(H)R⁹, —S(=O)NR¹⁰R⁹,
  —N(H)S(=O)₂R⁹, —N(R⁹)S(=O)₂R¹⁰, —S(=O)₂N(H)R⁹, —S(=O)₂NR¹⁰R⁹,
  —S(=O)(=NR¹⁰)R⁹, —N=S(=O)(R¹⁰)R⁹;
R⁷ represents a hydrogen atom or a $C_1$-$C_3$-alkyl- or $C_1$-$C_3$-alkoxy-$C_1$-$C_3$-alkyl- group;
R⁹, R¹⁰, R¹¹
  represent, independently from each other, a hydrogen atom or a $C_1$-$C_3$-alkyl- or $C_1$-$C_3$-alkoxy-$C_1$-$C_3$-alkyl- group;
  or
  R⁹R¹⁰ together with the atom or the group of atoms they are attached to, form a 3- to 10-membered heterocycloalkyl- or 4- to 10-membered heterocycloalkenyl- group;
  or a tautomer, an N-oxide, a hydrate, a solvate, or a salt thereof, or a mixture of same.

The present invention further relates to a pharmaceutical composition comprising a compound of formula (I), supra.

The present invention further relates to the use of a compound of formula (I), supra, for the prophylaxis or treatment of a disease.

The present invention further relates to the use of a compound of formula (I), supra, for the preparation of a medicament for the prophylaxis or treatment of a disease.

DETAILED DESCRIPTION OF THE INVENTION

The terms as mentioned in the present text have preferably the following meanings:

The term "halogen atom" or "halo-" is to be understood as meaning a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5 or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methyl butyl, 1-ethyl propyl, 1,2-dimethylpropyl, neo-pentyl, 1,1-dimethylpropyl, 4-methyl pentyl, 3-methylpentyl, 2-methylpentyl, 1-methylpentyl, 2-ethyl butyl, 1-ethyl butyl, 3,3-dimethyl butyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more of the hydrogen atoms is replaced, identically or differently, by a halogen atom. Particularly, said halogen atom is F. Said halo-$C_1$-$C_6$-alkyl group is, for example, —CF₃, —CHF₂, —CH₂F, —CF₂CF₃, or —CH₂CF₃.

The term "$C_1$-$C_6$-alkoxy" is to be understood as preferably meaning a linear or branched, saturated, monovalent group of formula —O—(C₁-C₆-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, identically or differently, by a halogen atom. Particularly, said halogen atom is F. Said halo-$C_1$-$C_6$-alkoxy group is, for example, —$OCF_3$, —$OCHF_2$, —$OCH_2F$, —$OCF_2CF_3$, or —$OCH_2CF_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, identically or differently, by a halogen atom. Particularly, said halogen atom is F. Said halo-$C_1$-$C_6$-alkoxy-$C_1$-$C_6$-alkyl group is, for example, —$CH_2CH_2OCF_3$, —$CH_2CH_2OCHF_2$, —$CH_2CH_2OCH_2F$, —$CH_2CH_2OCF_2CF_3$, or —$CH_2CH_2OCH_2CF_3$.

The term "$C_1$-$C_6$-alkoxy-$C_2$-$C_6$-alkoxy" is to be understood as preferably meaning a saturated, monovalent $C_2$-$C_6$-alkoxy group, as defined supra, in which one of the hydrogen atoms is replaced by a $C_1$-$C_6$-alkoxy group, as defined supra, e.g. methoxyalkoxy, ethoxyalkoxy, pentoxyalkoxy, hexoxyalkoxy group or methoxyethoxy, ethoxyethoxy, isopropoxyhexoxy group, in which the term "alkoxy" is defined supra, or an isomer thereof.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, iso-propenyl, 2-methyl prop-2-enyl, 1-methyl prop-2-enyl, 2-methyl prop-1-enyl, (E)-1-methylprop-1-enyl, (Z)-1-methylprop-1-enyl, 3-methyl but-3-enyl, 2-methyl but-3-enyl, 1-methyl but-3-enyl, 3-methyl but-2-enyl, (E)-2-methyl but-2-enyl, (Z)-2-methyl but-2-enyl, (E)-1-methyl but-2-enyl, (Z)-1-methyl but-2-enyl, (E)-3-methyl but-1-enyl, (Z)-3-methyl but-1-enyl, (E)-2-methyl but-1-enyl, (Z)-2-methyl but-1-enyl, (E)-1-methyl but-1-enyl, (Z)-1-methyl but-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methyl pent-4-enyl, 1-methyl pent-4-enyl, 4-methyl pent-3-enyl, (E)-3-methyl pent-3-enyl, (Z)-3-methyl pent-3-enyl, (E)-2-methyl pent-3-enyl, (Z)-2-methyl pent-3-enyl, (E)-1-methyl pent-3-enyl, (Z)-1-methyl pent-3-enyl, (E)-4-methyl pent-2-enyl, (Z)-4-methyl pent-2-enyl, (E)-3-methyl pent-2-enyl, (Z)-3-methyl pent-2-enyl, (E)-2-methyl pent-2-enyl, (Z)-2-methyl pent-2-enyl, (E)-1-methyl pent-2-enyl, (Z)-1-methyl pent-2-enyl, (E)-4-methyl pent-1-enyl, (Z)-4-methyl pent-1-enyl, (E)-3-methyl pent-1-enyl, (Z)-3-methyl pent-1-enyl, (E)-2-methyl pent-1-enyl, (Z)-2-methyl pent-1-enyl, (E)-1-methyl pent-1-enyl, (Z)-1-methyl pent-1-enyl, 3-ethyl but-3-enyl, 2-ethyl but-3-enyl, 1-ethyl but-3-enyl, (E)-3-ethyl but-2-enyl, (Z)-3-ethyl but-2-enyl, (E)-2-ethyl but-2-enyl, (Z)-2-ethyl but-2-enyl, (E)-1-ethyl but-2-enyl, (Z)-1-ethyl but-2-enyl, (E)-3-ethyl but-1-enyl, (Z)-3-ethyl but-1-enyl, 2-ethyl but-1-enyl, (E)-1-ethyl but-1-enyl, (Z)-1-ethyl but-1-enyl, 2-propyl prop-2-enyl, 1-propyl prop-2-enyl, 2-isopropyl prop-2-enyl, 1-isopropyl prop-2-enyl, (E)-2-propyl prop-1-enyl, (Z)-2-propyl prop-1-enyl, (E)-1-propyl prop-1-enyl, (Z)-1-propyl prop-1-enyl, (E)-2-isopropyl prop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethyl prop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methyl prop-2-ynyl, 2-methyl but-3-ynyl, 1-methyl but-3-ynyl, 1-methyl but-2-ynyl, 3-methyl but-1-ynyl, 1-ethyl prop-2-ynyl, 3-methylpent-4-ynyl, 2-methyl pent-4-ynyl, 1-methyl-pent-4-ynyl, 2-methyl pent-3-ynyl, 1-methylpent-3-ynyl, 4-methyl pent-2-ynyl, 1-methylpent-2-ynyl, 4-methyl pent-1-ynyl, 3-methyl pent-1-ynyl, 2-ethyl but-3-ynyl, 1-ethyl but-3-ynyl, 1-ethyl but-2-ynyl, 1-propyl prop-2-ynyl, 1-isopropyl prop-2-ynyl, 2,2-dimethyl but-3-ynyl, 1,1-dimethyl but-3-ynyl, 1,1-dimethylbut-2-ynyl, or 3,3-dimethylbut-1-ynyl group. Particularly, said alkynyl group is ethynyl, prop-1-ynyl, or prop-2-ynyl.

The term "$C_3$-$C_7$-cycloalkyl" is to be understood as meaning a saturated, monovalent, monocyclic hydrocarbon ring which contains 3, 4, 5, 6 or 7 carbon atoms. Said $C_3$-$C_7$-cycloalkyl group is for example a cyclopropyl, cyclobutyl, cyclopentyl, cyclohexyl or cycloheptyl ring. Particularly, said ring contains 3, 4, 5 or 6 carbon atoms ("$C_3$-$C_6$-cycloalkyl").

The term "$C_4$-$C_8$-cycloalkenyl" is to be understood as preferably meaning a monovalent, monocyclic hydrocarbon ring which contains 4, 5, 6, 7 or 8 carbon atoms and one or two double bonds, in conjugation or not, as the size of said cycloalkenyl ring allows. Particularly, said ring contains 4, 5 or 6 carbon atoms ("$C_4$-$C_6$-cycloalkenyl"). Said $C_4$-$C_8$-cycloalkenyl group is for example a cyclobutenyl, cyclopentenyl, or cyclohexenyl group.

The term "$C_3$-$C_6$-cycloalkoxy" is to be understood as meaning a saturated, monovalent, monocyclic group of formula —O—($C_3$-$C_6$-cycloalkyl), in which the term "$C_3$-$C_6$-cycloalkyl" is defined supra, e.g. a cyclopropyloxy, cyclobutyloxy, cyclopentyloxy or cyclohexyloxy group.

The term "3- to 10-membered heterocycloalkyl", is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(=O), O, S, S(=O), S(=O)$_2$, NH; it being possible for said heterocycloalkyl group to be attached to the rest of the molecule via any one of the carbon atoms or, if present, a nitrogen atom.

Particularly, said 3- to 10-membered heterocycloalkyl can contain 2, 3, 4, 5 or 6 carbon atoms, and one or more of the above-mentioned heteroatom-containing groups (a "3- to 7-membered heterocycloalkyl"), more particularly said heterocycloalkyl can contain 4, 5 or 6 carbon atoms, and one or more of the above-mentioned heteroatom-containing groups (a "4- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example.

The term "4- to 10-membered heterocycloalkenyl", is to be understood as meaning an unsaturated, monovalent, mono- or bicyclic hydrocarbon ring which contains 3, 4, 5, 6, 7, 8 or 9 carbon atoms, and one or more heteroatom-containing groups selected from C(=O), O, S, S(=O), S(=O)$_2$, NH; it being possible for said heterocycloalkenyl group to be attached to the rest of the molecule via any one of the carbon atoms or, if present, a nitrogen atom. Examples of said heterocycloalkenyl may contain one or more double bonds, e.g. 4H-pyranyl, 2H-pyranyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group.

The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a biphenyl group (a "$C_{12}$-aryl" group), or a ring having 13 carbon atoms, (a "$C_{13}$-aryl" group), e.g. a fluorenyl group, or a ring having 14 carbon atoms, (a "$C_{14}$-aryl" group), e.g. an anthracenyl group. Preferably, the aryl group is a phenyl group.

The term "heteroaryl" is understood as preferably meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridinyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridyl includes pyridin-2-yl, pyridin-3-yl, and pyridin-4-yl; or the term thienyl includes thien-2-yl and thien-3-yl. Preferably, the heteroaryl group is a pyridinyl group.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$, particularly $C_1$-$C_2$, $C_1$-$C_3$, $C_1$-$C_4$, $C_1$-$C_5$, $C_1$-$C_6$, more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$, particularly $C_2$-$C_3$.

Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms. It is to be understood further that said term "$C_3$-$C_7$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_7$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 3.

Ring system substituent means a substituent attached to an aromatic or nonaromatic ring system which, for example, replaces an available hydrogen on the ring system.

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitrobenzene)-sulfonyloxy, (4-isopropyl-benzene)sulfonyloxy, (2,4,6-tri-isopropyl-benzene)-sulfonyloxy, (2,4,6-trimethylbenzene)sulfonyloxy, (4-tertbutyl-benzene)sulfonyloxy, benzenesulfonyloxy, and (4-methoxy-benzene)sulfonyloxy.

Where the plural form of the word compounds, salts, polymorphs, hydrates, solvates and the like, is used herein, this is taken to mean also a single compound, salt, polymorph, isomer, hydrate, solvate or the like.

The compounds of this invention contain one or more asymmetric centres, depending upon the location and nature of the various substituents desired. Asymmetric carbon atoms may be present in the (R) or (S) configuration. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, viz.:

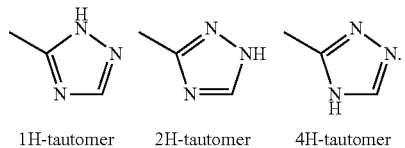

1H-tautomer     2H-tautomer     4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The present invention includes all possible salts of the compounds of the present invention as single salts, or as any mixture of said salts, in any ratio.

Furthermore, the present invention includes all possible crystalline forms, or polymorphs, of the compounds of the present invention, either as single polymorphs, or as a mixture of more than one polymorphs, in any ratio.

In accordance with a first aspect, the present invention covers compounds of general formula (I):

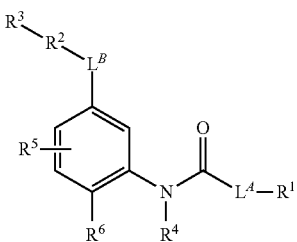

(I)

in which:
$L^A$ represents a methylene or ethylene group, said methylene or ethylene group being optionally substituted, one or more times, identically or differently, with a substituent selected from:
hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-, 3- to 10-membered heterocycloalkyl-;
or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from: halo-, hydroxy-, cyano-, $C_1$-$C_3$-alkyl-, $C_1$-$C_3$-alkoxy-;
$L^B$ represents —N(H)—C(=O)— or —C(=O)—N(H)—;
$R^1$ represents a group selected from:
5- to 8-membered heterocycloalkyl-, 4- to 10-membered heterocycloalkenyl-, aryl-, heteroaryl-, and —N($R^7$)—($C_1$-$C_6$-alkyl);
wherein said 5- to 8-membered heterocycloalkyl-, 4- to 10-membered heterocycloalkenyl-, aryl-, heteroaryl-, and —N($R^7$)—($C_1$-$C_6$-alkyl) group is optionally substituted, one or more times, identically or differently, with a substituent selected from: halo-, hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-;
$R^2$ represents a group selected from:

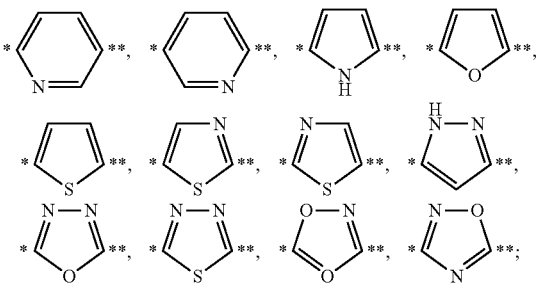

wherein "*" indicates the point of attachment to $R^3$, and "**" indicates the point of attachment to $L^B$; wherein said group is optionally substituted, one or more times, identically or differently, with a $C_1$-$C_3$-alkyl- group;
$R^3$ represents a phenyl-group,
said phenyl-group being optionally substituted, one or more times, identically or differently, with a substituent selected from:
halo-, hydroxy-, —N($R^9$)($R^{10}$), —N(H)C(=O)$R^9$, cyano-, nitro-, $C_1$-$C_3$-alkyl-, $C_1$-$C_3$-alkoxy-, halo-$C_1$-$C_3$-alkyl-, hydroxy-$C_1$-$C_3$-alkyl-, amino-$C_1$-$C_3$-alkyl-, halo-$C_1$-$C_3$-alkoxy-;
$R^4$ represents a hydrogen atom or a $C_1$-$C_3$-alkyl- group;
$R^5$ represents a hydrogen atom or a halogen atom or a group selected from:
cyano-, $C_1$-$C_3$-alkyl-, $C_1$-$C_3$-alkoxy-;
$R^6$ represents a group selected from:
$C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkoxy-, halo-, hydroxy-, cyano-, aryl-,
heteroaryl-, —N($R^9$)($R^{10}$), —C(=O)—O—$C_1$-$C_4$-alkyl, —C(=O)—N($R^9$)($R^{10}$), $R^9$—S—, $R^9$—S(=O)—, $R^9$—S(=O)$_2$—;
said $C_1$-$C_6$-alkyl-, $C_2$-$C_6$-alkenyl-, $C_2$-$C_6$-alkynyl-, aryl-, heteroaryl-, and $C_1$-$C_6$-alkoxy- group being optionally substituted, one or more times, identically or differently, with a substituent selected from: halo-, cyano-, nitro-, hydroxy-, $C_1$-$C_3$-alkyl-, $C_1$-$C_3$-alkoxy-, halo-$C_1$-$C_3$-alkoxy-, hydroxy-$C_1$-$C_3$-alkoxy-, $C_1$-$C_3$-alkoxy-$C_2$-$C_3$-alkoxy-,
$C_3$-$C_7$-cycloalkyl-, $C_4$-$C_7$-cycloalkenyl-,
3- to 10-membered heterocycloalkyl-, 4- to 10-membered heterocycloalkenyl-,
aryl-, heteroaryl-, —C(=O)$R^9$, —C(=O)O—($C_1$-$C_4$-alkyl), —OC(=O)—$R^9$, —N(H)C(=O)$R^9$, —N($R^{10}$)C(=O)$R^9$,
—N(H)C(=O)N$R^{10}R^9$, —N($R^{11}$)C(=O)N$R^{10}R^9$, —N(H)$R^9$, —N$R^{10}R^9$,
—C(=O)N(H)$R^9$, —C(=O)N$R^{10}R^9$, $R^9$—S—, $R^9$—S(=O)—, $R^9$—S(=O)$_2$—,
—N(H)S(=O)$R^9$, —N($R^{10}$)S(=O)$R^9$, —S(=O)N(H)$R^9$, —S(=O)N$R^{10}R^9$,
—N(H)S(=O)$_2R^9$, —N($R^9$)S(=O)$_2R^{10}$, —S(=O)$_2$N(H)$R^9$, —S(=O)$_2$N$R^{10}R^9$,
—S(=O)(=N$R^{10}$)$R^9$, —N=S(=O)($R^{10}$)$R^9$;
$R^7$ represents a hydrogen atom or a $C_1$-$C_3$-alkyl- or $C_1$-$C_3$-alkoxy-$C_1$-$C_3$-alkyl- group;
$R^9$, $R^{10}$, $R^{11}$
represent, independently from each other, a hydrogen atom or a $C_1$-$C_3$-alkyl- or $C_1$-$C_3$-alkoxy-$C_1$-$C_3$-alkyl- group;
or
$R^9R^{10}$ together with the atom or the group of atoms they are attached to, form a 3- to 10-membered heterocycloalkyl- or 4- to 10-membered heterocycloalkenyl- group;
or a tautomer, an N-oxide, a hydrate, a solvate, or a salt thereof, or a mixture of same.
In an embodiment, the present invention relates to compounds of the general formula (I), supra, in which:
$L^A$ represents a methylene or ethylene group, said methylene or ethylene group being optionally substituted, one or more times, identically or differently, with a substituent selected from:
hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-, 3- to 10-membered heterocycloalkyl-;
or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from: halo-, hydroxy-, cyano-, $C_1$-$C_3$-alkyl-, $C_1$-$C_3$-alkoxy-.

In another embodiment, the present invention relates to compounds of the general formula (I), supra, in which:

$L^A$ represents a methylene or ethylene group, said methylene or ethylene group being optionally substituted, one or more times, identically or differently, with a substituent selected from:

hydroxy-, cyano-, $C_1$-$C_3$-alkyl-, $C_1$-$C_3$-alkoxy-, fluoro-$C_1$-$C_3$-alkyl-, hydroxy-$C_1$-$C_3$-alkyl-, fluoro-$C_1$-$C_3$-alkoxy-, $C_3$-$C_7$-cycloalkyl-, 3- to 10-membered heterocycloalkyl-;

or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from: halo-, hydroxy-, cyano-, $C_1$-$C_3$-alkyl-, $C_1$-$C_3$-alkoxy-.

In another embodiment, the present invention relates to compounds of the general formula (I), supra, in which:

$L^A$ represents a methylene group, said methylene group being optionally substituted, one or more times, identically or differently, with a substituent selected from:

cyano-, hydroxy-, $C_1$-$C_3$-alkyl-, $C_1$-$C_3$-alkoxy-, fluoro-$C_1$-$C_3$-alkyl-, hydroxy-$C_1$-$C_3$-alkyl-, $C_3$-$C_5$-cycloalkyl-, 3- to 6-membered heterocycloalkyl-;

or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from: halo-, hydroxy-, cyano-, $C_1$-$C_3$-alkyl-, $C_1$-$C_3$-alkoxy-.

In another embodiment, the present invention relates to compounds of general formula (I), supra, in which:

$L^A$ represents a methylene group, said methylene group being optionally substituted, one or more times, identically or differently, with a substituent selected from:

hydroxy-, $C_1$-$C_3$-alkyl-, $C_1$-$C_3$-alkoxy-, hydroxy-$C_1$-$C_3$-alkyl-, or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from: halo-, hydroxy-, cyano-, $C_1$-$C_3$-alkyl-, $C_1$-$C_3$-alkoxy-.

In a preferred embodiment, the present invention relates to compounds of general formula (I), supra, in which:

$L^A$ represents methylene, said methylene group being optionally substituted one or two times, identically or differently, with $C_1$-$C_3$-alkyl-, wherein, if said methylene is substituted with two $C_1$-$C_3$-alkyl- groups, these may, together with the carbon atom they are attached to, form a $C_3$-$C_6$-cycloalkyl- ring.

In a particularly preferred embodiment, the present invention relates to compounds of general formula (I), supra, in which:

$L^A$ represents —$CH_2$—, —$CH(CH_3)$—, —$C(CH_3)_2$—, —$CH(C_2H_5)$—,

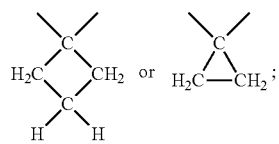

wherein the cyclobutyl- and the cyclopropyl- ring are optionally substituted one or more times, identically or differently, with a substituent selected from: halo-, hydroxy-, cyano-, $C_1$-$C_3$-alkyl-, $C_1$-$C_3$-alkoxy-.

In a particularly preferred embodiment, the present invention relates to compounds of general formula (I), supra, in which:

$L^A$ represents —$CH_2$—, —$CH(CH_3)$—, —$C(CH_3)_2$— or

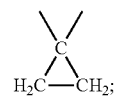

wherein the cyclopropyl- ring is optionally substituted one or more times, identically or differently, with a substituent selected from: halo-, hydroxy-, cyano-, $C_1$-$C_3$-alkyl-, $C_1$-$C_3$-alkoxy-.

In another particularly preferred embodiment, the present invention relates to compounds of general formula (I), supra, in which:

$L^A$ represents —$CH_2$—, —$CH(CH_3)$—, —$C(CH_3)_2$— or

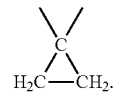

In another particularly preferred embodiment, the present invention relates to compounds of general formula (I), supra, in which:

$L^A$ represents —$CH_2$—, —$CH(CH_3)$—, or

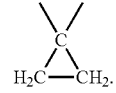

In another particularly preferred embodiment, the present invention relates to compounds of general formula (I), supra, in which:

$L^A$ represents —$CH_2$— or —$CH(CH_3)$—.

In another particularly preferred embodiment, the present invention relates to compounds of general formula (I), supra, in which:

$L^A$ represents —$CH_2$—.

In another particularly preferred embodiment, the present invention relates to compounds of general formula (I), supra, in which:

$L^A$ represents —$CH(CH_3)$—.

In another particularly preferred embodiment, the present invention relates to compounds of general formula (I), supra, in which:

$L^A$ represents

wherein the cyclopropyl- ring is optionally substituted one or more times, identically or differently, with a substituent selected from: halo-, hydroxy-, cyano-, $C_1$-$C_3$-alkyl-, $C_1$-$C_3$-alkoxy-.

In another particularly preferred embodiment, the present invention relates to compounds of general formula (I), supra, in which:
$L^A$ represents

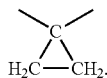

In another embodiment, the present invention relates to compounds of the general formula (I), supra, in which:
$L^B$ represents —N(H)—C(=O)— or —C(=O)—N(H)—.

In a preferred embodiment, the present invention relates to compounds of the general formula (I), supra, in which:
$L^B$ represents *N(H)—C(=O)**;
wherein "*" indicates the point of attachment to $R^2$, and "**" indicates the point of attachment to the phenyl group.

In another embodiment, the present invention relates to compounds of the general formula (I), supra, in which:
$R^1$ represents a group selected from:
5- to 8-membered heterocycloalkyl-, 4- to 10-membered heterocycloalkenyl-, aryl-, heteroaryl-, and —N($R^7$)—($C_1$-$C_6$-alkyl);
wherein said 5- to 8-membered heterocycloalkyl-, 4- to 10-membered heterocycloalkenyl-, aryl-, heteroaryl-, and —N($R^7$)—($C_1$-$C_6$-alkyl) group is optionally substituted, one or more times, identically or differently, with a substituent selected from: halo-, hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-.

In another embodiment, the present invention relates to compounds of the general formula (I), supra, in which:
$R^1$ represents a group selected from:

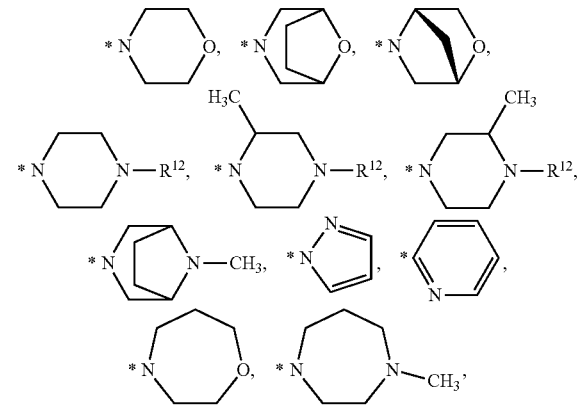

—N(CH$_3$)$_2$, —N(H)—(CH$_2$—CH$_2$—O—CH$_3$), —N(CH$_3$)—(CH$_2$—CH$_2$—O—CH$_3$);
wherein *indicates the point of attachment to $L^A$; and
wherein $R^{12}$ represents a methyl-, ethyl-, trifluoroethyl-, difluoroethyl- or cyclopropyl- group.

In another embodiment, the present invention relates to compounds of the general formula (I), supra, in which:
$R^1$ represents a group selected from:

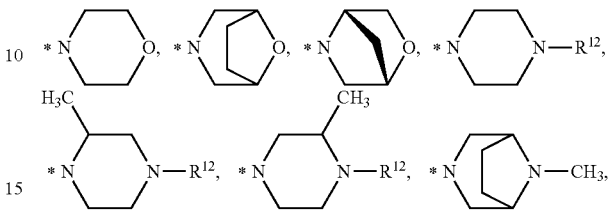

—N(CH$_3$)$_2$, —N(H)—(CH$_2$—CH$_2$—O—CH$_3$), —N(CH$_3$)—(CH$_2$—CH$_2$—O—CH$_3$);
wherein * indicates the point of attachment to $L^A$; and
wherein $R^{12}$ represents a methyl-, ethyl-, trifluoroethyl-, difluoroethyl- or cyclopropyl- group.

In another embodiment, the present invention relates to compounds of the general formula (I), supra, in which:
$R^1$ represents a 6-membered heterocycloalkyl- group; said group being optionally substituted with a $C_1$-$C_3$-alkyl-, —$C_1$-$C_2$-alkylene- (which means a bridging methylene or ethylene group) or $C_3$-$C_6$-cycloalkyl- group.

In another embodiment, the present invention relates to compounds of the general formula (I), supra, in which:
$R^1$ represents a group selected from:

—N(CH$_3$)$_2$, —N(H)—(CH$_2$—CH$_2$—O—CH$_3$), —N(CH$_3$)—(CH$_2$—CH$_2$—O—CH$_3$);
wherein * indicates the point of attachment to $L^A$; and
wherein $R^{12}$ represents methyl, ethyl or cyclopropyl.

In another embodiment, the present invention relates to compounds of the general formula (I), supra, in which:
$R^1$ represents a morpholino group, which is attached to $L^A$ via its nitrogen atom, and which may be optionally substituted one or two times, identically or differently, with $C_1$-$C_3$-alkyl-, or two of said $C_1$-$C_3$-alkyl groups together may form a $C_1$-$C_3$-alkylene group (forming a bridge between two different ring carbon atoms of said morpholino group);
or
$R^1$ represents thiomorpholino, 4-cyclopropylpiperazino, 4-methylpiperazino or pyrazol-1-yl group, said groups being attached to $L^A$ via their ring nitrogen atom.

In another embodiment, the present invention relates to compounds of the general formula (I), supra, in which:
$R^1$ represents a

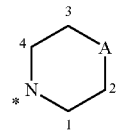

group;

wherein * indicates the point of attachment to $L^A$; wherein A represents a group selected from:

—O—, —S—, —S(=O)$_2$—, —NR$^{12}$—; wherein R$^{12}$ represents a hydrogen atom or group selected from:

C$_1$-C$_6$-alkyl-, C$_3$-C$_7$-cycloalkyl-; and wherein the carbon atoms 1 and 4, 1 and 3, 2 and 3, or 2 and 4 are optionally bridged via a methylene or ethylene group.

In another embodiment, the present invention relates to compounds of the general formula (I), supra, in which:

R$^1$ represents a

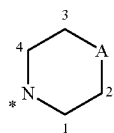

group;

wherein * indicates the point of attachment to $L^A$; wherein A represents a group selected from:

—O— and —NR$^{12}$—; wherein R$^{12}$ represents a group selected from: C$_1$-C$_3$-alkyl-, C$_3$-C$_6$-cycloalkyl-; and wherein the carbon atoms 2 and 3, or 2 and 4 are optionally bridged via a methylene or ethylene group;

In a particularly preferred embodiment, the present invention relates to compounds of the general formula (I), supra, in which:

R$^1$ represents a

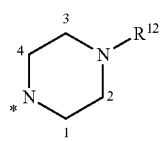

group;

wherein * indicates the point of attachment to $L^A$; wherein R$^{12}$ represents a methyl-, ethyl- or cyclopropyl- group; and wherein the carbon atoms 1 and 4, 1 and 3, 2 and 3, or 2 and 4 are optionally bridged via a methylene or ethylene group.

In a particularly preferred embodiment, the present invention relates to compounds of the general formula (I), supra, in which:

R$^1$ represents a

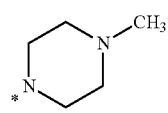

group;

wherein * indicates the point of attachment to $L^A$.

In a particularly preferred embodiment, the present invention relates to compounds of the general formula (I), supra, in which:

R$^1$ represents a

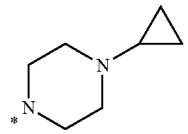

group;

wherein * indicates the point of attachment to $L^A$.

In a preferred embodiment, the present invention relates to compounds of the general formula (I), supra, in which:

R$^1$ represents a morpholino group, which is attached to $L^A$ via its nitrogen atom, and which may be optionally substituted one or two times, identically or differently, with C$_1$-C$_3$-alkyl-, or two of said C$_1$-C$_3$-alkyl- groups together may form a C$_1$-C$_3$-alkylene group (forming a bridge between two different ring carbon atoms of said morpholino group).

In a particularly preferred embodiment, the present invention relates to compounds of the general formula (I), supra, in which:

R$^1$ represents a group selected from:

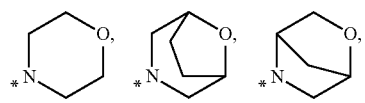

wherein "*" indicates the point of attachment to $L^A$.

In another particularly preferred embodiment, the present invention relates to compounds of the general formula (I), supra, in which:

R$^1$ represents a group selected from:

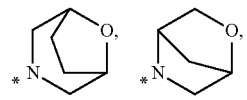

wherein "*" indicates the point of attachment to $L^A$.

In another particularly preferred embodiment, the present invention relates to compounds of the general formula (I), supra, in which:

R$^1$ represents a group selected from:

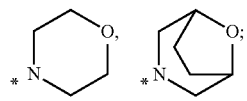

wherein "*" indicates the point of attachment to $L^A$.

In another particularly preferred embodiment, the present invention relates to compounds of the general formula (I), supra, in which:

R$^1$ represents

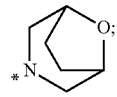

wherein "*" indicates the point of attachment to $L^A$.

In another particularly preferred embodiment, the present invention relates to compounds of the general formula (I), supra, in which:
$R^1$ represents

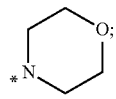

wherein "*" indicates the point of attachment to $L^A$.

In a particularly preferred embodiment, the present invention relates to compounds of the general formula (I), supra, in which:
$R^1$ represents

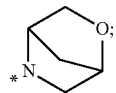

wherein "*" indicates the point of attachment to $L^A$.

In another particularly preferred embodiment, the present invention relates to compounds of the general formula (I), supra, in which:
$R^1$ represents a group selected from:

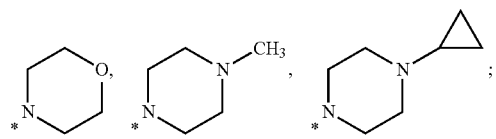

wherein "*" indicates the point of attachment to $L^A$.

In another embodiment, the present invention relates to compounds of the general formula (I), supra, in which:
$R^2$ represents a group selected from:

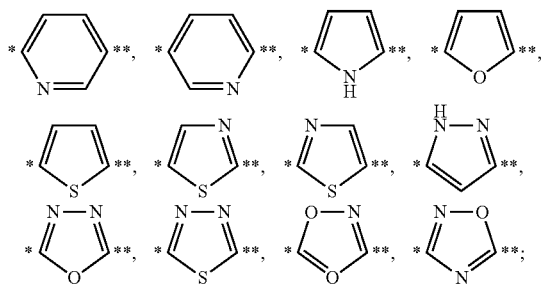

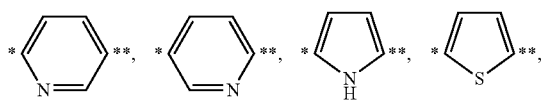

wherein "*" indicates the point of attachment to $R^3$, and "**" indicates the point of attachment to $L^B$; wherein said group is optionally substituted, one or more times, identically or differently, with a $C_1$-$C_3$-alkyl- group.

In another embodiment, the present invention relates to compounds of the general formula (I), supra, in which:
$R^2$ represents a group selected from:

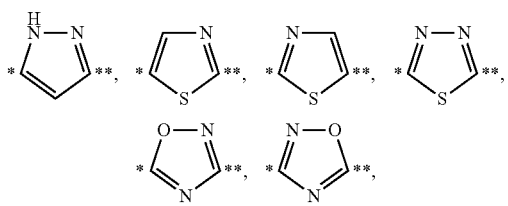

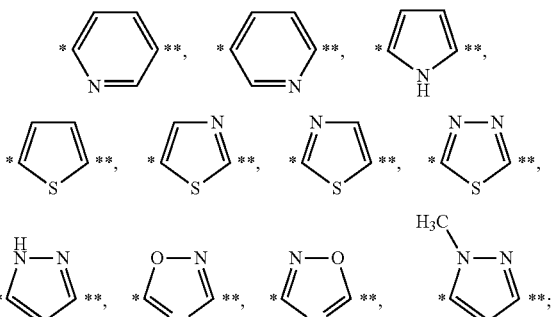

wherein "*" indicates the point of attachment to $R^3$, and "**" indicates the point of attachment to $L^B$.

In another embodiment, the present invention relates to compounds of the general formula (I), supra, in which:
$R^2$ represents a group selected from:

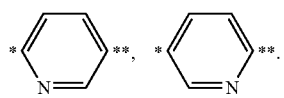

In another embodiment, the present invention relates to compounds of the general formula (I), supra, in which:
$R^2$ represents a group selected from:

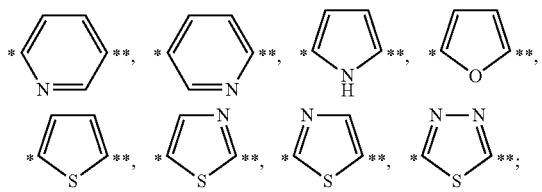

wherein "*" indicates the point of attachment to $R^3$, and "**" indicates the point of attachment to $L^B$.

In another embodiment, the present invention relates to compounds of the general formula (I), supra, in which:

$R^2$ represents a group selected from:

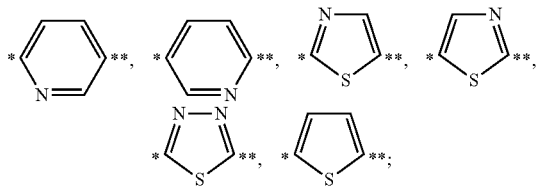

wherein "*" indicates the point of attachment to $R^3$, and "**" indicates the point of attachment to $L^B$.

In another embodiment, the present invention relates to compounds of the general formula (I), supra, in which:
$R^2$ represents

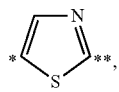

wherein "*" indicates the point of attachment to $R^3$, and "**" indicates the point of attachment to $L^B$.

In another embodiment, the present invention relates to compounds of the general formula (I), supra, in which:
$R^2$ represents

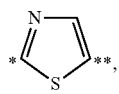

wherein "*" indicates the point of attachment to $R^3$, and "**" indicates the point of attachment to $L^B$.

In another embodiment, the present invention relates to compounds of the general formula (I), supra, in which:
$R^2$ represents

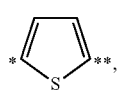

wherein "*" indicates the point of attachment to $R^3$, and "**" indicates the point of attachment to $L^B$.

In another preferred embodiment, the present invention relates to compounds of the general formula (I), supra, in which:
$R^2$ represents

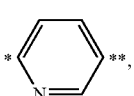

wherein "*" indicates the point of attachment to $R^3$, and "**" indicates the point of attachment to $L^B$.

In another particular preferred embodiment, the present invention relates to compounds of the general formula (I), supra, in which:
$R^2$ represents

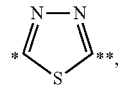

wherein "*" indicates the point of attachment to $R^3$, and "**" indicates the point of attachment to $L^B$.

In another embodiment, the present invention relates to compounds of the general formula (I), supra, in which:
$R^3$ represents a phenyl-group,
said phenyl-group being optionally substituted, one or more times, identically or differently, with a substituent selected from:
halo-, hydroxy-, —N($R^9$)($R^{10}$), —N(H)C(=O)$R^9$, cyano-, nitro-, $C_1$-$C_3$-alkyl-, $C_1$-$C_3$-alkoxy-, halo-$C_1$-$C_3$-alkyl-, hydroxy-$C_1$-$C_3$-alkyl-, amino-$C_1$-$C_3$-alkyl-, halo-$C_1$-$C_3$-alkoxy-.

In another embodiment, the present invention relates to compounds of the general formula (I), supra, in which:
$R^3$ represents a phenyl-group,
said phenyl-group being optionally substituted, one or more times, identically or differently, with a substituent selected from: halo-, hydroxy-, —$NH_2$, cyano-, $C_1$-$C_3$-alkyl-, $C_1$-$C_3$-alkoxy-, fluoro-$C_1$-$C_3$-alkyl-, hydroxy-$C_1$-$C_3$-alkyl-, fluoro-$C_1$-$C_3$-alkoxy-.

In another embodiment, the present invention relates to compounds of the general formula (I), supra, in which:
$R^3$ represents a phenyl-group,
said phenyl-group being optionally substituted, one or more times, identically or differently, with a substituent selected from: halo-, hydroxy-, —$NH_2$, cyano-, $C_1$-$C_2$-alkyl-, $C_1$-$C_2$-alkoxy-, fluoro-$C_1$-$C_2$-alkyl-, hydroxy-$C_1$-$C_2$-alkyl-, fluoro-$C_1$-$C_2$-alkoxy-.

In another embodiment, the present invention relates to compounds of the general formula (I), supra, in which:
$R^3$ represents a phenyl-group,
said phenyl-group being optionally substituted, one or two times, identically or differently, with fluoro, chloro, —$NH_2$ or methoxy.

In another embodiment, the present invention relates to compounds of the general formula (I), supra, in which:
$R^3$ represents a phenyl-group,
said phenyl-group being optionally substituted, one or more times, identically or differently, with a substituent selected from: halo-, $C_1$-$C_3$-alkoxy-.

In a preferred embodiment, the present invention relates to compounds of the general formula (I), supra, in which:
$R^3$ represents a phenyl-group,
said phenyl-group being optionally substituted one or two times, identically or differently, with fluoro or methoxy.

In a particularly preferred embodiment, the present invention relates to compounds of the general formula (I), supra, in which:
$R^3$ represents a phenyl-group,
said phenyl-group being optionally substituted, one or two times, with fluoro.

In another particularly preferred embodiment, the present invention relates to compounds of the general formula (I), supra, in which:
$R^3$ represents an unsubstituted phenyl-group.

In another particularly preferred embodiment, the present invention relates to compounds of the general formula (I), supra, in which:
$R^3$ represents a phenyl-group which is substituted in 2-, 3-, 5- and/or 6-position to the point of attachment of said phenyl-group to $R^2$ with a substituent selected from: Cl, F, —$CH_3$, with the proviso that the number of substituents is 1 or 2.

In another embodiment, the present invention relates to compounds of the general formula (I), supra, in which:
$R^3$ represents:

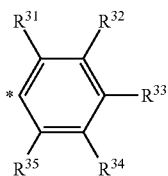

wherein "*" represents the point of attachment to $R^2$;
$R^{31}$, $R^{32}$, $R^{34}$ and $R^{35}$ represent, independently from each other, a hydrogen atom or a group selected from: halo-, hydroxy-, —$NH_2$, cyano-, nitro-,
$C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-; and
$R^{33}$ represents a hydrogen atom or a substituent selected from:
hydroxy-, —$CHF_2$, —$NH_2$, —$NR^{10}R^9$, —$CH_2NH_2$, —$N(H)C(=O)CH_3$.

In another embodiment, the present invention relates to compounds of the general formula (I), supra, in which:
$R^3$ represents:

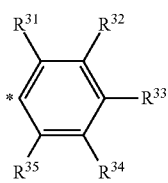

wherein "*" represents the point of attachment to $R^2$;
$R^{31}$, $R^{32}$, $R^{34}$ and $R^{35}$ represent, independently from each other, a hydrogen atom or a group selected from: halo-, hydroxy-, —$NH_2$, nitro-, $C_1$-$C_3$-alkyl-, $C_1$-$C_3$-alkoxy-, halo-$C_1$-$C_3$-alkyl-; and
$R^{33}$ represents a hydrogen atom or a substituent selected from:
fluoro-, hydroxy-, —$CHF_2$, —$NH_2$.

In another embodiment, the present invention relates to compounds of the general formula (I), supra, in which:
$R^3$ represents:

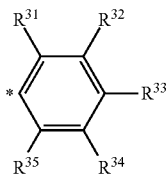

wherein "*" represents the point of attachment to $R^2$;
$R^{31}$, $R^{32}$, $R^{34}$ and $R^{35}$ represent, independently from each other, a hydrogen atom or a group selected from: fluoro-, chloro, hydroxy-, nitro-,
$C_1$-$C_3$-alkyl-, $C_1$-$C_3$-alkoxy-, halo-$C_1$-$C_3$-alkyl-, —$NH_2$;
$R^{33}$ represents a hydrogen atom.

In another embodiment, the present invention relates to compounds of the general formula (I), supra, in which:
$R^3$ represents:

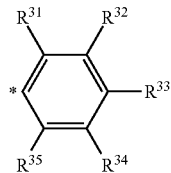

wherein "*" represents the point of attachment to $R^2$;
$R^{31}$, $R^{32}$, $R^{34}$ and $R^{35}$ represent, independently from each other, a hydrogen atom or a group selected from: fluoro-, chloro, methyl-, methoxy-, trifluoromethyl-;
$R^{33}$ represents a hydrogen atom.

In another embodiment, the present invention relates to compounds of the general formula (I), supra, in which:
$R^3$ represents:

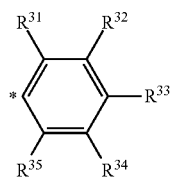

wherein "*" represents the point of attachment to $R^2$;
$R^{31}$, $R^{32}$, $R^{34}$ and $R^{35}$ represent, independently from each other, a hydrogen atom or a group selected from: fluoro-, chloro, methyl-, methoxy-, trifluoromethyl-; with the proviso that at least two of $R^{31}$, $R^{32}$, $R^{34}$ and $R^{35}$ represent a hydrogen atom; and
$R^{33}$ represents a hydrogen atom.

In another particularly preferred embodiment, the present invention relates to compounds of the general formula (I), supra, in which:
$R^3$ represents an ortho-fluorophenyl-group.

In another particularly preferred embodiment, the present invention relates to compounds of the general formula (I), supra, in which:
$R^3$ represents a meta-fluorophenyl-group.

In another particularly preferred embodiment, the present invention relates to compounds of the general formula (I), supra, in which:
$R^3$ represents a 2,3-difluorophenyl-group.

In another particularly preferred embodiment, the present invention relates to compounds of the general formula (I), supra, in which:
$R^3$ represents a 3,5-difluorophenyl-group.

In another particularly preferred embodiment, the present invention relates to compounds of the general formula (I), supra, in which:
$R^3$ represents a 2,6-difluorophenyl-group.

In another particularly preferred embodiment, the present invention relates to compounds of the general formula (I), supra, in which:
$R^3$ represents a 2-methylphenyl-group.

In another embodiment, the present invention relates to compounds of the general formula (I), supra, in which:
$R^4$ represents a hydrogen atom or a $C_1$-$C_3$-alkyl- group.

In another embodiment, the present invention relates to compounds of the general formula (I), supra, in which:

$R^4$ represents a hydrogen atom or a methyl- group.

In another embodiment, the present invention relates to compounds of the general formula (I), supra, in which:
$R^4$ represents methyl-.

In a preferred embodiment, the present invention relates to compounds of the general formula (I), supra, in which:
$R^4$ represents a hydrogen atom.

In another embodiment, the present invention relates to compounds of the general formula (I), supra, in which:
$R^5$ represents a hydrogen atom or a halogen atom or a group selected from:
cyano-, $C_1$-$C_3$-alkyl-, $C_1$-$C_3$-alkoxy-.

In another embodiment, the present invention relates to compounds of the general formula (I), supra, in which:
$R^5$ represents a group selected from: cyano-, $C_1$-$C_3$-alkyl-, $C_1$-$C_3$-alkoxy-.

In another embodiment, the present invention relates to compounds of the general formula (I), supra, in which:
$R^5$ represents a hydrogen atom or a halogen atom.

In another embodiment, the present invention relates to compounds of the general formula (I), supra, in which:
$R^5$ represents hydrogen, fluoro or chloro.

In another embodiment, the present invention relates to compounds of the general formula (I), supra, in which:
$R^5$ represents fluoro or chloro.

In another embodiment, the present invention relates to compounds of the general formula (I), supra, in which:
$R^5$ represents chloro.

In another embodiment, the present invention relates to compounds of the general formula (I), supra, in which:
$R^5$ represents fluoro.

In a preferred embodiment, the present invention relates to compounds of the general formula (I), supra, in which:
$R^5$ represents hydrogen.

In another embodiment, the present invention relates to compounds of the general formula (I), supra, in which:
$R^6$ represents a group selected from:
$C_1$-$C_6$-alkyl-, $C_2$-$C_6$-alkenyl-, $C_2$-$C_6$-alkynyl-,
$C_1$-$C_6$-alkoxy-, $C_3$-$C_6$-cycloalkoxy-, halo-, hydroxy-, cyano-, aryl-,
heteroaryl-, —N($R^9$)($R^{10}$), —C(=O)—O—$C_1$-$C_4$-alkyl, —C(=O)—N($R^9$)($R^{10}$), $R^9$—S—, $R^9$—S(=O)—, $R^9$—S(=O)$_2$—;
said $C_1$-$C_6$-alkyl-, $C_2$-$C_6$-alkenyl-, $C_2$-$C_6$-alkynyl-, aryl-, heteroaryl-, and $C_1$-$C_6$-alkoxy- group being optionally substituted, one or more times, identically or differently, with a substituent selected from: halo-, cyano-, nitro-, hydroxy-, $C_1$-$C_3$-alkyl-, $C_1$-$C_3$-alkoxy-, halo-$C_1$-$C_3$-alkoxy-, hydroxy-$C_1$-$C_3$-alkoxy-, $C_1$-$C_3$-alkoxy-$C_2$-$C_3$-alkoxy-,
$C_3$-$C_7$-cycloalkyl-, $C_4$-$C_7$-cycloalkenyl-,
3- to 10-membered heterocycloalkyl-, 4- to 10-membered heterocycloalkenyl-,
aryl-, heteroaryl-, —C(=O)$R^9$, —C(=O)O—($C_1$-$C_4$-alkyl), —OC(=O)—$R^9$, —N(H)C(=O)$R^9$, —N($R^{10}$)C(=O)$R^9$,
—N(H)C(=O)N$R^{10}R^9$, —N($R^{11}$)C(=O)N$R^{10}R^9$, —N(H)$R^9$, —N$R^{10}R^9$,
—C(=O)N(H)$R^9$, —C(=O)N$R^{10}R^9$, $R^9$—S—, $R^9$—S(=O)—, $R^9$—S(=O)$_2$—,
—N(H)S(=O)$R^9$, —N($R^{10}$)S(=O)$R^9$, —S(=O)N(H)$R^9$, —S(=O)N$R^{10}R^9$,
—N(H)S(=O)$_2R^9$, —N($R^9$)S(=O)$_2R^{10}$, —S(=O)$_2$N(H)$R^9$, —S(=O)$_2$N$R^{10}R^9$,
—S(=O)(=N$R^{10}$)$R^9$, —N=S(=O)($R^{10}$)$R^9$;

In another embodiment, the present invention relates to compounds of the general formula (I), supra, in which:
$R^6$ represents a group selected from:
$C_1$-$C_6$-alkyl-, $C_2$-$C_6$-alkenyl-, $C_2$-$C_6$-alkynyl-
$C_1$-$C_6$-alkoxy-, halo-, hydroxy-, halo-$C_1$-$C_6$-alkyl-, halo-$C_1$-$C_6$-alkoxy-, cyano-, -aryl, -heteroaryl, —N($R^9$)($R^{10}$), —C(=O)—O—$C_1$-$C_4$-alkyl, —C(=O)—N($R^9$)($R^{10}$);
said $C_1$-$C_6$-alkyl-, $C_2$-$C_6$-alkenyl-, $C_2$-$C_6$-alkynyl-, aryl-, heteroaryl- or $C_1$-$C_6$-alkoxy- group being optionally substituted, one or more times, identically or differently, with halo-, cyano-, nitro-, hydroxy-, $C_1$-$C_3$-alkyl-, $C_1$-$C_3$-alkoxy-, halo-$C_1$-$C_3$-alkoxy-, hydroxy-$C_1$-$C_3$-alkoxy-, $C_1$-$C_3$-alkoxy-$C_2$-$C_3$-alkoxy-,
$C_3$-$C_7$-cycloalkyl-, $C_4$-$C_7$-cycloalkenyl-, 3- to 10-membered heterocycloalkyl-,
4- to 10-membered heterocycloalkenyl-, aryl-, heteroaryl-,
—C(=O)$R^9$, —C(=O)O—($C_1$-$C_4$-alkyl), —OC(=O)—$R^9$, —N(H)C(=O)$R^9$, —N($R^{10}$)C(=O)$R^9$,
—N(H)C(=O)N$R^{10}R^9$, —N($R^{11}$)C(=O)N$R^{10}R^9$, —N(H)$R^9$, —N$R^{10}R^9$,
—C(=O)N(H)$R^9$, —C(=O)N$R^{10}R^9$, $R^9$—S—, $R^9$—S(=O)—, $R^9$—S(=O)$_2$—,
—N(H)S(=O)$R^9$, —N($R^{10}$)S(=O)$R^9$, —S(=O)N(H)$R^9$, —S(=O)N$R^{10}R^9$,
—N(H)S(=O)$_2R^9$, —N($R^9$)S(=O)$_2R^{10}$, —S(=O)$_2$N(H)$R^9$, —S(=O)$_2$N$R^{10}R^9$,
—S(=O)(=N$R^{10}$)$R^9$, —S(=O)(=N$R^{10}$)$R^9$, —N=S(=O)($R^{10}$)$R^9$.

In another embodiment, the present invention relates to compounds of the general formula (I), supra, in which:
$R^6$ represents a group selected from:
$C_1$-$C_6$-alkyl-, $C_1$-$C_6$-alkoxy-, halo-, hydroxy-, fluoro-$C_1$-$C_6$-alkyl-, fluoro-$C_1$-$C_6$-alkoxy-, phenyl-, 5- to 6-membered heteroaryl-, cyano-, —C(=O)—O—$C_1$-$C_4$-alkyl, —C(=O)—N($R^9$)($R^{10}$);
said $C_1$-$C_6$-alkyl- or $C_1$-$C_6$-alkoxy- group being optionally substituted, one or more times, identically or differently, with
$C_1$-$C_3$-alkyl-, $C_1$-$C_3$-alkoxy-, halo-$C_1$-$C_3$-alkoxy-, hydroxy-$C_1$-$C_3$-alkoxy-, $C_1$-$C_3$-alkoxy-$C_2$-$C_3$-alkoxy-,
$C_3$-$C_7$-cycloalkyl-, 3- to 10-membered heterocycloalkyl-, aryl-, heteroaryl-,
—C(=O)$R^9$, —C(=O)O—($C_1$-$C_4$-alkyl), —OC(=O)—$R^9$, —N(H)C(=O)$R^9$, —N($R^{10}$)C(=O)$R^9$,
—N(H)C(=O)N$R^{10}R^9$, —N($R^{11}$)C(=O)N$R^{10}R^9$, —N(H)$R^9$, —N$R^{10}R^9$,
—C(=O)N(H)$R^9$, —C(=O)N$R^{10}R^9$.

In another embodiment, the present invention relates to compounds of the general formula (I), supra, in which:
$R^6$ represents a group selected from:
$C_1$-$C_6$-alkyl-, $C_1$-$C_6$-alkoxy-, $C_3$-$C_6$-cycloalkoxy-, halo-, hydroxy-, fluoro-$C_1$-$C_6$-alkyl-, fluoro-$C_1$-$C_6$-alkoxy-, phenyl-, 5- to 6-membered heteroaryl-, cyano-, —C(=O)—O—$C_1$-$C_4$-alkyl, —C(=O)—N($R^9$)($R^{10}$), $R^9$—S—, $R^9$—S(=O)—, $R^9$—S(=O)$_2$—; said $C_1$-$C_6$-alkyl- or $C_1$-$C_6$-alkoxy- group being optionally substituted, one or more times, identically or differently, with
$C_1$-$C_3$-alkyl-, $C_1$-$C_3$-alkoxy-, halo-$C_1$-$C_3$-alkoxy-, hydroxy-$C_1$-$C_3$-alkoxy-, $C_1$-$C_3$-alkoxy-$C_2$-$C_3$-alkoxy-,
$C_3$-$C_7$-cycloalkyl-, 3- to 10-membered heterocycloalkyl-, aryl-, heteroaryl-,
—C(=O)$R^9$, —C(=O)O—($C_1$-$C_4$-alkyl), —OC(=O)—$R^9$, —N(H)C(=O)$R^9$, —N($R^{10}$)C(=O)$R^9$,
—N(H)C(=O)N$R^{10}R^9$, —N($R^{11}$)C(=O)N$R^{10}R^9$, —N(H)$R^9$, —N$R^{10}R^9$,
—C(=O)N(H)$R^9$, —C(=O)N$R^{10}R^9$.

In another embodiment, the present invention relates to compounds of the general formula (I), supra, in which:
$R^6$ represents a group selected from:
- $C_1$-$C_6$-alkyl-, $C_1$-$C_6$-alkoxy-, halo-, hydroxy-, fluoro-$C_1$-$C_6$-alkyl-, fluoro-$C_1$-$C_6$-alkoxy-, cyano-, —C(=O)—O—$C_1$-$C_4$-alkyl, —C(=O)—N($R^9$)($R^{10}$);
- said $C_1$-$C_6$-alkyl- or $C_1$-$C_6$-alkoxy- group being optionally substituted, one or more times, identically or differently, with
- $C_3$-$C_7$-cycloalkyl-, 3- to 10-membered heterocycloalkyl-, aryl-, heteroaryl-,
- —C(=O)$R^9$, —C(=O)O—($C_1$-$C_4$-alkyl), —OC(=O)—$R^9$, —N(H)C(=O)$R^9$, —N($R^{10}$)C(=O)$R^9$, —N(H)C(=O)N$R^{10}R^9$, —N($R^{11}$)C(=O)N$R^{10}R^9$, —N(H)$R^9$, —N$R^{10}R^9$,
- —C(=O)N(H)$R^9$, —C(=O)N$R^{10}R^9$.

In another embodiment, the present invention relates to compounds of the general formula (I), supra, in which:
$R^6$ represents a group selected from:
- $C_1$-$C_6$-alkyl-, $C_1$-$C_6$-alkoxy-, $C_3$-$C_6$-cycloalkoxy-, halo-, hydroxy-, cyano-, —C(=O)—O—$C_1$-$C_4$-alkyl, —C(=O)—N($R^9$)($R^{10}$), $R^9$—S—, $R^9$—S(=O)—, $R^9$—S(=O)$_2$—;
- said $C_1$-$C_6$-alkyl-, and $C_1$-$C_6$-alkoxy- group being optionally substituted, one or more times, identically or differently, with a substituent selected from: halo-, cyano-, nitro-, hydroxy-,
- $C_1$-$C_3$-alkoxy-, halo-$C_1$-$C_3$-alkoxy-,
- hydroxy-$C_1$-$C_3$-alkoxy-, $C_1$-$C_3$-alkoxy-$C_2$-$C_3$-alkoxy-,
- $C_3$-$C_7$-cycloalkyl-, 3- to 10-membered heterocycloalkyl-, —C(=O)$R^9$, —C(=O)O—$R^9$, —C(=O)O—($C_1$-$C_4$-alkyl), —N(H)C(=O)$R^9$, —N($R^{10}$)C(=O)$R^9$, —N(H)C(=O)N$R^{10}R^9$, —N($R^{11}$)C(=O)N$R^{10}R^9$, —N(H)$R^9$, —N$R^{10}R^9$,
- —C(=O)N(H)$R^9$, —C(=O)N$R^{10}R^9$, $R^9$—S—, $R^9$—S(=O)—, $R^9$—S(=O)$_2$—,
- —N(H)S(=O)$R^9$, —N($R^{10}$)S(=O)$R^9$, —S(=O)N(H)$R^9$, —S(=O)N$R^{10}R^9$,
- —N(H)S(=O)$_2R^9$, —N($R^9$)S(=O)$_2R^{10}$, —S(=O)$_2$N(H)$R^9$, —S(=O)$_2$N$R^{10}R^9$,
- —S(=O)(=N$R^{10}$)$R^9$, —N=S(=O)($R^{10}$)$R^9$.

In another embodiment, the present invention relates to compounds of the general formula (I), supra, in which:
$R^6$ represents a group selected from:
- $C_1$-$C_6$-alkyl-, $C_1$-$C_6$-alkoxy-, $C_3$-$C_6$-cycloalkoxy-, halo-, hydroxy-, cyano-,
- —C(=O)—O—$C_1$-$C_4$-alkyl, —C(=O)—N($R^9$)($R^{10}$), $R^9$—S—, $R^9$—S(=O)—, $R^9$—S(=O)$_2$—;
- said $C_1$-$C_6$-alkyl-, and $C_1$-$C_6$-alkoxy- group being optionally substituted, one or more times, identically or differently, with a substituent selected from: halo-, $C_1$-$C_3$-alkoxy-, $C_1$-$C_3$-alkoxy-$C_2$-$C_3$-alkoxy-, $C_3$-$C_7$-cycloalkyl-, 3- to 10-membered heterocycloalkyl-,
- —C(=O)$R^9$, —C(=O)O—$R^9$, —C(=O)O—($C_1$-$C_4$-alkyl), —N(H)C(=O)$R^9$, —N($R^{10}$)C(=O)$R^9$, —N(H)C(=O)N$R^{10}R^9$, —N($R^{11}$)C(=O)N$R^{10}R^9$, —N(H)$R^9$, —N$R^{10}R^9$,
- —C(=O)N(H)$R^9$, —C(=O)N$R^{10}R^9$, $R^9$—S—, $R^9$—S(=O)—, $R^9$—S(=O)$_2$—,
- —N(H)S(=O)$R^9$, —N($R^{10}$)S(=O)$R^9$, —S(=O)N(H)$R^9$, —S(=O)N$R^{10}R^9$,
- —N(H)S(=O)$_2R^9$, —N($R^9$)S(=O)$_2R^{10}$, —S(=O)$_2$N(H)$R^9$, —S(=O)$_2$N$R^{10}R^9$,
- —S(=O)(=N$R^{10}$)$R^9$, —N=S(=O)($R^{10}$)$R^9$.

In another embodiment, the present invention relates to compounds of the general formula (I), supra, in which:
$R^6$ represents a group selected from:
- $C_1$-$C_6$-alkyl-, $C_1$-$C_6$-alkoxy-, $C_3$-$C_6$-cycloalkoxy-, halo-, hydroxy-, cyano-, —C(=O)—O—$C_1$-$C_4$-alkyl, —C(=O)—N($R^9$)($R^{10}$), $R^9$—S—, $R^9$—S(=O)—, $R^9$—S(=O)$_2$—;
- said $C_1$-$C_6$-alkyl-, and $C_1$-$C_6$-alkoxy- group being optionally substituted, one or more times, identically or differently, with a substituent selected from: halo-, $C_1$-$C_3$-alkoxy-, $C_1$-$C_3$-alkoxy-$C_2$-$C_3$-alkoxy-, $C_3$-$C_7$-cycloalkyl-.

In another embodiment, the present invention relates to compounds of the general formula (I), supra, in which:
$R^6$ represents a group selected from:
- $C_1$-$C_3$-alkyl-, $C_1$-$C_3$-alkoxy-, halo-, hydroxy-, cyano-, —N($R^9$)($R^{10}$), —C(=O)—O—$C_1$-$C_4$-alkyl, —C(=O)—N($R^9$)($R^{10}$); said $C_1$-$C_3$-alkyl- and $C_1$-$C_3$-alkoxy- group being optionally substituted, one or more times, identically or differently, with halo-, cyano-, $C_1$-$C_3$-alkoxy-, $R^9$—S(=O)$_2$—.

In another embodiment, the present invention relates to compounds of the general formula (I), supra, in which:
$R^6$ represents halo-, cyano-, $C_1$-$C_4$-alkyl-, fluoro-$C_1$-$C_3$-alkyl-, $C_1$-$C_4$-alkoxy- or fluoro-$C_1$-$C_3$-alkoxy-, —C(=O)N$R^9R^{10}$ or a 5-membered heteroaryl-,
wherein said $C_1$-$C_4$-alkyl- and $C_1$-$C_4$-alkoxy- group may be optionally substituted by one phenyl-group.

In a preferred embodiment, the present invention relates to compounds of the general formula (I), supra, in which:
$R^6$ represents halogen, $C_1$-$C_4$-alkyl-, fluoro-$C_1$-$C_3$-alkyl-, $C_1$-$C_4$-alkoxy- or fluoro-$C_1$-$C_3$-alkoxy-.

In a preferred embodiment, the present invention relates to compounds of the general formula (I), supra, in which:
$R^6$ represents a group selected from:
methoxy-, difluoromethoxy-, trifluoromethoxy-, methyl-, trifluormethyl-, tert-butyl-, chloro-, bromo-, cyano-, methoxymethyl-, —C(=O)NH$_2$, —CH$_2$—S(=O)$_2$—CH$_3$.

In another preferred embodiment, the present invention relates to compounds of the general formula (I), supra, in which:
$R^6$ represents halogen.

In another preferred embodiment, the present invention relates to compounds of the general formula (I), supra, in which:
$R^6$ represents fluoro-$C_1$-$C_3$-alkyl-.

In another preferred embodiment, the present invention relates to compounds of the general formula (I), supra, in which:
$R^6$ represents fluoro-$C_1$-$C_3$-alkoxy-.

In another preferred embodiment, the present invention relates to compounds of the general formula (I), supra, in which:
$R^6$ represents $C_1$-$C_4$-alkoxy-.

In another preferred embodiment, the present invention relates to compounds of the general formula (I), supra, in which:
$R^6$ represents cyclopropyloxy-.

In another preferred embodiment, the present invention relates to compounds of the general formula (I), supra, in which:
$R^6$ represents cyclopropylmethoxy-.

In a particularly preferred embodiment, the present invention relates to compounds of the general formula (I), supra, in which:
$R^6$ represents chloro, $C_1$-$C_4$-alkyl-, methoxy-, difluoromethoxy-, trifluoromethoxy-, trifluoromethyl-, —C(=O)—NH$_2$, —CH$_2$—O—CH$_3$ or —CH$_2$—S(=O)$_2$—CH$_3$.

In another particularly preferred embodiment, the present invention relates to compounds of the general formula (I), supra, in which:
R$^6$ represents difluoromethoxy- or trifluoromethoxy-.

In another particularly preferred embodiment, the present invention relates to compounds of the general formula (I), supra, in which:
R$^6$ represents chloro, C$_1$-C$_4$-alkyl-, methoxy-, trifluoromethoxy- or trifluoromethyl-.

In another particularly preferred embodiment, the present invention relates to compounds of the general formula (I), supra, in which:
R$^6$ represents chloro.

In another particularly preferred embodiment, the present invention relates to compounds of the general formula (I), supra, in which:
R$^6$ represents C$_1$-C$_4$-alkyl-.

In another particularly preferred embodiment, the present invention relates to compounds of the general formula (I), supra, in which:
R$^6$ represents methoxy.

In another particularly preferred embodiment, the present invention relates to compounds of the general formula (I), supra, in which:
R$^6$ represents trifluoromethyl.

In another particularly preferred embodiment, the present invention relates to compounds of the general formula (I), supra, in which:
R$^6$ represents trifluoromethoxy or tert-butyl;

In another particularly preferred embodiment, the present invention relates to compounds of the general formula (I), supra, in which:
R$^6$ represents tert-butyl.

In another particularly preferred embodiment, the present invention relates to compounds of the general formula (I), supra, in which:
R$^6$ represents trifluoromethoxy.

In a particularly preferred embodiment, the present invention relates to compounds of the general formula (I), supra, in which:
R$^6$ represents difluoromethoxy-.

In another particularly preferred embodiment, the present invention relates to compounds of the general formula (I), supra, in which:
R$^6$ represents —C(=O)—N(R$^9$)(R$^{10}$).

In a particularly preferred embodiment, the present invention relates to compounds of the general formula (I), supra, in which:
R$^6$ represents —C(=O)—NH$_2$.

In a particularly preferred embodiment, the present invention relates to compounds of the general formula (I), supra, in which:
R$^6$ represents —CH$_2$—O—CH$_3$.

In a particularly preferred embodiment, the present invention relates to compounds of the general formula (I), supra, in which:
R$^6$ represents —CH$_2$—S(=O)$_2$—CH$_3$.

In a particularly preferred embodiment, the present invention relates to compounds of the general formula (I), supra, in which:
R$^6$ represents a group selected from: R$^9$—S—, R$^9$—S(=O)—, R$^9$—S(=O)$_2$—, wherein R$^9$ represents a C$_1$-C$_3$-alkyl- group, preferably a methyl- group.

In another embodiment, the present invention relates to compounds of the general formula (I), supra, in which:
R$^7$ represents —H, C$_1$-C$_3$-alkyl- or C$_1$-C$_3$-alkoxy-C$_1$-C$_3$-alkyl-.

In another embodiment, the present invention relates to compounds of the general formula (I), supra, in which:
R$^7$ represents —H or C$_1$-C$_3$-alkyl-.

In another embodiment, the present invention relates to compounds of the general formula (I), supra, in which:
R$^9$ represents —H or C$_1$-C$_3$-alkyl-.

In another embodiment, the present invention relates to compounds of the general formula (I), supra, in which:
R$^{10}$ represents —H or C$_1$-C$_3$-alkyl-.

In another embodiment, the present invention relates to compounds of the general formula (I), supra, in which:
R$^{11}$ represents —H or C$_1$-C$_3$-alkyl-.

In another embodiment, the present invention relates to compounds of the general formula (Ia):

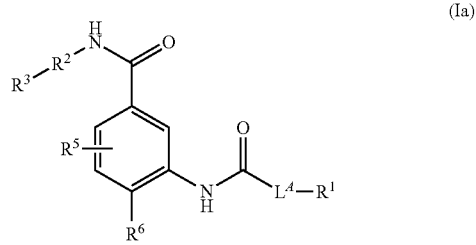

in which R$^1$, R$^2$, R$^3$, R$^5$, R$^6$ and L$^A$ are as defined for general formula (I), supra.

In another embodiment, the present invention relates to compounds of the general formula (Ib):

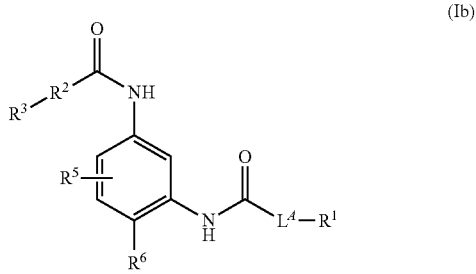

in which R$^1$, R$^2$, R$^3$, R$^5$, R$^6$ and L$^A$ are as defined for general formula (I), supra.

In another embodiment, the present invention relates to compounds of the general formula (Ic):

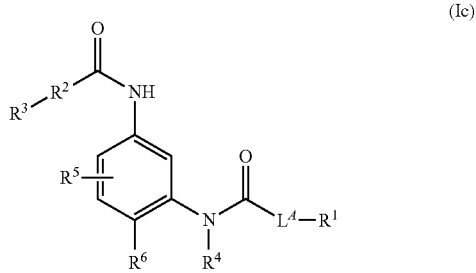

in which R$^1$, R$^2$, R$^3$, R$^4$, R$^5$, R$^6$ and L$^A$ are as defined for general formula (I), supra.

It is to be understood that the present invention relates also to any combination of the preferred embodiments described above.

Some examples of combinations are given hereinafter. However, the invention is not limited to these combinations.

In a preferred embodiment, the present invention relates to compounds of general formula (I):

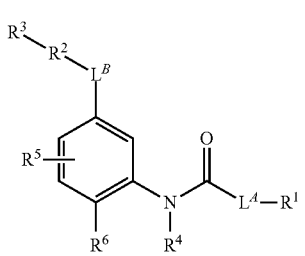

(I)

in which:
$L^A$ represents a methylene or ethylene group, said methylene or ethylene group being optionally substituted, one or more times, identically or differently, with a substituent selected from:
hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-, 3- to 10-membered heterocycloalkyl-;
or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from: halo-, hydroxy-, cyano-, $C_1$-$C_3$-alkyl-, $C_1$-$C_3$-alkoxy-;
$L^B$ represents —N(H)—C(=O)— or —C(=O)—N(H)—;
$R^1$ represents a group selected from:
5- to 8-membered heterocycloalkyl-, 4- to 10-membered heterocycloalkenyl-, aryl-, heteroaryl-, and —N($R^7$)—($C_1$-$C_6$-alkyl);
wherein said 5- to 8-membered heterocycloalkyl-, 4- to 10-membered heterocycloalkenyl-, aryl-, heteroaryl-, and —N($R^7$)—($C_1$-$C_6$-alkyl) group is optionally substituted, one or more times, identically or differently, with a substituent selected from: halo-, hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-;
$R^2$ represents a group selected from:

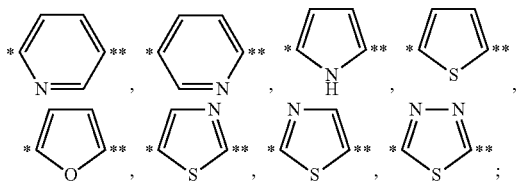

wherein "*" indicates the point of attachment to $R^3$, and "**" indicates the point of attachment to $L^B$; wherein said group is optionally substituted, one or more times, identically or differently, with a $C_1$-$C_3$-alkyl- group;
$R^3$ represents a phenyl-group,
said phenyl-group being optionally substituted, one or more times, identically or differently, with a substituent selected from:
halo-, hydroxy-, —N($R^9$)($R^{10}$), —N(H)C(=O)$R^9$, cyano-, nitro-, $C_1$-$C_3$-alkyl-, $C_1$-$C_3$-alkoxy-, halo-$C_1$-$C_3$-alkyl-, hydroxy-$C_1$-$C_3$-alkyl-, amino-$C_1$-$C_3$-alkyl-, halo-$C_1$-$C_3$-alkoxy-;
$R^4$ represents a hydrogen atom or a $C_1$-$C_3$-alkyl- group;
$R^5$ represents a hydrogen atom or a halogen atom or a group selected from:
cyano-, $C_1$-$C_3$-alkyl-, $C_1$-$C_3$-alkoxy-;
$R^6$ represents a group selected from:
$C_1$-$C_6$-alkyl-, $C_2$-$C_6$-alkenyl-, $C_2$-$C_6$-alkynyl- $C_1$-$C_6$-alkoxy-, halo-, hydroxy-, cyano-, aryl-, heteroaryl-, —N($R^9$)($R^{10}$), —C(=O)—O—$R^9$, —C(=O)—N($R^9$)($R^{10}$);
said $C_1$-$C_6$-alkyl-, $C_2$-$C_6$-alkenyl-, $C_2$-$C_6$-alkynyl-, aryl-, heteroaryl-, and $C_1$-$C_6$-alkoxy- group being optionally substituted, one or more times, identically or differently, with halo-, cyano-, nitro-, hydroxy-, $C_1$-$C_3$-alkyl-, $C_1$-$C_3$-alkoxy-, halo-$C_1$-$C_3$-alkoxy-, hydroxy-$C_1$-$C_3$-alkoxy-, $C_1$-$C_3$-alkoxy-$C_1$-$C_3$-alkoxy-, $C_3$-$C_7$-cycloalkyl-, $C_4$-$C_7$-cycloalkenyl-, 3- to 10-membered heterocycloalkyl-, 4- to 10-membered heterocycloalkenyl-, aryl-, heteroaryl-, —C(=O)$R^9$, —C(=O)O—$R^9$, —OC(=O)—$R^9$, —N(H)C(=O)$R^9$, —N($R^{10}$)C(=O)$R^9$, —N(H)C(=O)N$R^{10}R^9$, —N($R^{11}$)C(=O)N$R^{10}R^9$, —N(H)$R^9$, —N$R^{10}R^9$, —C(=O)N(H)$R^9$, —C(=O)N$R^{10}R^9$, $R^9$—S—, $R^9$—S(=O)—, $R^9$—S(=O)$_2$—, —N(H)S(=O)$R^9$, —N($R^{10}$)S(=O)$R^9$, —S(=O)N(H)$R^9$, —S(=O)N$R^{10}R^9$, —N(H)S(=O)$_2R^9$, —N($R^9$)S(=O)$_2R^{10}$, —S(=O)$_2$N(H)$R^9$, —S(=O)$_2$N$R^{10}R^9$, —S(=O)(=N$R^{10}$)$R^9$, —S(=O)(=N$R^{10}$)$R^9$, —N=S(=O)($R^{10}$)$R^9$;
$R^7$ represents —H or $C_1$-$C_3$-alkyl-;
$R^9$, $R^{10}$, $R^{11}$
represent, independently from each other, —H or $C_1$-$C_3$-alkyl-;
or
$R^9R^{10}$ together with the atom or the group of atoms they are attached to, form a 3- to 10-membered heterocycloalkyl- or 4- to 10-membered heterocycloalkenyl- group;
or a tautomer, an N-oxide, a hydrate, a solvate, or a salt thereof, or a mixture of same.

In another preferred embodiment, the present invention relates to compounds of general formula (I):

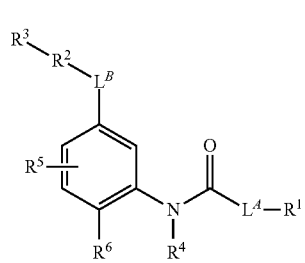

(I)

in which:
$L^A$ represents a methylene or ethylene group, said methylene or ethylene group being optionally substituted, one or more times, identically or differently, with a substituent selected from:
hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-, 3- to 10-membered heterocycloalkyl-;

or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from: halo-, hydroxy-, cyano-, $C_1$-$C_3$-alkyl-, $C_1$-$C_3$-alkoxy-;

$L^B$ represents —N(H)—C(=O)— or —C(=O)—N(H)—;

$R^1$ represents a group selected from:
  5- to 8-membered heterocycloalkyl-, 4- to 10-membered heterocycloalkenyl-, aryl-, heteroaryl-, and —N($R^7$)—($C_1$-$C_6$-alkyl);
  wherein said 5- to 8-membered heterocycloalkyl-, 4- to 10-membered heterocycloalkenyl-, aryl-, heteroaryl-, and —N($R^7$)—($C_1$-$C_6$-alkyl) group is optionally substituted, one or more times, identically or differently, with a substituent selected from: halo-, hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-;

$R^2$ represents a group selected from:

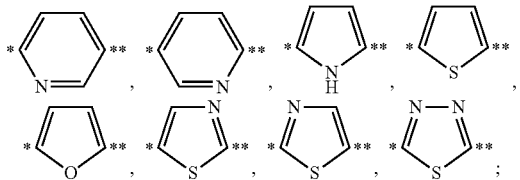

wherein "*" indicates the point of attachment to $R^3$, and "**" indicates the point of attachment to $L^B$; wherein said group is optionally substituted, one or more times, identically or differently, with a $C_1$-$C_3$-alkyl- group;

$R^3$ represents a phenyl-group,
  said phenyl-group being optionally substituted, one or more times, identically or differently, with a substituent selected from:
  halo-, hydroxy-, —N($R^9$)($R^{10}$), —N(H)C(=O)$R^9$, cyano-, nitro-, $C_1$-$C_3$-alkyl-, $C_1$-$C_3$-alkoxy-, halo-$C_1$-$C_3$-alkyl-, hydroxy-$C_1$-$C_3$-alkyl-, amino-$C_1$-$C_3$-alkyl-, halo-$C_1$-$C_3$-alkoxy-;

$R^4$ represents a hydrogen atom or a $C_1$-$C_3$-alkyl- group;

$R^5$ represents a hydrogen atom or a halogen atom or a group selected from:
  cyano-, $C_1$-$C_3$-alkyl-, $C_1$-$C_3$-alkoxy-;

$R^6$ represents a group selected from:
  $C_1$-$C_6$-alkyl-, $C_2$-$C_6$-alkenyl-, $C_2$-$C_6$-alkynyl-
  $C_1$-$C_6$-alkoxy-, halo-, hydroxy-, cyano-, aryl-, heteroaryl-, —N($R^9$)($R^{10}$), —C(=O)—O—$R^9$, —C(=O)—N($R^9$)($R^{10}$);
  said $C_1$-$C_6$-alkyl-, $C_2$-$C_6$-alkenyl-, $C_2$-$C_6$-alkynyl-, aryl-, heteroaryl- or $C_1$-$C_6$-alkoxy- group being optionally substituted, one or more times, identically or differently, with halo-, cyano-, nitro-, hydroxy-, $C_1$-$C_3$-alkyl-, $C_1$-$C_3$-alkoxy-, halo-$C_1$-$C_3$-alkoxy-, hydroxy-$C_1$-$C_3$-alkoxy-, $C_1$-$C_3$-alkoxy-$C_2$-$C_3$-alkoxy-, $C_3$-$C_7$-cycloalkyl-, $C_4$-$C_7$-cycloalkenyl-,
  3- to 10-membered heterocycloalkyl-, 4- to 10-membered heterocycloalkenyl-,
  aryl-, heteroaryl-, —C(=O)$R^9$, —C(=O)O—($C_1$-$C_4$-alkyl), —OC(=O)—$R^9$, —N(H)C(=O)$R^9$, —N($R^{10}$)C(=O)$R^9$, —N(H)C(=O)N$R^{10}R^9$, —N($R^{11}$)C(=O)N$R^{10}R^9$, —N(H)$R^9$, —N$R^{10}R^9$,
—C(=O)N(H)$R^9$, —C(=O)N$R^{10}R^9$, $R^9$—S—, $R^9$—S(=O)—, $R^9$—S(=O)$_2$—,
—N(H)S(=O)$R^9$, —N($R^{10}$)S(=O)$R^9$, —S(=O)N(H)$R^9$, —S(=O)N$R^{10}R^9$,
—N(H)S(=O)$_2R^9$, —N($R^9$)S(=O)$_2R^{10}$, —S(=O)$_2$N(H)$R^9$, —S(=O)$_2$N$R^{10}R^9$,
—S(=O)(=N$R^{10}R^9$), —S(=O)(=N$R^{10}R^9$), —N=S(=O)($R^{10}R^9$);

$R^7$ represents —H or $C_1$-$C_3$-alkyl-;

$R^9$, $R^{10}$, $R^{11}$
  represent, independently from each other, —H or $C_1$-$C_3$-alkyl-;
or
$R^9R^{10}$ together with the atom or the group of atoms they are attached to, form a 3- to 10-membered heterocycloalkyl- or 4- to 10-membered heterocycloalkenyl- group;

or a tautomer, an N-oxide, a hydrate, a solvate, or a salt thereof, or a mixture of same.

In another preferred embodiment, the present invention relates to compounds of general formula (I), supra, in which:

$L^A$ represents a methylene or ethylene group, said methylene or ethylene group being optionally substituted, one or more times, identically or differently, with a substituent selected from:
  hydroxy-, cyano-, $C_1$-$C_3$-alkyl-, $C_1$-$C_3$-alkoxy-, fluoro-$C_1$-$C_3$-alkyl-,
  hydroxy-$C_1$-$C_3$-alkyl-, fluoro-$C_1$-$C_3$-alkoxy-, $C_3$-$C_7$-cycloalkyl-,
  3- to 10-membered heterocycloalkyl-;
  or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from: halo-, hydroxy-, cyano-, $C_1$-$C_3$-alkyl-, $C_1$-$C_3$-alkoxy-;

$L^B$ represents —N(H)—C(=O)— or —C(=O)—N(H)—;

$R^1$ represents a group selected from:
  5- to 8-membered heterocycloalkyl-, 4- to 10-membered heterocycloalkenyl-, aryl-, heteroaryl-, and —N($R^7$)—($C_1$-$C_6$-alkyl);
  wherein said 5- to 8-membered heterocycloalkyl-, 4- to 10-membered heterocycloalkenyl-, aryl-, heteroaryl-, and —N($R^7$)—($C_1$-$C_6$-alkyl) group is optionally substituted, one or more times, identically or differently, with a substituent selected from: halo-, hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-;

$R^2$ represents a group selected from:

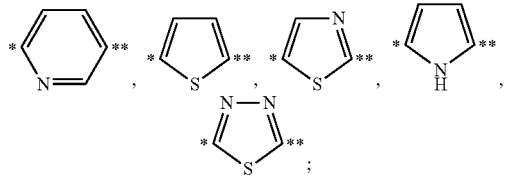

wherein "*" indicates the point of attachment to $R^3$, and "**" indicates the point of attachment to $L^B$; wherein said group is optionally substituted, one or more times, identically or differently, with a $C_1$-$C_3$-alkyl- group;

$R^3$ represents a phenyl-group,
said phenyl-group being optionally substituted, one or more times, identically or differently, with a substituent selected from: halo-, hydroxy-, cyano-, $C_1$-$C_3$-alkyl-, $C_1$-$C_3$-alkoxy-, fluoro-$C_1$-$C_3$-alkyl-, hydroxy-$C_1$-$C_3$-alkyl-, fluoro-$C_1$-$C_3$-alkoxy-;

$R^4$ represents a hydrogen atom or a methyl- group;

$R^5$ represents a hydrogen atom or a halogen atom or a group selected from:
cyano-, $C_1$-$C_3$-alkyl-, $C_1$-$C_3$-alkoxy-;

$R^6$ represents a group selected from:
$C_1$-$C_6$-alkyl-, $C_1$-$C_6$-alkoxy-, halo-, hydroxy-, fluoro-$C_1$-$C_6$-alkyl-, fluoro-$C_1$-$C_6$-alkoxy-, phenyl-, 5- to 6-membered heteroaryl-, cyano-, —C(=O)—O—$R^9$, —C(=O)—N($R^9$)($R^{10}$);
said $C_1$-$C_6$-alkyl- or $C_1$-$C_6$-alkoxy- group being optionally substituted, one or more times, identically or differently, with hydroxy-, $C_1$-$C_3$-alkyl-, $C_1$-$C_3$-alkoxy-, halo-$C_1$-$C_3$-alkoxy-, hydroxy-$C_1$-$C_3$-alkoxy-, $C_1$-$C_3$-alkoxy-$C_2$-$C_3$-alkoxy-,
$C_3$-$C_7$-cycloalkyl-, 3- to 10-membered heterocycloalkyl-, aryl-, heteroaryl-,
—C(=O)$R^9$, —C(=O)O—$R^9$, —C(=O)O—($C_1$-$C_4$-alkyl), —N(H)C(=O)$R^9$, —N($R^{10}$)C(=O)$R^9$,
—N(H)C(=O)N$R^{10}R^9$, —N($R^{11}$)C(=O)N$R^{10}R^9$,
—N(H)$R^9$, —N$R^{10}R^9$,
—C(=O)N(H)$R^9$, —C(=O)N$R^{10}R^9$;

$R^7$ represents —H or $C_1$-$C_3$-alkyl-;

$R^9$, $R^{10}$, $R^{11}$
represent, independently from each other, —H or $C_1$-$C_3$-alkyl-;

or a tautomer, an N-oxide, a hydrate, a solvate, or a salt thereof, or a mixture of same.

In another preferred embodiment, the present invention relates to compounds of general formula (I), supra, in which:

$L^A$ represents a methylene group, said methylene group being optionally substituted, one or more times, identically or differently, with a substituent selected from:
cyano-, hydroxy-, $C_1$-$C_3$-alkyl-, $C_1$-$C_3$-alkoxy-, fluoro-$C_1$-$C_3$-alkyl-, hydroxy-$C_1$-$C_3$-alkyl-, $C_3$-$C_5$-cycloalkyl-, 3- to 6-membered heterocycloalkyl-;
or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from: halo-, hydroxy-, cyano-, $C_1$-$C_3$-alkyl-, $C_1$-$C_3$-alkoxy-;

$L^B$ represents —N(H)—C(=O)— or —C(=O)—N(H)—;

$R^1$ represents a group selected from:
5- to 8-membered heterocycloalkyl-, 4- to 10-membered heterocycloalkenyl-, aryl-, heteroaryl-, and —N($R^7$)—($C_1$-$C_6$-alkyl);
wherein said 5- to 8-membered heterocycloalkyl-, 4- to 10-membered heterocycloalkenyl-, aryl-, heteroaryl-, and —N($R^7$)—($C_1$-$C_6$-alkyl) group is optionally substituted, one or more times, identically or differently, with a substituent selected from: halo-, hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-;

$R^2$ represents a group selected from:

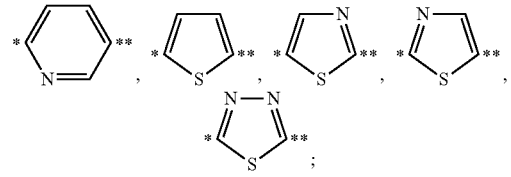

wherein "*" indicates the point of attachment to $R^3$, and "**" indicates the point of attachment to $L^B$;

$R^3$ represents a phenyl-group,
said phenyl-group being optionally substituted, one or more times, identically or differently, with a substituent selected from: halo-, hydroxy-, —NH$_2$, cyano-, $C_1$-$C_2$-alkyl-, $C_1$-$C_2$-alkoxy-, fluoro-$C_1$-$C_2$-alkyl-, hydroxy-$C_1$-$C_2$-alkyl, fluoro-$C_1$-$C_2$-alkoxy-;

$R^4$ represents a hydrogen atom or a methyl- group;

$R^5$ represents a hydrogen atom or a halogen atom or a group selected from:
cyano-, $C_1$-$C_3$-alkyl-, $C_1$-$C_3$-alkoxy-;

$R^6$ represents a group selected from:
$C_1$-$C_6$-alkyl-, $C_1$-$C_6$-alkoxy-, halo-, hydroxy-, fluoro-$C_1$-$C_6$-alkyl-, fluoro-$C_1$-$C_6$-alkoxy-, cyano-, —C(=O)—O—$R^9$, —C(=O)—N($R^9$)($R^{10}$);
said $C_1$-$C_6$-alkyl-, or $C_1$-$C_6$-alkoxy- group being optionally substituted, one or more times, identically or differently, with
$C_3$-$C_7$-cycloalkyl-, 3- to 10-membered heterocycloalkyl-, aryl-, heteroaryl-,
—C(=O)$R^9$, —C(=O)O—$R^9$, —OC(=O)—$R^9$, —N(H)C(=O)$R^9$, —N($R^{10}$)C(=O)$R^9$,
—N(H)C(=O)N$R^{10}R^9$, —N($R^{11}$)C(=O)N$R^{10}R^9$,
—N(H)$R^9$, —N$R^{10}R^9$,
—C(=O)N(H)$R^9$, —C(=O)N$R^{10}R^9$;

$R^9$, $R^{10}$, $R^{11}$
represent, independently from each other, —H or $C_1$-$C_3$-alkyl-;

or a tautomer, an N-oxide, a hydrate, a solvate, or a salt thereof, or a mixture of same.

In another preferred embodiment, the present invention relates to compounds of general formula (I), supra, in which:

$L^A$ represents a methylene group, said methylene group being optionally substituted, one or more times, identically or differently, with a substituent selected from:
hydroxy-, $C_1$-$C_3$-alkyl-, $C_1$-$C_3$-alkoxy-, hydroxy-$C_1$-$C_3$-alkyl-;
or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from: halo-, hydroxy-, cyano-, $C_1$-$C_3$-alkyl-, $C_1$-$C_3$-alkoxy-;

$L^B$ represents —N(H)—C(=O)— or —C(=O)—N(H)—;

$R^1$ represents a morpholino group, which is attached to $L^A$ via its nitrogen atom, and which may be optionally substituted one or two times, identically or differently, with $C_1$-$C_3$-alkyl-, or two of said $C_1$-$C_3$-alkyl- groups together may form a $C_1$-$C_3$-alkylene group (forming a bridge between two different ring carbon atoms of said morpholino group);
or $R^1$ represents thiomorpholino, 4-cyclopropylpiperazino, 4-methylpiperazino or pyrazol-1-yl group, said groups being attached to $L^A$ via their ring nitrogen atom;

$R^2$ represents a group selected from:

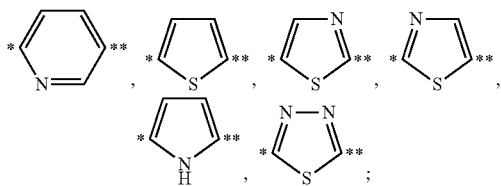

wherein "*" indicates the point of attachment to $R^3$, and "**" indicates the point of attachment to $L^B$;
$R^3$ represents a phenyl-group,
  said phenyl-group being optionally substituted, one or two times, identically or differently, with fluoro, chloro, —$NH_2$ or methoxy;
$R^4$ represents hydrogen atom or a methyl- group;
$R^5$ represents hydrogen, fluoro or chloro;
$R^6$ represents halo-, cyano-, $C_1$-$C_4$-alkyl-, fluoro-$C_1$-$C_3$-alkyl-, $C_1$-$C_4$-alkoxy- or fluoro-$C_1$-$C_3$-alkoxy-, —C(=O)$NR^9R^{10}$ or 5-membered heteroaryl-,
  wherein said $C_1$-$C_4$-alkyl- and $C_1$-$C_4$-alkoxy- group may be optionally substituted by one phenyl-group;
or a tautomer, an N-oxide, a hydrate, a solvate, or a salt thereof, or a mixture of same.

In another preferred embodiment, the present invention relates to compounds of general formula (I), supra, in which:
$L^A$ represents methylene, said methylene group being optionally substituted one or two times, identically or differently, with $C_1$-$C_3$-alkyl-,
  wherein, if said methylene is substituted with two $C_1$-$C_3$-alkyl- groups, these may, together with the carbon atom they are attached to, form a $C_3$-$C_6$-cycloalkyl- ring;
$L^B$ represents —N(H)—C(=O)— or —C(=O)—N(H)—;
$R^1$ represents a morpholino group, which is attached to $L^A$ via its nitrogen atom, and which may be optionally substituted one or two times, identically or differently, with $C_1$-$C_3$-alkyl-, or two of said $C_1$-$C_3$-alkyl- groups together may form a $C_1$-$C_3$-alkylene group (forming a bridge between two different ring carbon atoms of said morpholino group);
$R^2$ represents a group selected from:

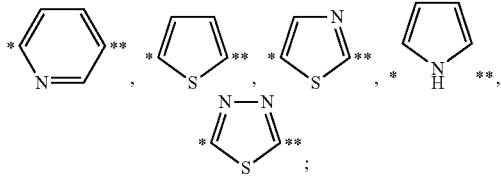

wherein "*" indicates the point of attachment to $R^3$, and "**" indicates the point of attachment to $L^B$;
$R^3$ represents a phenyl-group,
  said phenyl-group being optionally substituted one or two times, identically or differently, with fluoro or methoxy;
$R^4$ represents hydrogen;
$R^5$ represents hydrogen;
$R^6$ represents halogen, $C_1$-$C_4$-alkyl-, fluoro-$C_1$-$C_3$-alkyl-, $C_1$-$C_4$-alkoxy- or fluoro-$C_1$-$C_3$-alkoxy-;
or a tautomer, an N-oxide, a hydrate, a solvate, or a salt thereof, or a mixture of same.

In another preferred embodiment, the present invention relates to compounds of general formula (I), supra, in which:

$L^A$ represents methylene, said methylene group being optionally substituted one or two times, identically or differently, with $C_1$-$C_3$-alkyl-,
  wherein, if said methylene is substituted with two $C_1$-$C_3$-alkyl- groups, these may, together with the carbon atom they are attached to, form a $C_3$-$C_6$-cycloalkyl- ring;
$L^B$ represents —N(H)—C(=O)— or —C(=O)—N(H)—;
$R^1$ represents a morpholino group, which is attached to $L^A$ via its nitrogen atom, and which may be optionally substituted one or two times, identically or differently, with $C_1$-$C_3$-alkyl-, or two of said $C_1$-$C_3$-alkyl- groups together may form a $C_1$-$C_3$-alkylene group (forming a bridge between two different ring carbon atoms of said morpholino group);
$R^2$ represents a group selected from:

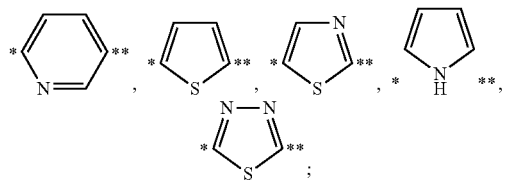

wherein "*" indicates the point of attachment to $R^3$, and "**" indicates the point of attachment to $L^B$;
$R^3$ represents a phenyl-group,
  said phenyl-group being optionally substituted one or two times, identically or differently, with fluoro or methoxy;
$R^4$ represents hydrogen;
$R^5$ represents hydrogen;
$R^6$ represents trifluoromethoxy;
or a tautomer, an N-oxide, a hydrate, a solvate, or a salt thereof, or a mixture of same.

In a particularly preferred embodiment, the present invention relates to compounds of general formula (I), supra, in which:
$L^A$ represents —$CH_2$—, —CH($CH_3$)—, —C($CH_3$)$_2$— or

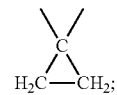

wherein the cyclopropyl- ring is optionally substituted one or more times, identically or differently, with a substituent selected from: halo-, hydroxy-, cyano-, $C_1$-$C_3$-alkyl-, $C_1$-$C_3$-alkoxy-.
$L^B$ represents —N(H)—C(=O)— or —C(=O)—N(H)—;
$R^1$ represents a group selected from:

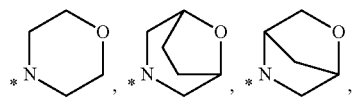

wherein "*" indicates the point of attachment to $L^A$;
$R^2$ represents a group selected from:

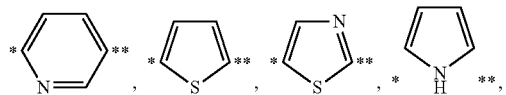

-continued

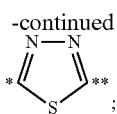

wherein "*" indicates the point of attachment to $R^3$, and "**" indicates the point of attachment to $L^B$;
$R^3$ represents a phenyl-group,
said phenyl-group being optionally substituted, one or two times, with fluoro;
$R^4$ represents hydrogen;
$R^5$ represents hydrogen;
$R^6$ represents chloro, $C_1$-$C_4$-alkyl-, methoxy-, trifluoromethoxy- or trifluoromethyl-;
or a tautomer, an N-oxide, a hydrate, a solvate, or a salt thereof, or a mixture of same.

In another particularly preferred embodiment, the present invention relates to compounds of general formula (I), supra, in which:
$L^A$ represents —$CH_2$—, —$CH(CH_3)$—, —$C(CH_3)_2$— or

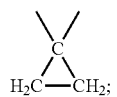

$L^B$ represents —N(H)—C(=O)— or —C(=O)—N(H)—;
$R^1$ represents a group selected from:

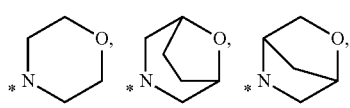

wherein "*" indicates the point of attachment to $L^A$;
$R^2$ represents a group selected from:

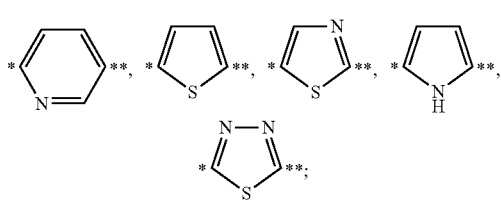

wherein "*" indicates the point of attachment to $R^3$, and "**" indicates the point of attachment to $L^B$;
$R^3$ represents a phenyl-group,
said phenyl-group being optionally substituted, one or two times, with fluoro;
$R^4$ represents hydrogen;
$R^5$ represents hydrogen;
$R^6$ represents trifluoromethoxy;
or a tautomer, an N-oxide, a hydrate, a solvate, or a salt thereof, or a mixture of same.

In another particularly preferred embodiment, the present invention relates to compounds of general formula (I), supra, in which:
$L^A$ represents —$CH_2$—, —$CH(CH_3)$— or

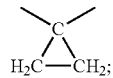

$L^B$ represents —N(H)—C(=O)— or —C(=O)—N(H)—;
$R^1$ represents a group selected from:

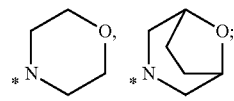

wherein "*" indicates the point of attachment to $L^A$;
$R^2$ represents a group selected from:

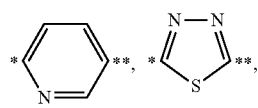

wherein "*" indicates the point of attachment to $R^3$, and "**" indicates the point of attachment to $L^B$;
$R^3$ represents a phenyl-group,
said phenyl-group being optionally substituted, one or two times, with fluoro;
$R^4$ represents hydrogen;
$R^5$ represents hydrogen;
$R^6$ represents trifluoromethoxy or tert-butyl;
or a tautomer, an N-oxide, a hydrate, a solvate, or a salt thereof, or a mixture of same.

In another particularly preferred embodiment, the present invention relates to compounds of general formula (I), supra, in which:
$L^A$ represents —$CH_2$— or —$CH(CH_3)$—;
$L^B$ represents —N(H)—C(=O)— or —C(=O)—N(H)—;
$R^1$ represents a group selected from:

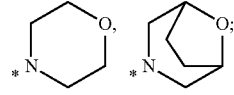

wherein "*" indicates the point of attachment to $L^A$;
$R^2$ represents a group selected from:

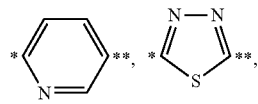

wherein "*" indicates the point of attachment to $R^3$, and "**" indicates the point of attachment to $L^B$;
$R^3$ represents a phenyl-group,
said phenyl-group being optionally substituted, one or two times, with fluoro;
$R^4$ represents hydrogen;
$R^5$ represents hydrogen;
$R^6$ represents trifluoromethoxy;
or a tautomer, an N-oxide, a hydrate, a solvate, or a salt thereof, or a mixture of same.

In another particularly preferred embodiment, the present invention relates to compounds of general formula (I), supra, in which:

$L^A$ represents a methylene or ethylene group, said methylene or ethylene group being optionally substituted, one or more times, identically or differently, with a substituent selected from:
  halo-, hydroxy-, cyano-, $C_1$-$C_3$-alkyl-, $C_1$-$C_3$-alkoxy-, fluoro-$C_1$-$C_3$-alkyl-, hydroxy-$C_1$-$C_3$-alkyl-, fluoro-$C_1$-$C_3$-alkoxy-, $C_3$-$C_7$-cycloalkyl-,
  3- to 10-membered heterocycloalkyl-;
  or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from:
  halo-, hydroxy-, cyano-, $C_1$-$C_3$-alkyl-, $C_1$-$C_3$-alkoxy-;

$L^B$ represents —N(H)—C(=O)— or —C(=O)—N(H)—;

$R^1$ represents a group selected from:
  5- to 8-membered heterocycloalkyl-, 4- to 10-membered heterocycloalkenyl-, aryl-, heteroaryl-, and —N($R^7$)—($C_1$-$C_6$-alkyl);
  wherein said 5- to 8-membered heterocycloalkyl-, 4- to 10-membered heterocycloalkenyl-, aryl-, heteroaryl-, and —N($R^7$)—($C_1$-$C_6$-alkyl) group is optionally substituted, one or more times, identically or differently, with a substituent selected from: halo-, hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-;

$R^2$ represents a group selected from:

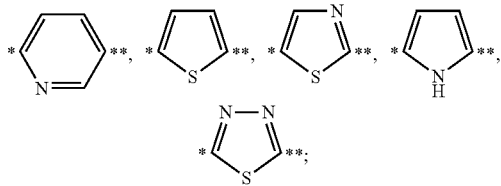

wherein "*" indicates the point of attachment to $R^3$, and "**" indicates the point of attachment to $L^B$; wherein said group is optionally substituted, one or more times, identically or differently, with a $C_1$-$C_3$-alkyl- group;

$R^3$ represents a phenyl-group,
  said phenyl-group being optionally substituted, one or more times, identically or differently, with a substituent selected from: halo-, hydroxy-, cyano-, $C_1$-$C_3$-alkyl-, $C_1$-$C_3$-alkoxy-, fluoro-$C_1$-$C_3$-alkyl-, hydroxy-$C_1$-$C_3$-alkyl-, fluoro-$C_1$-$C_3$-alkoxy-;

$R^4$ represents a hydrogen atom or a methyl- group;

$R^5$ represents a hydrogen atom or a halogen atom or a group selected from:
  cyano-, $C_1$-$C_3$-alkyl-, $C_1$-$C_3$-alkoxy-;

$R^6$ represents a group selected from:
  $C_1$-$C_6$-alkyl-, $C_1$-$C_6$-alkoxy-, halo-, hydroxy-, fluoro-$C_1$-$C_6$-alkyl-, fluoro-$C_1$-$C_6$-alkoxy-, phenyl-, 5- to 6-membered heteroaryl-, cyano-, —C(=O)—O—$R^9$, —C(=O)—N($R^9$)($R^{10}$);
  said $C_1$-$C_6$-alkyl- or $C_1$-$C_6$-alkoxy- group being optionally substituted, one or more times, identically or differently, with fluoro-, cyano-, nitro-, hydroxy-, $C_1$-$C_3$-alkyl-, $C_1$-$C_3$-alkoxy-, fluoro-$C_1$-$C_3$-alkoxy-, hydroxy-$C_1$-$C_3$-alkoxy-, $C_1$-$C_3$-alkoxy-$C_2$-$C_3$-alkoxy-,
  $C_3$-$C_7$-cycloalkyl-, 3- to 10-membered heterocycloalkyl-, aryl-, heteroaryl-, —C(=O)$R^9$, —C(=O)O—($C_1$-$C_4$-alkyl), —OC(=O)—$R^9$, —N(H)C(=O)$R^9$, —N($R^{10}$)C(=O)$R^9$, —N(H)C(=O)N$R^{10}R^9$, —N($R^{11}$)C(=O)N$R^{10}R^9$, —N(H)$R^9$, —N$R^{10}R^9$, —C(=O)N(H)$R^9$, —C(=O)N$R^{10}R^9$, $R^9$—S(=O)$_2$—;

$R^7$ represents —H or $C_1$-$C_3$-alkyl-;

$R^9$, $R^{10}$, $R^{11}$
  represent, independently from each other, —H or $C_1$-$C_3$-alkyl-;
  or
  $R^9R^{10}$ together with the atom or the group of atoms they are attached to, form a 3- to 10-membered heterocycloalkyl- or 4- to 10-membered heterocycloalkenyl- group;

or a tautomer, an N-oxide, a hydrate, a solvate, or a salt thereof, or a mixture of same.

In another particularly preferred embodiment, the present invention relates to compounds of general formula (I), supra, in which:

$L^A$ represents a methylene group, said methylene group being optionally substituted, one or more times, identically or differently, with a substituent selected from:
  cyano-, hydroxy-, $C_1$-$C_3$-alkyl-, $C_1$-$C_3$-alkoxy-, fluoro-$C_1$-$C_3$-alkyl-,
  hydroxy-$C_1$-$C_3$-alkyl-, $C_3$-$C_5$-cycloalkyl-, 3- to 6-membered heterocycloalkyl-;
  or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from: halo-, hydroxy-, cyano-, $C_1$-$C_3$-alkyl-, $C_1$-$C_3$-alkoxy-;

$L^B$ represents —N(H)—C(=O)— or —C(=O)—N(H)—;

$R^1$ represents a group selected from:
  5- to 8-membered heterocycloalkyl-, or 5- to 6-membered heteroaryl-,
  wherein each group is optionally substituted, one or more times, identically or differently, with a substituent selected from: halo-, hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, $C_3$-$C_7$-cycloalkyl-;

$R^2$ represents a group selected from:

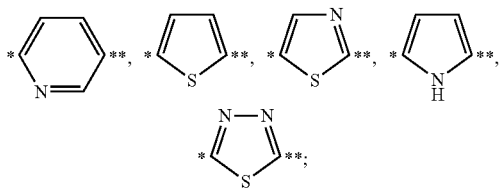

wherein "*" indicates the point of attachment to $R^3$, and "**" indicates the point of attachment to $L^B$; wherein said group is optionally substituted, one or more times, identically or differently, with a $C_1$-$C_3$-alkyl- group;

$R^3$ represents a phenyl-group,
  said phenyl-group being optionally substituted, one or more times, identically or differently, with a substituent selected from: halo-, hydroxy-, cyano-, $C_1$-$C_2$-alkyl-, $C_1$-$C_2$-alkoxy-, fluoro-$C_1$-$C_2$-alkyl-, hydroxy-$C_1$-$C_2$-alkyl-, fluoro-$C_1$-$C_2$-alkoxy-;

$R^4$ represents a hydrogen atom or a methyl- group;

$R^5$ represents a hydrogen atom or a halogen atom or a group selected from:
cyano-, $C_1$-$C_3$-alkyl-, $C_1$-$C_3$-alkoxy-;

$R^6$ represents a group selected from:
$C_1$-$C_6$-alkyl-, $C_1$-$C_6$-alkoxy-, halo-, hydroxy-, fluoro-$C_1$-$C_6$-alkyl-, fluoro-$C_1$-$C_6$-alkoxy-, cyano-, —C(=O)—O—$R^9$, —C(=O)—N($R^9$)($R^{10}$);

said $C_1$-$C_6$-alkyl- or $C_1$-$C_6$-alkoxy- group being optionally substituted, one or more times, identically or differently, with $C_1$-$C_3$-alkoxy-, $C_3$-$C_7$-cycloalkyl-, 3- to 10-membered heterocycloalkyl-, aryl-, heteroaryl-, —C(=O)$R^9$, —C(=O)O—($C_1$-$C_4$-alkyl), —OC(=O)—$R^9$, —N(H)C(=O)$R^9$, —N($R^{10}$)C(=O)$R^9$, —N(H)C(=O)N$R^{10}R^9$, —N($R^{11}$)C(=O)N$R^{10}R^9$, —N(H)$R^9$, —N$R^{10}R^9$, —C(=O)N(H)$R^9$, —C(=O)N$R^{10}R^9$, $R^9$—S(=O)$_2$;

$R^9$, $R^{10}$, $R^{11}$
represent, independently from each other, —H or $C_1$-$C_3$-alkyl-;

or a tautomer, an N-oxide, a hydrate, a solvate, or a salt thereof, or a mixture of same.

In another particularly preferred embodiment, the present invention relates to compounds of general formula (I), supra, in which:

$L^A$ represents a methylene group, said methylene group being optionally substituted, one or more times, identically or differently, with a substituent selected from:
hydroxy-, $C_1$-$C_3$-alkyl-, $C_1$-$C_3$-alkoxy-, hydroxy-$C_1$-$C_3$-alkyl-,
or, when two substituents are present at the same carbon atom, the two substituents, together with the carbon atom they are attached to, may form a $C_3$-$C_6$-cycloalkyl- or 3- to 6-membered heterocycloalkyl- ring; wherein said ring is optionally substituted one or more times, identically or differently, with a substituent selected from: halo-, hydroxy-, cyano-, $C_1$-$C_3$-alkyl-, $C_1$-$C_3$-alkoxy-;

$L^B$ represents —N(H)—C(=O)— or —C(=O)—N(H)—;

$R^1$ represents a morpholino group, which is attached to $L^A$ via its nitrogen atom, and which may be optionally substituted one or two times, identically or differently, with $C_1$-$C_3$-alkyl-, or two of said $C_1$-$C_3$-alkyl- groups together may form a $C_1$-$C_3$-alkylene group,
or
$R^1$ represents thiomorpholino, 4-cyclopropylpiperazino, 4-methylpiperazino or pyrazol-1-yl-group; said groups being attached to $L^A$ via their ring nitrogen atom;

$R^2$ represents a group selected from:

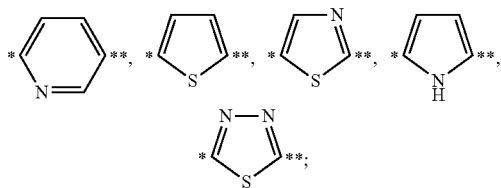

wherein "*" indicates the point of attachment to $R^3$, and "**" indicates the point of attachment to $L^B$; wherein said group is optionally substituted, one or more times, identically or differently, with a $C_1$-$C_3$-alkyl- group;

$R^3$ represents a phenyl-group,
said phenyl-group being optionally substituted, one or two times, identically or differently, with fluoro, chloro, —NH$_2$ or methoxy;

$R^4$ represents a hydrogen atom or a methyl- group;

$R^5$ represents a hydrogen atom, fluoro or chloro;

$R^6$ represents halo-, cyano-, $C_1$-$C_4$-alkyl-, fluoro-$C_1$-$C_3$-alkyl-, $C_1$-$C_4$-alkoxy-, fluoro-$C_1$-$C_3$-alkoxy-, —C(=O)N$R^9R^{10}$, $C_1$-$C_3$-alkoxy-$C_1$-$C_3$-alkyl-, $R^9$—S(=O)$_2$—$C_1$-$C_3$-alkyl-, 5-membered heteroaryl-, $R^9$, $R^{10}$ represent, independently from each other, —H or $C_1$-$C_3$-alkyl-;

or a tautomer, an N-oxide, a hydrate, a solvate, or a salt thereof, or a mixture of same.

In another particularly preferred embodiment, the present invention relates to compounds of general formula (I), supra, in which:

$L^A$ represents methylene, said methylene group being optionally substituted one or two times, identically or differently, with $C_1$-$C_3$-alkyl-,
wherein, if said methylene is substituted with two $C_1$-$C_3$-alkyl- groups, these may, together with the carbon atom they are attached to, form a $C_3$-$C_6$-cycloalkyl- ring;

$L^B$ represents —N(H)—C(=O)— or —C(=O)—N(H)—;

$R^1$ represents a morpholino group, which is attached to $L^A$ via its nitrogen atom, and which may be optionally substituted one or two times, identically or differently, with $C_1$-$C_3$-alkyl-, or two of said $C_1$-$C_3$-alkyl groups together may form a $C_1$-$C_3$-alkylene group;
or
$R^1$ represents thiomorpholino, 4-cyclopropylpiperazino, 4-methylpiperazino or pyrazol-1-yl-group; said groups being attached to $L^A$ via their ring nitrogen atom;

$R^2$ represents a group selected from:

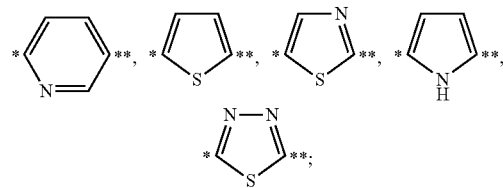

wherein "*" indicates the point of attachment to $R^3$, and "**" indicates the point of attachment to $L^B$;

$R^3$ represents a phenyl-group,
said phenyl-group being optionally substituted one or two times, identically or differently, with fluoro or methoxy;

$R^4$ represents hydrogen;

$R^5$ represents hydrogen;

$R^6$ represents halogen, $C_1$-$C_4$-alkyl-, fluoro-$C_1$-$C_3$-alkyl-, $C_1$-$C_4$-alkoxy-, fluoro-$C_1$-$C_3$-alkoxy-, —C(=O)N$R^9R^{10}$, $C_1$-$C_3$-alkoxy-$C_1$-$C_3$-alkyl-, $R^9$—S(=O)$_2$—$C_1$-$C_3$-alkyl-;

$R^9$, $R^{10}$ represent, independently from each other, —H or $C_1$-$C_3$-alkyl-;

or a tautomer, an N-oxide, a hydrate, a solvate, or a salt thereof, or a mixture of same.

In another particularly preferred embodiment, the present invention relates to compounds of general formula (I), supra, in which:

$L^A$ represents a group selected from: —CH$_2$—, —CH(CH$_3$)—, —C(CH$_3$)$_2$—,

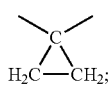

$L^B$ represents —N(H)—C(=O)— or —C(=O)—N(H)—;
$R^1$ represents a group selected from:

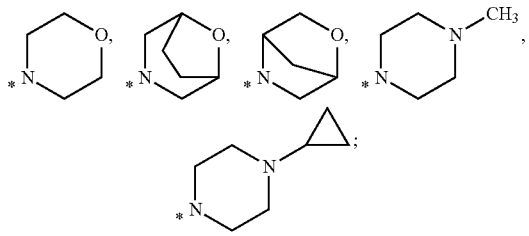

wherein "*" indicates the point of attachment to $L^A$;
$R^2$ represents a group selected from:

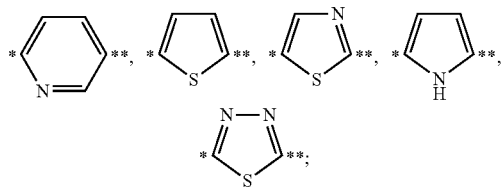

wherein "*" indicates the point of attachment to $R^3$, and "**" indicates the point of attachment to $L^B$;
$R^3$ represents a phenyl-group,
said phenyl-group being optionally substituted, one or two times, with fluoro;
$R^4$ represents hydrogen;
$R^5$ represents hydrogen;
$R^6$ represents a group selected from:
methoxy-, difluoromethoxy-, trifluoromethoxy-, methyl-, trifluormethyl-, tert-butyl-, chloro-, methoxymethyl-, —C(=O)—NH$_2$, —CH$_2$—S(=O)$_2$—CH$_3$;
or a tautomer, an N-oxide, a hydrate, a solvate, or a salt thereof, or a mixture of same.

In another particularly preferred embodiment, the present invention relates to compounds of general formula (I), supra, in which:
$L^A$ represents a group selected from: —CH$_2$—, —CH(CH$_3$)—,

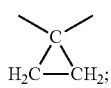

$L^B$ represents —N(H)—C(=O)— or —C(=O)—N(H)—;
$R^1$ represents a group selected from:

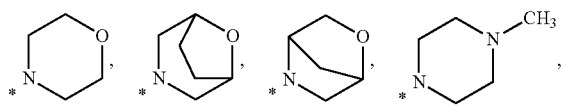

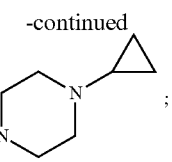

wherein "*" indicates the point of attachment to $L^A$;
$R^2$ represents a group selected from:

wherein "*" indicates the point of attachment to $R^3$, and "**" indicates the point of attachment to $L^B$;
$R^3$ represents a phenyl-group,
said phenyl-group being optionally substituted, one or two times, with fluoro;
$R^4$ represents hydrogen;
$R^5$ represents hydrogen;
$R^6$ represents a group selected from:
methoxy-, difluoromethoxy-, trifluoromethoxy-, methyl-, trifluormethyl-, tert-butyl-, chloro-, methoxymethyl-, —C(=O)—NH$_2$, —CH$_2$—S(=O)$_2$—CH$_3$;
or a tautomer, an N-oxide, a hydrate, a solvate, or a salt thereof, or a mixture of same.

In a preferred embodiment, the present invention relates to compounds of general formula (Ia):

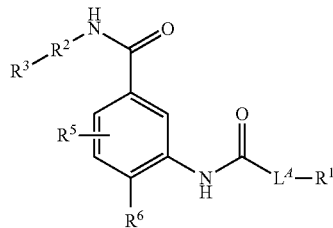

(Ia)

in which:
$L^A$ represents a methylene group, said methylene group being optionally substituted, one or more times, identically or differently, with a $C_1$-$C_3$-alkyl- group;
or, when two substituents are present at the same carbon atom, the two substituents, together with the carbon atom they are attached to, may form a $C_3$-$C_6$-cycloalkyl- ring;
$R^1$ represents a 6-membered heterocycloalkyl- group; said group being optionally substituted with a $C_1$-$C_3$-alkyl-, —$C_1$-$C_2$-alkylene- or $C_3$-$C_6$-cycloalkyl- group;
$R^2$ represents a group selected from:

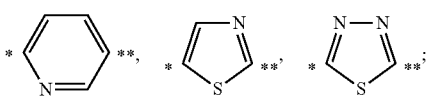

wherein "*" indicates the point of attachment to $R^3$, and "**" indicates the point of attachment to $L^B$;
$R^3$ represents a phenyl-group, said phenyl-group being optionally substituted, one or two times with fluoro-;
$R^5$ represents a hydrogen atom;

$R^6$ represents a group selected from:
  $C_1$-$C_3$-alkyl-, $C_1$-$C_3$-alkoxy-, —C(=O)—N($R^9$)($R^{10}$);
    said $C_1$-$C_3$-alkyl- and $C_1$-$C_3$-alkoxy- group being optionally substituted, one or more times, identically or differently, with fluoro-, $C_1$-$C_3$-alkoxy-, $R^9$—S(=O)$_2$—;
$R^9$, $R^{10}$
  represent, independently from each other, —H or $C_1$-$C_3$-alkyl-;
or a tautomer, an N-oxide, a hydrate, a solvate, or a salt thereof, or a mixture of same.

In another particularly preferred embodiment, the present invention relates to compounds of general formula (I), supra, in which:
$L^A$ represents —CH$_2$—, —CH(CH$_3$)—, —C(CH$_3$)$_2$— or

$L^B$ represents —N(H)—C(=O)— or —C(=O)—N(H)—;
$R^1$ represents a group selected from:

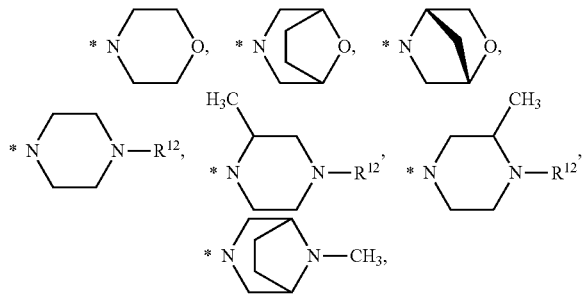

—N(CH$_3$)$_2$, —N(H)—(CH$_2$—CH$_2$—O—CH$_3$), —N(CH$_3$)—(CH$_2$—CH$_2$—O—CH$_3$);
  wherein * indicates the point of attachment to $L^A$; and
  wherein $R^{12}$ represents a methyl-, ethyl-, trifluoroethyl-, difluoroethyl- or cyclopropyl- group;
$R^2$ represents a group selected from:

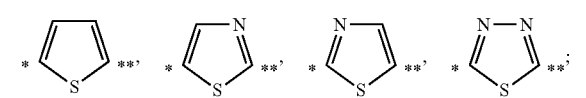

wherein "*" indicates the point of attachment to $R^3$, and "**" indicates the point of attachment to $L^B$;
$R^3$ represents a phenyl-group,
  said phenyl-group being optionally substituted, one or more times, identically or differently, with a substituent selected from:
    halo-, hydroxy-, —N($R^9$)($R^{10}$), —N(H)C(=O)$R^9$, cyano-, nitro-, $C_1$-$C_3$-alkyl-, $C_1$-$C_3$-alkoxy-, halo-$C_1$-$C_3$-alkyl-, hydroxy-$C_1$-$C_3$-alkyl-, amino-$C_1$-$C_3$-alkyl-, halo-$C_1$-$C_3$-alkoxy-;
$R^4$ represents a hydrogen atom;
$R^5$ represents a hydrogen atom;
$R^6$ represents a group selected from:
  $C_1$-$C_3$-alkyl-, $C_1$-$C_3$-alkoxy-, halo-, hydroxy-, cyano-, —N($R^9$)($R^{10}$), —C(=O)—O—$C_1$-$C_4$-alkyl, —C(=O)—N($R^9$)($R^{10}$), cyclopropyloxy-, cyclopropylmethoxy-; said $C_1$-$C_3$-alkyl- and $C_1$-$C_3$-alkoxy- group being optionally substituted, one or more times, identically or differently, with halo-, cyano-, $C_1$-$C_3$-alkoxy-, $R^9$—S(=O)$_2$—;
$R^9$, $R^{10}$
  represent, independently from each other, a hydrogen atom or a $C_1$-$C_3$-alkyl- or $C_1$-$C_3$-alkoxy-$C_1$-$C_3$-alkyl- group;
or a tautomer, an N-oxide, a hydrate, a solvate, or a salt thereof, or a mixture of same.

In another particularly preferred embodiment, the present invention relates to compounds of general formula (I), supra, in which:
$L^A$ represents —CH$_2$—, —CH(CH$_3$)—, —C(CH$_3$)$_2$— or

$L^B$ represents —N(H)—C(=O)— or —C(=O)—N(H)—;
$R^1$ represents a group selected from:

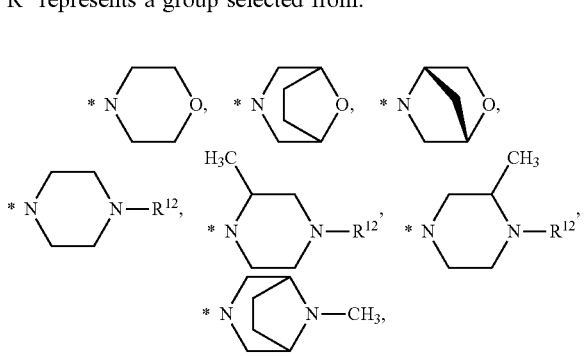

—N(CH$_3$)$_2$, —N(H)—(CH$_2$—CH$_2$—O—CH$_3$), —N(CH$_3$)—(CH$_2$—CH$_2$—O—CH$_3$);
  wherein * indicates the point of attachment to $L^A$; and
  wherein $R^{12}$ represents a methyl-, ethyl-, trifluoroethyl-, difluoroethyl- or cyclopropyl- group;
$R^2$ represents a group selected from:

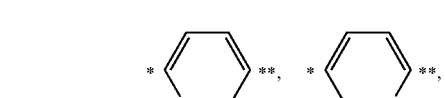

wherein "*" indicates the point of attachment to $R^3$, and "**" indicates the point of attachment to $L^B$; wherein said group is optionally substituted, one or more times, identically or differently, with a $C_1$-$C_3$-alkyl- group;
$R^3$ represents a phenyl-group,
  said phenyl-group being optionally substituted, one or more times, identically or differently, with a substituent selected from:
    halo-, hydroxy-, —N($R^9$)($R^{10}$), —N(H)C(=O)$R^9$, cyano-, nitro-, $C_1$-$C_3$-alkyl-, $C_1$-$C_3$-alkoxy-, halo-$C_1$-$C_3$-alkyl-, hydroxy-$C_1$-$C_3$-alkyl-, amino-$C_1$-$C_3$-alkyl-, halo-$C_1$-$C_3$-alkoxy-;
$R^4$ represents a hydrogen atom;
$R^5$ represents a hydrogen atom;

$R^6$ represents a group selected from:
C$_1$-C$_3$-alkyl-, C$_1$-C$_3$-alkoxy-, halo-, hydroxy-, cyano-, —N(R$^9$)(R$^{10}$), —C(=O)—O—C$_1$-C$_4$-alkyl, —C(=O)—N(R$^9$)(R$^{10}$), cyclopropyloxy-, cyclopropylmethoxy-; said C$_1$-C$_3$-alkyl- and C$_1$-C$_3$-alkoxy- group being optionally substituted, one or more times, identically or differently, with halo-, cyano-, C$_1$-C$_3$-alkoxy-, R$^9$—S(=O)$_2$—;

$R^9$, $R^{10}$
represent, independently from each other, a hydrogen atom or a C$_1$-C$_3$-alkyl- or C$_1$-C$_3$-alkoxy-C$_1$-C$_3$-alkyl- group;

or a tautomer, an N-oxide, a hydrate, a solvate, or a salt thereof, or a mixture of same.

In a particularly preferred embodiment, the present invention relates to compounds of general formula (Ia), supra, in which:

$L^A$ represents a group selected from:
—CH$_2$—, —C(CH$_3$)(H)—,

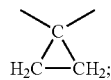

$R^1$ represents a group selected from:

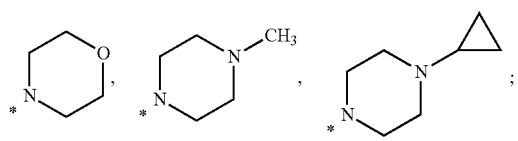

wherein "*" indicates the point of attachment to $L^A$;

$R^2$ represents a group selected from:

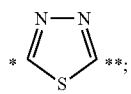

wherein "*" indicates the point of attachment to $R^3$, and "**" indicates the point of attachment to the nitrogen;

$R^3$ represents a phenyl-group;

$R^5$ represents a hydrogen atom;

$R^6$ represents a group selected from: trifluoromethoxy-, difluoromethoxy-, —CH$_2$—O—CH$_3$, —CH$_2$—S(=O)$_2$—CH$_3$, —C(=O)—NH$_2$;

or a tautomer, an N-oxide, a hydrate, a solvate, or a salt thereof, or a mixture of same.

In another preferred embodiment, the present invention relates to compounds of general formula (I):

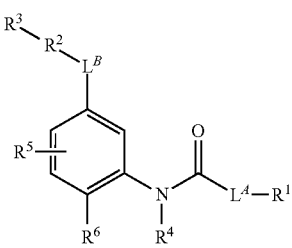
(I)

in which:

$L^A$ represents —CH$_2$—, —CH(CH$_3$)—, —C(CH$_3$)$_2$— or

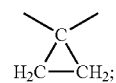

$L^B$ represents —N(H)—C(=O)— or —C(=O)—N(H)—;

$R^1$ represents a group selected from:

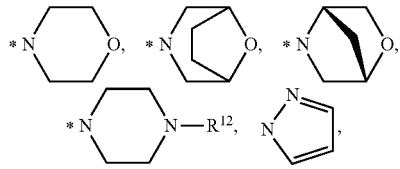

—N(CH$_3$)$_2$, —N(H)—(CH$_2$—CH$_2$—O—CH$_3$), —N(CH$_3$)—(CH$_2$—CH$_2$—O—CH$_3$);

wherein * indicates the point of attachment to $L^A$;

$R^{12}$ represents a methyl-, ethyl- or cyclopropyl- group;

$R^2$ represents a group selected from:

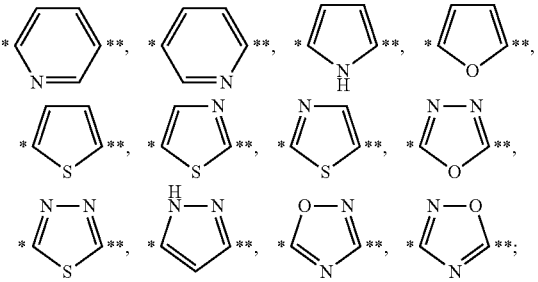

wherein "*" indicates the point of attachment to $R^3$, and "**" indicates the point of attachment to $L^B$; wherein said group is optionally substituted, one or more times, identically or differently, with a C$_1$-C$_3$-alkyl- group;

$R^3$ represents:

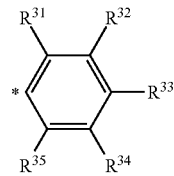

wherein "*" represents the point of attachment to $R^2$;

$R^{31}$, $R^{32}$, $R^{34}$ and $R^{35}$
represent, independently from each other, a hydrogen atom or a group selected from: halo-, hydroxy-, —NH$_2$, cyano-, nitro-, C$_1$-C$_3$-alkyl-, C$_1$-C$_3$-alkoxy-, halo-C$_1$-C$_3$-alkyl-, hydroxy-C$_1$-C$_3$-alkyl-, halo-C$_1$-C$_3$-alkoxy-;

$R^{33}$ represents a hydrogen atom or a substituent selected from: hydroxy-, —CHF$_2$, —NH$_2$, —N(R$^{10}$)R$^9$, —CH$_2$NH$_2$, —N(H)C(=O)CH$_3$;

$R^4$ represents a hydrogen atom or a methyl- group;

$R^5$ represents a hydrogen atom;

53

$R^6$ represents a group selected from:
  $C_1$-$C_6$-alkyl-, $C_1$-$C_6$-alkoxy-, $C_3$-$C_6$-cycloalkoxy-, halo-, hydroxy-, cyano-, —C(=O)—O—$C_1$-$C_4$-alkyl, —C(=O)—N($R^9$)($R^{10}$), $R^9$—S—, $R^9$—S(=O)—, $R^9$—S(=O)$_2$—;
  said $C_1$-$C_6$-alkyl-, and $C_1$-$C_6$-alkoxy- group being optionally substituted, one or more times, identically or differently, with a substituent selected from: halo-, $C_1$-$C_3$-alkoxy-, $C_1$-$C_3$-alkoxy-$C_2$-$C_3$-alkoxy-, $C_3$-$C_7$-cycloalkyl-;

$R^9$, $R^{10}$
  represent, independently from each other, a hydrogen atom or a $C_1$-$C_3$-alkyl- or $C_1$-$C_3$-alkoxy-$C_1$-$C_3$-alkyl- group;
  or
$R^9R^{10}$ together with the atom or the group of atoms they are attached to, form a 3- to 10-membered heterocycloalkyl- or 4- to 10-membered heterocycloalkenyl- group;
  or a tautomer, an N-oxide, a hydrate, a solvate, or a salt thereof, or a mixture of same.

In another preferred embodiment, the present invention relates to compounds of general formula (I):

(I)

in which:
$L^A$ represents —CH$_2$—, —CH(CH$_3$)—, —C(CH$_3$)$_2$— or $L^B$ represents —N(H)—C(=O)— or —C(=O)—N(H)—;
$R^1$ represents a group selected from:

—N(CH$_3$)$_2$, —N(H)—(CH$_2$—CH$_2$—O—CH$_3$), —N(CH$_3$)—(CH$_2$—CH$_2$—O—CH$_3$);
  wherein * indicates the point of attachment to $L^A$;
$R^{12}$ represents a methyl-, ethyl- or cyclopropyl- group;
$R^2$ represents a group selected from:

54 wherein "*" indicates the point of attachment to $R^3$, and "**" indicates the point of attachment to $L^B$;
$R^3$ represents:

wherein "*" represents the point of attachment to $R^2$;
$R^{31}$, $R^{32}$, $R^{34}$ and $R^{35}$ represent, independently from each other, a hydrogen atom or a group selected from: fluoro-, chloro, methyl-, methoxy-; with the proviso that at least two of $R^{31}$, $R^{32}$, $R^{34}$ and $R^{35}$ represent a hydrogen atom;
$R^{33}$ represents a hydrogen atom;
$R^4$ represents a hydrogen atom or a methyl- group;
$R^5$ represents a hydrogen atom;
$R^6$ represents a group selected from:
  $C_1$-$C_6$-alkyl-, $C_1$-$C_6$-alkoxy-, $C_3$-$C_6$-cycloalkoxy-, halo-, hydroxy-, cyano-,
  —C(=O)—O—$C_1$-$C_4$-alkyl, —C(=O)—N($R^9$)($R^{10}$), $R^9$—S—, $R^9$—S(=O)—, $R^9$—S(=O)$_2$—;
  said $C_1$-$C_6$-alkyl-, and $C_1$-$C_6$-alkoxy- group being optionally substituted, one or more times, identically or differently, with a substituent selected from: halo-, $C_1$-$C_3$-alkoxy-, $C_1$-$C_3$-alkoxy-$C_2$-$C_3$-alkoxy-, $C_3$-$C_7$-cycloalkyl-;
$R^9$, $R^{10}$
  represent, independently from each other, a hydrogen atom or a $C_1$-$C_3$-alkyl- or $C_1$-$C_3$-alkoxy-$C_1$-$C_3$-alkyl- group;
  or
$R^9R^{10}$ together with the atom or the group of atoms they are attached to, form a 3- to 10-membered heterocycloalkyl- or 4- to 10-membered heterocycloalkenyl- group;
  or a tautomer, an N-oxide, a hydrate, a solvate, or a salt thereof, or a mixture of same.

In another preferred embodiment, the present invention relates to compounds of general formula (I):

(I)

in which:
$L^A$ represents —CH$_2$—, —CH(CH$_3$)—, —C(CH$_3$)$_2$— or $L^B$ represents —N(H)—C(=O)— or —C(=O)—N(H)—;

$R^1$ represents a group selected from:

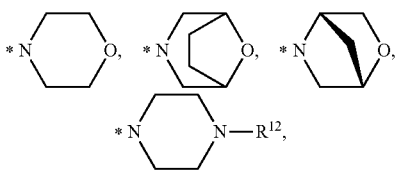

wherein * indicates the point of attachment to $L^A$;
$R^{12}$ represents a methyl-, ethyl- or cyclopropyl- group;
$R^2$ represents a group selected from:

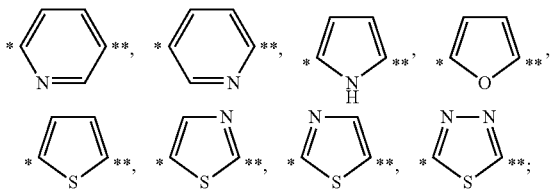

wherein "*" indicates the point of attachment to $R^3$, and "**" indicates the point of attachment to $L^B$; wherein said group is optionally substituted, one or more times, identically or differently, with a $C_1$-$C_3$-alkyl- group;
$R^3$ represents:

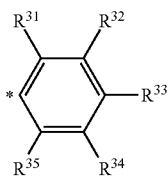

wherein "*" represents the point of attachment to $R^2$;
$R^{31}$, $R^{32}$, $R^{34}$ and $R^{35}$
represent, independently from each other, a hydrogen atom or a group selected from: fluoro-, chloro, methyl-, methoxy-; with the proviso that at least two of $R^{31}$, $R^{32}$, $R^{34}$ and $R^{35}$ represent a hydrogen atom;
$R^{33}$ represents a hydrogen atom;
$R^4$ represents a hydrogen atom;
$R^5$ represents a hydrogen atom;
$R^6$ represents chloro, $C_1$-$C_4$-alkyl-, methoxy-, difluoromethoxy-, trifluoromethoxy-, trifluoromethyl-, —C(=O)—NH$_2$, —CH$_2$—O—CH$_3$ or —CH$_2$—S(=O)$_2$—CH$_3$;
or a tautomer, an N-oxide, a hydrate, a solvate, or a salt thereof, or a mixture of same.

It is to be understood that the present invention relates also to any combination of the preferred embodiments described above.

More particularly still, the present invention covers compounds of general formula (I) which are disclosed in the Examples section of this text, infra.

In accordance with another aspect, the present invention covers methods of preparing compounds of the present invention, said methods comprising the steps as described in the Experimental Section herein.

In a preferred embodiment, the present invention relates to a method of preparing a compound of general formula (I), supra, said method comprising the step of allowing an intermediate compound of general formula (VI):

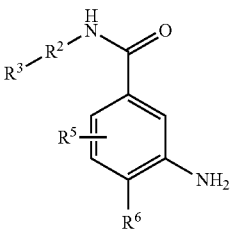

in which $R^2$, $R^3$, $R^5$, and $R^6$ are as defined for general formula (I), supra;

to react with a carboxylic acid HO$_2$C-$L^A$-$R^1$ or the corresponding acyl chloride Cl—C(=O)-$L^A$-$R^1$, wherein $L^A$ and $R^1$ are as defined for the compounds of general formula (I), supra; or alternatively to react with suitable reagents, such as Cl—C(=O)-$L^A$-LG, in which $L^A$ is as defined for the compounds of general formula (I), and LG stands for a leaving group, preferably chloro or bromo, and subsequently with agents suitable for the introduction of $R^1$, exemplified by but not limited to cyclic secondary amines;

thereby giving, upon optional deprotection, a compound of general formula (Ia):

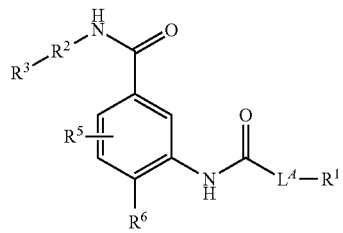

in which $L^A$, $R^1$, $R^2$, $R^3$, $R^5$, and $R^6$ are as defined for the compounds of general formula (I), supra.

In accordance with another embodiment, the present invention also relates to a method of preparing a compound of general formula (I), supra, said method comprising the step of allowing an intermediate compound of general formula (XI):

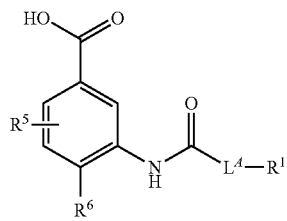

in which $L^A$, $R^1$, $R^5$, and $R^6$ are as defined for general formula (I), supra;

to react with a compound of general formula $R^3R^2NH_2$, in which $R^2$ and $R^3$ are as defined for the compounds of general formula (I), supra;

thereby giving, upon optional deprotection, a compound of general formula (Ia):

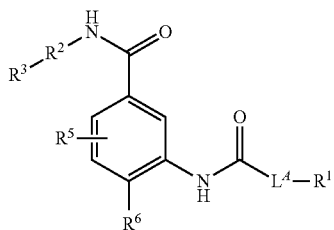

(Ia)

in which $L^A$, $R^1$, $R^2$, $R^3$, $R^5$, and $R^6$ are as defined for the compounds of general formula (I), supra.

In accordance with another embodiment, the present invention also relates to a method of preparing a compound of general formula (I), supra, said method comprising the step of allowing an intermediate compound of general formula (XIa):

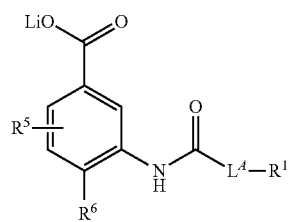

(XIa)

in which $L^A$, $R^1$, $R^5$, and $R^6$ are as defined for general formula (I), supra;

to react with a compound of general formula $R^3R^2NH_2$, in which $R^2$ and $R^3$ are as defined for the compounds of general formula (I), supra;

thereby giving, upon optional deprotection, a compound of general formula (Ia):

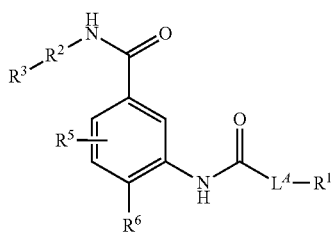

(Ia)

in which $L^A$, $R^1$, $R^2$, $R^3$, $R^5$, and $R^6$ are as defined for the compounds of general formula (I), supra.

In accordance with another embodiment, the present invention also relates to a method of preparing a compound of general formula (I), supra, said method comprising the step of allowing an intermediate compound of general formula (XVII):

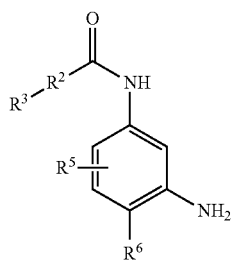

(XVII)

in which $R^2$, $R^3$, $R^5$, and $R^6$ are as defined for general formula (I), supra;

to react with a carboxylic acid $HO_2C$-$L^A$-$R^1$ or the corresponding acyl chloride Cl—C(=O)-$L^A$-$R^1$, wherein $L^A$ and $R^1$ are as defined for the compounds of general formula (I), supra; or alternatively to react with suitable reagents, such as Cl—C(=O)-$L^A$-LG, in which $L^A$ is as defined for the compounds of general formula (I), and LG stands for a leaving group, preferably chloro or bromo, and subsequently with agents suitable for the introduction of $R^1$, exemplified by but not limited to cyclic secondary amines;

thereby giving, upon optional deprotection, a compound of general formula (Ib):

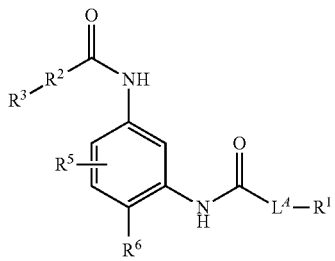

(Ib)

in which $L^A$, $R^1$, $R^2$, $R^3$, $R^5$, and $R^6$ are as defined for the compounds of general formula (I), supra.

In accordance with another embodiment, the present invention also relates to a method of preparing a compound of general formula (I), supra, said method comprising the step of allowing an intermediate compound of general formula (XXII):

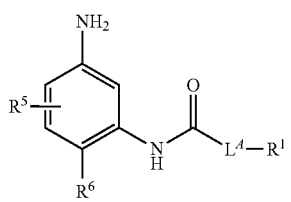

(XXII)

in which $L^A$, $R^1$, $R^5$ and $R^6$ are as defined for general formula (I), supra;

to react with a carboxylic acid $HO_2C$—$R^2$—$R^3$, wherein $R^2$ and $R^3$ are as defined for the compounds of general formula (I), supra; or alternatively to react with a carboxylic acid X—$R^2$—$CO_2H$, in which $R^2$ is as defined for the compounds of general formula (I), supra, and subsequently subjected to a palladium catalysed coupling reaction, such as a Suzuki coupling, with R³—X′, in which R³ is as defined for the compounds of general formula (I), supra. In X—R²—CO₂H and R³—X′, both X and X′ represent groups enabling palladium catalysed coupling reactions, such as chloro, bromo, iodo, trifluoromethylsulfonyloxy, nonaflyl or a boronic acid or an ester thereof, with the proviso that if X represents a boronic ester or an ester thereof, X′ stands for bromo, iodo, trifluoromethylsulfonyloxy or nonaflyl and the like, or vice versa;

thereby giving, upon optional deprotection, a compound of general formula (Ib):

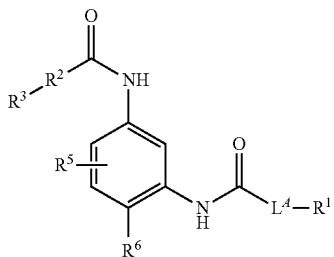

(Ib)

in which $L^A$, $R^1$, $R^2$, $R^3$, $R^5$, and $R^6$ are as defined for the compounds of general formula (I), supra.

In accordance with another embodiment, the present invention also relates to a method of preparing a compound of general formula (I), supra, said method comprising the step of allowing an intermediate compound of general formula (XXIV):

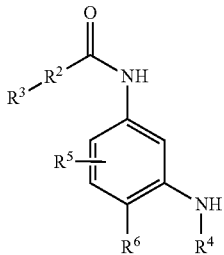

(XXIV)

in which $R^2$, $R^3$, $R^4$, $R^5$ and $R^6$ are as defined for general formula (I), supra;

to react with a carboxylic acid HO₂C-$L^A$-$R^1$ or the corresponding acyl chloride Cl—C(=O)-$L^A$-$R^1$, wherein $L^A$ and $R^1$ are as defined for the compounds of general formula (I), supra;

thereby giving, upon optional deprotection, a compound of general formula (Ic):

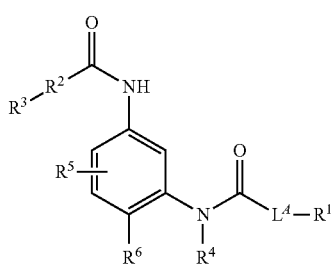

(Ic)

in which $L^A$, $R^1$, $R^2$, $R^3$, $R^4$, $R^5$ and $R^6$ are as defined for the compounds of general formula (I), supra.

In accordance with another embodiment, the present invention also relates to a method of preparing a compound of general formula (I), supra, said method comprising the step of allowing an intermediate compound of general formula (XXV):

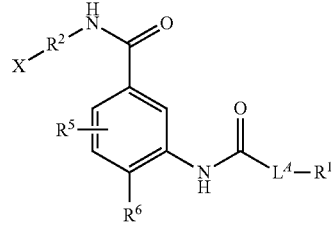

(XXV)

in which $L^A$, $R^1$, $R^2$, $R^5$ and $R^6$ are as defined for general formula (I), supra;

to react with a compound of general formula R³—X′, wherein R³ is as defined for the compounds of general formula (I), supra;

wherein both, X and X′ represent groups enabling palladium catalysed coupling reactions, such as chloro, bromo, iodo, trifluoromethylsulfonyloxy, nonaflyl or a boronic acid or an ester thereof, with the proviso that if X represents a boronic ester or an ester thereof, X′ stands for chloro, bromo, iodo, trifluoromethylsulfonyloxy or nonaflyl and the like, or vice versa.

thereby giving, upon optional deprotection, a compound of general formula (Ia):

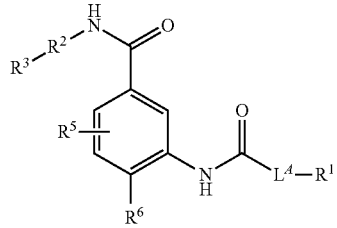

(Ia)

in which $L^A$, $R^1$, $R^2$, $R^3$, $R^4$, $R^5$ and $R^6$ are as defined for the compounds of general formula (I), supra.

In accordance with a further aspect, the present invention covers intermediate compounds which are useful in the preparation of compounds of the present invention of general formula (I), particularly in the method described herein. In particular, the present invention covers intermediate compounds of general formula (VI):

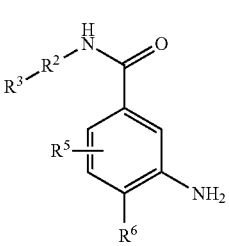

(VI)

in which R², R³, R⁵, and R⁶ are as defined for general formula (I), supra.

The present invention also covers intermediate compounds of general formula (XI):

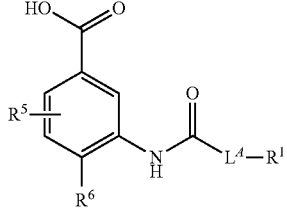

(XI)

in which L^A, R¹, R⁵, and R⁶ are as defined for the compounds of general formula (I), supra.

The present invention also covers intermediate compounds of general formula (XIa):

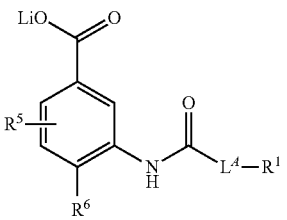

(XIa)

in which L^A, R¹, R⁵, and R⁶ are as defined for general formula (I), supra.

The present invention also covers intermediate compounds of general formula (XVII):

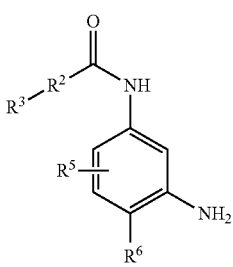

(XVII)

in which R², R³, R⁵, and R⁶ are as defined for general formula (I), supra.

The present invention also covers intermediate compounds of general formula (XXII):

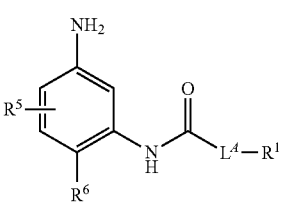

(XXII)

in which L^A, R¹, R⁵ and R⁶ are as defined for general formula (I), supra.

The present invention also covers intermediate compounds of general formula (XXIV):

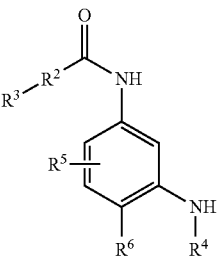

(XXIV)

in which R², R³, R⁴, R⁵ and R⁶ are as defined for general formula (I), supra.

The present invention also covers intermediate compounds of general formula (XXV):

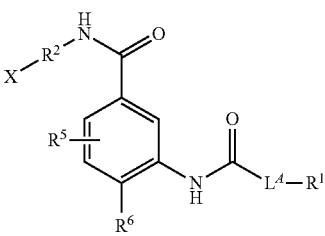

(XXV)

in which L^A, R¹, R², R⁵ and R⁶ are as defined for general formula (I), supra, and X represents a group enabling palladium catalysed coupling reactions, such as chloro, bromo, iodo, trifluoromethylsulfonyloxy, nonaflyl or a boronic acid or an ester thereof.

In accordance with yet another aspect, the present invention covers the use of the intermediate compounds of general formula (VI):

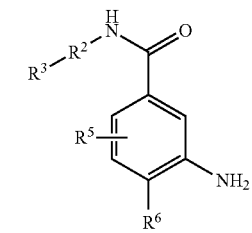

(VI)

in which R², R³, R⁵, and R⁶ are as defined for general formula (I) supra, for the preparation of a compound of general formula (I) as defined supra.

In accordance with yet another aspect, the present invention covers the use of the intermediate compounds of general formula (XI):

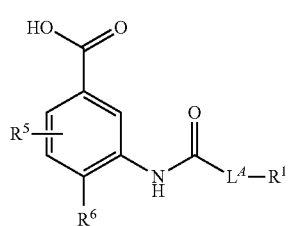

(XI)

in which $L^A$, $R^1$, $R^5$, and $R^6$ are as defined for the compounds of general formula (I) supra, for the preparation of a compound of general formula (I) as defined supra.

In accordance with yet another aspect, the present invention covers the use of the intermediate compounds of general formula (XIa):

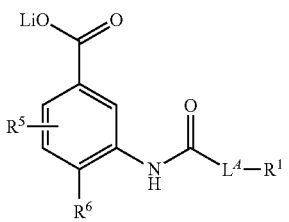

(XIa)

in which $L^A$, $R^1$, $R^5$, and $R^6$ are as defined for general formula (I) supra, for the preparation of a compound of general formula (I) as defined supra.

In accordance with yet another aspect, the present invention covers the use of the intermediate compounds of general formula (XVII):

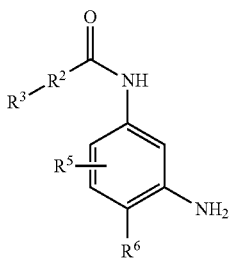

(XVII)

in which $R^2$, $R^3$, $R^5$, and $R^6$ are as defined for general formula (I) supra, for the preparation of a compound of general formula (I) as defined supra.

In accordance with yet another aspect, the present invention covers the use of the intermediate compounds of general formula (XXII):

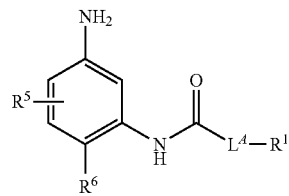

(XXII)

in which $L^A$, $R^1$, $R^5$ and $R^6$ are as defined for general formula (I) supra, for the preparation of a compound of general formula (I) as defined supra.

In accordance with yet another aspect, the present invention covers the use of the intermediate compounds of general formula (XXIV):

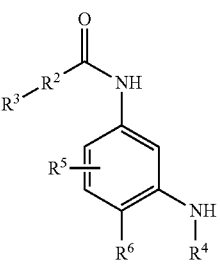

(XXIV)

in which $R^2$, $R^3$, $R^4$, $R^5$ and $R^6$ are as defined for general formula (I) supra, for the preparation of a compound of general formula (I) as defined supra.

In accordance with yet another aspect, the present invention covers the use of the intermediate compounds of general formula (XXV):

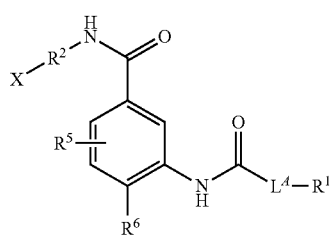

(XXV)

in which $L^A$, $R^1$, $R^2$, $R^5$ and $R^6$ are as defined for general formula (I), supra, and X represents a group enabling palladium catalysed coupling reactions, such as chloro, bromo, iodo, trifluoromethylsulfonyloxy, nonaflyl or a boronic acid or an ester thereof;

for the preparation of a compound of general formula (I) as defined supra.

General Synthesis of the Compounds of the Invention

The following paragraphs outline a variety of synthetic approaches suitable to prepare compounds of formulae (Ia), (Ib) and (Ic), in which $L^A$, $R^1$, $R^2$, $R^3$, $R^5$ and $R^6$ are as defined for the compounds of general formula (I), supra. Formulae (Ia) and (Ib), in which $R^4$ represents hydrogen, both constitute subsets of formula (I) in that they feature different orientations of the amide linker $L^B$, which stands for —NH—C(=O)— in formula (Ia) whilst representing —C(=O)—NH— in formula (Ib), as shown in Scheme A. In formula (Ic), $L^B$ represents —C(=O)—NH—, alike formula (Ib), and $R^4$ is as defined for the compounds of general formula (I), supra, but different from hydrogen.

Scheme A: Formulae (I), (Ia), Ib), and (Ic).

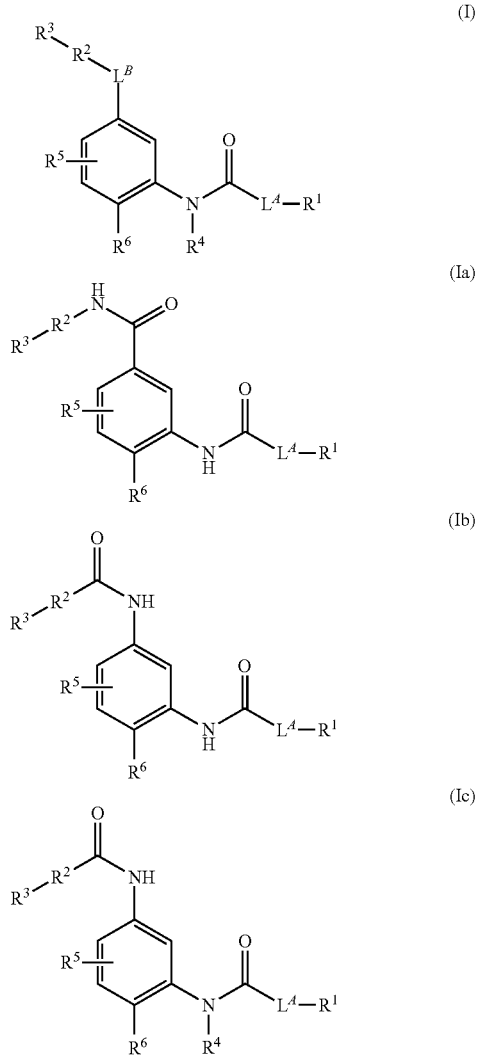

In addition to the routes described below, also other routes may be used to synthesise the target compounds, in accordance with common general knowledge of a person skilled in the art of organic synthesis. The order of transformations exemplified in the following Schemes is therefore not intended to be limiting, and suitable synthesis steps from various schemes can be combined to form additional synthesis sequences. In addition, interconversion of any of the substituents $R^1$, $R^2$, $R^3$, $R^4$, $R^5$ and/or $R^6$, can be achieved before and/or after the exemplified transformations. These modifications can be such as the introduction of protective groups, cleavage of protective groups, reduction or oxidation of functional groups, halogenation, metallation, metal catalysed coupling reactions, substitution or other reactions known to a person skilled in the art. These transformations include those which introduce a functionality allowing for further interconversion of substituents. Appropriate protective groups and their introduction and cleavage are well-known to a person skilled in the art (see for example T. W. Greene and P. G. M. Wuts in Protective Groups in Organic Synthesis, $3^{rd}$ edition, Wiley 1999). Specific examples are described in the subsequent paragraphs. Further, it is possible that two or more successive steps may be performed without work-up being performed between said steps, e.g. in a "one-pot" reaction, as it is well-known to a person skilled in the art.

Scheme B outlines the preparation of compounds of the formula (Ia), in which $L^A$, $R^1$, $R^2$, $R^3$, $R^5$, and $R^6$ are as defined for the compounds of general formula (I), supra, starting from meta-nitrobenzoic acid derivatives (II), in which $R^5$ and $R^6$ are as defined for the compounds of general formula (I), which can be converted into the corresponding benzoyl chlorides (III), by treatment with a suitable chlorinating agent, such as oxalyl chloride. Benzoic acid derivatives of the formula (II) are well known to the person skilled in the art, and are often commercially available. Said benzoyl chlorides of the formula (III) can be subsequently converted into amides of the general formula (V), e.g. directly by aminolysis with amines $R^3$—$R^2$—$NH_2$, in which $R^2$ and $R^3$ are as defined for the compounds of general formula (I). Alternatively, amides of the formula (V) can be accomplished in two steps by aminolysis of (III) using an amine X—$R^2$—$NH_2$, in which $R^2$ is as defined for the compounds of general formula (I), giving rise to amides of the formula (IV). Said amides can be subsequently coupled with $R^3$—X', in which $R^3$ is as defined for the compounds of general formula (I), in a palladium catalysed coupling reaction such as a Suzuki coupling to furnish amides of general formula (V). In X—$R^2$—$NH_2$ and $R^3$—X', both X and X' represent groups enabling palladium catalysed coupling reactions, such as chloro, bromo, iodo, trifluoromethylsulfonyloxy, —S(=O)$_2$C$_4$F$_9$ (nonaflyl) or a boronic acid or an ester thereof, with the proviso that if X represents a boronic ester or an ester thereof, X' stands for bromo, iodo, trifluoromethylsulfonyloxy or nonaflyl and the like, or vice versa.

The nitro group present in said amides (V) is then reduced by treatment with a suitable reducing agent, such as titanium (III)chloride, or hydrogenation in the presence of a suitable catalyst, e.g. palladium on charcoal, to give anilines of the formula (VI). Said anilines of the formula (VI) are then elaborated into compounds of the formula (Ia). This can be accomplished directly by reacting a compound of the formula (VI) with a carboxylic acid $HO_2C$-$L^A$-$R^1$, wherein $L^A$ and $R^1$ are as defined for the compounds of general formula (I), in an amide coupling reaction, for example in the presence of a tertiary aliphatic amine, such as N,N-diisopropylethylamine, and 2,4,6-tripropyl-1,3,5,2,4,6-trioxaphosphinane 2,4,6-trioxide (also known as T3P), in a suitable solvent such as N,N-dimethylformamide. Alternatively, the transformation of anilines (VI) into compounds of the formula (Ia) can be performed by reaction of anilines (VI) with suitable reagents such as Cl—C(=O)-$L^A$-$R^1$, or, in a two step synthesis firstly with Cl—C(=O)-$L^A$-LG, in which $L^A$ is as defined for the compounds of general formula (I), and LG stands for a leaving group, preferably chloro or bromo, to give the corresponding compounds of formula (VII), which are subsequently reacted with agents suitable for the introduction of $R^1$, exemplified by but not limited to cyclic secondary amines, to give compounds of the formula (Ia).

Scheme B: Preparation of compounds of the formula (Ia) from meta-nitrobenzoic acid derivatives of formula (II)

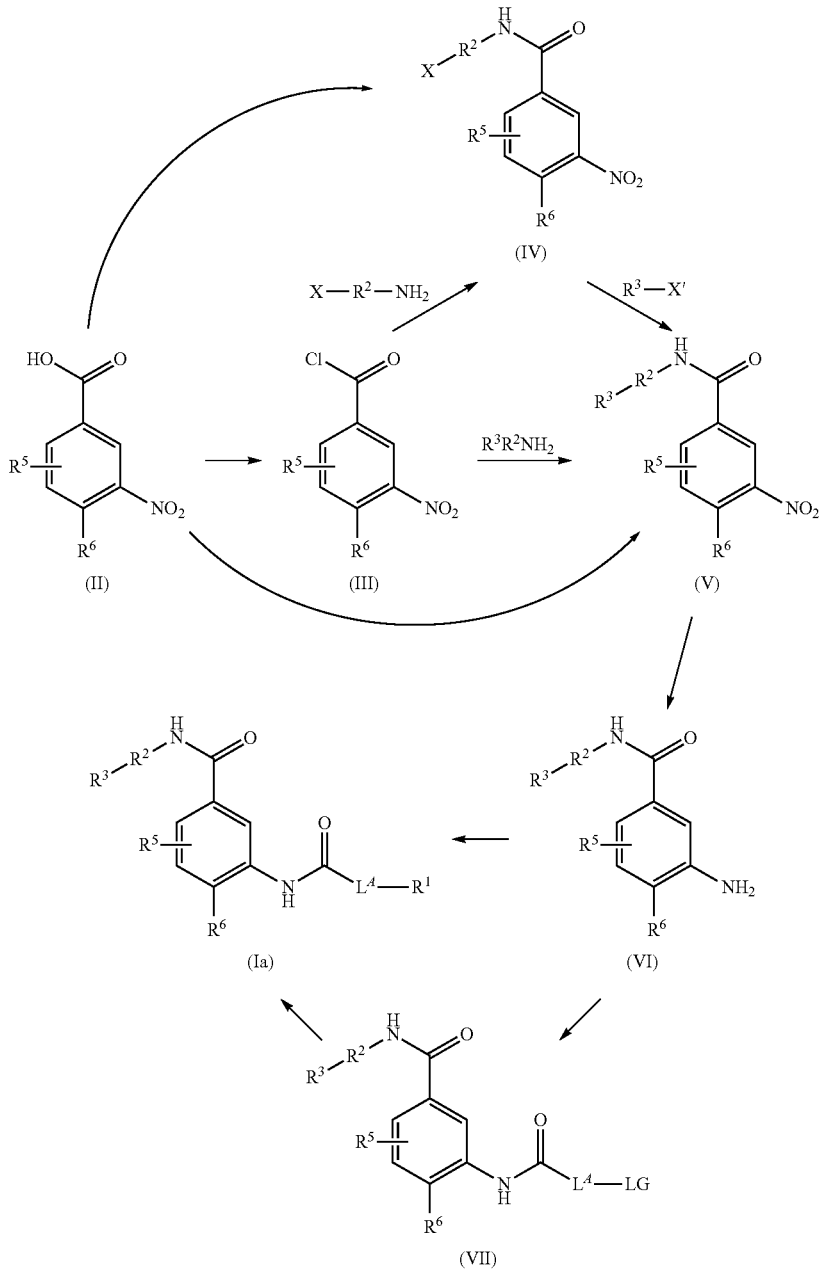

Alternatively, compounds of the formula (Ia) can be prepared starting from meta-aminobenzoic acid derivatives of formula (VIII), in which $R^5$ and $R^6$ are as defined for the compounds of general formula (I), supra, as outlined in Scheme C. Said meta-aminobenzoic acid derivatives of formula (VIII) are well known to the person skilled in the art and are commercially available in many cases. Compounds of formula (VIII) can be reacted with an amine $R^3R^2NH_2$, in which $R^2$ and $R^3$ are as defined for the compounds of general formula (I), supra, in a standard amide coupling reaction, to give amide derivatives of formula (VI). Said compounds of formula (VI) can also be obtained by coupling the aforementioned acids of formula (VIII) with an amine $X-R^2-NH_2$, in which $R^2$ is as defined for the compounds of general formula (I), supra, giving rise to amides of the formula (IX). These are subsequently subjected to a palladium catalysed coupling reaction, such as a Suzuki coupling, with $R^3-X'$, in which $R^3$ is as defined for the compounds of general formula (I), in order to furnish amides of general formula (VI), respectively. In $X-R^2-NH_2$ and $R^3-X'$, both X and X' represent groups enabling palladium catalysed coupling reactions, such as bromo, iodo, trifluoromethylsulfonyloxy, nonaflyl or a boronic acid or an ester thereof, with the proviso that if X represents a boronic ester or an ester thereof, X' stands for bromo, iodo, trifluoromethylsulfonyloxy or nonaflyl and the like, or vice versa. Amides of the formula (VI) are subsequently converted into compounds of formula (Ia) as described supra in context with Scheme B.

Scheme C: Preparation of compounds of the formula (Ia) from meta-aminobenzoic acid derivatives of formula (VIII)

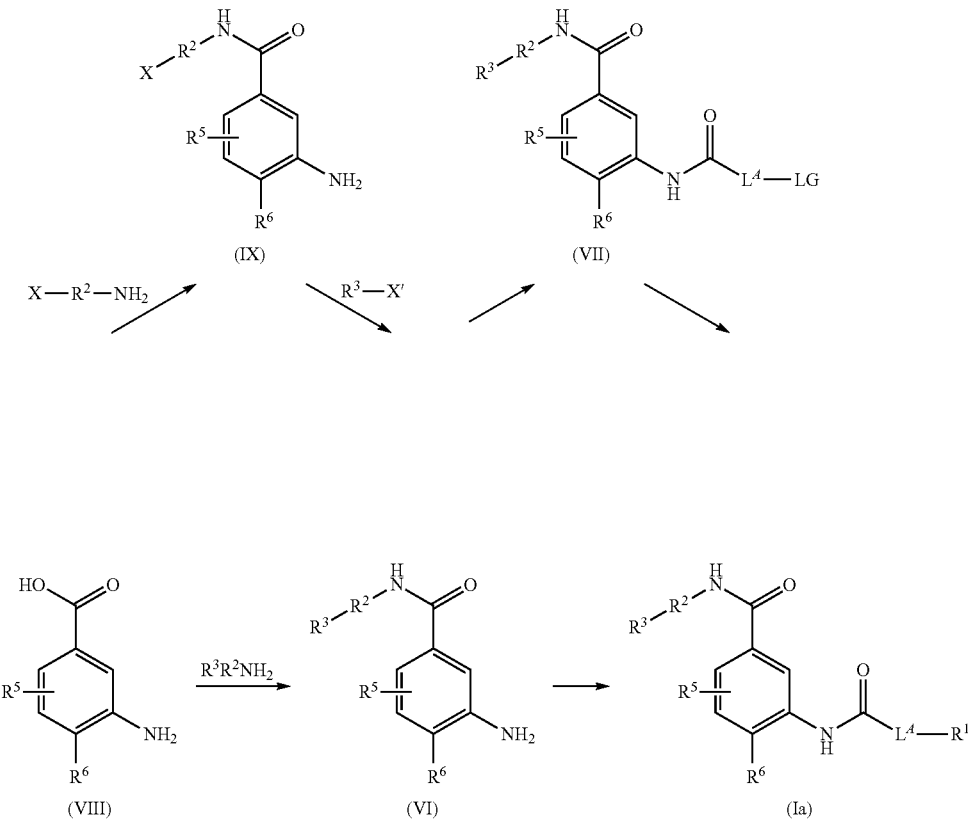

The sequence of synthetic steps can be varied as outlined in Scheme D, in order to convert meta-aminobenzoic acid derivatives of formula (VIII), in which $R^5$ and $R^6$ are as defined for the compounds of general formula (I), into compounds of the formula (Ia). Said benzoic acid derivatives of the formula (VIII) can be converted into compounds of the formula (X), in which LG stands for a leaving group, preferably chloro or bromo, followed e.g. by aminolysis of compounds of the formula (X) using reagents suitable for the introduction of $R^1$, exemplified by but not limited to suitable cyclic secondary amines, to give compounds of the formula (XI). Subsequently, the carboxy group present in compounds of the formula (XI) can be coupled with an amine $R^3R^2NH_2$, in which $R^2$ and $R^3$ are as defined for the compounds of general formula (I), supra, in an amide coupling reaction, for example in the presence of a tertiary aliphatic amine, such as N,N-diisopropylethylamine, and 2,4,6-tripropyl-1,3,5,2,4,6-trioxaphosphinane 2,4,6-trioxide (also known as T3P), in a suitable solvent such as N,N-dimethylformamide, to afford compounds of the formula (Ia).

Scheme D: Alternative preparation of compounds of the formula (Ia) from meta-aminobenzoic acid derivatives of formula (VIII)

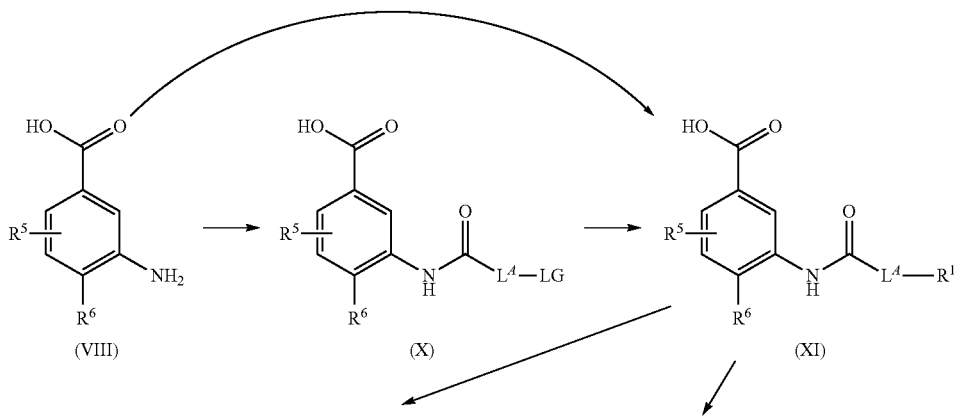

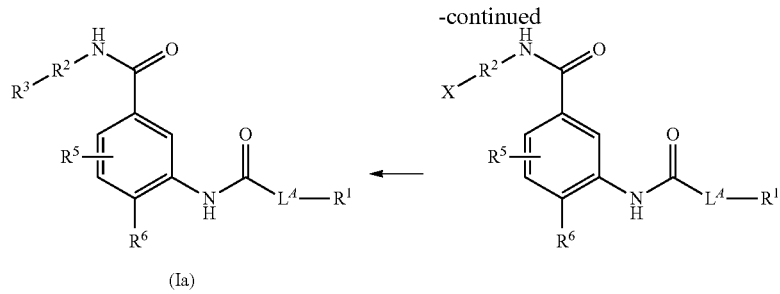

Instead of said benzoic acid derivatives of formula (VIII), also the corresponding ester analogues of formula (XII), in which $R^5$ and $R^6$ are as defined for the compounds of general formula (I), and in which $R^E$ stands for a $C_1$-$C_6$-alkyl group, preferably methyl or ethyl, can be employed in a similar fashion in order to prepare compounds of the formula (Ia), as outlined in Scheme E. Esters of the formula (XII) are well known to the person skilled in the art, and are commercially available in many cases. Elaboration of said benzoic acid esters of formula (XII) into compounds of formula (XIV), in which $R^1$ is as defined for the compounds of general formula (I), supra, can proceed via compounds of formula (XIII), in which LG stands for a leaving group, preferably chloro or bromo, and can be performed analogously as described in context with Scheme D. Subsequently, the ester group present in compounds of formula (XIV) can be saponified by reaction with e.g. lithium hydroxide to yield the lithium salt of the formula (XIa). Said lithium salt of formula (XIa) or the corresponding carboxylic acid is then converted into compounds of formula (Ia).

Scheme E: Preparation of compounds of the formula (Ia) from meta-aminobenzoic acid esters of formula (XII)

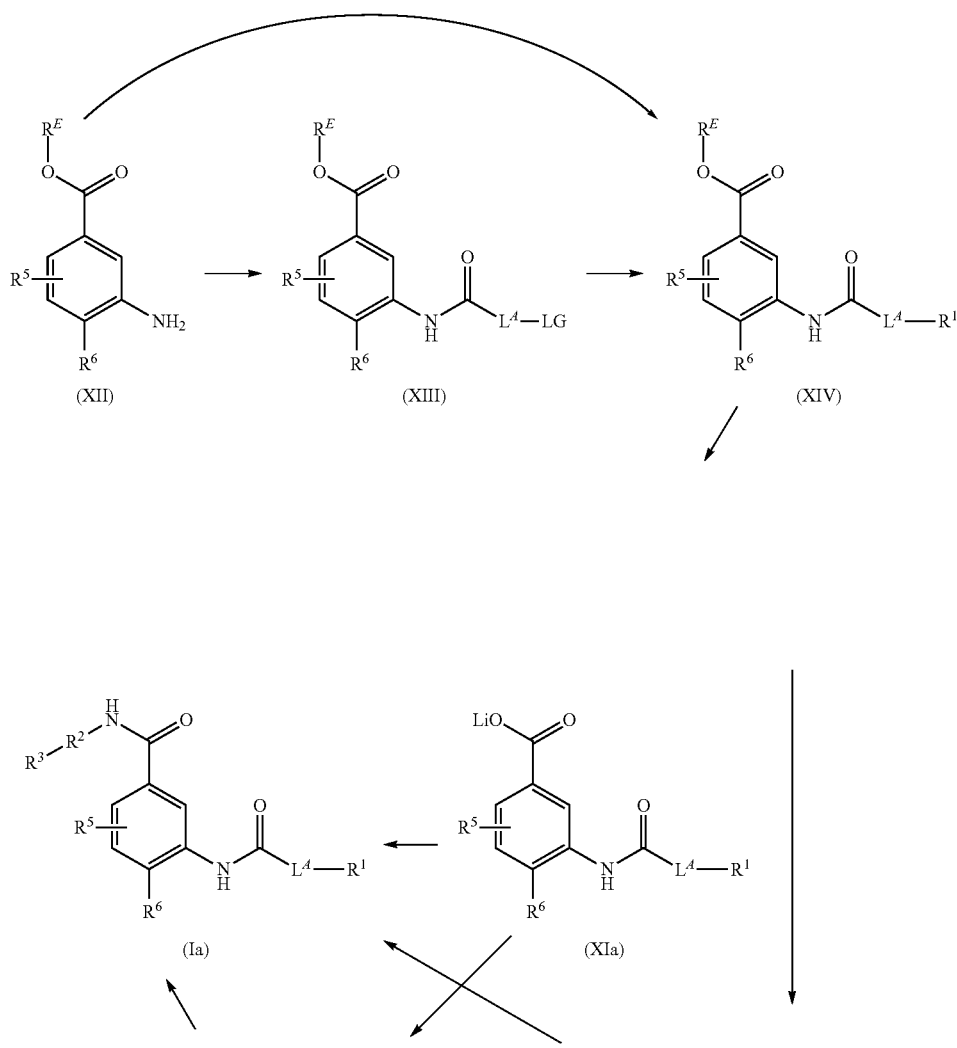

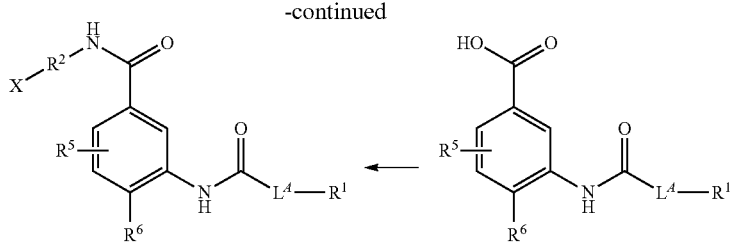

A first approach to compounds of the formula (Ib) from meta-nitroaniline derivatives of formula (XV), in which $R^5$ and $R^6$ are as defined for the compounds of general formula (I), supra, is outlined in Scheme F. Said meta-nitroaniline derivatives of formula (XV) are well known to the person skilled in the art, and are often commercially available. They can be converted into amide derivatives of formula (XVI) e.g. by a reacting with a carboxylic acid chloride $R^3$—$R^2$—C(=O)Cl, in which $R^2$ and $R^3$ are as defined for the compounds of general formula (I), supra, in the presence of a suitable base, such as potassium carbonate, and in a suitable solvent, such as acetonitrile. Basic solvents, such as pyridine, can take over both the role of a base and of a solvent, respectively. Alternatively, conversion of (XV) into (XVI) can be performed via standard amide coupling reactions. The nitro group present in amides of the formula (XVI) can be subsequently reduced e.g. by hydrogenation in the presence of a suitable catalyst, e.g. palladium on charcoal, to give the corresponding aniline derivatives of formula (XVII). Said anilines of the formula (XVII) can then be elaborated into compounds of the formula (Ib). This can be accomplished directly by reacting a compound of the formula (XVII) with a carboxylic acid $HO_2C$-$L^A$-$R^1$, wherein $L^A$ and $R^1$ are as defined for the compounds of general formula (I), in an amide coupling reaction, for example in the presence of a tertiary aliphatic amine, such as N,N-diisopropylethylamine, and 2,4,6-tripropyl-1,3,5,2,4,6-trioxaphosphinane 2,4,6-trioxide (also known as T3P), in a suitable solvent such as N,N-dimethylformamide. Alternatively, the transformation of anilines (XVII) into compounds of the formula (Ia) can be performed by reaction of anilines (XVII) with suitable reagents, such as Cl—C(=O)-$L^A$-LG, in which $L^A$ is as defined for the compounds of general formula (I), and LG stands for a leaving group, preferably chloro or bromo, to give the corresponding compounds of formula (XVIII), which are subsequently reacted with agents suitable for the introduction of $R^1$, exemplified by but not limited to cyclic secondary amines, to give compounds of the formula (Ib).

Scheme F: Preparation of compounds of the formula (Ib) from meta-nitroaniline derivatives of formula (XV)

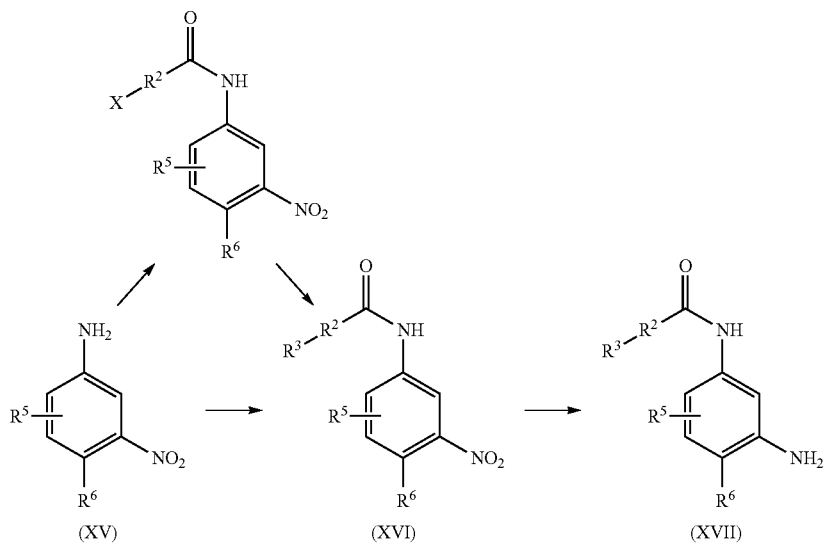

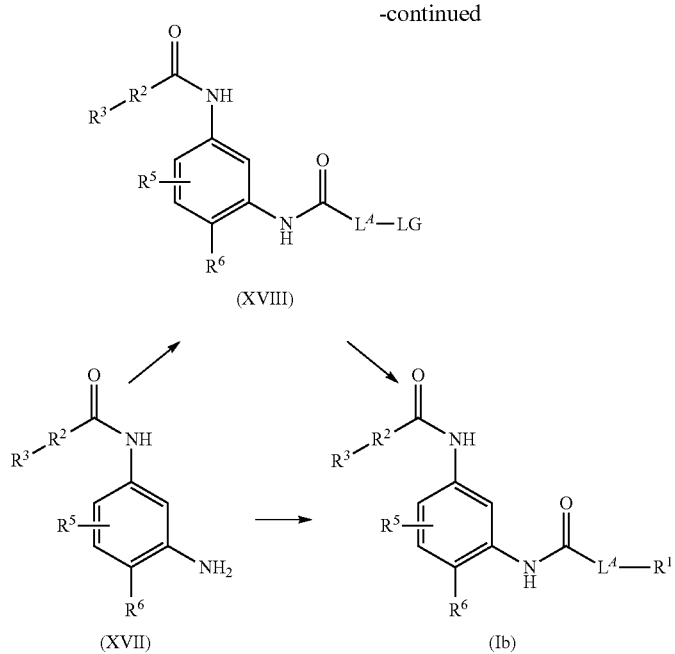

Scheme G outlines an approach complimentary to Scheme F as an alternative synthesis route for compounds of the formula (Ib), from meta-nitroaniline derivatives of formula (XIX), in which $R^5$ and $R^6$ are as defined for the compounds of general formula (I), supra, and which differ from the compounds of formula (XV) by the inverse arrangement of their nitro and amino groups, respectively. Said meta-nitroaniline derivatives of formula (XIX) are well known to the person skilled in the art, and are often commercially available. They can be converted into amide derivatives of formula (XX), in which $L^A$ is as defined for the compounds of general formula (I), supra, and in which LG stands for a leaving group, preferably chloro or bromo, by a reacting with a carboxylic acid LG-$L^A$-$CO_2H$, in a standard amide coupling reaction. Said amides of the formula (XX) can be subsequently converted into compounds of the formula (XXI), in which $R^1$ is as defined for the compounds of general formula (I), supra, using reagents suitable for the introduction of $R^1$, exemplified by but not limited to cyclic secondary amines. The nitro group present in amides of the formula (XXI) is then reduced e.g. by hydrogenation in the presence of a suitable catalyst, e.g. palladium on charcoal, to give the corresponding aniline derivatives of formula (XXII). Compounds of formula (XXII) can be reacted with a carboxylic acid $R^3R^2CO_2H$, wherein $R^2$ and $R^3$ are as defined for the compounds of general formula (I), supra, in an amide coupling reaction, for example in the presence of a tertiary aliphatic amine, such as N,N-diisopropylethylamine, and 2,4,6-tripropyl-1,3,5,2,4,6-trioxaphosphinane 2,4,6-trioxide (also known as T3P), in a suitable solvent such as N,N-dimethylformamide, to give compounds of the formula (Ib). The compounds of formula (Ib) can also be obtained by coupling the aforementioned anilines of formula (XXII) with a carboxylic acid X—$R^2$—$CO_2H$, in which $R^2$ is as defined for the compounds of general formula (I), supra, giving rise to amides of the formula (XXIII). These can be subsequently subjected to a palladium catalysed coupling reaction, such as a Suzuki coupling, with $R^3$—X', in which $R^3$ is as defined for the compounds of general formula (I), in order to furnish compounds of the formula (Ib), respectively. In X—$R^2$—$CO_2H$ and $R^3$—X', both X and X' represent groups enabling palladium catalysed coupling reactions, such as chloro, bromo, iodo, trifluoromethylsulfonyloxy, nonaflyl or a boronic acid or an ester thereof, with the proviso that if X represents a boronic ester or an ester thereof, X' stands for chloro, bromo, iodo, trifluoromethylsulfonyloxy or nonaflyl and the like, or vice versa.

Scheme G: Preparation of compounds of the formula (Ib) from meta-nitroaniline derivatives of formula (XIX)

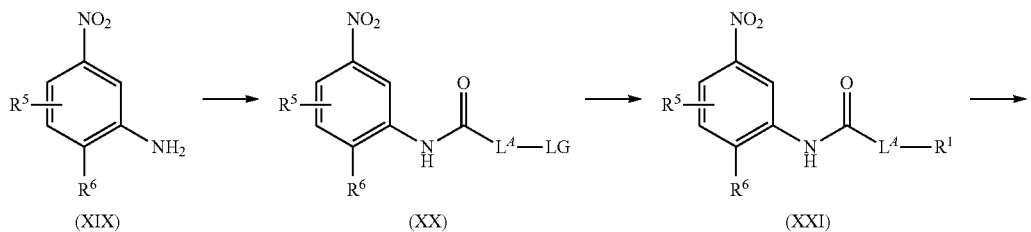

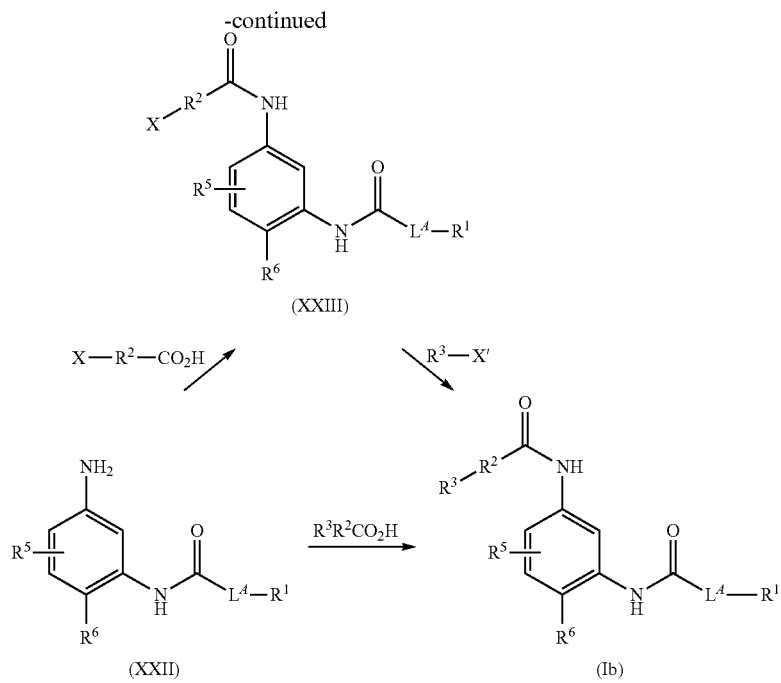

Scheme H illustrates the introduction of $R^4$ groups different from hydrogen. In order so to do, primary anilines of the formula (XVII), in which $L^A$, $R^1$, $R^2$, $R^3$, $R^5$, and $R^6$ are as defined for the compounds of general formula (I), supra, and which can be prepared according to Scheme F, can be converted into secondary anilines of the formula (XXIV), in which $R^4$ is as defined for the compounds of general formula (I), supra, but different from hydrogen. This can be accomplished by various methods known to the person skilled in the art, such as a reductive amination with an aldehyde suitable to confer $R^4$, e.g. benzaldehyde for $R^4$=benzyl, in the presence of a suitable borohydride reagent, such as sodium triacetoxyborohydride, and in the presence of a suitable acid, such as acetic acid, in a suitable solvent, such as a chlorinated hydrocarbon, preferably dichloromethane. The resulting compounds of the formula (XXIV) are subsequently elaborated into compounds of the formula (Ic), in which $L^A$, $R^1$, $R^2$, $R^3$, $R^4$, $R^5$ and $R^6$ are as defined for the compounds of general formula (I), supra, with the proviso that $R^4$ is different from hydrogen.

Scheme H: Preparation of compounds of the formula (Ic) from aniline derivatives of formula (XVII)

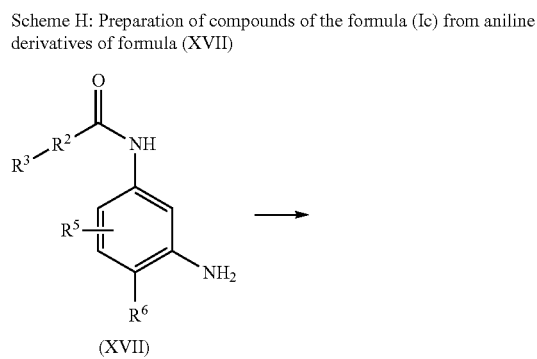

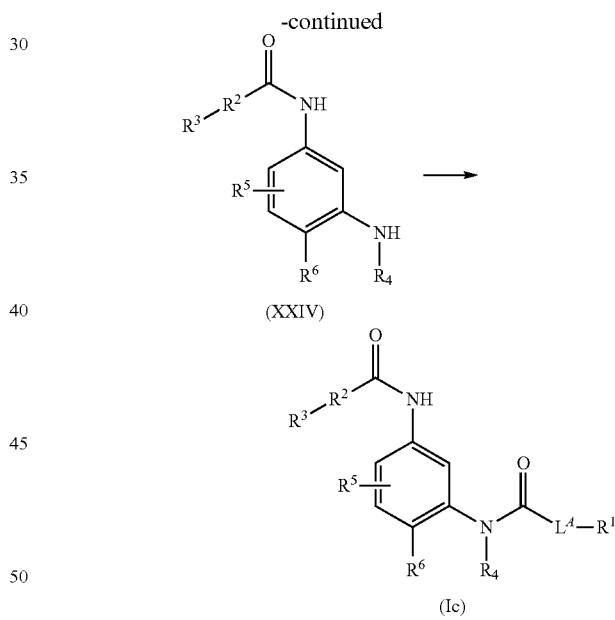

Further details (reaction conditions, suitable solvents etc.) can be obtained from the experimental section below.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF3COOH", "x Na+", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

EXPERIMENTAL SECTION

The following table lists the abbreviations used in this paragraph, and in the examples section.

| Abbreviation | Meaning |
|---|---|
| anh | anhydrous |
| br. | broad signal (in NMR data) |
| d | day(s) |
| DAD | Diode Array Detector |
| DCM | dichloromethane |
| DME | 1,2-dimethoxyethane |
| DMF | N,N-dimethylformamide |
| DMSO | dimethyl sulfoxide |
| ELSD | Evaporative Light Scattering Detector |
| ESI | electrospray ionisation |
| EtOAc | ethyl acetate |
| h | hour |
| HPLC, LC | high performance liquid chromatography |
| m/z | mass-to-charge ratio (in mass spectrum) |
| mc | multiplet centred |
| MeOH | methanol |
| min | Minute |
| MPLC | medium pressure liquid chromatography |
| MS | mass spectroscopy |
| neg | negative |
| NMR | nuclear magnetic resonance |
| PE | petroleum ether |
| pos | positive |
| ppm | Chemical shift δ in parts per million |
| PYBOP | (1H-benzotriazol-1-yloxy)(tripyrrolidin-1-yl)phosphonium hexafluorophosphate |
| $R_t$ | retention time |
| rt | room temperature |
| THF | tetrahydrofurane |
| TLC | thin layer chromatography |

Methods:

Method 1:

Instrument: Waters Acquity UPLC-MS SQD; column: Acquity UPLC BEH C18 1.7 50×2.1 mm; Eluent A: water+0.05% vol. formic acid (98%), Eluent B: acetonitrile+0.05% vol. formic acid (98%); gradient: 0-1.6 min 1-99% B, 1.6-2.0 min 99% B; rate 0.8 mL/min; temperature: 60° C.; DAD scan: 210-400 nm; ELSD.

Method 2:

Instrument: Waters Autopurification system SOD; column: Waters XBrigde C18 5μ 100×30 mm; water+0.1% vol. formic acid (99%)/acetonitrile gradient; temperature: room temperature; injection: 2500 μL; DAD scan: 210-400 nm.

Method 3:

Instrument: Waters Acquity UPLC-MS SOD; column: Acquity UPLC BEH C18 1.7 50×2.1 mm; Eluent A: water+0.2% vol. ammonia (32%), Eluent B: acetonitrile; gradient: 0-1.6 min 1-99% B, 1.6-2.0 min 99% B; rate 0.8 mL/min; temperature: 60° C.; DAD scan: 210-400 nm; ELSD.

Method 4:

Instrument: Waters Acquity UPLC-MS SQD; column: Acquity UPLC BEH C18 1.7 50×2.1 mm; Eluent A: water+0.1% vol. formic acid (99%), Eluent B: acetonitrile; gradient: 0-1.6 min 1-99% B, 1.6-2.0 min 99% B; rate 0.8 mL/min; temperature: 60° C.; DAD scan: 210-400 nm; ELSD.

Method 5:

Instrument: Waters Autopurification system SOD; column: Waters XBrigde C18 5μ 100×30 mm; water+0.2% vol. ammonia (32%)/acetonitrile gradient; temperature: room temperature; injection: 2500 μL; DAD scan: 210-400 nm.

Method 6:

Instrument: JASCO P2000 Polarimeter; wavelength 589 nm; temperature: 20° C.; integration time 10 s; path length 100 mm.

Method 7:

Instrument: Acquity UPLC from Waters; mass detector: LCT from Micromass (now Waters); column: Kinetex C18 from Phenomenex, 50×2.1 mm, 2.6 μm particle, 60° C.; solvent: A: water+0.05% formic acid; B: acetonitrile+0.05% formic acid; injection: 0.5 μl; rate: 1.3 mL/min; gradient 99% A, 1% B until 1.9 min linear to 1% A, 99% B; 1.9-2.10 min unchanged; until 2.20 min back to 99% A, 1% B.

Intermediates

Intermediate 1

5-phenyl-1,3-thiazole-2-carboxylic acid

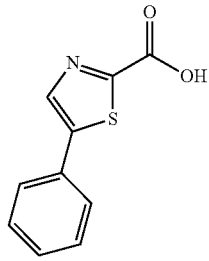 [SMILES: O=C(O)c1ncc(-c2ccccc2)s1]

500 mg (2.14 mmol) of ethyl 5-phenyl-1,3-thiazole-2-carboxylate were provided in 4.4 mL of dioxane, a solution of 103 mg (4.29 mmol) of lithium hydroxide in 2.6 mL of water was added at room temperature and the mixture was stirred for 5 h at room temperature. Water and a 2N aqueous hydrogen chloride solution were then added until an acidic pH of 1.5-2 was achieved. After stirring for 15 minutes, the precipitate was filtered off, washed with water and dried. 360 mg of the title compound were obtained as a mixture of the free acid and its lithium salt.

LC-MS (Method 4): $R_t$=0.85 min; MS (ESIpos): m/z=206 [M+H]$^+$.

Intermediate 2 lithium 5-phenyl-1,3-thiazole-2-carboxylate

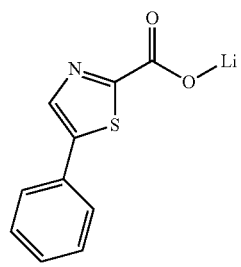

To a solution of ethyl 5-phenyl-1,3-thiazole-2-carboxylate (500 mg, 2.14 mmol) in dioxane (4.4 mL) was added a solution of lithium hydroxide (103 mg, 4.29 mmol, 2.0 equiv) in water (2.6 mL) at room temperature. The mixture was stirred for 4 h at room temperature. The resulting mixture was concentrated under reduced pressure, and washed with $CH_2Cl_2$ (10 mL). The resulting aqueous layer was concentrated to dryness under reduced pressure to give lithium 5-phenyl-1,3-thiazole-2-carboxylate, which was used without further purification.

Intermediate 3

4-methoxy-3-nitrobenzoyl chloride

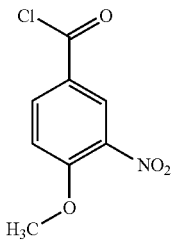

3.00 g (15.2 mmol) of 4-methoxy-3-nitrobenzoic acid were stirred in 20 mL of dichloromethane at room temperature. 59 μL (0.76 mmol) of DMF and 2.66 mL (30.4 mmol) of oxalyl chloride were added and the mixture was stirred for additional 2 h at 50° C. after the gas formation had stopped. 1.33 mL (15.2 mmol) of oxalyl chloride were added and the mixture was stirred for 6 h at 50° C. Then the solvents were evaporated and the remaining material was provided in 20 mL of dichloromethane at room temperature. 59 μL (0.76 mmol) of DMF and 2.66 mL (30.4 mmol) of oxalyl chloride were added and the mixture was stirred for additional 2 h at 50° C. after the gas formation had stopped. After concentration, 3.25 g of raw material were obtained, which were used without further purification.

Intermediate 4

N-(6-chloropyridin-3-yl)-4-methoxy-3-nitrobenzamide

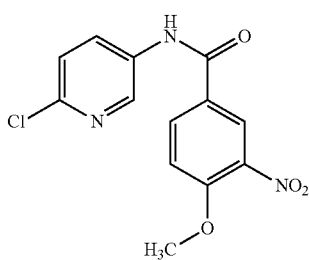 [SMILES: COc1ccc(C(=O)Nc2ccc(Cl)nc2)cc1[N+](=O)[O-]]

1.94 g (15.1 mmol) of 6-chloropyridin-3-amine and 3.15 mL (22.6 mmol) of triethylamine in 100 mL of THF were stirred at room temperature. A solution of 3.25 g (15.1 mmol) of the compound from intermediate 3 in 50 mL of THF and 50 mL of THF were added and the mixture was stirred at room temperature over night. The mixture was poured into water and ethyl acetate was added. The organic solvents were evaporated and the precipitate in the remaining aqueous phase was filtered off, washed with water and ethanol and dried. 4.30 g (87% of theory) of the title compound were obtained, which were used without further purification.

$^1$H-NMR (300 MHz, DMSO-$d_6$): δ [ppm]=4.03 (s, 3H), 7.55 (dd, 2H), 8.21-8.33 (m, 2H), 8.55 (d, 1H), 8.77 (d, 1H), 10.68 (s, 1H).

LC-MS (Method 4): $R_t$=1.06 min; MS (ESIpos): m/z=308 $[M+H]^+$.

Intermediate 5

N-[6-(2-fluorophenyl)pyridin-3-yl]-4-methoxy-3-nitrobenzamide

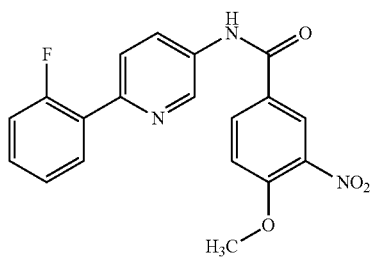

4.25 g (13.8 mmol) of the compound from intermediate 4 were provided in 140 mL of degassed THF under an argon atmosphere at room temperature. 2.90 g (20.7 mmol) of (2-fluorophenyl)boronic acid, 326 mg (0.41 mmol) of chloro (2-dicyclohexylphosphino-2',4',6'-triisopropyl-1,1'-biphenyl)[2-(2'-amino-1,1'-biphenyl)palladium(II) and 55.2 mL (27.6 mmol) of a 0.5M aqueous, degassed solution of potassium phosphate were added, and the mixture was stirred at room temperature for 1 h. The mixture was poured into water, and dichloromethane was added. The organic solvents were evaporated and the precipitate in the remaining aqueous phase was filtered off, washed with water and ethanol and dried. 5.07 g (98% of theory) of the title compound were obtained, which were used without further purification.

$^1$H-NMR (300 MHz, DMSO-$d_6$): δ [ppm]=4.03 (s, 3H), 7.29-7.38 (m, 2H), 7.41-7.52 (m, 1H), 7.56 (d, 1H), 7.84 (dd, 1H), 7.91-8.03 (m, 1H), 8.26-8.37 (m, 2H), 8.58 (d, 1H), 9.06 (d, 1H), 10.69 (s, 1H).

LC-MS (Method 1): $R_t$=1.19 min; MS (ESIpos): m/z=368 $[M+H]^+$.

Intermediate 6

4-methoxy-3-nitro-N-(6-phenylpyridin-3-yl)benzamide

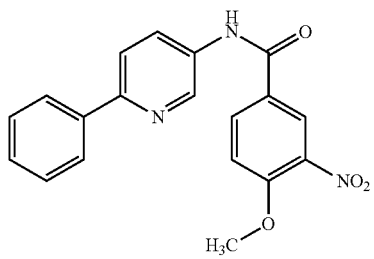 [SMILES: COc1ccc(C(=O)Nc2ccc(-c3ccccc3)nc2)cc1[N+](=O)[O-]]

2.55 g (15.0 mmol) of 6-phenylpyridin-3-amine and 3.13 mL (22.5 mmol) of triethylamine in 100 mL of THF were stirred at room temperature. A solution of 3.23 g (15.0 mmol) of the compound from intermediate 3 in 50 mL of THF was added and the mixture was stirred at room temperature over night. The mixture was poured into water and ethyl acetate was added. The organic solvents were evaporated and the precipitate in the remaining aqueous phase was filtered off, washed with water and ethanol and dried. 5.08 g (96% of theory) of the title compound were obtained, which were used without further purification.

$^1$H-NMR (300 MHz, DMSO-$d_6$): δ [ppm]=4.03 (s, 3H), 7.36-7.61 (m, 4H), 8.01 (d, 1H), 8.05-8.12 (m, 2H), 8.24-8.37 (m, 2H), 8.58 (d, 1H), 9.01 (d, 1H), 10.65 (s, 1H).

LC-MS (Method 4): $R_t$=1.18 min; MS (ESIpos): m/z=350 [M+H]$^+$.

Intermediate 7

3-amino-N-[6-(2-fluorophenyl)pyridin-3-yl]-4-methoxybenzamide

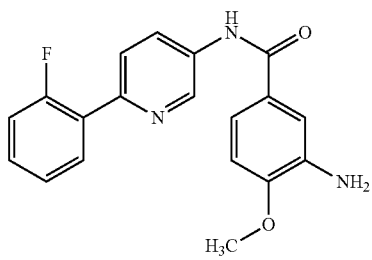 [SMILES: COc1ccc(C(=O)Nc2ccc(-c3ccccc3F)nc2)cc1N]

5.00 g (13.6 mmol) of the compound from intermediate 5 were provided in 150 mL of THF and cooled to 0° C. 92.6 mL (109 mmol) of a 10% aqueous hydrogen chloride solution containing 15% of titanium(III) trichloride were added and the mixture was stirred at room temperature over night. 200 mL of THF were added, and the mixture was stirred at room temperature for 2 days. 200 mL of THF and 92.6 mL (109 mmol) of a 10% aqueous hydrogen chloride solution containing 15% of titanium(III) trichloride were added, and the mixture was stirred at room temperature over night. 92.6 mL (109 mmol) of a 10% aqueous hydrogen chloride solution containing 15% of titanium(III) trichloride were added, and the mixture was stirred at room temperature over night. Dichloromethane was added, the pH was adjusted to a value of 10 by addition of a 2N aqueous solution of sodium hydroxide, and the mixture was stirred for 2 h. After filtration and separation of the organic and aqueous phase, the aqueous phase was extracted with dichloromethane. The combined organic phases were washed with brine, dried over sodium sulfate, filtered and concentrated. 4.67 g of the title compound were obtained and used without further purification.

$^1$H-NMR (400 MHz, DMSO-$d_6$): δ [ppm]=3.85 (s, 3H), 4.96 (s, 2H), 6.90-6.95 (m, 1H), 7.26-7.36 (m, 4H), 7.41-7.49 (m, 1H), 7.79 (dd, 1H), 7.91-8.01 (m, 1H), 8.30 (dd, 1H), 9.05 (d, 1H), 10.29 (s, 1H).

LC-MS (Method 1): $R_t$=1.02 min; MS (ESIpos): m/z=338 [M+H]$^+$.

Intermediate 8

3-amino-4-methoxy-N-(6-phenylpyridin-3-yl)benzamide

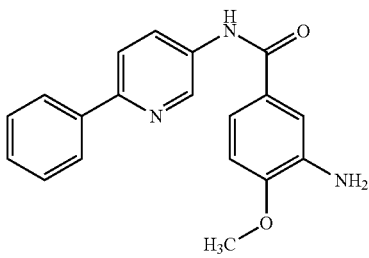 [SMILES: COc1ccc(C(=O)Nc2ccc(-c3ccccc3)nc2)cc1N]

5.00 g (14.3 mmol) of the compound from intermediate 6 were provided in 150 mL of THF and cooled to 0° C. 97.3 mL (115 mmol) of a 10% aqueous hydrogen chloride solution containing 15% of titanium(III) trichloride were added and after addition of further 200 mL of THF the mixture was stirred at room temperature over night. 200 mL of THF were added, and the mixture was stirred at room temperature for 2 days. 400 mL of THF and 48.7 mL (57.3 mmol) of a 10% aqueous hydrogen chloride solution containing 15% of titanium(III) trichloride were added, and the mixture was stirred at room temperature over night. The reaction mixture was neutralized by addition of solid sodium bicarbonate, saturated with sodium chloride and stirred with 600 mL of a 1:1 mixture of THF and ethyl acetate for 2 h. The precipitate was filtered off. Dichloromethane was added to the precipitate, the pH was adjusted to a value of 10 by addition of a 2N aqueous solution of sodium hydroxide, and the mixture was stirred for 2 h. After filtration and separation of the organic and aqueous phase, the aqueous phase was extracted with dichloromethane. The combined organic phases were washed with brine, dried over sodium sulfate, filtered and concentrated. 1.90 g of the title compound (42% of theory) were obtained and used without further purification.

$^1$H-NMR (300 MHz, DMSO-$d_6$): δ [ppm]=3.85 (s, 3H), 4.98 (s, 2H), 6.89-6.97 (m, 1H), 7.23-7.31 (m, 2H), 7.35-7.44 (m, 1H), 7.44-7.53 (m, 2H), 7.96 (d, 1H), 8.02-8.12 (m, 2H), 8.29 (dd, 1H), 9.00 (d, 1H), 10.26 (s, 1H).

LC-MS (Method 1): $R_t$=0.97 min; MS (ESIpos): m/z=320 [M+H]$^+$.

Intermediate 9

3-amino-N-(6-chloropyridin-3-yl)-4-(trifluoromethoxy)benzamide

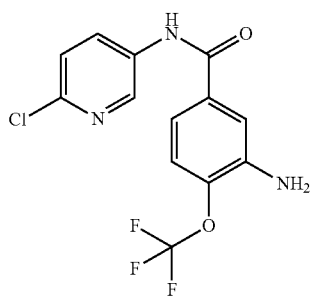 [SMILES: Nc1cc(C(=O)Nc2ccc(Cl)nc2)ccc1OC(F)(F)F]

A mixture of 3-amino-4-(trifluoromethoxy)benzoic acid (10.2 g, 46.1 mmol) which can be synthesized according to the method disclosed on page 213 of WO2008/75064A1 and 6-chloropyridin-3-amine (11.9 g, 92.3 mmol, 2.0 equiv) in DMF (325 mL) was treated with propanephosphonic anhydride (50%, 54 mL, 92.3 mmol, 2.0 equiv), followed by diisopropylethylamine (40 mL, 230.6 mmol, 5.0 equiv). The resulting mixture was allowed to stir at room temperature for 24 h. The resulting solution was concentrated under reduced pressure until a precipitate began to form (removal of approximately 50 mL). The resulting mixture was treated with water (100 mL). The resulting solids were separated, washed with water, and dried at 50° C. under reduced pressure to give 3-amino-N-(6-chloropyridin-3-yl)-4-(trifluoromethoxy)benzamide (10.0 g, 65%).

$^1$H-NMR (300 MHz, DMSO-d$_6$): δ [ppm]=5.63 (br s, 2H), 7.09 (dd, J=2.3, 8.5 Hz, 1H), 7.23 (ddm, J=1.3, 8.5 Hz, 1H), 7.32 (d, J=2.1 Hz, 1H), 7.47 (d J=8.7 Hz, 1H), 8.18 (dd, J=2.6, 8.9 Hz, 1H), 8.72 (d, J=2.3 Hz, 1H), 10.47 (s, 1H).

LC-MS (Method 3): R$_t$=1.11 min; MS (ESIpos): m/z=332 ([M+H]$^+$, 100%); MS (ESIneg): m/z=330 ([M−H]$^−$, 100%).

Intermediate 10

3-amino-N-[6-(2-fluorophenyl)pyridin-3-yl]-4-(trifluoromethoxy)benzamide

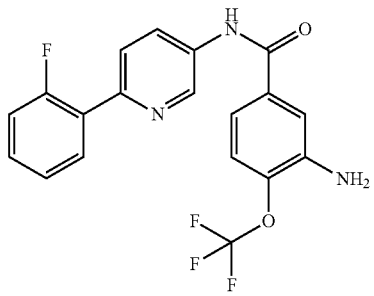 [SMILES: Nc1cc(C(=O)Nc2ccc(-c3ccccc3F)nc2)ccc1OC(F)(F)F]

To a flask was added 3-amino-N-(6-chloropyridin-3-yl)-4-(trifluoromethoxy)benzamide (prepared in a manner analogous to that described in intermediate 9, 5.0 g, 15.1 mmol), (2-fluorophenyl)boronic acid (3.2 g, 22.6 mmol, 1.5 equiv), potassium carbonate (4.2 g, 30.1 mmol, 2.0 equiv) and a DME/water mixture (3:1, 150 mL). The resulting suspension was purged with argon, treated with [1,1'-bis(diphenylphosphino)ferrocene]palladium(II) chloride CH$_2$Cl$_2$ complex (Pd(dppf)Cl$_2$·CH$_2$Cl$_2$, 0.62 g, 0.75 mmol, 5.0 mol %) and sealed. The resulting mixture was stirred in a sealed flask at 90° C. for 12 h, then cooled to room temperature. In parallel, a second reaction was run with 3-amino-N-(6-chloropyridin-3-yl)-4-(trifluoromethoxy)benzamide (prepared in a manner analogous to that described in intermediate 9, 5.0 g, 15.1 mmol). The combined reaction mixtures were poured onto ice water (200 mL), and extracted with ethyl acetate (3×100 mL). The combined organic phases were washed with a saturated NaCl solution (100 mL), dried (Na$_2$SO$_4$ anh), and concentrated under reduced pressure. The resulting material was recrystallized from ethanol to give 3-amino-N-[6-(2-fluorophenyl)pyridin-3-yl]-4-(trifluoromethoxy)benzamide (3.5 g, 29%).

$^1$H-NMR (300 MHz, DMSO-d$_6$): δ [ppm]=5.67 (s, 2H), 7.12 (dd, J=2.1, 8.3 Hz, 1H), 7.21-7.33 (m, 3H), 7.35 (d, J=2.1 Hz, 1H), 7.39-7.47 (m, 1H), 7.78 (dd, J=1.9, 8.5 Hz, 1H), 7.92 (td, J=1.7, 8.1 Hz, 1H), 8.25 (dd, J=2.5, 8.7 Hz, 1H), 9.00 (d, J=2.1 Hz, 1H), 10.50 (s, 1H).

LC-MS (Method 3): R$_t$=1.23 min; MS (ESIpos): m/z=392 ([M+H]$^+$, 70%); MS (ESIneg): m/z=390 ([M−H]$^−$, 100%).

The mother liquor from the recrystallization was concentrated to dryness under reduced pressure to give additional 3-amino-N-[6-(2-fluorophenyl)pyridin-3-yl]-4-(trifluoromethoxy)benzamide (approximately 92% pure (HPLC), 8.2 g, 69%). This material was used in subsequent reactions without further purification.

Intermediate 11

3-amino-N-(6-phenylpyridin-3-yl)-4-(trifluoromethoxy)benzamide

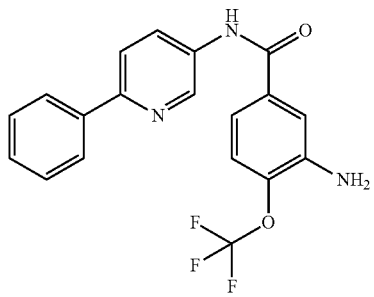 [SMILES: Nc1cc(C(=O)Nc2ccc(-c3ccccc3)nc2)ccc1OC(F)(F)F]

To a flask was added 3-amino-N-(6-chloropyridin-3-yl)-4-(trifluoromethoxy)benzamide (prepared in a manner analogous to that described in intermediate 9, 2.50 g, 7.5 mmol), phenylboronic acid (1.38 g, 11.3 mmol, 1.5 equiv), potassium carbonate (2.1 g, 15.1 mmol, 2.0 equiv) and a DME/water mixture (3:1, 75 mL). The resulting suspension was purged with argon, treated with [1,1'-bis(diphenylphosphino)ferrocene]palladium(II) chloride CH$_2$Cl$_2$ complex (0.15 g, 0.19 mmol, 2.5 mol %) and sealed. The resulting mixture was stirred in a sealed flask at 90° C. for 16 h, then cooled to room temperature. The reaction mixture was poured onto ice water (75 mL), and extracted with ethyl acetate (3×50 mL). The combined organic phases were washed with a saturated NaCl solution (50 mL), dried (Na$_2$SO$_4$ anh), and concentrated under reduced pressure. The resulting material was recrystallized from methanol to give 3-amino-N-[6-(2-fluorophenyl)pyridin-3-yl]-4-(trifluoromethoxy)benzamide (1.2 g, 41%).

$^1$H-NMR (300 MHz, DMSO-d$_6$): δ [ppm]=5.71 (s, 2H), 7.15 (dd, 1H), 7.27 (dd, 1H), 7.34-7.53 (m, 4H), 7.98 (d, 1H), 8.02-8.11 (m, 2H), 8.28 (dd, 1H), 8.99 (d, 1H), 10.50 (s, 1H).

LC-MS (Method 3): R$_t$=1.25 min; MS (ESIpos): m/z=374 ([M+H]$^+$, 100%); MS (ESIneg): m/z=372 ([M−H]$^−$, 100%).

Intermediate 12

3-[(chloroacetyl)amino]-N-[6-(2-fluorophenyl)pyridin-3-yl]-4-methoxybenzamide

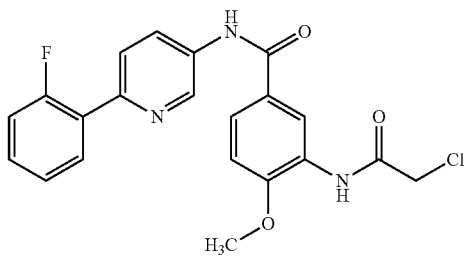 [SMILES: COc1ccc(C(=O)Nc2ccc(-c3ccccc3F)nc2)cc1NC(=O)CCl]

500 mg (1.48 mmol) of the compound from intermediate 7 were provided in 10 mL of toluene, 0.24 mL (2.96 mmol) of chloroacetyl chloride were added, and the mixture was stirred for 2 h at 100° C. After concentration, 593 mg of raw material were obtained, which were used without further purification.

LC-MS (Method 1): $R_t$=1.14 min; MS (ESIpos): m/z=414 [M+H]$^+$.

Intermediate 13

3-[(chloroacetyl)amino]-4-methoxy-N-(6-phenylpyridin-3-yl)benzamide

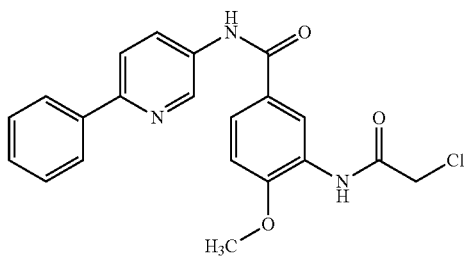 [SMILES: COc1ccc(C(=O)Nc2ccc(-c3ccccc3)nc2)cc1NC(=O)CCl]

To a solution of 3-amino-4-methoxy-N-(6-phenylpyridin-3-yl)benzamide (prepared in a manner analogous to that described in intermediate 8, 0.50 g, 1.57 mmol) and pyridine (0.27 mL, 3.29 mmol, 2.1 equiv) in CH$_2$Cl$_2$ (9 mL) at 0° C. was added chloroacetyl chloride (0.13 mL, 1.64 mmol, 1.05 equiv) dropwise. The resulting mixture was allowed to warm to room temperature and was stirred at that temperature for 5 h. The resulting material was concentrated under reduced pressure to give impure 3-[(chloroacetyl)amino]-4-methoxy-N-(6-phenylpyridin-3-yl)benzamide (0.75 g). This material was used in subsequent reactions without further purification.

Intermediate 14

3-[(chloroacetyl)amino]-N-[6-(2-fluorophenyl)pyridin-3-yl]-4-(trifluoromethoxy)benzamide

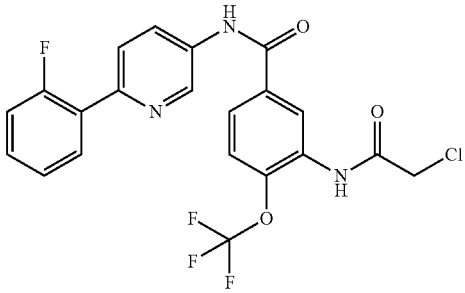 [SMILES: O=C(CCl)Nc1cc(C(=O)Nc2ccc(-c3ccccc3F)nc2)ccc1OC(F)(F)F]

To a solution of 3-amino-N-[6-(2-fluorophenyl)pyridin-3-yl]-4-(trifluoromethoxy)benzamide (prepared in a manner analogous to that described in intermediate 10, 1.08 g, 2.76 mmol) and pyridine (0.47 mL, 5.80 mmol, 2.1 equiv) in CH$_2$Cl$_2$ (20 mL) at 0° C. was added chloroacetyl chloride (0.23 mL, 2.90 mmol, 1.05 equiv) dropwise. The resulting mixture was allowed to warm to room temperature and was stirred at that temperature for 12 h. The resulting mixture was concentrated under reduced pressure to give impure 3-[(chloroacetyl)amino]-N-[6-(2-fluorophenyl)pyridin-3-yl]-4-(trifluoromethoxy)benzamide (1.75 g). This material was used in subsequent reactions without further purification.

LC-MS (Method 3): $R_t$=1.28 min; MS (ESIpos): m/z=468 ([M+H]$^+$, 30%), 935 ([2M+H]$^+$, 10%); MS (ESIneg): m/z=466 ([M−H]$^-$, 100%).

Intermediate 15

3-[(2-chloropropanoy)amino]-N-[6-(2-fluorophenyl)pyridin-3-yl]-4-(trifluoromethoxy)benzamide

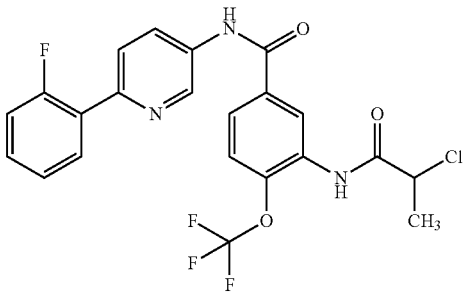 [SMILES: CC(Cl)C(=O)Nc1cc(C(=O)Nc2ccc(-c3ccccc3F)nc2)ccc1OC(F)(F)F]

To a solution of 3-amino-N-[6-(2-fluorophenyl)pyridin-3-yl]-4-(trifluoromethoxy)benzamide (prepared in a manner analogous to that described in intermediate 10, 0.50 g, 1.28 mmol) and pyridine (0.22 mL, 2.68 mmol, 2.1 equiv) in CH$_2$Cl$_2$ (7.5 mL) at 0° C. was added 2-chloropropanoyl chloride (0.13 mL, 1.34 mmol, 1.05 equiv) dropwise. The resulting mixture was allowed to warm to room temperature and was stirred at that temperature for 12 h. The resulting mixture was concentrated under reduced pressure to give impure 3-[(2-chloropropanoy)amino]-N-[6-(2-fluorophenyl)pyridin-3-yl]-4-(trifluoromethoxy)benzamide (0.62 g). This material was used in subsequent reactions without further purification.

LC-MS (Method 3): $R_t$=1.34 min; MS (ESIpos): m/z=443 ([M+H]$^+$, 20%); MS (ESIneg): m/z=480 ([M−H]$^−$, 100%).

Intermediate 16

3-[(2-chloropropanoy)amino]-N-(6-phenylpyridin-3-yl)-4-(trifluoromethoxy)benzamide

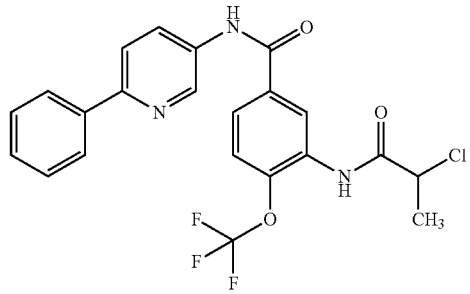 [SMILES: CC(Cl)C(=O)Nc1cc(C(=O)Nc2ccc(-c3ccccc3)nc2)ccc1OC(F)(F)F]

To a solution of 3-amino-N-(6-phenylpyridin-3-yl)-4-(trifluoromethoxy)benzamide (prepared in a manner analogous to that described in intermediate 11, 535 mg, 1.43 mmol) and pyridine (0.24 mL, 3.01 mmol, 2.1 equiv) in CH$_2$Cl$_2$ (8.4 mL) at 0° C. was added 2-chloropropanoyl chloride (0.15 mL, 1.51 mmol, 1.05 equiv) dropwise. The resulting mixture was allowed to warm to room temperature and was stirred at that temperature for 12 h. The resulting mixture was concentrated under reduced pressure to give impure 3-[(2-chloropropanoyl)amino]-N-(6-phenylpyridin-3-yl)-4-(trifluoromethoxy)benzamide (0.81 g). This material was used in subsequent reactions without further purification.

LC-MS (Method 1): $R_t$=1.33 min; MS (ESIpos): m/z=464 ([M+H]$^+$, 100%), 927 ([2M+H]$^+$, 10%); MS (ESIneg): m/z=462 ([M−H]$^−$, 100%).

Intermediate 17

3-[(2-bromo-2-methylpropanoyl)amino]-N-[6-(2-fluorophenyl)pyridin-3-yl]-4-(trifluoromethoxy)benzamide

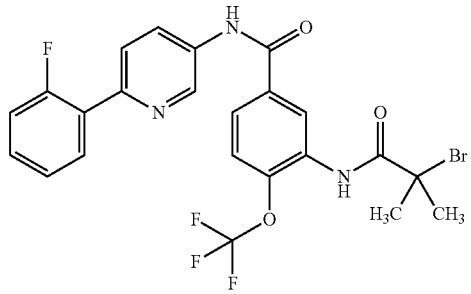 [SMILES: CC(C)(Br)C(=O)Nc1cc(C(=O)Nc2ccc(-c3ccccc3F)nc2)ccc1OC(F)(F)F]

500 mg (1.28 mmol) of the compound from intermediate 10 and 114 μL (1.41 mmol) of pyridine were provided in 5 mL of dichloromethane. 308 mg (1.34 mmol) of 2-bromo-2-methylpropanoyl bromide were added at 0° C., and the mixture was stirred at room temperature over night. Water was added, and the phases were separated. The aqueous phase was extracted twice with dichloromethane, and the combined organic phases were washed with brine, dried over sodium sulfate, filtered and concentrated. 720 mg of the title compound were obtained, which were used without further purification.

LC-MS (Method 4): $R_t$=1.44 min; MS (ESIpos): m/z=540 [M+H]$^+$.

Intermediate 18

3-[(chloroacetyl)amino]-4-(trifluoromethyl)benzoic acid

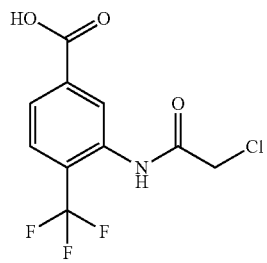 [SMILES: O=C(CCl)Nc1cc(C(=O)O)ccc1C(F)(F)F]

To a solution of 3-amino-4-(trifluoromethyl)benzoic acid (2.50 g, 12.19 mmol) and pyridine (2.07 mL, 25.6 mmol, 2.1 equiv) in CH$_2$Cl$_2$ (50 mL) at 0° C. was added chloroacetyl chloride (1.02 mL, 12.80 mmol, 1.05 equiv) dropwise. The resulting mixture was allowed to warm to room temperature and was stirred at that temperature for 5 h. The resulting solution was treated with a CH$_2$Cl$_2$/isopropanol mixture (4:1, 50 mL). The resulting solution was washed with an aqueous 1N HCl solution (50 mL), dried (MgSO$_4$ anh), and concentrated under reduced pressure to give impure 3-[(chloroacetyl)amino]-4-(trifluoromethyl)benzoic acid (3.83 g). This material was used in subsequent reactions without further purification.

LC-MS (Method 3): $R_t$=0.89 min; MS (ESIpos): m/z=282 ([M+H]$^+$, 100%); MS (ESIneg): m/z=280 ([M−H]$^−$, 100%).

Intermediate 19

3-[(chloroacetyl)amino]-4-(trifluoromethoxy)benzoic acid

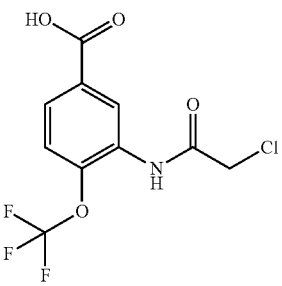 [SMILES: O=C(CCl)Nc1cc(C(=O)O)ccc1OC(F)(F)F]

To a solution of 3-amino-4-(trifluoromethoxy)benzoic acid (2.50 g, 11.3 mmol) and pyridine (1.92 mL, 23.7 mmol, 2.1 equiv) in CH$_2$Cl$_2$ (50 mL) at 0° C. was added chloroacetyl chloride (0.95 mL, 11.9 mmol, 1.05 equiv) dropwise. The resulting mixture was allowed to warm to room temperature and was stirred at that temperature for 5 h. The resulting solution was treated with a CH₂Cl₂/isopropanol mixture (4:1, 50 mL). The resulting solution was washed with an aqueous 1N HCl solution (50 mL), dried (MgSO₄ anh), and concentrated under reduced pressure to give impure 3-[(chloroacetyl)amino]-4-(trifluoromethyl)benzoic acid (3.52 g). This material was used in subsequent reactions without further purification.

¹H-NMR (300 MHz, DMSO-d₆): δ [ppm]=4.35 (s, 2H), 7.52 (ddm, J=1.5, 8.7 Hz, 1H), 7.80 (dd, J=2.1, 8.7 Hz, 1H), 8.47 (d, J=2.1 Hz, 1H), 10.17 (s, 1H), 13.28 (br s, 1H).

LC-MS (Method 3): R$_t$=0.95 min; MS (ESIpos): m/z=298 ([M+H]⁺, 100%); MS (ESIneg): m/z=296 ([M−H]⁻, 100%), 593 ([2M−H]⁻, 100%).

Intermediate 20

3-[(morpholin-4-ylacetyl)amino]-4-(trifluoromethyl)benzoic acid

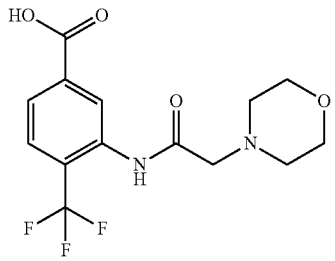

To a solution of 3-[(chloroacetyl)amino]-4-(trifluoromethyl)benzoic acid (prepared in a manner analogous to that described in intermediate 18, 3.52 g, 11.0 mmol) in DMF (50 mL) was added morpholine (2.0 mL, 23.1 mmol, 2.1 equiv), triethylamine (3.2 mL, 23.1 mmol, 2.1 equiv) and potassium iodide (0.28 g, 1.71 mmol, 0.16 equiv). The reaction mixture was stirred at room temperature for 16 h. The resulting mixture was diluted with water (75 mL). The aqueous solution was extracted with a CH₂Cl₂/isopropanol solution (4:1, 5×50 mL). The combined organic phases were washed with saturated brine (50 mL), dried (Na2SO₄ anh), and concentrated under reduced pressure to give impure 3-[(morpholin-4-ylacetyl)amino]-4-(trifluoromethyl)benzoic acid (2.38 g). This material was used in subsequent reactions without further purification.

LC-MS (Method 3): R$_t$=0.55 min; MS (ESIpos): m/z=333 ([M+H]⁺, 100%); MS (ESIneg): m/z=331 ([M−H]⁻, 100%).

Intermediate 21

3-[(morpholin-4-ylacetyl)amino]-4-(trifluoromethoxy)benzoic acid

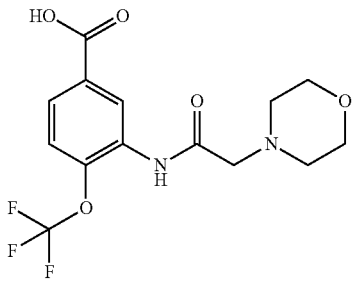 [SMILES: O=C(CN1CCOCC1)Nc1cc(C(=O)O)ccc1OC(F)(F)F]

To a solution of 3-[(chloroacetyl)amino]-4-(trifluoromethoxy)benzoic acid (prepared in a manner analogous to that described in intermediate 19, 3.52 g, 11.8 mmol) in DMF (50 mL) was added morpholine (2.2 mL, 24.8 mmol, 2.1 equiv), triethylamine (3.5 mL, 24.8 mmol, 2.1 equiv) and potassium iodide (0.30 g, 1.83 mmol, 0.16 equiv). The reaction mixture was stirred at room temperature for 16 h. The resulting mixture was diluted with water (75 mL). The aqueous solution was extracted with a CH₂Cl₂/isopropanol solution (4:1, 5×50 mL). The combined organic phases were washed with saturated brine (50 mL), dried (Na₂SO₄ anh), and concentrated under reduced pressure to give impure 3-[(morpholin-4-ylacetyl)amino]-4-(trifluoromethoxy)benzoic acid (2.87 g). This material was used in subsequent reactions without further purification.

¹H-NMR (300 MHz, DMSO-d₆): δ [ppm]=2.54-2.59 (m, 4H), 3.20 (s, 2H), 3.61-3.66 (m, 4H), 7.49-7.54 (m, 1H), 7.76 (dd, J=2.1, 8.6 Hz, 1H), 8.80 (d, J=2.1 Hz, 1H), 9.81 (s, 1H).

LC-MS (Method 3): R$_t$=0.58 min; MS (ESIpos): m/z=349 ([M+H]⁺, 100%); MS (ESIneg): m/z=347 ([M−H]⁻, 100%).

Intermediate 22

2-chloro-N-[5-nitro-2-(trifluoromethoxy)phenyl]acetamide

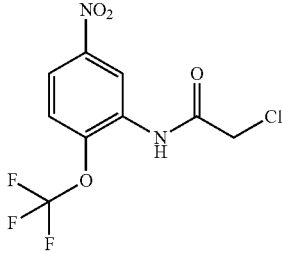 [SMILES: O=C(CCl)Nc1cc([N+](=O)[O-])ccc1OC(F)(F)F]

To a solution of 5-nitro-2-(trifluoromethoxy)aniline (17.3 g, 77.7 mmol) and pyridine (6.60 mL, 81.5 mmol, 1.05 equiv) in CH₂Cl₂ (250 mL) at 0° C. was added chloroacetyl chloride (6.50 mL, 81.5 mmol, 1.05 equiv) dropwise. The resulting mixture was warmed to room temperature and was stirred at that temperature for 12 h. The resulting mixture was diluted with CH₂Cl₂ (250 mL), washed with water (200 mL) followed by a saturated NaCl solution (250 mL), dried (MgSO₄ anh), and concentrated under reduced pressure to give impure 2-chloro-N-[5-nitro-2-(trifluoromethoxy)phenyl]acetamide (23.8 g). This material was used in subsequent reactions without further purification.

¹H-NMR (300 MHz, DMSO-d₆): δ [ppm]=4.40 (s, 2H), 7.69 (dd, J=1.7, 9.0 Hz, 1H), 8.09 (dd, J=3.0, 9.2 Hz, 1H), 8.88 (d, J=2.8 Hz, 1H), 10.41 (s, 1H).

LC-MS (Method 3): R$_t$=1.09 min; MS (ESIneg): m/z=297 ([M−H]⁻, 100%).

Intermediate 23

N-(2-tert-butyl-5-nitrophenyl)-2-chloroacetamide

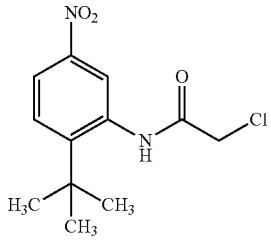 [SMILES: CC(C)(C)c1ccc([N+](=O)[O-])cc1NC(=O)CCl]

To a solution of 2-tert-butyl-5-nitroaniline (2.55 g, 13.1 mmol) and pyridine (2.20 mL, 27.6 mmol, 2.1 equiv) in CH$_2$Cl$_2$ (55 mL) at 0° C. was added chloroacetyl chloride (1.10 mL, 13.8 mmol, 1.05 equiv) dropwise. The resulting mixture was allowed to warm to room temperature and was stirred at that temperature for 12 h. The resulting solution was diluted with CH$_2$Cl$_2$ (50 mL), washed with water (50 mL), dried (Na2SO$_4$ anh), and concentrated under reduced pressure to afford impure N-(2-tert-butyl-5-nitrophenyl)-2-chloroacetamide (3.94 g). This material was used in subsequent reactions without further purification.

LC-MS (Method 3): R$_t$=1.16 min; MS (ESIpos): m/z=271 ([M+H]$^+$, 40%); MS (ESIneg): m/z=469 ([M−H]$^−$, 100%).

Intermediate 24

2-chloro-N-(2-chloro-5-nitrophenyl)acetamide

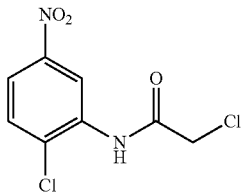 [SMILES: O=C(CCl)Nc1cc([N+](=O)[O-])ccc1Cl]

To a solution of 2-chloro-5-nitroaniline (3.00 g, 17.4 mmol) and pyridine (1.69 mL, 20.9 mmol, 1.2 equiv) in CH$_2$Cl$_2$ (60 mL) at 0° C. was added chloroacetyl chloride (1.66 mL, 20.9 mmol, 1.2 equiv) dropwise. The resulting mixture was allowed to warm to room temperature and was stirred at that temperature for 12 h. The resulting solution was diluted with CH$_2$Cl$_2$ (60 mL), washed with water (500 mL) followed by a saturated NaCl solution (50 mL), dried (MgSO$_4$ anh), and concentrated under reduced pressure to afford 2-chloro-N-(2-chloro-5-nitrophenyl)acetamide (4.4 g, 100%).

$^1$H-NMR (300 MHz, DMSO-d$_6$): δ [ppm]=4.42 (s, 2H), 7.80 (d J=8.8 Hz, 1H), 8.02 (dd, J=2.8, 8.8 Hz, 1H), 8.69 (d, J=2.5 Hz, 1H), 10.16 (s, 1H).

LC-MS (Method 3): R$_t$=0.97 min; MS (ESIneg): m/z=247 ([M−H]$^−$, 100%).

Intermediate 25

2-chloro-N-(2-methyl-5-nitrophenyl)acetamide

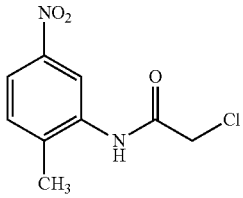

To a solution of 2-methyl-5-nitroaniline (2.00 g, 13.1 mmol) and pyridine (1.28 mL, 15.8 mmol, 1.2 equiv) in CH$_2$Cl$_2$ (30 mL) at 0° C. was added chloroacetyl chloride (1.1 mL, 13.8 mmol, 1.05 equiv) dropwise. The resulting mixture was warmed to room temperature, and was stirred at that temperature for 12 h. The resulting solution was diluted with CH$_2$Cl$_2$ (30 mL), washed with water (25 mL) followed by a saturated NaCl solution (25 mL), dried (MgSO$_4$ anh), and concentrated under reduced pressure to afford 2-chloro-N-(2-methyl-5-nitrophenyl)acetamide (2.2 g, 72%).

$^1$H-NMR (400 MHz, DMSO-d$_6$): δ [ppm]=2.32 (s, 3H), 4.35 (s, 2H), 7.50 (d, J=8.6 Hz, 1H), 7.94 (dd, J=2.5, 8.3 Hz, 1H), 8.39 (d, J=2.5 Hz, 1H), 9.87 (s, 1H).

LC-MS (Method 3): R$_t$=1.25 min; MS (ESIpos): m/z=229 ([M+H]$^+$, 70%); MS (ESIneg): m/z=227 ([M−H]$^−$, 100%).

Intermediate 26

2-chloro-N-(2-methoxy-5-nitrophenyl)acetamide

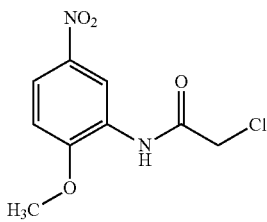 [SMILES: COc1ccc([N+](=O)[O-])cc1NC(=O)CCl]

To a solution of 2-methoxy-5-nitroaniline (10.00 g, 59.5 mmol) and pyridine (5.1 mL, 62.4 mmol, 1.05 equiv) in CH$_2$Cl$_2$ (175 mL) at 0° C. was added chloroacetyl chloride (4.97 mL, 62.4 mmol, 1.05 equiv) dropwise. The resulting mixture was warmed to room temperature, and was stirred at that temperature for 12 h. The resulting solution was concentrated under reduced pressure. The remaining solids were triturated with ethanol, filtered, washed with ethanol, followed by water, followed by ethanol, and dried at 50° C. under reduced pressure to give 2-chloro-N-(2-methoxy-5-nitrophenyl)acetamide (14.1 g, 97%).

$^1$H-NMR (400 MHz, DMSO-d$_6$): δ [ppm]=3.98 (s, 3H), 4.41 (s, 2H), 7.27 (d, J=9.1 Hz, 1H), 8.04 (dd, J=2.8, 9.1 Hz, 1H), 8.95 (d, J=2.8 Hz, 1H), 9.85 (s, 1H).

LC-MS (Method 3): R$_t$=0.95 min; MS (ESIpos): m/z=245 ([M+H]$^+$, 100%); MS (ESIneg): m/z=243 ([M−H]$^−$, 100%).

Intermediate 27

2-(morpholin-4-yl)-N-[5-nitro-2-(trifluoromethoxy)phenyl]acetamide

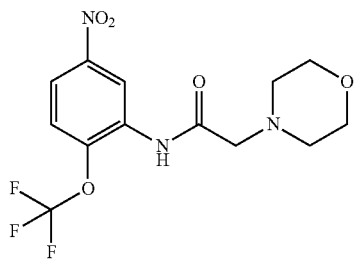 [SMILES: O=C(CN1CCOCC1)Nc1cc([N+](=O)[O-])ccc1OC(F)(F)F]

To a solution of 2-chloro-N-[5-nitro-2-(trifluoromethoxy)phenyl]acetamide (prepared in a manner analogous to that described in intermediate 22, 20.6 g, 69.0 mmol) in DMF (300 mL) was added morpholine (9.0 mL, 103.5 mmol, 1.5 equiv), triethylamine (14.4 mL, 103.5 mmol, 1.5 equiv) and potassium iodide (1.78 g, 10.7 mmol, 0.16 equiv). The reaction mixture was stirred at room temperature for 16 h. The resulting mixture was poured onto water (300 mL). The resulting mixture was extracted with ethyl acetate (3×100 mL). The combined organic phases were washed with half-saturated NaCl solution, dried (Na2SO4 anh) and concentrated under reduced pressure to give 2-(morpholin-4-yl)-N-[5-nitro-2-(trifluoromethoxy)phenyl]acetamide (20.0 g, 83%).

$^1$H-NMR (400 MHz, DMSO-$d_6$): δ [ppm]=2.53-2.56 (m, 4H), 3.22 (s, 2H), 3.59-3.62 (m, 4H), 7.72 (dq, J=1.7, 9.1 Hz, 1H), 8.05 (dd, J=2.8, 9.1 Hz, 1H), 9.11 (d, J=2.8 Hz, 1H), 10.05 (s, 1H).

LC-MS (Method 3): $R_t$=1.15 min; MS (ESIpos): m/z=350 ([M+H]$^+$, 100%); MS (ESIneg): m/z=348 ([M−H]$^−$, 100%).

Intermediate 28

N-(2-tert-butyl-5-nitrophenyl)-2-(morpholin-4-yl)acetamide

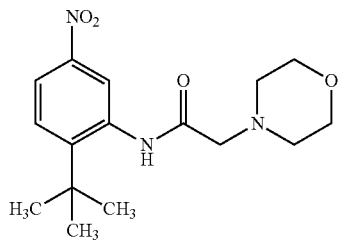

To a solution of N-(2-tert-butyl-5-nitrophenyl)-2-chloroacetamide (prepared in a manner analogous to that described in intermediate 23, 3.94 g, 14.6 mmol) in DMF (60 mL) was added morpholine (1.90 mL, 21.8 mmol, 1.5 equiv), triethylamine (3.04 mL, 21.8 mmol, 1.5 equiv) and potassium iodide (0.37 g, 2.56 mmol, 0.16 equiv). The reaction mixture was stirred at room temperature for 16 h. The resulting mixture was poured onto water (75 mL). The resulting mixture was extracted with ethyl acetate (3×50 mL). The combined organic phases were dried (Na2SO4 anh) and concentrated under reduced pressure to give N-(2-tert-butyl-5-nitrophenyl)-2-(morpholin-4-yl)acetamide (1.61 g, 34%).

$^1$H-NMR (400 MHz, DMSO-$d_6$): δ [ppm]=1.42 (s, 9H), 2.57-2.62 (m, 4H), 3.21 (s, 2H), 3.60-3.65 (m, 4H), 7.63 (d, J=9.0 Hz, 1H), 7.93 (dd, J=2.6, 8.9 Hz, 1H), 8.82 (d, J=2.5 Hz, 1H), 9.69 (s, 1H).

LC-MS (Method 3): $R_t$=1.19 min; MS (ESIpos): m/z=322 ([M+H]$^+$, 100%); MS (ESIneg): m/z=320 ([M−H]$^−$, 100%).

Intermediate 29

N-(2-chloro-5-nitrophenyl)-2-(morpholin-4-yl)acetamide

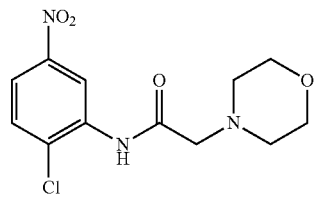 [SMILES: O=C(CN1CCOCC1)Nc1cc([N+](=O)[O-])ccc1Cl]

To a solution of 2-chloro-N-(2-chloro-5-nitrophenyl)acetamide (prepared in a manner analogous to that described in intermediate 24, 4.40 g, 17.7 mmol) in DMF (75 mL) was added morpholine (2.3 mL, 26.5 mmol, 1.5 equiv), triethylamine (3.7 mL, 26.5 mmol, 1.5 equiv) and potassium iodide (0.45 g, 2.74 mmol, 0.16 equiv). The reaction mixture was stirred at room temperature for 16 h. The resulting mixture was poured onto water (75 mL). The resulting precipitate was removed by filtration, washed with water followed by ethanol, and dried at 50° C. under reduced pressure to give N-(2-chloro-5-nitrophenyl)-2-(morpholin-4-yl)acetamide (4.8 g, 90%).

$^1$H-NMR (400 MHz, DMSO-$d_6$): δ [ppm]=2.54-2.58 (m, 4H), 3.22 (s, 2H), 3.63-3.66 (m, 4H), 7.82 (d, J=8.8 Hz, 1H), 7.96 (dd, J=2.8, 8.8 Hz, 1H), 9.11 (d, J=2.5 Hz, 1H), 10.17 (s, 1H).

LC-MS (Method 3): $R_t$=1.07 min; MS (ESIneg): m/z=298 ([M−H]$^−$, 100%).

Intermediate 30

N-(2-methyl-5-nitrophenyl)-2-(morpholin-4-yl)acetamide

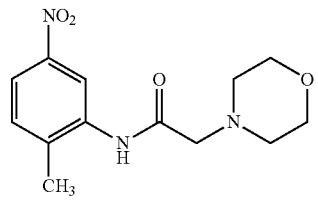 [SMILES: Cc1ccc([N+](=O)[O-])cc1NC(=O)CN1CCOCC1]

To a solution of 2-chloro-N-(2-methyl-5-nitrophenyl)acetamide (prepared in a manner analogous to that described in intermediate 25, 2.16 g, 9.5 mmol) in DMF (35 mL) was added morpholine (1.2 mL, 14.2 mmol, 1.5 equiv), triethylamine (2.0 mL, 14.2 mmol, 1.5 equiv) and potassium iodide (0.24 g, 1.46 mmol, 0.16 equiv). The reaction mixture was stirred at room temperature for 16 h. The resulting mixture was poured onto water (35 mL). The resulting precipitate was removed by filtration, washed with water followed by ethanol, and dried at 50° C. under reduced pressure to give N-(2-methyl-5-nitrophenyl)-2-(morpholin-4-yl)acetamide (2.1 g, 79%).

$^1$H-NMR (400 MHz, DMSO-d$_6$): δ [ppm]=2.34 (s, 3H), 2.53-2.56 (m, 4H), 3.17 (s, 2H), 3.61-3.65 (m, 4H), 7.50 (d, J=8.8 Hz, 1H), 7.90 (dd, J=2.5, 8.3 Hz, 1H), 8.71 (d, J=2.5 Hz, 1H), 9.65 (s, 1H).

LC-MS (Method 3): R$_t$=0.95 min; MS (ESIpos): m/z=280 ([M+H]$^+$, 50%); MS (ESIneg): m/z=278 ([M−H]$^−$, 100%).

Intermediate 31

N-(2-methoxy-5-nitrophenyl)-2-(morpholin-4-yl)acetamide

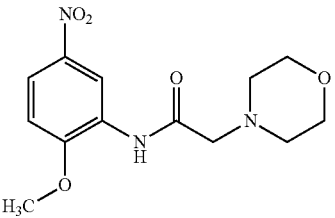

To a solution of 2-chloro-N-(2-methoxy-5-nitrophenyl)acetamide (prepared in a manner analogous to that described in intermediate 26, 14.1 g, 57.6 mmol) in DMF (250 mL) was added morpholine (7.5 mL, 66.5 mmol, 1.5 equiv), triethylamine (12.1 mL, 86.5 mmol, 1.5 equiv) and potassium iodide (1.48 g, 8.93 mmol, 0.16 equiv). The reaction mixture was stirred at room temperature for 16 h. The resulting mixture was poured onto water (250 mL). The resulting mixture was extracted with ethyl acetate (3×100 mL). The combined organic phases were washed with a half-saturated NaCl solution, dried (Na2SO$_4$ anh), and concentrated under reduced pressure. The resulting material was triturated with ethanol to give N-(2-methoxy-5-nitrophenyl)-2-(morpholin-4-yl)acetamide as a precipitate (15.5 g, 91%).

$^1$H-NMR (400 MHz, DMSO-d$_6$): δ [ppm]=2.51-2.54 (m, 4H), 3.17 (s, 2H), 3.61-3.64 (m, 4H), 4.02 (s, 3H), 7.26 (d, J=9.1 Hz, 1H), 8.00 (dd, J=2.8, 9.1 Hz, 1H), 9.08 (d, J=3.0 Hz, 1H), 9.89 (s, 1H).

LC-MS (Method 3): R$_t$=0.96 min; MS (ESIpos): m/z=296 ([M+H]$^+$, 70%); MS (ESIneg): m/z=294 ([M−H]$^−$, 100%).

Intermediate 32

N-[5-amino-2-(trifluoromethoxy)phenyl]-2-(morpholin-4-yl)acetamide

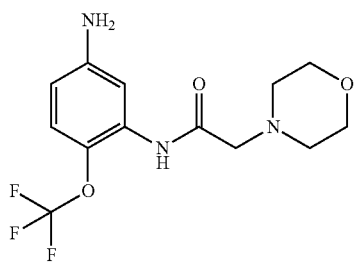 [SMILES: Nc1ccc(OC(F)(F)F)c(NC(=O)CN2CCOCC2)c1]

To a solution of 2-(morpholin-4-yl)-N-[5-nitro-2-(trifluoromethoxy)phenyl]acetamide (prepared in a manner analogous to that described in intermediate 27, 20.0 g, 57.1 mmol) in ethyl acetate (500 mL) was added 10% palladium on carbon (6.1 g, 5.72 mmol Pd, 10 mol % Pd). The resulting slurry was stirred under a hydrogen atmosphere for 3.25 h. The resulting slurry was filtered and concentrated under reduced pressure to afford N-[5-amino-2-(trifluoromethoxy)phenyl]-2-(morpholin-4-yl)acetamide (17.8 g, 98%).

$^1$H-NMR (400 MHz, DMSO-d$_6$): δ [ppm]=2.49-2.52 (m, 4H), 3.10 (s, 2H), 3.57-3.60 (m, 4H), 5.37 (s, 2H), 6.26 (dd, J=2.5, 8.8 Hz, 1H), 6.99 (dd, J=1.3, 8.8 Hz, 1H), 7.51 (d, J=2.5 Hz, 1H), 9.50 (s, 1H).

LC-MS (Method 4): R$_t$=0.99 min; MS (ESIpos): m/z=320 ([M+H]$^+$, 90%); MS (ESIneg): m/z=318 ([M−H]$^−$, 100%).

Intermediate 33

N-(5-amino-2-tert-butylphenyl)-2-(morpholin-4-yl)acetamide

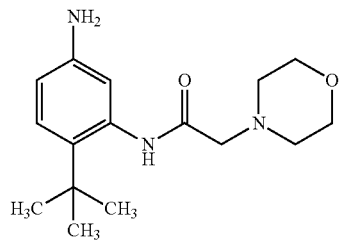 [SMILES: CC(C)(C)c1ccc(N)cc1NC(=O)CN1CCOCC1]

To a solution of N-(2-tert-butyl-5-nitrophenyl)-2-(morpholin-4-yl)acetamide (prepared in a manner analogous to that described in intermediate 28, 1.61 g, 5.01 mmol) in ethyl acetate (50 mL) was added 10% palladium on carbon (0.53 g, 0.50 mmol Pd, 10 mol % Pd). The resulting slurry was stirred under a hydrogen atmosphere for 4 h. The resulting slurry was filtered and concentrated under reduced pressure to afford N-(5-amino-2-tert-butylphenyl)-2-(morpholin-4-yl)acetamide (0.39 g, 27%).

$^1$H-NMR (400 MHz, DMSO-d$_6$): δ [ppm]=1.28 (s, 9H), 2.52-2.56 (m, 4H), 3.07 (s, 2H), 3.58-3.63 (m, 4H), 4.89 (s, 2H), 6.27 (dd, J=2.5, 8.5 Hz, 1H), 6.95 (d, J=8.5 Hz, 1H), 7.02 (d, J=2.5 Hz, 1H), 9.18 (s, 1H).

LC-MS (Method 4): R$_t$=0.98 min; MS (ESIpos): m/z=292 ([M+H]$^+$, 100%), 583 ([2M+H]$^+$, 10%); MS (ESIneg): m/z=290 ([M−H]$^−$, 100%).

Intermediate 34

N-(5-amino-2-chlorophenyl)-2-(morpholin-4-yl)acetamide

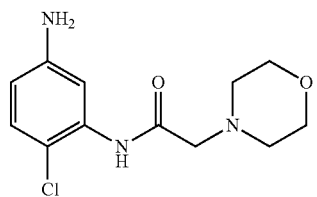 [SMILES: Nc1ccc(Cl)c(NC(=O)CN2CCOCC2)c1]

To a solution of N-(2-chloro-5-nitrophenyl)-2-(morpholin-4-yl)acetamide (prepared in a manner analogous to that described in intermediate 29, 1.00 g, 3.33 mmol) in methanol (10 mL) at 0° C. was added tin(II) chloride dihydrate (3.76 g, 16.7 mmol, 5.0 equiv). The resulting mixture was heated at the reflux temperature for 16 h, was then cooled to room temperature. The resulting mixture was treated with ethanol (20 mL). The resulting precipitate was removed with filtration, washed with a saturated $Na_2CO_3$ solution, followed by water, followed by ethanol, then dried at 50° C. under reduced pressure to give N-(5-amino-2-chlorophenyl)-2-(morpholin-4-yl)acetamide (0.45 g, 50%).

LC-MS (Method 4): $R_t$=0.87 min; MS (ESIpos): m/z=270 ([M+H]$^+$, 100%); MS (ESIneg): m/z=268 ([M−H]$^−$, 60%).

Intermediate 35

N-(5-amino-2-methylphenyl)-2-(morpholin-4-yl)acetamide

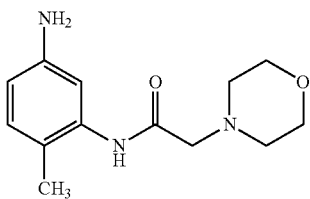

To a solution of N-(2-methyl-5-nitrophenyl)-2-(morpholin-4-yl)acetamide (prepared in a manner analogous to that described in intermediate 30, 2.09 g, 7.47 mmol) in ethyl acetate (80 mL) was added 10% palladium on carbon (0.80 g, 0.75 mmol Pd, 10 mol % Pd). The resulting slurry was stirred under a hydrogen atmosphere for 1.5 h. The resulting slurry was filtered and concentrated under reduced pressure to afford N-(5-amino-2-methylphenyl)-2-(morpholin-4-yl)acetamide (1.80 g, 97%).

$^1$H-NMR (400 MHz, DMSO-d$_6$): δ [ppm]=2.06 (s, 3H), 2.52-2.55 (m, 4H), 3.08 (s, 2H), 3.62-3.65 (m, 4H), 4.86 (s, 2H), 6.25 (dd, J=2.2, 7.9 Hz, 1H), 6.82 (d, J=8.2 Hz, 1H), 7.14 (d, J=2.2 Hz, 1H), 9.16 (s, 1H).

Intermediate 36

N-(5-amino-2-methoxyphenyl)-2-(morpholin-4-yl)acetamide

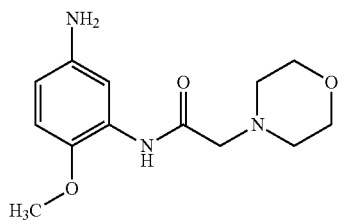

To a solution of N-(2-methoxy-5-nitrophenyl)-2-(morpholin-4-yl)acetamide (prepared in a manner analogous to that described in intermediate 31, 15.5 g, 52.5 mmol) in ethyl acetate (500 mL) was added 10% palladium on carbon (5.59 g, 5.25 mmol Pd, 10 mol % Pd). The resulting slurry was stirred under a hydrogen atmosphere for 2 h. The resulting slurry was filtered and concentrated under reduced pressure to afford N-(5-amino-2-methoxyphenyl)-2-(morpholin-4-yl)acetamide (12.2 g, 88%).

$^1$H-NMR (400 MHz, DMSO-d$_6$): δ [ppm]=3.05 (s, 2H), 3.59-3.63 (m, 4H), 3.70 (s, 3H), 4.68 (s, 2H), 6.19 (dd, J=2.6, 8.7 Hz, 1H), 6.71 (d, J=8.5 Hz, 1H), 7.54 (d, J=2.8 Hz, 1H), 9.56 (s, 1H), protons at 2.48-2.50 ppm partially obscured by solvent.

LC-MS (Method 4): $R_t$=0.74 min; MS (ESIpos): m/z=266 ([M+H]$^+$, 100%); MS (ESIneg): m/z=264 ([M−H]$^−$, 90%).

Intermediate 37

6-chloro-N-{3-[(morpholin-4-ylacetyl)amino]-4-(trifluoromethoxy)phenyl}nicotinamide

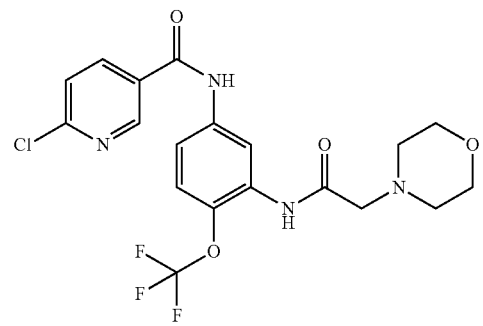 [SMILES: O=C(CN1CCOCC1)Nc1cc(NC(=O)c2ccc(Cl)nc2)ccc1OC(F)(F)F]

To a solution of N-[5-amino-2-(trifluoromethoxy)phenyl]-2-(morpholin-4-yl)acetamide (prepared in a manner analogous to that described in intermediate 32, 1.92 g, 6.00 mmol) and 6-chloronicotinic acid (1.23 g, 7.80 mmol, 1.3 equiv) in DMF (57.5 mL) was added (benzotriazol-1-yloxy)tripyrrolidinophosphonium hexafluorophosphate (PYBOP, 4.06 g, 7.80 mmol, 1.30 equiv) followed by diisopropylethylamine (3.13 mL, 18.0 mmol, 3.00 equiv). The resulting mixture was stirred at room temperature for 24 h, was then treated with water (50 mL). The aqueous mixture was extracted with ethyl acetate (100 mL). The organic phase was dried (Na2SO$_4$ anh) and concentrated under reduced pressure. The remaining material was purified using MPLC (hexane/ethyl acetate 1:1) to give impure 6-chloro-N-{3-[(morpholin-4-ylacetyl)amino]-4-(trifluoromethoxy)phenyl}nicotinamide (1.84 g). This material was used in subsequent reactions without further purification.

LC-MS (Method 3): $R_t$=1.19 min; MS (ESIpos): m/z=459 ([M+H]$^+$, 30%); MS (ESIneg): m/z=457 ([M−H]$^−$, 100%).

Intermediate 38

6-chloro-N-{4-methoxy-3-[(morpholin-4-ylacetyl)amino]phenyl}nicotinamide

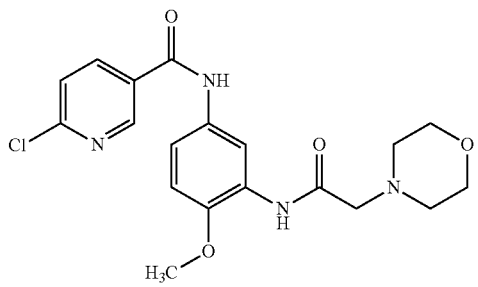 [SMILES: COc1ccc(NC(=O)c2ccc(Cl)nc2)cc1NC(=O)CN1CCOCC1]

To a solution of N-(5-amino-2-methoxyphenyl)-2-(morpholin-4-yl)acetamide (prepared in a manner analogous to that described in intermediate 36, 1.00 g, 3.77 mmol) and 6-chloronicotinic acid (0.77 g, 4.90 mmol, 1.3 equiv) in DMF (30 mL) was added propanephosphonic acid cyclic anhydride solution (50% in ethyl acetate, 2.86 mL, 4.90 mmol, 1.30 equiv) followed by diisopropylethylamine (1.97 mL, 11.3 mmol, 3.0 equiv). The resulting mixture was stirred at room temperature for 24 h, was then treated with water (50 mL). The resulting mixture was extracted with ethyl acetate (50 mL). The organic phase was dried (Na2SO4 anh), and concentrated under reduced pressure. The residue was crystalized from ethanol to give 6-chloro-N-{4-methoxy-3-[(morpholin-4-ylacetyl)amino]phenyl}nicotinamide (1.13 g, 74%).

$^1$H-NMR (400 MHz, DMSO-d$_6$): δ [ppm]=2.49-2.54 (m, 4H), 3.12 (s, 2H), 3.61-3.65 (m, 4H), 3.86 (s, 3H), 7.03 (d, J=8.9 Hz, 1H), 7.55 (dd, J=2.5, 8.9 Hz, 1H), 7.65 (d, J=8.3 Hz, 1H), 8.31 (dd, J=2.6, 8.3 Hz, 1H), 8.51 (d, J=2.6 Hz, 1H), 8.90 (d, J=2.3 Hz, 1H), 9.73 (s, 1H), 10.41 (s, 1H).

LC-MS (Method 3): R$_t$=0.98 min; MS (ESIpos): m/z=405 ([M+H]$^+$, 100%), 809 ([2M+H]$^+$, 40%); MS (ESIneg): m/z=403 ([M-H]$^-$, 100%), 807 ([2M-H]$^-$, 10%).

Intermediate 39

5-bromo-N-{4-methoxy-3-[(morpholin-4-ylacetyl)amino]phenyl}thiophene-2-carboxamide

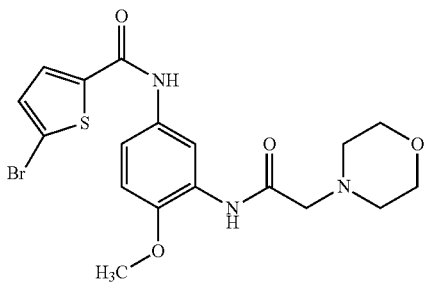 [SMILES: COc1ccc(NC(=O)c2ccc(Br)s2)cc1NC(=O)CN1CCOCC1]

To a solution of N-(5-amino-2-methoxyphenyl)-2-(morpholin-4-yl)acetamide (prepared in a manner analogous to that described in intermediate 36, 0.75 g, 2.83 mmol) and 5-bromothiophene-2-carboxylic acid (0.77 g, 4.90 mmol, 1.3 equiv) in DMF (30 mL) was added propanephosphonic acid cyclic anhydride solution (50% in ethyl acetate, 1.98 mL, 3.39 mmol, 1.2 equiv) followed by diisopropylethylamine (1.48 mL, 8.48 mmol, 3.0 equiv). The resulting mixture was stirred at room temperature for 24 h, was then treated with water (50 mL). The resulting mixture was extracted with ethyl acetate (50 mL). The organic phase was dried (Na2SO4 anh), and concentrated under reduced pressure. The residue was crystalized from ethanol to give 5-bromo-N-{4-methoxy-3-[(morpholin-4-ylacetyl)amino]phenyl}thiophene-2-carboxamide (0.48 g, 35%).

$^1$H-NMR (400 MHz, DMSO-d$_6$): δ [ppm]=2.50-2.53 (m, 4H), 3.12 (s, 2H), 3.61-3.65 (m, 4H), 3.85 (s, 3H), 7.01 (d, J=9.1 Hz, 1H), 7.31 (d, J=4.0 Hz, 1H), 7.49 (dd, J=2.8, 8.8 Hz, 1H), 7.83 (d, J=4.0 Hz, 1H), 8.44 (d, J=2.5 Hz, 1H), 9.71 (s, 1H), 10.21 (s, 1H).

LC-MS (Method 3): R$_t$=1.16 min; MS (ESIpos): m/z=454 ([M+H]$^+$, 90%); MS (ESIneg): m/z=452 ([M-H]$^-$, 70%).

Intermediate 40

3-amino-N-(5-phenyl-1,3,4-thiadiazol-2-yl)-4-(trifluoromethoxy)benzamide

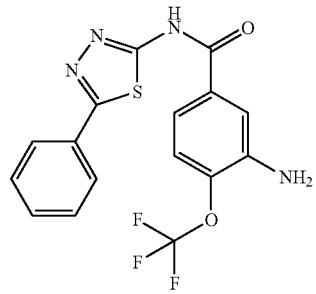 [SMILES: Nc1cc(C(=O)Nc2nnc(-c3ccccc3)s2)ccc1OC(F)(F)F]

To a solution of 3-amino-4-(trifluoromethoxy)benzoic acid (known from WO2007/31791, 20.0 g, 90.4 mmol) and 5-phenyl-1,3,4-thiadiazol-2-amine (20.8 g, 118 mmol, 1.3 equiv) in DMF (200 mL) was added (benzotriazol-1-yloxy)tripyrrolidinophosphonium hexafluorophosphate (PYBOP, 70.6 g, 136 mmol, 1.5 equiv) and diisopropylethylamine (47.3 mL, 271 mmol, 3.0 equiv). The resulting mixture was stirred at room temperature over night, was then treated with (benzotriazol-1-yloxy)tripyrrolidinophosphonium hexafluorophosphate (PYBOP, 70.6 g, 136 mmol, 1.5 equiv) and diisopropylethylamine (47.3 mL, 271 mmol, 3.0 equiv). The resulting mixture was stirred at room temperature over night. The resulting mixture was concentrated under reduced pressure, was then triturated with dichloromethane and was concentrated under reduced pressure. The remaining solids were then triturated with a mixture of water (200 mL) and ethanol (600 mL), and the resulting mixture was stirred for 30 minutes. The remaining solids were removed by filtration, washed with ethanol, and were dried at 50° C. under reduced pressure to give the title compound (29.4 g, 84%).

$^1$H-NMR (300 MHz, DMSO-d$_6$): δ [ppm]=5.75 (s, 2H), 7.27 (dd, 1H), 7.35 (dd, 1H), 7.50-7.59 (m, 4H), 7.94-8.02 (m, 2H), 13.09 (s, 1H).

LC-MS (Method 1): R$_t$=1.24 min; MS (ESIpos): m/z=381 [M+H]$^+$.

Intermediate 41

3-[(chloroacetyl)amino]-N-(5-phenyl-1,3,4-thiadiazol-2-yl)-4-(trifluoromethoxy)benzamide

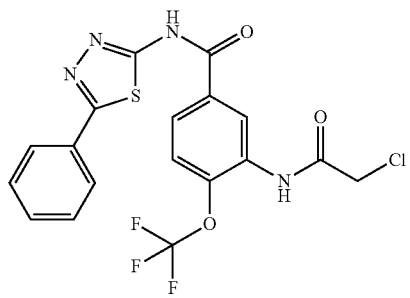 [SMILES: O=C(CCl)Nc1cc(C(=O)Nc2nnc(-c3ccccc3)s2)ccc1OC(F)(F)F]

12.9 g (33.9 mmol) of the compound from intermediate 40 were provided in 430 mL of toluene, 4.05 mL (50.9 mmol) of chloroacetyl chloride were added, another 100 mL of toluene were added, and the mixture was stirred for 2 h at 100° C. After concentration, 15.5 g of raw material were obtained, which were used without further purification.

$^1$H-NMR (400 MHz, DMSO-d$_6$): δ [ppm]=4.41 (s, 2H), 7.53-7.59 (m, 3H), 7.64 (dd, 1H), 7.96-8.02 (m, 2H), 8.08 (dd, 1H), 8.68 (d, 1H), 10.26 (s, 1H), 13.35 (s, 1H).

LC-MS (Method 4): R$_t$=1.26 min; MS (ESIpos): m/z=457 [M+H]$^+$.

Intermediate 42

1-(4-methylpiperazin-1-yl)cyclopropanecarboxylic acid hydrochloride (1:1)

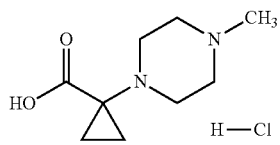

The title compound was prepared according to the following scheme by methods which are known to the person skilled in the art:

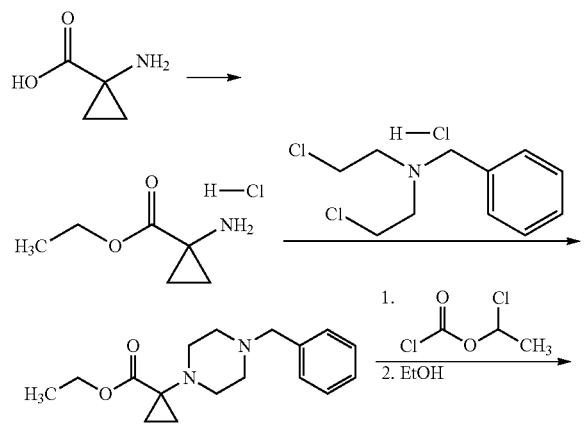

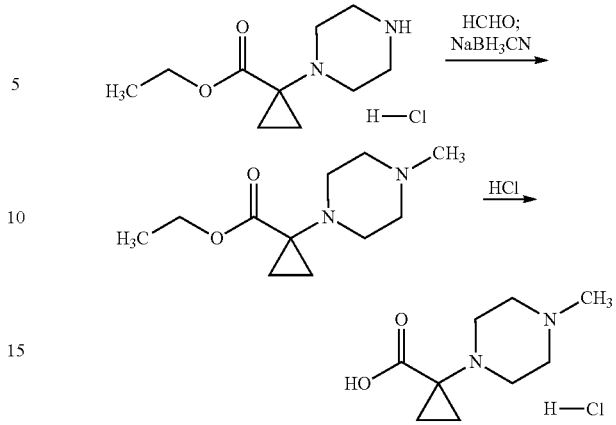

LC-MS Methods for Intermediates 42 and 43:

MS instrument type: Agilent 1956A; HPLC instrument type: Agilent 1200 Series; UV DAD; column: Agilent TC-C18, 2.1×50 mm, 5 μm; mobile phase A: 0.0375% TFA in water, mobile phase B: 0.0188% TFA in acetonitrile; gradient: 0.0 min 100% A->1.0 min 100% A->3.4 min 20% A->3.9 min 0% A->3.91 min 100% A->4.0 min 100% A->4.5 min 100% A; flow rate: 0.0 min 0.6 ml/min->1.0 min/3.4 min/3.9 min/3.91 min 0.6 ml/min->4.0 min/4.5 min 1.0 ml/min; column temp: 40° C.; UV detection: 220 nm.

Step 1 ethyl 1-aminocyclopropanecarboxylate hydrochloride (1:1)

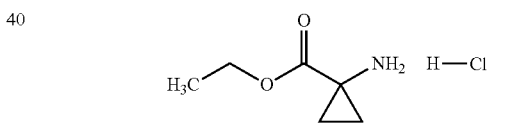

Thionyl chloride (150 mL, 2.056 mol) was added slowly below 0° C. to a suspension of 1-aminocyclopropanecarboxylic acid (100 g, 0.989 mol) in anhydrous ethanol (1 L). The mixture was stirred at 70° C. for 20 h. TLC (methanol, R$_f$=0.4) showed that most of the starting material was consumed. Then the solution was concentrated to give 210 g of crude product. The residue was dissolved in water and adjusted to a pH between 9 and 10 with potassium carbonate. The aqueous layer was extracted with dichloromethane (1 L×3). The combined organic layers were concentrated to dryness. The residue was dissolved in ethyl acetate (300 mL) and hydrochloride in ethyl acetate (250 mL, 4M) was added slowly to the solution below −30° C. It was stirred for 30 min at 0° C. A solid precipitated and it was filtered under nitrogen atmosphere to give ethyl 1-aminocyclopropanecarboxylate hydrochloride (132 g, 80.6% yield) as a white solid.

The following $^1$H-NMR is from the free amine.

$^1$H-NMR (400 MHz, chloroform-d$_1$): δ [ppm]=0.91-1.02 (m, 2H), 1.15-1.30 (m, 5H), 2.17 (s, 2H), 4.10 (d, 2H).

Step 2 ethyl 1-(4-benzylpiperazin-1-yl)cyclopropanecarboxylate

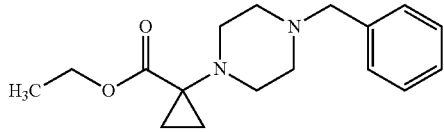 [SMILES: CCOC(=O)C1(N2CCN(Cc3ccccc3)CC2)CC1]

A mixture of ethyl 1-aminocyclopropanecarboxylate hydrochloride (120 g, 0.725 mol), N,N-diisopropylethylamine (942 g, 7.29 mol), N-benzyl-2-chloro-N-(2-chloroethyl)ethanamine hydrochloride (213 g, 0.793 mol) in anhydrous ethanol (1.6 L) was stirred under reflux for 16 h. TLC (PE:EtOAc=5:1, $R_f$=0.4) showed that most of the starting material was consumed. Then the mixture was concentrated. The residue was partitioned between dichloromethane (1 L) and water (0.5 L). The layers were separated and the aqueous layer was extracted with dichloromethane (0.5 L×2). The combined organic layers were concentrated. The residue was purified by chromatography on silica gel (PE:EtOAc=20:1 to 10:1) to give ethyl 1-(4-benzylpiperazin-1-yl)cyclopropanecarboxylate (100 g, 47.8%) as a light yellow oil.

$^1$H-NMR (400 MHz, chloroform-$d_1$): δ [ppm]=0.88-0.97 (m, 2H), 1.23-1.36 (m, 5H), 2.37 (br. S, 4H), 2.98 (br. S, 4H), 3.51 (s, 2H), 4.15 (q, 2H), 7.23-7.36 (m, 5H).

Step 3 ethyl 1-(piperazin-1-yl)cyclopropanecarboxylate hydrochloride (1:1)

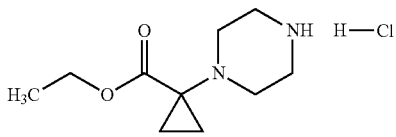

To a solution of ethyl 1-(4-benzylpiperazin-1-yl)cyclopropanecarboxylate (83 g, 0.288 mol) in anhydrous dichloromethane (700 mL) 1-chloroethyl carbonochloridate (60.4 g, 0.422 mol) was slowly added below 0° C. After the addition, the mixture was stirred at 18° C. for 1 h. TLC (PE:EtOAc=4:1, $R_f$=0.85) showed that the reaction was complete. Then it was concentrated to dryness. The residue was dissolved in ethanol (700 mL). It was stirred under reflux for 16 h. TLC (PE:EtOAc=4:1, $R_f$=0) showed the reaction was complete. Then it was concentrated to dryness. The residue was stirred with ethanol:methyl-tert-butylether=5:1 to give ethyl 1-(piperazin-1-yl)cyclopropanecarboxylate hydrochloride (1:1) (62 g, 92%) as a white solid.

$^1$H-NMR (400 MHz, methanol-$d_4$): δ [ppm]=1.27 (t, 3H), 1.50-1.65 (m, 4H), 3.50 (mc, 4H), 3.65-3.85 (m, 4H), 4.21 (q, 2H).

Step 4 ethyl 1-(4-methylpiperazin-1-yl)cyclopropanecarboxylate

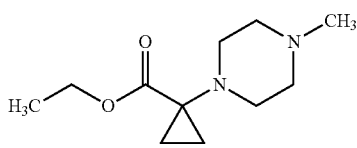

To a solution of ethyl 1-(piperazin-1-yl)cyclopropanecarboxylate hydrochloride (25 g, 0.107 mol) in water (250 mL) was added solid sodium hydrogen carbonate (10 g, 0.119 mol) so that a pH of 7-8 was reached. Then formaldehyde (13.5 g, 0.166 mol, 37% in water) and sodium cyanoborohydride (17.3 g, 0.275 mol) were added below 10° C. The mixture was stirred 18 h at 18° C. TLC (PE:EtOAc=1:1, $R_f$=0.1) showed that most of the starting material was consumed. Then it was extracted with DCM (50 mL×3). The combined organic phases were concentrated to dryness. The residue was purified by chromatography on silica gel (PE:EtOAc=3:1 to dichloromwthane:methanol=15:1) to give ethyl 1-(4-methylpiperazin-1-yl)cyclopropanecarboxylate (12 g, 53%).

$^1$H-NMR (400 MHz, methanol-$d_4$): δ [ppm]=0.98-1.04 (m, 2H), 1.24 (t, 3H), 1.26-1.31 (m, 2H), 2.70 (s, 3H), 2.97 (mc, 4H), 3.20 (mc, 4H), 4.11 (q, 2H).

Step 5

1-(4-methylpiperazin-1-yl)cyclopropanecarboxylic acid hydrochloride (1:1)

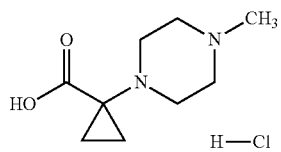

To a round bottom flask containing ethyl 1-(4-methylpiperazin-1-yl)cyclopropanecarboxylate (14 g, 65.9 mmol) was added aqueous hydrochloric acid (6M, 100 mL) slowly below 20° C. After the addition, the mixture was stirred at 100-140° C. for 24 h. TLC (dichloromethane:methanol=8:1, $R_f$=0.0) showed that the reaction was complete. Then the reaction mixture was concentrated to dryness. The residue was stirred in ethanol and the solid was filtered off to give 1-(4-methylpiperazin-1-yl)cyclopropanecarboxylic acid hydrochloride (1:1) (6.4 g, 44%) as a white solid.

$^1$H-NMR (400 MHz, water-$d_2$): δ [ppm]=1.27-1.37 (m, 2H), 1.45-1.56 (m, 2H), 2.88 (d, 3H), 3.08-3.23 (m, 2H), 3.45-3.53 (m, 2H), 3.55-3.68 (m, 2H), 3.72-3.87 (m, 2H).

ELSD: M/Z=211.1 (M+H$^+$).

Intermediate 43

1-(4-cyclopropylpiperazin-1-yl)cyclopropanecarboxylic acid hydrochloride (1:1)

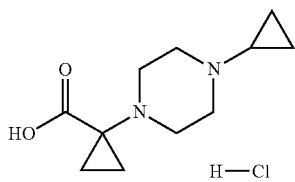

Step 1 ethyl 1-(4-cyclopropylpiperazin-1-yl)cyclopropanecarboxylate

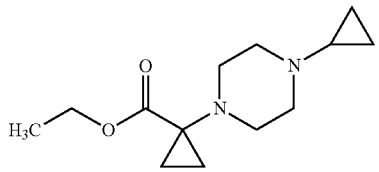 [SMILES: CCOC(=O)C1(N2CCN(C3CC3)CC2)CC1]

To a solution of ethyl 1-(piperazin-1-yl)cyclopropanecarboxylate hydrochloride (12.8 g, 54.5 mmol) in a mixture of anhydrous THF (68 mL) and methanol (68 mL) (1-ethoxycyclopropoxy)trimethylsilane (21.9 ml, 108.9 mmol) and acetic acid (10 mL) were added. Then sodium cyanoborohydride (5.14 g, 81.8 mmol) was added in portions. After the addition, the mixture was stirred at 60° C. for 16 h. TLC (dichloromethane:methanol=4:1, $R_f$=0.9) showed that the reaction was complete. It was cooled to 18° C. and quenched with water (5 mL). It was concentrated to dryness and the residue was partitioned between dichloromethane (100 mL) and aqueous saturated sodium hydrogen carbonate (20 mL). The layers were separated and the aqueous layer was extracted with dichloromethane (100 mL). The combined organic layers were washed with water (15 mL) and concentrated to dryness. The residue was purified by column chromatography on silica gel (PE:EtOAc=20:1 to 8:1) to give ethyl 1-(4-cyclopropylpiperazin-1-yl)cyclopropanecarboxylate (12 g, 92%) as a light yellow oil.

$^1$H-NMR (400 MHz, methanol-$d_4$): δ [ppm]=0.40-0.45 (m, 4H), 0.91-0.97 (m, 2H), 1.19-1.28 (m, 5H), 1.58-1.66 (m, 1H), 2.40-2.70 (m, 4H), 2.87-3.09 (m, 4H), 4.10 (q, 2H).

Step 2

1-(4-cyclopropylpiperazin-1-yl)cyclopropanecarboxylic acid hydrochloride (1:1)

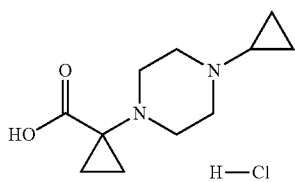

To a rond bottom flask containing ethyl 1-(piperazin-1-yl)cyclopropanecarboxylate (12 g, 50.4 mmol) was added aqueous hydrochloric acid (6M, 100 mL) below 0° C. After the addition, the mixture was stirred at 100° C. for 16 h. TLC (dichloromethane:methanol=10:1, $R_f$=0.4) showed that the reaction was complete. Then the reaction mixture was concentrated under reduced pressure and the residue was stirred in ethanol (40 mL). The solid was filtered off to give 1-(4-cyclopropylpiperazin-1-yl)cyclopropanecarboxylic acid hydrochloride (1:1) (10.2 g, 82%) as a white solid.

$^1$H-NMR (400 MHz, water-$d_2$): δ [ppm]=0.87-0.98 (m, 4H), 1.25-1.33 (m, 2H), 1.45-1.53 (m, 2H), 2.77-2.85 (m, 1H), 3.28-3.78 (m, 8H).

ELSD: M/Z=211.1 (M+H$^+$).

Intermediate 44

1-(morpholin-4-yl)cyclopropanecarboxylic acid hydrochloride (1:1)

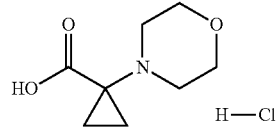

The title compound is known from WO2010/136778.

Intermediate 45

3-({[1-(morpholin-4-yl)cyclopropyl]carbonyl}amino)-4-(trifluoromethoxy)benzoic acid

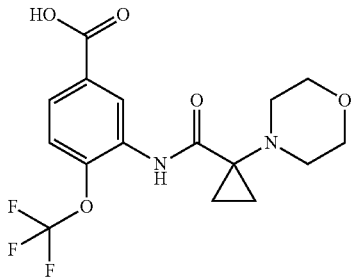 [SMILES: O=C(O)c1ccc(OC(F)(F)F)c(NC(=O)C2(N3CCOCC3)CC2)c1]

1.88 g (9.04 mmol, 2 equiv) of the compound of intermediate 44 were stirred in 10 mL of dichloromethane at room temperature. 0.7 mL (9.04 mmol, 2 equiv) of DMF and 0.79 mL (9.04 mmol, 2 equiv) of oxalyl chloride were added and the mixture was stirred for additional 0.5 h at room temperature. 2.49 mL (22.6 mmol, 5 equiv) of 4-methylmorpholine and 1.00 g (4.52 mmol) of 3-amino-4-(trifluoromethoxy)benzoic acid (known from WO2007/31791) were added and the mixture was stirred for additional 36 h at room temperature. The reaction mixture was poured into water, acidified with a 1M aqueous solution of hydrogen chloride and extracted with dichloromethane. The combined organic phases were dried (Na2SO$_4$ anh), and concentrated under reduced pressure. Purification by HPLC (column: chromatorex C18, 10 μm, 195×51 mm, mobile phase: acetonitrile/water+0.1% formic acid gradient) yielded 186 mg (11% of theory) of the title compound.

¹H-NMR (300 MHz, DMSO-d₆): δ [ppm]=1.10-1.17 (m, 2H), 1.23-1.31 (m, 2H), 2.41-2.48 (m, 4H), 3.63-3.73 (m, 4H), 7.58 (dd, 1H), 7.76 (dd, 1H), 8.97 (d, 1H), 10.54 (s, 1H), 13.28 (s, 1H).

LC-MS (Method 1): $R_t$=1.12 min; MS (ESIpos): m/z=375 [M+H]⁺.

Intermediate 46

3-amino-4-(difluoromethoxy)-N-(5-phenyl-1,3,4-thiadiazol-2-yl)benzamide

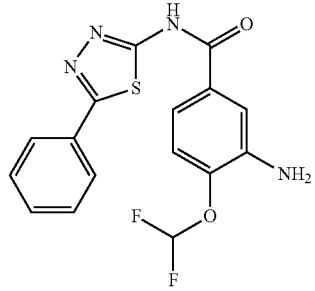 [SMILES: Nc1cc(C(=O)Nc2nnc(-c3ccccc3)s2)ccc1OC(F)F]

The title compound was prepared in a manner analogous to that described in intermediate 40 starting from 2.00 g (9.85 mmol) of 3-amino-4-(difluoromethoxy)benzoic acid and 2.62 g (14.8 mmol, 1.5 equiv) of 5-phenyl-1,3,4-thiadiazol-2-amine. 2.78 g (78% of theory) of the title compound were obtained.

¹H-NMR (300 MHz, DMSO-d₆): δ [ppm]=5.42 (s, 2H), 7.13 (d, 1H), 7.21 (t, 1H), 7.39 (dd, 1H), 7.48 (d, 1H), 7.51-7.60 (m, 3H), 7.93-8.03 (m, 2H), 13.00 (s, 1H).

LC-MS (Method 4): $R_t$=1.14 min; MS (ESIpos): m/z=363 [M+H]⁺.

Intermediate 47

3-[(chloroacetyl)amino]-4-(difluoromethoxy)-N-(5-phenyl-1,3,4-thiadiazol-2-yl)benzamide

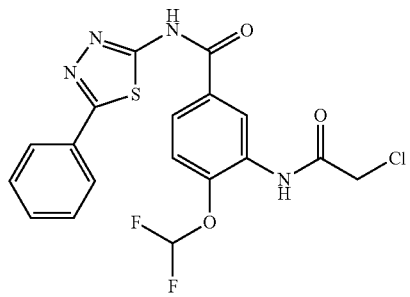 [SMILES: O=C(CCl)Nc1cc(C(=O)Nc2nnc(-c3ccccc3)s2)ccc1OC(F)F]

The title compound was prepared in a manner analogous to that described in intermediate 41 starting from 1.00 g (2.76 mmol) of the compound of intermediate 46. 723 mg (60% of theory) of the title compound were obtained.

¹H-NMR (400 MHz, DMSO-d₆): δ [ppm]=4.43 (s, 2H), 7.38 (t, 1H), 7.45 (d, 1H), 7.52-7.60 (m, 3H), 7.95-8.02 (m, 2H), 8.06 (dd, 1H), 8.71 (d, 1H), 9.99 (s, 1H), 13.24 (s, 1H).

LC-MS (Method 4): $R_t$=1.19 min; MS (ESIpos): m/z=439 [M+H]⁺.

Intermediate 48

3-[(2-chloropropanoyl)amino]-4-(difluoromethoxy)-N-(5-phenyl-1,3,4-thiadiazol-2-yl)benzamide

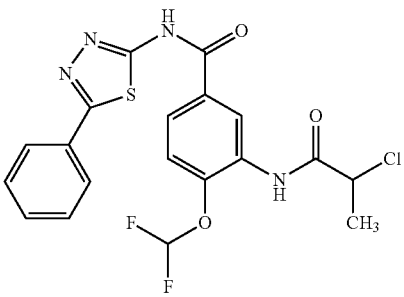 [SMILES: CC(Cl)C(=O)Nc1cc(C(=O)Nc2nnc(-c3ccccc3)s2)ccc1OC(F)F]

The title compound was prepared in a manner analogous to that described in intermediate 41 starting from 1.00 g (2.76 mmol) of the compound of intermediate 46 and 526 mg (4.14 mmol, 1.5 equiv) of 2-chloropropanoyl chloride. 1.08 g (86% of theory) of the title compound were obtained.

¹H-NMR (400 MHz, DMSO-d₆): δ [ppm]=1.65 (d, 3H), 4.95 (q, 1H), 7.36 (t, 1H), 7.45 (d, 1H), 7.52-7.59 (m, 3H), 7.95-8.02 (m, 2H), 8.06 (dd, 1H), 8.66 (d, 1H), 10.02 (s, 1H), 13.25 (s, 1H).

LC-MS (Method 4): $R_t$=1.26 min; MS (ESIpos): m/z=453 [M+H]⁺.

Intermediate 49

4-(methoxymethyl)-3-nitrobenzoic acid

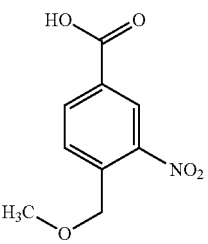

To a solution of 10.0 g (38.5 mmol) of 4-(bromomethyl)-3-nitrobenzoic acid in 200 mL of methanol were added 231 mL (115 mmol, 3 equiv) of a 0.5M solution of sodium methanolate in methanol. The resulting mixture was stirred at 60° C. for 1 h. After cooling to room temperature, the reaction mixture was poured into water and the organic solvents were evaporated under reduced pressure. A 1N aqueous hydrogen chloride solution was then added until an acidic pH was achieved. After stirring for 5 minutes, the precipitate was filtered off, washed with water and dried. 5.96 g (73% of theory) of the title compound were obtained.

¹H-NMR (400 MHz, DMSO-d₆): δ [ppm]=3.39 (s, 3H), 4.82 (s, 2H), 7.87 (d, 1H), 8.26 (dd, 1H), 8.48 (d, 1H).

LC-MS (Method 4): $R_t$=0.87 min; MS (ESIneg): m/z=210 [M−H]⁻.

Intermediate 50

4-(methoxymethyl)-3-nitro-N-(5-phenyl-1,3,4-thiadiazol-2-yl)benzamide

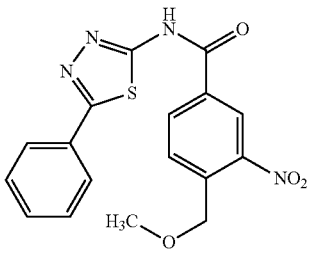 [SMILES: COCc1ccc(C(=O)Nc2nnc(-c3ccccc3)s2)cc1[N+](=O)[O-]]

The title compound was prepared in a manner analogous to that described in intermediate 40 starting from 5.80 g (27.5 mmol, 2 equiv) of the compound of intermediate 49 and 2.43 g (13.7 mmol) of 5-phenyl-1,3,4-thiadiazol-2-amine. 5.20 g (95% of theory) of the title compound were obtained.

$^1$H-NMR (400 MHz, DMSO-$d_6$): δ [ppm]=3.41 (s, 3H), 4.85 (s, 2H), 7.53-7.57 (m, 3H), 7.92 (d, 1H), 7.96-8.01 (m, 2H), 8.48 (dd, 1H), 8.83 (d, 1H), 13.53 (s, 1H).

LC-MS (Method 4): $R_f$=1.25 min; MS (ESIpos): m/z=371 [M+H]$^+$.

Intermediate 51

3-amino-4-(methoxymethyl)-N-(5-phenyl-1,3,4-thiadiazol-2-yl)benzamide

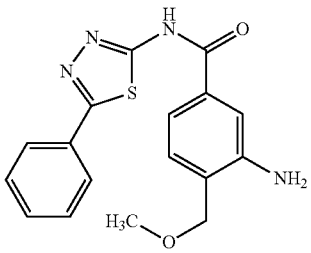

5.20 g (14.0 mmol) of the compound from intermediate 50 were provided in a mixture of 60 mL of ethanol and 90 mL of THF. 0.80 g of palladium on charcoal (10% Pd, 50% water) were added, and the mixture was stirred under a hydrogen atmosphere at room temperature for 0.5 h. 0.80 g of palladium on charcoal (10% Pd, 50% water) were added, and the mixture was stirred under a hydrogen atmosphere at room temperature for 1 h. A mixture of 300 mL of ethanol and 450 mL of THF and 2.00 g of palladium on charcoal (10% Pd, 50% water) were added, and the mixture was stirred under a hydrogen atmosphere at room temperature for 5.5 h. After filtration, the solvents were evaporated. 4.80 g (90% of theory) of the title compound were obtained.

$^1$H-NMR (400 MHz, DMSO-$d_6$): δ [ppm]=3.31 (s, 3H), 4.39 (s, 2H), 5.25 (s, 2H), 7.22 (d, 1H), 7.32-7.37 (m, 2H), 7.52-7.58 (m, 3H), 7.95-8.00 (m, 2H), 12.92 (s, 1H).

LC-MS (Method 4): $R_f$=1.08 min; MS (ESIpos): m/z=341 [M+H]$^+$.

Intermediate 52

3-[(chloroacetyl)amino]-4-(methoxymethyl)-N-(5-phenyl-1,3,4-thiadiazol-2-yl)benzamide

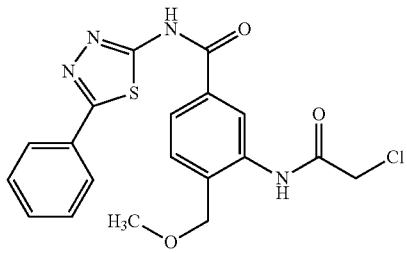 [SMILES: COCc1ccc(C(=O)Nc2nnc(-c3ccccc3)s2)cc1NC(=O)CCl]

The title compound was prepared in a manner analogous to that described in intermediate 41 starting from 2.00 g (5.88 mmol) of the compound of intermediate 51. 2.30 g (94% of theory) of the title compound were obtained.

$^1$H-NMR (300 MHz, DMSO-$d_6$): δ [ppm]=3.37 (s, 3H), 4.40 (s, 2H), 4.52 (s, 2H), 7.52-7.62 (m, 4H), 7.95-8.05 (m, 3H), 8.35 (s, 1H), 9.90 (s, 1H), 13.23 (s, 1H).

LC-MS (Method 4): $R_f$=1.17 min; MS (ESIpos): m/z=417 [M+H]$^+$.

Intermediate 53

4-[(methylsulfonyl)methyl]-3-nitrobenzoic acid

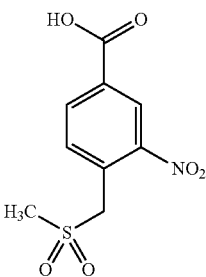 [SMILES: CS(=O)(=O)Cc1ccc(C(=O)O)cc1[N+](=O)[O-]]

To a solution of 10.0 g (38.5 mmol) of 4-(bromomethyl)-3-nitrobenzoic acid in 100 mL of DMF were added 19.6 g (192 mmol, 5 equiv) of sodium methanesulfinate. The resulting mixture was stirred at 60° C. for 1 h. After cooling to room temperature and concentration, water and a 1N aqueous hydrogen chloride solution were added until an acidic pH was achieved. The resulting mixture was extracted with ethyl acetate and the combined organic phases were dried (Na2SO$_4$ anh) and concentrated under reduced pressure. The remaining solids were then triturated with 100 mL of ethanol, and the resulting mixture was stirred for 30 minutes. The remaining solids were removed by filtration, washed with ethanol, and were dried under reduced pressure. The remaining solids were then triturated with 200 mL of ethanol, and the resulting mixture was stirred for 1 h. The remaining solids were removed by filtration, washed with ethanol, and were dried under reduced pressure to give 7.72 g of the title compound.

$^1$H-NMR (300 MHz, DMSO-$d_6$): δ [ppm]=3.03 (s, 3H), 5.07 (s, 2H), 7.82 (d, 1H), 8.28 (dd, 1H), 8.47 (d, 1H), 13.75 (s, 1H).

LC-MS (Method 4): $R_t$=0.61 min; MS (ESIneg): m/z=258 [M−H]⁻.

Intermediate 54

4-[(methylsulfonyl)methyl]-3-nitro-N-(5-phenyl-1,3,4-thiadiazol-2-yl)benzamide

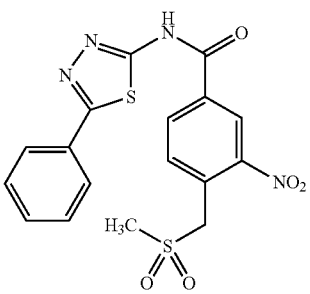 [SMILES: CS(=O)(=O)Cc1ccc(C(=O)Nc2nnc(-c3ccccc3)s2)cc1[N+](=O)[O-]]

The title compound was prepared in a manner analogous to that described in intermediate 40 starting from 5.00 g (15.4 mmol) of the compound of intermediate 53 and 3.56 g (20.1 mmol, 1.3 equiv) of 5-phenyl-1,3,4-thiadiazol-2-amine. 4.86 g (75% of theory) of the title compound were obtained.

¹H-NMR (400 MHz, DMSO-d₆): δ [ppm]=3.06 (s, 3H), 5.10 (s, 2H), 7.53-7.59 (m, 3H), 7.88 (d, 1H), 7.96-8.03 (m, 2H), 8.48 (dd, 1H), 8.82 (d, 1H), 13.63 (s, 1H).

LC-MS (Method 4): $R_t$=1.08 min; MS (ESIpos): m/z=419 [M+H]⁺.

Intermediate 55

3-amino-4-[(methylsulfonyl)methyl]-N-(5-phenyl-1,3,4-thiadiazol-2-yl)benzamide

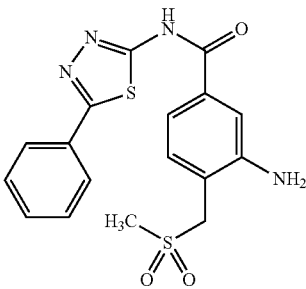

The title compound was prepared in a manner analogous to that described in intermediate 51 starting from 4.83 g (11.5 mmol) of the compound of intermediate 54. Warm DMF was used to extract the title compound from the catalyst. The organic solvents were evaporated under reduced pressure and the remaining solids were triturated with 50 mL of ethanol. The resulting mixture was stirred for 0.5 h. The remaining solids were removed by filtration, washed with ethanol, and were dried under reduced pressure to give 3.56 g of the title compound.

¹H-NMR (400 MHz, DMSO-d₆): δ [ppm]=2.95 (s, 3H), 4.51 (s, 2H), 5.57 (s, 2H), 7.27 (d, 1H), 7.35-7.43 (m, 2H), 7.51-7.59 (m, 3H), 7.93-8.02 (m, 2H), 13.00 (s, 1H).

LC-MS (Method 4): $R_t$=0.97 min; MS (ESIpos): m/z=389 [M+H]⁺.

Intermediate 56

2-nitro-N⁴-(5-phenyl-1,3,4-thiadiazol-2-yl)terephthalamide

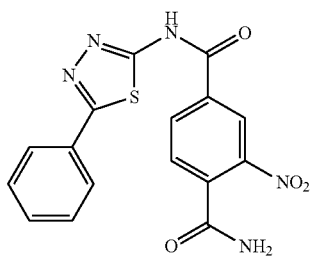 [SMILES: NC(=O)c1ccc(C(=O)Nc2nnc(-c3ccccc3)s2)cc1[N+](=O)[O-]]

To a solution of 4-carbamoyl-3-nitrobenzoic acid (5.00 g, 23.8 mmol) in 30.0 mL of DMF were added 5-phenyl-1,3,4-thiadiazol-2-amine (5.06 g, 28.6 mmol), (benzotriazol-1-yloxy)tripyrrolidinophosphonium hexafluorophosphate (PyBOP, 14.9 g, 28.6 mmol) followed by N,N-diisopropylethylamine (12.4 mL, 71.4 mmol). The reaction mixture was stirred at room temperature overnight. The mixture was diluted with 150 mL of water. The resulting precipitate was collected by filtration and washed with water. The filtrate was suspended in 100 mL of methanol and stirred for 30 min at 50° C. After filtration, the solid was washed with methanol and dried to yield the desired amide 56 (3.08 g, 7.92 mmol, 27%).

¹H-NMR (300 MHz, DMSO-d₆): δ [ppm]=7.52-7.60 (m, 3H), 7.79-7.90 (m, 2H), 7.99 (dd, 2H), 8.29 (s, 1H), 8.45 (dd, 1H), 8.75 (d, 1H), 13.70 (br. s, 1H).

LC-MS (Method 4): $R_t$=0.95 min; MS (ESIpos): m/z=370 [M+H]⁺.

Intermediate 57

2-amino-N⁴-(5-phenyl-1,3,4-thiadiazol-2-yl)terephthalamide

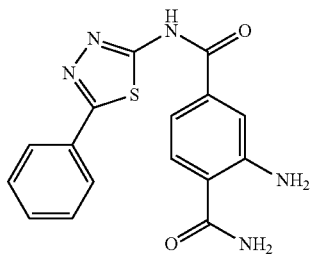

To a solution of intermediate 56 (3.50 g, 9.48 mmol) in 50.0 mL of 1-methyl-2-pyrrolidon (NMP) were added 10% palladium on carbon (605 mg, 10% Pd) and 10.0 mL methanol. The resulting slurry was stirred overnight at 60° C. under a hydrogen atmosphere. Additionally 300 mg of the catalyst and 5.0 mL of NMP were added to the mixture and it was stirred at 60° C. under a hydrogen atmosphere for 2 h. After addition of further 115 mg of the catalyst, the reaction mixture was stirred at 60° C. under a hydrogen atmosphere until complete consumption of the starting material was observed (2 days). The mixture was diluted with 50.0 mL of DMF and stirred for 10 min at 60° C. The resulting suspension was filtered over a pad of celite, the DMF of the filtrate was evaporated. Water (100 mL) was added to the concentrated filtrate and the resulting precipitate was collected by filtration and washed with water; afterwards the precipitate was suspended in methanol (50.0 mL) and stirred under reflux. After cooling to room temperature the suspension was filtrated, the resulting solid was washed with methanol. After drying the desired aniline derivative 57 (3.00 g, 8.57 mmol, 91%) was obtained and used without any further purification.

$^1$H-NMR (300 MHz, DMSO-d$_6$): δ [ppm]=6.76-6.85 (m, 2H), 7.20-7.32 (m, 2H), 7.35-7.43 (m, 1H), 7.54 (d, 3H), 7.66-7.70 (m, 1H), 7.88-8.03 (m, 3H), 12.88-13.33 (m, 1H).

LC-MS (Method 1): R$_t$=0.94 min; MS (ESIpos): m/z=340 [M+H]$^+$.

Intermediate 58

3-[(2-chloropropanoyl)amino]-N-(5-phenyl-1,3,4-thiadiazol-2-yl)-4-(trifluoromethoxy)benzamide

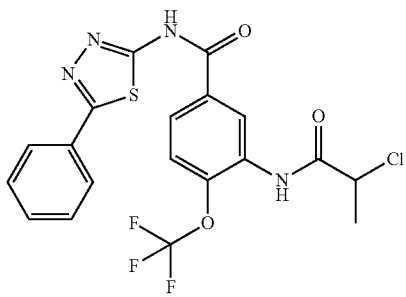 [SMILES: CC(Cl)C(=O)Nc1cc(C(=O)Nc2nnc(-c3ccccc3)s2)ccc1OC(F)(F)F]

A solution of intermediate 40 (500 mg, 1.31 mmol) and 2-chloropropionyl chloride (263 μL, 2.63 mmol) in 6.6 mL of toluene was stirred for 4 h at 100° C. and overnight at room temperature. The reaction mixture was taken to dryness to provide the crude desired product (620 mg, 1.31 mmol, quant.) which was used without further purification.

$^1$H-NMR (300 MHz, DMSO-d$_6$): δ [ppm]=1.65 (d, 3H), 4.91 (d, 1H), 7.60-7.50 (m, 3H), 7.65 (dd, 1H), 8.03-7.93 (m, 2H), 8.10 (dd, 1H), 8.62 (d, 1H), 10.31 (s, 1H), 13.55-13.26 (m, 1H).

LC-MS (Method 1): R$_t$=1.33 min; MS (ESIpos): m/z=471 [M+H]$^+$.

Intermediate 59

3-nitro-N-(5-phenyl-1,3,4-thiadiazol-2-yl)-4-(trifluoromethyl)benzamide

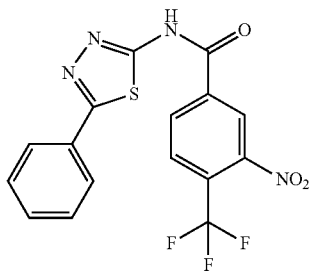 [SMILES: O=C(Nc1nnc(-c2ccccc2)s1)c1ccc(C(F)(F)F)c([N+](=O)[O-])c1]

To a solution of 3-nitro-4-(trifluoromethyl)benzoic acid (10.0 g, 42.5 mmol) and 5-phenyl-1,3,4-thiadiazol-2-amine (10.6 g, 59.5 mmol) in 163 mL of DMF were added (benzotriazol-1-yloxy)tripyrrolidinophosphonium hexafluorophosphate (PyBOP, 33.2 g, 63.8 mmol) and N,N-diisopropylethylamine (22.2 mL, 128 mmol). The mixture was stirred overnight at room temperature and poured into water. The resulting precipitate was collected by filtration, washed with water and dried at 60° C. in vacuum to provide the crude desired product (13.2 g, 76% pure, 60%), which was used without further purification.

$^1$H-NMR (300 MHz, DMSO-d$_6$): δ [ppm]=7.40-7.34 (m, 1H), 7.50-7.41 (m, 1H), 7.59-7.51 (m, 2H), 7.78-7.71 (m, 1H), 8.03-7.97 (m, 1H), 8.29-8.22 (m, 1H), 8.62-8.53 (m, 1H), 8.84-8.78 (m, 1H).

LC-MS (Method 4): R$_t$=1.34 min; MS (ESIpos): m/z=395 [M+H]$^+$.

Intermediate 60

3-amino-N-(5-phenyl-1,3,4-thiadiazol-2-yl)-4-(trifluoromethyl)benzamide

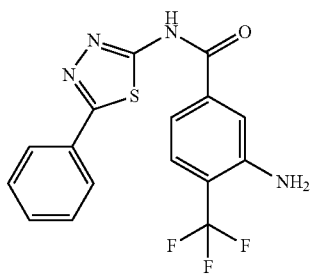 [SMILES: Nc1cc(C(=O)Nc2nnc(-c3ccccc3)s2)ccc1C(F)(F)F]

To a solution of intermediate 59 (11.7 g, 22.6 mmol) in 169 mL of tetrahydrofuran was added a 15% solution of titanium(III) chloride in 10% hydrogen chloride dropwise (225 mL, 265 mmol) at 0° C. The reaction mixture was allowed to warm up to room temperature and was stirred overnight. The pH of the mixture was adjusted under stirring with solid sodium bicarbonate to 7. The suspension was saturated with solid sodium chloride and stirred with 1 L of tetrahydrofuran/ethyl acetate (1:1) for 2 h. The layers were separated and the organic layer was washed with brine, dried over magnesium sulfate and concentrated in vacuum. The residue was suspended in ethanol and stirred at 40° C. until a fine suspension was obtained. The precipitate was collected by filtration and dried to yield the desired product 60 (6.59 g, 17.4 mmol, 77%).

$^1$H-NMR (400 MHz, DMSO-d$_6$): δ [ppm]=5.93 (s, 2H), 8.03-7.95 (m, 2H), 7.59-7.47 (m, 5H), 7.33 (d, 1H), 13.30-13.02 (m, 1H).

LC-MS (Method 4): R$_t$=1.23 min; MS (ESIpos): m/z=365 [M+H]$^+$.

Intermediate 61

3-[(chloroacetyl)amino]-N-(5-phenyl-1,3,4-thiadiazol-2-yl)-4-(trifluoromethyl)benzamide

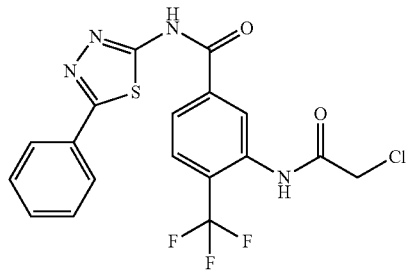 [SMILES: O=C(CCl)Nc1cc(C(=O)Nc2nnc(-c3ccccc3)s2)ccc1C(F)(F)F]

A solution of intermediate 60 (2.00 g, 5.49 mmol) and chloroacetyl chloride (892 µL, 10.98 mmol) in 27.5 mL of toluene was stirred for 4 h at 100° C. Two equivalents of chloroacetyl chloride were added to the mixture and it was stirred at 100° C. until the starting material was consumed (16 h). The reaction mixture was concentrated to provide the desired compound 61 (2.37 g, 5.11 mmol, 93%) as crude product which was used without further purification.

$^1$H-NMR (400 MHz, DMSO-d$_6$): δ [ppm]=4.38 (s, 2H), 7.61-7.50 (m, 3H), 8.04-7.93 (m, 3H), 8.31-8.19 (m, 2H), 10.14 (s, 1H), 13.73-13.28 (m, 1H).

LC-MS (Method 4): R$_t$=1.18 min; MS (ESIpos): m/z=441 [M+H]$^+$.

Intermediate 62

6-chloro-N-[3-nitro-4-(trifluoromethoxy)phenyl]nicotinamide

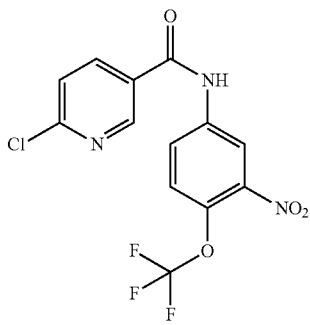 [SMILES: O=C(Nc1ccc(OC(F)(F)F)c([N+](=O)[O-])c1)c1ccc(Cl)nc1]

5.00 g (22.5 mmol) of 3-nitro-4-(trifluoromethoxy)aniline and 4.7 mL (33.8 mmol) of triethylamine in 250 mL of THF were stirred at room temperature. 4.36 g (24.8 mmol) of 6-chloronicotinoyl chloride were added and the mixture was stirred at room temperature over night. The mixture was poured into water and extracted with ethyl acetate. The combined organic phases were washed with a saturated, aqueous NH$_4$Cl solution and with a saturated, aqueous NaHCO$_3$ solution, was dried (Na$_2$SO$_4$ anh), and concentrated under reduced pressure. 7.99 g (96% of theory) of the title compound were obtained, which were used without further purification.

$^1$H-NMR (400 MHz, DMSO-d$_6$): δ [ppm]=7.74-7.81 (m, 2H), 8.17 (dd, 1H), 8.38 (dd, 1H), 8.65 (d, 1H), 8.98 (d, 1H), 11.02 (s, 1H).

LC-MS (Method 1): R$_t$=1.25 min; MS (ESIpos): m/z=362 [M+H]$^+$.

Intermediate 63

6-(3,5-difluorophenyl)-N-[3-nitro-4-(trifluoromethoxy)phenyl]nicotinamide

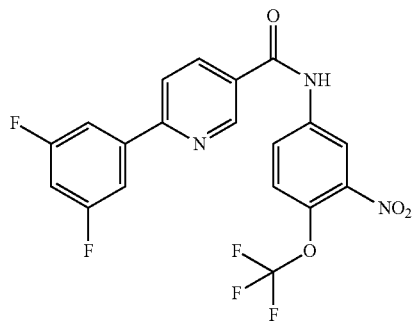 [SMILES: Nc1cc(NC(=O)c2ccc(-c3cc(F)cc(F)c3)nc2)ccc1OC(F)(F)F]

To a pressure vessel were added 4.00 g (10.8 mmol) of the compound of intermediate 62, 2.56 g (16.2 mmol, 1.5 equiv) of (3,5-difluorophenyl)boronic acid, 2.99 g (21.7 mmol, 2.0 equiv) of potassium carbonate and a DME/water mixture (3:1, 100 mL). The resulting suspension was purged with argon, treated with 442 mg (0.54 mmol, 5.0 mol %) of [1,1'-bis(diphenylphosphino)ferrocene]palladium(II) chloride CH$_2$Cl$_2$ complex (Pd(dppf)C$_{12}$.CH$_2$Cl$_2$), and sealed. The resulting mixture was heated at 90° C. over night, was then cooled to room temperature. The reaction mixture was poured onto ice water, and extracted with ethyl acetate. The combined organic phases were washed with a saturated NaCl solution, dried (Na2SO$_4$ anh), and concentrated under reduced pressure. 4.99 g (94% of theory) of the title compound were obtained, which were used without further purification.

$^1$H-NMR (400 MHz, DMSO-d$_6$): δ [ppm]=7.36-7.44 (m, 1H), 7.79 (dd, 1H), 7.89-7.98 (m, 2H), 8.21 (dd, 1H), 8.31 (d, 1H), 8.47 (dd, 1H), 8.70 (d, 1H), 9.23 (d, 1H), 11.03 (s, 1H).

LC-MS (Method 1): R$_t$=1.44 min; MS (ESIpos): m/z=440 [M+H]$^+$.

Intermediate 64

N-[3-amino-4-(trifluoromethoxy)phenyl]-6-(3,5-difluorophenyl)nicotinamide

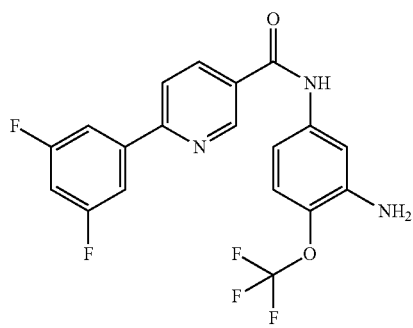

To a solution of the compound of intermediate 63 (4.99 g, 10.2 mmol) in 170 mL of tetrahydrofuran was added a 15% solution of titanium(III) chloride in 10% hydrogen chloride dropwise (87 mL, 102 mmol, 10 equiv) at 0° C. The reaction mixture was allowed to warm up to room temperature and was stirred overnight. The pH of the mixture was adjusted under stirring with solid sodium bicarbonate to 7. The suspension was saturated with solid sodium chloride and stirred with 200 mL of a mixture of tetrahydrofuran/ethyl acetate for 2 h. The suspension was filtered and the filtrate was washed with brine, dried over sodium sulfate and concentrated under reduced pressure. 4.20 g (100% of theory) of the title compound were obtained, which were used without further purification.

LC-MS (Method 1): $R_t$=1.30 min; MS (ESIpos): m/z=410 [M+H]$^+$.

Intermediate 65

N-[3-nitro-4-(trifluoromethoxy)phenyl]-6-phenylnicotinamide

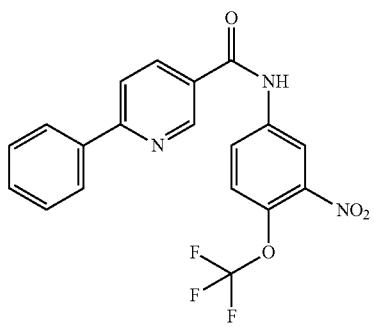 [SMILES: O=C(Nc1ccc(OC(F)(F)F)c([N+](=O)[O-])c1)c1ccc(-c2ccccc2)nc1]

To a pressure vessel were added 3.26 g (8.74 mmol) of the compound of intermediate 62, 1.60 g (13.1 mmol, 1.5 equiv) of phenylboronic acid, 2.42 g (17.5 mmol, 2.0 equiv) of potassium carbonate and a DME/water mixture (3:1, 100 mL). The resulting suspension was purged with argon, treated with 357 mg (0.44 mmol, 5.0 mol %) of [1,1'-bis(diphenylphosphino)ferrocene]palladium(II) chloride CH$_2$Cl$_2$ complex (Pd(dppf)C$_{12}$.CH$_2$Cl$_2$), and sealed. The resulting mixture was heated at 90° C. over night, was then cooled to room temperature. The reaction mixture was poured onto ice water, and extracted with ethyl acetate. The combined organic phases were washed with a saturated NaCl solution, dried (Na2SO$_4$ anh), and concentrated under reduced pressure. The residue was purified using MPLC (Biotage Isolera; silica gel; hexane/EtOAc gradient). 3.17 g (90% of theory) of the title compound were obtained.

$^1$H-NMR (300 MHz, DMSO-d$_6$): δ [ppm]=7.47-7.61 (m, 3H), 7.74-7.84 (m, 1H), 8.15-8.27 (m, 4H), 8.43 (dd, 1H), 8.71 (d, 1H), 9.23 (d, 1H), 11.01 (s, 1H).

LC-MS (Method 1): $R_t$=1.37 min; MS (ESIpos): m/z=404 [M+H]$^+$.

Intermediate 66

N-[3-amino-4-(trifluoromethoxy)phenyl]-6-phenyl-nicotinamide

To a solution of the compound of intermediate 65 (2.35 g, 5.83 mmol) in 200 mL of tetrahydrofuran was added a 15% solution of titanium(III) chloride in 10% hydrogen chloride dropwise (50 mL, 58.3 mmol, 10 equiv) at 0° C. The reaction mixture was allowed to warm up to room temperature and was stirred overnight. The pH of the mixture was adjusted under stirring with solid sodium bicarbonate to 7. The suspension was saturated with solid sodium chloride and stirred with 200 mL of a mixture of tetrahydrofuran/ethyl acetate for 2 h. The suspension was filtered and the filtrate was washed with brine, dried over sodium sulfate and concentrated under reduced pressure. 2.07 g (95% of theory) of the title compound were obtained, which were used without further purification.

$^1$H-NMR (400 MHz, DMSO-d$_6$): δ [ppm]=5.44 (s, 2H), 6.94 (dd, 1H), 7.08 (dd, 1H), 7.38 (d, 1H), 7.47-7.59 (m, 3H), 8.11-8.22 (m, 3H), 8.36 (dd, 1H), 9.16 (d, 1H), 10.32 (s, 1H).

LC-MS (Method 1): $R_t$=1.23 min; MS (ESIpos): m/z=374 [M+H]$^+$.

Intermediate 67

6-chloro-N-(4-methoxy-3-nitrophenyl)nicotinamide 15.0 g (89.2 mmol) of 4-methoxy-3-nitroaniline, 77.7 mL (446 mmol, 5 equiv) of N,N-diisopropylethylamine and 28.1 g (178 mmol, 2 equiv) of 6-chloronicotinic acid were provided in 300 mL of DMF at room temperature. 104 mL (178 mmol, 2 equiv) of a 50% solution of 2,4,6-tripropyl-1,3,5,2,4,6-trioxatriphosphinane 2,4,6-trioxide (T3P) in DMF were added, and the mixture was stirred for 16 h at room temperature. The resulting mixture was concentrated to half of the original volume, poured onto water, and stirred for 15 minutes. The precipitate was filtered off, washed with water and dried. 34.1 g of the title compound were obtained, which were used without further purification.

$^1$H-NMR (300 MHz, DMSO-$d_6$): δ [ppm]=3.92 (s, 3H), 7.39 (d, 1H), 7.65-7.75 (m, 1H), 7.97 (dd, 1H), 8.31-8.43 (m, 2H), 8.97 (d, 1H), 10.81 (s, 1H).

LC-MS (Method 1): $R_t$=1.02 min; MS (ESIpos): m/z=308 [M+H]$^+$.

Intermediate 68

6-(2-fluorophenyl)-N-(4-methoxy-3-nitrophenyl) nicotinamide

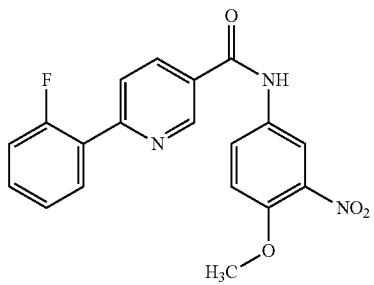 [SMILES: COc1ccc(NC(=O)c2ccc(-c3ccccc3F)nc2)cc1[N+](=O)[O-]]

To a pressure vessel were added 11.0 g (35.8 mmol) of the compound of intermediate 67, 7.50 g (53.6 mmol, 1.5 equiv) of (2-fluorophenyl)boronic acid, 9.88 g (71.5 mmol, 2.0 equiv) of potassium carbonate and a DME/water mixture (3:1, 400 mL). The resulting suspension was purged with argon, treated with 1.46 g (1.79 mmol, 5.0 mol %) of [1,1'-bis(diphenylphosphino)ferrocene]palladium(II) chloride CH$_2$Cl$_2$ complex (Pd(dppf)C$_{12}$.CH$_2$Cl$_2$), and sealed. The resulting mixture was heated at 90° C. over night, was then cooled to room temperature. The reaction mixture was poured onto ice water, and extracted with ethyl acetate. The combined organic phases were washed with a saturated NaCl solution, dried (Na2SO$_4$ anh), and concentrated under reduced pressure. 3.82 g (29% of theory) of the title compound were obtained, which were used without further purification.

LC-MS (Method 1): $R_t$=1.19 min; MS (ESIpos): m/z=368 [M+H]$^+$.

Intermediate 69

N-(3-amino-4-methoxyphenyl)-6-(2-fluorophenyl) nicotinamide

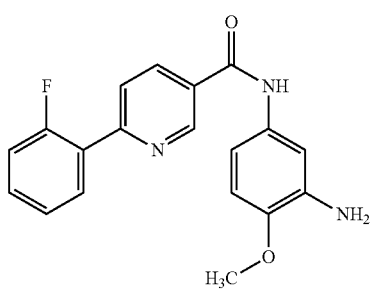

To a solution of the compound of intermediate 68 (3.82 g, 10.4 mmol) in 300 mL of tetrahydrofuran was added a 15% solution of titanium(III) chloride in 10% hydrogen chloride dropwise (88 mL, 104 mmol, 10 equiv) at 0° C. The reaction mixture was allowed to warm up to room temperature and was stirred for 3 days. The pH of the mixture was adjusted under stirring with solid sodium bicarbonate to 7. The suspension was saturated with solid sodium chloride and stirred with 300 mL of a mixture of tetrahydrofuran/ethyl acetate for 2 h. The suspension was filtered and the filtrate was washed with brine, dried over sodium sulfate and concentrated under reduced pressure. The residue was purified using MPLC (Biotage Isolera; silica gel; hexane/EtOAc gradient). 0.6 g (17% of theory) of the title compound were obtained.

$^1$H-NMR (300 MHz, DMSO-$d_6$): δ [ppm]=3.75 (s, 3H), 4.82 (s, 2H), 6.76 (d, 1H), 6.92 (dd, 1H), 7.14 (d, 1H), 7.34-7.43 (m, 2H), 7.49-7.60 (m, 1H), 7.90-8.04 (m, 2H), 8.37 (dd, 1H), 9.19 (d, 1H), 10.15 (s, 1H).

LC-MS (Method 1): $R_t$=0.99 min; MS (ESIpos): m/z=338 [M+H]$^+$.

Intermediate 70

3-amino-N-[6-(3-fluorophenyl)pyridin-3-yl]-4-(trifluoromethoxy)benzamide

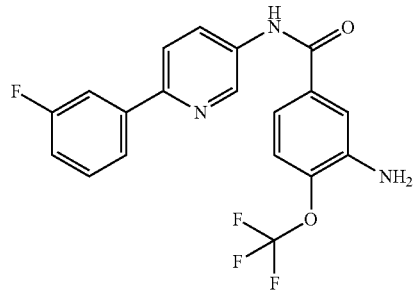 [SMILES: Nc1cc(C(=O)Nc2ccc(-c3cccc(F)c3)nc2)ccc1OC(F)(F)F]

To a pressure vessel were added 2.95 g (8.89 mmol) of the compound of intermediate 9, 1.87 g (13.3 mmol, 1.5 equiv) of (3-fluorophenyl)boronic acid, 2.46 g (17.8 mmol, 2.0 equiv) of potassium carbonate and a DME/water mixture (3:1, 100 mL). The resulting suspension was purged with argon, treated with 363 mg (0.45 mmol, 5.0 mol %) of [1,1'-bis(diphenylphosphino)ferrocene]palladium(II) chloride CH$_2$Cl$_2$ complex (Pd(dppf)C$_{12}$.CH$_2$Cl$_2$), and sealed. The resulting mixture was heated at 90° C. over night, was then cooled to room temperature. The reaction mixture was poured onto ice water, and extracted with ethyl acetate. The combined organic phases were washed with a saturated NaCl solution, dried (Na2SO$_4$ anh), and concentrated under reduced pressure. 3.46 g (99% of theory) of the title compound were obtained, which were used without further purification.

LC-MS (Method 1): $R_t$=1.25 min; MS (ESIpos): m/z=392 [M+H]$^+$.

Intermediate 71

3-[(2-chloropropanoy)amino]-N-[6-(3-fluorophenyl)pyridin-3-yl]-4-(trifluoromethoxy)benzamide

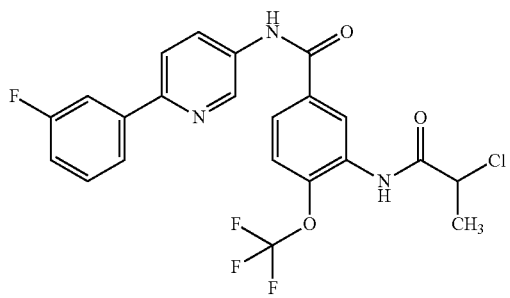 [SMILES: CC(Cl)C(=O)Nc1cc(C(=O)Nc2ccc(-c3cccc(F)c3)nc2)ccc1OC(F)(F)F]

3.46 g (8.84 mmol) of the compound of intermediate 70 were provided in 64 mL of toluene, 1.72 mL (17.7 mmol) of 2-chloropropanoyl chloride were added, and the mixture was stirred for 1.5 h at 100° C. After concentration, 4.13 g of the title compound were obtained, which were used without further purification.

LC-MS (Method 1): $R_t$=1.34 min; MS (ESIpos): m/z=482 [M+H]$^+$.

Intermediate 72

3-amino-N-[6-(3,5-difluorophenyl)pyridin-3-yl]-4-(trifluoromethoxy)benzamide

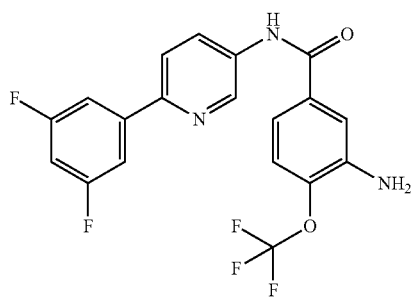 [SMILES: Nc1cc(C(=O)Nc2ccc(-c3cc(F)cc(F)c3)nc2)ccc1OC(F)(F)F]

To a pressure vessel were added 3.30 g (8.95 mmol) of the compound of intermediate 9, 2.12 g (13.4 mmol, 1.5 equiv) of (3,5-difluorophenyl)boronic acid, 2.48 g (17.9 mmol, 2.0 equiv) of potassium carbonate and a DME/water mixture (3:1, 100 mL). The resulting suspension was purged with argon, treated with 366 mg (0.45 mmol, 5.0 mol %) of [1,1'-bis(diphenylphosphino)ferrocene]palladium(II) chloride CH$_2$Cl$_2$ complex (Pd(dppf)C$_{12}$.CH$_2$Cl$_2$), and sealed. The resulting mixture was heated at 90° C. over night, was then cooled to room temperature. The reaction mixture was poured onto ice water, and extracted with ethyl acetate. The combined organic phases were washed with a saturated NaCl solution, dried (Na2SO$_4$ anh), and concentrated under reduced pressure. The residue was purified using MPLC (Biotage Isolera; silica gel; hexane/EtOAc gradient). 3.62 g (92% of theory) of the title compound were obtained.

$^1$H-NMR (400 MHz, DMSO-d$_6$): δ [ppm]=5.69 (s, 2H), 7.15 (dd, 1H), 7.23-7.30 (m, 2H), 7.38 (d, 1H), 7.75-7.83 (m, 2H), 8.09 (d, 1H), 8.31 (dd, 1H), 9.01 (d, 1H), 10.55 (s, 1H).

LC-MS (Method 4): $R_t$=1.32 min; MS (ESIpos): m/z=410 [M+H]$^+$.

Intermediate 73

3-[(chloroacetyl)amino]-N-[6-(3,5-difluorophenyl)pyridin-3-yl]-4-(trifluoromethoxy)benzamide

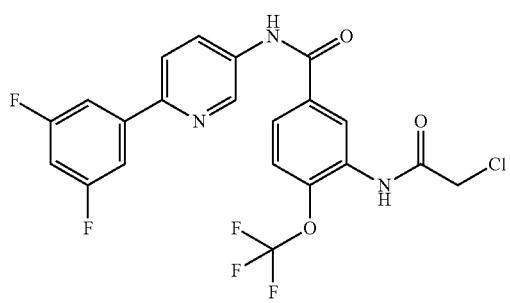 [SMILES: O=C(CCl)Nc1cc(C(=O)Nc2ccc(-c3cc(F)cc(F)c3)nc2)ccc1OC(F)(F)F]

600 mg (1.36 mmol) of the compound of intermediate 72 were provided in 8 mL of toluene, 0.22 mL (2.73 mmol) of chloroacetyl chloride were added, and the mixture was stirred for 2 h at 100° C. After concentration, 650 mg of the title compound were obtained, which were used without further purification.

LC-MS (Method 1): $R_t$=1.34 min; MS (ESIpos): m/z=486 [M+H]$^+$.

Intermediate 74

3-nitro-4-(trifluoromethyl)benzoyl chloride

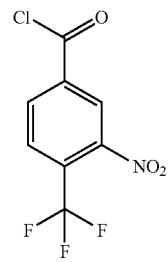 [SMILES: O=C(Cl)c1ccc(C(F)(F)F)c([N+](=O)[O-])c1]

5.00 g (21.3 mmol) of 3-nitro-4-(trifluoromethyl)benzoic acid were stirred in 28 mL of dichloromethane at room temperature. 0.08 mL (1.06 mmol) of DMF and 3.7 mL (42.5 mmol) of oxalyl chloride were added, and the mixture was stirred for additional 1.5 h at 50° C. after the gas formation had stopped. The mixture was left at room temperature over night. After concentration, 4.58 g of raw material were obtained, which were used without further purification.

Intermediate 75

N-(6-chloropyridin-3-yl)-3-nitro-4-(trifluoromethyl)benzamide

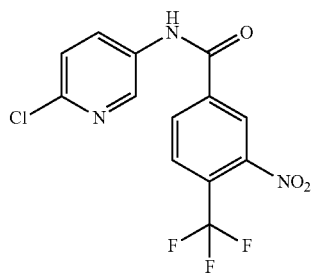 [SMILES: O=C(Nc1ccc(Cl)nc1)c1ccc(C(F)(F)F)c([N+](=O)[O-])c1]

1.78 g (13.8 mmol) of 6-chloropyridin-3-amine and 2.6 mL (18.9 mmol, 1.5 equiv) of triethylamine in 150 mL of THF were stirred at room temperature. 3.19 g (12.6 mmol) of the compound of intermediate 74 were added and the mixture was stirred at room temperature over night. The mixture was poured into water and extracted with ethyl acetate. The combined organic phases were washed with a saturated, aqueous NH$_4$Cl solution and with a saturated, aqueous NaHCO$_3$ solution, was dried (Na2SO$_4$ anh), and concentrated under reduced pressure. 4.04 g (88% of theory) of the title compound were obtained, which were used without further purification.

$^1$H-NMR (400 MHz, DMSO-d$_6$): δ [ppm]=7.57 (d, 1H), 8.23-8.30 (m, 2H), 8.44-8.48 (m, 1H), 8.67-8.70 (m, 1H), 8.78 (d, 1H), 11.02 (s, 1H).

LC-MS (Method 1): R$_t$=1.21 min; MS (ESIpos): m/z=346 [M+H]$^+$.

Intermediate 76

N-[6-(2-fluorophenyl)pyridin-3-yl]-3-nitro-4-(trifluoromethyl)benzamide

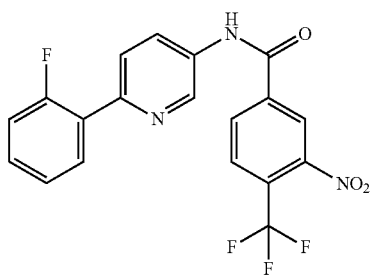 [SMILES: O=C(Nc1ccc(-c2ccccc2F)nc1)c1ccc(C(F)(F)F)c([N+](=O)[O-])c1]

4.04 g (11.1 mmol) of the compound of intermediate 75 were provided in 120 mL of degassed THF under an argon atmosphere at room temperature. 2.33 g (16.7 mmol) of (2-fluorophenyl)boronic acid, 262 mg (0.33 mmol) of chloro (2-dicyclohexylphosphino-2',4',6'-triisopropyl-1,1'-biphenyl)[2-(2'-amino-1,1'-biphenyl)palladium(II) and 44.4 mL (22.2 mmol) of a 0.5M aqueous, degassed solution of potassium phosphate were added, and the mixture was stirred at room temperature for 16 h. The mixture was poured into a mixture of water and tert-butyl methyl ether. After separation of the phases, the aqueous phase was extracted with tert-butyl methyl ether, and the combined organic phases were dried over sodium sulfate and concentrated. 4.49 g (94% of theory) of the title compound were obtained, which were used without further purification.

$^1$H-NMR (300 MHz, DMSO-d$_6$): δ [ppm]=7.29-7.39 (m, 2H), 7.43-7.53 (m, 1H), 7.87 (dd, 1H), 7.97 (td, 1H), 8.25-8.36 (m, 2H), 8.49 (d, 1H), 8.72 (s, 1H), 9.07 (d, 1H), 11.02 (s, 1H).

LC-MS (Method 4): R$_t$=1.35 min; MS (ESIpos): m/z=406 [M+H]$^+$.

Intermediate 77

3-amino-N-[6-(2-fluorophenyl)pyridin-3-yl]-4-(trifluoromethyl)benzamide

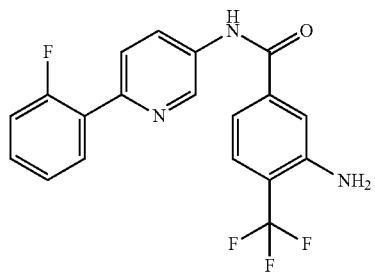 [SMILES: Nc1cc(C(=O)Nc2ccc(-c3ccccc3F)nc2)ccc1C(F)(F)F]

To a solution of the compound of intermediate 76 (4.49 g, 10.4 mmol) in 100 mL of tetrahydrofuran was added a 15% solution of titanium(III) chloride in 10% hydrogen chloride dropwise (71 mL, 83.3 mmol, 8 equiv) at 0° C. The reaction mixture was allowed to warm up to room temperature and was stirred for 16 hours. A 15% solution of titanium(III) chloride in 10% hydrogen chloride was added dropwise (71 mL, 83.3 mmol, 8 equiv) and the reaction mixture was stirred for 16 hours. The pH of the mixture was adjusted under stirring with solid sodium bicarbonate to 7. The suspension was saturated with solid sodium chloride and stirred with 300 mL of a mixture of tetrahydrofuran/ethyl acetate for 2 h. The suspension was filtered and the filtrate was washed with brine, dried over sodium sulfate and concentrated under reduced pressure. The residue was purified using MPLC (Biotage Isolera; silica gel; hexane/EtOAc gradient). 3.40 g (87% of theory) of the title compound were obtained.

LC-MS (Method 4): R$_t$=1.22 min; MS (ESIpos): m/z=376 [M+H]$^+$.

Intermediate 78

3-[(chloroacetyl)amino]-N-[6-(2-fluorophenyl)pyridin-3-yl]-4-(trifluoromethyl)benzamide

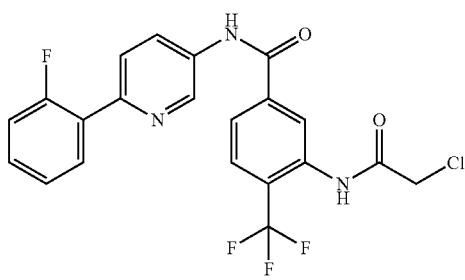 [SMILES: O=C(CCl)Nc1cc(C(=O)Nc2ccc(-c3ccccc3F)nc2)ccc1C(F)(F)F]

1.00 g (2.66 mmol) of the compound of intermediate 77 was provided in 20 mL of toluene, 0.42 mL (5.33 mmol) of chloroacetyl chloride were added, and the mixture was stirred for 1.5 h at 100° C. After concentration, 1.10 g of the title compound were obtained, which were used without further purification.

LC-MS (Method 1): $R_t$=1.22 min; MS (ESIpos): m/z=452 [M+H]$^+$.

Intermediate 79

N$^4$-[6-(2-fluorophenyl)pyridin-3-yl]-2-nitro-terephthalamide

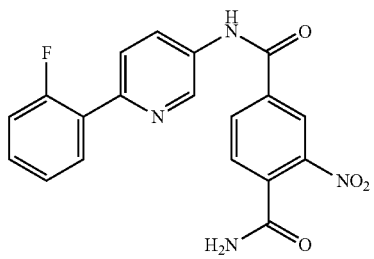 [SMILES: NC(=O)c1ccc(C(=O)Nc2ccc(-c3ccccc3F)nc2)cc1[N+](=O)[O-]]

1.79 g (9.52 mmol, 2 equiv) of 6-(2-fluorophenyl)pyridin-3-amine, 4.1 mL (23.8 mmol, 5 equiv) of N,N-diisopropylethylamine and 1.00 g (4.76 mmol) of 4-carbamoyl-3-nitrobenzoic acid were provided in 25 mL of DMF at room temperature. 5.6 mL (9.52 mmol, 2 equiv) of a 50% solution of 2,4,6-tripropyl-1,3,5,2,4,6-trioxatriphosphinane 2,4,6-trioxide (T3P) in DMF were added, and the mixture was stirred for 16 h at room temperature. The resulting mixture was concentrated and water and saturated, aqueous sodium bicarbonate solution were added. The precipitate was filtered off, washed with water and dried. The residue was purified using MPLC (Biotage Isolera; silica gel; dichloromethane/methanol gradient). 0.73 g (39% of theory) of the title compound were obtained.

$^1$H-NMR (400 MHz, DMSO-d$_6$): δ [ppm]=7.30-7.38 (m, 2H), 7.44-7.51 (m, 1H), 7.80-7.89 (m, 3H), 7.94-8.00 (m, 1H), 8.27 (s, 1H), 8.30-8.40 (m, 2H), 8.61 (d, 1H), 9.08 (d, 1H), 10.90 (s, 1H).

LC-MS (Method 1): $R_t$=0.99 min; MS (ESIpos): m/z=381 [M+H]$^+$.

Intermediate 80

2-amino-N$^4$-[6-(2-fluorophenyl)pyridin-3-yl]terephthalamide

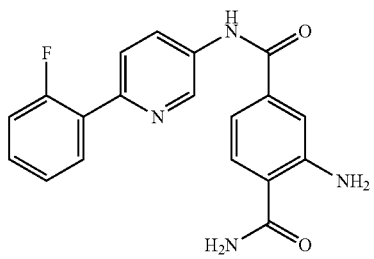 [SMILES: NC(=O)c1ccc(C(=O)Nc2ccc(-c3ccccc3F)nc2)cc1N]

To a solution of the compound of intermediate 79 (0.70 g, 1.84 mmol) in 30 mL of tetrahydrofuran was added a 15% solution of titanium(III) chloride in 10% hydrogen chloride dropwise (15.6 mL, 18.4 mmol, 10 equiv) at 0° C. The reaction mixture was allowed to warm up to room temperature and was stirred overnight. The pH of the mixture was adjusted under stirring with solid sodium bicarbonate to 7. The suspension was saturated with solid sodium chloride and stirred with 50 mL of a mixture of tetrahydrofuran/ethyl acetate for 2 h. The suspension was filtered and the filtrate was washed with brine, dried over sodium sulfate and concentrated under reduced pressure. 589 mg (82% of theory) of the title compound were obtained, which were used without further purification.

$^1$H-NMR (400 MHz, DMSO-d$_6$): δ [ppm]=6.79 (s, 2H), 7.07 (dd, 1H), 7.18-7.29 (m, 2H), 7.29-7.37 (m, 2H), 7.43-7.50 (m, 1H), 7.69 (d, 1H), 7.82 (dd, 1H), 7.89 (s, 1H), 7.93-7.99 (m, 1H), 8.31 (dd, 1H), 9.06 (d, 1H), 10.52 (s, 1H).

LC-MS (Method 4): $R_t$=0.93 min; MS (ESIpos): m/z=351 [M+H]$^+$.

Intermediate 81 methyl 4-methyl-3-({[1-(morpholin-4-yl)cyclopropyl]carbonyl}amino)benzoate

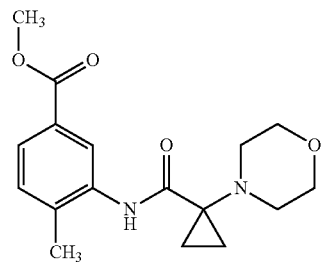 [SMILES: COC(=O)c1ccc(C)c(NC(=O)C2(N3CCOCC3)CC2)c1]

To a solution of methyl 3-amino-4-methylbenzoate (3.00 g, 18.2 mmol) and 1-(morpholin-4-yl)cyclopropanecarboxylic acid hydrochloride (1:1) (intermediate 44, 7.54 g, 36.3 mmol, 2 equiv) in DMF (50 mL) was added (benzotriazol-1-yloxy)tripyrrolidinophosphonium hexafluorophosphate (PYBOP, 18.9 g, 36.3 mmol, 2 equiv) and diisopropylethylamine (15.8 mL, 90.8 mmol, 5 equiv). The resulting mixture was stirred at room temperature over night, was concentrated under reduced pressure, was then dissolved in dichloromethane, was washed with 1N aqueous hydrogen chloride solution and saturated, aqueous sodium bicarbonate solution, was dried over sodium sulfate and concentrated under reduced pressure. The remaining solids were then triturated with ethanol (30 mL), and the resulting mixture was stirred for 30 minutes. The remaining solids were removed by filtration, washed with ethanol, and were dried at 50° C. under reduced pressure to give the title compound (4.60 g, 80% of theory).

$^1$H-NMR (400 MHz, DMSO-d$_6$): δ [ppm]=1.08-1.16 (m, 2H), 1.17-1.24 (m, 2H), 2.39 (s, 3H), 2.44-2.49 (m, 4H), 3.67-3.74 (m, 4H), 3.83 (s, 3H), 7.39 (d, 1H), 7.63 (dd, 1H), 8.62 (d, 1H), 10.15 (s, 1H).

LC-MS (Method 4): $R_t$=1.09 min; MS (ESIpos): m/z=319 [M+H]$^+$.

Intermediate 82

4-methyl-3-({[1-(morpholin-4-yl)cyclopropyl]carbonyl}amino)benzoic acid

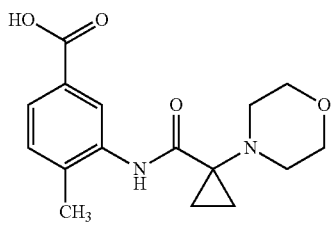

4.57 g (14.4 mmol) of the compound of intermediate 81 were provided in 60 mL of dioxane, a solution of 690 mg (28.7 mmol) of lithium hydroxide in 25 mL of water was added at room temperature and the mixture was stirred for 5 h at room temperature. Water and a 2N aqueous hydrogen chloride solution were then added until an acidic pH of 1.5-2 was achieved. After stirring for 15 minutes, the precipitate was filtered off, washed with water and dried. 3.92 g (90% of theory) of the title compound were obtained, which were used without further purification.

$^1$H-NMR (400 MHz, DMSO-$d_6$): δ [ppm]=1.08-1.13 (m, 2H), 1.17-1.22 (m, 2H), 2.38 (s, 3H), 2.45-2.49 (m, 4H), 3.68-3.74 (m, 4H), 7.35 (d, 1H), 7.61 (dd, 1H), 8.56 (d, 1H), 10.10 (s, 1H), 12.82 (s, 1H).

LC-MS (Method 4): $R_t$=0.90 min; MS (ESIpos): m/z=305 [M+H]$^+$.

Intermediate 83 methyl 4-fluoro-3-({[1-(morpholin-4-yl)cyclopropyl]carbonyl}amino)benzoate

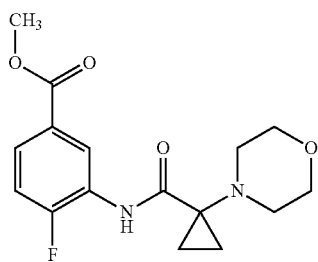 [SMILES: COC(=O)c1ccc(F)c(NC(=O)C2(N3CCOCC3)CC2)c1]

4.67 g (22.5 mmol) of 1-(morpholin-4-yl)cyclopropanecarboxylic acid hydrochloride (1:1) (intermediate 44) were stirred in 90 mL of dichloromethane at room temperature. 0.17 mL (2.25 mmol) of DMF and 3.9 mL (45.0 mmol) of oxalyl chloride were added, and the mixture was stirred for additional 2 h at 50° C. after the gas formation had stopped. After concentration, 4.80 g of raw material were obtained, which were added to a solution of 3.00 g (17.7 mmol) of methyl 3-amino-4-fluorobenzoate and 12.4 mL (88.7 mmol) of triethylamine in a mixture of 42 mL of dichloromethane and 42 mL of THF. The resulting mixture was stirred at room temperature over night, was washed with water and 1N aqueous hydrogen chloride solution, was dried over sodium sulfate and concentrated under reduced pressure. The remaining solids were then triturated with ethanol, and the remaining solids were removed by filtration and were dried at 50° C. under reduced pressure to give the title compound (4.55 g, 80% of theory).

$^1$H-NMR (400 MHz, DMSO-$d_6$): δ [ppm]=1.10-1.15 (m, 2H), 1.20-1.26 (m, 2H), 2.43-2.48 (m, 4H), 3.65-3.72 (m, 4H), 3.85 (s, 3H), 7.46 (dd, 1H), 7.75 (ddd, 1H), 8.77 (dd, 1H), 10.35 (s, 1H).

LC-MS (Method 4): $R_t$=1.13 min; MS (ESIpos): m/z=323 [M+H]$^+$.

Intermediate 84

4-fluoro-3-({[1-(morpholin-4-yl)cyclopropyl]carbonyl}amino)benzoic acid

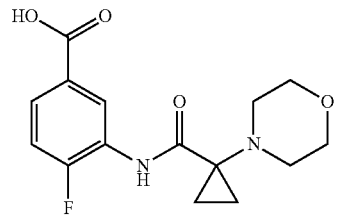

4.55 g (14.1 mmol) of the compound of intermediate 83 were provided in 60 mL of dioxane, 676 mg (28.2 mmol) of lithium hydroxide and 25 mL of water were added at room temperature and the mixture was stirred at room temperature over night. Water and a 2N aqueous hydrogen chloride solution were then added until an acidic pH of 1.5-2 was achieved. After stirring for 15 minutes, the precipitate was filtered off, washed with water and dried. 3.02 g (66% of theory) of the title compound were obtained, which were used without further purification.

$^1$H-NMR (400 MHz, DMSO-$d_6$): δ [ppm]=1.08-1.15 (m, 2H), 1.19-1.25 (m, 2H), 2.43-2.48 (m, 4H), 3.65-3.72 (m, 4H), 7.41 (dd, 1H), 7.72 (ddd, 1H), 8.73 (dd, 1H), 10.32 (s, 1H), 13.02 (s, 1H).

LC-MS (Method 4): $R_t$=0.93 min; MS (ESIpos): m/z=309 [M+H]$^+$.

Intermediate 85 methyl 4-chloro-3-({[1-(morpholin-4-yl)cyclopropyl]carbonyl}amino)benzoate

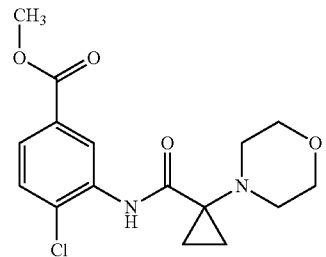 [SMILES: COC(=O)c1ccc(Cl)c(NC(=O)C2(N3CCOCC3)CC2)c1]

To a solution of methyl 3-amino-4-chlorobenzoate (3.00 g, 16.2 mmol) and 1-(morpholin-4-yl)cyclopropanecarboxylic acid hydrochloride (1:1) (intermediate 44, 6.71 g, 32.3 mmol, 2 equiv) in DMF (50 mL) was added (benzotriazol-1-yloxy)tripyrrolidinophosphonium hexafluorophosphate (PYBOP, 16.8 g, 32.3 mmol, 2 equiv) and diisopropylethylamine (14.1 mL, 80.8 mmol, 5 equiv). The resulting mixture was stirred at room temperature for 3 days. (Benzotriazol-1-yloxy)tripyrrolidinophosphonium hexafluorophosphate (PYBOP, 16.8 g, 32.3 mmol, 2 equiv) and diisopropylethylamine (14.1 mL, 80.8 mmol, 5 equiv) were added and the resulting mixture was stirred at 60° C. over night. The mixture was concentrated under reduced pressure, was then dissolved in dichloromethane, was washed with 1N aqueous hydrogen chloride solution and saturated, aqueous sodium bicarbonate solution, was dried over sodium sulfate and concentrated under reduced pressure. The remaining solids were then triturated with ethanol (40 mL), and the resulting mixture was stirred for 30 minutes. The remaining solids were removed by filtration, washed with ethanol, and were dried at 50° C. under reduced pressure. The remaining solids were then triturated with ethanol (70 mL), and the resulting mixture was stirred under reflux. After cooling to room temperature, the remaining solids were removed by filtration, washed with ethanol, and were dried at 50° C. under reduced pressure to give the title compound (3.60 g).

LC-MS (Method 4): $R_t$=1.23 min; MS (ESIpos): m/z=339 [M+H]$^+$.

Intermediate 86

4-chloro-3-({[1-(morpholin-4-yl)cyclopropyl]carbonyl}amino)benzoic acid

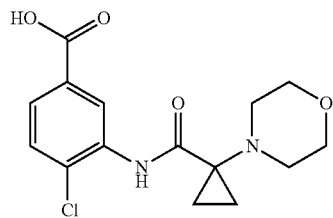

3.60 g (10.6 mmol) of the compound of intermediate 85 were provided in 45 mL of dioxane, 509 mg (21.3 mmol) of lithium hydroxide and 19 mL of water were added at room temperature and the mixture was stirred at room temperature for 5 hours. Water and a 2N aqueous hydrogen chloride solution were then added until an acidic pH of 1.5-2 was achieved. After stirring for 15 minutes, the precipitate was filtered off, washed with water and dried. 2.67 g (77% of theory) of the title compound were obtained, which were used without further purification.

$^1$H-NMR (300 MHz, DMSO-d$_6$): δ [ppm]=1.10-1.18 (m, 2H), 1.23-1.31 (m, 2H), 2.43-2.49 (m, 4H), 3.68-3.77 (m, 4H), 7.61-7.70 (m, 2H), 8.97 (s, 1H), 10.75 (s, 1H), 13.17 (s, 1H).

LC-MS (Method 1): $R_t$=1.01 min; MS (ESIpos): m/z=325 [M+H]$^+$.

Intermediate 87

3-[(2-chloropropanoy)amino]-4-[(methylsulfonyl)methyl]-N-(5-phenyl-1,3,4-thiadiazol-2-yl)benzamide

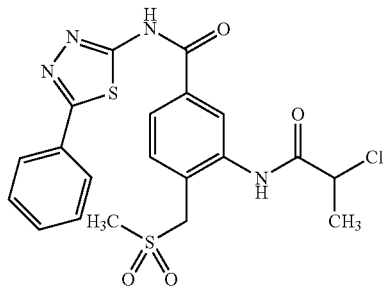 [SMILES: CC(Cl)C(=O)Nc1cc(C(=O)Nc2nnc(-c3ccccc3)s2)ccc1CS(C)(=O)=O]

1.50 g (3.86 mmol) of the compound from intermediate 55 were provided in 40 mL of toluene, 0.56 mL (5.79 mmol) of 2-chloropropanoyl chloride were added, and the mixture was stirred for 2 h at 100° C. After concentration, 1.85 g (100% of theory) of the title compound were obtained, which were used without further purification.

$^1$H-NMR (400 MHz, DMSO-d$_6$): δ [ppm]=1.67 (d, 3H), 2.95 (s, 3H), 4.65-4.75 (m, 2H), 4.84 (q, 1H), 7.53-7.58 (m, 3H), 7.67 (d, 1H), 7.96-8.02 (m, 2H), 8.06 (dd, 1H), 8.30-8.33 (m, 1H), 9.96 (s, 1H), 13.28 (s, 1H).

Intermediate 88

4-methoxy-3-nitro-N-(5-phenyl-1,3,4-thiadiazol-2-yl)benzamide

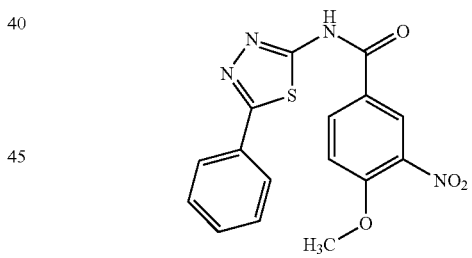

To a solution of 4-methoxy-3-nitrobenzoic acid (5.00 g, 25.4 mmol) and 5-phenyl-1,3,4-thiadiazol-2-amine (6.29 g, 35.5 mmol) in 110 mL of DMF were added (benzotriazol-1-yloxy)tripyrrolidinophosphonium hexafluorophosphate (PyBOP, 19.8 g, 38.0 mmol) and N,N-diisopropylethylamine (13.3 mL, 76.1 mmol). The mixture was stirred overnight at room temperature. (Benzotriazol-1-yloxy)tripyrrolidinophosphonium hexafluorophosphate (PyBOP, 6.60 g, 12.7 mmol) and N,N-diisopropylethylamine (4.4 mL, 25.4 mmol) were added, the mixture was stirred at room temperature for 2 hours and poured into water. The resulting precipitate was collected by filtration, washed with water and dried in vacuum to provide the crude desired product (8.57 g), which was used without further purification.

$^1$H-NMR (300 MHz, DMSO-d$_6$): δ [ppm]=4.04 (s, 3H), 7.51-7.59 (m, 4H), 7.92-8.02 (m, 2H), 8.44 (dd, 1H), 8.72 (d, 1H), 13.39 (s, 1H).

Intermediate 89

3-amino-4-methoxy-N-(5-phenyl-1,3,4-thiadiazol-2-yl)benzamide

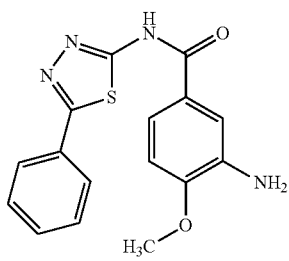 [SMILES: COc1ccc(C(=O)Nc2nnc(-c3ccccc3)s2)cc1N]

8.50 g (23.9 mmol) of the compound of intermediate 88 were provided in a mixture of 100 mL of ethanol and 150 mL of THF. 2.54 g of palladium on charcoal (10% Pd, 50% water) were added, and the mixture was stirred under a hydrogen atmosphere at room temperature for 1.5 h. 4.00 g of palladium on charcoal (10% Pd, 50% water) and 75 mL of ethanol and 100 mL of THF were added, and the mixture was stirred under a hydrogen atmosphere at room temperature for 1 h. A mixture of 75 mL of ethanol and 100 mL of THF and 4.00 g of palladium on charcoal (10% Pd, 50% water) were added, and the mixture was stirred under a hydrogen atmosphere at room temperature for 1.5 h. 3.00 g of palladium on charcoal (10% Pd) were added, and the mixture was stirred under a hydrogen atmosphere at room temperature for 5.25 h. After filtration, the solvents were evaporated. 6.67 g (86% of theory) of the title compound were obtained.

$^1$H-NMR (300 MHz, DMSO-$d_6$): δ [ppm]=3.86 (s, 3H), 5.02 (s, 2H), 6.93 (d, 1H), 7.38 (d, 1H), 7.47-7.60 (m, 4H), 7.93-8.00 (m, 2H), 12.79 (s, 1H).

LC-MS (Method 4): $R_t$=1.05 min; MS (ESIpos): m/z=327 [M+H]$^+$.

Intermediate 90

3-[(chloroacetyl)amino]-4-methoxy-N-(5-phenyl-1,3,4-thiadiazol-2-yl)benzamide

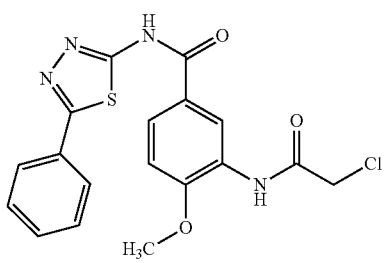 [SMILES: COc1ccc(C(=O)Nc2nnc(-c3ccccc3)s2)cc1NC(=O)CCl]

1.50 g (4.60 mmol) of the compound of intermediate 89 were provided in 40 mL of toluene, 0.55 mL (6.89 mmol) of chloroacetyl chloride were added, and the mixture was stirred for 2 h at 100° C. After concentration, 1.10 g of the title compound were obtained, which were used without further purification.

$^1$H-NMR (400 MHz, DMSO-$d_6$): δ [ppm]=3.97 (s, 3H), 4.43 (s, 2H), 7.26 (d, 1H), 7.52-7.59 (m, 3H), 7.96-8.00 (m, 2H), 8.05 (dd, 1H), 8.74-8.78 (m, 1H), 9.71 (s, 1H), 13.03 (s, 1H).

LC-MS (Method 4): $R_t$=1.15 min; MS (ESIpos): m/z=403 [M+H]$^+$.

Intermediate 91 methyl 4-(benzyloxy)-3-({[1-(morpholin-4-yl)cyclopropyl]carbonyl}amino)benzoate

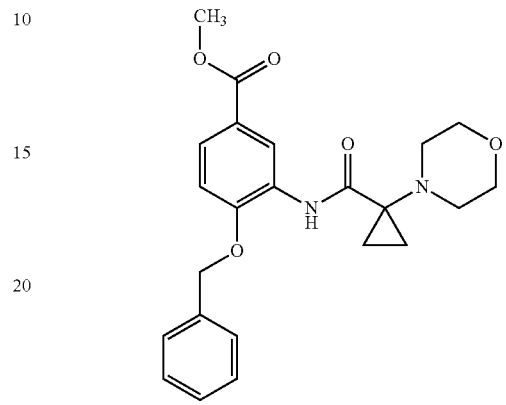

To a solution of methyl 3-amino-4-(benzyloxy)benzoate (5.00 g, 19.4 mmol) and 1-(morpholin-4-yl)cyclopropanecarboxylic acid hydrochloride (1:1) (intermediate 44, 4.84 g, 23.3 mmol) in DMF (50 mL) was added (benzotriazol-1-yloxy)tripyrrolidinophosphonium hexafluorophosphate (PYBOP, 20.2 g, 38.9 mmol) and diisopropylethylamine (16.9 mL, 97.2 mmol). The resulting mixture was stirred at room temperature over night, was concentrated under reduced pressure, was then dissolved in dichloromethane, was washed with 1N aqueous hydrogen chloride solution and saturated, aqueous sodium bicarbonate solution, was dried over sodium sulfate and concentrated under reduced pressure. The remaining solids were then triturated with ethanol (100 mL), and the resulting mixture was stirred for 30 minutes. The remaining solids were removed by filtration, washed with ethanol, and were dried at 50° C. under reduced pressure to give the title compound (7.98 g, 100% of theory).

LC-MS (Method 4): $R_t$=1.32 min; MS (ESIpos): m/z=411 [M+H]$^+$.

Intermediate 92

4-(benzyloxy)-3-({[1-(morpholin-4-yl)cyclopropyl]carbonyl}amino)benzoic acid

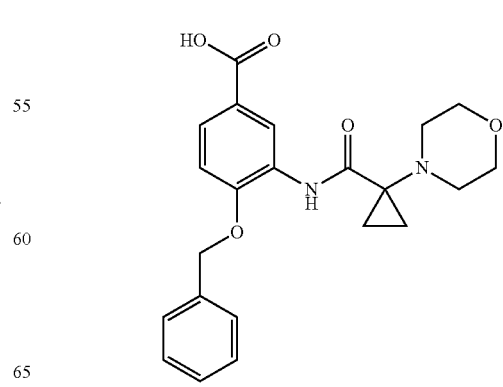

7.98 g (19.4 mmol) of the compound of intermediate 91 were provided in 80 mL of dioxane, 931 mg (38.9 mmol) of lithium hydroxide and 34 mL of water were added at room temperature and the mixture was stirred at room temperature for 22 hours. Water and a 2N aqueous hydrogen chloride solution were then added until an acidic pH of 1.5-2 was achieved. After stirring for 15 minutes, the precipitate was filtered off, washed with water and dried. 5.70 g (74% of theory) of the title compound were obtained, which were used without further purification.

$^1$H-NMR (400 MHz, DMSO-$d_6$): δ [ppm]=1.04-1.09 (m, 2H), 1.10-1.16 (m, 2H), 2.21-2.29 (m, 4H), 3.14-3.23 (m, 4H), 5.25 (s, 2H), 7.29 (d, 1H), 7.38-7.47 (m, 3H), 7.54-7.59 (m, 2H), 7.67 (dd, 1H), 8.92 (d, 1H), 10.37 (s, 1H).

LC-MS (Method 1): $R_t$=1.13 min; MS (ESIpos): m/z=397 [M+H]$^+$.

Intermediate 93

3-amino-4-bromo-N-(5-phenyl-1,3,4-thiadiazol-2-yl)benzamide

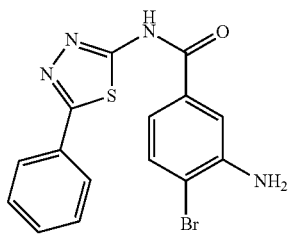 [SMILES: Nc1cc(C(=O)Nc2nnc(-c3ccccc3)s2)ccc1Br]

To a solution of 3-amino-4-bromobenzoic acid (10.0 g, 46.3 mmol) and 5-phenyl-1,3,4-thiadiazol-2-amine (6.84 g, 38.6 mmol) in DMF (140 mL) was added (benzotriazol-1-yloxy)tripyrrolidinophosphonium hexafluorophosphate (PYBOP, 40.1 g, 77.2 mmol) and diisopropylethylamine (26.9 mL, 154 mmol). The resulting mixture was stirred at room temperature over night. (Benzotriazol-1-yloxy)tripyrrolidinophosphonium hexafluorophosphate (PYBOP, 40.1 g, 77.2 mmol) and diisopropylethylamine (26.9 mL, 154 mmol) were added and the resulting mixture was stirred at room temperature for 3 days. The mixture was concentrated under reduced pressure, was then triturated with dichloromethane, and was concentrated under reduced pressure. The remaining solids were then triturated with ethanol (300 mL) and water (300 mL), and the resulting mixture was stirred for 30 minutes. The remaining solids were removed by filtration, washed with ethanol, and were dried at 50° C. under reduced pressure. The remaining solids were then triturated with ethanol (500 mL), and the resulting mixture was stirred under reflux. After cooling to room temperature, the remaining solids were removed by filtration, washed with ethanol, and were dried at 50° C. under reduced pressure. The remaining solids were then triturated with toluene (300 mL), and the resulting mixture was stirred under reflux. After cooling to room temperature, the remaining solids were removed by filtration, washed with toluene, and were dried at 50° C. under reduced pressure to give the title compound (13.7 g).

$^1$H-NMR (400 MHz, DMSO-$d_6$): δ [ppm]=5.64 (s, 2H), 7.25 (dd, 1H), 7.47 (d, 1H), 7.50-7.58 (m, 4H), 7.94-8.01 (m, 2H), 13.05 (s, 1H).

LC-MS (Method 4): $R_t$=1.18 min; MS (ESIpos): m/z=375 [M+H]$^+$.

Intermediate 94

4-bromo-3-[(chloroacetyl)amino]-N-(5-phenyl-1,3,4-thiadiazol-2-yl)benzamide

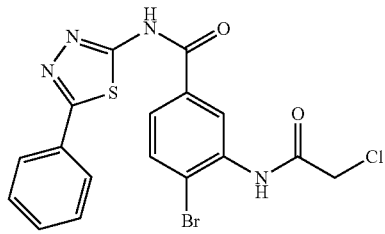 [SMILES: O=C(CCl)Nc1cc(C(=O)Nc2nnc(-c3ccccc3)s2)ccc1Br]

4.00 g (10.7 mmol) of the compound of intermediate 93 were provided in 100 mL of toluene, 1.27 mL (16.0 mmol) of chloroacetyl chloride were added, and the mixture was stirred for 2 h at 100° C. 20 mL of toluene were added and after concentration 4.80 g of the title compound were obtained, which were used without further purification.

$^1$H-NMR (400 MHz, DMSO-$d_6$): δ [ppm]=4.42 (s, 2H), 7.51-7.59 (m, 3H), 7.89-8.02 (m, 4H), 8.40 (d, 1H), 10.03 (s, 1H), 13.31 (s, 1H).

LC-MS (Method 4): $R_t$=1.21 min; MS (ESIpos): m/z=451 [M+H]$^+$.

Intermediate 95

3-amino-N-(5-phenylpyridin-2-yl)-4-(trifluoromethoxy)benzamide

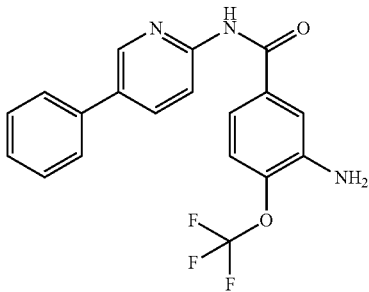 [SMILES: Nc1cc(C(=O)Nc2ccc(-c3ccccc3)cn2)ccc1OC(F)(F)F]

To a solution of 3-amino-4-(trifluoromethoxy)benzoic acid (known from WO2007/31791, 500 mg, 2.26 mmol) and 5-phenylpyridin-2-amine (654 mg, 3.84 mmol) in DMF (5 mL) was added (benzotriazol-1-yloxy)tripyrrolidinophosphonium hexafluorophosphate (PYBOP, 2.35 g, 4.52 mmol) and diisopropylethylamine (2.0 mL, 11.3 mmol). The resulting mixture was stirred at room temperature for 3 days. The mixture was triturated with water and extracted with ethyl acetate. The combined organic phases were dried over sodium sulfate and concentrated under reduced pressure. The residue was purified using MPLC (Biotage Isolera; silica gel; hexane/EtOAc gradient). 98.0 mg (11% of theory) of the title compound were obtained.

$^1$H-NMR (300 MHz, DMSO-$d_6$): δ [ppm]=5.65 (s, 2H), 7.17-7.29 (m, 2H), 7.35-7.45 (m, 2H), 7.46-7.55 (m, 2H), 7.69-7.79 (m, 2H), 8.15 (dd, 1H), 8.25 (d, 1H), 8.71 (d, 1H), 10.76 (s, 1H).

LC-MS (Method 4): $R_t$=1.31 min; MS (ESIpos): m/z=374 [M+H]$^+$.

Intermediate 96

3-amino-N-(5-bromo-1,3,4-thiadiazol-2-yl)-4-(trifluoromethoxy)benzamide

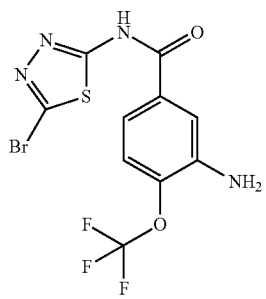 [SMILES: Nc1cc(C(=O)Nc2nnc(Br)s2)ccc1OC(F)(F)F]

To a solution of 3-amino-4-(trifluoromethoxy)benzoic acid (known from WO2007/31791, 2.00 g, 9.04 mmol) and 5-bromo-1,3,4-thiadiazol-2-amine (2.77 g, 15.4 mmol) in DMF (20 mL) was added (benzotriazol-1-yloxy)tripyrrolidinophosphonium hexafluorophosphate (PYBOP, 9.41 g, 18.1 mmol) and diisopropylethylamine (7.9 mL, 45.2 mmol). The resulting mixture was stirred at room temperature over night, was concentrated under reduced pressure, was then triturated with water, and was extracted with ethyl acetate. The combined organic phases were dried over sodium sulfate and concentrated under reduced pressure. The remaining solids were then triturated with ethanol (50 mL) and water (50 mL), and the resulting mixture was stirred for 15 minutes. The remaining solids were removed by filtration, washed with water, and were dried at 50° C. under reduced pressure. The residue was purified using MPLC (Biotage Isolera; silica gel; hexane/EtOAc gradient). 310 mg (9% of theory) of the title compound were obtained.

$^1$H-NMR (400 MHz, DMSO-d$_6$): δ [ppm]=5.74 (s, 2H), 7.27 (dd, 1H), 7.32 (dd, 1H), 7.49 (d, 1H), 13.29 (s, 1H).

LC-MS (Method 1): $R_t$=1.14 min; MS (ESIpos): m/z=383 [M+H]$^+$.

Intermediate 97

3-[(chloroacetyl)amino]-4-[(methylsulfonyl)methyl]-N-(5-phenyl-1,3,4-thiadiazol-2-yl)benzamide

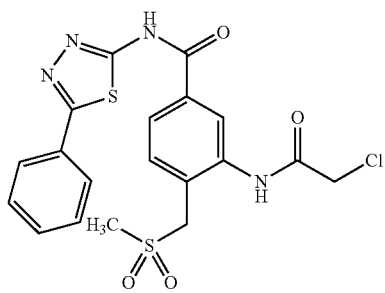 [SMILES: CS(=O)(=O)Cc1ccc(C(=O)Nc2nnc(-c3ccccc3)s2)cc1NC(=O)CCl]

1.50 g (3.86 mmol) of the compound of intermediate 55 were provided in 50 mL of toluene, 0.46 mL (5.79 mmol) of chloroacetyl chloride were added, and the mixture was stirred for 2 h at 100° C. 20 mL of toluene were added and after concentration 1.80 g of the title compound were obtained, which were used without further purification.

$^1$H-NMR (400 MHz, DMSO-d$_6$): δ [ppm]=2.96 (s, 3H), 4.40 (s, 2H), 4.71 (s, 2H), 7.53-7.58 (m, 3H), 7.67 (d, 1H), 7.96-8.02 (m, 2H), 8.06 (dd, 1H), 8.31-8.33 (m, 1H), 9.88 (s, 1H), 13.27 (s, 1H).

Intermediate 98 methyl 2-amino-4-[(5-phenyl-1,3,4-thiadiazol-2-yl)carbamoyl]benzoate

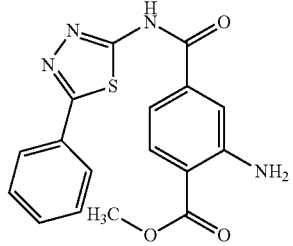 [SMILES: COC(=O)c1ccc(C(=O)Nc2nnc(-c3ccccc3)s2)cc1N]

To a solution of 3-amino-4-(methoxycarbonyl)benzoic acid (5.00 g, 25.6 mmol) and 5-phenyl-1,3,4-thiadiazol-2-amine (6.81 g, 38.4 mmol) in DMF (150 mL) was added (benzotriazol-1-yloxy)tripyrrolidinophosphonium hexafluorophosphate (PYBOP, 26.7 g, 51.2 mmol) and diisopropylethylamine (22.3 mL, 128 mmol). The resulting mixture was stirred at room temperature over night, was then triturated with water, and was stirred for 15 minutes. The precipitate was removed by filtration, washed with water, and was dried at 50° C. under reduced pressure. 2.87 g (32% of theory) of the title compound were obtained.

$^1$H-NMR (300 MHz, DMSO-d$_6$): δ [ppm]=3.83 (s, 3H), 6.88 (s, 2H), 7.23 (dd, 1H), 7.47 (d, 1H), 7.52-7.58 (m, 3H), 7.83 (d, 1H), 7.94-8.02 (m, 2H), 13.21 (s, 1H).

LC-MS (Method 1): $R_t$=1.21 min; MS (ESIpos): m/z=355 [M+H]$^+$.

Intermediate 99 methyl 2-[(chloroacetyl)amino]-4-[(5-phenyl-1,3,4-thiadiazol-2-yl)carbamoyl]benzoate

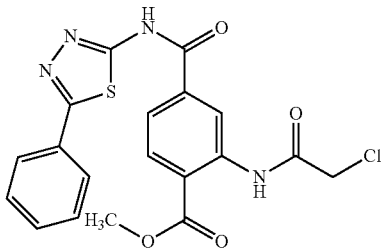 [SMILES: COC(=O)c1ccc(C(=O)Nc2nnc(-c3ccccc3)s2)cc1NC(=O)CCl]

To a suspension of the compound of the intermediate 98 (2.87 g, 8.10 mmol) and pyridine (1.64 mL, 20.3 mmol) in CH$_2$Cl$_2$ (50 mL) at 0° C. was added chloroacetyl chloride (0.77 mL, 9.72 mmol) dropwise. The resulting mixture was allowed to warm to room temperature, was stirred at that temperature over night, was then concentrated and afterwards triturated with 100 mL of a 2/1 mixture of water and ethanol. The precipitate was removed by filtration, washed with water, and was dried at 50° C. under reduced pressure.

4.07 g of the title compound were obtained. This material was used in subsequent reactions without further purification.

$^1$H-NMR (300 MHz, DMSO-d$_6$): δ [ppm]=3.92 (s, 3H), 4.49 (s, 2H), 7.52-7.61 (m, 3H), 7.94-8.04 (m, 3H), 8.11 (d, 1H), 8.95-9.00 (m, 1H), 11.28 (s, 1H), 13.51 (s, 1H).

LC-MS (Method 1): R$_t$=1.28 min; MS (ESIpos): m/z=431 [M+H]$^+$.

Intermediate 100

N-(4-methoxy-3-nitrophenyl)-2-phenyl-1,3-thiazole-5-carboxamide

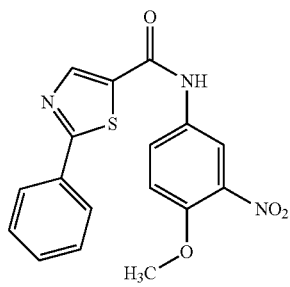 [SMILES: COc1ccc(NC(=O)c2cnc(-c3ccccc3)s2)cc1[N+](=O)[O-]]

To a solution of 2-phenyl-1,3-thiazole-5-carboxylic acid (502 mg, 2.45 mmol) in diisopropylethylamine (1.25 mL, 7.19 mmol) and DMF (8.2 mL) were added 4-methoxy-3-nitroaniline (403 mg, 2.40 mmol) and 2.10 mL of a 50% solution of 2,4,6-tripropyl-1,3,5,2,4,6-trioxatriphosphinane 2,4,6-trioxide (T3P) in DMF (3.60 mmol). The mixture was stirred over night at room temperature. Water was added and the mixture was extracted three times with ethyl acetate. The combined organic layers were dried over MgSO$_4$ and concentrated in vacuum. After flash-chromatography of the residue the product was suspended in ethyl acetate and stirred with saturated NaHCO$_3$ solution to remove acidic impurities. The layers were separated, the organic layer was dried over MgSO$_4$ and provided after removal of the solvent the desired product (202 mg, 23%).

$^1$H-NMR (400 MHz, DMSO-d$_6$): δ [ppm]=3.93 (s, 3H), 7.45 (s, 1H), 7.52-7.61 (m, 3H), 8.05 (s, 3H), 8.33 (d, 1H), 8.67 (s, 1H), 10.69 (s, 1H).

LC-MS (Method 4): R$_t$=1.24 min; MS (ESIpos): m/z=356 [M+H]$^+$.

Intermediate 101

N-(3-amino-4-methoxyphenyl)-2-phenyl-1,3-thiazole-5-carboxamide

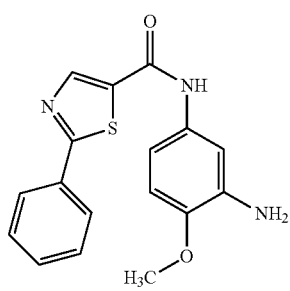 [SMILES: COc1ccc(NC(=O)c2cnc(-c3ccccc3)s2)cc1N]

The compound of intermediate 100 (88.0 mg, 248 μmol) was dissolved in THF (1.85 mL) and cooled to 0° C. At that temperature 1.68 mL of a 10% aqueous hydrogen chloride solution containing 15% of titanium(III) trichloride (1.98 mmol) were added. The mixture was stirred over night. Under ice bath cooling 2 mL of the titanium(III) trichloride solution were added and the mixture was stirred at 40° C. over night. Afterwards 2 mL of the titanium(III) trichloride solution were added again under ice bath cooling. The mixture was stirred additionally over night at 40° C. The reaction mixture was neutralized by addition of solid sodium bicarbonate, saturated with sodium chloride and stirred with 50 mL of a 1:1 mixture of THF and ethyl acetate for 2 h. The precipitate was filtered off. The filtrate was washed with brine, dried over MgSO$_4$ and concentrated in vacuum to yield the desired compound 101 (123 mg, quant.) as crude product, which was used in the next step without any further purification.

LC-MS (Method 1): R$_t$=1.16 min; MS (ESIpos): m/z=326 [M+H]$^+$.

Intermediate 102

N-{3-[(2-chloropropanoy)amino]-4-methoxyphenyl}-2-phenyl-1,3-thiazole-5-carboxamide

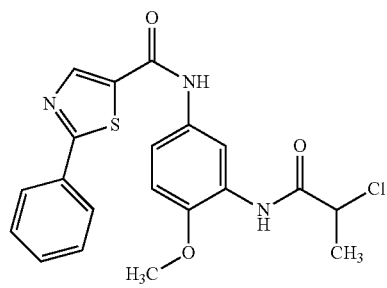 [SMILES: COc1ccc(NC(=O)c2cnc(-c3ccccc3)s2)cc1NC(=O)C(C)Cl]

To a solution of the compound of intermediate 101 (123 mg, 380 μmol) in toluene (1.90 mL) was added under argon 2-chloropropionyl chloride (76 μL, 759 μmol). The mixture was stirred for 2 h at 100° C. and was subsequently concentrated. The residue yielded the desired product 102 (469 mg, 78% pure, 84%) as crude material which was used without further purification.

LC-MS (Method 1): R$_t$=1.35 min; MS (ESIpos): m/z=416 [M+H]$^+$.

Intermediate 103

N-[3-nitro-4-(trifluoromethoxy)phenyl]-2-phenyl-1,3-thiazole-5-carboxamide

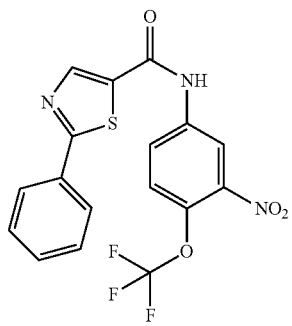

To a solution of 3-nitro-4-(trifluoromethoxy)aniline (668 mg, 3.01 mmol) and 2-phenyl-1,3-thiazole-5-carboxylic acid (772 mg, 3.76 mmol) in DMF (7.0 mL) were added diisopropylethylamine (1.57 mL, 9.03 mmol) and (benzotriazol-1-yloxy)tripyrrolidinophosphonium hexafluorophosphate (PYBOP, 2.35 g, 4.51 mmol). The mixture was stirred for 3 d at 60° C. After cooling to room temperature the mixture was poured into water. The resulting precipitate was filtered off, washed with water and dried at 40° C. under vacuum. The crude material was suspended in methanol, stirred at room temperature. Insoluble material was collected by filtration and dried to provide the desired intermediate 103 90% pure (1.16 g, 85%).

$^1$H-NMR (300 MHz, DMSO-$d_6$): δ [ppm]=7.49-7.59 (m, 3H), 7.79 (d, 1H), 8.00-8.08 (m, 2H), 8.17 (dd, 1H), 8.61 (d, 1H), 8.72 (s, 1H), 11.02 (s, 1H).

LC-MS (Method 4): $R_t$=1.43 min; MS (ESIpos): m/z=410 [M+H]$^+$.

Intermediate 104

N-[3-amino-4-(trifluoromethoxy)phenyl]-2-phenyl-1,3-thiazole-5-carboxamide

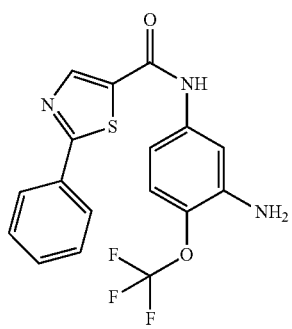 [SMILES: O=C(Nc1ccc(OC(F)(F)F)c([N+](=O)[O-])c1)c1cnc(-c2ccccc2)s1]

The compound of intermediate 103 (1.16 g, 2.83 mmol) was suspended in a mixture of THF/MeOH (15 mL/25 mL) and palladium on charcoal (10% Pd, 151 mg) was added. The mixture was stirred over night under hydrogen atmosphere. The mixture was filtered over a pad of Celite. The filtrate was concentrated and the residue was purified by flash-chromatography to provide the desired compound 104 72% pure (310 mg, 21%).

$^1$H-NMR (300 MHz, DMSO-$d_6$): δ [ppm]=5.46 (s, 2H), 6.88 (dd, 1H), 7.09 (dd, 1H), 7.28 (d, 1H), 7.49-7.60 (m, 3H), 7.96-8.10 (m, 2H), 8.66 (s, 1H), 10.33 (s, 1H).

LC-MS (Method 1): $R_t$=1.28 min; MS (ESIpos): m/z=380 [M+H]$^+$.

Intermediate 105 ethyl 3-amino-4-(trifluoromethoxy)benzoate

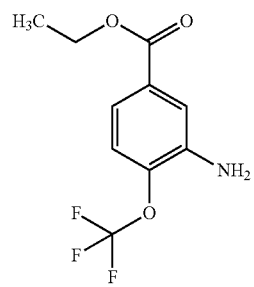 [SMILES: CCOC(=O)c1ccc(OC(F)(F)F)c(N)c1]

3-Amino-4-(trifluormethoxy)benzoic acid (20.0 g, 90.4 mmol) were treated carefully under argon with thionyl chloride (38.0 mL, 520 mmol). The resulting suspension was stirred for 15 min at room temperature. Ethanol (136 mL, 2.33 mol) was added dropwise at 0° C. into the mixture. The reaction mixture was stirred for 30 min at 0° C., over night at room temperature and subsequently 5 h under reflux. After cooling to room temperature the mixture was concentrated, the residue was diluted with water and extracted three times with ethyl acetate. The combined organic layers were washed with saturated NaHCO$_3$-solution, dried over MgSO$_4$ and the solvent was removed under reduced pressure to provide the desired compound 105 (25.7 g, quant.) as crude product which was used without further purification.

$^1$H-NMR (400 MHz, DMSO-$d_6$): δ [ppm]=1.30 (t, 3H), 4.28 (q, 2H), 5.68 (s, 2H), 7.11-7.16 (m, 1H), 7.19-7.23 (m, 1H), 7.45 (d, 1H).

LC-MS (Method 4): $R_t$=1.22 min; MS (ESIpos): m/z=250 [M+H]$^+$.

Intermediate 106 ethyl 3-[(2-chloropropanoyl)amino]-4-(trifluoromethoxy)benzoate

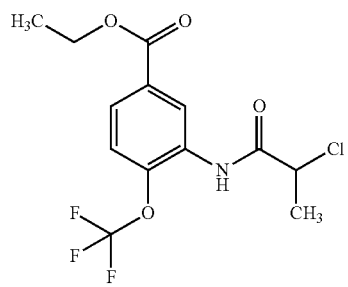 [SMILES: CCOC(=O)c1ccc(OC(F)(F)F)c(NC(=O)C(C)Cl)c1]

A solution of the compound of intermediate 105 (25.5 g, 102 mmol) in toluene (513 mL) was treated with 2-chloropropionyl chloride (20.5 mL, 205 mmol). The resulting mixture was stirred for 2 h at 100° C. and concentrated after cooling to room temperature under reduced pressure to provide the desired compound 106 as crude product (34.9 g, 97%) which was used without further purification.

¹H-NMR (300 MHz, DMSO-d₆): δ [ppm]=1.32 (t, 3H), 1.62 (d, 3H), 4.34 (q, 2H), 4.89 (q, 1H), 7.59 (dd, 1H), 7.88 (dd, 1H), 8.46 (d, 1H), 10.28 (s, 1H).

LC-MS (Method 1): $R_t$=1.30 min; MS (ESIpos): m/z=340 [M+H]⁺.

Intermediate 107 ethyl 3-{[2-(morpholin-4-yl)propanoyl]amino}-4-(trifluoromethoxy)benzoate

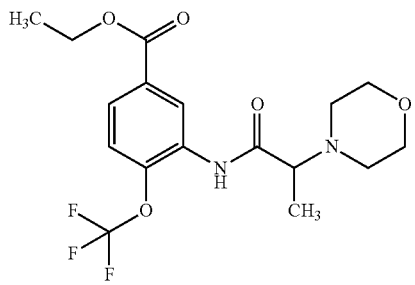 [SMILES: CCOC(=O)c1ccc(OC(F)(F)F)c(NC(=O)C(C)N2CCOCC2)c1]

To a solution of the compound of intermediate 106 (34.9 g, 103 mmol) in DMF (442 mL) morpholine (13.4 mL, 154 mmol), potassium iodide (2.64 g, 15.9 mmol) and triethylamine (21.4 mL, 154 mmol) were added. The mixture was stirred over night at room temperature and for 7 h at 90° C. After cooling to room temperature the mixture was poured into water and extracted three times with ethyl acetate. The combined organic layers were dried over MgSO₄ and concentrated under reduced pressure. The obtained desired product 107 (36.3 g, 80%) was used in the next step without any further purification.

¹H-NMR (300 MHz, DMSO-d₆) δ [ppm]=1.21 (d, 3H), 1.32 (t, 3H), 2.52-2.58 (m, 4H), 3.40 (d, 1H), 3.61-3.68 (m, 4H), 4.34 (q, 2H), 7.59 (dd, 1H), 7.80 (dd, 1H), 8.81 (d, 1H), 10.05 (s, 1H).

LC-MS (Method 1): $R_t$=1.05 min; MS (ESIpos): m/z=391 [M+H]⁺.

Intermediate 108 lithium 3-{[2-(morpholin-4-yl)propanoyl]amino}-4-(trifluoromethoxy)benzoate

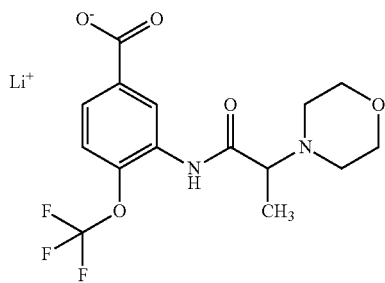 [SMILES: [Li+] ; CC(C(=O)Nc1cc(C(=O)[O-])ccc1OC(F)(F)F)N1CCOCC1]

A solution of the compound of intermediate 107 (4.38 g, 11.2 mmol) in a mixture of THF/methanol (93 mL/24 mL) was treated with a 1M aqueous lithium hydroxide solution (13.5 mL, 13.5 mmol) and was stirred for 2.5 h at room temperature. The mixture was concentrated under reduced pressure to provide the desired compound 108 as 85% pure material (4.76 g, 98%).

¹H-NMR (400 MHz, DMSO-d₆): δ [ppm]=1.18-1.22 (m, 3H), 2.51-2.59 (m, 4H), 3.63-3.68 (m, 4H), 7.25 (dd, 1H), 7.67 (dd, 1H), 8.50 (d, 1H), 9.73 (s, 1H).

LC-MS (Method 4): $R_t$=0.76 min; MS (ESIpos): m/z=363 [M−Li⁺+H⁺+H]⁺.

Intermediate 109

N-(6-chloropyridin-3-yl)-3-{[2-(morpholin-4-yl)propanoyl]amino}-4-(trifluoromethoxy)benzamide

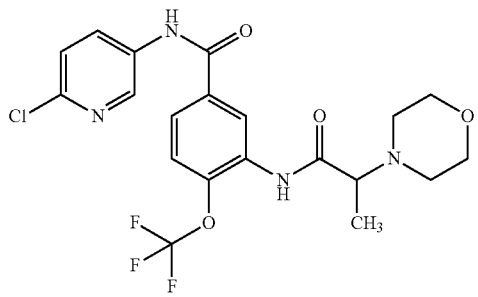 [SMILES: CC(C(=O)Nc1cc(C(=O)Nc2ccc(Cl)nc2)ccc1OC(F)(F)F)N1CCOCC1]

To a solution of the compound of intermediate 108 (13.5 g, 37.2 mmol) and 5-amino-2-chloropyridine (9.57 g, 74.4 mmol) in DMF (273 mL) were added (benzotriazol-1-yloxy)tripyrrolidinophosphonium hexafluorophosphate (PYBOP, 29.0 g, 55.8 mmol) and diisopropylethylamine (19.4 mL, 112 mmol). The reaction mixture was stirred over night at 60° C. After cooling to room temperature the mixture was added dropwise into water. The water was removed by decantation. The residue was dissolved in ethanol and was added dropwise into water. After stirring over night at room temperature, the precipitate was collected by filtration and dried at 60° C. under reduced pressure. The title compound 109 was obtained 93% pure (12.9 g, 25.3 mmol, 68%).

¹H-NMR (300 MHz, DMSO-d₆) δ [ppm]=1.22 (d, 3H), 2.53-2.57 (m, 4H), 3.35-3.44 (m, 1H), 3.63-3.68 (m, 4H), 7.54 (d, 1H), 7.62-7.68 (m, 1H), 7.82 (m, 1H), 8.20-8.28 (m, 1H), 8.75 (dd, 2H), 10.05 (s, 1H), 10.73 (s, 1H).

LC-MS (Method 4): $R_t$=0.99 min; MS (ESIpos): m/z=473 [M+H]⁺.

Intermediate 110

N-(6-chloropyridin-3-yl)-3-[(morpholin-4-ylacetyl)amino]-4-(trifluoromethoxy)benzamide

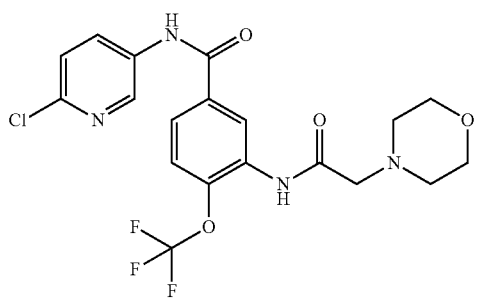 [SMILES: O=C(CN1CCOCC1)Nc1cc(C(=O)Nc2ccc(Cl)nc2)ccc1OC(F)(F)F]

To a solution of intermediate 21 (500 mg, 1.44 mmol) and 5-amino-2-chloropyridine (277 mg, 2.15 mmol) in DMF (3.0 mL) were added (benzotriazol-1-yloxy)tripyrrolidinophosphonium hexafluorophosphate (PYBOP, 1.21 g, 2.15 mmol) and diisopropylethylamine (750 μL, 4.31 mmol). The reaction mixture was stirred for 3 d at 60° C. After cooling to room temperature the mixture was poured into water. The precipitate was collected by filtration and was dried at 40° C. under reduced pressure to yield the desired crude intermediate 110 (349 mg, 52%).

$^1$H-NMR (300 MHz, DMSO-d$_6$) δ [ppm]=2.54-2.62 (m, 4H), 3.23 (s, 2H), 3.61-3.68 (m, 4H), 7.54 (d, 1H), 7.63-7.69 (m, 1H), 7.79-7.87 (m, 1H), 8.20-8.28 (m, 1H), 8.77 (t, 2H), 9.93 (s, 1H), 10.74 (s, 1H).

LC-MS (Method 4): R$_t$=1.16 min; MS (ESIpos): m/z=459 [M+H]$^+$.

Intermediate 111

3-[(2-chloropropanoy)amino]-N-(5-phenyl-1,3,4-thiadiazol-2-yl)-4-(trifluoromethyl)benzamide

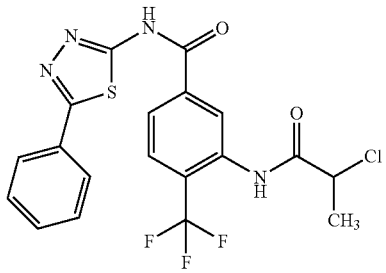 [SMILES: CC(Cl)C(=O)Nc1cc(C(=O)Nc2nnc(-c3ccccc3)s2)ccc1C(F)(F)F]

To a solution of intermediate 60 (1.00 g, 2.75 mmol) in toluene (13.7 mL) was added 2-chloropropanoyl chloride under inert gas atmosphere. The reaction mixture was stirred for 4 h at 100° C. The mixture was treated again with the same amount of chloropropanoyl chloride and was stirred over night at 100° C. After cooling to room temperature the mixture was concentrated to obtain the desired crude product (1.30 g, 99%) which was used in the next step without further purification.

$^1$H-NMR (400 MHz, DMSO-d$_6$) δ [ppm]=1.66 (d, 3H), 7.51-7.61 (m, 3H), 7.94-8.05 (m, 3H), 8.19-8.29 (m, 2H), 10.17 (s, 1H), 13.50 (br. s, 1H).

LC-MS (Method 4): R$_t$=1.18 min; MS (ESIpos): m/z=455 [M+H]$^+$.

Intermediate 112

3-{[(4-methylpiperazin-1-yl)acetyl]amino}-4-(trifluoromethoxy)benzoic acid

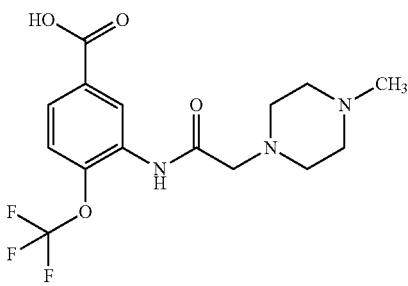 [SMILES: CN1CCN(CC(=O)Nc2cc(C(=O)O)ccc2OC(F)(F)F)CC1]

To a suspension of intermediate 19 (4.10 g, 13.8 mmol) in DMF (78.6 ml) was added triethylamine (2.88 ml, 20.7 mmol) to yield a clear solution. This solution was treated under inert gas atmosphere with potassium iodide (354 mg, 2.14 mmol) and 1-methylpiperazine (2.29 ml, 20.7 mmol). The reaction mixture was stirred over night at room temperature and filtrated afterwards. The filtrate was concentrated in vacuum to yield the desired product (7.90 g, 76% pure, quant.) as crude material with was used without any further purification.

$^1$H NMR (400 MHz, DMSO-d$_6$) δ [ppm]=2.28 (s, 3H), 2.57-2.58 (m, 4H), 3.22 (s, 2H), 7.55 (dd, 1H), 7.78 (dd, 1H), 8.84 (d, 1H), 9.89 (s, 1H).

LC-MS (Method 4): R$_t$=0.57 min; MS (ESIneg): m/z=360 [M–H]$^-$.

Intermediate 113

2-(2-fluorophenyl)-5-nitropyridine

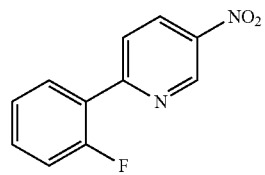 [SMILES: O=[N+]([O-])c1ccc(-c2ccccc2F)nc1]

To 7.4 g (36.45 mmol) of 2-bromo-5-nitropyridine and 5.6 g (40.10 mmol) of (2-fluorophenyl)boronic acid in 222 mL of toluene and 55 mL of ethanol were added 409 mg (1.82 mmol) of palladium(II)diacetate, 956 mg (3.65 mmol) of triphenylphosphine and 36.4 mL (36.4 mmol) of an aqueous sodium carbonate solution (1M). The reaction mixture was stirred for 5 h under reflux. The reaction mixture was allowed to reach rt. The reaction mixture was concentrated and elutriated in water. EtOAc was added, the layers were separated and the aqueous layer was extracted twice with EtOAc. The combined organic phases were washed with water, dried over magnesium sulfate and concentrated. The residue was purified on silica gel (n-hexane/EtOAc 7:3) to provide 7.25 g (89%) of the desired intermediate.

$^1$H-NMR (300 MHz, DMSO-d$_6$): δ [ppm]=7.36-7.48 (m, 2H), 7.55-7.66 (m, 1H), 7.98-8.13 (m, 2H), 8.69 (dd, 1H), 9.48 (d, 1H).

LC-MS (Method 4): R$_t$=1.20 min; MS (ESIpos): m/z=219 [M+H]$^+$.

Intermediate 114

6-(2-fluorophenyl)pyridin-3-amine

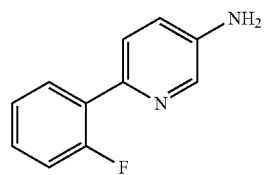 [SMILES: Nc1ccc(-c2ccccc2F)nc1]

To a suspension of 7.66 g (35.11 mmol) of 2-(2-fluorophenyl)-5-nitropyridine (intermediate 113) in 500 mL of a mixture of THF/methanol 1:1 were added 2.3 g of palladium on charcoal (10% Pd with 50% water). It was hydrogenated for 4.5 h at rt. The catalyst was filtered off and washed with 100 mL of THF and 100 mL of methanol. The filtrate was concentrated. The residue was suspended twice in toluene and concentrated again. 6.76 g (99%) of the desired product were isolated.

$^1$H-NMR (400 MHz, DMSO-$d_6$): δ [ppm]=5.54 (br. s, 2H), 6.98 (dd, 1H), 7.18-7.26 (m, 2H), 7.28-7.35 (m, 1H), 7.45-7.50 (m, 1H), 7.86 (td, 1H), 8.05 (d, 1H).

LC-MS (Method 4): $R_t$=0.56 min; MS (ESIpos): m/z=189 [M+H]$^+$.

Intermediate 115

4-(cyclopropyloxy)-N-[6-(2-fluorophenyl)pyridin-3-yl]-3-nitrobenzamide

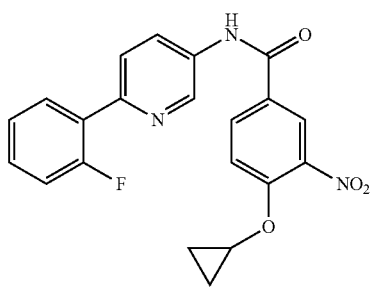 [SMILES: O=C(Nc1ccc(-c2ccccc2F)nc1)c1ccc(OC2CC2)c([N+](=O)[O-])c1]

2.5 g (11.20 mmol) 4-(cyclopropyloxy)-3-nitrobenzoic acid was dissolved in 40 mL of anh DMF. 2.53 g (13.44 mmol) of 6-(2-fluorophenyl)pyridin-3-amine (intermediate 114), 7.8 mL (44.81 mmol) of N-ethyl-N-isopropylpropan-2-amine and 7.00 g (13.44 mmol) of PYBOP were added. It was stirred at rt over night. The volatile was removed under vacuum and the residue was triturated with water/methanol 7:3. The remaining solid was filtered off, washed with water/methanol 7:3 and dried under vacuum at 45° C. yielding 4.4 g (95%) of the title compound.

$^1$H-NMR (300 MHz, DMSO-$d_6$): δ [ppm]=0.74-0.96 (m, 4H), 4.21 (mc, 1H), 7.27-7.38 (m, 2H), 7.41-7.52 (m, 1H), 7.76-7.88 (m, 2H), 7.92-8.00 (m, 1H), 8.28-8.38 (m, 2H), 8.56 (d, 1H), 9.05 (d, 1H), 10.68 (s, 1H).

LC-MS (Method 4): $R_t$=1.30 min; MS (ESIpos): m/z=394 [M+H]$^+$.

Intermediate 116

3-amino-4-(cyclopropyloxy)-N-[6-(2-fluorophenyl)pyridin-3-yl]benzamide

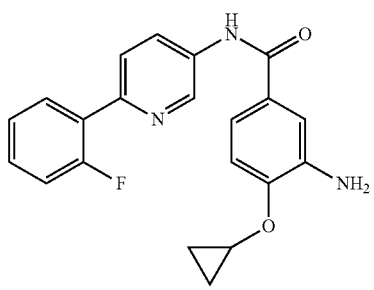 [SMILES: Nc1cc(C(=O)Nc2ccc(-c3ccccc3F)nc2)ccc1OC1CC1]

2.0 g (5.08 mmol) of 4-(cyclopropyloxy)-N-[6-(2-fluorophenyl)pyridin-3-yl]-3-nitrobenzamide (intermediate 115) were dissolved in 80 mL of a mixture of THF/methanol 1:1 and 0.325 g of palladium on charcoal (10% Pd with 50% water) were added. It was hydrogenated for 4 h at rt. The catalyst was filtered off, washed with 30 mL of THF and 30 mL of methanol. The filtrate was concentrated and twice suspended in toluene and concentrated again. 1.64 g (85%) of the title compound was obtained.

$^1$H-NMR (300 MHz, DMSO-$d_6$): δ [ppm]=0.65-0.86 (m, 4H), 3.87-3.96 (m, 1H), 4.90 (s, 2H), 7.14-7.36 (m, 5H), 7.40-7.50 (m, 1H), 7.79 (dd, 1H), 7.90-7.99 (m, 1H), 8.29 (dd, 1H), 9.04 (d, 1H), 10.30 (s, 1H).

LC-MS (Method 4): $R_t$=1.16 min; MS (ESIpos): m/z=364 [M+H]$^+$.

Intermediate 117

N-[6-(2-fluorophenyl)pyridin-3-yl]-4-(methylsulfanyl)-3-nitrobenzamide

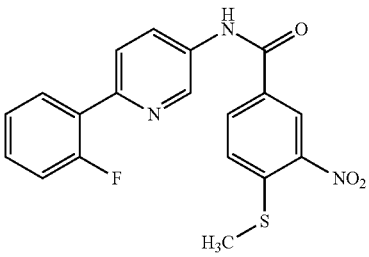 [SMILES: CSc1ccc(C(=O)Nc2ccc(-c3ccccc3F)nc2)cc1[N+](=O)[O-]]

5.296 g (28.148 mmol) of 6-(2-fluorophenyl)pyridin-3-amine (intermediate 114), 5.0 g (23.45 mmol) of 4-(methylsulfanyl)-3-nitrobenzoic acid and 14.644 g (28.14 mmol) of PYBOP were dissolved in 150 mL of anh DMF. 4.9 mL (28.14 mmol) of N-ethyl-N-isopropylpropan-2-amine were added. It was stirred at rt over night. The reaction mixture was concentrated to approximately 50% of the original volume. The reaction mixture was added dropwise into water. The solid material was filtered off and 60 mL of EtOAc were added. It was stirred under heat so that some material was dissolved and then it was allowed to reach rt. The solid was filtered off yielding 8.57 g (75%) of the title compound.

$^1$H-NMR (300 MHz, DMSO-$d_6$): δ [ppm]=2.62 (s, 3H), 7.28-7.38 (m, 2H), 7.42-7.51 (m, 1H), 7.77 (d, 1H), 7.81-7.88 (m, 1H), 7.92-8.00 (m, 1H), 8.28-8.36 (m, 2H), 8.90 (d, 1H), 9.08 (d, 1H), 10.84 (s, 1H).

LC-MS (Method 4): $R_t$=1.27 min; MS (ESIpos): m/z=384 [M+H]$^+$.

Intermediate 118

3-amino-N-[6-(2-fluorophenyl)pyridin-3-yl]-4-(methylsulfanyl)benzamide

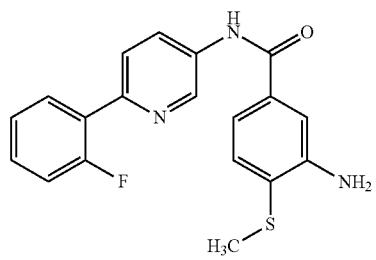 [SMILES: CSc1ccc(C(=O)Nc2ccc(-c3ccccc3F)nc2)cc1N]

8.07 g (21.04 mmol) of N-[6-(2-fluorophenyl)pyridin-3-yl]-4-(methylsulfanyl)-3-nitrobenzamide (intermediate 117) were dissolved in 389 mL of methanol and 389 mL of THF. 1.277 g of 10% palladium on charcoal (with 50% water) were added and the resulting mixture was stirred at 60° C. over night under an atmosphere of hydrogen. This reaction was combined with a reaction mixture of a 0.5 g batch of the same material. The catalyst was filtered off. The filtrate was concentrated to yield 7.61 g (96%) of the title compound.

$^1$H-NMR (300 MHz, DMSO-d$_6$): δ [ppm]=2.43 (s, 3H), 5.33 (s, 2H), 7.18-7.36 (m, 5H), 7.41-7.50 (m, 1H), 7.80 (dd, 1H), 7.95 (td, 1H), 8.29 (dd, 1H), 9.05 (d, 1H), 10.43 (s, 1H).

LC-MS (Method 4): R$_t$=1.14 min; MS (ESIpos): m/z=344 [M+H]$^+$.

Intermediate 119

4-tert-butyl-N-(6-chloropyridin-3-yl)-3-nitrobenzamide

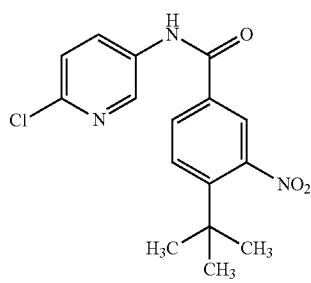 [SMILES: CC(C)(C)c1ccc(C(=O)Nc2ccc(Cl)nc2)cc1[N+](=O)[O-]]

500 mg (2.24 mmol) of 4-tert-butyl-3-nitrobenzoic acid and 345 mg (2.69 mmol) of 6-chloropyridin-3-amine were dissolved in 13.8 mL of anh DMF. 1.83 mL (3.14 mmol) of 2,4,6-tripropyl-1,3,5,2,4,6-trioxatriphosphinane 2,4,6-trioxide (50% in DMF) and 1.95 mL (11.20 mmol) of N-ethyl-N-isopropylpropan-2-amine were added. It was stirred 24 h at rt. The reaction mixture was poured into water and extracted three times with EtOAc. The combined organic phases were dried over sodium sulfate and concentrated affording 720 mg (96%) of the title compound.

LC-MS (Method 3): R$_t$=1.31 min; MS (ESIpos): m/z=334 [M+H]$^+$.

Intermediate 120

4-tert-butyl-N-[6-(2-fluorophenyl)pyridin-3-yl]-3-nitrobenzamide

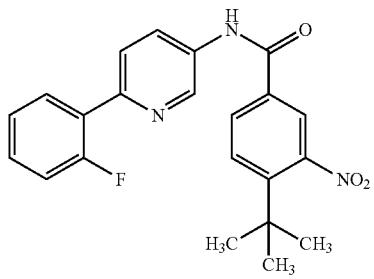 [SMILES: CC(C)(C)c1ccc(C(=O)Nc2ccc(-c3ccccc3F)nc2)cc1[N+](=O)[O-]]

720 mg (2.16 mmol) of 4-tert-butyl-N-(6-chloropyridin-3-yl)-3-nitrobenzamide (intermediate 119), 453 mg (3.24 mmol) of (2-fluorophenyl)boronic acid and 596 mg (4.31 mmol) of potassium carbonate were suspended in 21.8 mL of a mixture of DME/water 3:1 and purged with argon. 88 mg (0.11 mmol) [1,1'-bis(diphenylphosphino)ferrocene]dichloropalladium(II) complex with dichloromethane were added and the reaction tube was closed immediately. It was stirred for 1 h at 150° C. in the microwave reactor. The reaction mixture was poured into water and extracted three times with a mixture of dichloromethane/isopropanol 4:1. The combined organic phases were washed with aqueous saturated sodium chloride solution, dried over sodium sulfate and concentrated. The solid was triturated with ethanol yielding 402 mg (45%) of the title compound.

$^1$H-NMR (300 MHz, DMSO-d$_6$): δ [ppm]=1.36 (s, 9H), 7.25-7.34 (m, 2H), 7.39-7.48 (m, 1H), 7.78-7.83 (m, 1H), 7.85 (d, 1H), 7.89-7.97 (m, 1H), 8.09-8.17 (m, 2H), 8.27 (dd, 1H), 9.02 (d, 1H), 10.68 (s, 1H).

LC-MS (Method 3): R$_t$=1.43 min; MS (ESIpos): m/z=394 [M+H]$^+$.

Intermediate 121

3-amino-4-tert-butyl-N-[6-(2-fluorophenyl)pyridin-3-yl]benzamide

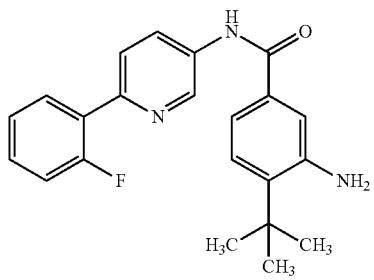 [SMILES: CC(C)(C)c1ccc(C(=O)Nc2ccc(-c3ccccc3F)nc2)cc1N]

375 mg (0.95 mmol) of 4-tert-butyl-N-[6-(2-fluorophenyl)pyridin-3-yl]-3-nitrobenzamide (intermediate 120) were dissolved in 5 mL of THF. At 0° C. 6.5 mL (7.63 mmol) of titanium(III)chloride (15% in 10% aqueous hydrochloride) were added. It was stirred over night at rt. 3.25 mL (3.81 mmol) of titanium(III)chloride (15% in 10% aqueous hydrochloride) were added and it was stirred for 12 h at rt and for 5 h at 50° C. The reaction mixture was cooled down and on an ice bath the reaction was neutralized with solid sodium hydrogen carbonate under vigorous stirring. The suspension was diluted with water and extracted with a mixture of EtOAc/THF twice. The combined organic layers were dried over sodium sulfate and concentrated affording 280 mg (81%) of the title compound.

LC-MS (Method 3): R$_t$=1.28 min; MS (ESIpos): m/z=364 [M+H]$^+$.

Intermediate 122

4-tert-butyl-3-[(2-chloropropanoyl)amino]-N-[6-(2-fluorophenyl)pyridin-3-yl]benzamide

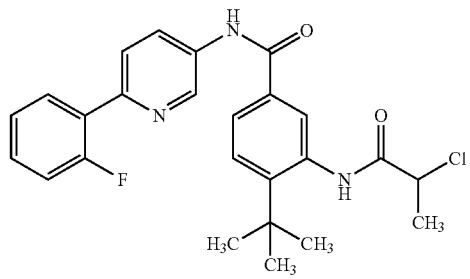 [SMILES: CC(Cl)C(=O)Nc1cc(C(=O)Nc2ccc(-c3ccccc3F)nc2)ccc1C(C)(C)C]

280 mg (0.77 mmol) of 3-amino-4-tert-butyl-N-[6-(2-fluorophenyl)pyridin-3-yl]benzamide (intermediate 121) were suspended in 5.0 mL of anh dichloromethane. 0.125 mL (1.54 mmol) of anh pyridine were added. On an ice bath 82 μL (0.85 mmol) of 2-chloropropanoyl chloride were added. It was stirred for 5 h at rt. 63 μL (0.78 mmol) of anh pyridine and 75 μL (0.77 mmol) of 2-chloropropanoyl chloride were added. It was stirred for 12 h at rt. The reaction mixture was evaporated to dryness and used without further purification.

LC-MS (Method 3): R$_t$=1.32 min; MS (ESIpos): m/z=454 [M+H]$^+$.

Intermediate 123

4-tert-butyl-3-nitro-N-(5-phenyl-1,3-thiazol-2-yl)benzamide

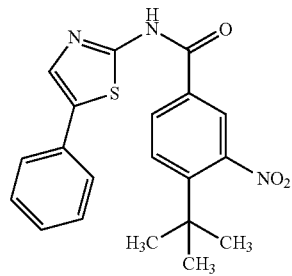 [SMILES: CC(C)(C)c1ccc(C(=O)Nc2ncc(-c3ccccc3)s2)cc1[N+](=O)[O-]]

500 mg (2.24 mmol) of 4-tert-butyl-3-nitrobenzoic acid and 474 mg (2.69 mmol) of 5-phenyl-1,3-thiazol-2-amine were dissolved in 13.8 mL of anh DMF. 1.63 g (3.14 mmol) of PYBOP and 1.17 mL (6.72 mmol) of N-ethyl-N-isopropylpropan-2-amine were added. It was stirred for 24 h at rt. The reaction mixture was poured into water and extracted three times with EtOAc. The combined organic phases were dried over sodium sulfate and concentrated affording 650 mg (73%) of the title compound.

$^1$H-NMR (300 MHz, DMSO-d$_6$): δ [ppm]=1.35 (s, 9H), 7.25-7.32 (m, 1H), 7.36-7.44 (m, 2H), 7.59-7.66 (m, 2H), 7.84 (d, 1H), 7.95 (s, 1H), 8.19-8.24 (m, 1H), 8.26 (d, 1H), 12.89 (s, 1H).

Intermediate 124

3-amino-4-tert-butyl-N-(5-phenyl-1,3-thiazol-2-yl)benzamide

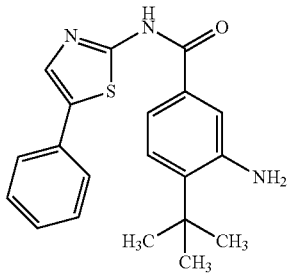 [SMILES: CC(C)(C)c1ccc(C(=O)Nc2ncc(-c3ccccc3)s2)cc1N]

565 mg (1.48 mmol) of 4-tert-butyl-3-nitro-N-(5-phenyl-1,3-thiazol-2-yl)benzamide (intermediate 123) were dissolved in 7.5 mL of THF. At 0° C. 4.6 mL (11.8 mmol) of titanium(III)chloride (15% in 10% aqueous hydrochloride) were added. It was stirred over night at rt. 1.15 mL (2.95 mmol) of titanium(III)chloride (15% in 10% aqueous hydrochloride) were added and it was stirred at rt and 40° C. till the starting material was consumed. The reaction mixture was cooled down and on an ice bath the reaction was neutralized with solid sodium hydrogen carbonate under vigorous stirring. The suspension was diluted with water and extracted with a mixture of EtOAc/THF twice. The combined organic layers were dried over sodium sulfate and concentrated affording 700 mg of the title compound.

LC-MS (Method 3): R$_t$=1.26 min; MS (ESIpos): m/z=352 [M+H]$^+$.

Intermediate 125

4-tert-butyl-3-[(2-chloropropanoy)amino]-N-(5-phenyl-1,3-thiazol-2-yl)benzamide

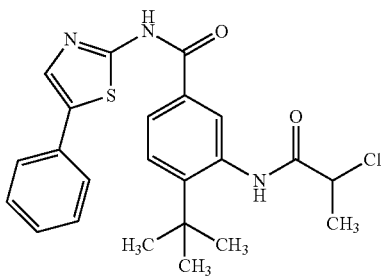 [SMILES: CC(Cl)C(=O)Nc1cc(C(=O)Nc2ncc(-c3ccccc3)s2)ccc1C(C)(C)C]

527 mg (1.50 mmol) of 3-amino-4-tert-butyl-N-(5-phenyl-1,3-thiazol-2-yl)benzamide (intermediate 124) were suspended in 8.8 mL of anh dichloromethane. 0.255 mL (3.15 mmol) of anh pyridine were added. On an ice bath 153

µL (1.58 mmol) of 2-chloropropanoyl chloride were added. It was stirred for 5 h at rt. 121 µL (1.50 mmol) of anh pyridine and 146 µL (1.50 mmol) of 2-chloropropanoyl chloride were added. It was stirred for 12 h at rt. The reaction mixture was evaporated to dryness and used without further purification.

Intermediate 126

3-{[(4-methylpiperazin-1-yl)acetyl]amino}-4-(trifluoromethoxy)benzoic acid hydrochloride (1:1)

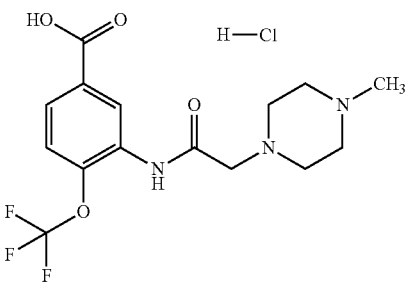 [SMILES: CN1CCN(CC(=O)Nc2cc(C(=O)O)ccc2OC(F)(F)F)CC1 ; Cl]

To a solution of intermediate 19 (1.50 g, 5.04 mmol) in DMF (45 mL) was added triethylamine (1.05 mL, 7.56 mmol), potassium iodide (126 mg, 0.76 mmol) and 1-methylpiperazine (0.84 mL, 7.56 mmol). The reaction mixture was stirred over night at room temperature. The mixture was concentrated. The remaining residue was triturated with water, and a 1M aqueous solution of hydrogen chloride was added until a pH of 4 was achieved. The mixture was saturated with sodium chloride and extracted three times with a mixture of DCM/isopropanol 4:1. The combined organic phases were dried over sodium sulfate and concentrated to yield the desired crude material (1.62 g, 69%), which was used in the next step without further purification.

$^1$H-NMR (300 MHz, DMSO-$d_6$) δ [ppm]=2.60 (s, 3H), 2.70-2.85 (m, 4H), 2.90-3.03 (m, 4H), 3.31 (s, 2H), 7.50-7.60 (m, 1H), 7.81 (dd, 1H), 8.67 (d, 1H), 9.83 (s, 1H).

LC-MS (Method 4): $R_t$=0.58 min; MS (ESIpos): m/z=362 [M–HCl+H]$^+$.

Intermediate 127

2-{[(4-methylpiperazin-1-yl)acetyl]amino}-4-[(5-phenyl-1,3,4-thiadiazol-2-yl)carbamoyl]benzoic acid hydrochloride (1:1)

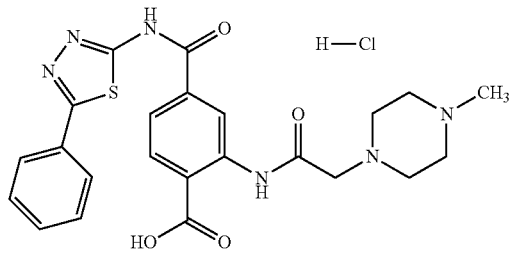 [SMILES: CN1CCN(CC(=O)Nc2cc(C(=O)Nc3nnc(-c4ccccc4)s3)ccc2C(=O)O)CC1 ; Cl]

1.47 g (2.95 mmol) of the compound of example 105 were provided in a mixture of 40 mL of THF and 20 mL of methanol, 5.9 mL (29.5 mmol) of a 5N aqueous solution of sodium hydroxide was added at room temperature and the mixture was stirred at room temperature over night. The mixture was diluted with ethyl acetate and water, and a 5N aqueous hydrogen chloride solution was then added until an acidic pH of 4 was achieved. The precipitate was filtered off, washed with water and dried. 400 mg (28% of theory) of the title compound were obtained and used without further purification. $^1$H-NMR (300 MHz, DMSO-$d_6$): δ [ppm] =2.67-2.90 (m, 6H), 2.94-3.22 (m, 5H), 3.36 (s, 2H), 7.51-7.61 (m, 3H), 7.90 (dd, 1H), 7.95-8.04 (m, 2H), 8.15 (d, 1H), 9.32 (s, 1H), 11.17 (s, 1H), 11.96 (s, 1H), 13.38 (s, 1H), 14.16 (s, 1H).

LC-MS (Method 4): $R_t$=0.84 min; MS (ESIpos): m/z=481 [M–HCl+H]$^+$.

Intermediate 128

2-[(morpholin-4-ylacetyl)amino]-4-[(5-phenyl-1,3,4-thiadiazol-2-yl)carbamoyl]benzoic acid

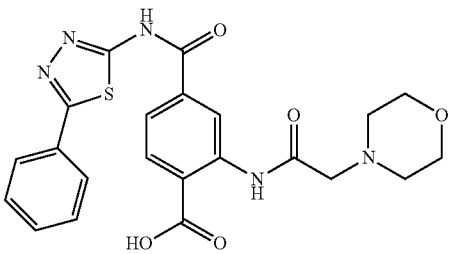 [SMILES: O=C(CN1CCOCC1)Nc1cc(C(=O)Nc2nnc(-c3ccccc3)s2)ccc1C(=O)O]

1.40 g (2.68 mmol) of the compound of example 106 were provided in a mixture of 40 mL of THF and 20 mL of methanol, 5.5 mL (26.8 mmol) of a 5N aqueous solution of sodium hydroxide was added at room temperature and the mixture was stirred at room temperature over night. The mixture was diluted with ethyl acetate and water, and a 5N aqueous hydrogen chloride solution was then added until an acidic pH of 4 was achieved. The precipitate was filtered off, washed with water and dried. 1.15 g (92% of theory) of the title compound were obtained and used without further purification.

LC-MS (Method 4): $R_t$=0.88 min; MS (ESIpos): m/z=468 [M+H]$^+$.

Intermediate 129

4-methyl-3-nitro-N-(5-phenyl-1,3,4-thiadiazol-2-yl) benzamide

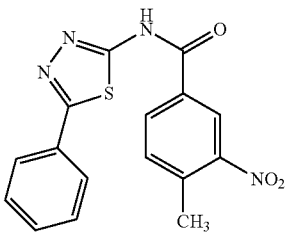

To a solution of 4-methyl-3-nitrobenzoic acid (2.00 g, 11.0 mmol) and 5-phenyl-1,3,4-thiadiazol-2-amine (2.54 g, 14.4 mmol, 1.3 equiv) in DMF (43 mL) was added (benzotriazol-1-yloxy)tripyrrolidinophosphonium hexafluorophosphate (PYBOP, 11.5 g, 22.1 mmol, 2 equiv) and diisopropylethylamine (7.7 mL, 44.2 mmol, 4 equiv). The resulting mixture was stirred at room temperature over night, then triturated with a mixture of water and ethanol. The precipitate was collected by filtration, washed with water and dried under reduced pressure at 50° C. 2.71 g (69% of theory) of the title compound were obtained.

$^1$H-NMR (400 MHz, DMSO-d$_6$): δ [ppm]=2.62 (s, 3H), 7.52-7.60 (m, 3H), 7.72 (d, 1H), 7.95-8.03 (m, 2H), 8.35 (dd, 1H), 8.77 (d, 1H), 13.49 (s, 1H).

LC-MS (Method 4): R$_t$=1.26 min; MS (ESIpos): m/z=341 [M+H]$^+$.

Intermediate 130

3-amino-4-methyl-N-(5-phenyl-1,3,4-thiadiazol-2-yl)benzamide

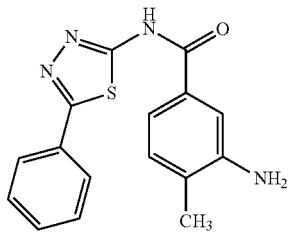 [SMILES: Cc1ccc(C(=O)Nc2nnc(-c3ccccc3)s2)cc1N]

2.71 g (7.96 mmol) of the compound of intermediate 129 were provided in a mixture of 200 mL of a mixture of THF and ethanol (3/2). 2.11 g of palladium on charcoal (10% Pd, 50% water) were added, and the mixture was stirred under a hydrogen atmosphere at room temperature for 3 h. After filtration, the solvents were evaporated yielding 2.36 g (86% of theory) of the title compound.

$^1$H-NMR (300 MHz, DMSO-d$_6$): δ [ppm]=2.13 (s, 3H), 5.17 (s, 2H), 7.09 (d, 1H), 7.25-7.37 (m, 2H), 7.47-7.61 (m, 3H), 7.91-8.04 (m, 2H), 12.87 (s, 1H).

LC-MS (Method 3): R$_t$=0.61 min; MS (ESIpos): m/z=311 [M+H]$^+$.

Intermediate 131

4-(cyclopropyloxy)-3-nitro-N-(5-phenyl-1,3,4-thiadiazol-2-yl)benzamide

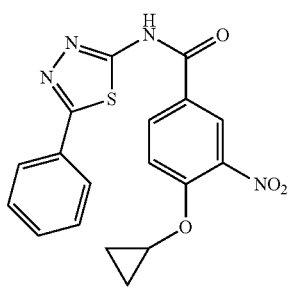 [SMILES: O=C(Nc1nnc(-c2ccccc2)s1)c1ccc(OC2CC2)c([N+](=O)[O-])c1]

2.00 g (8.96 mmol) of 4-(cyclopropyloxy)-3-nitrobenzoic acid were dissolved in 20 mL of anhydrous DMF. 1.9 g (10.75 mmol) of 5-phenyl-1,3,4-thiadiazol-2-amine and 5.6 g (10.75 mmol) of PYBOP were added. Finally, 4.7 mL (26.98 mmol) of N-ethyl-N-isopropylpropan-2-amine were added. It was stirred for 2 h at rt. 30 mL of water were added and the solid was filtered off, washed three times with water and dried at 45° C. under vacuum yielding 4.27 g of the title compound.

$^1$H-NMR (300 MHz, DMSO-d$_6$): δ [ppm]=0.75-0.96 (m, 4H), 4.18-4.27 (m, 1H), 7.50-7.59 (m, 3H), 7.81 (d, 1H), 7.94-8.02 (m, 2H), 8.45 (dd, 1H), 8.72 (d, 1H), 13.37 (br. s, 1H).

LC-MS (Method 4): R$_t$=1.28 min; MS (ESIpos): m/z=383 [M+H]$^+$.

Intermediate 132

3-amino-4-(cyclopropyloxy)-N-(5-phenyl-1,3,4-thiadiazol-2-yl)benzamide

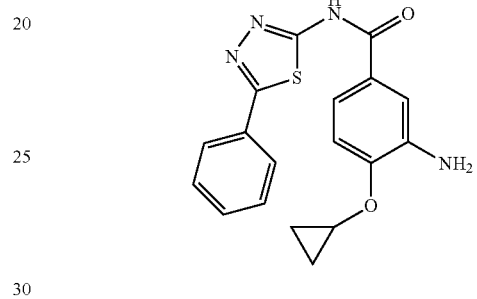

2.00 g (5.23 mmol) of 4-(cyclopropyloxy)-3-nitro-N-(5-phenyl-1,3,4-thiadiazol-2-yl)benzamide (intermediate 131) were dissolved in a mixture of 200 mL of methanol/THF 1:1. 334 mg of 10% palladium on charcoal and two drops of water were added. It was stirred for 6 h under an atmosphere of hydrogen. 223 mg of 10% palladium on charcoal were added and it was stirred under an atmosphere of hydrogen over night. 111 mg of 10% palladium on charcoal were added it was stirred for 5 h under an atmosphere of hydrogen. The catalyst was filtered off over celite and washed with methanol. The filtrate was concentrated and and the residue was stirred in a mixture of 400 mL of methanol/water 1:1 at 50° C. for 1 h. It was allowed to reach rt. The solid was filtered off and dried affording 1.12 g (61%) of the title compound.

$^1$H-NMR (400 MHz, DMSO-d$_6$): δ [ppm]=0.68-0.87 (m, 4H), 3.92-3.98 (m, 1H), 5.00 (s, 2H), 7.20 (d, 1H), 7.37 (d, 1H), 7.48-7.59 (m, 4H), 7.95-8.02 (m, 2H), 12.84 (s, 1H).

LC-MS (Method 4): R$_t$=1.17 min; MS (ESIpos): m/z=353 [M+H]$^+$.

Intermediate 133

4-chloro-3-nitrobenzoyl chloride

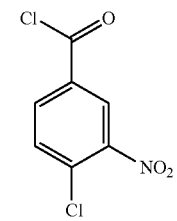 [SMILES: O=C(Cl)c1ccc(Cl)c([N+](=O)[O-])c1]

4.40 g (21.8 mmol) of 4-chloro-3-nitrobenzoic acid were stirred in 110 mL of dichloromethane at room temperature. 0.17 mL (2.18 mmol) of DMF and 2.3 mL (26.2 mmol) of oxalyl chloride were added, and the mixture was stirred for additional 3 h at 50° C. after the gas formation had stopped. 1.1 mL (13.1 mmol) of oxalyl chloride were added, and the mixture was stirred for additional 2 h at 50° C. after the gas formation had stopped. After concentration, 4.4 g of raw material were obtained, which were used without further purification.

Intermediate 134

4-chloro-3-nitro-N-(5-phenyl-1,3,4-thiadiazol-2-yl)benzamide

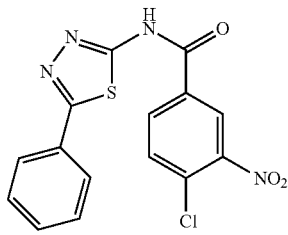 [SMILES: O=C(Nc1nnc(-c2ccccc2)s1)c1ccc(Cl)c([N+](=O)[O-])c1]

To a suspension of 1.95 g (11.0 mmol, 1.1 equiv) of 5-phenyl-1,3,4-thiadiazol-2-amine and 7.0 mL (50.0 mmol, 5 equiv) of triethylamine in 80 mL of a 1:1 mixture of THF/dichloromethane were added 2.20 g (10.0 mmol) of the compound of intermediate 133. The reaction mixture was stirred at room temperature over night. 7.0 mL (50.0 mmol, 5 equiv) of triethylamine, 100 mL of a 1:1 mixture of THF/dichloromethane and 2.20 g (10.0 mmol) of the compound of intermediate 133 were added and the reaction mixture was stirred at room temperature over night. After concentration, the remaining solid was triturated with a mixture of 300 mL of a saturated, aqueous solution of sodium bicarbonate and 300 mL of ethanol, stirred for 30 minutes, collected by filtration and dried. The remaining solid was triturated with 500 mL of water, stirred for 30 minutes, collected by filtration and dried. 2.55 g (69% of theory) of the title compound were obtained.

$^1$H-NMR (300 MHz, DMSO-d$_6$): δ [ppm]=7.51-7.62 (m, 3H), 7.94-8.06 (m, 3H), 8.39 (dd, 1H), 8.81 (d, 1H), 13.69 (s, 1H).

LC-MS (Method 4): R$_t$=1.28 min; MS (ESIpos): m/z=361 [M+H]$^+$.

Intermediate 135

3-amino-4-chloro-N-(5-phenyl-1,3,4-thiadiazol-2-yl)benzamide

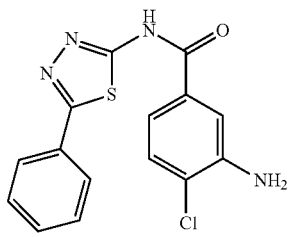

To a suspension of the compound of intermediate 134 (2.50 g, 6.93 mmol) in 100 mL of tetrahydrofuran was added a 15% solution of titanium(III) chloride in 10% hydrogen chloride dropwise (58.9 mL, 69.3 mmol, 10 equiv) at 0° C. The reaction mixture was allowed to warm up to room temperature and was stirred overnight. The pH of the mixture was adjusted under stirring with solid sodium bicarbonate to 7. The suspension was saturated with solid sodium chloride and stirred with 250 mL of a 1:1 mixture of tetrahydrofuran/ethyl acetate for 2 h. The suspension was filtered and the filtrate was washed with brine, dried over sodium sulfate and concentrated under reduced pressure. 1.15 g (50% of theory) of the title compound were obtained, which were used without further purification.

$^1$H-NMR (400 MHz, DMSO-d$_6$): δ [ppm]=5.69 (s, 2H), 7.30-7.40 (m, 2H), 7.49 (d, 1H), 7.52-7.57 (m, 3H), 7.96-8.01 (m, 2H), 13.04 (s, 1H).

LC-MS (Method 1): R$_t$=1.20 min; MS (ESIpos): m/z=331 [M+H]$^+$.

Intermediate 136

4-chloro-3-[(chloroacetyl)amino]-N-(5-phenyl-1,3,4-thiadiazol-2-yl)benzamide

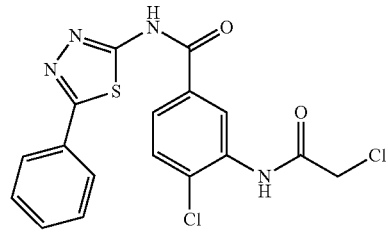 [SMILES: O=C(CCl)Nc1cc(C(=O)Nc2nnc(-c3ccccc3)s2)ccc1Cl]

0.50 g (1.51 mmol) of the compound of intermediate 135 were provided in 20 mL of toluene, 0.18 mL (2.27 mmol) of chloroacetyl chloride were added, and the mixture was stirred for 2 h at 100° C. After concentration, 0.62 g of the title compound were obtained, which were used without further purification.

$^1$H-NMR (300 MHz, DMSO-d$_6$): δ [ppm]=4.43 (s, 2H), 7.50-7.61 (m, 3H), 7.75 (d, 1H), 7.94-8.05 (m, 3H), 8.51 (d, 1H), 10.10 (s, 1H), 13.36 (s, 1H).

LC-MS (Method 4): R$_t$=1.19 min; MS (ESIpos): m/z=407 [M+H]$^+$.

Intermediate 137

4-cyano-3-nitrobenzoyl chloride

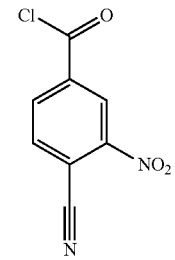 [SMILES: N#Cc1ccc(C(=O)Cl)cc1[N+](=O)[O-]]

1.00 g (5.20 mmol) of 4-cyano-3-nitrobenzoic acid was stirred in 25 mL of dichloromethane at room temperature. 0.04 mL (0.49 mmol) of DMF and 0.51 mL (5.82 mmol) of oxalyl chloride were added, and the mixture was stirred for additional 2 h at 50° C. after the gas formation had stopped. After concentration, 1.02 g of raw material were obtained, which were used without further purification.

Intermediate 138

4-cyano-3-nitro-N-(5-phenyl-1,3,4-thiadiazol-2-yl) benzamide

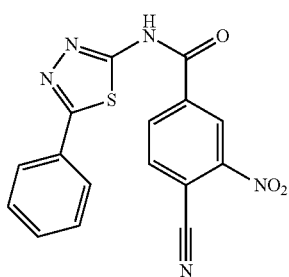 [SMILES: N#Cc1ccc(C(=O)Nc2nnc(-c3ccccc3)s2)cc1[N+](=O)[O-]]

To a suspension of 926 mg (5.22 mmol, 1.1 equiv) of 5-phenyl-1,3,4-thiadiazol-2-amine and 3.3 mL (23.7 mmol, 5 equiv) of triethylamine in 40 mL of a 1:1 mixture of THF/dichloromethane was added 1.00 g (4.75 mmol) of the compound of intermediate 137. The reaction mixture was stirred at room temperature over night. The reaction mixture was diluted with dichloromethane and was washed with a diluted, aqueous solution of hydrogen chloride. The precipitate was collected by filtration, washed with water and dried. 0.45 g (27% of theory) of the title compound were obtained.

$^1$H-NMR (400 MHz, DMSO-d$_6$): δ [ppm]=7.52-7.59 (m, 3H), 7.94-8.03 (m, 2H), 8.37 (d, 1H), 8.61 (dd, 1H), 9.02-9.08 (m, 1H), 14.05 (s, 1H).

LC-MS (Method 4): R$_t$=1.17 min; MS (ESIpos): m/z=352 [M+H]$^+$.

Intermediate 139

3-amino-4-cyano-N-(5-phenyl-1,3,4-thiadiazol-2-yl) benzamide

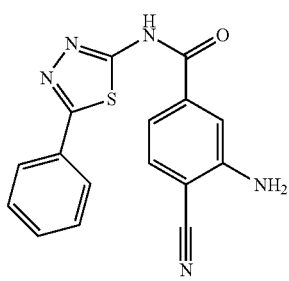 [SMILES: N#Cc1ccc(C(=O)Nc2nnc(-c3ccccc3)s2)cc1N]

To a suspension of the compound of intermediate 138 (50 mg, 0.14 mmol) in 2 mL of tetrahydrofuran was added a 15% solution of titanium(III) chloride in 10% hydrogen chloride dropwise (1.2 mL, 1.42 mmol, 10 equiv) at 0° C. The reaction mixture was allowed to warm up to room temperature and was stirred for 2 h. To a suspension of the compound of intermediate 138 (400 mg, 1.14 mmol) in 16 mL of tetrahydrofuran was added a 15% solution of titanium (III) chloride in 10% hydrogen chloride dropwise (9.7 mL, 11.4 mmol, 10 equiv) at 0° C. The reaction mixture was allowed to warm up to room temperature and was stirred for 2 h. Both reaction mixtures were combined and the pH was adjusted under stirring with solid sodium bicarbonate to 7. The suspension was saturated with solid sodium chloride and stirred with 30 mL of a 1:1 mixture of tetrahydrofuran/ ethyl acetate for 2 h. The suspension was filtered and the filtrate was washed with brine, dried over sodium sulfate and concentrated under reduced pressure. 63.0 mg of the title compound were obtained, which were used without further purification. The precipitate from the extraction with a 1:1 mixture of tetrahydrofuran/ethyl acetate was triturated with a 4:1 mixture of dichloromethane and isopropanol. The filtrate was washed with brine, dried over sodium sulfate and concentrated under reduced pressure. 40.0 mg of the title compound were obtained, which were used without further purification.

LC-MS (Method 4): R$_t$=1.08 min; MS (ESIpos): m/z=322 [M+H]$^+$.

Intermediate 140

3-[(chloroacetyl)amino]-4-cyano-N-(5-phenyl-1,3,4-thiadiazol-2-yl)benzamide

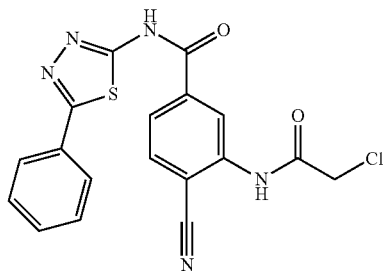 [SMILES: N#Cc1ccc(C(=O)Nc2nnc(-c3ccccc3)s2)cc1NC(=O)CCl]

0.10 g (0.31 mmol) of the compound of intermediate 139 were provided in 3.6 mL of toluene, 0.04 mL (0.47 mmol) of chloroacetyl chloride were added, and the mixture was stirred for 2 h at 100° C. After concentration, 120 mg of the title compound were obtained, which were used without further purification.

LC-MS (Method 1): R$_t$=1.17 min; MS (ESIpos): m/z=398 [M+H]$^+$.

Intermediate 141

3-amino-4-(difluoromethoxy)benzoic acid

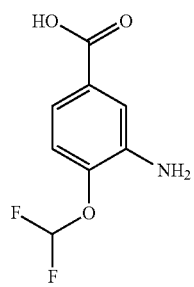 [SMILES: Nc1cc(C(=O)O)ccc1OC(F)F]

2.50 g (10.7 mmol) of 4-(difluoromethoxy)-3-nitrobenzoic acid were provided in 50 mL of methanol. 0.57 g of palladium on charcoal (10% Pd, 50% water) were added, and the mixture was stirred under a hydrogen atmosphere at room temperature for 1.25 h. After filtration, the solvents were evaporated. 2.16 g (99% of theory) of the title compound were obtained.

$^1$H-NMR (400 MHz, DMSO-d$_6$): δ [ppm]=5.29 (s, 2H), 7.04 (d, 1H), 7.13 (dd, 2H), 7.14 (t, 1H), 7.38 (d, 1H), 12.69 (s, 1H).

LC-MS (Method 1): R$_t$=0.76 min; MS (ESIpos): m/z=204 [M+H]$^+$.

Intermediate 142

3-amino-4-(difluoromethoxy)-N-[5-(2-methylphenyl)-1,3,4-thiadiazol-2-yl]benzamide

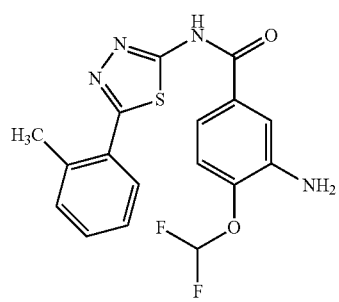 [SMILES: Cc1ccccc1-c1nnc(NC(=O)c2ccc(OC(F)F)c(N)c2)s1]

To a solution of the compound of intermediate 141 (0.50 g, 2.46 mmol) and 5-(2-methylphenyl)-1,3,4-thiadiazol-2-amine (941 mg, 4.92 mmol, 2 equiv) in DMF (8 mL) was added (benzotriazol-1-yloxy)tripyrrolidinophosphonium hexafluorophosphate (PYBOP, 2.56 g, 4.92 mmol, 2 equiv) followed by diisopropylethylamine (2.1 mL, 12.3 mmol, 5 equiv). The resulting mixture was stirred at room temperature over night and was then concentrated. The remaining solid was triturated with 15 mL of ethanol, stirred for 15 minutes, collected by filtration and dried. The remaining solid was triturated with 30 mL of ethanol, stirred for 15 minutes at 80° C., collected by filtration at 55° C. and dried. The residue (0.25 g) was purified using HPLC (column: chromatorex C18, 10 µm, 195×51 mm, mobile phase: acetonitrile/water gradient) to give the title compound (404 mg, 42%).

$^1$H-NMR (400 MHz, DMSO-d$_6$): δ [ppm]=2.53 (s, 3H), 5.42 (s, 2H), 7.13 (d, 1H), 7.21 (t, 1H), 7.33-7.45 (m, 4H), 7.48 (d, 1H), 7.70 (d, 1H), 12.97 (s, 1H).

LC-MS (Method 1): R$_t$=1.26 min; MS (ESIpos): m/z=377 [M+H]$^+$.

Intermediate 143

3-[(chloroacetyl)amino]-4-(difluoromethoxy)-N-[5-(2-methylphenyl)-1,3,4-thiadiazol-2-yl]benzamide

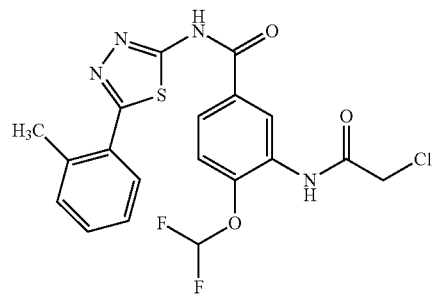 [SMILES: Cc1ccccc1-c1nnc(NC(=O)c2ccc(OC(F)F)c(NC(=O)CCl)c2)s1]

200 mg (0.52 mmol) of the compound of intermediate 142 were provided in 4 mL of toluene, 0.06 mL (0.77 mmol) of chloroacetyl chloride were added, and the mixture was stirred for 2 h at 100° C. The precipitate was collected by filtration, washed with ethyl acetate and dried to yield 121 mg of the title compound, which were used without further purification.

$^1$H-NMR (400 MHz, DMSO-d$_6$): δ [ppm]=2.54 (s, 3H), 4.43 (s, 2H), 7.34-7.48 (m, 4H), 7.38 (t, 1H), 7.71 (d, 1H), 8.05 (dd, 1H), 8.71 (d, 1H), 9.99 (s, 1H), 13.22 (s, 1H).

LC-MS (Method 3): R$_t$=0.74 min; MS (ESIpos): m/z=453 [M+H]$^+$.

Intermediate 144

4-(methoxymethyl)-N-[5-(2-methylphenyl)-1,3,4-thiadiazol-2-yl]-3-nitrobenzamide

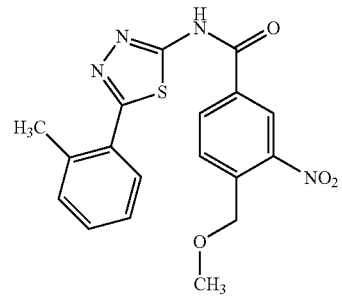

To a solution of the compound of intermediate 49 (1.00 g, 4.74 mmol) and 5-(2-methylphenyl)-1,3,4-thiadiazol-2-amine (755 mg, 3.95 mmol) in DMF (15 mL) was added (benzotriazol-1-yloxy)tripyrrolidinophosphonium hexafluorophosphate (PYBOP, 4.11 g, 7.89 mmol, 2 equiv) followed by diisopropylethylamine (3.4 mL, 19.7 mmol, 5 equiv). The resulting mixture was stirred at room temperature for 3 days. After concentration, the remaining solid was triturated with a mixture of 100 mL of water and 70 mL of ethanol, stirred for 30 minutes, collected by filtration and dried. The remaining solid was triturated with 100 mL of ethanol, stirred under reflux, collected by filtration and dried to yield the title compound (1.27 g, 75% of theory).

$^1$H-NMR (400 MHz, DMSO-d$_6$): δ [ppm]=2.54 (s, 3H), 3.41 (s, 3H), 4.86 (s, 2H), 7.34-7.40 (m, 1H), 7.40-7.47 (m, 2H), 7.71 (d, 1H), 7.92 (d, 1H), 8.48 (dd, 1H), 8.84 (d, 1H), 13.64 (s, 1H).

Intermediate 145

3-amino-4-(methoxymethyl)-N-[5-(2-methylphenyl)-1,3,4-thiadiazol-2-yl]benzamide

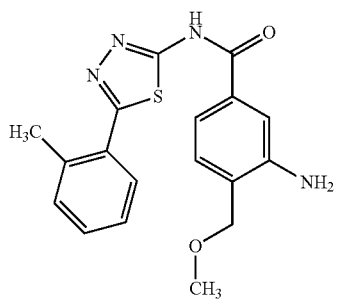 [SMILES: COCc1ccc(C(=O)Nc2nnc(-c3ccccc3C)s2)cc1[N+](=O)[O-]]

1.20 g (3.12 mmol) of the compound of intermediate 144 were provided in 80 ml of a 1:1 mixture of THF and ethanol and 10 ml of 2-methyltetrahydrofuran. 0.25 g of palladium on charcoal (10% Pd, 50% water) were added, and the mixture was stirred under a hydrogen atmosphere at room temperature for 1 h. 0.5 g of palladium on charcoal (10% Pd, 50% water) were added, and the mixture was stirred under a hydrogen atmosphere at room temperature for 4 h. The reaction mixture was left under a nitrogen atmosphere over night. 0.25 g of palladium on charcoal (10% Pd, 50% water) were added, and the mixture was stirred under a hydrogen atmosphere at room temperature for 2 h. The reaction mixture was left under a nitrogen atmosphere over night. After filtration, the solvents were evaporated. 1.06 g (86% of theory) of the title compound were obtained.

$^1$H-NMR (300 MHz, DMSO-$d_6$): δ [ppm]=2.53 (s, 3H), 3.31 (s, 3H), 4.38 (s, 2H), 5.26 (s, 2H), 7.18-7.25 (m, 1H), 7.30-7.45 (m, 5H), 7.70 (d, 1H), 12.92 (s, 1H).

LC-MS (Method 1): $R_t$=1.15 min; MS (ESIpos): m/z=355 [M+H]$^+$.

Intermediate 146

3-[(chloroacetyl)amino]-4-(methoxymethyl)-N-[5-(2-methylphenyl)-1,3,4-thiadiazol-2-yl]benzamide

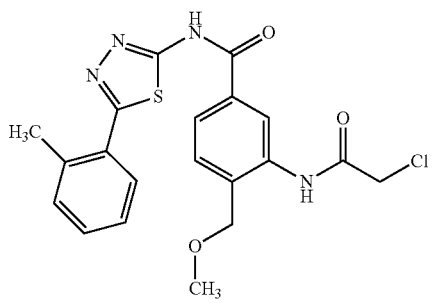 [SMILES: COCc1ccc(C(=O)Nc2nnc(-c3ccccc3C)s2)cc1NC(=O)CCl]

0.30 g (0.85 mmol) of the compound of intermediate 145 were provided in 12 mL of toluene, 0.1 mL (1.27 mmol) of chloroacetyl chloride were added, and the mixture was stirred for 2 h at 100° C. After concentration 360 mg of the title compound were obtained, which were used without further purification.

$^1$H-NMR (400 MHz, DMSO-$d_6$): δ [ppm]=2.54 (s, 3H), 3.37 (s, 3H), 4.40 (s, 2H), 4.52 (s, 2H), 7.33-7.47 (m, 3H), 7.59 (d, 1H), 7.71 (d, 1H), 8.02 (dd, 1H), 8.35 (s, 1H), 9.90 (s, 1H), 13.26 (s, 1H).

LC-MS (Method 1): $R_t$=1.23 min; MS (ESIpos): m/z=431 [M+H]$^+$.

Intermediate 147

3-amino-4-(difluoromethoxy)-N-[5-(2-fluorophenyl)-1,3,4-thiadiazol-2-yl]benzamide

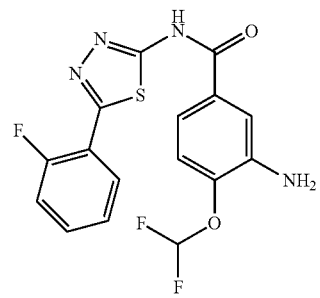 [SMILES: Nc1cc(C(=O)Nc2nnc(-c3ccccc3F)s2)ccc1OC(F)F]

To a solution of the compound of intermediate 141 (0.80 g, 3.94 mmol) and 5-(2-fluorophenyl)-1,3,4-thiadiazol-2-amine (1.15 g, 5.91 mmol, 1.5 equiv) in DMF (12 mL) was added (benzotriazol-1-yloxy)tripyrrolidinophosphonium hexafluorophosphate (PYBOP, 3.07 g, 5.91 mmol, 1.5 equiv) followed by diisopropylethylamine (2.1 mL, 11.8 mmol, 3 equiv). The resulting mixture was stirred at room temperature for 6 h. (Benzotriazol-1-yloxy)tripyrrolidinophosphonium hexafluorophosphate (PYBOP, 3.07 g, 5.91 mmol, 1.5 equiv) and diisopropylethylamine (2.1 mL, 11.8 mmol, 3 equiv) were added, the resulting mixture was stirred at room temperature over night and was then concentrated. The remaining solid was triturated with a mixture of 100 mL of water and 70 mL of ethanol, stirred for 30 minutes, collected by filtration and dried. The remaining solid was triturated with 100 mL of ethanol, stirred at 80° C., collected by filtration at 40° C. and dried to give the title compound (965 mg, 64%).

$^1$H-NMR (400 MHz, DMSO-$d_6$): δ [ppm]=5.44 (s, 2H), 7.13 (d, 1H), 7.21 (t, 1H), 7.37-7.53 (m, 4H), 7.58-7.66 (m, 1H), 8.23-8.33 (m, 1H), 13.06 (s, 1H).

LC-MS (Method 4): $R_t$=1.15 min; MS (ESIpos): m/z=381 [M+H]$^+$.

Intermediate 148

3-[(chloroacetyl)amino]-4-(difluoromethoxy)-N-[5-(2-fluorophenyl)-1,3,4-thiadiazol-2-yl]benzamide

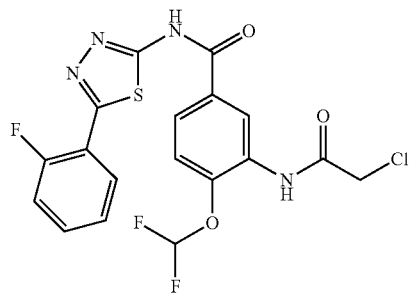 [SMILES: O=C(CCl)Nc1cc(C(=O)Nc2nnc(-c3ccccc3F)s2)ccc1OC(F)F]

0.70 g (1.84 mmol) of the compound of intermediate 147 were provided in 26 mL of toluene, 0.22 mL (2.76 mmol) of chloroacetyl chloride were added, and the mixture was stirred for 2 h at 100° C. After concentration 840 mg of the title compound were obtained, which were used without further purification.

$^1$H-NMR (300 MHz, DMSO-d$_6$): δ [ppm]=4.43 (s, 2H), 7.38-7.54 (m, 3H), 7.39 (t, 1H), 7.55-7.67 (m, 1H), 8.06 (dd, 1H), 8.25-8.34 (m, 1H), 8.72 (d, 1H), 10.01 (s, 1H), 13.34 (s, 1H).

LC-MS (Method 4): R$_t$=1.20 min; MS (ESIpos): m/z=457 [M+H]$^+$.

EXAMPLES

Example 1

N-[6-(2-fluorophenyl)pyridin-3-yl]-4-methoxy-3-[(morpholin-4-ylacetyl)amino]benzamide

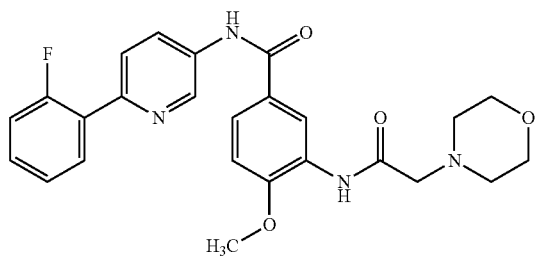 [SMILES: COc1ccc(C(=O)Nc2ccc(-c3ccccc3F)nc2)cc1NC(=O)CN1CCOCC1]

296 mg (715 µmol) of the compound from intermediate 12 were provided in 2 mL of DMF. 150 µL (1.07 mmol) of triethylamine, 93.5 mg (1.07 mmol) of morpholine and 18.4 mg (111 µmol) of potassium iodide were added and the mixture was stirred at room temperature over night. After filtration, purification by HPLC (method 2) yielded 63.0 mg (19% of theory) of the title compound.

$^1$H-NMR (400 MHz, DMSO-d$_6$): δ [ppm]=2.54-2.61 (m, 4H), 3.19 (s, 2H), 3.65-3.72 (m, 4H), 4.00 (s, 3H), 7.24 (d, 1H), 7.28-7.37 (m, 2H), 7.42-7.50 (m, 1H), 7.77-7.85 (m, 2H), 7.92-8.00 (m, 1H), 8.30 (dd, 1H), 8.81 (d, 1H), 9.06 (d, 1H), 9.80 (s, 1H), 10.48 (s, 1H).

LC-MS (Method 1): R$_t$=0.89 min; MS (ESIpos): m/z=465 [M+H]$^+$.

Example 2

N-[6-(2-fluorophenyl)pyridin-3-yl]-4-methoxy-3-[(8-oxa-3-azabicyclo[3.2.1]oct-3-ylacetyl)amino]benzamide

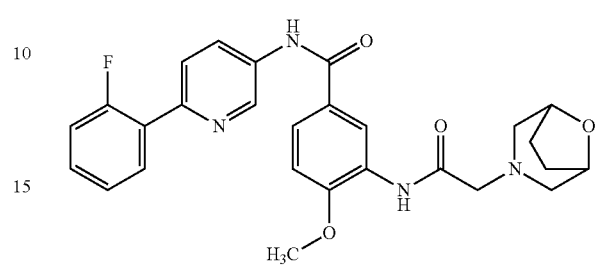

296 mg (715 µmol) of the compound from intermediate 12 were provided in 2 mL of DMF. 0.25 mL (1.79 mmol) of triethylamine, 161 mg (1.07 mmol) of 8-oxa-3-azabicyclo[3.2.1]octane hydrochloride and 18.4 mg (111 µmol) of potassium iodide were added and the mixture was stirred at room temperature over night. After filtration, purification by HPLC (method 2) yielded 81.0 mg (22% of theory) of the title compound.

$^1$H-NMR (400 MHz, DMSO-d$_6$): δ [ppm]=1.84-1.93 (m, 2H), 2.04-2.12 (m, 2H), 2.43-2.49 (m, 2H), 2.62-2.69 (m, 2H), 3.11 (s, 2H), 3.99 (s, 3H), 4.26-4.32 (m, 2H), 7.26 (d, 1H), 7.29-7.36 (m, 2H), 7.42-7.50 (m, 1H), 7.77-7.84 (m, 2H), 7.93-8.00 (m, 1H), 8.30 (dd, 1H), 8.92 (d, 1H), 9.07 (d, 1H), 9.79 (s, 1H), 10.48 (s, 1H).

LC-MS (Method 1): R$_t$=1.13 min; MS (ESIpos): m/z=491 [M+H]$^+$.

Example 3

N-[6-(2-fluorophenyl)pyridin-3-yl]-4-methoxy-3-{[(1S,4S)-2-oxa-5-azabicyclo[2.2.1]hept-5-ylacetyl]amino}benzamide

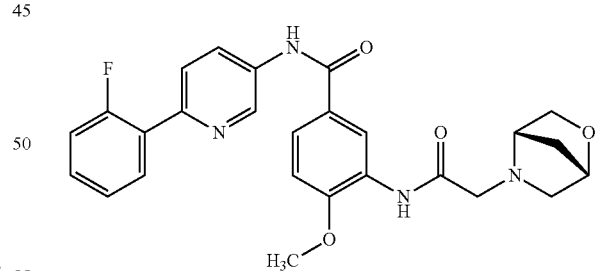

The preparation of the title compound was conducted in analogy to the synthesis of the compound from example 1 starting with 253 mg (611 µmol) of the compound from intermediate 12, 124 mg (917 µmol) of (1S,4S)-2-oxa-5-azabicyclo[2.2.1]heptane hydrochloride and 256 µL (1.83 mmol) of triethylamine. 111 mg (37% of theory) of the title compound were obtained.

$^1$H-NMR (400 MHz, DMSO-d$_6$): δ [ppm]=1.64-1.71 (m, 1H), 1.81-1.87 (m, 1H), 2.68-2.74 (m, 1H), 2.85-2.92 (m, 1H), 3.40 (s, 2H), 3.57-3.65 (m, 2H), 3.84 (d, 1H), 3.97 (s, 3H), 4.44 (s, 1H), 7.24 (d, 1H), 7.29-7.37 (m, 2H), 7.43-7.50

(m, 1H), 7.81 (ddd, 2H), 7.93-7.99 (m, 1H), 8.30 (dd, 1H), 8.84 (d, 1H), 9.06 (d, 1H), 9.84 (s, 1H), 10.50 (s, 1H).

LC-MS (Method 4): $R_t$=0.82 min; MS (ESIpos): m/z=477 [M+H]$^+$.

Example 4

4-methoxy-3-[(morpholin-4-ylacetyl)amino]-N-(6-phenylpyridin-3-yl)benzamide

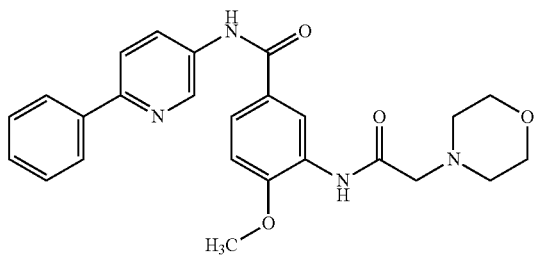 [SMILES: COc1ccc(C(=O)Nc2ccc(-c3ccccc3)nc2)cc1NC(=O)CN1CCOCC1]

To a solution of 3-[(chloroacetyl)amino]-4-methoxy-N-(6-phenylpyridin-3-yl)benzamide (prepared in a manner analogous to that described in intermediate 13, 0.62 g, 1.56 mmol) in DMF (20 mL) was added morpholine (0.20 mL, 2.34 mmol, 1.5 equiv), triethylamine (0.33 mL, 2.34 mmol, 1.5 equiv) and potassium iodide (0.040 g, 0.24 mmol, 0.16 equiv). The reaction mixture was stirred at room temperature for 16 h. The resulting mixture was diluted with water (25 mL). The resulting solution was extracted with a CH$_2$Cl$_2$/isopropanol solution (4:1, 4×25 mL). The combined organic phases were concentrated under reduced pressure. The residue (0.45 g) was triturated with methanol. The resulting solids were washed with water, followed by methanol, then were dried at 50° C. to give 4-methoxy-3-[(morpholin-4-ylacetyl)amino]-N-(6-phenylpyridin-3-yl)benzamide (0.52 g, 73%).

$^1$H-NMR (400 MHz, DMSO-d$_6$): δ [ppm]=2.51-2.55 (m, 4H), 3.15 (s, 2H), 3.63-3.66 (m, 4H), 3.96 (s, 3H), 7.20 (d, J=8.6 Hz, 1H), 7.37 (tt, J=2.0, 7.3 Hz, 1H), 7.45 (t, J=7.5 Hz, 2H), 7.77 (dd, J=2.3, 8.6 Hz, 1H), 7.94 (d, J=8.6 Hz, 1H), 8.03 (dm, J=7.1, 2H), 8.25 (dd, J=2.8, 8.6 Hz, 1H), 8.77 (d, J=2.3 Hz, 1H), 8.97 (d, J=2.5 Hz, 1H), 9.76 (s, 1H), 10.40 (s, 1H).

LC-MS (Method 3): $R_t$=1.15 min; MS (ESIpos): m/z=447 ([M+H]$^+$, 90%), 893 ([2M+H]$^+$, 60%); MS (ESIneg): m/z=445 ([M–H]$^-$, 100%).

Example 5

N-[6-(2-fluorophenyl)pyridin-3-yl]-3-[(morpholin-4-ylacetyl)amino]-4-(trifluoromethoxy)benzamide

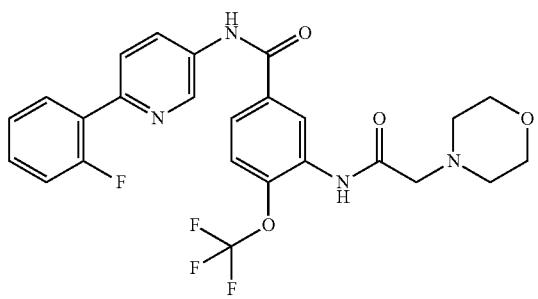 [SMILES: O=C(CN1CCOCC1)Nc1cc(C(=O)Nc2ccc(-c3ccccc3F)nc2)ccc1OC(F)(F)F]

To a solution of 3-[(chloroacetyl)amino]-N-[6-(2-fluorophenyl)pyridin-3-yl]-4-(trifluoromethoxy)benzamide (prepared in a manner analogous to that described in intermediate 14, 1.29 g, 2.75 mmol) in DMF (15 mL) was added morpholine (0.36 mL, 4.13 mmol, 1.5 equiv), triethylamine (0.58 mL, 4.13 mmol, 1.5 equiv) and potassium iodide (0.071 g, 0.43 mmol, 0.16 equiv). The reaction mixture was stirred at room temperature for 16 h. The resulting mixture was diluted with water (25 mL). The resulting precipitate was washed with water followed by ethanol, was then dried at 50° C. The resulting solids were triturated with DMSO (10 mL) to give N-[6-(2-fluorophenyl)pyridin-3-yl]-3-[(morpholin-4-ylacetyl)amino]-4-(trifluoromethoxy)benzamide (0.61 g, 43%).

$^1$H-NMR (400 MHz, DMSO-d$_6$): δ [ppm]=2.53-2.57 (m, 4H), 3.20 (s, 2H), 3.60-3.64 (m, 4H), 7.25-7.34 (m, 2H), 7.39-7.47 (m, 1H), 7.62 (d, J=8.3 Hz, 1H), 7.78-7.85 (m, 2H), 7.93 (t, J=8.2 Hz, 1H), 8.26 (dd, J=2.5, 8.7 Hz, 1H), 8.75 (d, J=1.9 Hz, 1H), 9.02 (d, J=2.1 Hz, 1H), 9.89 (s, 1H), 10.69 (s, 1H).

LC-MS (Method 3): $R_t$=1.30 min; MS (ESIpos): m/z=519 ([M+H]$^+$, 100%); MS (ESIneg): m/z=517 ([M–H]$^-$, 100%).

The DMSO mother liquor was concentrated under reduced pressure. The residue was purified by HPLC to give additional N-(biphenyl-4-yl)-4-methoxy-3-[(morpholin-4-ylacetyl)amino]benzamide (0.19 g, 13%).

Example 6

N-[6-(2-fluorophenyl)pyridin-3-yl]-3-[(8-oxa-3-azabicyclo[3.2.1]oct-3-ylacetyl)amino]-4-(trifluoromethoxy)benzamide

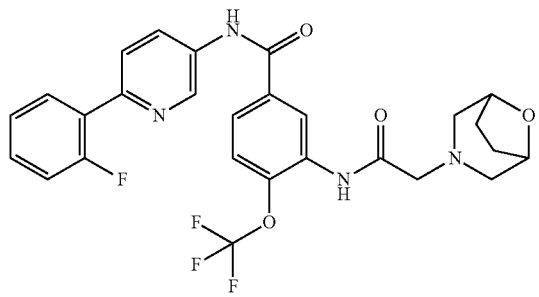 [SMILES: O=C(CN1CC2CCC(C1)O2)Nc1cc(C(=O)Nc2ccc(-c3ccccc3F)nc2)ccc1OC(F)(F)F]

To a solution of 3-[(chloroacetyl)amino]-N-[6-(2-fluorophenyl)pyridin-3-yl]-4-(trifluoromethoxy)benzamide (prepared in a manner analogous to that described in intermediate 14, 0.15 g, 0.32 mmol) in DMF (1.5 mL) was added 8-oxa-3-azabicyclo[3.2.1]octane HCl salt (0.072 g, 0.48 mmol, 1.5 equiv), triethylamine (0.13 mL, 0.96 mmol, 3.0 equiv) and potassium iodide (8.2 mg, 0.050 mmol, 0.16 equiv). The reaction mixture was stirred at room temperature for 16 h, then concentrated under reduced pressure. The residue was purified by HPLC (method 2). The resulting solids (96 mg) were further purified by crystallization from methanol to give N-[6-(2-fluorophenyl)pyridin-3-yl]-3-[(8-oxa-3-azabicyclo[3.2.1]oct-3-ylacetyl)amino]-4-(trifluoromethoxy)benzamide (55 mg, 30%).

$^1$H-NMR (400 MHz, DMSO-d$_6$): δ [ppm]=1.76-1.81 (m, 2H), 1.93-1.98 (m, 2H), 2.41 (d, J=10.9 Hz, 2H), 2.63 (d, J=10.6 Hz, 2H), 3.14 (s, 2H), 4.20-4.26 (m, 2H), 7.27-7.32 (m, 2H), 7.41-7.47 (m, 1H), 7.62 (dd, J=1.8, 8.6 Hz, 1H), 7.80 (dd, J=1.5, 8.8 Hz, 1H), 7.83 (dd, J=2.3, 8.8 Hz, 1H), 7.93 (td, J=2.0, 7.8 Hz, 1H), 8.27 (dd, J=2.5, 8.6 Hz, 1H), 8.82 (d, J=2.0 Hz, 1H), 9.02 (d, J=2.5, 1H), 9.56 (s, 1H), 10.69 (s, 1H).

LC-MS (Method 3): $R_t$=1.35 min; MS (ESIpos): m/z=545 ([M+H]$^+$, 100%); MS (ESIneg): m/z=543 ([M−H]$^−$, 100%).

Example 7

N-[6-(2-fluorophenyl)pyridin-3-yl]-3-{[2-(morpholin-4-yl)propanoyl]amino}-4-(trifluoromethoxy)benzamide Example 8

N-[6-(2-fluorophenyl)pyridin-3-yl]-3-{[(2S)-2-(morpholin-4-yl)propanoyl]amino}-4-(trifluoromethoxy)benzamide or N-[6-(2-fluorophenyl)pyridin-3-yl]-3-{[(2R)-2-(morpholin-4-yl)propanoyl]amino}-4-(trifluoromethoxy)benzamide

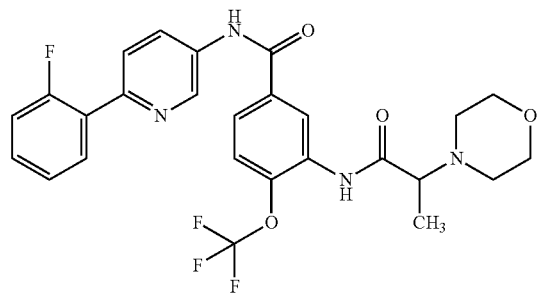

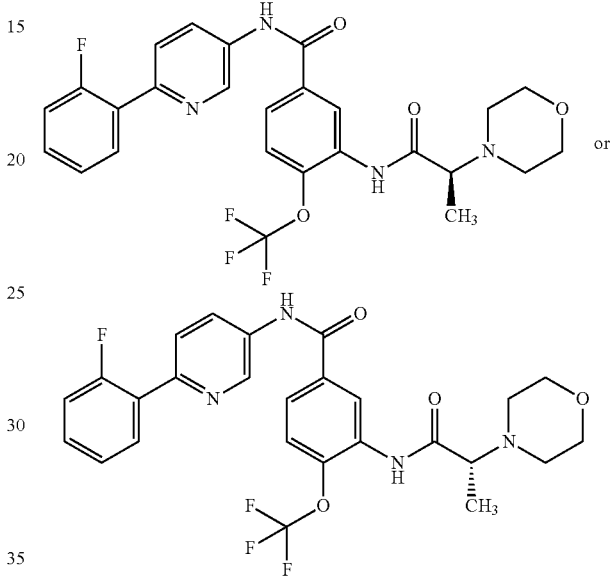

To a solution of 3-[(2-chloropropanoyl)amino]-N-[6-(2-fluorophenyl)pyridin-3-yl]-4-(trifluoromethoxy)benzamide (prepared in a manner analogous to that described in intermediate 15, 0.616 g, 1.28 mmol) in DMF (5.5 mL) was added morpholine (0.17 mL, 1.92 mmol, 1.5 equiv), triethylamine (0.27 mL, 1.92 mmol, 1.5 equiv) and potassium iodide (32 mg, 0.20 mmol, 0.16 equiv). The reaction mixture was stirred at room temperature for 16 h, then treated with water (10 mL). The resulting mixture was extracted with ethyl acetate (3×25 mL). The combined organic phases were dried (Na2SO4 anh) and concentrated under reduced pressure. The residue (0.7 g) was purified using MPLC (Biotage Isolera; 25 g SNAP cartridge: 100% hexane 2.0 min., gradient to 70% hexane/30% EtOAc 4.0 min., 70% hexane/30% EtOAc 2.5 min., gradient to 50% hexane/50% EtOAc 3.5 min., 50% hexane/50% EtOAc 3.0 min., gradient to 24% hexane/74% EtOAc 2.8 min., gradient to 100% EtOAc 2.6 min., 100% EtOAc 12.0 min.) to give racemic N-[6-(2-fluorophenyl)pyridin-3-yl]-3-{[2-(morpholin-4-yl)propanoyl]amino}-4-(trifluoromethoxy)benzamide (0.41 g, 60%).

$^1$H-NMR (400 MHz, DMSO-d$_6$): δ [ppm]=1.20 (d, J=6.8 Hz, 3H), 2.50-2.55 (m, 4H), 3.37 (q, J=7.1 Hz, 1H), 3.60-3.64 (m, 4H), 7.27-7.33 (m, 2H), 7.41-7.47 (m, 1H), 7.62 (dm, J=8.6 Hz, 1H), 7.81 (td, J=1.8, 8.6 Hz, 2H), 7.93 (td, J=1.5, 7.8 Hz, 1H), 8.27 (dd, J=2.5, 6.3 Hz, 1H), 8.71 (d, J=2.0 Hz, 1H), 9.02 (d, J=2.5 Hz, 1H), 10.01 (s, 1H), 10.69 (s, 1H).

LC-MS (Method 3): $R_t$=1.14 min; MS (ESIpos): m/z=533 ([M+H]$^+$, 80%); MS (ESIneg): m/z=531 ([M−H]$^−$, 100%).

A sample of racemic N-[6-(2-fluorophenyl)pyridin-3-yl]-3-{[2-(morpholin-4-yl)propanoyl]amino}-4-(trifluoromethoxy)benzamide (prepared as described in example 7, 0.39 g, 0.73 mmol) was separated using chiral HPLC (System: Agilent Prep 1200, Column: Chiralpak IC 5 μm 250×30 mm, Solvent: hexane/ethanol/diethylamine 70:30:0.1 (v/v/v)) to give the second eluting enantiomer of N-[6-(2-fluorophenyl)pyridin-3-yl]-3-{[2-(morpholin-4-yl)propanoyl]amino}-4-(trifluoromethoxy)benzamide (0.14 g, 34% from racemate).

$^1$H-NMR (400 MHz, DMSO-d$_6$): δ [ppm]=1.20 (d, J=7.1 Hz, 3H), 2.51-2.55 (m, 4H), 3.37 (q, J=7.1 Hz, 1H), 3.61-3.64 (m, 4H), 7.27-7.32 (m, 2H), 7.41-7.47 (m, 1H), 7.62 (dd, J=1.5, 8.8 Hz, 1H), 7.81 (td, J=1.8, 8.6 Hz, 2H), 7.93 (td, J=2.0, 8.1 Hz, 1H), 8.27 (dd, J=2.5, 8.8 Hz, 1H), 8.71 (d, J=2.3 Hz, 1H), 9.02 (d, J=2.3 Hz, 1H), 10.01 (s, 1H), 10.69 (s, 1H).

LC-MS (Method 4): $R_t$=1.15 min; MS (ESIpos): m/z=533 [M+H]$^+$.

Optical rotation (Method 6): [α]=+6.4° (c=1.00, CHCl$_3$).

Chiral HPLC (System: Waters Alliance 2695 DAD 996 ESA: Corona, Column: Chiralpak IC 3 μm 100×4.6 mm, Solvent: hexane/ethanol/diethylamine 70:30:0.1 (v/v/v)): $R_t$=10.23 min, 94.6% enantiomeric excess.

Example 9

N-[6-(2-fluorophenyl)pyridin-3-yl]-3-{[(2S)-2-(morpholin-4-yl)propanoyl]amino}-4-(trifluoromethoxy)benzamide or N-[6-(2-fluorophenyl)pyridin-3-yl]-3-{[(2R)-2-(morpholin-4-yl)propanoyl]amino}-4-(trifluoromethoxy)benzamide

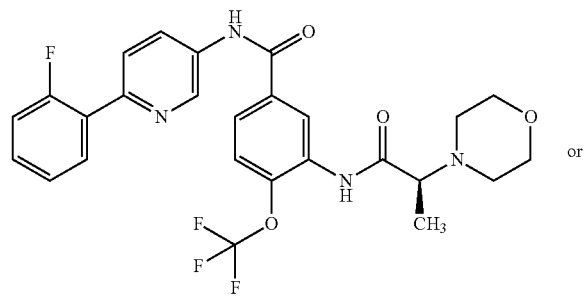

or

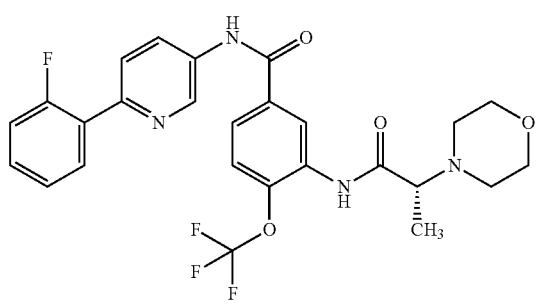 [SMILES: CC(C(=O)Nc1cc(C(=O)Nc2ccc(-c3ccccc3F)nc2)ccc1OC(F)(F)F)N1CCOCC1]

A sample of racemic N-[6-(2-fluorophenyl)pyridin-3-yl]-3-{[2-(morpholin-4-yl)propanoyl]amino}-4-(trifluoromethoxy)benzamide (prepared as described in example 7, 0.39 g, 0.73 mmol) was separated using chiral HPLC (System: Agilent Prep 1200, Column: Chiralpak IC 5 μm 250×30 mm, Solvent: hexane/ethanol/diethylamine 70:30:0.1 (v/v/v)) to give the first eluting enantiomer of N-[6-(2-fluorophenyl)pyridin-3-yl]-3-{[2-(morpholin-4-yl)propanoyl]amino}-4-(trifluoromethoxy)benzamide (0.16 g, 39% from racemate).

$^1$H-NMR (400 MHz, DMSO-d$_6$): δ [ppm]=1.20 (d, J=7.1 Hz, 3H), 2.51-2.55 (m, 4H), 3.37 (q, J=7.1 Hz, 1H), 3.61-3.64 (m, 4H), 7.27-7.32 (m, 2H), 7.41-7.47 (m, 1H), 7.62 (dd, J=1.5, 8.8 Hz, 1H), 7.81 (td, J=1.8, 8.6 Hz, 2H), 7.93 (td, J=2.0, 8.1 Hz, 1H), 8.27 (dd, J=2.5, 8.8 Hz, 1H), 8.71 (d, J=2.3 Hz, 1H), 9.02 (d, J=2.3 Hz, 1H), 10.01 (s, 1H), 10.69 (s, 1H).

LC-MS (Method 1): R$_t$=1.16 min; MS (ESIpos): m/z=533 [M+H]$^+$.

Optical rotation (Method 6): [α]=−9.9° (c=1.00, CHCl$_3$).

Chiral HPLC (System: Waters Alliance 2695 DAD 996 ESA: Corona, Column: Chiralpak IC 3 μm 100×4.6 mm, Solvent: hexane/ethanol/diethylamine 70:30:0.1 (v/v/v)): R$_t$=9.03 min, 100% enantiomeric excess.

Example 10

3-{[2-(morpholin-4-yl)propanoyl]amino}-N-(6-phenylpyridin-3-yl)-4-(trifluoromethoxy)benzamide

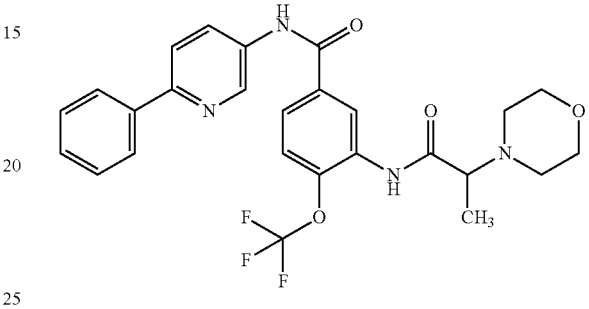

To a solution of 3-[(2-chloropropanoyl)amino]-N-(6-phenylpyridin-3-yl)-4-(trifluoromethoxy)benzamide (prepared in a manner analogous to that described in intermediate 16, 0.66 g, 1.43 mmol) in DMF (6 mL) was added morpholine (0.19 mL, 2.15 mmol, 1.5 equiv), triethylamine (0.30 mL, 2.15 mmol, 1.5 equiv) and potassium iodide (37 mg, 0.22 mmol, 0.16 equiv). The reaction mixture was stirred at room temperature for 16 h, then treated with water (10 mL). The resulting mixture was extracted with ethyl acetate (3×10 mL). The combined organic phases were dried (Na2SO4 anh) and concentrated under reduced pressure. The residue (0.85 g) was purified using MPLC (Biotage Isolera; 25 g SNAP cartridge: 100% hexane 2.0 min., gradient to 70% hexane/30% EtOAc 3.5 min., 70% hexane/30% EtOAc 2.0 min., gradient to 49% hexane/51% EtOAc 2.1 min., gradient to 45% hexane/55% EtOAc 0.2 min., 45% hexane/55% EtOAc 8.5 min., gradient to 100% EtOAc 4.5 min., 100% EtOAc 5.5 min.) to give racemic N-[6-(2-fluorophenyl)pyridin-3-yl]-3-{[2-(morpholin-4-yl)propanoyl]amino}-4-(trifluoromethoxy)benzamide (0.48 g, 65%).

$^1$H-NMR (400 MHz, DMSO-d$_6$): δ [ppm]=1.19 (d, J=7.2 Hz, 3H), 2.50-2.56 (m, 4H), 3.37 (q, J=7.0 Hz, 1H), 3.60-3.65 (m, 4H), 7.37 (t, J=7.2 Hz, 1H), 7.45 (t, J=7.7 Hz, 2H), 7.61 (dd, J=1.5, 8.5 Hz, 1H), 7.82 (dd, J=2.1, 8.7 Hz, 1H), 7.96 (d, J=8.7 Hz, 1H), 8.04 (dm, J=7.0 Hz, 2H), 8.25 (dd, J=2.6, 8.7 Hz, 1H), 8.70 (d, J=2.1 Hz, 1H), 8.96 (d, J=2.1 Hz, 1H), 10.00 (s, 1H), 10.65 (s, 1H).

LC-MS (Method 3): R$_t$=1.34 min; MS (ESIpos): m/z=515 ([M+H]$^+$, 100%); MS (ESIneg): m/z=513 ([M−H]$^-$, 100%).

Example 11

N-[6-(2-fluorophenyl)pyridin-3-yl]-3-{[2-methyl-2-(morpholin-4-yl)propanoyl]amino}-4-(trifluoromethoxy)benzamide

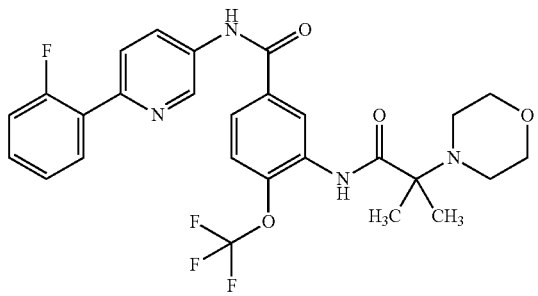 [SMILES: CC(C)(C(=O)Nc1cc(C(=O)Nc2ccc(-c3ccccc3F)nc2)ccc1OC(F)(F)F)N1CCOCC1]

950 mg (1.33 mmol) of the compound from intermediate 17 were provided in 15 mL of DMF. 278 μL (1.99 mmol) of triethylamine and 347 μL (3.99 mmol) of morpholine were added and the mixture was stirred at 120° C. for 6 h. After concentration, purification by HPLC (1. column: chromatorex C18, 10 μm, 195×51 mm, mobile phase: acetonitrile/water gradient; 2. Waters Autopurification system, column: XBrigde C18 5 μm 100×30 mm, solvent: water/acetonitrile+0.1% formic acid gradient, rate: 50 mL/min, temperature: room temperature) yielded 21.8 mg (3% of theory) of the title compound.

$^1$H-NMR (300 MHz, DMSO-d$_6$): δ [ppm]=1.24 (s, 6H), 3.62-3.74 (m, 4H), 2.51-2.55 (m, 4H), 7.28-7.38 (m, 2H), 7.42-7.52 (m, 1H), 7.62-7.69 (m, 1H), 7.80-7.88 (m, 2H), 7.92-8.01 (m, 1H), 8.30 (dd, 1H), 8.76 (d, 1H), 9.06 (d, 1H), 10.01 (s, 1H), 10.75 (s, 1H).

LC-MS (Method 1): R$_t$=1.34 min; MS (ESIpos): m/z=547 [M+H]$^+$.

Example 12

3-[(morpholin-4-ylacetyl)amino]-N-(5-phenyl-1,3-thiazol-2-yl)-4-(trifluoromethyl)benzamide

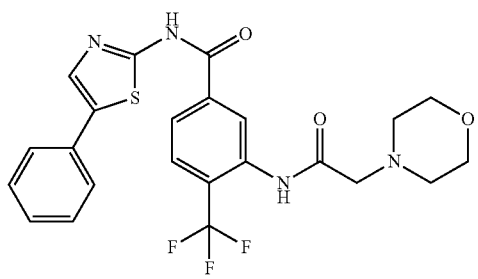 [SMILES: O=C(CN1CCOCC1)Nc1cc(C(=O)Nc2ncc(-c3ccccc3)s2)ccc1C(F)(F)F]

63.0 mg (359 μmol) of 5-phenyl-1,3-thiazol-2-amine and 188 μL (1.08 mmol) of N,N-diisopropylethylamine were provided in 1.8 mL of DMF at room temperature. 143 mg (431 μmol) of the compound from intermediate 20 and 251 μL (431 μmol) of a 50% solution of 2,4,6-tripropyl-1,3,5,2,4,6-trioxatriphosphinane 2,4,6-trioxide (T3P) in DMF were added and the mixture was stirred for 3 days at room temperature. After filtration, purification by HPLC (method 2) yielded 62.0 mg (33% of theory) of the title compound.

$^1$H-NMR (300 MHz, DMSO-d$_6$): δ [ppm]=2.53-2.70 (m, 4H), 3.60-3.77 (m, 4H), 7.30-7.37 (m, 1H), 7.40-7.49 (m, 2H), 7.62-7.73 (m, 2H), 7.94 (d, 1H), 8.01 (s, 1H), 8.08 (d, 1H), 8.82 (s, 1H), 10.02 (s, 1H), 12.93 (s, 1H).

LC-MS (Method 1): R$_t$=1.18 min; MS (ESIpos): m/z=491 [M+H]$^+$.

Example 13

3-[(morpholin-4-ylacetyl)amino]-N-(6-phenylpyridin-3-yl)-4-(trifluoromethyl)benzamide

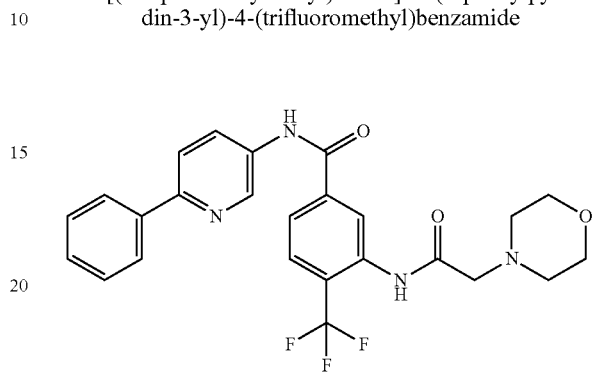

To a solution of 3-[(morpholin-4-ylacetyl)amino]-4-(trifluoromethyl)benzoic acid (prepared in a manner analogous to that described in intermediate 20, 0.20 g, 0.48 mmol) and 6-phenylpyridin-3-amine (0.098 g, 0.58 mmol, 1.2 equiv) in DMF (3.4 mL) was added (benzotriazol-1-yloxy)tripyrrolidinophosphonium hexafluorophosphate (PYBOP, 0.30 g, 0.58 mmol, 1.2 equiv) followed by diisopropylethylamine (0.34 mL, 1.93 mmol, 4.0 equiv). The resulting mixture was stirred at room temperature for 24 h, was then treated with water (5 mL). The resulting mixture was extracted with ethyl acetate (10 mL). The organic phase was dried (Na2SO$_4$ anh), and concentrated under reduced pressure. The residue (0.25 g) was purified using HPLC (method 2) to give 3-[(morpholin-4-ylacetyl)amino]-N-(6-phenylpyridin-3-yl)-4-(trifluoromethyl)benzamide (0.069 g, 29%).

$^1$H-NMR (400 MHz, DMSO-d$_6$): δ [ppm]=2.53-2.58 (m, 4H), 3.20 (s, 2H), 3.60-3.65 (m, 4H), 7.38 (t, J=7.2 Hz, 1H), 7.46 (t, J=7.3 Hz, 2H), 7.92 (s, 2H), 7.98 (d, J=8.7 Hz, 1H), 8.04 (d, J=7.2 Hz, 2H), 8.27 (dd, J=2.6, 8.5 Hz, 1H), 8.70 (s, 1H), 8.98 (d, J=2.3 Hz, 1H), 9.97 (s, 1H), 10.77 (s, 1H).

LC-MS (Method 3): R$_t$=1.25 min; MS (ESIpos): m/z=485 ([M+H]$^+$, 30%), 969 ([2M+H]$^+$, 70%); MS (ESIneg): m/z=483 ([M−H]$^-$, 100%).

Example 14

3-[(morpholin-4-ylacetyl)amino]-N-(5-phenyl-1,3-thiazol-2-yl)-4-(trifluoromethoxy)benzamide

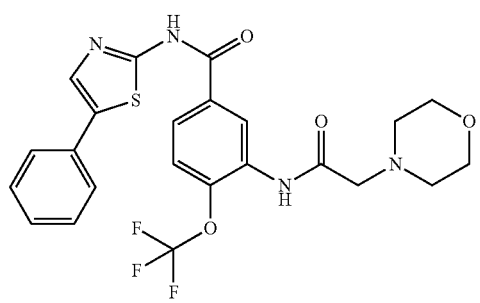 [SMILES: O=C(CN1CCOCC1)Nc1cc(C(=O)Nc2ncc(-c3ccccc3)s2)ccc1OC(F)(F)F]

63.0 mg (359 µmol) of 5-phenyl-1,3-thiazol-2-amine and 188 µL (1.08 mmol) of N,N-diisopropylethylamine were provided in 1.8 mL of DMF at room temperature. 150 mg (431 µmol) of the compound from intermediate 21 and 251 µL (431 µmol) of a 50% solution of 2,4,6-tripropyl-1,3,5,2,4,6-trioxatriphosphinane 2,4,6-trioxide (T3P) in DMF were added and the mixture was stirred over night at room temperature. 251 µL (431 µmol) of a 50% solution of 2,4,6-tripropyl-1,3,5,2,4,6-trioxatriphosphinane 2,4,6-trioxide (T3P) in DMF were added and the mixture was stirred for 2 days at room temperature. After filtration, purification by HPLC (method 2) yielded 52.4 mg (27% of theory) of the title compound.

$^1$H-NMR (300 MHz, DMSO-$d_6$): δ [ppm]=2.55-2.66 (m, 4H), 3.25 (s, 2H), 3.62-3.70 (m, 4H), 7.28-7.37 (m, 1H), 7.39-7.49 (m, 2H), 7.59-7.71 (m, 3H), 7.94-8.04 (m, 2H), 8.91 (d, 1H), 9.93 (s, 1H), 12.85 (s, 1H).

LC-MS (Method 4): $R_t$=1.18 min; MS (ESIpos): m/z=507 [M+H]$^+$.

Example 15

3-[(morpholin-4-ylacetyl)amino]-N-(6-phenylpyridin-3-yl)-4-(trifluoromethoxy)benzamide

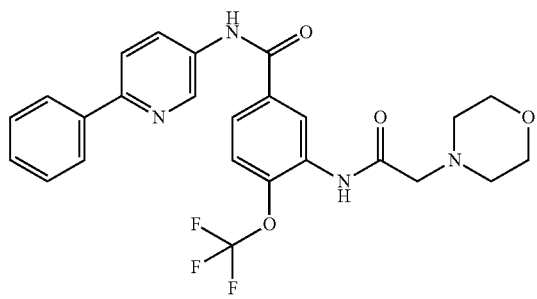 [SMILES: O=C(CN1CCOCC1)Nc1cc(C(=O)Nc2ccc(-c3ccccc3)nc2)ccc1OC(F)(F)F]

To a solution of 3-[(morpholin-4-ylacetyl)amino]-4-(trifluoromethoxy)benzoic acid (prepared in a manner analogous to that described in intermediate 21, 0.20 g, 0.46 mmol) and 6-phenylpyridin-3-amine (0.094 g, 0.55 mmol, 1.2 equiv) in DMF (3.3 mL) was added (benzotriazol-1-yloxy)tripyrrolidinophosphonium hexafluorophosphate (PYBOP, 0.29 g, 0.55 mmol, 1.2 equiv) followed by diisopropylethylamine (0.32 mL, 1.84 mmol, 4.0 equiv). The resulting mixture was stirred at room temperature for 24 h, was then treated with water (5 mL). The resulting mixture was extracted with ethyl acetate (10 mL). The organic phase was dried (Na2SO4 anh), and concentrated under reduced pressure. The residue (0.25 g) was purified using HPLC (method 2) to give 3-[(morpholin-4-ylacetyl)amino]-N-(6-phenylpyridin-3-yl)-4-(trifluoromethoxy)benzamide (0.085 g, 36%).

$^1$H-NMR (400 MHz, DMSO-$d_6$): δ [ppm]=2.52-2.56 (m, 4H), 3.20 (s, 2H), 3.59-3.64 (m, 4H), 7.37 (t, J=7.1 Hz, 1H), 7.45 (t, J=7.3 Hz, 2H), 7.63 (dd, J=1.3, 8.5 Hz, 1H), 7.82 (dd, J=2.3, 8.7 Hz, 1H), 7.97 (d, J=8.7 Hz, 1H), 8.04 (d, J=7.2 Hz, 2H), 8.25 (dd, J=2.6, 8.7 Hz, 1H), 8.75 (d, J=2.1 Hz, 1H), 8.96 (d, J=2.5 Hz, 1H), 9.90 (s, 1H), 10.66 (s, 1H).

LC-MS (Method 3): $R_t$=1.27 min; MS (ESIpos): m/z=501 ([M+H]$^+$, 30%); MS (ESIneg): m/z=499 ([M−H]$^-$, 100%).

Example 16

N-{3-[(morpholin-4-ylacetyl)amino]-4-(trifluoromethoxy)phenyl}-5-phenyl-1,3-thiazole-2-carboxamide

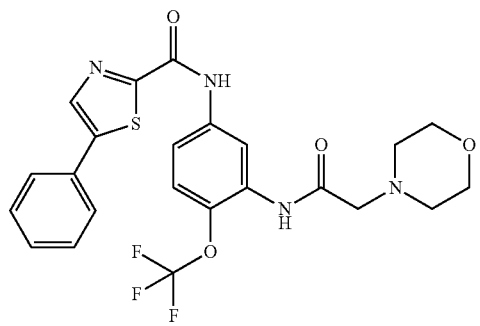 [SMILES: O=C(CN1CCOCC1)Nc1cc(NC(=O)c2ncc(-c3ccccc3)s2)ccc1OC(F)(F)F]

194 mg (609 µmol) of the compound from intermediate 32 and 318 µL (1.83 mmol) of N,N-diisopropylethylamine were provided in 3 mL of DMF at room temperature. 150 mg (731 µmol) of the compound from intermediate 1 and 427 µL (731 µmol) of a 50% solution of 2,4,6-tripropyl-1,3,5,2,4,6-trioxatriphosphinane 2,4,6-trioxide (T3P) in DMF were added and the mixture was stirred for 3 days at room temperature. After filtration, purification by HPLC (method 2) yielded 219 mg (70% of theory) of the title compound.

$^1$H-NMR (400 MHz, DMSO-$d_6$): δ [ppm]=2.54-2.61 (m, 4H), 3.20 (s, 2H), 3.61-3.68 (m, 4H), 7.42-7.55 (m, 4H), 7.71 (dd, 1H), 7.80-7.86 (m, 2H), 8.52 (s, 1H), 8.84 (d, 1H), 9.79 (s, 1H), 11.04 (s, 1H).

LC-MS (Method 1): $R_t$=1.24 min; MS (ESIpos): m/z=507 [M+H]$^+$.

Example 17

N-{3-[(morpholin-4-ylacetyl)amino]-4-(trifluoromethoxy)phenyl}-5-phenylthiophene-2-carboxamide

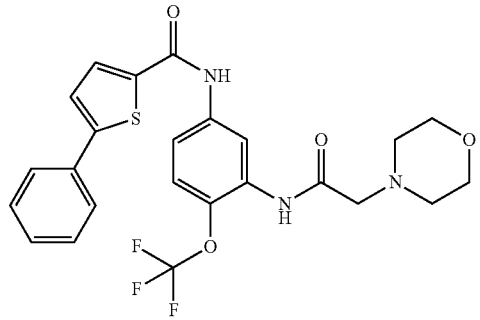 [SMILES: O=C(CN1CCOCC1)Nc1cc(NC(=O)c2ccc(-c3ccccc3)s2)ccc1OC(F)(F)F]

To a solution of N-[5-amino-2-(trifluoromethoxy)phenyl]-2-(morpholin-4-yl)acetamide (prepared in a manner analogous to that described in intermediate 32, 0.075 g, 0.24 mmol) and 5-phenylthiophene-2-carboxylic acid (0.097 g, 0.57 mmol, 1.0 equiv) in DMF (2.5 mL) was added (benzotriazol-1-yloxy)tripyrrolidinophosphonium hexafluorophosphate (PYBOP, 0.18 g, 0.35 mmol, 1.5 equiv) followed by diisopropylethylamine (0.16 mL, 0.94 mmol, 4.0 equiv).

The resulting mixture was stirred at room temperature for 24 h, was then concentrated under reduced pressure. The residue was treated with water (10 mL). The resulting mixture was extracted with ethyl acetate (10 mL). The organic phase was dried (Na2SO$_4$ anh), and concentrated under reduced pressure. The residue (0.25 g) was purified using HPLC (method 2) to give N-{3-[(morpholin-4-ylacetyl)amino]-4-(trifluoromethoxy)phenyl}-5-phenylthiophene-2-carboxamide (0.041 g, 33%).

$^1$H-NMR (400 MHz, DMSO-d$_6$): δ [ppm]=2.51-2.56 (m, 4H), 3.18 (s, 2H), 3.59-3.64 (m, 4H), 7.32-7.47 (m, 4H), 7.59 (d, J=4.0 Hz, 1H), 7.66-7.74 (m, 3H), 8.04 (d, J=4.0 Hz, 1H), 8.61 (d, J=2.6 Hz, 1H), 9.76 (s, 1H), 10.46 (s, 1H).

LC-MS (Method 3): R$_t$=1.40 min; MS (ESIpos): m/z=506 ([M+H]$^+$, 100%); MS (ESIneg): m/z=504 ([M−H]$^−$, 100%).

Example 18

N-{4-tert-butyl-3-[(morpholin-4-ylacetyl)amino]phenyl}-6-phenylnicotinamide

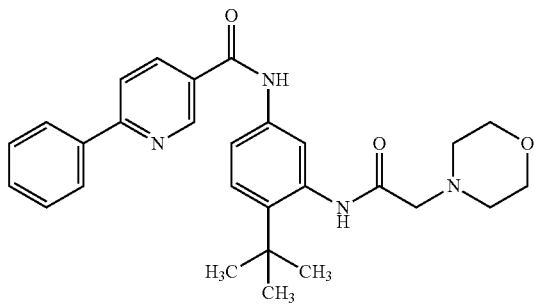 [SMILES: CC(C)(C)c1ccc(NC(=O)c2ccc(-c3ccccc3)nc2)cc1NC(=O)CN1CCOCC1]

To a solution of N-(5-amino-2-tert-butylphenyl)-2-(morpholin-4-yl)acetamide (prepared in a manner analogous to that described in intermediate 33, 0.090 g, 0.31 mmol) and 6-phenylnicotinic acid HCl salt (0.091 g, 0.39 mmol, 1.25 equiv) in DMF (2.4 mL) was added propanephosphonic acid cyclic anhydride solution (50% in ethyl acetate, 0.23 mL, 0.39 mmol, 1.25 equiv) followed by diisopropylethylamine (0.22 mL, 1.24 mmol, 4.0 equiv). The resulting mixture was stirred at room temperature for 24 h, was then concentrated under reduced pressure. The residue was then treated with water (50 mL). The resulting mixture was extracted with ethyl acetate (50 mL). The organic phase was dried (Na2SO$_4$ anh), and concentrated under reduced pressure. The residue was purified by HPLC (method 2) to give N-{4-tert-butyl-3-[(morpholin-4-ylacetyl)amino]phenyl}-6-phenylnicotinamide (22 mg, 15%).

$^1$H-NMR (400 MHz, DMSO-d$_6$): δ [ppm]=1.37 (s, 9H), 2.55-2.61 (m, 4H), 3.15 (s, 2H), 3.61-3.65 (m, 4H), 7.33 (d, J=8.9 Hz, 1H), 7.43-7.54 (m, 3H), 7.60 (dd, J=2.3, 8.7 Hz, 1H), 8.08-8.17 (m, 4H), 8.36 (dd, J=2.5, 8.3 Hz, 1H), 9.15 (d, J=1.7 Hz, 1H), 9.39 (s, 1H), 10.43 (s, 1H).

LC-MS (Method 3): R$_t$=1.28 min; MS (ESIpos): m/z=473 ([M+H]$^+$, 100%); MS (ESIneg): m/z=471 ([M−H]$^−$, 100%).

Example 19

N-{4-tert-butyl-3-[(morpholin-4-ylacetyl)amino]phenyl}-5-phenylthiophene-2-carboxamide

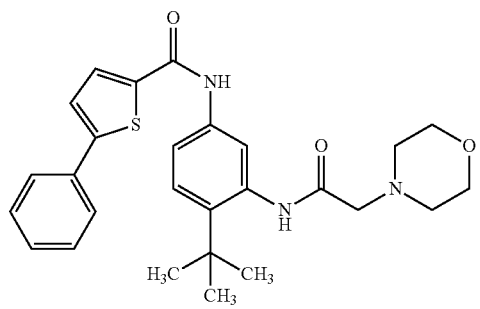 [SMILES: CC(C)(C)c1ccc(NC(=O)c2ccc(-c3ccccc3)s2)cc1NC(=O)CN1CCOCC1]

To a solution of N-(5-amino-2-tert-butylphenyl)-2-(morpholin-4-yl)acetamide (prepared in a manner analogous to that described in intermediate 33, 0.090 g, 0.31 mmol) and 5-phenylthiophene-2-carboxylic acid (0.078 g, 0.39 mmol, 1.25 equiv) in DMF (2.4 mL) was added propanephosphonic acid cyclic anhydride solution (50% in ethyl acetate, 0.23 mL, 0.39 mmol, 1.25 equiv) followed by diisopropylethylamine (0.16 mL, 0.93 mmol, 3.0 equiv). The resulting mixture was stirred at room temperature for 24 h, was then concentrated under reduced pressure. The residue was then treated with water (50 mL). The resulting mixture was extracted with ethyl acetate (50 mL). The organic phase was dried (Na2SO$_4$ anh), and concentrated under reduced pressure. The residue was purified by HPLC (method 2) to give N-{4-tert-butyl-3-[(morpholin-4-ylacetyl)amino]phenyl}-5-phenylthiophene-2-carboxamide (28 mg, 18%).

$^1$H-NMR (400 MHz, DMSO-d$_6$): δ [ppm]=1.36 (s, 9H), 2.55-2.60 (m, 4H), 3.14 (s, 2H), 3.60-3.65 (m, 4H), 7.29-7.38 (m, 2H), 7.43 (t, J=7.3 Hz, 2H), 7.54-7.59 (m, 2H), 7.71 (d, J=7.2 Hz, 2H), 8.00-8.03 (m, 2H), 9.38 (s, 1H), 10.23 (s, 1H).

LC-MS (Method 3): R$_t$=1.40 min; MS (ESIpos): m/z=478 ([M+H]$^+$, 100%), 955 ([2M+H]$^+$, 30%); MS (ESIneg): m/z=476 ([M−H]$^−$, 100%).

Example 20

N-{4-methoxy-3-[(morpholin-4-ylacetyl)amino]phenyl}-5-phenyl-1,3-oxazole-2-carboxamide

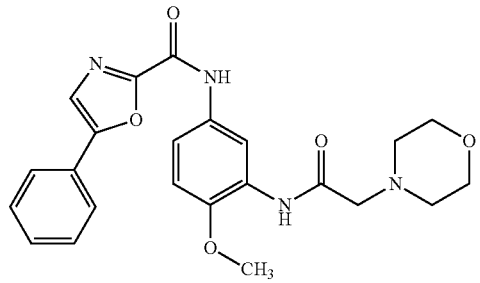 [SMILES: COc1ccc(NC(=O)c2ncc(-c3ccccc3)o2)cc1NC(=O)CN1CCOCC1]

To a solution of N-(5-amino-2-methoxyphenyl)-2-(morpholin-4-yl)acetamide (prepared in a manner analogous to that described in intermediate 36, 0.085 g, 0.32 mmol) and 5-phenyl-1,3-oxazole-2-carboxylic acid (0.075 g, 0.40 mmol, 1.25 equiv) in DMF (2.5 mL) was added propanephosphonic acid cyclic anhydride solution (50% in ethyl acetate, 0.23 mL, 0.39 mmol, 1.25 equiv) followed by diisopropylethylamine (0.17 mL, 0.96 mmol, 3.0 equiv). The resulting mixture was stirred at room temperature for 24 h, was then concentrated under reduced pressure. The residue was then treated with water (50 mL). The resulting mixture was extracted with ethyl acetate (50 mL). The organic phase was dried (Na2SO4 anh), and concentrated under reduced pressure. The residue was purified by HPLC (method 2) to give N-{4-methoxy-3-[(morpholin-4-ylacetyl)amino]phenyl}-5-phenyl-1,3-oxazole-2-carboxamide (23 mg, 16%).

$^1$H-NMR (400 MHz, DMSO-d$_6$): δ [ppm]=2.50-2.55 (m, 4H), 3.12 (s, 2H), 3.62-3.66 (m, 4H), 3.86 (s, 3H), 7.04 (d, J=8.9 Hz, 1H), 7.39-7.54 (m, 4H), 7.84 (d, J=7.2 Hz, 2H), 7.95 (s, 1H), 8.61 (d, J=2.6 Hz, 1H), 9.71 (s, 1H), 10.72 (s, 1H).

LC-MS (Method 3): R$_t$=1.16 min; MS (ESIpos): m/z=437 ([M+H]$^+$, 100%), 873 ([2M+H]$^+$, 60%); MS (ESIneg): m/z=435 ([M−H]$^−$, 100%).

Example 21

N-{4-chloro-3-[(morpholin-4-ylacetyl)amino]phenyl}-5-phenylthiophene-2-carboxamide

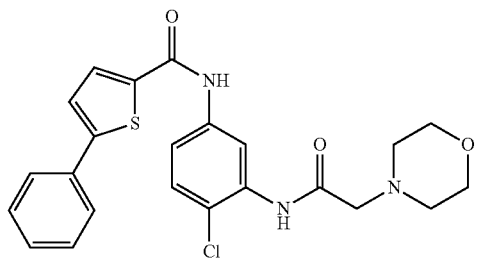 [SMILES: O=C(CN1CCOCC1)Nc1cc(NC(=O)c2ccc(-c3ccccc3)s2)ccc1Cl]

To a solution of N-(5-amino-2-chlorophenyl)-2-(morpholin-4-yl)acetamide (prepared in a manner analogous to that described in intermediate 34, 0.13 g, 0.48 mmol) and 5-phenylthiophene-2-carboxylic acid (0.15 g, 0.72 mmol, 1.5 equiv) in DMF (5 mL) was added (benzotriazol-1-yloxy)tripyrrolidinophosphonium hexafluorophosphate (PYBOP, 0.38 g, 0.723 mmol, 1.5 equiv) followed by diisopropylethylamine (0.34 mL, 1.93 mmol, 4.0 equiv). The resulting mixture was stirred at room temperature for 24 h, was then concentrated under reduced pressure. The residue was treated with water (10 mL). The resulting mixture was extracted with ethyl acetate (10 mL). The organic phase was dried (Na2SO4 anh), and concentrated under reduced pressure. The residue (3.5 g) was purified by HPLC (method 2) to give N-{4-chloro-3-[(morpholin-4-ylacetyl)amino]phenyl}-5-phenylthiophene-2-carboxamide (37 mg, 16%).

$^1$H-NMR (400 MHz, DMSO-d$_6$): δ [ppm]=2.53-2.58 (m, 4H), 3.18 (s, 2H), 3.62-3.67 (m, 4H), 7.31-7.48 (m, 4H), 7.59 (d, J=4.0 Hz, 1H), 7.65 (dd, J=2.6, 8.7 Hz, 1H), 7.72 (d, J=7.0 Hz, 2H), 8.03 (d, J=4.1 Hz, 1H), 8.61 (d, J=2.5 Hz, 1H), 9.89 (s, 1H), 10.41 (s, 1H).

LC-MS (Method 3): R$_t$=1.34 min; MS (ESIpos): m/z=456 ([M+H]$^+$, 100%), 911 ([2M+H]$^+$, 20%); (ESIneg): m/z=454 ([M−H]$^−$, 50%).

Example 22

N-{4-methyl-3-[(morpholin-4-ylacetyl)amino]phenyl}-5-phenylthiophene-2-carboxamide

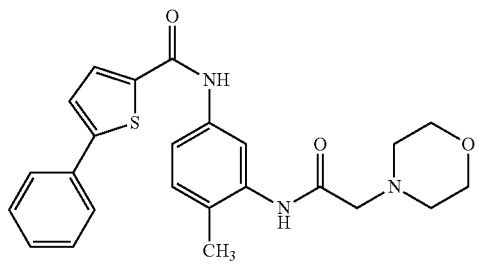 [SMILES: Cc1ccc(NC(=O)c2ccc(-c3ccccc3)s2)cc1NC(=O)CN1CCOCC1]

To a solution of N-(5-amino-2-methylphenyl)-2-(morpholin-4-yl)acetamide (prepared in a manner analogous to that described in intermediate 35, 0.085 g, 0.34 mmol) and 5-phenyl-thiophene-2-carboxylic acid (0.084 g, 0.41 mmol, 1.22 equiv) in DMF (2.7 mL) was added propanephosphonic acid cyclic anhydride solution (50% in ethyl acetate, 0.24 mL, 0.41 mmol, 1.20 equiv) followed by diisopropylethylamine (0.18 mL, 1.02 mmol, 3.0 equiv). The resulting mixture was stirred at room temperature for 24 h, was then concentrated under reduced pressure. The residue was then treated with water (10 mL). The resulting mixture was extracted with ethyl acetate (10 mL). The organic phase was dried (Na2SO4 anh), and concentrated under reduced pressure. The residue was purified by HPLC (method 2) to give N-{4-methyl-3-[(morpholin-4-ylacetyl)amino]phenyl}-5-phenylthiophene-2-carboxamide (34 mg, 23%).

$^1$H-NMR (400 MHz, DMSO-d$_6$): δ [ppm]=2.18 (s, 3H), 2.53-2.56 (m, 4H), 3.12 (s, 2H), 3.61-3.66 (m, 4H), 7.16 (d, J=8.3 Hz, 1H), 7.35 (t, J=7.2 Hz, 1H), 7.43 (t, J=7.5 Hz, 2H), 7.50 (dd, J=2.0, 8.3 Hz, 1H), 7.57 (d, 4.0 Hz, 1H), 7.71 (d, J=7.3 Hz, 2H), 8.01 (d, J=4.0 Hz, 1H), 8.10 (d, J=1.8 Hz, 1H), 9.38 (s, 1H), 10.21 (s, 1H).

LC-MS (Method 3): R$_t$=1.23 min; MS (ESIpos): m/z=436 ([M+H]$^+$, 100%), 871 ([2M+H]$^+$, 70%); MS (ESIneg): m/z=434 ([M−H]$^−$, 100%), 869 ([2M−H]$^−$, 10%).

Example 23

N-{4-methoxy-3-[(morpholin-4-ylacetyl)amino]phenyl}-5-phenyl-1,3-thiazole-2-carboxamide

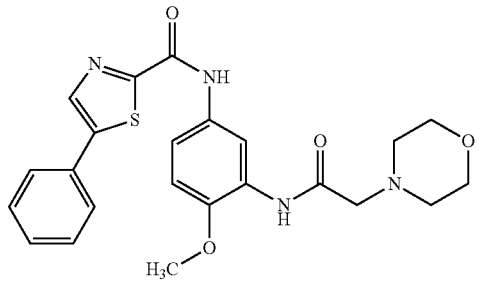 [SMILES: COc1ccc(NC(=O)c2ncc(-c3ccccc3)s2)cc1NC(=O)CN1CCOCC1]

To a solution of N-(5-amino-2-methoxyphenyl)-2-(morpholin-4-yl)acetamide (prepared in a manner analogous to that described in intermediate 36, 0.15 g, 0.57 mmol) and lithium 5-phenyl-1,3-thiazole-2-carboxylate (prepared in a manner analogous to that described in intermediate 2, 0.18 g, 0.85 mmol, 1.5 equiv) in DMF (4 mL) was added (benzotriazol-1-yloxy)tripyrrolidinophosphonium hexafluorophosphate (PYBOP, 0.44 g, 0.85 mmol, 1.5 equiv) followed by diisopropylethylamine (0.30 mL, 1.70 mmol, 3.0 equiv). The resulting mixture was stirred at room temperature for 24 h, was then concentrated under reduced pressure. The residue was treated with water (10 mL). The resulting mixture was extracted with ethyl acetate (10 mL). The organic phase was dried (Na2SO4 anh), and concentrated under reduced pressure. The residue was purified by HPLC (method 2) to give N-{4-methoxy-3-[(morpholin-4-ylacetyl)amino]phenyl}-5-phenyl-1,3-thiazole-2-carboxamide (48 mg, 19%).

$^1$H-NMR (400 MHz, DMSO-d$_6$): δ [ppm]=2.51-2.54 (m, 4H), 3.12 (s, 2H), 3.62-3.66 (m, 4H), 3.86 (s, 3H), 7.03 (d, J=9.1 Hz, 1H), 7.38-7.51 (m, 4H), 7.78 (d, J=7.3 Hz, 2H), 8.45 (s, 1H), 8.67 (d, J=2.5 Hz, 1H), 9.70 (s, 1H), 10.66 (s, 1H).

LC-MS (Method 3): R$_t$=1.29 min; MS (ESIpos): m/z=453 ([M+H]$^+$, 100%), 905 ([2M+H]$^+$, 60%); MS (ESIneg): m/z=451 ([M−H]$^−$, 100%).

Example 24

N-{4-methoxy-3-[(morpholin-4-ylacetyl)amino]phenyl}-5-phenyl-1H-pyrrole-2-carboxamide

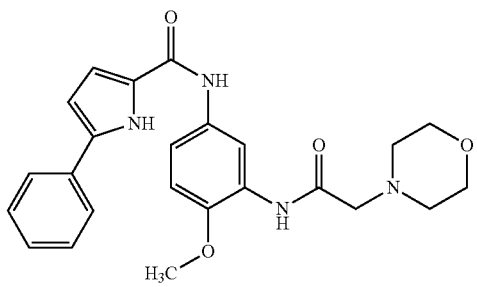 [SMILES: COc1ccc(NC(=O)c2ccc(-c3ccccc3)[nH]2)cc1NC(=O)CN1CCOCC1]

To a solution of N-(5-amino-2-methoxyphenyl)-2-(morpholin-4-yl)acetamide (prepared in a manner analogous to that described in intermediate 36, 0.090 g, 0.34 mmol) and 5-phenyl-1H-pyrrole-2-carboxylic acid (0.076 g, 0.41 mmol, 1.20 equiv) in DMF (1.2 mL) was added propanephosphonic acid cyclic anhydride solution (50% in ethyl acetate, 0.24 mL, 0.41 mmol, 1.20 equiv) followed by diisopropylethylamine (0.18 mL, 1.02 mmol, 3.0 equiv). The resulting mixture was stirred at room temperature for 24 h, was then concentrated under reduced pressure. The residue was then treated with water (10 mL). The resulting mixture was extracted with ethyl acetate (10 mL). The organic phase was dried (Na2SO4 anh), and concentrated under reduced pressure. The residue (0.16 g) was purified by HPLC (method 2) to give N-{4-methoxy-3-[(morpholin-4-ylacetyl)amino]phenyl}-5-phenyl-1H-pyrrole-2-carboxamide (13 mg, 9%).

$^1$H-NMR (400 MHz, DMSO-d$_6$): δ [ppm]=3.12 (s, 2H), 3.60-3.78 (m, 4H), 3.84 (s, 3H), 6.58-6.61 (m, 1H), 6.99-7.08 (m, 2H), 7.21 (t, J=7.3 Hz, 1H), 7.35 (t, J=7.6 Hz, 2H), 7.50-7.56 (m, 1H), 7.79 (d, J=7.4 Hz, 2H), 8.53 (br s, 1H), 9.70 (s, 2H), 11.75 (s, 1H), peak at 2.4-2.6 ppm partially obscured by solvent.

LC-MS (Method 3): R$_t$=1.14 min; MS (ESIpos): m/z=435 ([M+H]$^+$, 100%), 869 ([2M+H]$^+$, 30%); MS (ESIneg): m/z=433 ([M−H]$^−$, 100%).

Example 25

N-{4-methoxy-3-[(morpholin-4-ylacetyl)amino]phenyl}-5-phenylthiophene-2-carboxamide

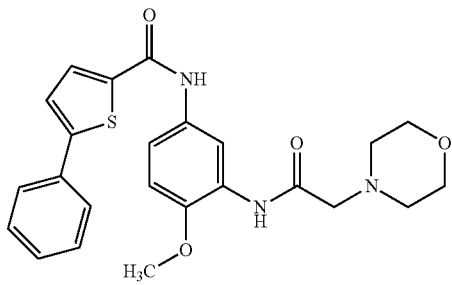 [SMILES: COc1ccc(NC(=O)c2ccc(-c3ccccc3)s2)cc1NC(=O)CN1CCOCC1]

To a solution of N-(5-amino-2-methoxyphenyl)-2-(morpholin-4-yl)acetamide (prepared in a manner analogous to that described in intermediate 36, 0.075 g, 0.28 mmol) and 5-phenylthiophene-2-carboxylic acid (0.072 g, 0.35 mmol, 1.25 equiv) in DMF (3 mL) was added (benzotriazol-1-yloxy)tripyrrolidinophosphonium hexafluorophosphate (PYBOP, 0.18 g, 0.35 mmol, 1.25 equiv) followed by diisopropylethylamine (0.19 mL, 1.13 mmol, 4.0 equiv). The resulting mixture was stirred at room temperature for 24 h, was then concentrated under reduced pressure. The residue was treated with water (10 mL). The resulting mixture was extracted with ethyl acetate (10 mL). The organic phase was dried (Na2SO4 anh), and concentrated under reduced pressure. The residue (0.3 g) was purified by HPLC (method 2) to give N-{4-methoxy-3-[(morpholin-4-ylacetyl)amino]phenyl}-5-phenylthiophene-2-carboxamide (62 mg, 49%).

$^1$H-NMR (400 MHz, DMSO-d$_6$): δ [ppm]=2.49-2.57 (m, 4H), 3.12 (br s, 2H), 3.61-3.68 (m, 4H), 3.85 (s, 3H). 7.02 (d, J=9.0 Hz, 1H), 7.34 (t, J=7.8 Hz, 1H), 7.43 (t, J=7.3 Hz, 2H), 7.52 (br d, J=8.5 Hz, 1H), 7.57 (d, J=7.6 Hz, 1H), 7.71 (d, J=7.0 Hz, 2H), 8.00 (d, J=4.0 Hz, 1H), 8.47 (br s, 1H), 9.73 (br s, 1H), 10.19 (s, 1H).

LC-MS (Method 3): R$_t$=1.23 min; MS (ESIpos): m/z=452 ([M+H]$^+$, 100%), 903 ([2M+H]$^+$, 30%); MS (ESIneg): m/z=450 ([M−H]$^−$, 100%), 901 ([2M−H]$^−$, 10%).

Example 26

6-(2,3-difluorophenyl)-N-{3-[(morpholin-4-ylacetyl)amino]-4-(trifluoromethoxy)phenyl}nicotinamide

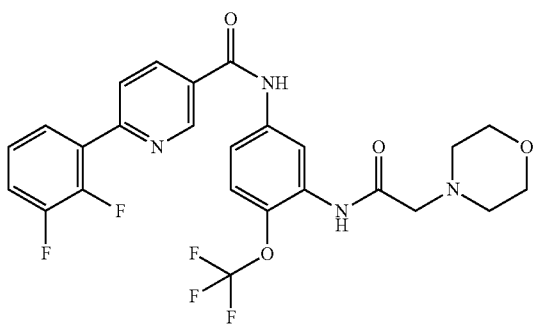 [SMILES: O=C(CN1CCOCC1)Nc1cc(NC(=O)c2ccc(-c3cccc(F)c3F)nc2)ccc1OC(F)(F)F]

To a microwave vial was added 6-chloro-N-{3-[(morpholin-4-ylacetyl)amino]-4-(trifluoromethoxy)phenyl}nicotinamide (prepared in a manner analogous to that described in intermediate 37, 0.15 g, 0.33 mmol), (2,3-difluorophenyl)boronic acid (0.077 g, 0.49 mmol, 1.5 equiv), potassium carbonate (90 mg, 0.65 mmol, 2.0 equiv) and a DME/water mixture (3:1, 3.3 mL). The resulting suspension was purged with argon, treated with [1,1'-bis(diphenylphosphino)ferrocene]palladium(II) chloride $CH_2Cl_2$ complex (Pd(dppf)$Cl_2$·$CH_2Cl_2$, 0.013 g, 0.016 mmol, 5.0 mol %) and sealed. The resulting mixture was heated with a microwave apparatus at 150° C. for 1 h, was then cooled to room temperature. The reaction mixture was poured onto ice water (10 mL), and extracted with ethyl acetate (3×10 mL). The combined organic phases were washed with a saturated NaCl solution, dried (Na2SO$_4$ anh), and concentrated under reduced pressure. The resulting material was purified by HPLC (method 2) to give 6-(2,3-difluorophenyl)-N-{3-[(morpholin-4-ylacetyl)amino]-4-(trifluoromethoxy)phenyl}nicotinamide (8 mg, 4%).

$^1$H-NMR (400 MHz, DMSO-d$_6$): δ [ppm]=2.52-2.56 (m, 4H), 3.18 (s, 2H), 3.59-3.64 (m, 4H), 7.31-7.39 (m, 1H), 7.43 (dm, J=8.0 Hz, 1H), 7.50-7.60 (m, 1H), 7.70-7.80 (m, 2H), 7.95 (dm, J=7.5 Hz, 1H), 8.41 (dd, J=2.3, 8.3 Hz, 1H), 8.69 (d, J=2.5 Hz, 1H), 9.21 (d, J=1.7 Hz, 1H), 9.77 (s, 1H), 10.73 (s, 1H).

LC-MS (Method 3): R$_t$=1.34 min; MS (ESIpos): m/z=537 ([M+H]$^+$, 100%); MS (ESIneg): m/z=535 ([M–H]$^-$, 100%).

Example 27

6-(3,5-difluorophenyl)-N-{3-[(morpholin-4-ylacetyl)amino]-4-(trifluoromethoxy)phenyl}nicotinamide

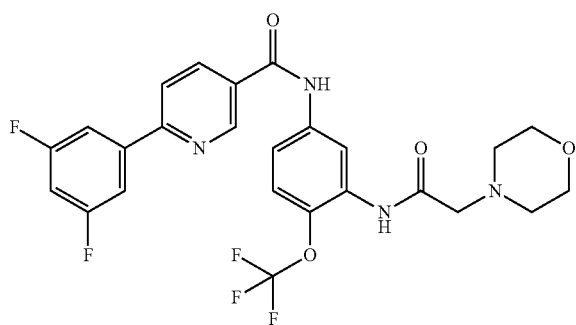 [SMILES: O=C(CN1CCOCC1)Nc1cc(NC(=O)c2ccc(-c3cc(F)cc(F)c3)nc2)ccc1OC(F)(F)F]

To a microwave vial was added 6-chloro-N-{3-[(morpholin-4-ylacetyl)amino]-4-(trifluoromethoxy)phenyl}nicotinamide (prepared in a manner analogous to that described in intermediate 37, 0.15 g, 0.33 mmol), (3,5-difluorophenyl)boronic acid (0.077 g, 0.49 mmol, 1.5 equiv), potassium carbonate (90 mg, 0.65 mmol, 2.0 equiv) and a DME/water mixture (3:1, 3.3 mL). The resulting suspension was purged with argon, treated with [1,1'-bis(diphenylphosphino)ferrocene]palladium(II) chloride $CH_2Cl_2$ complex (Pd(dppf)$Cl_2$·$CH_2Cl_2$, 0.013 g, 0.016 mmol, 5.0 mol %) and sealed. The resulting mixture was heated with a microwave apparatus at 150° C. for 1 h, was then cooled to room temperature. The reaction mixture was poured onto ice water (10 mL), and extracted with ethyl acetate (3×10 mL). The combined organic phases were washed with a saturated NaCl solution, dried (Na2SO$_4$ anh), and concentrated under reduced pressure. The resulting material was purified by HPLC (method 2) to give 6-(3,5-difluorophenyl)-N-{3-[(morpholin-4-ylacetyl)amino]-4-(trifluoromethoxy)phenyl}nicotinamide (28 mg, 15%).

$^1$H-NMR (400 MHz, DMSO-d$_6$): δ [ppm]=2.52-2.56 (m, 4H), 3.17 (s, 2H), 3.59-3.63 (m, 4H), 7.37 (tt, J=2.3, 10.9 Hz, 1H), 7.43 (dm, J=9.0 Hz, 1H), 7.72 (dd, J=2.5, 6.6 Hz, 1H), 7.90 (dm, J=9.0 Hz, 2H), 8.25 (d, J=8.1 Hz, 1H), 8.42 (dd, J=2.3, 8.3 Hz, 1H), 8.69 (d, J=2.6 Hz, 1H), 9.17 (d, J=1.7 Hz, 1H), 9.78 (s, 1H), 10.71 (s, 1H).

LC-MS (Method 3): R$_t$=1.38 min; MS (ESIpos): m/z=537 ([M+H]$^+$, 100%); MS (ESIneg): m/z=535 ([M–H]$^-$, 100%).

Example 28

6-(3-fluorophenyl)-N-{3-[(morpholin-4-ylacetyl)amino]-4-(trifluoromethoxy)phenyl}nicotinamide

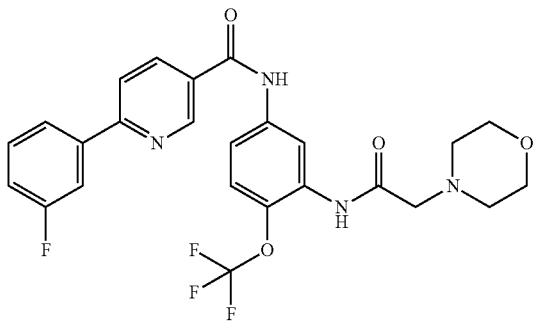 [SMILES: O=C(CN1CCOCC1)Nc1cc(NC(=O)c2ccc(-c3cccc(F)c3)nc2)ccc1OC(F)(F)F]

To a microwave vial was added 6-chloro-N-{3-[(morpholin-4-ylacetyl)amino]-4-(trifluoromethoxy)phenyl}nicotinamide (prepared in a manner analogous to that described in intermediate 37, 0.15 g, 0.33 mmol), (3-fluorophenyl)boronic acid (0.068 g, 0.49 mmol, 1.5 equiv), potassium carbonate (90 mg, 0.65 mmol, 2.0 equiv) and a DME/water mixture (3:1, 3.3 mL). The resulting suspension was purged with argon, treated with [1,1'-bis(diphenylphosphino)ferrocene]palladium(II) chloride $CH_2Cl_2$ complex (Pd(dppf)$Cl_2$·$CH_2Cl_2$, 0.013 g, 0.016 mmol, 5.0 mol %) and sealed. The resulting mixture was heated with a microwave apparatus at 150° C. for 1 h, was then cooled to room temperature. The reaction mixture was poured onto ice water (10 mL), and extracted with ethyl acetate (3×10 mL). The combined organic phases were washed with a saturated NaCl solution, dried (Na2SO$_4$ anh), and concentrated under reduced pressure. The resulting material was purified by HPLC (method 2) to give 6-(3-fluorophenyl)-N-{3-[(morpholin-4-ylacetyl)amino]-4-(trifluoromethoxy)phenyl}nicotinamide (31 mg, 18%).

$^1$H-NMR (400 MHz, DMSO-d$_6$): δ [ppm]=2.52-2.56 (m, 4H), 3.18 (s, 2H), 3.60-3.63 (m, 4H), 7.31 (td, J=2.5, 8.5 Hz, 1H), 7.43 (dd, J=1.5, 8.8 Hz, 1H), 7.53-7.59 (m, 1H), 7.73 (dd, J=2.5, 9.1 Hz, 1H), 7.97 (dm, J=10.6 Hz, 2H), 8.18 (d, J=8.3 Hz, 1H), 8.39 (dd, J=2.3, 8.3 Hz, 1H), 8.69 (d, J=2.5 Hz, 1H), 9.17 (d, J=1.5 Hz, 1H), 9.77 (s, 1H), 10.68 (s, 1H).

LC-MS (Method 3): R$_t$=1.34 min; MS (ESIpos): m/z=519 ([M+H]$^+$, 100%); MS (ESIneg): m/z=517 ([M–H]$^-$, 100%).

Example 29

6-(2,6-difluorophenyl)-N-{3-[(morpholin-4-ylacetyl)amino]-4-(trifluoromethoxy)phenyl}nicotinamide

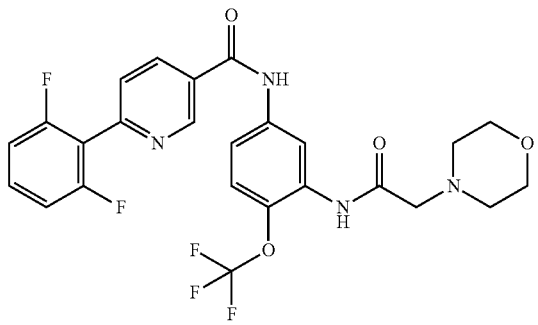 [SMILES: O=C(CN1CCOCC1)Nc1cc(NC(=O)c2ccc(-c3c(F)cccc3F)nc2)ccc1OC(F)(F)F]

To a microwave vial was added 6-chloro-N-{3-[(morpholin-4-ylacetyl)amino]-4-(trifluoromethoxy)phenyl}nicotinamide (prepared in a manner analogous to that described in intermediate 37, 0.15 g, 0.33 mmol), (2,6-difluorophenyl)boronic acid (0.077 g, 0.49 mmol, 1.5 equiv), potassium carbonate (90 mg, 0.65 mmol, 2.0 equiv) and a DME/water mixture (3:1, 3.3 mL). The resulting suspension was purged with argon, treated with [1,1'-bis(diphenylphosphino)ferrocene]palladium(II) chloride $CH_2Cl_2$ complex $(Pd(dppf)Cl_2 \cdot CH_2Cl_2$, 0.013 g, 0.016 mmol, 5.0 mol %) and sealed. The resulting mixture was heated with a microwave apparatus at 150° C. for 1 h, was then cooled to room temperature. The reaction mixture was poured onto ice water (10 mL), and extracted with ethyl acetate (3×10 mL). The combined organic phases were washed with a saturated NaCl solution, dried (Na2SO4 anh), and concentrated under reduced pressure. The resulting material was purified by HPLC (method 2) to give 6-(2,6-difluorophenyl)-N-{3-[(morpholin-4-ylacetyl)amino]-4-(trifluoromethoxy)phenyl}nicotinamide (6 mg, 3%).

$^1$H-NMR (400 MHz, DMSO-$d_6$): δ [ppm]=2.55-2.59 (m, 4H), 3.20 (s, 2H), 3.62-3.66 (m, 4H), 7.24-7.31 (m, 2H), 7.46 (dd, J=1.3, 9.0 Hz, 1H), 7.55-7.63 (m, 1H), 7.73-7.79 (m, 2H), 8.41 (dd, J=2.3, 8.3 Hz, 1H), 8.71 (d, J=2.5 Hz, 1H), 9.20 (d, J=1.5 Hz, 1H), 9.80 (s, 1H), 10.77 (s, 1H).

LC-MS (Method 3): $R_t$=1.28 min; MS (ESIpos): m/z=537 ([M+H]$^+$, 100%); MS (ESIneg): m/z=535 ([M−H]$^−$, 100%).

Example 30

6-(2-fluorophenyl)-N-{3-[(morpholin-4-ylacetyl)amino]-4-(trifluoromethoxy)phenyl}nicotinamide

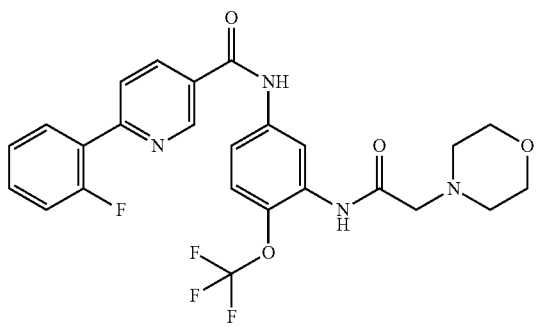 [SMILES: O=C(CN1CCOCC1)Nc1cc(NC(=O)c2ccc(-c3ccccc3F)nc2)ccc1OC(F)(F)F]

To a microwave vial was added 6-chloro-N-{3-[(morpholin-4-ylacetyl)amino]-4-(trifluoromethoxy)phenyl}nicotinamide (prepared in a manner analogous to that described in intermediate 37, 0.126 g, 0.28 mmol), (2-fluorophenyl)boronic acid (0.058 g, 0.41 mmol, 1.5 equiv), potassium carbonate (76 mg, 0.54 mmol, 2.0 equiv) and a DME/water mixture (3:1, 2.8 mL). The resulting suspension was purged with argon, treated with [1,1'-bis(diphenylphosphino)ferrocene]palladium(II) chloride $CH_2Cl_2$ complex $(Pd(dppf)Cl_2 \cdot CH_2Cl_2$, 0.011 g, 0.014 mmol, 5.0 mol %) and sealed. The resulting mixture was heated with a microwave apparatus at 150° C. for 1 h, was then cooled to room temperature. The reaction mixture was poured onto ice water (10 mL), and extracted with ethyl acetate (3×10 mL). The combined organic phases were washed with a saturated NaCl solution, dried (Na2SO4 anh), and concentrated under reduced pressure. The resulting material was purified by HPLC (method 2) to give a precipitate (40 mg), which was crystallized from ethanol to give the title compound (9 mg, 6%).

$^1$H-NMR (400 MHz, DMSO-$d_6$): δ [ppm]=2.52-2.56 (m, 4H), 3.17 (s, 2H), 3.59-3.64 (m, 4H), 7.31-7.39 (m, 2H), 7.43 (dd, J=1.5, 9.0 Hz, 1H), 7.48-7.56 (m, 1H), 7.72 (dd, J=2.6, 9.0 Hz, 1H), 7.90-8.01 (m, 2H), 8.38 (dd, J=2.5, 8.3 Hz, 1H), 8.69 (d, J=2.6 Hz, 1H), 9.20 (d, J=1.7 Hz, 1H), 9.77 (s, 1H), 10.71 (s, 1H).

LC-MS (Method 3): $R_t$=1.35 min; MS (ESIpos): m/z=519 ([M+H]$^+$, 100%); MS (ESIneg): m/z=517 ([M−H]$^−$, 100%).

Example 31

6-(2-fluorophenyl)-N-{4-methoxy-3-[(morpholin-4-ylacetyl)amino]phenyl}nicotinamide

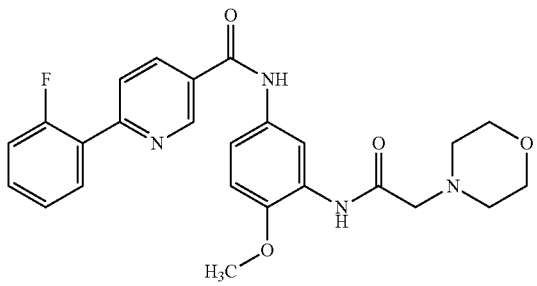 [SMILES: COc1ccc(NC(=O)c2ccc(-c3ccccc3F)nc2)cc1NC(=O)CN1CCOCC1]

To a microwave vial was added 6-chloro-N-{4-methoxy-3-[(morpholin-4-ylacetyl)amino]phenyl}nicotinamide (prepared in a manner analogous to that described in intermediate 38, 0.070 g, 0.17 mmol), (2-fluorophenyl)boronic acid (0.036 g, 0.26 mmol, 1.5 equiv), potassium carbonate (48 mg, 0.35 mmol, 2.0 equiv) and a DME/water mixture (3:1, 1.75 mL). The resulting suspension was purged with argon, treated with [1,1'-bis(diphenylphosphino)ferrocene]palladium(II) chloride $CH_2Cl_2$ complex $(Pd(dppf)Cl_2 \cdot CH_2Cl_2$, 7.1 mg, 0.009 mmol, 5 mol %) and sealed. The resulting mixture was heated with a microwave apparatus at 150° C. for 1 h, was then cooled to room temperature. The reaction mixture was poured onto ice water (10 mL), and extracted with ethyl acetate (3×10 mL). The combined organic phases were washed with a saturated NaCl solution, dried (Na$_2$SO$_4$ anh), and concentrated under reduced pressure. The resulting material was purified by HPLC (method 2) to give 6-(2-fluorophenyl)-N-{4-methoxy-3-[(morpholin-4-ylacetyl)amino]phenyl}nicotinamide (32 mg, 40%).

¹H-NMR (400 MHz, DMSO-d₆): δ [ppm]=2.51-2.54 (m, 4H), 3.13 (s, 2H), 3.62-3.66 (m, 4H), 3.87 (s, 3H), 7.04 (d, J=8.8 Hz, 1H), 7.32-7.38 (m, 2H), 7.49-7.55 (m, 1H), 7.58 (dd, J=2.5, 6.3 Hz, 1H), 7.90 (dd, J=1.5, 8.3 Hz, 1H), 7.98 (td, J=1.8, 7.8 Hz, 1H), 8.37 (dd, J=2.3, 8.3 Hz, 1H), 8.55 (d, J=2.5 Hz, 1H), 9.19 (d, J=1.8 Hz, 1H), 9.72 (s, 1H), 10.42 (s, 1H).

LC-MS (Method 3): $R_f$=1.14 min; MS (ESIpos): m/z=465 ([M+H]⁺, 100%), 929 ([2M+H]⁺, 20%); MS (ESIneg): m/z=463 ([M–H]⁻, 100%).

Example 32

6-(3-fluorophenyl)-N-{4-methoxy-3-[(morpholin-4-ylacetyl)amino]phenyl}nicotinamide

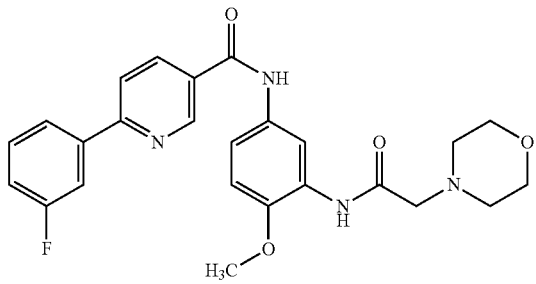 [SMILES: COc1ccc(NC(=O)c2ccc(-c3cccc(F)c3)nc2)cc1NC(=O)CN1CCOCC1]

To a microwave vial was added 6-chloro-N-{4-methoxy-3-[(morpholin-4-ylacetyl)amino]phenyl}nicotinamide (prepared in a manner analogous to that described in intermediate 38, 0.070 g, 0.17 mmol), 3-fluorophenyl)boronic acid (0.036 g, 0.26 mmol, 1.5 equiv), potassium carbonate (48 mg, 0.35 mmol, 2.0 equiv) and a DME/water mixture (3:1, 1.75 mL). The resulting suspension was purged with argon, treated with [1,1'-bis(diphenylphosphino)ferrocene]palladium(II) chloride CH₂Cl₂ complex (Pd(dppf)Cl₂.CH₂Cl₂, 7.1 mg, 0.009 mmol, 5 mol %) and sealed. The resulting mixture was heated with a microwave apparatus at 150° C. for 1 h, was then cooled to room temperature. The reaction mixture was poured onto ice water (10 mL), and extracted with ethyl acetate (3×10 mL). The combined organic phases were washed with a saturated NaCl solution, dried (Na2SO₄ anh), and concentrated under reduced pressure. The resulting material was purified by HPLC (method 2) to give the title compound (49 mg, 60%).

¹H-NMR (400 MHz, DMSO-d₆): δ [ppm]=2.51-2.55 (m, 4H), 3.12 (s, 2H), 3.63-3.66 (m, 4H), 3.87 (s, 3H), 7.04 (d, J=8.8 Hz, 1H), 7.30 (td, J=2.3, 8.3 Hz, 1H), 7.52-7.60 (m, 2H), 7.96 (dm, J=10.6 Hz, 1H), 8.01 (d, J=8.1 Hz, 1H), 8.16 (d, J=8.3 Hz, 1H), 8.38 (dd, J=2.3, 8.3 Hz, 1H), 8.55 (d, J=2.5 Hz, 1H), 9.16 (d, J=1.8 Hz, 1H), 9.72 (s, 1H), 10.39 (s, 1H).

LC-MS (Method 3): $R_f$=1.16 min; MS (ESIpos): m/z=465 ([M+H]⁺, 100%); MS (ESIneg): m/z=463 ([M–H]⁻, 100%).

Example 33

N-{3-[(morpholin-4-ylacetyl)amino]-4-(trifluoromethoxy)phenyl}-6-phenylnicotinamide

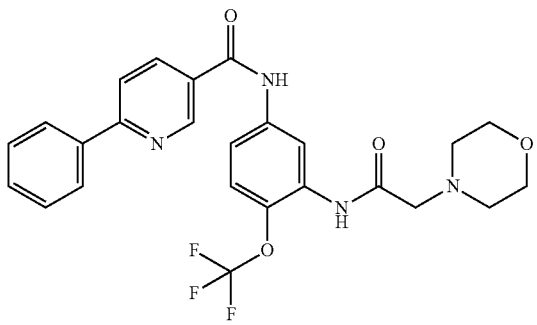 [SMILES: O=C(CN1CCOCC1)Nc1cc(NC(=O)c2ccc(-c3ccccc3)nc2)ccc1OC(F)(F)F]

To a microwave vial was added 6-chloro-N-{3-[(morpholin-4-ylacetyl)amino]-4-(trifluoromethoxy) phenyl}nicotinamide (prepared in a manner analogous to that described in intermediate 37, 0.126 g, 0.275 mmol), phenylboronic acid (0.050 g, 0.412 mmol, 1.5 equiv), potassium carbonate (76 mg, 0.55 mmol, 2.0 equiv) and a DME/water mixture (3:1, 2.8 mL). The resulting suspension was purged with argon, treated with [1,1'-bis(diphenylphosphino)ferrocene]palladium(II) chloride CH₂Cl₂ complex (Pd(dppf)Cl₂.CH₂Cl₂, 11 mg, 0.014 mmol, 5 mol %) and sealed. The resulting mixture was heated with a microwave apparatus at 150° C. for 1 h, was then cooled to room temperature. The reaction mixture was poured onto ice water (10 mL), and extracted with a CH₂Cl₂/isopropanol mixture (4:1, 3×10 mL). The combined organic phases were washed with a saturated NaCl solution, dried (Na2SO₄ anh), and concentrated under reduced pressure. The resulting material was purified by HPLC (method 2) to give N-{3-[(morpholin-4-ylacetyl)amino]-4-(trifluoromethoxy)phenyl}-6-phenylnicotinamide (54 mg, 39%).

¹H-NMR (400 MHz, DMSO-d₆): δ [ppm]=2.53-2.56 (m, 4H), 3.18 (s, 2H), 3.60-3.63 (m, 4H), 7.41-7.54 (m, 4H), 7.73 (dd, J=2.5, 8.8 Hz, 1H), 8.10-8.17 (m, 3H), 8.37 (dd, J=2.3, 8.3 Hz, 1H), 8.69 (d, J=2.5 Hz, 1H), 9.17 (d, J=1.8 Hz, 1H), 9.77 (s, 1H), 10.66 (s, 1H).

LC-MS (Method 3): $R_f$=1.28 min; MS (ESIpos): m/z=501 ([M+H]⁺, 100%); MS (ESIneg): m/z=499 ([M–H]⁻, 100%).

Example 34

N-{4-methoxy-3-[(morpholin-4-ylacetyl)amino]phenyl}-6-phenylnicotinamide

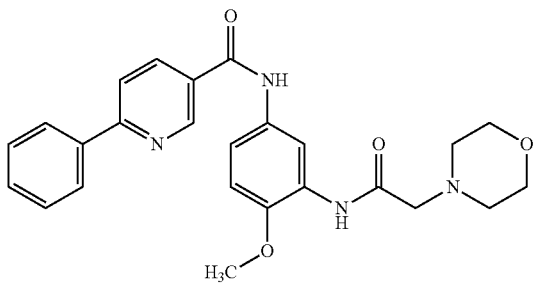 [SMILES: COc1ccc(NC(=O)c2ccc(-c3ccccc3)nc2)cc1NC(=O)CN1CCOCC1]

To a microwave vial was added 6-chloro-N-{4-methoxy-3-[(morpholin-4-ylacetyl)amino]phenyl}nicotinamide (prepared in a manner analogous to that described in intermediate 38, 3.30 g, 8.15 mmol), phenylboronic acid (1.49 g, 12.2 mmol, 1.5 equiv), potassium carbonate (2.25 g, 16.3 mmol, 2.0 equiv) and a DME/water mixture (3:1, 82.3 mL). The resulting suspension was purged with argon, treated with [1,1'-bis(diphenylphosphino)ferrocene]palladium(II) chloride $CH_2Cl_2$ complex (Pd(dppf)$Cl_2$.$CH_2Cl_2$, 0.332 g, 0.41 mmol, 5 mol %) and sealed. The resulting mixture was heated with a microwave apparatus at 150° C. for 1 h, was then cooled to room temperature. The reaction mixture was poured onto ice water (100 mL), and extracted with a $CH_2Cl_2$/isopropanol mixture (4:1, 3×50 mL). The combined organic phases were washed with a saturated NaCl solution, dried (Na2SO$_4$ anh), and concentrated under reduced pressure. The residue was treated with DMF (50 mL). The resulting precipitate was removed by filtration to give N-{4-methoxy-3-[(morpholin-4-ylacetyl)amino]phenyl}-6-phenylnicotinamide (1.07 g, 29%) $^1$H-NMR (400 MHz, DMSO-d$_6$): δ [ppm]=2.51-2.54 (m, 4H), 3.12 (s, 2H), 3.62-3.66 (m, 4H), 3.86 (s, 3H), 7.04 (d, J=8.8 Hz, 1H), 7.44-7.53 (m, 3H), 7.58 (dd, J=2.5, 6.3 Hz, 1H), 8.09 (d, J=7.8 Hz, 1H), 8.15 (dm, J=8.8 Hz, 2H), 8.36 (dd, J=2.5, 8.3 Hz, 1H), 8.55 (d, J=2.5 Hz, 1H), 9.15 (d, J=1.8 Hz, 1H), 9.72 (s, 1H), 10.37 (s, 1H).

LC-MS (Method 3): $R_t$=1.12 min; MS (ESIpos): m/z=447 ([M+H]$^+$, 100%), 893 ([2M+H]$^+$, 20%); MS (ESIneg): m/z=445 ([M−H]$^−$, 100%).

The DMF mother liquor was concentrated under reduced pressure. The residue was purified by HPLC (method 2) to give additional N-{4-methoxy-3-[(morpholin-4-ylacetyl)amino]phenyl}-6-phenylnicotinamide (1.30 g, 36%).

Example 35

N-{4-methoxy-3-[(morpholin-4-ylacetyl)amino]phenyl}-5-(4-methoxyphenyl)thiophene-2-carboxamide

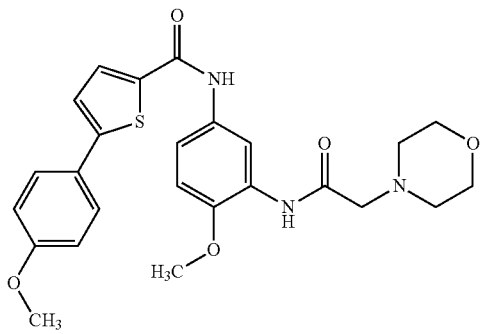 [SMILES: COc1ccc(-c2ccc(C(=O)Nc3ccc(OC)c(NC(=O)CN4CCOCC4)c3)s2)cc1]

To a microwave vial was added 5-bromo-N-{4-methoxy-3-[(morpholin-4-ylacetyl)amino]phenyl}thiophene-2-carboxamide (prepared in a manner analogous to that described in intermediate 39, 0.075 g, 0.165 mmol), (4-methoxyphenyl)boronic acid (0.050 g, 0.33 mmol, 2.0 equiv), a 2N sodium carbonate solution (0.25 mL, 0.50 mmol, 3.0 equiv) and dioxane (1.0 mL). The resulting suspension was purged with argon, treated with [1,1'-bis(diphenylphosphino)ferrocene]palladium(II) chloride $CH_2Cl_2$ complex (Pd(dppf)$Cl_2$.$CH_2Cl_2$, 0.013 g, 0.016 mmol, 10 mol %) and sealed. The resulting mixture was heated with a microwave apparatus at 105° C. for 1 h, was then cooled to room temperature. The reaction mixture was poured onto ice water (10 mL), and extracted with ethyl acetate (3×10 mL). The combined organic phases were dried (Na2SO$_4$ anh), and concentrated under reduced pressure. The resulting material was purified by HPLC (method 2) to give N-{4-methoxy-3-[(morpholin-4-ylacetyl)amino]phenyl}-5-(4-methoxyphenyl)thiophene-2-carboxamide (32 mg, 40%).

$^1$H-NMR (400 MHz, DMSO-d$_6$): δ [ppm]=2.56-2.58 (m, 4H), 3.17 (s, 2H), 3.67-3.70 (m, 4H), 3.82 (s, 3H), 3.90 (s, 3H), 7.03 (d, J=8.7 Hz, 2H), 7.06 (d, J=9.0 Hz, 1H), 7.48 (d, J=3.8 Hz, 1H), 7.57 (dd, J=2.6, 8.7 Hz, 1H), 7.68 (d, J=8.6 Hz, 2H), 8.00 (d, J=4.1 Hz, 1H), 8.51 (d, J=2.6 Hz, 1H), 9.76 (s, 1H), 10.17 (s, 1H).

LC-MS (Method 3): $R_t$=1.36 min; MS (ESIpos): m/z=482 ([M+H]$^+$, 100%); MS (ESIneg): m/z=480 ([M−H]$^−$, 100%).

Example 36

5-(4-fluorophenyl)-N-{4-methoxy-3-[(morpholin-4-ylacetyl)amino]phenyl}thiophene-2-carboxamide

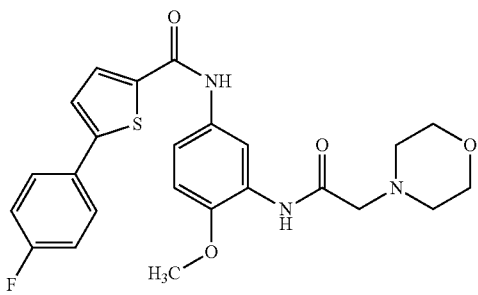 [SMILES: COc1ccc(NC(=O)c2ccc(-c3ccc(F)cc3)s2)cc1NC(=O)CN1CCOCC1]

To a microwave vial was added 5-bromo-N-{4-methoxy-3-[(morpholin-4-ylacetyl)amino]phenyl}thiophene-2-carboxamide (prepared in a manner analogous to that described in intermediate 39, 0.075 g, 0.165 mmol), (4-fluorophenyl)boronic acid (0.046 g, 0.33 mmol, 2.0 equiv), a 2N sodium carbonate solution (0.25 mL, 0.50 mmol, 3.0 equiv) and dioxane (1.0 mL). The resulting suspension was purged with argon, treated with [1,1'-bis(diphenylphosphino)ferrocene]palladium(II) chloride $CH_2Cl_2$ complex (Pd(dppf)$Cl_2$.$CH_2Cl_2$, 0.013 g, 0.016 mmol, 10 mol %) and sealed. The resulting mixture was heated with a microwave apparatus at 105° C. for 1 h, was then cooled to room temperature. The reaction mixture was poured onto water (10 mL), and extracted with ethyl acetate (3×10 mL). The combined organic phases were dried (Na2SO$_4$ anh), and concentrated under reduced pressure. The resulting material was purified by HPLC (method 2) to give 5-(4-fluorophenyl)-N-{4-methoxy-3-[(morpholin-4-ylacetyl)amino]phenyl}thiophene-2-carboxamide (41 mg, 53%).

$^1$H-NMR (400 MHz, DMSO-d$_6$): δ [ppm]=2.50-2.55 (m, 4H), 3.12 (s, 2H), 3.61-3.66 (m, 4H), 3.86 (s, 3H), 7.02 (d, J=8.9 Hz, 1H), 7.26 (t, J=8.9 Hz, 2H), 7.50-7.54 (m, 2H), 7.72-7.78 (m, 2H), 7.99 (d, J=4.0 Hz, 1H), 8.47 (d, J=2.5 Hz, 1H), 9.72 (s, 1H), 10.17 (s, 1H).

LC-MS (Method 3): $R_t$=1.40 min; MS (ESIpos): m/z=470 ([M+H]$^+$, 100%); MS (ESIneg): m/z=468 ([M−H]$^−$, 100%).

Example 37

4-(difluoromethoxy)-3-({[1-(morpholin-4-yl)cyclo-propyl]carbonyl}amino)-N-(5-phenyl-1,3,4-thiadi-azol-2-yl)benzamide

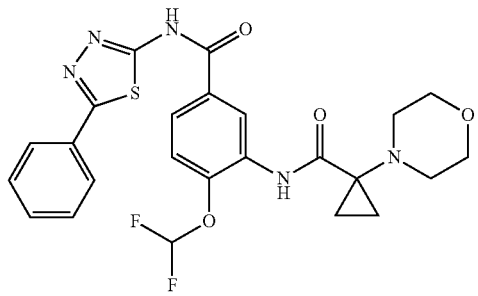 [SMILES: O=C(Nc1nnc(-c2ccccc2)s1)c1ccc(OC(F)F)c(NC(=O)C2(N3CCOCC3)CC2)c1]

The title compound was prepared in a manner analogous to that described in intermediate 40 starting from 100 mg (0.28 mmol) of the compound of intermediate 46 and 115 mg (0.55 mmol, 2 equiv) of the compound of intermediate 44. 8.1 mg (5% of theory) of the title compound were obtained.

$^1$H-NMR (300 MHz, DMSO-d$_6$): δ [ppm]=1.11-1.21 (m, 2H), 1.22-1.32 (m, 2H), 2.40-2.48 (m, 4H), 3.66-3.78 (m, 4H), 7.46 (d, 1H), 7.50-7.60 (m, 3H), 7.53 (t, 1H), 7.92-8.03 (m, 3H), 9.09 (d, 1H), 10.64 (s, 1H), 13.27 (s, 1H).

LC-MS (Method 4): R$_t$=1.30 min; MS (ESIpos): m/z=516 [M+H]$^+$.

Example 38

3-({[1-(4-cyclopropylpiperazin-1-yl)cyclopropyl]carbonyl}amino)-4-(difluoromethoxy)-N-(5-phenyl-1,3,4-thiadiazol-2-yl)benzamide

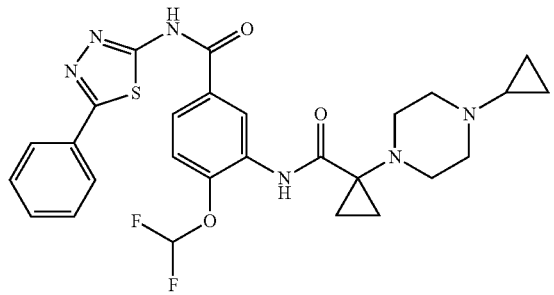 [SMILES: O=C(Nc1nnc(-c2ccccc2)s1)c1ccc(OC(F)F)c(NC(=O)C2(N3CCN(C4CC4)CC3)CC2)c1]

The title compound was prepared in a manner analogous to that described in intermediate 40 starting from 150 mg (0.41 mmol) of the compound of intermediate 46 and 348 mg of the compound of intermediate 43. 32.6 mg (14% of theory) of the title compound were obtained.

$^1$H-NMR (400 MHz, DMSO-d$_6$): δ [ppm]=0.45-0.85 (m, 4H), 1.15-1.33 (m, 4H), 2.47-2.74 (m, 8H), 7.40 (t, 1H), 7.45 (d, 1H), 7.51-7.58 (m, 3H), 7.93-8.03 (m, 3H), 8.96 (s, 1H), 10.24 (s, 1H), 13.0 (s, 1H).

LC-MS (Method 4): R$_t$=1.00 min; MS (ESIpos): m/z=555 [M+H]$^+$.

Example 39

4-(difluoromethoxy)-3-({[1-(4-methylpiperazin-1-yl)cyclopropyl]carbonyl}amino)-N-(5-phenyl-1,3,4-thiadiazol-2-yl)benzamide

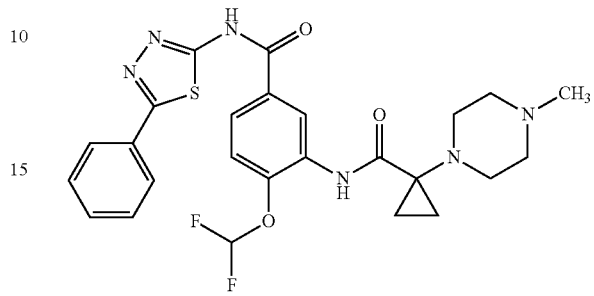

The title compound was prepared in a manner analogous to that described in intermediate 40 starting from 150 mg (0.41 mmol) of the compound of intermediate 46 and 305 mg of the compound of intermediate 42. 50.7 mg (23% of theory) of the title compound were obtained.

$^1$H-NMR (400 MHz, DMSO-d$_6$): δ [ppm]=1.14-1.20 (m, 2H), 1.21-1.27 (m, 2H), 2.46 (s, 3H), 2.53-2.65 (m, 4H), 2.71-2.94 (m, 4H), 7.46 (d, 1H), 7.49 (t, 1H), 7.52-7.59 (m, 3H), 7.95-8.02 (m, 3H), 9.01 (d, 1H), 10.43 (s, 1H), 12.24 (s, 1H).

LC-MS (Method 4): R$_t$=0.94 min; MS (ESIpos): m/z=529 [M+H]$^+$.

Example 40

4-(difluoromethoxy)-3-{[(4-methylpiperazin-1-yl)acetyl]amino}-N-(5-phenyl-1,3,4-thiadiazol-2-yl)benzamide

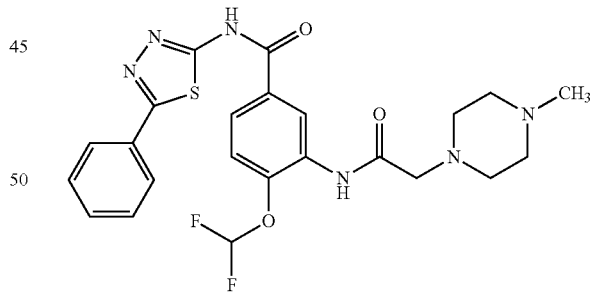

The title compound was prepared in a manner analogous to that described in example 53 starting from 140 mg (0.32 mmol) of the compound of intermediate 47 and 71 μL (0.64 mmol, 2 equiv) 1-methylpiperazine. 93.2 mg (58% of theory) of the title compound were obtained.

$^1$H-NMR (300 MHz, DMSO-d$_6$): δ [ppm]=2.24 (s, 3H), 2.40-2.55 (m, 4H), 2.56-2.68 (m, 4H), 3.21 (s, 2H), 7.43 (d, 1H), 7.46 (t, 1H), 7.50-7.59 (m, 3H), 7.93-8.02 (m, 3H), 9.01 (d, 1H), 9.90 (s, 1H), 12.85 (s, 1H).

LC-MS (Method 4): R$_t$=0.88 min; MS (ESIpos): m/z=503 [M+H]$^+$.

Example 41

3-{[(4-cyclopropylpiperazin-1-yl)acetyl]amino}-4-(difluoromethoxy)-N-(5-phenyl-1,3,4-thiadiazol-2-yl)benzamide

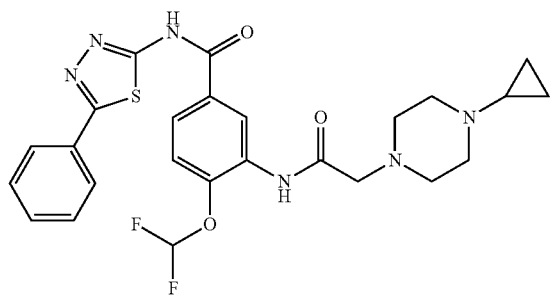 [SMILES: O=C(CN1CCN(C2CC2)CC1)Nc1cc(C(=O)Nc2nnc(-c3ccccc3)s2)ccc1OC(F)F]

The title compound was prepared in a manner analogous to that described in example 53 starting from 140 mg (0.32 mmol) of the compound of intermediate 47. 90.3 mg (54% of theory) of the title compound were obtained.

$^1$H-NMR (300 MHz, DMSO-$d_6$): δ [ppm]=0.26-0.38 (m, 2H), 0.39-0.50 (m, 2H), 1.57-1.75 (m, 1H), 2.50-2.75 (m, 8H), 3.21 (s, 2H), 7.46 (d, 1H), 7.48 (t, 1H), 7.51-7.60 (m, 3H), 7.94-8.03 (m, 3H), 8.97-9.04 (m, 1H), 9.95 (s, 1H), 13.21 (s, 1H).

LC-MS (Method 4): $R_t$=0.93 min; MS (ESIpos): m/z=529 [M+H]$^+$.

Example 42

4-(difluoromethoxy)-3-{[2-(4-methylpiperazin-1-yl)propanoyl]amino}-N-(5-phenyl-1,3,4-thiadiazol-2-yl)benzamide trifluoroacetate (1:1)

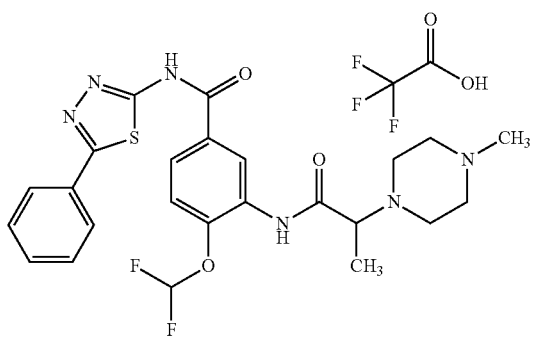

The title compound was prepared in a manner analogous to that described in example 53 starting from 500 mg (1.10 mmol) of the compound of intermediate 48 and 250 µL (2.21 mmol, 2 equiv) 1-methylpiperazine. The reaction mixture was stirred over night at 60° C. Purification by HPLC under the addition of trifluoroacetic acid yielded 40.0 mg (6% of theory) of the title compound. $^1$H-NMR (300 MHz, DMSO-$d_6$): δ [ppm]=1.25 (d, 3H), 2.51-2.66 (m, 1H), 2.67-2.88 (m, 1H), 2.81 (s, 3H), 2.90-3.14 (m, 4H), 3.41-3.54 (m, 2H), 3.59 (q, 1H), 7.41 (t, 1H), 7.45 (d, 1H), 7.51-7.61 (m, 3H), 7.94-8.02 (m, 2H), 8.05 (dd, 1H), 8.74 (d, 1H), 9.70 (s, 1H), 9.78 (s, 1H), 13.25 (s, 1H).

LC-MS (Method 4): $R_t$=0.95 min; MS (ESIpos): m/z=517 [M-CF$_3$CO$_2$H+H]$^+$.

Example 43

4-(methoxymethyl)-3-({[1-(morpholin-4-yl)cyclopropyl]carbonyl}amino)-N-(5-phenyl-1,3,4-thiadiazol-2-yl)benzamide

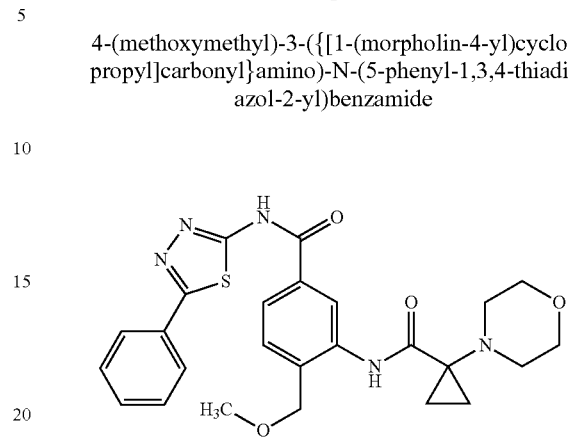

The title compound was prepared in a manner analogous to that described in intermediate 40 starting from 250 mg (0.73 mmol) of the compound of intermediate 51 and 610 mg (2.94 mmol, 4 equiv) of the compound of intermediate 44. 298 mg (80% of theory) of the title compound were obtained.

$^1$H-NMR (300 MHz, DMSO-$d_6$): δ [ppm]=1.11-1.17 (m, 2H), 1.21-1.27 (m, 2H), 2.43-2.48 (m, 4H), 3.33 (s, 3H), 3.68-3.78 (m, 4H), 4.64 (s, 2H), 7.51-7.58 (m, 4H), 7.88 (dd, 1H), 7.94-8.02 (m, 2H), 8.86 (d, 1H), 10.63 (s, 1H), 13.20 (s, 1H).

LC-MS (Method 4): $R_t$=1.27 min; MS (ESIpos): m/z=494 [M+H]$^+$.

Example 44

3-({[1-(4-cyclopropylpiperazin-1-yl)cyclopropyl]carbonyl}amino)-4-(methoxymethyl)-N-(5-phenyl-1,3,4-thiadiazol-2-yl)benzamide

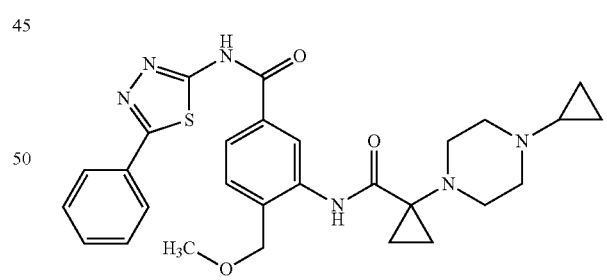

The title compound was prepared in a manner analogous to that described in intermediate 40 starting from 170 mg (0.50 mmol) of the compound of intermediate 51 and 210 mg of the compound of intermediate 43. 167 mg (61% of theory) of the title compound were obtained.

$^1$H-NMR (300 MHz, DMSO-$d_6$): δ [ppm]=0.24-0.31 (m, 2H), 0.38-0.46 (m, 2H), 1.08-1.15 (m, 2H), 1.15-1.21 (m, 2H), 1.61-1.70 (m, 1H), 2.35-2.46 (m, 4H), 2.64-2.74 (m, 4H), 3.37 (s, 3H), 4.63 (s, 2H), 7.51-7.58 (m, 4H), 7.87 (dd, 1H), 7.95-8.01 (m, 2H), 8.86 (d, 1H), 10.58 (s, 1H), 13.22 (s, 1H).

LC-MS (Method 3): $R_t$=0.83 min; MS (ESIpos): m/z=533 [M+H]$^+$.

Example 45

4-(methoxymethyl)-3-({[1-(4-methylpiperazin-1-yl)cyclopropyl]carbonyl}amino)-N-(5-phenyl-1,3,4-thiadiazol-2-yl)benzamide hydrochloride (1:1)

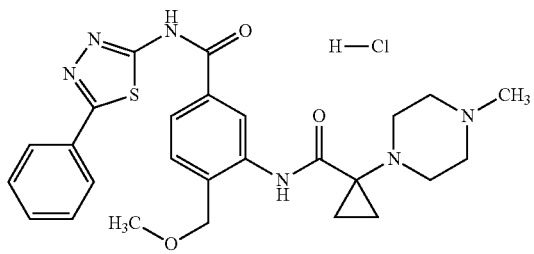 [SMILES: COCc1ccc(C(=O)Nc2nnc(-c3ccccc3)s2)cc1NC(=O)C1(N2CCN(C)CC2)CC1 ; Cl]

The title compound was prepared in a manner analogous to that described in intermediate 40 starting from 170 mg (0.50 mmol) of the compound of intermediate 51 and 368 mg of the compound of intermediate 42. 201 mg (79% of theory) of the title compound were obtained.

$^1$H-NMR (400 MHz, DMSO-d$_6$): δ [ppm]=1.18-1.25 (m, 4H), 2.45-3.65 (m, 8H), 2.80 (s, 3H), 3.32 (s, 3H), 4.66 (s, 2H), 7.53-7.59 (m, 4H), 7.95 (dd, 1H), 7.96-8.00 (m, 2H), 8.70 (d, 1H), 9.55 (s, 1H), 10.29 (s, 1H), 13.18 (s, 1H).

LC-MS (Method 3): $R_t$=0.74 min; MS (ESIpos): m/z=507 [M−HCl+H]$^+$.

Example 46

4-(methoxymethyl)-3-{[(4-methylpiperazin-1-yl)acetyl]amino}-N-(5-phenyl-1,3,4-thiadiazol-2-yl)benzamide

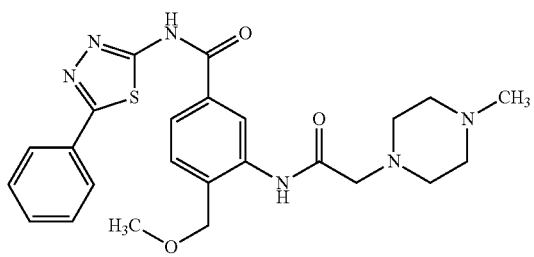 [SMILES: COCc1ccc(C(=O)Nc2nnc(-c3ccccc3)s2)cc1NC(=O)CN1CCN(C)CC1]

The title compound was prepared in a manner analogous to that described in example 53 starting from 200 mg (0.48 mmol) of the compound of intermediate 52 and 110 µL (0.96 mmol, 2 equiv) 1-methylpiperazine. 154 mg (67% of theory) of the title compound were obtained.

$^1$H-NMR (300 MHz, DMSO-d$_6$): δ [ppm]=2.23 (s, 3H), 2.42-2.65 (m, 8H), 3.18 (s, 2H), 3.39 (s, 3H), 4.55 (s, 2H), 7.47-7.60 (m, 4H), 7.89 (dd, 1H), 7.94-8.01 (m, 2H), 8.79-8.83 (m, 1H), 9.94 (s, 1H).

LC-MS (Method 1): $R_t$=0.86 min; MS (ESIpos): m/z=481 [M+H]$^+$.

Example 47

4-[(methylsulfonyl)methyl]-3-({[1-(morpholin-4-yl)cyclopropyl]carbonyl}amino)-N-(5-phenyl-1,3,4-thiadiazol-2-yl)benzamide

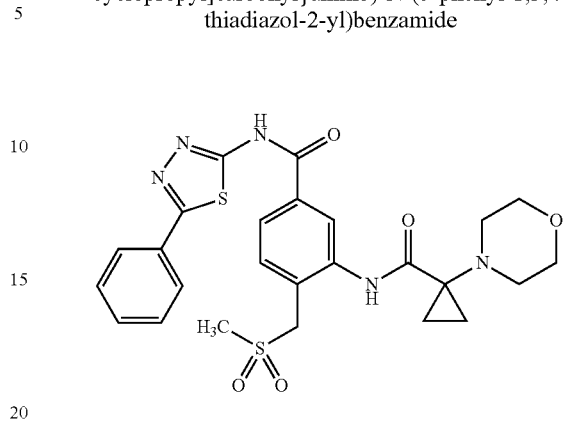

The title compound was prepared in a manner analogous to that described in intermediate 40 starting from 150 mg (0.39 mmol) of the compound of intermediate 55 and 320 mg (1.54 mmol, 4 equiv) of the compound of intermediate 44. 193 mg (90% of theory) of the title compound were obtained.

$^1$H-NMR (300 MHz, DMSO-d$_6$): δ [ppm]=1.11-1.18 (m, 2H), 1.21-1.27 (m, 2H), 3.09 (s, 3H), 3.70-3.79 (m, 4H), 4.70 (s, 2H), 7.51-7.58 (m, 3H), 7.65 (d, 1H), 7.94-8.01 (m, 3H), 8.50-8.55 (m, 1H), 10.48 (s, 1H), 13.21 (s, 1H).

LC-MS (Method 3): $R_t$=0.64 min; MS (ESIpos): m/z=542 [M+H]$^+$.

Example 48

3-({[1-(4-cyclopropylpiperazin-1-yl)cyclopropyl]carbonyl}amino)-4-[(methylsulfonyl)methyl]-N-(5-phenyl-1,3,4-thiadiazol-2-yl)benzamide

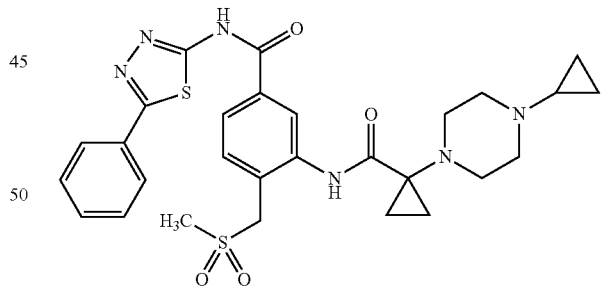

The title compound was prepared in a manner analogous to that described in intermediate 40 starting from 150 mg (0.39 mmol) of the compound of intermediate 55 and 573 mg (2.31 mmol, 6 equiv) of the compound of intermediate 43. 59 mg (26% of theory) of the title compound were obtained.

$^1$H-NMR (400 MHz, DMSO-d$_6$): δ [ppm]=0.22-0.31 (m, 2H), 0.37-0.45 (m, 2H), 1.08-1.15 (m, 2H), 1.15-1.23 (m, 2H), 1.63-1.71 (m, 1H), 2.37-2.48 (m, 4H), 2.69-2.79 (m, 4H), 3.09 (s, 3H), 4.67 (s, 2H), 7.52-7.59 (m, 3H), 7.66 (d, 1H), 7.94-8.03 (m, 3H), 8.56 (d, 1H), 10.46 (s, 1H), 13.25 (s, 1H).

Example 49

3-({[1-(4-methylpiperazin-1-yl)cyclopropyl]carbonyl}amino)-4-[(methylsulfonyl)methyl]-N-(5-phenyl-1,3,4-thiadiazol-2-yl)benzamide

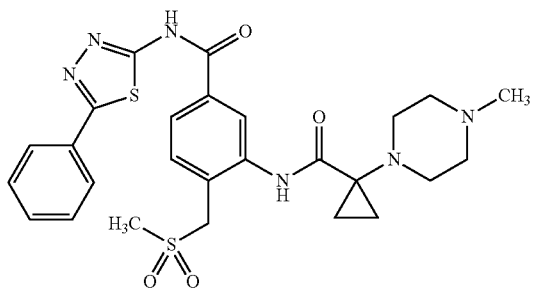 [SMILES: CN1CCN(C2(C(=O)Nc3cc(C(=O)Nc4nnc(-c5ccccc5)s4)ccc3CS(C)(=O)=O)CC2)CC1]

The title compound was prepared in a manner analogous to that described in intermediate 40 starting from 150 mg (0.39 mmol) of the compound of intermediate 55 and 510 mg (2.31 mmol, 6 equiv) of the compound of intermediate 42. 12.5 mg (6% of theory) of the title compound were obtained.

$^1$H-NMR (300 MHz, DMSO-d$_6$): δ [ppm]=1.10-1.27 (m, 4H), 2.24 (s, 3H), 2.56-2.63 (m, 4H), 3.07 (s, 3H), 4.65 (s, 2H), 7.48-7.57 (m, 3H), 7.59-7.65 (m, 1H), 7.92-8.01 (m, 3H), 8.53 (d, 1H), 10.36 (s, 1H).

LC-MS (Method 3): R$_t$=0.63 min; MS (ESIpos): m/z=555 [M+H]$^+$.

Example 50

3-({[1-(morpholin-4-yl)cyclopropyl]carbonyl}amino)-N-(5-phenyl-1,3,4-thiadiazol-2-yl)-4-(trifluoromethoxy)benzamide

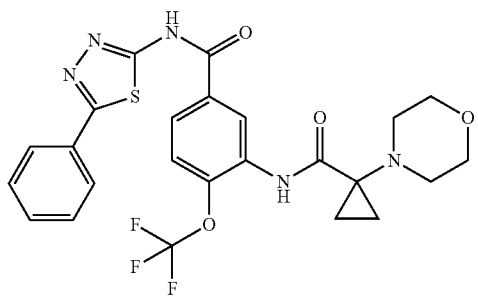 [SMILES: O=C(Nc1nnc(-c2ccccc2)s1)c1ccc(OC(F)(F)F)c(NC(=O)C2(N3CCOCC3)CC2)c1]

The title compound was prepared in a manner analogous to that described in intermediate 40 starting from 180 mg (0.48 mmol) of the compound of intermediate 45 and 170 mg (0.96 mmol, 2 equiv) of 5-phenyl-1,3,4-thiadiazol-2-amine. 35.0 mg (14% of theory) of the title compound were obtained.

$^1$H-NMR (400 MHz, DMSO-d$_6$): δ [ppm]=1.13-1.21 (m, 2H), 1.26-1.34 (m, 2H), 2.44-2.50 (m, 4H), 3.63-3.76 (m, 4H), 7.51-7.60 (m, 3H), 7.67 (dd, 1H), 7.93-8.04 (m, 3H), 9.08 (d, 1H), 10.57 (s, 1H), 13.36 (s, 1H).

LC-MS (Method 1): R$_t$=1.39 min; MS (ESIpos): m/z=534 [M+H]$^+$.

Example 51

3-({[1-(4-cyclopropylpiperazin-1-yl)cyclopropyl]carbonyl}amino)-N-(5-phenyl-1,3,4-thiadiazol-2-yl)-4-(trifluoromethoxy)benzamide

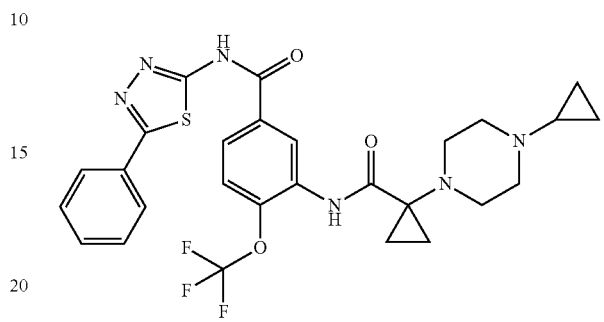

To a suspension of 151 mg (0.61 mmol) of the compound from intermediate 43 in 8 mL of dichloromethane were added 0.32 mL of 1-chloro-N,N,2-trimethylprop-1-en-1-amine (2.45 mmol, 6 equiv). The reaction mixture was stirred at room temperature for 2 h. The resulting mixture was concentrated under reduced pressure, was then triturated with dichloromethane and was concentrated under reduced pressure. The remaining material was provided in 8 mL of dichloromethane and 0.15 mL of pyridine (1.83 mmol, 4.5 equiv) and 155 mg of the compound from intermediate 40 were added. The resulting suspension was stirred at room temperature over night.

The resulting mixture was concentrated under reduced pressure. Purification by HPLC (Waters Autopurification system, column: XBrigde C18 5 μm 100×30 mm, solvent: water/methanol+0.2% ammonia (32%) gradient, rate: 70 mL/min, temperature: room temperature) yielded 22.2 mg (9% of theory) of the title compound.

$^1$H-NMR (300 MHz, DMSO-d$_6$): δ [ppm]=0.24-0.33 (m, 2H), 0.38-0.50 (m, 2H), 1.11-1.19 (m, 2H), 1.20-1.28 (m, 2H), 1.55-1.64 (m, 1H), 2.35-2.47 (m, 4H), 2.60-2.71 (m, 4H), 7.48-7.60 (m, 3H), 7.61-7.69 (m, 1H), 7.92-8.03 (m, 3H), 9.14 (d, 1H), 10.63 (s, 1H), 13.4 (s, 1H).

LC-MS (Method 3): R$_t$=0.88 min; MS (ESIpos): m/z=573 [M+H]$^+$.

Example 52

3-({[1-(4-methylpiperazin-1-yl)cyclopropyl]carbonyl}amino)-N-(5-phenyl-1,3,4-thiadiazol-2-yl)-4-(trifluoromethoxy)benzamide

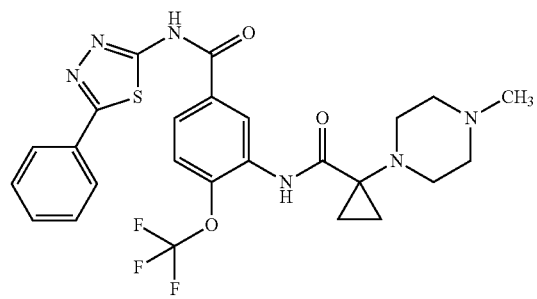 [SMILES: CN1CCN(C2(C(=O)Nc3cc(C(=O)Nc4nnc(-c5ccccc5)s4)ccc3OC(F)(F)F)CC2)CC1]

To a suspension of 100 mg (0.45 mmol) of the compound from intermediate 42 in 6 mL of dichloromethane were added 0.24 mL of 1-chloro-N,N,2-trimethylprop-1-en-1-amine (1.81 mmol, 4 equiv). The reaction mixture was stirred at room temperature for 2 h. The resulting mixture was concentrated under reduced pressure, was then triturated with dichloromethane and was concentrated under reduced pressure. The remaining material was provided in 6 mL of dichloromethane and 0.11 mL of pyridine (1.36 mmol, 3 equiv) and 172 mg of the compound from intermediate 40 were added. The resulting suspension was stirred at room temperature over night.

The resulting mixture was concentrated under reduced pressure, was then triturated with a mixture of 5 mL of water and 5 mL of ethanol, and the resulting mixture was stirred for 30 minutes. The remaining solids were removed by filtration, washed with ethanol, and were dried under reduced pressure. Purification by HPLC (Waters Autopurification system, column: XBrigde C18 5 µm 100×30 mm, solvent: water/methanol+0.2% ammonia (32%) gradient, rate: 70 mL/min, temperature: room temperature) yielded 25.9 mg (10% of theory) of the title compound. $^1$H-NMR (300 MHz, DMSO-$d_6$): δ [ppm]=1.13-1.21 (m, 2H), 1.22-1.29 (m, 2H), 2.22 (s, 3H), 7.48-7.59 (m, 3H), 7.63 (dd, 1H), 7.91-8.02 (m, 3H), 9.12 (d, 1H), 10.55 (s, 1H), 13.15 (s, 1H).

LC-MS (Method 3): $R_t$=0.79 min; MS (ESIpos): m/z=547 [M+H]$^+$.

Example 53

3-{[(4-cyclopropylpiperazin-1-yl)acetyl]amino}-N-(5-phenyl-1,3,4-thiadiazol-2-yl)-4-(trifluoromethoxy)benzamide

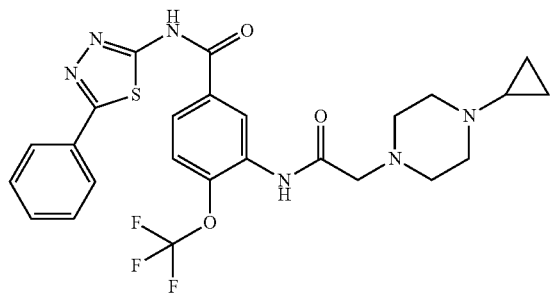 [SMILES: O=C(CN1CCN(C2CC2)CC1)Nc1cc(C(=O)Nc2nnc(-c3ccccc3)s2)ccc1OC(F)(F)F]

To a suspension of 120 mg (0.26 mmol) of the compound from intermediate 41 in 1.5 mL of DMF were added 0.22 mL of triethylamine (1.58 mmol, 6 equiv), 105 mg of 1-cyclopropylpiperazine dihydrochloride (0.53 mmol, 2 equiv), and 9.0 mg of potassium iodide (0.05 mmol, 0.2 equiv). The reaction mixture was stirred at room temperature over night. After filtration, purification by HPLC (method 2) yielded 86 mg (60% of theory) of the title compound.

$^1$H-NMR (300 MHz, DMSO-$d_6$): δ [ppm]=0.26-0.35 (m, 2H), 0.39-0.47 (m, 2H), 2.47-2.67 (m, 8H), 3.21 (s, 2H), 7.51-7.59 (m, 3H), 7.62-7.69 (m, 1H), 7.94-8.05 (m, 3H), 9.01 (d, 1H), 9.97 (s, 1H), 13.41 (s, 1H).

LC-MS (Method 1): $R_t$=0.98 min; MS (ESIpos): m/z=547 [M+H]$^+$.

Example 54

3-{[(4-methylpiperazin-1-yl)acetyl]amino}-N-(5-phenyl-1,3,4-thiadiazol-2-yl)-4-(trifluoromethoxy)benzamide

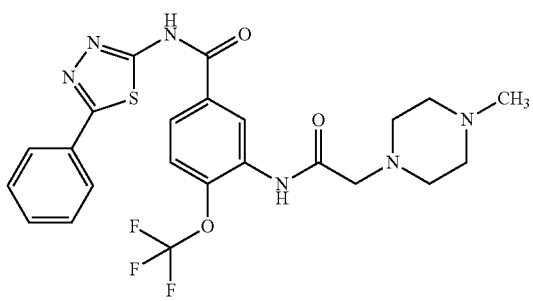 [SMILES: CN1CCN(CC(=O)Nc2cc(C(=O)Nc3nnc(-c4ccccc4)s3)ccc2OC(F)(F)F)CC1]

To a suspension of 15.5 g (33.9 mmol) of the compound from intermediate 41 in 250 mL of DMF were added 9.5 mL of triethylamine (67.9 mmol, 2 equiv), 7.5 mL of 1-methylpiperazine (67.9 mmol, 2 equiv), and 1.13 g of potassium iodide (6.79 mmol, 0.2 equiv). The reaction mixture was stirred at room temperature over night. The resulting mixture was concentrated under reduced pressure, was then triturated with a mixture of 500 mL of water and 300 mL of ethanol, and the resulting mixture was stirred for 30 minutes. The remaining solids were removed by filtration, washed with ethanol, and were dried at 50° C. under reduced pressure. The remaining solids were dissolved at 40° C. in 480 mL of DMF, and the solution was added dropwise into 1580 mL of a 0.1M aqueous solution of sodium bicarbonate. The resulting suspension was stirred for 30 minutes, the remaining solids were removed by filtration, washed with water, and were dried at 50° C. under reduced pressure to give 13.6 g of the title compound (75% of theory).

$^1$H-NMR (300 MHz, DMSO-$d_6$): δ [ppm]=2.26 (s, 3H), 2.56-2.70 (m, 4H), 3.24 (s, 2H), 7.48-7.58 (m, 3H), 7.58-7.66 (m, 1H), 7.91-8.05 (m, 3H), 8.98 (d, 1H), 9.91 (s, 1H), 12.95 (s, 1H).

LC-MS (Method 4): $R_t$=1.00 min; MS (ESIpos): m/z=521 [M+H]$^+$.

Example 55

3-[(morpholin-4-ylacetyl)amino]-N-(5-phenyl-1,3,4-thiadiazol-2-yl)-4-(trifluoromethoxy)benzamide

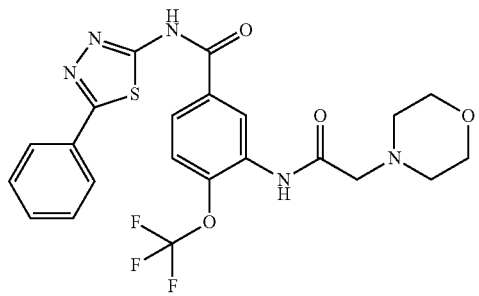 [SMILES: O=C(CN1CCOCC1)Nc1cc(C(=O)Nc2nnc(-c3ccccc3)s2)ccc1OC(F)(F)F]

To a suspension of 5.00 g (11.0 mmol) of the compound from intermediate 41 in 110 mL of DMF were added 3.1 mL of triethylamine (21.9 mmol, 2 equiv), 1.9 mL of morpholine (21.9 mmol, 2 equiv), and 363 mg of potassium iodide (2.19 mmol, 0.2 equiv). Another 50 mL of DMF were added and the reaction mixture was stirred at room temperature over night. The resulting mixture was concentrated under reduced pressure, was then triturated with a mixture of 100 mL of water and 100 mL of ethanol, and the resulting mixture was stirred for 30 minutes. The remaining solids were removed by filtration, washed with ethanol, and were dried at 50° C. under reduced pressure to give 5.13 g of the title compound (92% of theory).

$^1$H-NMR (400 MHz, DMSO-d$_6$): δ [ppm]=2.55-2.62 (m, 4H), 3.24 (s, 2H), 3.62-3.69 (m, 4H), 7.52-7.59 (m, 3H), 7.66 (dd, 1H), 7.95-8.06 (m, 3H), 8.95 (d, 1H), 9.93 (s, 1H), 13.43 (s, 1H).

LC-MS (Method 4): R$_t$=1.12 min; MS (ESIpos): m/z=508 [M+H]$^+$.

Example 56

2-({[1-(morpholin-4-yl)cyclopropyl]carbonyl}amino)-N-4-(5-phenyl-1,3,4-thiadiazol-2-yl)terephthalamide

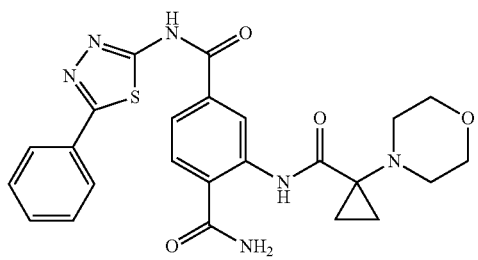 [SMILES: NC(=O)c1ccc(C(=O)Nc2nnc(-c3ccccc3)s2)cc1NC(=O)C1(N2CCOCC2)CC1]

To a suspension of the compound of intermediate 57 (116 mg, 280 μmol) in 5.0 mL of dichloromethane was added 1-chloro-N,N,2-trimethylpropenylamine (299 mg, 2.24 mmol). The mixture was stirred for 2 h at room temperature. The resulting solution was evaporated to dryness. The residue was two times co-distilled with dichloromethane and finally dissolved in 5.0 mL of dichloromethane. To this solution pyridine (102 μL, 1.26 mmol) and 1-(morpholin-4-yl)cyclopropanecarboxylic acid hydrochloride (116 mg, 560 μmol) were added. The reaction mixture was stirred for 2 d at room temperature. The mixture was concentrated and the residue was dissolved in DMSO (1.5 mL) and stirred overnight to provide a fine suspension, which was filtrated. The precipitate was washed with water and dried at 45° C. under vacuum to yield the desired compound 56 (115 mg, 220 mmol, 79%).

$^1$H-NMR (300 MHz, DMSO-d$_6$): δ [ppm]=1.09-1.16 (m, 2H), 1.18-1.25 (m, 2H), 2.41 (br. s, 4H), 3.81 (br. s, 4H), 7.45-7.60 (m, 3H), 7.80-8.06 (m, 5H), 8.35 (s, 1H), 9.26 (s, 1H), 12.63 (s, 1H), 13.31 (br. s, 1H).

LC-MS (Method 1): R$_t$=1.10 min; MS (ESIpos): m/z=493 [M+H]$^+$.

Example 57

3-{[2-(morpholin-4-yl)propanoyl]amino}-N-(5-phenyl-1,3,4-thiadiazol-2-yl)-4-(trifluoromethoxy)benzamide

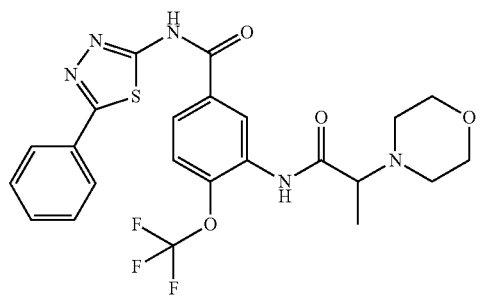

To a solution of intermediate 58 (590 mg, 1.25 mmol) and triethylamine (262 μL, 1.88 mmol) in 5.4 mL of DMF were added potassium iodide (32.2 mg, 194 μmol) and morpholine (164 μL, 1.88 mmol). The reaction mixture was stirred over night under an inert gas atmosphere at room temperature. The same amount of potassium iodide and 1 equivalent of morpholine were added to the mixture and it was stirred at 50° C. until complete consumption of the starting material was observed. The reaction mixture was taken onto water and extracted three times with dichloromethane/isopropanol (4:1). The combined organic layers were washed with brine, dried over a silicon filter and taken to dryness. The residue was suspended in ethanol (2.0 mL) and stirred at room temperature. The resulting fine suspension was filtrated to collect the precipitate. The same procedure was repeated with 4.0 mL of dichloromethane/ethanol 1:1 to yield the desired product 57 (232 mg, 430 μmol, 34%).

$^1$H-NMR (300 MHz, DMSO-d$_6$): δ [ppm]=1.23 (d, 3H), 2.62-2.53 (m, 4H), 3.41 (d, 1H), 3.66 (t, 4H), 7.55 (dd, 3H), 7.65 (dd, 1H), 8.07-7.93 (m, 3H), 8.90 (d, 1H), 10.05 (s, 1H), 13.54-13.32 (m, 1H).

LC-MS (Method 1): R$_t$=1.14 min; MS (ESIpos): m/z=522 [M+H]$^+$.

Example 58

3-{[2-(4-methylpiperazin-1-yl)propanoyl]amino}-N-(5-phenyl-1,3,4-thiadiazol-2-yl)-4-(trifluoromethoxy)benzamide

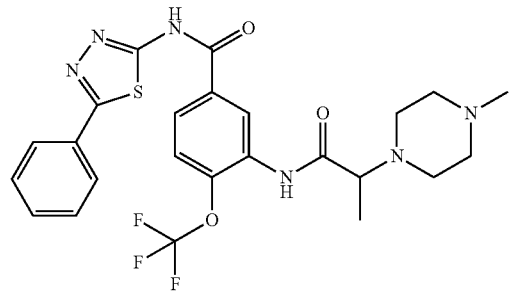 [SMILES: CC(C(=O)Nc1cc(C(=O)Nc2nnc(-c3ccccc3)s2)ccc1OC(F)(F)F)N1CCN(C)CC1]

To a solution of intermediate 58 (250 mg, 531 μmol) and triethylamine (111 μL, 796 μmol) in 2.3 mL of DMF were added potassium iodide (10.1 mg, 61 µmol) and 1-methylpiperazine (79.8 mg, 796 µmol). The reaction mixture was stirred overnight under an inert gas atmosphere at 50° C. The reaction mixture was diluted with water and filtered. The filtrate was three times extracted with dichloromethane/isopropanol 4:1. The combined organic phases were washed with brine, dried over a silicon filter and concentrated in vacuum. The residue was suspended in ethanol and stirred. The resulting fine suspension was filtrated to collect the precipitate, which provided after drying the desired compound 58 (119 mg, 210 µmol, 40%).

$^1$H-NMR (300 MHz, DMSO-d$_6$): δ [ppm]=1.22 (d, 3H), 2.33-2.24 (s, 3H), 2.56-2.52 (m, 4H), 2.61 (br. s, 4H), 3.45 (q, 1H), 7.57-7.48 (m, 3H), 7.61 (dd, 1H), 8.05-7.92 (m, 3H), 8.93 (d, 1H), 10.05 (s, 1H), 13.07-12.61 (m, 1H).

LC-MS (Method 1): R$_t$=0.92 min; MS (ESIpos): m/z=535 [M+H]$^+$.

Example 59

3-{[(4-methylpiperazin-1-yl)acetyl]amino}-N-(5-phenyl-1,3,4-thiadiazol-2-yl)-4-(trifluoromethyl)benzamide

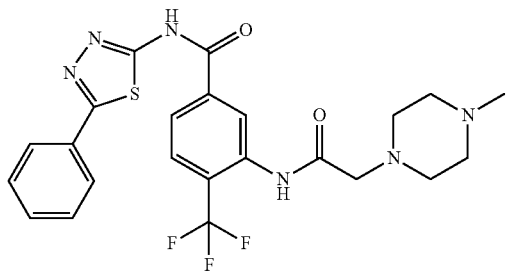 [SMILES: CN1CCN(CC(=O)Nc2cc(C(=O)Nc3nnc(-c4ccccc4)s3)ccc2C(F)(F)F)CC1]

To a solution of intermediate 61 (250 mg, 567 µmol), 1-methylpiperazine (85.2 mg, 851 µmol) and potassium iodide (14.6 mg, 87.9 µmol) in 2.44 mL of DMF was added triethylamine (119 µL, 851 µmol). The mixture was stirred for 36 h at 50° C. and afterwards poured into water. The resulting precipitate was removed by filtration (contains 56% of the desired product). The filtrate was three times extracted with dichloromethane/isopropanol 4:1. Thereby a precipitate occurred which was filtrated off, washed with ethanol and provided the desired compound 59 (103 mg, 35%) as an analytically pure sample.

$^1$H-NMR (300 MHz, DMSO-d$_6$): δ [ppm]=2.34 (s, 3H), 2.65 (br. s, 8H), 3.25 (s, 2H), 7.58-7.49 (m, 3H), 8.01-7.87 (m, 3H), 8.07 (s, 1H), 8.86 (s, 1H), 9.91 (s, 1H).

LC-MS (Method 4): R$_t$=0.90 min; MS (ESIpos): m/z=505 [M+H]$^+$.

Example 60

6-(3,5-difluorophenyl)-N-[3-({[1-(morpholin-4-yl)cyclopropyl]carbonyl}amino)-4-(trifluoromethoxy)phenyl]nicotinamide

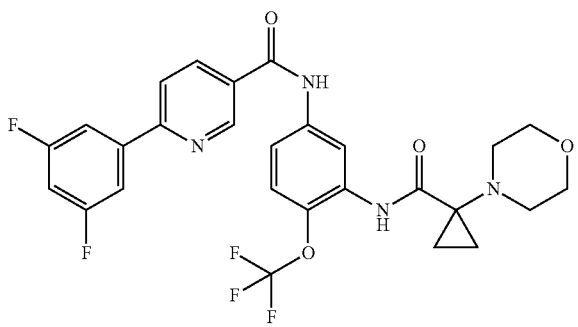 [SMILES: O=C(Nc1ccc(OC(F)(F)F)c(NC(=O)C2(N3CCOCC3)CC2)c1)c1ccc(-c2cc(F)cc(F)c2)nc1]

254 mg (1.22 mmol, 2 equiv) of the compound of intermediate 44 were stirred in 4 mL of dichloromethane at room temperature. 0.12 mL (1.53 mmol, 2.5 equiv) of DMF and 0.11 mL (1.22 mmol, 2 equiv) of oxalyl chloride were added and the mixture was stirred for additional 0.5 h at room temperature. 0.34 mL (3.05 mmol, 5 equiv) of 4-methylmorpholine and 250 mg (0.61 mmol) of the compound of intermediate 64 were added and the mixture was stirred at room temperature over night. 0.27 mL (2.44 mmol, 4 equiv) of 4-methylmorpholine and 210 mg of 1-(morpholin-4-yl)cyclopropanecarbonyl chloride hydrochloride (1:1) (prepared as described above) were added and the mixture was stirred at room temperature for 3 days. The reaction mixture was poured into water and extracted with ethyl acetate. The combined organic phases were dried (Na2SO$_4$ anh), and concentrated under reduced pressure. Purification by HPLC (method 2) yielded 24 mg (7% of theory) of the title compound.

$^1$H-NMR (300 MHz, DMSO-d$_6$): δ [ppm]=1.11-1.19 (m, 2H), 1.22-1.32 (m, 2H), 2.42-2.49 (m, 4H), 3.63-3.75 (m, 4H), 7.35-7.53 (m, 2H), 7.73 (dd, 1H), 7.87-7.99 (m, 2H), 8.28 (d, 1H), 8.45 (dd, 1H), 8.86 (d, 1H), 9.20 (d, 1H), 10.47 (s, 1H), 10.72 (s, 1H).

LC-MS (Method 1): R$_t$=1.46 min; MS (ESIpos): m/z=563 [M+H]$^+$.

Example 61

N-[3-({[1-(morpholin-4-yl)cyclopropyl]carbonyl}amino)-4-(trifluoromethoxy)phenyl]-6-phenylnicotinamide

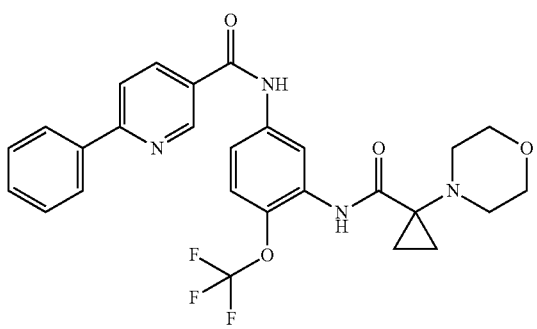 [SMILES: O=C(Nc1ccc(OC(F)(F)F)c(NC(=O)C2(N3CCOCC3)CC2)c1)c1ccc(-c2ccccc2)nc1]

2.30 g (11.1 mmol, 2 equiv) of the compound of intermediate 44 were stirred in 20 mL of dichloromethane at room temperature. 0.85 mL (11.1 mmol, 2 equiv) of DMF and 0.97 mL (11.1 mmol, 2 equiv) of oxalyl chloride were added and the mixture was stirred for additional 0.5 h at room temperature. 3.1 mL (27.7 mmol, 5 equiv) of 4-methylmorpholine and 2.07 g (5.55 mmol) of the compound of intermediate 66 were added and the mixture was stirred at room temperature over night. The reaction mixture was poured into water and extracted with dichloromethane. The combined organic phases were dried (Na2SO4 anh), and concentrated under reduced pressure. The residue was purified using MPLC (Biotage Isolera; silica gel; hexane/EtOAc gradient). The obtained material was dissolved in ethyl acetate and washed with saturated, aqueous sodium bicarbonate solution. The organic phase was dried over sodium sulfate and concentrated under reduced pressure. Purification by HPLC (column: chromatorex C18, 10 μm, 195×51 mm, mobile phase: acetonitrile/water+0.1% formic acid gradient) yielded 123 mg (4% of theory) of the title compound.

$^1$H-NMR (400 MHz, DMSO-d$_6$): δ [ppm]=1.11-1.18 (m, 2H), 1.23-1.30 (m, 2H), 2.42-2.48 (m, 4H), 3.65-3.73 (m, 4H), 7.44-7.58 (m, 4H), 7.71 (dd, 1H), 8.12-8.22 (m, 3H), 8.40 (dd, 1H), 8.85 (d, 1H), 9.19 (d, 1H), 10.46 (s, 1H), 10.67 (s, 1H).

LC-MS (Method 1): R$_t$=1.38 min; MS (ESIpos): m/z=527 [M+H]$^+$.

Example 62

6-(2-fluorophenyl)-N-[4-methoxy-3-({[1-(morpholin-4-yl)cyclopropyl]carbonyl}amino)phenyl]nicotinamide

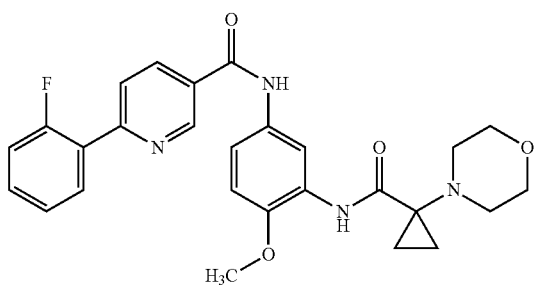 [SMILES: COc1ccc(NC(=O)c2ccc(-c3ccccc3F)nc2)cc1NC(=O)C1(N2CCOCC2)CC1]

To a solution of the compound of intermediate 69 (200 mg, 0.59 mmol) and the compound of intermediate 44 (246 mg, 1.19 mmol, 2 equiv) in DMF (2 mL) was added (benzotriazol-1-yloxy)tripyrrolidinophosphonium hexafluorophosphate (PYBOP, 617 mg, 1.19 mmol, 2 equiv) and diisopropylethylamine (0.52 mL, 2.96 mmol, 5 equiv). The resulting mixture was stirred at room temperature over night. After filtration, purification by HPLC (column: chromatorex C18, 10 μm, 195×51 mm, mobile phase: acetonitrile/water+0.1% formic acid gradient) yielded 149 mg (51% of theory) of the title compound.

$^1$H-NMR (400 MHz, DMSO-d$_6$): δ [ppm]=1.08-1.15 (m, 2H), 1.16-1.23 (m, 2H), 2.40-2.48 (m, 4H), 3.67-3.77 (m, 4H), 3.94 (s, 3H), 7.08 (d, 1H), 7.34-7.42 (m, 2H), 7.51-7.61 (m, 2H), 7.94 (dd, 1H), 8.01 (td, 1H), 8.40 (dd, 1H), 8.67 (d, 1H), 9.22 (d, 1H), 10.42 (s, 1H), 10.59 (s, 1H).

LC-MS (Method 1): R$_t$=1.25 min; MS (ESIpos): m/z=491 [M+H]$^+$.

Example 63

3-{[(4-cyclopropylpiperazin-1-yl)acetyl]amino}-N-[6-(2-fluorophenyl)pyridin-3-yl]-4-(trifluoromethoxy)benzamide

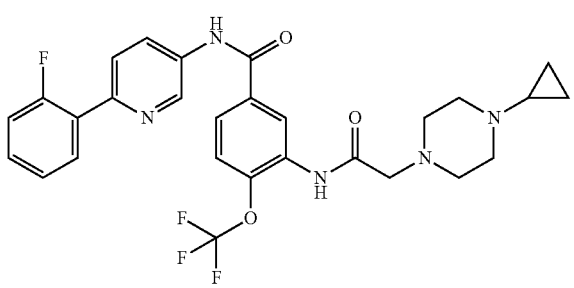 [SMILES: O=C(CN1CCN(C2CC2)CC1)Nc1cc(C(=O)Nc2ccc(-c3ccccc3F)nc2)ccc1OC(F)(F)F]

To a solution of 150 mg (0.32 mmol) of the compound of intermediate 14 in 1.8 mL of DMF were added 0.20 mL of triethylamine (1.44 mmol, 4.5 equiv), 96.0 mg of 1-cyclopropylpiperazine dihydrochloride (0.48 mmol, 1.5 equiv), and 8.3 mg of potassium iodide (0.05 mmol, 0.16 equiv). The reaction mixture was stirred at room temperature over night. After filtration, purification by HPLC (method 2) yielded 62.8 mg (33% of theory) of the title compound.

$^1$H-NMR (300 MHz, DMSO-d$_6$): δ [ppm]=0.20-0.38 (m, 2H), 0.38-0.56 (m, 2H), 1.49-1.70 (m, 1H), 2.45-2.76 (m, 8H), 3.22 (s, 2H), 7.26-7.39 (m, 2H), 7.42-7.53 (m, 1H), 7.61-7.71 (m, 1H), 7.79-7.90 (m, 2H), 7.91-8.02 (m, 1H), 8.30 (dd, 1H), 8.84 (s, 1H), 9.06 (d, 1H), 9.95 (s, 1H), 10.72 (s, 1H).

LC-MS (Method 4): R$_t$=1.04 min; MS (ESIpos): m/z=558 [M+H]$^+$.

Example 64

N-[6-(2-fluorophenyl)pyridin-3-yl]-3-{[2-(4-methylpiperazin-1-yl)propanoyl]amino}-4-(trifluoromethoxy)benzamide

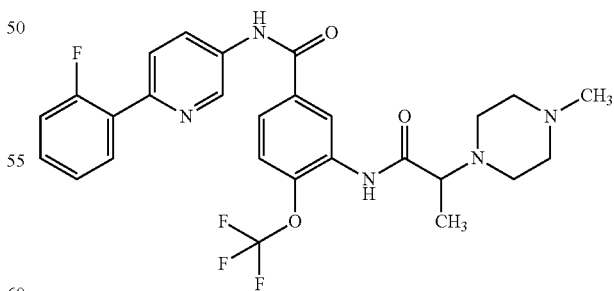

To a solution of 250 mg (0.52 mmol) of the compound of intermediate 15 in 3 mL of DMF were added 0.22 mL of triethylamine (1.56 mmol, 3 equiv), 0.17 mL of 1-methylpiperazine (1.56 mmol, 3 equiv), and 13.4 mg of potassium iodide (0.08 mmol, 0.16 equiv). The reaction mixture was stirred at room temperature over night. After filtration, purification by HPLC (method 2) yielded 155 mg (54% of theory) of the title compound.

$^1$H-NMR (300 MHz, DMSO-$d_6$): δ [ppm]=1.22 (d, 3H), 2.18 (s, 3H), 2.32-2.64 (m, 8H), 3.43 (q, 1H), 7.27-7.39 (m, 2H), 7.42-7.52 (m, 1H), 7.60-7.70 (m, 1H), 7.79-7.89 (m, 2H), 7.91-8.02 (m, 1H), 8.30 (dd, 1H), 8.84 (d, 1H), 9.06 (d, 1H), 10.09 (s, 1H), 10.72 (s, 1H).

LC-MS (Method 4): $R_t$=1.04 min; MS (ESIpos): m/z=546 [M+H]$^+$.

Example 65

N-[6-(2-fluorophenyl)pyridin-3-yl]-3-{[(2S)-2-(4-methylpiperazin-1-yl)propanoyl]amino}-4-(trifluoromethoxy)benzamide or N-[6-(2-fluorophenyl)pyridin-3-yl]-3-{[(2R)-2-(4-methylpiperazin-1-yl)propanoyl]amino}-4-(trifluoromethoxy)benzamide

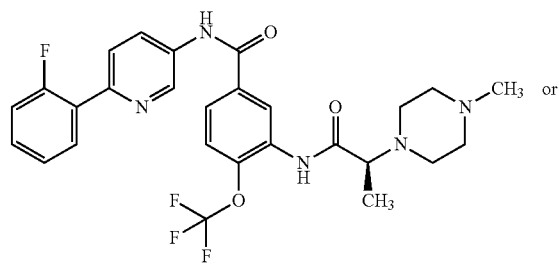

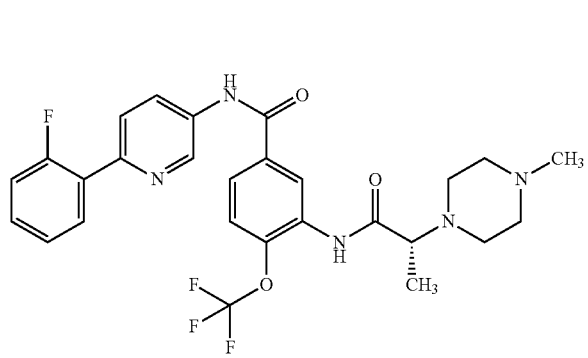 [SMILES: CC(C(=O)Nc1cc(C(=O)Nc2ccc(-c3ccccc3F)nc2)ccc1OC(F)(F)F)N1CCN(C)CC1]

120 mg of the racemate of the compound of example 64 were separated using chiral HPLC (System: Agilent Prep 1200, Column: Chiralpak IC 5 μm 250×20 mm, Solvent: hexane/2-propanol/diethylamine 50:50:0.1 (v/v/v)) to give the first eluting enantiomer of N-[6-(2-fluorophenyl)pyridin-3-yl]-3-{[2-(4-methylpiperazin-1-yl)propanoyl]amino}-4-(trifluoromethoxy)benzamide (36 mg).

$^1$H-NMR (400 MHz, DMSO-$d_6$): δ [ppm]=1.22 (d, 3H), 2.18 (s, 3H), 2.29-2.62 (m, 8H), 3.43 (q, 1H), 7.30-7.37 (m, 2H), 7.43-7.51 (m, 1H), 7.65 (dd, 1H), 7.80-7.87 (m, 2H), 7.93-8.00 (m, 1H), 8.30 (dd, 1H), 8.85 (d, 1H), 9.06 (d, 1H), 10.09 (s, 1H), 10.72 (s, 1H).

LC-MS (Method 4): $R_t$=1.01 min; MS (ESIpos): m/z=546 [M+H]$^+$.

Chiral HPLC (System: Waters Alliance 2695 DAD 996 ESA: Corona, Column: Chiralpak IC 3 μm 100×4.6 mm, Solvent: hexane/2-propanol/diethylamine 50:50:0.1 (v/v/v)): $R_t$=11.08 min, 99.7% enantiomeric excess.

Example 66

N-[6-(2-fluorophenyl)pyridin-3-yl]-3-{[(2S)-2-(4-methylpiperazin-1-yl)propanoyl]amino}-4-(trifluoromethoxy)benzamide or N-[6-(2-fluorophenyl)pyridin-3-yl]-3-{[(2R)-2-(4-methylpiperazin-1-yl)propanoyl]amino}-4-(trifluoromethoxy)benzamide

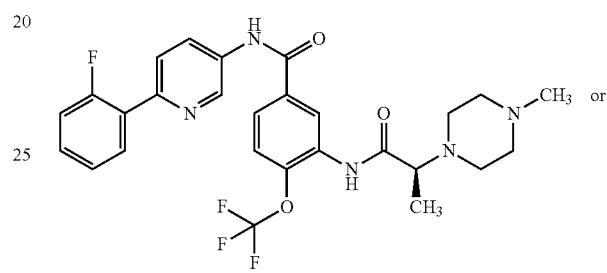

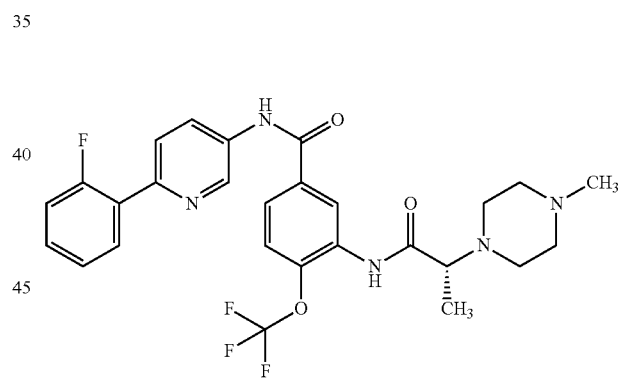

120 mg of the racemate of the compound of example 64 were separated using chiral HPLC (System: Agilent Prep 1200, Column: Chiralpak IC 5 μm 250×20 mm, Solvent: hexane/2-propanol/diethylamine 50:50:0.1 (v/v/v)) to give the second eluting enantiomer of N-[6-(2-fluorophenyl)pyridin-3-yl]-3-{[2-(4-methylpiperazin-1-yl)propanoyl]amino}-4-(trifluoromethoxy)benzamide (35 mg).

$^1$H-NMR (400 MHz, DMSO-$d_6$): δ [ppm]=1.22 (d, 3H), 2.18 (s, 3H), 2.30-2.63 (m, 8H), 3.43 (q, 1H), 7.29-7.37 (m, 2H), 7.44-7.50 (m, 1H), 7.65 (dd, 1H), 7.79-7.89 (m, 2H), 7.93-8.00 (m, 1H), 8.30 (dd, 1H), 8.85 (d, 1H), 9.06 (d, 1H), 10.09 (s, 1H), 10.72 (s, 1H).

Chiral HPLC (System: Waters Alliance 2695 DAD 996 ESA: Corona, Column: Chiralpak IC 3 μm 100×4.6 mm, Solvent: hexane/2-propanol/diethylamine 50:50:0.1 (v/v/v)): $R_t$=14.57 min, 92.3% enantiomeric excess.

Example 67

3-({[1-(4-cyclopropylpiperazin-1-yl)cyclopropyl]carbonyl}amino)-N-[6-(2-fluorophenyl)pyridin-3-yl]-4-(trifluoromethoxy)benzamide

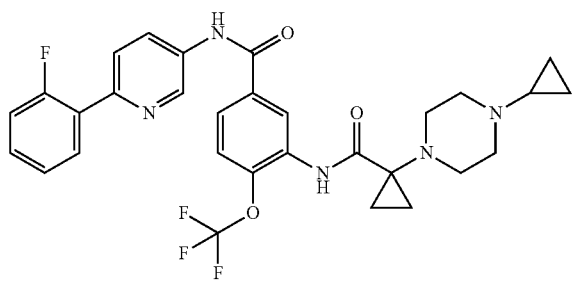 [SMILES: O=C(Nc1ccc(-c2ccccc2F)nc1)c1ccc(OC(F)(F)F)c(NC(=O)C2(N3CCN(C4CC4)CC3)CC2)c1]

To a suspension of 150 mg (0.61 mmol) of the compound of intermediate 43 in 8 mL of dichloromethane were added 0.32 mL of 1-chloro-N,N,2-trimethylprop-1-en-1-amine (2.43 mmol, 6 equiv). The reaction mixture was stirred at room temperature for 2 h. The resulting mixture was concentrated under reduced pressure, was then triturated with dichloromethane and was concentrated under reduced pressure. The remaining material was provided in 8 mL of dichloromethane and 0.15 mL of pyridine (1.82 mmol, 4.5 equiv) and 159 mg of the compound from intermediate 10 were added. The resulting solution was stirred at room temperature over night. The resulting mixture was concentrated under reduced pressure. Purification by HPLC (Waters Autopurification system, column: XBrigde C18 5 μm 100× 30 mm, solvent: water/acetonitrile+0.2% ammonia (32%) gradient, rate: 70 mL/min, temperature: room temperature) yielded 109 mg (46% of theory) of the title compound.

$^1$H-NMR (300 MHz, DMSO-d$_6$): δ [ppm]=0.24-0.33 (m, 2H), 0.40-0.48 (m, 2H), 1.11-1.19 (m, 2H), 1.19-1.28 (m, 2H), 1.54-1.65 (m, 1H), 2.36-2.46 (m, 4H), 2.60-2.71 (m, 4H), 7.28-7.38 (m, 2H), 7.42-7.52 (m, 1H), 7.67 (dd, 1H), 7.78-7.87 (m, 2H), 7.91-8.01 (m, 1H), 8.29 (dd, 1H), 8.99 (d, 1H), 9.05 (d, 1H), 10.64 (s, 1H), 10.72 (s, 1H).

LC-MS (Method 3): R$_t$=1.55 min; MS (ESIpos): m/z=584 [M+H]$^+$.

Example 68

N-[6-(2-fluorophenyl)pyridin-3-yl]-3-({[1-(morpholin-4-yl)cyclopropyl]carbonyl}amino)-4-(trifluoromethoxy)benzamide

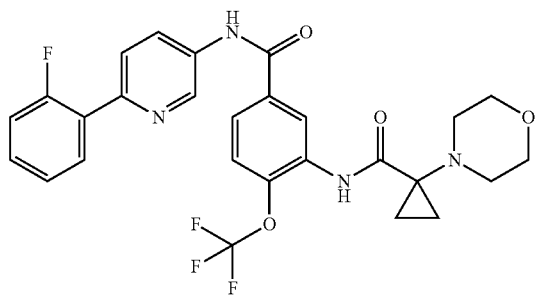 [SMILES: O=C(Nc1ccc(-c2ccccc2F)nc1)c1ccc(OC(F)(F)F)c(NC(=O)C2(N3CCOCC3)CC2)c1]

200 mg (0.96 mmol, 2 equiv) of the compound of intermediate 44 were stirred in 4 mL of dichloromethane at room temperature. 0.09 mL (1.20 mmol, 2.5 equiv) of DMF and 0.08 mL (0.96 mmol, 2 equiv) of oxalyl chloride were added and the mixture was stirred for additional 0.5 h at room temperature. 0.27 mL (2.41 mmol, 5 equiv) of 4-methylmorpholine and 188 mg (0.48 mmol) of the compound of intermediate 10 were added and the mixture was stirred at room temperature over night. The reaction mixture was poured into water and extracted with ethyl acetate. The combined organic phases were dried over sodium sulfate, and concentrated under reduced pressure. Purification by HPLC (method 2) yielded 25 mg (9% of theory) of the title compound.

$^1$H-NMR (300 MHz, DMSO-d$_6$): δ [ppm]=1.11-1.20 (m, 2H), 1.25-1.34 (m, 2H), 2.39-2.50 (m, 4H), 3.64-3.78 (m, 4H), 7.27-7.39 (m, 2H), 7.41-7.53 (m, 1H), 7.63-7.73 (m, 1H), 7.78-7.90 (m, 2H), 7.91-8.01 (m, 1H), 8.30 (dd, 1H), 8.93 (d, 1H), 9.05 (d, 1H), 10.57 (s, 1H), 10.73 (s, 1H).

LC-MS (Method 1): R$_t$=1.39 min; MS (ESIpos): m/z=545 [M+H]$^+$.

Example 69

N-[6-(3-fluorophenyl)pyridin-3-yl]-3-{[2-(morpholin-4-yl)propanoyl]amino}-4-(trifluoromethoxy)benzamide

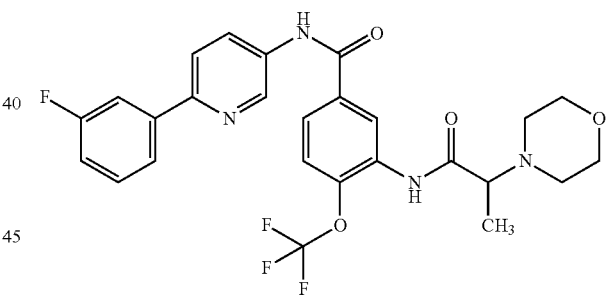

To a solution of 500 mg (1.04 mmol) of the compound of intermediate 71 in 6 mL of DMF were added 0.43 mL of triethylamine (3.11 mmol, 3 equiv), 0.27 mL of morpholine (3.11 mmol, 3 equiv), and 34.5 mg of potassium iodide (0.21 mmol, 0.2 equiv). The reaction mixture was stirred at 50° C. over night. After filtration, purification by HPLC (column: chromatorex C18, 10 μm, 195×51 mm, mobile phase: acetonitrile/water+0.1% formic acid gradient) yielded 214 mg (38% of theory) of the title compound.

$^1$H-NMR (300 MHz, DMSO-d$_6$): δ [ppm]=1.22 (d, 3H), 2.51-2.59 (m, 4H), 3.40 (q, 1H), 3.57-3.74 (m, 4H), 7.24 (td, 1H), 7.46-7.58 (m, 1H), 7.65 (dd, 1H), 7.79-7.97 (m, 3H), 8.06 (d, 1H), 8.31 (dd, 1H), 8.74 (d, 1H), 9.01 (d, 1H), 10.05 (s, 1H), 10.73 (s, 1H).

LC-MS (Method 1): R$_t$=1.15 min; MS (ESIpos): m/z=533 [M+H]$^+$.

Example 70

N-[6-(3-fluorophenyl)pyridin-3-yl]-3-{[2-(8-oxa-3-azabicyclo[3.2.1]oct-3-yl)propanoyl]amino}-4-(trifluoromethoxy)benzamide

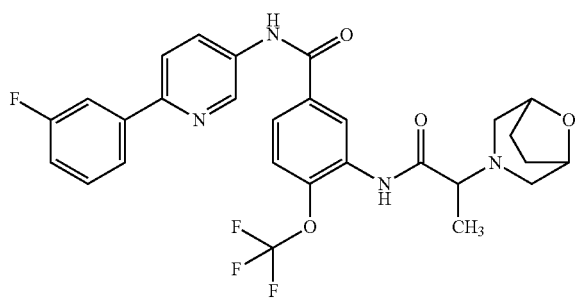 [SMILES: CC(C(=O)Nc1cc(C(=O)Nc2ccc(-c3cccc(F)c3)nc2)ccc1OC(F)(F)F)N1CC2CCC(C1)O2]

To a solution of 500 mg (1.04 mmol) of the compound of intermediate 71 in 6 mL of DMF were added 0.58 mL of triethylamine (4.15 mmol, 4 equiv), 466 mg of 8-oxa-3-azabicyclo[3.2.1]octane hydrochloride (3.11 mmol, 3 equiv), and 34.5 mg of potassium iodide (0.21 mmol, 0.2 equiv). The reaction mixture was stirred at 50° C. over night. 0.58 mL of triethylamine (4.15 mmol, 4 equiv), 466 mg of 8-oxa-3-azabicyclo[3.2.1]octane hydrochloride (3.11 mmol, 3 equiv), and 34.5 mg of potassium iodide (0.21 mmol, 0.2 equiv) were added and the reaction mixture was stirred at 50° C. over night. After filtration and concentration, purification by HPLC (Waters Autopurification system, column: Reprospher C18-DE 5 μm 125×30 mm, solvent: water/acetonitrile+0.1% formic acid (99%) gradient, rate: 70 mL/min, temperature: room temperature) yielded 288 mg (48% of theory) of the title compound.

$^1$H-NMR (300 MHz, DMSO-$d_6$): δ [ppm]=1.19 (d, 3H), 1.71-1.88 (m, 2H), 1.89-2.05 (m, 2H), 2.40-2.47 (m, 2H), 2.56-2.64 (m, 2H), 3.32 (q, 1H), 4.20-4.33 (m, 2H), 7.25 (td, 1H), 7.47-7.58 (m, 1H), 7.65 (dd, 1H), 7.81-7.99 (m, 3H), 8.07 (d, 1H), 8.31 (dd, 1H), 8.77 (d, 1H), 9.02 (d, 1H), 9.69 (s, 1H), 10.73 (s, 1H).

LC-MS (Method 4): $R_t$=1.36 min; MS (ESIpos): m/z=559 [M+H]$^+$.

Example 71

N-[6-(3,5-difluorophenyl)pyridin-3-yl]-3-({[1-(morpholin-4-yl)cyclopropyl]carbonyl}amino)-4-(trifluoromethoxy)benzamide

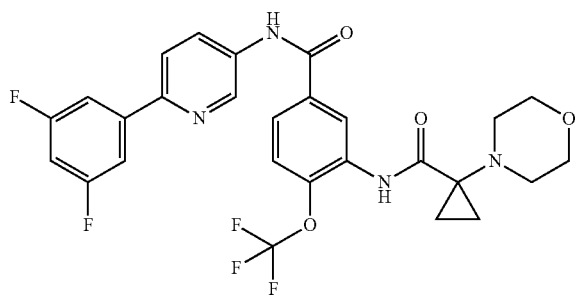 [SMILES: O=C(Nc1ccc(-c2cc(F)cc(F)c2)nc1)c1ccc(OC(F)(F)F)c(NC(=O)C2(N3CCOCC3)CC2)c1]

189 mg (0.91 mmol, 2 equiv) of the compound of intermediate 44 were stirred in 2 mL of dichloromethane at room temperature. 0.07 mL (0.91 mmol, 2 equiv) of DMF and 0.08 mL (0.91 mmol, 2 equiv) of oxalyl chloride were added and the mixture was stirred for additional 0.5 h at room temperature. 0.25 mL (2.27 mmol, 5 equiv) of 4-methylmorpholine and 200 mg (0.45 mmol) of the compound of intermediate 72 were added and the mixture was stirred at room temperature over night. The reaction mixture was poured into water and extracted with dichloromethane. The combined organic phases were dried over sodium sulfate, and concentrated under reduced pressure. Purification by HPLC (method 2) yielded 65 mg (25% of theory) of the title compound.

$^1$H-NMR (400 MHz, DMSO-$d_6$): δ [ppm]=1.14-1.19 (m, 2H), 1.26-1.31 (m, 2H), 2.44-2.48 (m, 4H), 3.65-3.75 (m, 4H), 7.23-7.32 (m, 1H), 7.67 (dd, 1H), 7.75-7.86 (m, 3H), 8.11 (d, 1H), 8.32 (dd, 1H), 8.93 (d, 1H), 9.02 (d, 1H), 10.56 (s, 1H), 10.75 (s, 1H).

LC-MS (Method 1): $R_t$=1.46 min; MS (ESIpos): m/z=563 [M+H]$^+$.

Example 72

N-[6-(3,5-difluorophenyl)pyridin-3-yl]-3-[(morpholin-4-ylacetyl)amino]-4-(trifluoromethoxy)benzamide

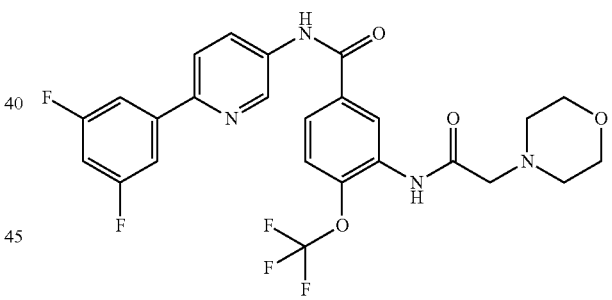

To a solution of 100 mg (0.21 mmol) of the compound of intermediate 73 in 1.5 mL of DMF were added 0.06 mL of triethylamine (0.41 mmol, 2 equiv), 0.04 mL of morpholine (0.41 mmol, 2 equiv), and 6.8 mg of potassium iodide (0.04 mmol, 0.2 equiv). The reaction mixture was stirred at room temperature over night. After filtration, purification by HPLC (method 2) yielded 54 mg (48% of theory) of the title compound.

$^1$H-NMR (400 MHz, DMSO-$d_6$): δ [ppm]=2.55-2.61 (m, 4H), 3.23 (s, 2H), 3.62-3.69 (m, 4H), 7.24-7.32 (m, 1H), 7.63-7.69 (m, 1H), 7.76-7.84 (m, 2H), 7.86 (dd, 1H), 8.12 (d, 1H), 8.33 (dd, 1H), 8.79 (d, 1H), 9.02 (d, 1H), 9.93 (s, 1H), 10.75 (s, 1H).

LC-MS (Method 1): $R_t$=1.24 min; MS (ESIpos): m/z=537 [M+H]$^+$.

Example 73

N-[6-(3,5-difluorophenyl)pyridin-3-yl]-3-[(8-oxa-3-azabicyclo[3.2.1]oct-3-ylacetyl)amino]-4-(trifluoromethoxy)benzamide

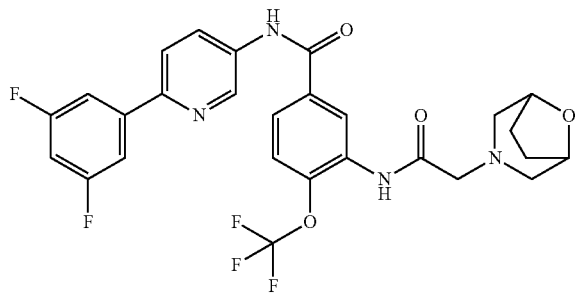 [SMILES: O=C(CN1CC2CCC(C1)O2)Nc1cc(C(=O)Nc2ccc(-c3cc(F)cc(F)c3)nc2)ccc1OC(F)(F)F]

To a solution of 100 mg (0.21 mmol) of the compound of intermediate 73 in 1.5 mL of DMF were added 0.09 mL of triethylamine (0.62 mmol, 3 equiv), 61.6 mg of 8-oxa-3-azabicyclo[3.2.1]octane hydrochloride (0.41 mmol, 2 equiv), and 6.8 mg of potassium iodide (0.04 mmol, 0.2 equiv). The reaction mixture was stirred at room temperature over night. After filtration, purification by HPLC (method 2) yielded 67 mg (57% of theory) of the title compound.

$^1$H-NMR (400 MHz, DMSO-$d_6$): δ [ppm]=1.78-1.86 (m, 2H), 1.96-2.03 (m, 2H), 2.41-2.47 (m, 2H), 2.64-2.69 (m, 2H), 3.18 (s, 2H), 4.24-4.29 (m, 2H), 7.24-7.32 (m, 1H), 7.63-7.69 (m, 1H), 7.76-7.83 (m, 2H), 7.86 (dd, 1H), 8.12 (d, 1H), 8.33 (dd, 1H), 8.85 (d, 1H), 9.02 (d, 1H), 9.59 (s, 1H), 10.75 (s, 1H).

LC-MS (Method 1): $R_t$=1.37 min; MS (ESIpos): m/z=563 [M+H]$^+$.

Example 74

N-[6-(2-fluorophenyl)pyridin-3-yl]-3-[(morpholin-4-ylacetyl)amino]-4-(trifluoromethyl)benzamide

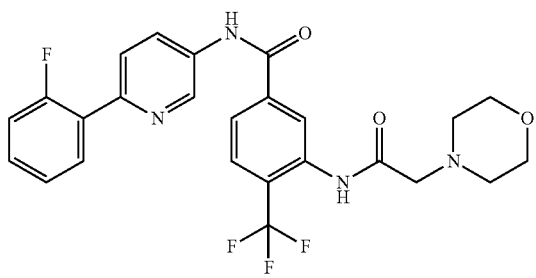 [SMILES: O=C(CN1CCOCC1)Nc1cc(C(=O)Nc2ccc(-c3ccccc3F)nc2)ccc1C(F)(F)F]

To a solution of 220 mg (0.49 mmol) of the compound of intermediate 78 in 2 mL of DMF were added 0.1 mL of triethylamine (0.73 mmol, 1.5 equiv), 0.06 mL of morpholine (0.73 mmol, 1.5 equiv), and 12.1 mg of potassium iodide (0.07 mmol, 0.15 equiv). The reaction mixture was stirred at room temperature for 3 days. After filtration, purification by HPLC (method 2) yielded 49 mg (20% of theory) of the title compound.

$^1$H-NMR (400 MHz, DMSO-$d_6$): δ [ppm]=2.55-2.62 (m, 4H), 3.23 (s, 2H), 3.62-3.70 (m, 4H), 7.29-7.38 (m, 2H), 7.44-7.51 (m, 1H), 7.85 (dd, 1H), 7.93-8.00 (m, 3H), 8.32 (dd, 1H), 8.74 (s, 1H), 9.07 (d, 1H), 9.99 (s, 1H), 10.83 (s, 1H).

LC-MS (Method 4): $R_t$=1.12 min; MS (ESIpos): m/z=503 [M+H]$^+$.

Example 75

N$^4$-[6-(2-fluorophenyl)pyridin-3-yl]-2-({[1-(morpholin-4-yl)cyclopropyl]carbonyl}amino)terephthalamide

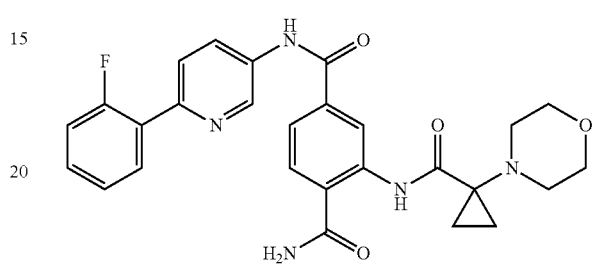

118 mg (0.57 mmol, 2 equiv) of the compound of intermediate 44 were stirred in 1.9 mL of dichloromethane at room temperature. 0.04 mL (0.57 mmol, 2 equiv) of DMF and 0.05 mL (0.57 mmol, 2 equiv) of oxalyl chloride were added and the mixture was stirred for additional 0.5 h at room temperature. 0.16 mL (1.43 mmol, 5 equiv) of 4-methylmorpholine and 100 mg (0.29 mmol) of the compound of intermediate 80 were added and the mixture was stirred at room temperature over night. The reaction mixture was poured into water and extracted with dichloromethane. The combined organic phases were dried over sodium sulfate, and concentrated under reduced pressure. Purification by HPLC (column: chromatorex C18, 10 μm, 125×30 mm, mobile phase: acetonitrile/water+0.1% formic acid gradient) yielded 15 mg (10% of theory) of the title compound.

$^1$H-NMR (400 MHz, DMSO-$d_6$): δ [ppm]=1.09-1.16 (m, 2H), 1.18-1.24 (m, 2H), 2.38-2.45 (m, 4H), 3.77-3.86 (m, 4H), 7.30-7.37 (m, 2H), 7.43-7.50 (m, 1H), 7.67-7.72 (m, 1H), 7.83 (d, 1H), 7.87-7.92 (m, 2H), 7.93-8.00 (m, 1H), 8.28-8.33 (m, 2H), 9.07 (d, 1H), 9.14 (s, 1H), 10.68 (s, 1H), 12.68 (s, 1H).

LC-MS (Method 4): $R_t$=1.11 min; MS (ESIpos): m/z=504 [M+H]$^+$.

Example 76

N-[6-(2-fluorophenyl)pyridin-3-yl]-4-methyl-3-({[1-(morpholin-4-yl)cyclopropyl]carbonyl}amino)benzamide

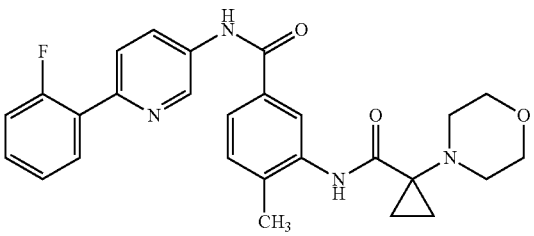 [SMILES: Cc1ccc(C(=O)Nc2ccc(-c3ccccc3F)nc2)cc1NC(=O)C1(N2CCOCC2)CC1]

To a solution of the compound of intermediate 82 (150 mg, 0.49 mmol) and 6-(2-fluorophenyl)pyridin-3-amine (intermediate 114, 111 mg, 0.59 mmol, 1.2 equiv) in DMF (1.8 mL) was added (benzotriazol-1-yloxy)tripyrrolidinophosphonium hexafluorophosphate (PYBOP, 513 mg, 0.99 mmol, 2 equiv) and diisopropylethylamine (0.34 mL, 1.97 mmol, 4 equiv). The resulting mixture was stirred at room temperature over night. After filtration, purification by HPLC (method 2) yielded 27 mg (11% of theory) of the title compound.

$^1$H-NMR (400 MHz, DMSO-$d_6$): δ [ppm]=1.12-1.15 (m, 2H), 1.19-1.26 (m, 2H), 2.40 (s, 3H), 3.69-3.76 (m, 4H), 7.29-7.36 (m, 2H), 7.41-7.50 (m, 2H), 7.72 (dd, 1H), 7.82 (dd, 1H), 7.93-8.00 (m, 1H), 8.31 (dd, 1H), 8.54 (d, 1H), 9.07 (d, 1H), 10.13 (s, 1H), 10.53 (s, 1H).

LC-MS (Method 1): $R_t$=1.22 min; MS (ESIpos): m/z=475 [M+H]$^+$.

Example 77

4-fluoro-N-[6-(2-fluorophenyl)pyridin-3-yl]-3-({[1-(morpholin-4-yl)cyclopropyl]carbonyl}amino)benzamide

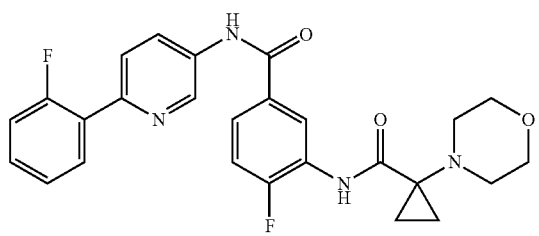 [SMILES: O=C(Nc1ccc(-c2ccccc2F)nc1)c1ccc(F)c(NC(=O)C2(N3CCOCC3)CC2)c1]

To a solution of the compound of intermediate 84 (170 mg, 0.55 mmol) and 6-(2-fluorophenyl)pyridin-3-amine (intermediate 114, 125 mg, 0.66 mmol, 1.2 equiv) in DMF (2.0 mL) was added (benzotriazol-1-yloxy)tripyrrolidinophosphonium hexafluorophosphate (PYBOP, 574 mg, 1.10 mmol, 2 equiv) and diisopropylethylamine (0.38 mL, 2.21 mmol, 4 equiv). The resulting mixture was stirred at room temperature for 2 days. After filtration, purification by HPLC (method 2) yielded 140 mg (52% of theory) of the title compound.

$^1$H-NMR (300 MHz, DMSO-$d_6$): δ [ppm]=1.10-1.19 (m, 2H), 1.19-1.29 (m, 2H), 3.65-3.76 (m, 4H), 7.28-7.39 (m, 2H), 7.42-7.57 (m, 2H), 7.77-7.87 (m, 2H), 7.96 (td, 1H), 8.30 (dd, 1H), 8.71 (dd, 1H), 9.06 (d, 1H), 10.35 (s, 1H), 10.64 (s, 1H).

LC-MS (Method 4): $R_t$=1.26 min; MS (ESIpos): m/z=479 [M+H]$^+$.

Example 78

4-fluoro-3-({[1-(morpholin-4-yl)cyclopropyl]carbonyl}amino)-N-(5-phenyl-1,3,4-thiadiazol-2-yl)benzamide

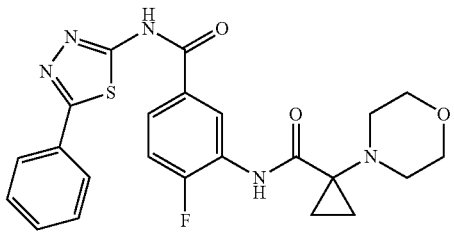 [SMILES: O=C(Nc1nnc(-c2ccccc2)s1)c1ccc(F)c(NC(=O)C2(N3CCOCC3)CC2)c1]

To a solution of the compound of intermediate 84 (150 mg, 0.49 mmol) and 5-phenyl-1,3,4-thiadiazol-2-amine (172 mg, 0.97 mmol, 2 equiv) in DMF (1.9 mL) was added (benzotriazol-1-yloxy)tripyrrolidinophosphonium hexafluorophosphate (PYBOP, 506 mg, 0.97 mmol, 2 equiv) and diisopropylethylamine (0.42 mL, 2.43 mmol, 5 equiv). The resulting mixture was stirred at room temperature over night. After concentration, the remaining solids were then triturated with ethanol and water. The precipitate was removed by filtration and dried under reduced pressure. The remaining solids were then triturated with DMSO and water. The precipitate was removed by filtration and dried under reduced pressure to give 91.6 mg (40% of theory) of the title compound.

$^1$H-NMR (300 MHz, DMSO-$d_6$): δ [ppm]=1.10-1.19 (m, 2H), 1.20-1.29 (m, 2H), 3.64-3.76 (m, 4H), 7.48-7.60 (m, 4H), 7.93-8.03 (m, 3H), 8.82-8.90 (m, 1H), 10.36 (s, 1H), 13.24 (s, 1H).

LC-MS (Method 4): $R_t$=1.27 min; MS (ESIpos): m/z=468 [M+H]$^+$.

Example 79

4-chloro-N-[6-(2-fluorophenyl)pyridin-3-yl]-3-({[1-(morpholin-4-yl)cyclopropyl]carbonyl}amino)benzamide

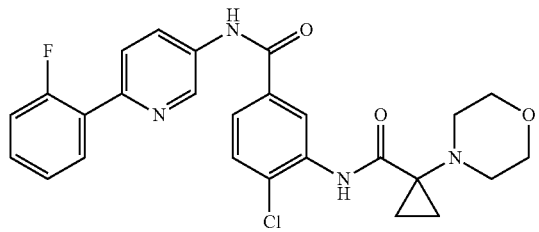

To a solution of the compound of intermediate 86 (150 mg, 0.46 mmol) and 6-(2-fluorophenyl)pyridin-3-amine (104 mg, 0.55 mmol, 1.2 equiv) in DMF (1.8 mL) was added (benzotriazol-1-yloxy)tripyrrolidinophosphonium hexafluorophosphate (PYBOP, 481 mg, 0.92 mmol, 2 equiv) and diisopropylethylamine (0.32 mL, 1.85 mmol, 4 equiv). The resulting mixture was stirred at room temperature over night. After filtration, purification by HPLC (method 2) yielded 60.3 mg (26% of theory) of the title compound.

¹H-NMR (300 MHz, DMSO-d₆): δ [ppm]=1.11-1.23 (m, 2H), 1.23-1.34 (m, 2H), 3.67-3.82 (m, 4H), 7.27-7.39 (m, 2H), 7.41-7.53 (m, 1H), 7.74-7.78 (m, 2H), 7.83 (dd, 1H), 7.91-8.01 (m, 1H), 8.30 (dd, 1H), 8.94 (s, 1H), 9.06 (d, 1H), 10.69 (s, 1H), 10.78 (s, 1H).

LC-MS (Method 1): $R_t$=1.30 min; MS (ESIpos): m/z=495 [M+H]⁺.

Example 80

N-[6-(2-fluorophenyl)pyridin-3-yl]-4-methoxy-3-({[1-(morpholin-4-yl)cyclopropyl]carbonyl}amino)benzamide

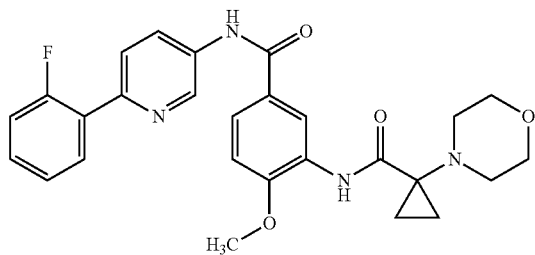 [SMILES: COc1ccc(C(=O)Nc2ccc(-c3ccccc3F)nc2)cc1NC(=O)C1(N2CCOCC2)CC1]

To a solution of the compound of intermediate 7 (100 mg, 0.30 mmol) and the compound of intermediate 44 (123 mg, 0.59 mmol, 2 equiv) in DMF (1.5 mL) was added (benzotriazol-1-yloxy)tripyrrolidinophosphonium hexafluorophosphate (PYBOP, 308 mg, 0.59 mmol, 2 equiv) and diisopropylethylamine (0.26 mL, 1.48 mmol, 5 equiv). The resulting mixture was stirred at room temperature over night. After filtration, purification by HPLC (method 2) yielded 46.0 mg (28% of theory) of the title compound.

¹H-NMR (300 MHz, DMSO-d₆): δ [ppm]=1.09-1.17 (m, 2H), 1.18-1.27 (m, 2H), 2.40-2.49 (m, 4H), 3.67-3.78 (m, 4H), 4.04 (s, 3H), 7.21-7.39 (m, 3H), 7.41-7.52 (m, 1H), 7.75-7.84 (m, 2H), 7.91-8.00 (m, 1H), 8.30 (dd, 1H), 8.89 (d, 1H), 9.06 (d, 1H), 10.49 (s, 1H), 10.65 (s, 1H).

LC-MS (Method 4): $R_t$=1.27 min; MS (ESIpos): m/z=491 [M+H]⁺.

Example 81

4-methoxy-3-({[1-(morpholin-4-yl)cyclopropyl]carbonyl}amino)-N-(6-phenylpyridin-3-yl)benzamide

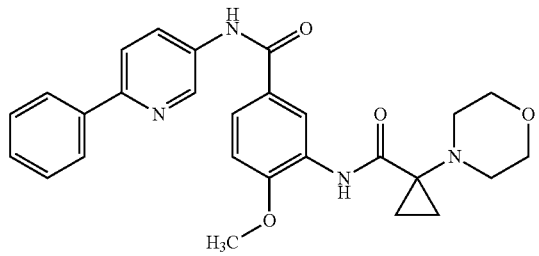 [SMILES: COc1ccc(C(=O)Nc2ccc(-c3ccccc3)nc2)cc1NC(=O)C1(N2CCOCC2)CC1]

To a solution of the compound of intermediate 8 (100 mg, 0.31 mmol) and the compound of intermediate 44 (97.5 mg, 0.47 mmol, 1.5 equiv) in DMF (1.7 mL) was added (benzotriazol-1-yloxy)tripyrrolidinophosphonium hexafluorophosphate (PYBOP, 326 mg, 0.63 mmol, 2 equiv) and diisopropylethylamine (0.27 mL, 1.57 mmol, 5 equiv). The resulting mixture was stirred at room temperature over night. After filtration, purification by HPLC (method 2) yielded 39.0 mg (26% of theory) of the title compound.

¹H-NMR (300 MHz, DMSO-d₆): δ [ppm]=1.08-1.18 (m, 2H), 1.18-1.27 (m, 2H), 2.40-2.49 (m, 4H), 3.67-3.79 (m, 4H), 4.04 (s, 3H), 7.25 (d, 1H), 7.35-7.44 (m, 1H), 7.44-7.53 (m, 2H), 7.77 (dd, 1H), 7.98 (d, 1H), 8.03-8.11 (m, 2H), 8.28 (dd, 1H), 8.88 (d, 1H), 9.00 (d, 1H), 10.45 (s, 1H), 10.65 (s, 1H).

LC-MS (Method 4): $R_t$=1.23 min; MS (ESIpos): m/z=473 [M+H]⁺.

Example 82

N-[6-(2-fluorophenyl)pyridin-3-yl]-4-methoxy-3-({[1-(morpholin-4-yl)cyclobutyl]carbonyl}amino)benzamide

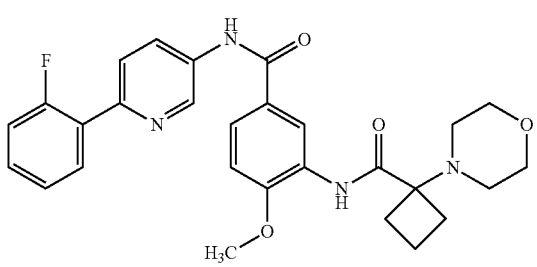 [SMILES: COc1ccc(C(=O)Nc2ccc(-c3ccccc3F)nc2)cc1NC(=O)C1(N2CCOCC2)CCC1]

To a solution of the compound of intermediate 7 (100 mg, 0.30 mmol) and 1-(morpholin-4-yl)cyclobutanecarboxylic acid (110 mg, 0.59 mmol, 2 equiv) in DMF (1.5 mL) was added (benzotriazol-1-yloxy)tripyrrolidinophosphonium hexafluorophosphate (PYBOP, 309 mg, 0.59 mmol, 2 equiv) and diisopropylethylamine (0.26 mL, 1.48 mmol, 5 equiv). The resulting mixture was stirred at room temperature over night. After filtration, purification by HPLC (method 2) yielded 38.0 mg (23% of theory) of the title compound.

¹H-NMR (300 MHz, DMSO-d₆): δ [ppm]=1.61-1.80 (m, 1H), 1.83-2.02 (m, 1H), 2.08-2.23 (m, 2H), 2.32-2.44 (m, 2H), 3.62-3.77 (m, 4H), 3.99 (s, 3H), 7.23 (d, 1H), 7.28-7.39 (m, 2H), 7.41-7.52 (m, 1H), 7.75-7.86 (m, 2H), 7.92-8.01 (m, 1H), 8.31 (dd, 1H), 8.82 (d, 1H), 9.07 (d, 1H), 9.79 (s, 1H), 10.51 (s, 1H).

LC-MS (Method 4): $R_t$=1.28 min; MS (ESIpos): m/z=505 [M+H]⁺.

Example 83

4-(methoxymethyl)-3-[(morpholin-4-ylacetyl)amino]-N-(5-phenyl-1,3,4-thiadiazol-2-yl)benzamide

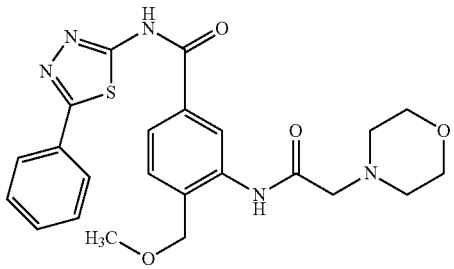 [SMILES: COCc1ccc(C(=O)Nc2nnc(-c3ccccc3)s2)cc1NC(=O)CN1CCOCC1]

To a solution of 200 mg (0.48 mmol) of the compound of intermediate 52 in 1.8 mL of DMF were added 0.13 mL of triethylamine (0.96 mmol, 2 equiv), 0.08 mL of morpholine (0.96 mmol, 2 equiv), and 16.0 mg of potassium iodide (0.10 mmol, 0.2 equiv). The reaction mixture was stirred at room temperature for 3 days. After filtration, purification by HPLC (method 2) yielded 126 mg (56% of theory) of the title compound.

$^1$H-NMR (300 MHz, DMSO-$d_6$): δ [ppm]=2.54-2.61 (m, 4H), 3.18 (s, 2H), 3.37 (s, 3H), 3.65-3.72 (m, 4H), 4.55 (s, 2H), 7.45-7.57 (m, 4H), 7.86-7.92 (m, 1H), 7.95 (dd, 2H), 8.78 (s, 1H), 9.96 (s, 1H).

LC-MS (Method 1): $R_t$=0.95 min; MS (ESIpos): m/z=468 [M+H]$^+$.

Example 84

3-{[(4-cyclopropylpiperazin-1-yl)acetyl]amino}-4-(methoxymethyl)-N-(5-phenyl-1,3,4-thiadiazol-2-yl)benzamide

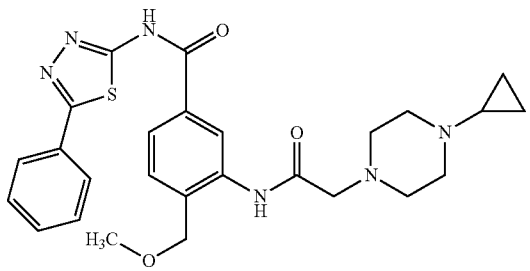 [SMILES: COCc1ccc(C(=O)Nc2nnc(-c3ccccc3)s2)cc1NC(=O)CN1CCN(C2CC2)CC1]

To a solution of 200 mg (0.48 mmol) of the compound of intermediate 52 in 1.8 mL of DMF were added 0.4 mL of triethylamine (2.88 mmol, 6 equiv), 191 mg of 1-cyclopropylpiperazine dihydrochloride (0.96 mmol, 2 equiv), and 16.0 mg of potassium iodide (0.10 mmol, 0.2 equiv). The reaction mixture was stirred at room temperature over night. After filtration, purification by HPLC (method 2) yielded 117 mg (48% of theory) of the title compound.

$^1$H-NMR (300 MHz, DMSO-$d_6$): δ [ppm]=0.25-0.33 (m, 2H), 0.38-0.46 (m, 2H), 1.59-1.68 (m, 1H), 2.60-2.68 (m, 4H), 3.16 (s, 2H), 3.41 (s, 3H), 4.56 (s, 2H), 7.48-7.60 (m, 4H), 7.85-7.91 (m, 1H), 7.94-8.02 (m, 2H), 8.82 (d, 1H), 9.98 (s, 1H), 13.12 (s, 1H).

LC-MS (Method 1): $R_t$=0.90 min; MS (ESIpos): m/z=507 [M+H]$^+$.

Example 85

3-{[N-(2-methoxyethyl)-N-methylglycyl]amino}-N-(5-phenyl-1,3,4-thiadiazol-2-yl)-4-(trifluoromethoxy)benzamide

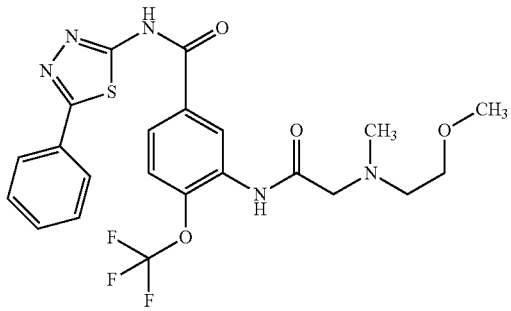 [SMILES: COCCN(C)CC(=O)Nc1cc(C(=O)Nc2nnc(-c3ccccc3)s2)ccc1OC(F)(F)F]

To a solution of 120 mg (0.26 mmol) of the compound of intermediate 41 in 1.5 mL of DMF were added 0.07 mL of triethylamine (0.53 mmol, 2 equiv), 0.06 mL of 2-methoxy-N-methylethanamine (0.53 mmol, 2 equiv), and 9.0 mg of potassium iodide (0.05 mmol, 0.2 equiv). The reaction mixture was stirred at room temperature over night. After filtration, purification by HPLC (method 2) yielded 58 mg (43% of theory) of the title compound.

$^1$H-NMR (400 MHz, DMSO-$d_6$): δ [ppm]=2.40 (s, 3H), 2.73 (t, 2H), 3.23 (s, 3H), 3.30 (s, 2H), 3.48 (t, 2H), 7.52-7.59 (m, 3H), 7.61-7.68 (m, 1H), 7.95-8.04 (m, 3H), 8.97 (d, 1H), 9.99 (s, 1H), 13.38 (s, 1H).

LC-MS (Method 1): $R_t$=0.97 min; MS (ESIpos): m/z=510 [M+H]$^+$.

Example 86

4-(difluoromethoxy)-3-[(8-oxa-3-azabicyclo[3.2.1]oct-3-ylacetyl)amino]-N-(5-phenyl-1,3,4-thiadiazol-2-yl)benzamide

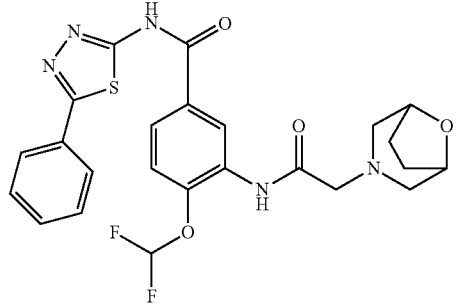 [SMILES: O=C(CN1CC2CCC(C1)O2)Nc1cc(C(=O)Nc2nnc(-c3ccccc3)s2)ccc1OC(F)F]

To a solution of 140 mg (0.32 mmol) of the compound of intermediate 47 in 2 mL of DMF were added 0.13 mL of triethylamine (0.96 mmol, 3 equiv), 95.5 mg of 8-oxa-3-azabicyclo[3.2.1]octane hydrochloride (0.64 mmol, 2 equiv), and 10.6 mg of potassium iodide (0.06 mmol, 0.2 equiv). The reaction mixture was stirred at room temperature over night. After filtration, purification by HPLC (method 2) yielded 4.2 mg (2% of theory) of the title compound.

$^1$H-NMR (300 MHz, DMSO-$d_6$): δ [ppm]=1.75-1.89 (m, 2H), 2.01-2.13 (m, 2H), 2.39-2.47 (m, 2H), 2.62-2.71 (m, 2H), 3.16 (s, 2H), 4.21-4.32 (m, 2H), 7.42 (d, 1H), 7.50 (t, 1H), 7.51-7.60 (m, 3H), 7.90-8.03 (m, 3H), 9.09 (d, 1H), 9.58 (s, 1H), 13.21 (s, 1H).

LC-MS (Method 4): $R_t$=1.19 min; MS (ESIpos): m/z=516 [M+H]$^+$.

Example 87

4-[(methylsulfonyl)methyl]-3-{[2-(morpholin-4-yl)propanoyl]amino}-N-(5-phenyl-1,3,4-thiadiazol-2-yl)benzamide

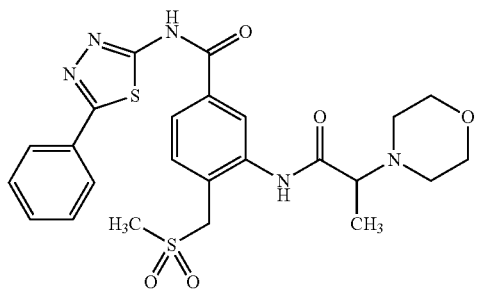 [SMILES: CC(C(=O)Nc1cc(C(=O)Nc2nnc(-c3ccccc3)s2)ccc1CS(C)(=O)=O)N1CCOCC1]

To a solution of 500 mg (1.04 mmol) of the compound of intermediate 87 in 10 mL of DMF were added 0.44 mL of triethylamine (3.13 mmol, 3 equiv), 0.27 mL of morpholine (3.13 mmol, 3 equiv), and 35.0 mg of potassium iodide (0.21 mmol, 0.2 equiv). The reaction mixture was stirred at 60° C. over night. After concentration, the remaining solids were then triturated with ethanol and water. The precipitate was removed by filtration and dried under reduced pressure. Purification by HPLC (Waters Autopurification system, column: YMC Triart, C18, 5 μm, 100×30 mm, solvent: water/acetonitrile+0.1% trifluoroacetic acid (99%) gradient, rate: 70 mL/min, temperature: room temperature) yielded 255 mg of the trifluoroacetic acid salt of the title compound. The material was triturated with water and a pH 7 hydrogen phosphate buffer solution and stirred for 30 minutes. The precipitate was removed by filtration, washed with water and dried under reduced pressure to yield 192 mg (35% of theory) of the title compound.

$^1$H-NMR (400 MHz, DMSO-d$_6$): δ [ppm]=1.24 (d, 3H), 2.53-2.64 (m, 4H), 3.06 (s, 3H), 3.30 (q, 1H), 3.66-3.73 (m, 4H), 4.63 (d, 1H), 4.70 (d, 1H), 7.53-7.58 (m, 3H), 7.65 (d, 1H), 7.95-8.02 (m, 3H), 8.50 (d, 1H), 10.02 (s, 1H), 13.24 (s, 1H).

LC-MS (Method 4): $R_t$=0.90 min; MS (ESIpos): m/z=530 [M+H]$^+$.

Example 88

3-{[2-(4-methylpiperazin-1-yl)propanoyl]amino}-4-[(methylsulfonyl)methyl]-N-(5-phenyl-1,3,4-thiadiazol-2-yl)benzamide

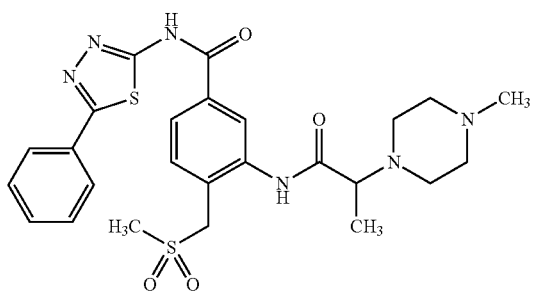 [SMILES: CC(C(=O)Nc1cc(C(=O)Nc2nnc(-c3ccccc3)s2)ccc1CS(C)(=O)=O)N1CCN(C)CC1]

To a solution of 500 mg (1.04 mmol) of the compound of intermediate 87 in 10 mL of DMF were added 0.44 mL of triethylamine (3.13 mmol, 3 equiv), 0.35 mL of methylpiperazine (3.13 mmol, 3 equiv), and 35.0 mg of potassium iodide (0.21 mmol, 0.2 equiv). The reaction mixture was stirred at 60° C. over night. After concentration, the remaining solids were then triturated with ethanol and water. The precipitate was removed by filtration and dried under reduced pressure to yield 351 mg (46% of theory) of the title compound.

$^1$H-NMR (400 MHz, DMSO-d$_6$): δ [ppm]=1.23 (d, 3H), 2.33 (s, 3H), 2.55-2.73 (m, 8H), 3.05 (s, 3H), 3.38 (q, 1H), 4.58-4.71 (m, 2H), 7.51-7.57 (m, 3H), 7.63 (d, 1H), 7.96-8.02 (m, 3H), 8.48 (d, 1H), 9.92 (s, 1H), 12.55 (s, 1H).

LC-MS (Method 4): $R_t$=0.87 min; MS (ESIpos): m/z=543 [M+H]$^+$.

Example 89

N-[5-(2-fluorophenyl)-1,3,4-thiadiazol-2-yl]-3-({[1-(morpholin-4-yl)cyclopropyl]carbonyl}amino)-4-(trifluoromethoxy)benzamide

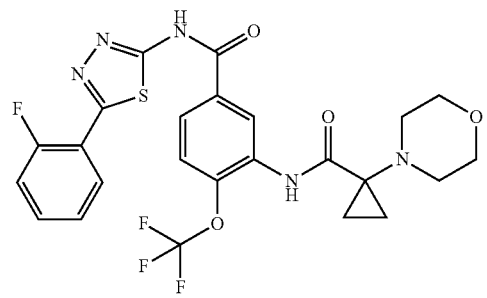 [SMILES: O=C(Nc1nnc(-c2ccccc2F)s1)c1ccc(OC(F)(F)F)c(NC(=O)C2(N3CCOCC3)CC2)c1]

To a solution of the compound of intermediate 45 (200 mg, 0.53 mmol) and 5-(2-fluorophenyl)-1,3,4-thiadiazol-2-amine (209 mg, 1.07 mmol, 2 equiv) in DMF (2.0 mL) was added (benzotriazol-1-yloxy)tripyrrolidinophosphonium hexafluorophosphate (PYBOP, 556 mg, 1.07 mmol, 2 equiv) and diisopropylethylamine (0.47 mL, 2.67 mmol, 5 equiv). The resulting mixture was stirred at room temperature over night. After concentration, the remaining solids were then triturated with DMSO and water. The precipitate was removed by filtration and dried under reduced pressure to give 211 mg (72% of theory) of the title compound.

$^1$H-NMR (300 MHz, DMSO-d$_6$): δ [ppm]=1.12-1.21 (m, 2H), 1.25-1.33 (m, 2H), 2.41-2.50 (m, 4H), 3.63-3.76 (m, 4H), 7.38-7.54 (m, 2H), 7.57-7.65 (m, 1H), 7.68 (dd, 1H), 8.00 (dd, 1H), 8.23-8.33 (m, 1H), 9.09 (d, 1H), 10.58 (s, 1H), 13.43 (s, 1H).

LC-MS (Method 1): $R_t$=1.41 min; MS (ESIpos): m/z=552 [M+H]$^+$.

Example 90

N-[5-(4-fluorophenyl)-1,3,4-thiadiazol-2-yl]-3-({[1-(morpholin-4-yl)cyclopropyl]carbonyl}amino)-4-(trifluoromethoxy)benzamide

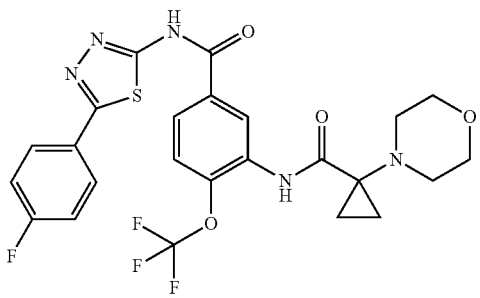 [SMILES: O=C(Nc1nnc(-c2ccc(F)cc2)s1)c1ccc(OC(F)(F)F)c(NC(=O)C2(N3CCOCC3)CC2)c1]

To a solution of the compound of intermediate 45 (200 mg, 0.53 mmol) and 5-(4-fluorophenyl)-1,3,4-thiadiazol-2-amine (209 mg, 1.07 mmol, 2 equiv) in DMF (2.0 mL) was added (benzotriazol-1-yloxy)tripyrrolidinophosphonium hexafluorophosphate (PYBOP, 556 mg, 1.07 mmol, 2 equiv) and diisopropylethylamine (0.47 mL, 2.67 mmol, 5 equiv). The resulting mixture was stirred at room temperature over night. After concentration, the remaining solids were then triturated with DMSO and water, and were extracted with ethyl acetate. The combined organic phases were dried over sodium sulfate and and concentrated under reduced pressure. The remaining material was purified by HPLC (column: chromatorex C18, 10 μm, 195×51 mm, mobile phase: acetonitrile/water gradient) to yield 20.8 mg (7% of theory) of the title compound.

$^1$H-NMR (300 MHz, DMSO-d$_6$): δ [ppm]=1.12-1.20 (m, 2H), 1.25-1.33 (m, 2H), 2.43-2.50 (m, 4H), 3.65-3.74 (m, 4H), 7.33-7.44 (m, 2H), 7.66 (dd, 1H), 7.95-8.09 (m, 3H), 9.08 (d, 1H), 10.56 (s, 1H), 13.40 (s, 1H).

LC-MS (Method 4): R$_t$=1.41 min; MS (ESIpos): m/z=552 [M+H]$^+$.

Example 91

4-methoxy-3-{[(4-methylpiperazin-1-yl)acetyl]amino}-N-(5-phenyl-1,3,4-thiadiazol-2-yl)benzamide

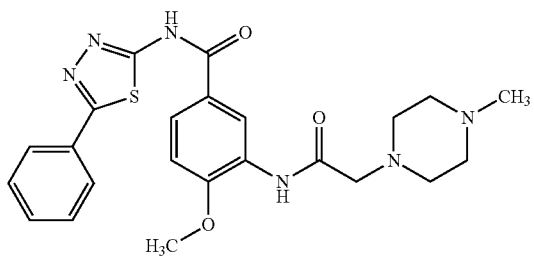 [SMILES: COc1ccc(C(=O)Nc2nnc(-c3ccccc3)s2)cc1NC(=O)CN1CCN(C)CC1]

To a solution of 120 mg (0.30 mmol) of the compound of intermediate 90 in 1.2 mL of DMF were added 0.07 mL of methylpiperazine (0.60 mmol, 2 equiv), 0.08 mL of triethylamine (0.60 mmol, 2 equiv), and 9.9 mg of potassium iodide (0.06 mmol, 0.2 equiv). The reaction mixture was stirred at room temperature over night and then triturated with water. The precipitate was removed by filtration and dried under reduced pressure to yield 85.5 mg (62% of theory) of the title compound. $^1$H-NMR (400 MHz, DMSO-d$_6$): δ [ppm]=2.27 (s, 3H), 2.56-2.65 (m, 4H), 3.19 (s, 2H), 4.00 (s, 3H), 7.24 (d, 1H), 7.52-7.59 (m, 3H), 7.94-8.03 (m, 3H), 8.94 (d, 1H), 9.80 (s, 1H), 12.34 (s, 1H).

LC-MS (Method 3): R$_t$=0.73 min; MS (ESIpos): m/z=467 [M+H]$^+$.

Example 92

4-(benzyloxy)-3-({[1-(morpholin-4-yl)cyclopropyl]carbonyl}amino)-N-(5-phenyl-1,3,4-thiadiazol-2-yl)benzamide

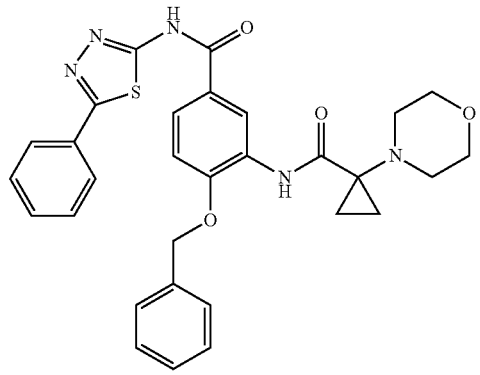 [SMILES: O=C(Nc1nnc(-c2ccccc2)s1)c1ccc(OCc2ccccc2)c(NC(=O)C2(N3CCOCC3)CC2)c1]

To a solution of the compound of intermediate 92 (1.50 g, 3.78 mmol) and 5-phenyl-1,3,4-thiadiazol-2-amine (805 mg, 4.54 mmol, 1.2 equiv) in DMF (14 mL) was added (benzotriazol-1-yloxy)tripyrrolidinophosphonium hexafluorophosphate (PYBOP, 3.94 g, 7.57 mmol, 2 equiv) and diisopropylethylamine (2.6 mL, 15.1 mmol, 4 equiv). The resulting mixture was stirred at room temperature over night. After concentration, the remaining solids were then triturated with 70 mL of water and 40 mL of ethanol and stirred for 30 minutes. The precipitate was removed by filtration, washed with ethanol, and dried under reduced pressure. The remaining solids were then triturated with ethanol and stirred under reflux. The precipitate was removed by filtration and dried under reduced pressure to give 1.38 g (60% of theory) of the title compound.

$^1$H-NMR (300 MHz, DMSO-d$_6$): δ [ppm]=0.97-1.27 (m, 4H), 2.20-2.35 (m, 4H), 3.10-3.27 (m, 4H), 5.31 (s, 2H), 7.36-7.50 (m, 4H), 7.51-7.63 (m, 5H), 7.94-8.04 (m, 3H), 9.07 (d, 1H), 10.44 (s, 1H), 13.10 (s, 1H).

LC-MS (Method 4): R$_t$=1.42 min; MS (ESIpos): m/z=556 [M+H]$^+$.

Example 93

4-hydroxy-3-({[1-(morpholin-4-yl)cyclopropyl]carbonyl}amino)-N-(5-phenyl-1,3,4-thiadiazol-2-yl)benzamide

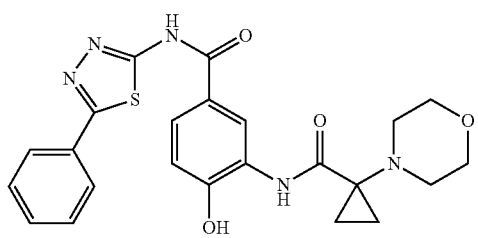 [SMILES: O=C(Nc1nnc(-c2ccccc2)s1)c1ccc(O)c(NC(=O)C2(N3CCOCC3)CC2)c1]

1.00 g (2.48 mmol) of the compound of example 92 was provided in 105 mL of a mixture of THF and methanol (3/2). 500 mg of palladium on charcoal (10% Pd, 50% water) were added, and the mixture was stirred under a hydrogen atmosphere at room temperature. Palladium on charcoal (10% Pd, 50% water) was added several times, and the mixture was stirred under a hydrogen atmosphere at room temperature till the starting material was consumed. After filtration, the solvents were evaporated. Purification by HPLC (Waters Autopurification system, column: Reprospher 5 µm 100×30 mm, solvent: water/acetonitrile+0.2% ammonia (32%) gradient, rate: 70 mL/min, temperature: room temperature) yielded 54.0 mg (4% of theory) of the title compound.

$^1$H-NMR (300 MHz, DMSO-$d_6$): δ [ppm]=1.09-1.16 (m, 2H), 1.18-1.26 (m, 2H), 2.42-2.49 (m, 4H), 3.67-3.76 (m, 4H), 6.99 (d, 1H), 7.49-7.60 (m, 3H), 7.81 (dd, 1H), 7.91-8.01 (m, 2H), 8.95 (d, 1H), 10.55 (s, 1H).

LC-MS (Method 3): $R_t$=0.58 min; MS (ESIpos): m/z=466 [M+H]$^+$.

Example 94

4-bromo-3-{[(4-methylpiperazin-1-yl)acetyl]amino}-N-(5-phenyl-1,3,4-thiadiazol-2-yl)benzamide

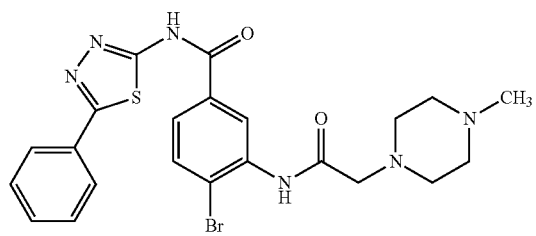 [SMILES: CN1CCN(CC(=O)Nc2cc(C(=O)Nc3nnc(-c4ccccc4)s3)ccc2Br)CC1]

To a solution of 500 mg (1.11 mmol) of the compound of intermediate 94 in 12 mL of DMF were added 0.31 mL of triethylamine (2.21 mmol, 2 equiv), 0.24 mL of methylpiperazine (2.21 mmol, 2 equiv), and 37 mg of potassium iodide (0.22 mmol, 0.2 equiv). The reaction mixture was stirred at room temperature over night. After concentration, the remaining material was triturated with 10 mL of water and 10 mL of ethanol and stirred for 30 minutes. The precipitate was removed by filtration, washed with ethanol and dried under reduced pressure to yield 513 mg (90% of theory) of the title compound.

$^1$H-NMR (400 MHz, DMSO-$d_6$): δ [ppm]=2.35 (s, 3H), 2.56-2.72 (m, 8H), 3.25 (s, 2H), 7.51-7.58 (m, 3H), 7.82-7.90 (m, 2H), 7.94-7.99 (m, 2H), 8.94 (d, 1H), 9.98 (s, 1H).

LC-MS (Method 4): $R_t$=0.94 min; MS (ESIpos): m/z=515 [M+H]$^+$.

Example 95

3-({[1-(morpholin-4-yl)cyclopropyl]carbonyl}amino)-N-(5-phenylpyridin-2-yl)-4-(trifluoromethoxy)benzamide

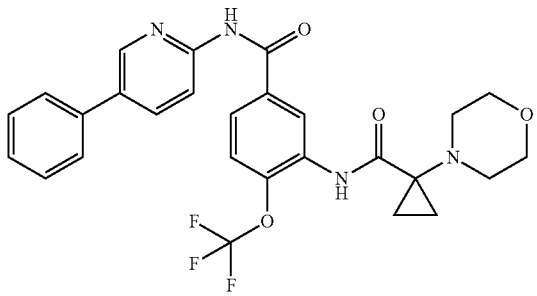 [SMILES: O=C(Nc1ccc(-c2ccccc2)cn1)c1ccc(OC(F)(F)F)c(NC(=O)C2(N3CCOCC3)CC2)c1]

66.5 mg (0.32 mmol) of 1-(morpholin-4-yl)cyclopropanecarboxylic acid hydrochloride (1:1) (intermediate 44) were stirred in 1.5 mL of dichloromethane at room temperature. 2.5 µL (32 µmol) of DMF and 55.8 µL (0.64 mmol) of oxalyl chloride were added, and the mixture was stirred for additional 2 h at 50° C. after the gas formation had stopped. After concentration, 71.0 mg of raw material were obtained, of which 64.2 mg (0.28 mmol) were added to a solution of 94.0 mg (0.24 mmol) of the compound of intermediate 95 and 0.17 mL (1.18 mmol) of triethylamine in a mixture of 1 mL of dichloromethane and 1 mL of THF. The resulting mixture was stirred at room temperature over night and for 24 h at 60° C. 0.17 mL (1.18 mmol) of triethylamine and 2 equivalents of 1-(morpholin-4-yl)cyclopropanecarbonyl chloride hydrochloride (1:1) (prepared as described above) were added and the resulting mixture was stirred at room temperature over night. After concentration, the remaining solids were then triturated with 5 mL of ethanol and stirred for 20 minutes. The remaining solids were removed by filtration and were dried at 50° C. under reduced pressure. Purification by HPLC (column: chromatorex C18, 10 µm, 125×30 mm, mobile phase: acetonitrile/water+0.1% formic acid gradient) yielded 17 mg (13% of theory) of the title compound.

$^1$H-NMR (400 MHz, DMSO-$d_6$): δ [ppm]=1.13-1.19 (m, 2H), 1.26-1.31 (m, 2H), 2.44-2.49 (m, 4H), 3.67-3.73 (m, 4H), 7.37-7.44 (m, 1H), 7.48-7.54 (m, 2H), 7.61 (dd, 1H), 7.73-7.77 (m, 2H), 7.89 (dd, 1H), 8.14-8.21 (m, 1H), 8.27 (d, 1H), 8.73 (d, 1H), 8.96 (d, 1H), 10.53 (s, 1H), 11.05 (s, 1H).

LC-MS (Method 1): $R_t$=1.44 min; MS (ESIpos): m/z=527 [M+H]$^+$.

Example 96

N-[5-(3-methylphenyl)-1,3,4-thiadiazol-2-yl]-3-[(morpholin-4-ylacetyl)amino]-4-(trifluoromethoxy)benzamide

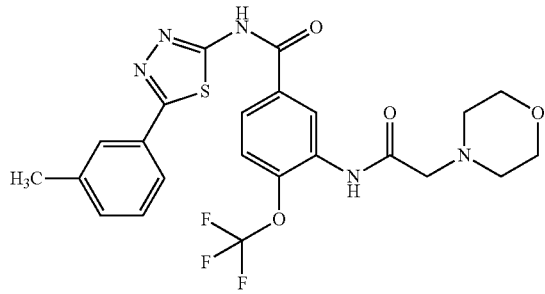 [SMILES: Cc1cccc(-c2nnc(NC(=O)c3ccc(OC(F)(F)F)c(NC(=O)CN4CCOCC4)c3)s2)c1]

To a solution of the compound of intermediate 21 (150 mg, 0.43 mmol) and 5-(3-methylphenyl)-1,3,4-thiadiazol-2-amine (165 mg, 0.86 mmol, 2 equiv) in DMF (2.0 mL) was added (benzotriazol-1-yloxy)tripyrrolidinophosphonium hexafluorophosphate (PYBOP, 448 mg, 0.86 mmol, 2 equiv) and diisopropylethylamine (0.38 mL, 2.15 mmol, 5 equiv). The resulting mixture was stirred at room temperature for 3 days, then triturated with ethanol and water and stirred for 15 minutes. The precipitate was collected by filtration and dried under reduced pressure. Purification by HPLC (method 2) yielded 6.0 mg (3% of theory) of the title compound.

$^1$H-NMR (300 MHz, DMSO-$d_6$): δ [ppm]=2.41 (s, 3H), 2.56-2.63 (m, 4H), 3.24 (s, 2H), 3.61-3.71 (m, 4H), 7.32-7.38 (m, 1H), 7.39-7.48 (m, 1H), 7.65 (dd, 1H), 7.73-7.84 (m, 2H), 8.02 (dd, 1H), 8.94 (d, 1H), 9.92 (s, 1H), 13.37 (s, 1H).

LC-MS (Method 3): $R_t$=0.79 min; MS (ESIpos): m/z=522 [M+H]$^+$.

Example 97

3-[(morpholin-4-ylacetyl)amino]-N-[5-(4-nitrophenyl)-1,3,4-thiadiazol-2-yl]-4-(trifluoromethoxy)benzamide

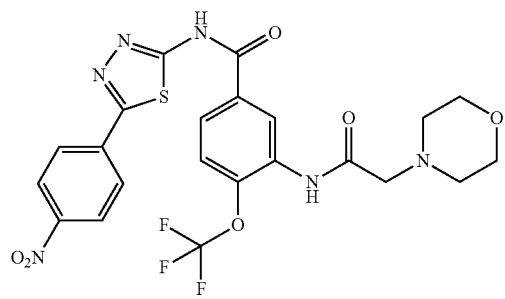 [SMILES: O=C(CN1CCOCC1)Nc1cc(C(=O)Nc2nnc(-c3ccc([N+](=O)[O-])cc3)s2)ccc1OC(F)(F)F]

To a solution of the compound of intermediate 21 (250 mg, 0.72 mmol) and 5-(4-nitrophenyl)-1,3,4-thiadiazol-2-amine (319 mg, 1.44 mmol, 2 equiv) in DMF (3.0 mL) was added (benzotriazol-1-yloxy)tripyrrolidinophosphonium hexafluorophosphate (PYBOP, 747 mg, 1.44 mmol, 2 equiv) and diisopropylethylamine (0.63 mL, 3.59 mmol, 5 equiv). The resulting mixture was stirred at room temperature over night, then triturated with ethanol and water and stirred for 15 minutes. The precipitate was collected by filtration and dried under reduced pressure. Purification by HPLC (method 2) yielded 34.8 mg (9% of theory) of the title compound.

$^1$H-NMR (400 MHz, DMSO-$d_6$): δ [ppm]=2.57-2.65 (m, 4H), 3.26 (s, 2H), 3.62-3.71 (m, 4H), 7.67 (dd, 1H), 8.04 (dd, 1H), 8.23-8.32 (m, 2H), 8.34-8.42 (m, 2H), 8.95 (d, 1H), 9.95 (s, 1H), 13.56 (s, 1H).

LC-MS (Method 4): $R_t$=1.16 min; MS (ESIpos): m/z=553 [M+H]$^+$.

Example 98

N-[5-(2-methylphenyl)-1,3,4-thiadiazol-2-yl]-3-[(morpholin-4-ylacetyl)amino]-4-(trifluoromethoxy)benzamide

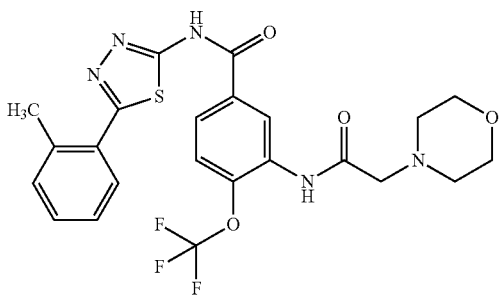 [SMILES: Cc1ccccc1-c1nnc(NC(=O)c2ccc(OC(F)(F)F)c(NC(=O)CN3CCOCC3)c2)s1]

To a solution of the compound of intermediate 21 (150 mg, 0.43 mmol) and 5-(2-methylphenyl)-1,3,4-thiadiazol-2-amine (165 mg, 0.86 mmol, 2 equiv) in DMF (2 mL) was added (benzotriazol-1-yloxy)tripyrrolidinophosphonium hexafluorophosphate (PYBOP, 448 mg, 0.86 mmol, 2 equiv) and diisopropylethylamine (0.38 mL, 2.15 mmol, 5 equiv). The resulting mixture was stirred at room temperature for 3 days, then triturated with ethanol and water and stirred for 15 minutes. The precipitate was collected by filtration and dried under reduced pressure. Purification by HPLC (method 2) yielded 10.3 mg (5% of theory) of the title compound.

$^1$H-NMR (500 MHz, DMSO-$d_6$): δ [ppm]=2.54 (s, 3H), 2.56-2.61 (m, 4H), 3.24 (s, 2H), 3.63-3.68 (m, 4H), 7.34-7.39 (m, 1H), 7.40-7.46 (m, 2H), 7.65 (d, 1H), 7.71 (d, 1H), 8.02 (dd, 1H), 8.95 (d, 1H), 9.93 (s, 1H), 13.34 (s, 1H).

LC-MS (Method 4): $R_t$=1.22 min; MS (ESIpos): m/z=522 [M+H]$^+$.

Example 99

N-[5-(4-fluorophenyl)-1,3,4-thiadiazol-2-yl]-3-[(morpholin-4-ylacetyl)amino]-4-(trifluoromethoxy)benzamide

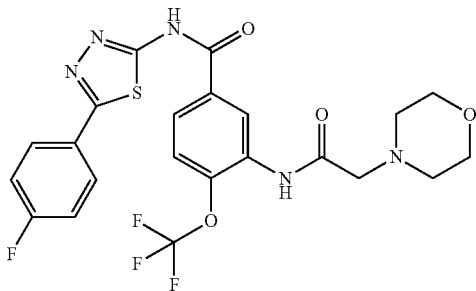 [SMILES: O=C(CN1CCOCC1)Nc1cc(C(=O)Nc2nnc(-c3ccc(F)cc3)s2)ccc1OC(F)(F)F]

To a solution of the compound of intermediate 21 (150 mg, 0.43 mmol) and 5-(4-fluorophenyl)-1,3,4-thiadiazol-2-amine (151 mg, 0.78 mmol, 1.8 equiv) in DMF (1.9 mL) was added (benzotriazol-1-yloxy)tripyrrolidinophosphonium hexafluorophosphate (PYBOP, 448 mg, 0.86 mmol, 2 equiv) and diisopropylethylamine (0.38 mL, 2.15 mmol, 5 equiv). The resulting mixture was stirred at room temperature over night. After filtration, purification by HPLC (method 2) yielded 133 mg (59% of theory) of the title compound.

$^1$H-NMR (400 MHz, DMSO-$d_6$): δ [ppm]=2.56-2.63 (m, 4H), 3.24 (s, 2H), 3.62-3.69 (m, 4H), 7.35-7.44 (m, 2H), 7.62-7.68 (m, 1H), 7.99-8.09 (m, 3H), 8.94 (d, 1H), 9.93 (s, 1H), 13.43 (s, 1H).

LC-MS (Method 3): $R_t$=0.77 min; MS (ESIpos): m/z=526 [M+H]$^+$.

Example 100

3-({[4-(2,2-difluoroethyl)piperazin-1-yl]acetyl}amino)-N-[6-(2-fluorophenyl)pyridin-3-yl]-4-(trifluoromethoxy)benzamide

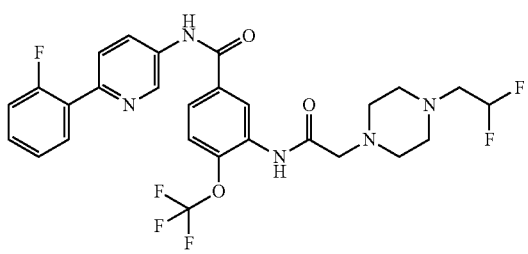 [SMILES: O=C(CN1CCN(CC(F)F)CC1)Nc1cc(C(=O)Nc2ccc(-c3ccccc3F)nc2)ccc1OC(F)(F)F]

To a suspension of 102 mg (0.22 mmol) of the compound of intermediate 14 in 1.3 mL of DMF were added 0.06 mL of triethylamine (0.44 mmol, 2 equiv), 0.06 mL of 1-(2,2-difluoroethyl)piperazine (0.44 mmol, 2 equiv), and 7.0 mg of potassium iodide (0.04 mmol, 0.2 equiv). The reaction mixture was stirred at room temperature over night. After filtration, purification by HPLC (method 2) yielded 71.3 mg (54% of theory) of the title compound.

$^1$H-NMR (300 MHz, DMSO-$d_6$): δ [ppm]=2.55-2.67 (m, 8H), 2.75 (dt, 2H), 3.22 (s, 2H), 6.14 (tt, 1H), 7.27-7.39 (m, 2H), 7.41-7.52 (m, 1H), 7.66 (dd, 1H), 7.79-7.90 (m, 2H), 7.91-8.01 (m, 1H), 8.30 (dd, 1H), 8.82 (d, 1H), 9.06 (d, 1H), 9.91 (s, 1H), 10.72 (s, 1H).

LC-MS (Method 3): $R_t$=1.37 min; MS (ESIpos): m/z=582 [M+H]$^+$.

Example 101

N-[5-(2-methoxyphenyl)-1,3,4-thiadiazol-2-yl]-3-{[(4-methylpiperazin-1-yl)acetyl]amino}-4-(trifluoromethoxy)benzamide

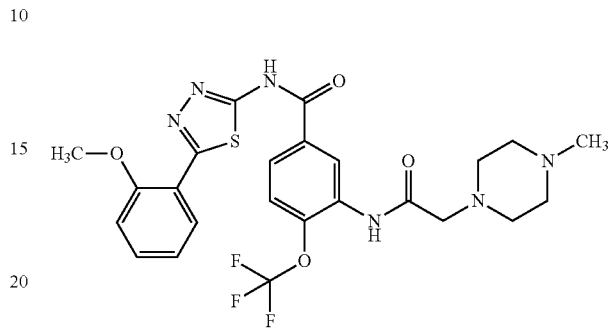

To a solution of the compound of intermediate 112 (150 mg, 0.32 mmol) and 5-(2-methoxyphenyl)-1,3,4-thiadiazol-2-amine (133 mg, 0.64 mmol, 2 equiv) in DMF (2 mL) was added (benzotriazol-1-yloxy)tripyrrolidinophosphonium hexafluorophosphate (PYBOP, 334 mg, 0.64 mmol, 2 equiv) and diisopropylethylamine (0.28 mL, 1.60 mmol, 5 equiv). The resulting mixture was stirred at room temperature over night, then triturated with 20 mL of a 9/1 mixture of water and ethanol. The precipitate was collected by filtration, washed with water and dried under reduced pressure at 50° C. The remaining material was triturated with 2 mL of DMSO. The precipitate was collected by filtration, washed with water and dried under reduced pressure at 50° C. 72 mg (40% of theory) of the title compound were obtained.

$^1$H-NMR (300 MHz, DMSO-$d_6$): δ [ppm]=2.21 (s, 3H), 2.32-2.47 (m, 4H), 2.56-2.69 (m, 4H), 3.23 (s, 2H), 4.04 (s, 3H), 7.15 (t, 1H), 7.29 (d, 1H), 7.50-7.57 (m, 1H), 7.64 (dd, 1H), 8.02 (dd, 1H), 8.30 (dd, 1H), 9.01 (d, 1H), 9.95 (s, 1H), 13.09 (s, 1H).

LC-MS (Method 3): $R_t$=0.78 min; MS (ESIpos): m/z=551 [M+H]$^+$.

Example 102

N-[5-(4-methylphenyl)-1,3,4-thiadiazol-2-yl]-3-{[(4-methylpiperazin-1-yl)acetyl]amino}-4-(trifluoromethoxy)benzamide

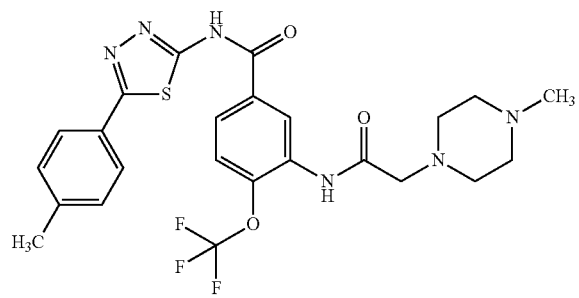 [SMILES: Cc1ccc(-c2nnc(NC(=O)c3ccc(OC(F)(F)F)c(NC(=O)CN4CCN(C)CC4)c3)s2)cc1]

To a solution of the compound of intermediate 112 (265 mg, 0.67 mmol) and 5-(4-methylphenyl)-1,3,4-thiadiazol-2- amine (255 mg, 1.33 mmol, 2 equiv) in DMF (3 mL) was added (benzotriazol-1-yloxy)tripyrrolidinophosphonium hexafluorophosphate (PYBOP, 693 mg, 1.33 mmol, 2 equiv) and diisopropylethylamine (0.58 mL, 3.33 mmol, 5 equiv). The precipitate was collected by filtration and dried under reduced pressure at 50° C. The remaining material was triturated with 2.5 mL of DMSO. The precipitate was collected by filtration and dried under reduced pressure at 50° C. 83.6 mg (23% of theory) of the title compound were obtained.

$^1$H-NMR (300 MHz, DMSO-d$_6$): δ [ppm]=2.28 (s, 3H), 2.38 (s, 3H), 2.47-2.58 (m, 4H), 2.60-2.70 (m, 4H), 3.25 (s, 2H), 7.32-7.38 (m, 2H), 7.63 (dd, 1H), 7.82-7.89 (m, 2H), 8.01 (dd, 1H), 8.96 (d, 1H), 9.93 (s, 1H), 12.85 (s, 1H).

LC-MS (Method 1): R$_t$=1.04 min; MS (ESIpos): m/z=535 [M+H]$^+$.

Example 103

4-methyl-3-({[1-(morpholin-4-yl)cyclopropyl]carbonyl}amino)-N-(5-phenyl-1,3,4-thiadiazol-2-yl)benzamide

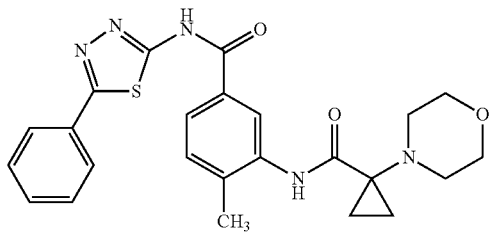 [SMILES: Cc1ccc(C(=O)Nc2nnc(-c3ccccc3)s2)cc1NC(=O)C1(N2CCOCC2)CC1]

To a solution of the compound of intermediate 82 (150 mg, 0.49 mmol) and 5-phenyl-1,3,4-thiadiazol-2-amine (105 mg, 0.59 mmol, 1.2 equiv) in DMF (1.8 mL) was added (benzotriazol-1-yloxy)tripyrrolidinophosphonium hexafluorophosphate (PYBOP, 513 mg, 0.99 mmol, 2 equiv) and diisopropylethylamine (0.34 mL, 1.97 mmol, 4 equiv). The resulting mixture was stirred at room temperature over night. (Benzotriazol-1-yloxy)tripyrrolidinophosphonium hexafluorophosphate (PYBOP, 513 mg, 0.99 mmol, 2 equiv) and diisopropylethylamine (0.34 mL, 1.97 mmol, 4 equiv) were added and the resulting mixture was stirred at room temperature over night. After filtration, purification by HPLC (1. method 2; 2. Waters Autopurification system, column: XBrigde C18 5 μm 100×30 mm, solvent: water/acetonitrile+0.2% ammonia (32%) gradient, rate: 70 mL/min, temperature: room temperature) yielded 5.5 mg (2% of theory) of the title compound.

$^1$H-NMR (300 MHz, DMSO-d$_6$): δ [ppm]=1.08-1.28 (m, 4H), 2.40 (s, 3H), 3.66-3.80 (m, 4H), 7.41 (d, 1H), 7.47-7.59 (m, 3H), 7.86 (dd, 1H), 7.91-8.01 (m, 2H), 8.62-8.71 (m, 1H), 10.11 (s, 1H), 13.10 (s, 1H).

LC-MS (Method 4): R$_t$=1.25 min; MS (ESIpos): m/z=464 [M+H]$^+$.

Example 104

3-{[(4-methylpiperazin-1-yl)acetyl]amino}-4-[(methylsulfonyl)methyl]-N-(5-phenyl-1,3,4-thiadiazol-2-yl)benzamide

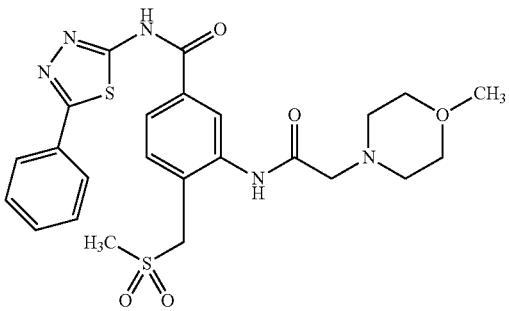

To a suspension of 150 mg (0.32 mmol) of the compound of intermediate 97 in 1.7 mL of DMF were added 0.09 mL of triethylamine (0.65 mmol, 2 equiv), 0.07 mL of 1-methylpiperazine (0.65 mmol, 2 equiv), and 11 mg of potassium iodide (0.07 mmol, 0.2 equiv). The reaction mixture was stirred at room temperature over night. After concentration, the remaining solids were then triturated with 10 mL of ethanol and 10 mL of water and stirred for 30 minutes. The precipitate was removed by filtration, washed with ethanol and dried under reduced pressure to yield 98.0 mg (55% of theory) of the title compound.

$^1$H-NMR (400 MHz, DMSO-d$_6$): δ [ppm]=2.30 (s, 3H), 2.55-2.71 (m, 8H), 3.05 (s, 3H), 3.19 (s, 2H), 4.66 (s, 2H), 7.51-7.57 (m, 3H), 7.63 (d, 1H), 7.95-7.99 (m, 2H), 8.01 (dd, 1H), 8.50 (d, 1H), 9.87 (s, 1H).

LC-MS (Method 4): R$_t$=0.84 min; MS (ESIpos): m/z=529 [M+H]$^+$.

Example 105 methyl 2-{[(4-methylpiperazin-1-yl)acetyl]amino}-4-[(5-phenyl-1,3,4-thiadiazol-2-yl)carbamoyl]benzoate

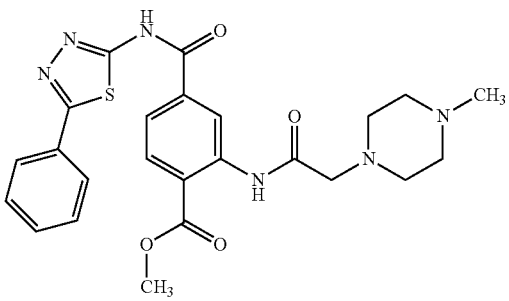 [SMILES: COC(=O)c1ccc(C(=O)Nc2nnc(-c3ccccc3)s2)cc1NC(=O)CN1CCN(C)CC1]

To a suspension of 2.00 g (4.64 mmol) of the compound of intermediate 99 in 25 mL of DMF were added 0.97 mL of triethylamine (6.96 mmol, 1.5 equiv), 0.77 mL of 1-methylpiperazine (6.96 mmol, 1.5 equiv), and 119 mg of potassium iodide (0.72 mmol, 0.16 equiv). The reaction mixture was stirred at room temperature over night, was then poured into 100 mL of a 5/1 mixture of ethanol and water and stirred for 15 minutes. The precipitate was removed by filtration, washed with water and dried under reduced pressure to yield 1.51 g (65% of theory) of the title compound.

$^1$H-NMR (300 MHz, DMSO-d$_6$): δ [ppm]=2.31 (s, 3H), 2.56-2.66 (m, 8H), 3.22 (s, 2H), 3.94 (s, 3H), 7.48-7.58 (m, 3H), 7.88-7.99 (m, 3H), 8.09 (d, 1H), 9.30 (d, 1H), 11.72 (s, 1H), 12.81 (s, 1H).

LC-MS (Method 3): R$_t$=0.71 min; MS (ESIpos): m/z=495 [M+H]$^+$.

Example 106 methyl 2-[(morpholin-4-ylacetyl)amino]-4-[(5-phenyl-1,3,4-thiadiazol-2-yl)carbamoyl]benzoate

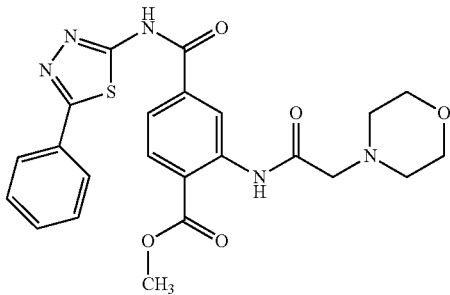 [SMILES: COC(=O)c1ccc(C(=O)Nc2nnc(-c3ccccc3)s2)cc1NC(=O)CN1CCOCC1]

To a suspension of 2.00 g (4.64 mmol) of the compound from intermediate 99 in 25 mL of DMF were added 0.97 mL of triethylamine (6.96 mmol, 1.5 equiv), 0.61 mL of morpholine (6.96 mmol, 1.5 equiv), and 119 mg of potassium iodide (0.72 mmol, 0.16 equiv). The reaction mixture was stirred at room temperature over night, was then poured into 100 mL of a 5/1 mixture of ethanol and water and stirred for 15 minutes. The precipitate was removed by filtration, washed with water and dried under reduced pressure to yield 1.44 g (59% of theory) of the title compound.

$^1$H-NMR (300 MHz, DMSO-d$_6$): δ [ppm]=2.54-2.61 (m, 4H), 3.21 (s, 2H), 3.70-3.78 (m, 4H), 3.94 (s, 3H), 7.47-7.57 (m, 3H), 7.88-8.00 (m, 3H), 8.09 (d, 1H), 9.32 (d, 1H), 11.84 (s, 1H), 13.48 (s, 1H).

LC-MS (Method 3): R$_t$=0.70 min; MS (ESIpos): m/z=482 [M+H]$^+$.

Example 107

N-(4-methoxy-3-{[2-(morpholin-4-yl)propanoyl]amino}phenyl)-2-phenyl-1,3-thiazole-5-carboxamide

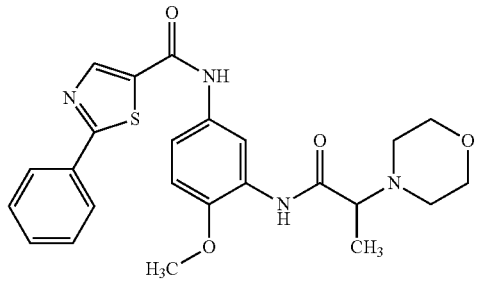 [SMILES: COc1ccc(NC(=O)c2cnc(-c3ccccc3)s2)cc1NC(=O)C(C)N1CCOCC1]

To a solution of the compound of intermediate 102 (169 mg, 407 μmol) in DMF (1.75 mL) were added morpholine (53.1 μL, 610 μmol), potassium iodide (10.5 mg, 63.0 μmol) and triethylamine (85.0 μL, 610 μmol). The mixture was stirred over night at room temperature. Water was added to the mixture and it was extracted three times with ethyl acetate. The combined organic layers were dried over MgSO$_4$ and concentrated in vacuum. The residue was purified by preparative HPLC (Methode 2) to yield the desired product 107 (11.7 mg, 6%).

$^1$H-NMR (300 MHz, DMSO-d$_6$): δ [ppm]=1.20 (d, 3H), 3.32 (m, 1H), 3.64-3.72 (m, 4H), 3.90 (s, 3H), 7.06 (d, 1H), 7.44-7.55 (m, 4H), 7.78-7.85 (m, 2H), 8.49 (s, 1H), 8.71 (d, 1H), 9.90 (s, 1H), 10.66 (s, 1H).

LC-MS (Method 4): R$_t$=1.05 min; MS (ESIpos): m/z=467 [M+H]$^+$.

Example 108

N-[3-({[1-(morpholin-4-yl)cyclopropyl]carbonyl}amino)-4-(trifluoromethoxy)phenyl]-2-phenyl-1,3-thiazole-5-carboxamide

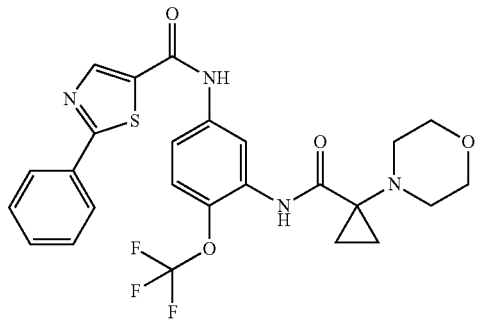 [SMILES: O=C(Nc1ccc(OC(F)(F)F)c(NC(=O)C2(N3CCOCC3)CC2)c1)c1cnc(-c2ccccc2)s1]

1-(Morpholin-4-yl)cyclopropanecarboxylic acid hydrochloride (intermediate 44, 67 mg, 324 μmol) was treated with diisopropylethylamine (188 μL, 1.08 mmol). Subsequently a solution of the compound of intermediate 104 (82 mg, 216 μmol) in DMF (1.5 mL) and (benzotriazol-1-yloxy) tripyrrolidinophosphonium hexafluorophosphate (PYBOP, 169 mg, 324 μmol) was added. The reaction mixture was stirred over night at 50° C. After cooling to room temperature additional 0.75 eq of diisopropylethylamine and 1.5 eq of 1-(morpholin-4-yl)cyclopropanecarboxylic acid hydrochloride were added. The mixture was stirred over night at 80° C. After cooling to room temperature 1.0 eq of diisopropylethylamine, 1.5 eq of 1-(morpholin-4-yl)cyclopropanecarboxylic acid hydrochloride and 1.5 eq of PYBOP were added. The mixture was again stirred at 50° C. over night. The reaction mixture was diluted with water and extracted three times with DCM. The combined organic layers were washed with brine, dried over a silicon filter and concentrated. The residue was purified by flash chromatography and additionally by preparative TLC to provide the desired compound 108 (12.5 mg, 10%).

$^1$H-NMR (300 MHz, DMSO-d$_6$): δ [ppm]=1.10-1.19 (m, 2H), 1.24-1.32 (m, 2H), 2.40-2.51 (m, 4H), 3.67-3.70 (m, 4H), 7.56 (d, 4H), 7.64-7.73 (m, 1H), 7.97-8.09 (m, 2H), 8.72 (s, 1H), 8.75-8.81 (m, 1H), 10.41-10.51 (m, 1H), 10.64-10.74 (m, 1H).

LC-MS (Method 4): R$_t$=1.43 min; MS (ESIpos): m/z=533 [M+H]$^+$.

Example 109

N-[6-(2-fluoro-4-hydroxyphenyl)pyridin-3-yl]-3-{[2-(morpholin-4-yl)propanoyl]amino}-4-(trifluoromethoxy)benzamide

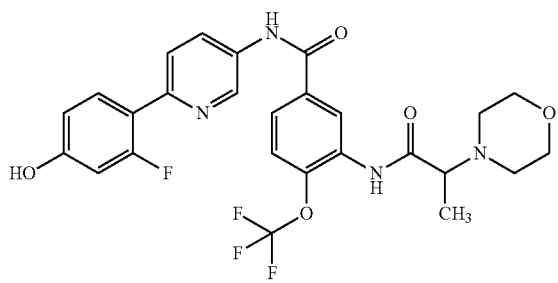 [SMILES: CC(C(=O)Nc1cc(C(=O)Nc2ccc(-c3ccc(O)cc3F)nc2)ccc1OC(F)(F)F)N1CCOCC1]

Argon was bubbled through a suspension of the compound of intermediate 109 (198 mg, 419 μmol), 2-fluoro-4-hydroxyphenylboronic acid (98.0 mg, 628 μmol) and potassium carbonate (116 mg, 837 μmol) in 1,2-dimethoxyethane (3.26 mL) and water (1.1 mL) for several minutes. Afterwards 1,1'-bis(diphenylphosphino)ferrocene-palladium(II)dichloride (153 mg, 209 μmol) was added to the mixture, the tube was sealed and the reaction mixture was stirred over night at 90° C. After cooling to room temperature, the mixture was diluted with water and extracted three times with ethyl acetate. The combined organic layers were washed with brine, dried over MgSO$_4$ and concentrated under reduced pressure. The residue was purified by preparative HPLC (Methode 2) to provide the title compound 109 (34.3 mg, 23%).

$^1$H-NMR (300 MHz, DMSO-d$_6$): δ [ppm]=1.23 (d, 3H), 2.56 (d, 4H), 3.37-3.48 (m, 1H), 3.65-3.67 (m, 4H), 6.68-6.81 (m, 2H), 7.66 (d, 1H), 7.86 (d, 1H), 8.05 (t, 1H), 8.22 (d, 1H), 8.35 (d, 1H), 8.75 (d, 1H), 9.00 (d, 1H), 10.06 (s, 1H), 10.81 (s, 1H), 14.28 (s, 1H).

LC-MS (Method 4): R$_t$=1.27 min; MS (ESIneg): m/z=547 [M−H]$^-$.

Example 110

N-[6-(3-fluoro-4-hydroxyphenyl)pyridin-3-yl]-3-{[2-(morpholin-4-yl)propanoyl]amino}-4-(trifluoromethoxy)benzamide

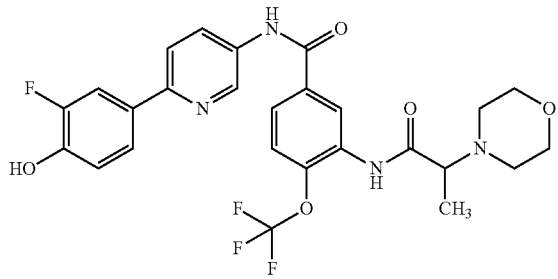 [SMILES: CC(C(=O)Nc1cc(C(=O)Nc2ccc(-c3ccc(O)c(F)c3)nc2)ccc1OC(F)(F)F)N1CCOCC1]

The title compound was prepared in a manner analogous to that described in example 109 starting from 198 mg (419 μmol) of intermediate 109 and 97.9 mg (628 μmol) of 3-fluoro-4-hydroxyphenylboronic acid. 32.2 mg (16%) of the desired compound 110 were obtained.

$^1$H-NMR (300 MHz, DMSO-d$_6$): δ [ppm]=1.23 (d, 3H), 2.53-2.60 (m, 4H), 3.35-3.47 (m, 1H), 3.65-3.67 (m, 4H), 6.93-7.08 (m, 1H), 7.20-7.44 (m, 1H), 7.62-7.68 (m, 1H), 7.72-7.77 (m, 1H), 7.82-1.93 (m, 3H), 8.15-8.26 (m, 1H), 8.73 (d, 1H), 8.93 (d, 1H), 10.03 (s, 1H), 10.63 (s, 1H).

LC-MS (Method 4): R$_t$=0.98 min; MS (ESIneg): m/z=547 [M−H]$^-$.

Example 111

N-[6-(4-aminophenyl)pyridin-3-yl]-3-{[2-(morpholin-4-yl)propanoyl]amino}-4-(trifluoromethoxy)benzamide

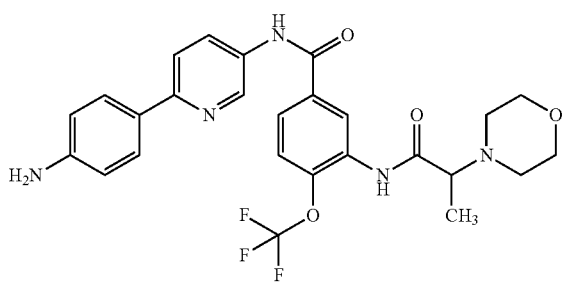 [SMILES: CC(C(=O)Nc1cc(C(=O)Nc2ccc(-c3ccc(N)cc3)nc2)ccc1OC(F)(F)F)N1CCOCC1]

Argon was bubbled through a suspension of the compound of intermediate 109 (210 mg, 444 μmol), 4-aminophenylboronic acid (91.2 mg, 666 μmol) and potassium carbonate (123 mg, 888 μmol) in 1,2-diethoxyethane (3.46 mL) and water (1.1 mL) for several minutes. Afterwards 1,1'-bis(diphenylphosphino)ferrocene-palladium(II)dichloride-DCM-complex (36.3 mg, 44 μmol) was added to the mixture, the tube was sealed and the reaction mixture was stirred over night at 90° C.

After cooling to room temperature, the mixture was diluted with water and extracted three times with ethyl acetate. The combined organic layers were washed with brine, dried over MgSO$_4$ and concentrated under reduced pressure. The residue was purified by preparative HPLC to provide the title compound 111 (30.8 mg, 13%).

$^1$H-NMR (300 MHz, DMSO-d$_6$): δ [ppm]=1.23 (d, 3H), 2.54-2.61 (m, 4H), 3.37-3.48 (m, 1H), 3.62-3.71 (m, 4H), 5.37 (s, 2H), 6.61-6.65 (m, 2H), 7.58-7.70 (m, 1H), 7.73-7.88 (m, 4H), 8.12-8.18 (m, 1H), 8.72 (s, 1H), 8.82-8.92 (m, 1H), 9.96-10.08 (m, 1H), 10.54 (s, 1H).

LC-MS (Method 4): R$_t$=0.82 min; MS (ESIneg): m/z=528 [M−H]$^-$.

Example 112

N-{6-[4-(difluoromethyl)phenyl]pyridin-3-yl}-3-{[2-(morpholin-4-yl)propanoyl]amino}-4-(trifluoromethoxy)benzamide

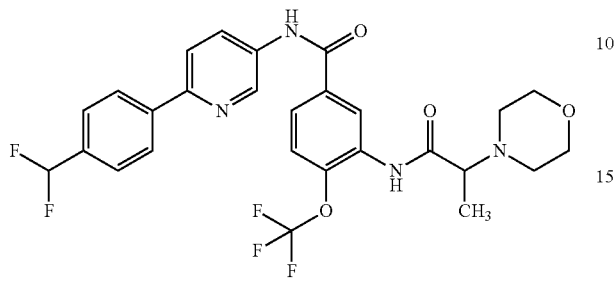

The title compound was prepared in a manner analogous to that described in example 111 starting from 197 mg (417 µmol) of the compound of intermediate 109 and 107 mg (626 µmol) of 4-difluoromethylphenylboronic acid. 29.7 mg (30%) of the desired compound 112 were obtained.

$^1$H-NMR (300 MHz, DMSO-d$_6$): δ [ppm]=1.23 (d, 3H), 2.54-2.58 (m, 4H), 3.36-3.49 (m, 1H), 3.65-3.68 (m, 4H), 7.10 (s, 1H), 7.63-7.70 (m, 3H), 7.82-7.91 (m, 1H), 8.09 (s, 1H), 8.22 (d, 2H), 8.29-8.36 (m, 1H), 8.75 (d, 1H), 9.04 (d, 1H), 10.04 (s, 1H), 10.72 (s, 1H).

LC-MS (Method 4): R$_t$=1.18 min; MS (ESIpos): m/z=563 [M−H]$^-$.

Example 113

N-[6-(4-acetamidophenyl)pyridin-3-yl]-3-{[2-(morpholin-4-yl)propanoyl]amino}-4-(trifluoromethoxy)benzamide

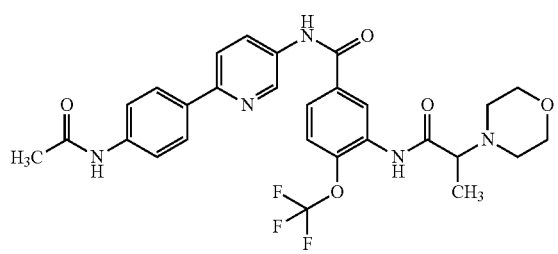 [SMILES: CC(=O)Nc1ccc(-c2ccc(NC(=O)c3ccc(OC(F)(F)F)c(NC(=O)C(C)N4CCOCC4)c3)cn2)cc1]

Argon was bubbled through a suspension of the compound of intermediate 109 (150 mg, 317 µmol), [4-(acetylamino)phenyl]boronic acid (85.2 mg, 476 µmol) and potassium carbonate (87.7 mg, 634 µmol) in 1,2-diethoxyethane (2.47 mL) and water (429 µL) for several minutes. Afterwards 1,1'-bis(diphenylphosphino)ferrocene-palladium(II) dichloride (116 mg, 159 µmol) was added to the mixture, the tube was sealed and the reaction mixture was stirred over night at 90° C. After cooling to room temperature, the mixture was filtered over a pad of Celite. The filtrate was concentrated in vacuum and the residue was purified by preparative HPLC (method 5) and preparative TLC to provide the title compound 113 (16.7 mg, 9.2%).

$^1$H-NMR (300 MHz, DMSO-d$_6$): δ [ppm]=1.23 (d, 3H), 2.07 (s, 3H), 2.54-2.59 (m, 4H), 3.36-3.45 (m, 1H), 3.65-3.68 (m, 4H), 7.61-7.72 (m, 3H), 7.81-7.88 (m, 1H), 7.91-7.95 (m, 1H), 7.98-8.05 (m, 2H), 8.21-8.27 (m, 1H), 8.71-8.76 (m, 1H), 8.93-8.98 (m, 1H), 10.00-10.08 (m, 2H), 10.61-10.69 (m, 1H).

LC-MS (Method 4): R$_t$=0.91 min; MS (ESIneg): m/z=570 [M−H]$^-$.

Example 114

N-{6-[4-(dimethylamino)phenyl]pyridin-3-yl}-3-{[2-(morpholin-4-yl)propanoyl]amino}-4-(trifluoromethoxy)benzamide

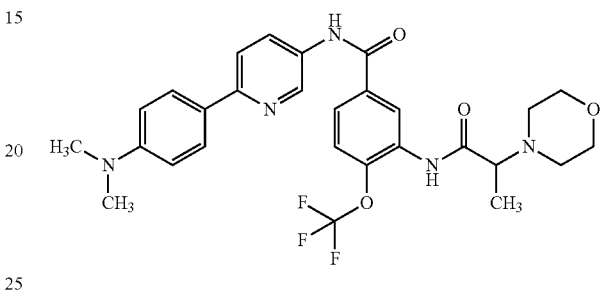

Argon was bubbled through a suspension of the compound of intermediate 109 (218 mg, 461 µmol), [4-(dimethylamino)phenyl]boronic acid (114 mg, 692 µmol) and potassium carbonate (191 mg, 1.38 mmol) in 1,2-dimethoxyethane (3.6 mL) and water (360 µL) for several minutes. Afterwards 1,1'-bis(diphenylphosphino)ferrocene-palladium(II)dichloride-DCM-complex (37.6 mg, 46 µmol) was added to the mixture, the tube was sealed and the reaction mixture was stirred over night at 90° C.

After cooling to room temperature, the mixture was concentrated under reduced pressure. The residue was purified by preparative HPLC (method 5) to provide the title compound 114 (134 mg, 230 µmol, 50%).

$^1$H-NMR (300 MHz, DMSO-d$_6$): δ [ppm]=1.23 (d, 3H), 2.52-2.61 (m, 4H), 2.97 (s, 6H), 3.39 (q, 1H), 3.65-3.68 (m, 4H), 6.77-6.82 (m, 2H), 7.45-7.70 (m, 1H), 7.82-7.86 (m, 2H), 7.91-7.94 (m, 2H), 8.14-8.24 (m, 1H), 8.73 (d, 1H), 8.89 (d, 1H), 10.04 (s, 1H), 10.58 (s, 1H).

LC-MS (Method 4): R$_t$=1.36 min; MS (ESIpos): m/z=558 [M+H]$^+$.

Example 115

N-{6-[4-(dimethylamino)phenyl]pyridin-3-yl}-3-{[(2S)-2-(morpholin-4-yl)propanoyl]amino}-4-(trifluoromethoxy)benzamide or N-{6-[4-(dimethylamino)phenyl]pyridin-3-yl}-3-{[(2R)-2-(morpholin-4-yl)propanoyl]amino}-4-(trifluoromethoxy)benzamide

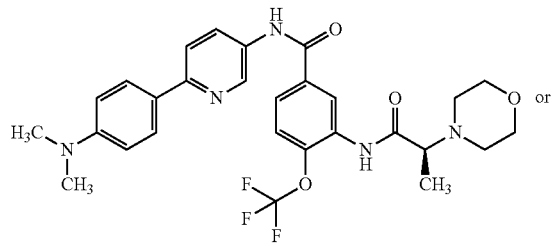

-continued

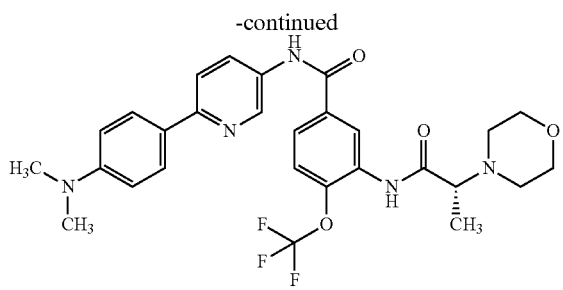

A sample of racemic N-{6-[4-(dimethylamino)phenyl]pyridin-3-yl}-3-{[2-(morpholin-4-yl)propanoyl]amino}-4-(trifluoromethoxy)benzamide (prepared as described in example 114, 70 mg, 126 µmol) was separated using chiral HPLC (system: Agilent Prep 1200, column: Chiralpak IC 5 µm 250×20 mm, solvent: hexane/ethyl acetate 50:50 (v/v)) to give the first eluting enantiomer of N-{6-[4-(dimethylamino)phenyl]pyridin-3-yl}-3-{[2-(morpholin-4-yl)propanoyl]amino}-4-(trifluoromethoxy)benzamide (16 mg, 21% from racemate).

$^1$H-NMR (300 MHz, DMSO-$d_6$): δ [ppm]=1.23 (d, 3H), 2.52-2.61 (m, 4H), 2.97 (s, 6H), 3.39 (q, 1H), 3.65-3.68 (m, 4H), 6.77-6.82 (m, 2H), 7.45-7.70 (m, 1H), 7.82-7.86 (m, 2H), 7.91-7.94 (m, 2H), 8.14-8.24 (m, 1H), 8.73 (d, 1H), 8.89 (d, 1H), 10.04 (s, 1H), 10.58 (s, 1H).

LC-MS (Method 4): $R_t$=1.36 min; MS (ESIpos): m/z=558 [M+H]$^+$.

Chiral HPLC (system: Waters Alliance 2695 DAD 996 ESA: Corona, column: Chiralpak IC 3 µm 100×4.6 mm, solvent: hexane/ethyl acetate 50:50 (v/v)): $R_t$=7.50 min, 97.8% enantiomeric excess.

Example 116

N-{6-[4-(dimethylamino)phenyl]pyridin-3-yl}-3-{[(2S)-2-(morpholin-4-yl)propanoyl]amino}-4-(trifluoromethoxy)benzamide or N-{6-[4-(dimethylamino)phenyl]pyridin-3-yl}-3-{[(2R)-2-(morpholin-4-yl)propanoyl]amino}-4-(trifluoromethoxy)benzamide

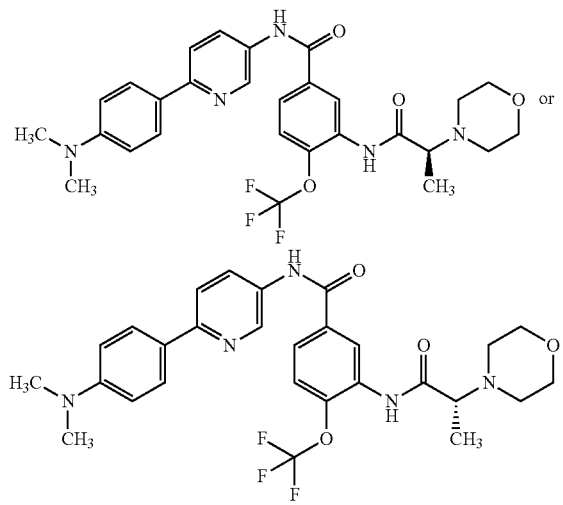

A sample of racemic N-{6-[4-(dimethylamino)phenyl]pyridin-3-yl}-3-{[2-(morpholin-4-yl)propanoyl]amino}-4-(trifluoromethoxy)benzamide (prepared as described in example 114, 70 mg, 126 µmol) was separated using chiral HPLC (system: Agilent Prep 1200, column: Chiralpak IC 5 µm 250×20 mm, solvent: hexane/ethyl acetate 50:50 (v/v)) to give the second eluting enantiomer of N-{6-[4-(dimethylamino)phenyl]pyridin-3-yl}-3-{[2-(morpholin-4-yl)propanoyl]amino}-4-(trifluoromethoxy)benzamide (12 mg, 16% from racemate).

$^1$H-NMR (300 MHz, DMSO-$d_6$): δ [ppm]=1.23 (d, 3H), 2.52-2.61 (m, 4H), 2.97 (s, 6H), 3.39 (q, 1H), 3.65-3.68 (m, 4H), 6.77-6.82 (m, 2H), 7.45-7.70 (m, 1H), 7.82-7.86 (m, 2H), 7.91-7.94 (m, 2H), 8.14-8.24 (m, 1H), 8.73 (d, 1H), 8.89 (d, 1H), 10.04 (s, 1H), 10.58 (s, 1H).

LC-MS (Method 4): $R_t$=1.36 min; MS (ESIpos): m/z=558 [M+H]$^+$.

Chiral HPLC (system: Waters Alliance 2695 DAD 996 ESA: Corona, column: Chiralpak IC 3 µm 100×4.6 mm, solvent: hexane/ethyl acetate 50:50 (v/v)): $R_t$=8.14 min, 91.8% enantiomeric excess.

Example 117

N-[6-(4-aminophenyl)pyridin-3-yl]-3-{[(2R)-2-(morpholin-4-yl)propanoyl]amino}-4-(trifluoromethoxy)benzamide or N-[6-(4-aminophenyl)pyridin-3-yl]-3-{[(2S)-2-(morpholin-4-yl)propanoyl]amino}-4-(trifluoromethoxy)benzamide

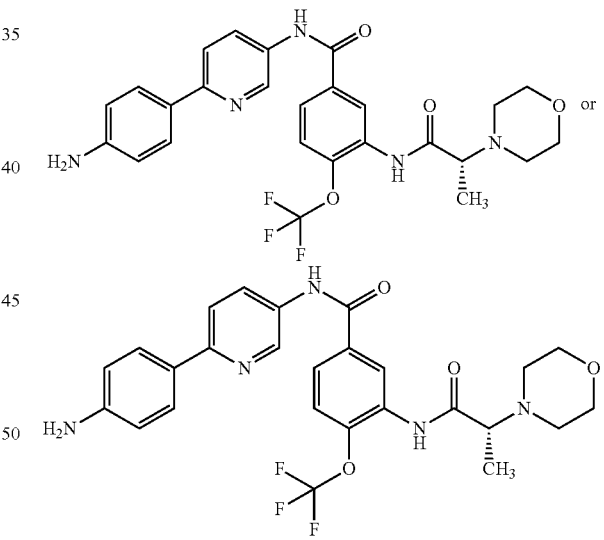

A sample of racemic N-[6-(4-aminophenyl)pyridin-3-yl]-3-{[2-(morpholin-4-yl)propanoyl]amino}-4-(trifluoromethoxy)benzamide (prepared as described in example 111, 111 mg, 209 µmol) was separated using chiral HPLC (system: Agilent Prep 1200, column: Chiralpak IC 5 µm 250×30 mm, solvent: ethanol/methanol/diethylamine 50:50:0.1 (v/v/v)) to give the first eluting enantiomer of N-[6-(4-aminophenyl)pyridin-3-yl]-3-{[2-(morpholin-4-yl)propanoyl]amino}-4-(trifluoromethoxy)benzamide (40 mg, 36% from racemate) which was purified again by preparative HPLC to obtain the desired pure enantiomer (18 mg, 16% from racemate).

¹H-NMR (300 MHz, DMSO-d₆): δ [ppm]=1.23 (d, 3H), 2.54-2.58 (m, 4H), 3.37-3.48 (m, 1H), 3.62-3.71 (m, 4H), 5.37 (s, 2H), 6.63 (d, 2H), 7.58-7.70 (m, 1H), 7.73-7.88 (m, 4H), 8.12-8.18 (m, 1H), 8.72 (s, 1H), 8.82-8.92 (m, 1H), 9.96-10.08 (m, 1H), 10.54 (s, 1H).

Optical rotation (Method 6): [α]=−4.1° (c=1.00, CHCl₃).

LC-MS (Method 4): R$_t$=0.82 min; MS (ESIneg): m/z=528 [M−H]⁻.

Chiral HPLC (system: Waters Alliance 2695 DAD 996 ESA: Corona, column: Chiralpak IC 3 μm 100×4.6 mm, solvent: ethanol/methanol/diethylamine 50:50:0.1 (v/v/v)): R$_t$=3.30 min, 93.4% enantiomeric excess.

Example 118

N-[6-(4-aminophenyl)pyridin-3-yl]-3-{[(2R)-2-(morpholin-4-yl)propanoyl]amino}-4-(trifluoromethoxy)benzamide or N-[6-(4-aminophenyl)pyridin-3-yl]-3-{[(2S)-2-(morpholin-4-yl)propanoyl]amino}-4-(trifluoromethoxy)benzamide

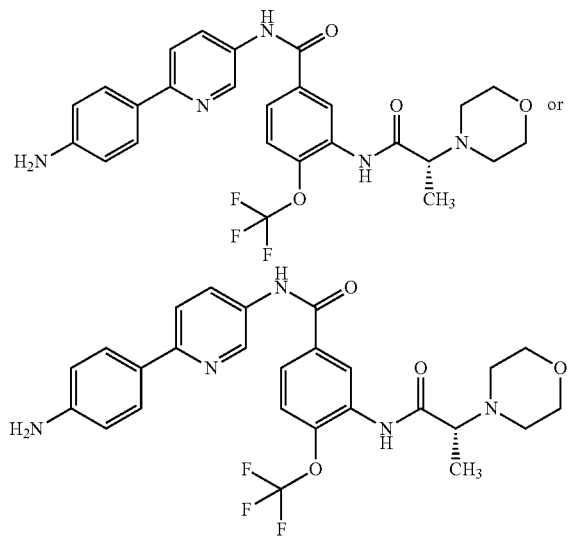

A sample of racemic N-[6-(4-aminophenyl)pyridin-3-yl]-3-{[2-(morpholin-4-yl)propanoyl]amino}-4-(trifluoromethoxy)benzamide (prepared as described in example 111, 111 mg, 209 μmol) was separated using chiral HPLC (system: Agilent Prep 1200, column: Chiralpak IC 5 μm 250×30 mm, solvent: ethanol/methanol/diethylamine 50:50: 0.1 (v/v/v)) to give the second eluting enantiomer of N-[6-(4-aminophenyl)pyridin-3-yl]-3-{[2-(morpholin-4-yl)propanoyl]amino}-4-(trifluoromethoxy)benzamide (38 mg, 34% from racemate) which was purified again by preparative HPLC (Method 2) to obtain the desired pure enantiomer (28 mg, 25% from racemate).

¹H-NMR (300 MHz, DMSO-d₆): δ [ppm]=1.23 (d, 3H), 2.54-2.58 (m, 4H), 3.37-3.48 (m, 1H), 3.62-3.71 (m, 4H), 5.37 (s, 2H), 6.63 (d, 2H), 7.58-7.70 (m, 1H), 7.73-7.88 (m, 4H), 8.12-8.18 (m, 1H), 8.72 (s, 1H), 8.82-8.92 (m, 1H), 9.96-10.08 (m, 1H), 10.54 (s, 1H).

Optical rotation (Method 6): [α]=+3.4° (c=1.00, CHCl₃).

LC-MS (Method 4): R$_t$=0.82 min; MS (ESIneg): m/z=528 [M−H]⁻.

Chiral HPLC (system: Waters Alliance 2695 DAD 996 ESA: Corona, column: Chiralpak IC 3 μm 100×4.6 mm, solvent: ethanol/methanol/diethylamine 50:50:0.1 (v/v/v)): R$_t$=4.85 min, 88.3% enantiomeric excess.

Example 119

N-{6-[4-(hydroxymethyl)phenyl]pyridin-3-yl}-3-{[(2S)-2-(morpholin-4-yl)propanoyl]amino}-4-(trifluoromethoxy)benzamide or N-{6-[4-(hydroxymethyl)phenyl]pyridin-3-yl}-3-{[(2R)-2-(morpholin-4-yl)propanoyl]amino}-4-(trifluoromethoxy)benzamide

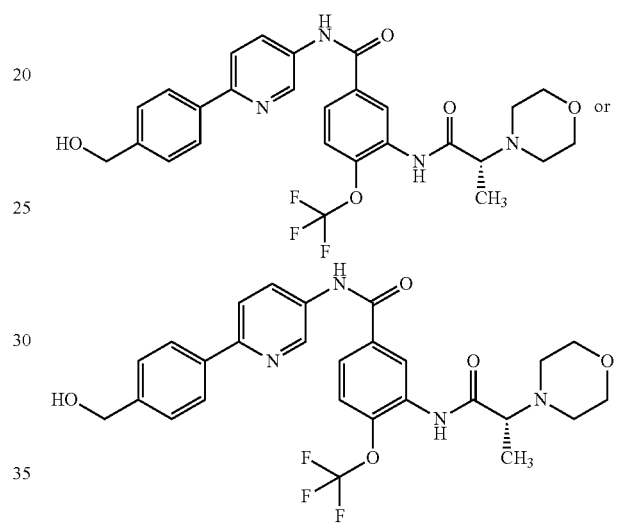

Argon was bubbled through a suspension of the compound of intermediate 109 (250 mg, 529 μmol), [4-(hydroxymethyl)phenyl]boronic acid (121 mg, 793 μmol) and potassium carbonate (146 mg, 1.06 mmol) in 1,2-diethoxyethane (4.12 mL) and water (714 μL) for several minutes. Afterwards 1,1'-bis(diphenylphosphino)ferrocene-palladium(II)dichloride (193 mg, 264 μmol) was added to the mixture, the tube was sealed and the reaction mixture was stirred over night at 90° C. After cooling to room temperature, the mixture was filtered over a pad of Celite. The filtrate was concentrated in vacuum and the residue was purified by preparative HPLC (method 5) to provide the racemic title compound (52.6 mg, 18.3%). The racemic mixture was separated using chiral HPLC (system: Agilent Prep 1200, column: Chiralpak IC 5 μm 250×30 mm, solvent: ethanol/methanol/diethylamine 50:50:0.1 (v/v/v)) to give the first eluting enantiomer of N-{6-[4-(hydroxymethyl)phenyl]pyridin-3-yl}-3-{[2-(morpholin-4-yl)propanoyl]amino}-4-(trifluoromethoxy)benzamide (14 mg, 27% from racemate).

¹H-NMR (300 MHz, DMSO-d₆): δ [ppm]=1.23 (d, 3H), 2.54-2.58 (m, 4H), 3.41 (q, 1H), 3.65-3.68 (m, 4H), 4.55 (s, 2H), 5.08-5.48 (m, 1H), 7.41-7.44 (m, 2H), 7.65 (d, 1H), 7.84 (d, 1H), 7.94-8.11 (m, 3H), 8.27 (dd, 1H), 8.74 (d, 1H), 8.98 (d, 1H), 10.05 (s, 1H), 10.69 (s, 1H).

Optical rotation (Method 6): [α]=−3.1° (c=1.00, CHCl₃).

LC-MS (Method 4): R$_t$=0.91 min; MS (ESIpos): m/z=543 [M−H]⁻.

Chiral HPLC (system: Waters Alliance 2695 DAD 996 ESA: Corona, column: Chiralpak IC 3 μm 100×4.6 mm, solvent: ethanol/methanol/diethylamine 50:50:0.1 (v/v/v)): $R_t$=4.11 min, 100% enantiomeric excess.

Example 120

N-{6-[4-(hydroxymethyl)phenyl]pyridin-3-yl}-3-{[(2S)-2-(morpholin-4-yl)propanoyl]amino}-4-(trifluoromethoxy)benzamide or N-{6-[4-(hydroxymethyl)phenyl]pyridin-3-yl}-3-{[(2R)-2-(morpholin-4-yl)propanoyl]amino}-4-(trifluoromethoxy)benzamide

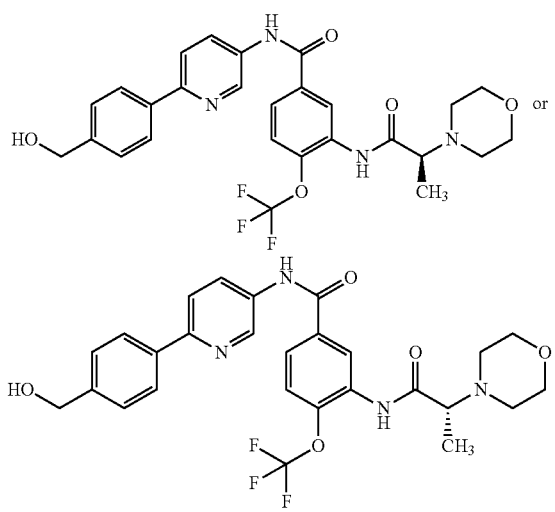

Argon was bubbled through a suspension of the compound of intermediate 109 (250 mg, 529 µmol), [4-(hydroxymethyl)phenyl]boronic acid (121 mg, 793 µmol) and potassium carbonate (146 mg, 1.06 mmol) in 1,2-diethoxyethane (4.12 mL) and water (714 µL) for several minutes. Afterwards 1,1'-bis(diphenylphosphino)ferrocene-palladium(II)dichloride (193 mg, 264 µmol) was added to the mixture, the tube was sealed and the reaction mixture was stirred over night at 90° C. After cooling to room temperature, the mixture was filtered over a pad of Celite. The filtrate was concentrated in vacuum and the residue was purified by preparative HPLC (Method 5) to provide the racemic title compound (52.6 mg, 18.3%). The racemic mixture was separated using chiral HPLC (system: Agilent Prep 1200, column: Chiralpak IC 5 µm 250×30 mm, solvent: ethanol/methanol/diethylamine 50:50:810.1 (v/v/v)) to give the second eluting enantiomer of N-{6-[4-(hydroxymethyl)phenyl]pyridin-3-yl}-3-{[2-(morpholin-4-yl)propanoyl]amino}-4-(trifluoromethoxy)benzamide (14 mg, 27% from racemate).

¹H-NMR (300 MHz, DMSO-$d_6$): δ [ppm]=1.23 (d, 3H), 2.54-2.58 (m, 4H), 3.41 (q, 1H), 3.65-3.68 (m, 4H), 4.55 (s, 2H), 5.08-5.48 (m, 1H), 7.41-7.44 (m, 2H), 7.65 (d, 1H), 7.84 (d, 1H), 7.94-8.11 (m, 3H), 8.27 (dd, 1H), 8.74 (d, 1H), 8.98 (d, 1H), 10.05 (s, 1H), 10.69 (s, 1H).

Optical rotation (Method 6): [α]=+0.2° (c=1.00, CHCl₃).
LC-MS (Method 4): $R_t$=0.91 min; MS (ESIneg): m/z=543 [M−H]⁻.
Chiral HPLC (system: Waters Alliance 2695 DAD 996 ESA: Corona, column: Chiralpak IC 3 µm 100×4.6 mm, solvent: ethanol/methanol/diethylamine 50:50:0.1 (v/v/v)): $R_t$=5.43 min, 94.9% enantiomeric excess.

Example 121

N-{3-[(morpholin-4-ylacetyl)amino]-4-(trifluoromethoxy)phenyl}-5-phenyl-1,2,4-oxadiazole-3-carboxamide

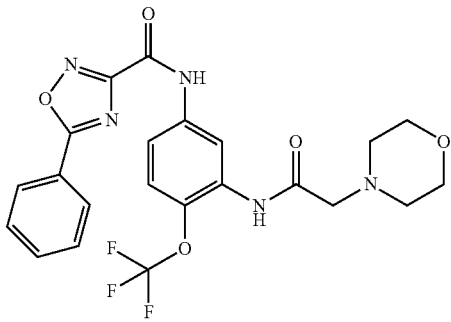 [SMILES: O=C(CN1CCOCC1)Nc1cc(NC(=O)c2noc(-c3ccccc3)n2)ccc1OC(F)(F)F]

To a solution of the compound of intermediate 32 (150 mg, 470 µmol) and 5-phenyl-1,2,4-oxadiazole-3-carboxylic acid (98.3 mg, 517 µmol) in DMF (3.0 mL) were added (benzotriazol-1-yloxy)tripyrrolidinophosphonium hexafluorophosphate (PYBOP, 367 mg, 705 µmol) and N,N-diisopropylethylamine (245 µL, 1.41 mmol). The reaction mixture was stirred over night at 60° C. After cooling to room temperature the mixture was poured into water. The resulting precipitate was collected by filtration, washed with water and dried at 60° C. under reduced pressure. After purification by preparative HPLC (Method 2) the titled compound 121 was obtained (21.6 mg, 9%).

¹H-NMR (300 MHz, DMSO-$d_6$): δ [ppm]=2.53-2.62 (m, 4H), 3.21 (s, 2H), 3.56-3.71 (m, 4H), 7.43-7.56 (m, 1H), 7.63-7.83 (m, 4H), 8.17-8.29 (m, 2H), 8.76 (s, 1H), 9.83 (m, 1H), 11.22 (m, 1H).
LC-MS (Method 4): $R_t$=1.10 min; MS (ESIpos): m/z=492 [M+H]⁺.

Example 122

3-[(morpholin-4-ylacetyl)amino]-N-(2-phenyl-1,3-thiazol-5-yl)-4-(trifluoromethoxy)benzamide

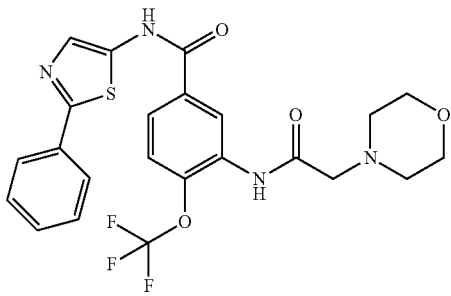 [SMILES: O=C(CN1CCOCC1)Nc1cc(C(=O)Nc2cnc(-c3ccccc3)s2)ccc1OC(F)(F)F]

To a solution of the compound of intermediate 21 (200 mg, 459 µmol) and 2-phenyl-1,3-thiazol-5-amine (98.3 mg, 517 µmol) in DMF (1.8 mL) were added (benzotriazol-1-yloxy)tripyrrolidinophosphonium hexafluorophosphate (PYBOP, 359 mg, 689 µmol) and N,N-diisopropylethylamine (240 µL, 1.34 mmol). The reaction mixture was stirred over night at room temperature. The mixture was poured

245 into water. The resulting precipitate was collected by filtration, washed with water and dried at 60° C. under reduced pressure. The resulting crude product was purified by crystallization from DMSO to obtain the title compound 122 (109 mg, 47%).

$^1$H-NMR (300 MHz, DMSO-d$_6$): δ [ppm]=2.55-2.62 (m, 4H), 3.24 (s, 2H), 3.57-3.69 (m, 4H), 7.42-7.52 (m, 3H), 7.68 (d, 1H), 7.82 (s, 1H), 7.87-7.94 (m, 3H), 8.83 (s, 1H), 9.94 (br. s, 1H), 11.99 (s, 1H).

LC-MS (Method 4): R$_t$=1.15 min; MS (ESIpos): m/z=507 [M+H]$^+$.

Example 123

1-methyl-N-{3-[(morpholin-4-ylacetyl)amino]-4-(trifluoromethoxy)phenyl}-5-phenyl-1H-pyrazole-3-carboxamide

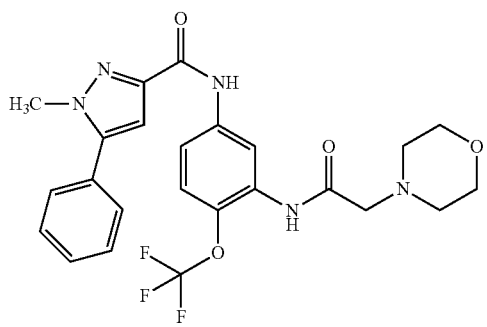 [SMILES: Cn1nc(C(=O)Nc2ccc(OC(F)(F)F)c(NC(=O)CN3CCOCC3)c2)cc1-c1ccccc1]

A solution of the compound of intermediate 32 (150 mg, 470 μmol) and 1-methyl-5-phenyl-1H-pyrazole-3-carboxylic acid (114 mg, 564 μmol) in DMF (3.0 mL) was treated with a 50% solution of 2,4,6-tripropyl-1,3,5,2,4,6-trioxatriphosphinane 2,4,6-trioxide (T3P) in DMF (164 μL, 1.41 mmol) and N,N-diisopropylethylamine (245 μL, 1.41 mmol). The reaction mixture was stirred for 3 d at room temperature and over night at 90° C. After cooling to room temperature the same amounts of T3P and N,N-diisopropylethylamine were added to the mixture again and it was stirred additionally for 16 h at 90° C. After cooling the mixture was poured into water and extracted three times with ethyl acetate. The combined organic layers were washed with brine, dried and concentrated in vacuum. The residue was purified by preparative HPLC (method 2) to obtain the title compound 123 (16.8 mg, 7%).

$^1$H-NMR (300 MHz, DMSO-d$_6$): δ [ppm]=2.51-2.62 (m, 4H), 3.19 (s, 2H), 3.58-3.71 (m, 4H), 3.97 (s, 3H), 6.94 (s, 1H), 7.38-7.72 (m, 7H), 8.76 (d, 1H), 9.76 (s, 1H), 10.36 (s, 1H).

LC-MS (Method 4): R$_t$=1.12 min; MS (ESIpos): m/z=504 [M+H]$^+$.

246
Example 124

N-{3-[(morpholin-4-ylacetyl)amino]-4-(trifluoromethoxy)phenyl}-5-phenyl-1H-pyrazole-3-carboxamide

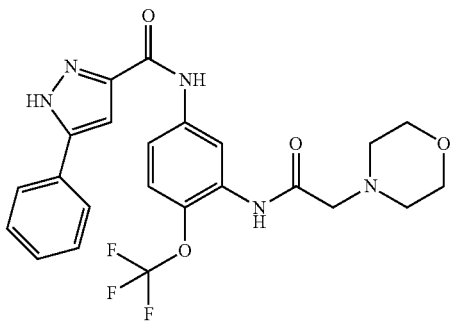 [SMILES: O=C(CN1CCOCC1)Nc1cc(NC(=O)c2cc(-c3ccccc3)[nH]n2)ccc1OC(F)(F)F]

A solution of the compound of intermediate 32 (150 mg, 470 μmol) and 5-phenyl-1H-pyrazole-3-carboxylic acid (106 mg, 564 μmol) in DMF (3.0 mL) was treated with a 50% solution of 2,4,6-tripropyl-1,3,5,2,4,6-trioxatriphosphinane 2,4,6-trioxide (T3P) in DMF (164 μL, 1.41 mmol) and N,N-diisopropylethylamine (245 μL, 1.41 mmol). The mixture was stirred for 24 h at room temperature and over night at 90° C. After cooling to room temperature the same amounts of T3P and N,N-diisopropylethylamine were added to the mixture again and it was additionally stirred for 16 h at 90° C. After cooling the mixture was poured into water. The resulting suspension was stirred for some minutes; the precipitate was collected by filtration and was washed several times with water. After drying, the crude product was crystallized from methanol to give the final product (81.9 mg, 35%).

$^1$H-NMR (500 MHz, DMSO-d$_6$): δ [ppm]=2.55-2.61 (m, 4H), 3.21 (s, 2H), 3.63-3.68 (m, 4H), 7.23 (br. s, 1H), 7.35-7.50 (m, 4H), 7.72 (d, 1H), 7.84 (d, 2H), 8.74 (br. s, 1H), 9.78 (br. s, 1H), 10.36 (br. s, 1H), 13.81 (br. s, 1H).

LC-MS (Method 1): R$_t$=1.04 min; MS (ESIpos): m/z=490 [M+H]$^+$.

Example 125

3-[(morpholin-4-ylacetyl)amino]-N-(3-phenyl-1,2,4-oxadiazol-5-yl)-4-(trifluoromethoxy)benzamide

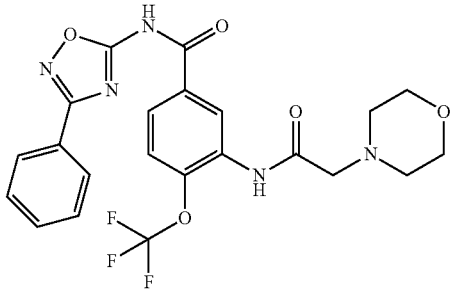 [SMILES: O=C(CN1CCOCC1)Nc1cc(C(=O)Nc2nc(-c3ccccc3)no2)ccc1OC(F)(F)F]

To a solution of the compound of intermediate 21 (200 mg, 459 μmol) and 3-phenyl-1,2,4-oxadiazol-5-amine (107 mg, 643 μmol) in DMF (1.8 mL) were added (benzotriazol- 1-yloxy)tripyrrolidinophosphonium hexafluorophosphate (PYBOP, 359 mg, 689 µmol) and N,N-diisopropylethylamine (240 µL, 1.34 mmol). The reaction mixture was stirred over night at room temperature. The mixture was poured into water. The resulting precipitate was collected by filtration, washed with water and dried at 60° C. under reduced pressure to yield the title compound 125 (53.8 mg, 24%).

$^1$H-NMR (400 MHz, DMSO-d$_6$): δ [ppm]=2.55-2.62 (m, 4H), 3.23 (s, 2H), 3.58-3.69 (m, 4H), 7.53-7.61 (m, 3H), 7.65 (s, 1H), 7.88-7.93 (m, 1H), 7.99-8.01 (m, 2H), 8.84 (d, 1H), 9.92 (s, 1H), 12.84 (m, 1H).

LC-MS (Method 4): R$_t$=1.04 min; MS (ESIpos): m/z=492 [M+H]$^+$.

Example 126

N-[6-(4-aminophenyl)pyridin-3-yl]-3-[(morpholin-4-ylacetyl)amino]-4-(trifluoromethoxy)benzamide

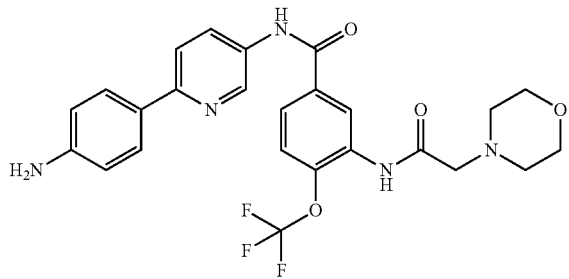 [SMILES: Nc1ccc(-c2ccc(NC(=O)c3ccc(OC(F)(F)F)c(NC(=O)CN4CCOCC4)c3)cn2)cc1]

The title compound was prepared in a manner analogous to that described in example 111 starting from 150 mg (327 µmol) of the compound of intermediate 110 and 67.2 mg (626 µmol) of 4-aminophenylboronic acid. To work up the reaction, the mixture was poured into water. The resulting precipitate was collected by filtration and subsequently purified by preparative HPLC (method 5) to yield 8.2 mg (20 µmol, 5%) of the desired compound 126.

$^1$H-NMR (400 MHz, DMSO-d$_6$): δ [ppm]=2.55-2.66 (m, 4H), 3.23 (s, 2H), 3.57-3.71 (m, 4H), 5.37 (s, 2H), 6.61-6.64 (m, 2H), 7.59-7.68 (m, 1H), 7.73-7.88 (m, 4H), 8.08-8.18 (m, 1H), 8.77 (d, 1H), 8.86 (d, 1H), 9.91 (s, 1H), 10.54 (s, 1H).

LC-MS (Method 1): R$_t$=0.82 min; MS (ESIpos): m/z=516 [M+H]$^+$.

Example 127

N-[5-(2-fluorophenyl)-1,3,4-thiadiazol-2-yl]-3-[(morpholin-4-ylacetyl)amino]-4-(trifluoromethoxy)benzamide

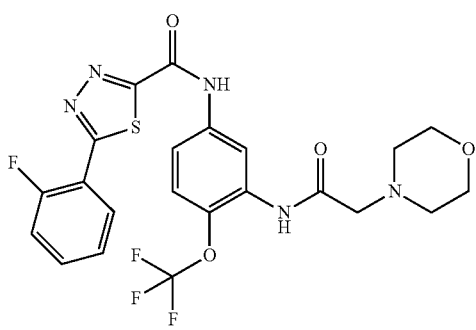 [SMILES: O=C(CN1CCOCC1)Nc1cc(NC(=O)c2nnc(-c3ccccc3F)s2)ccc1OC(F)(F)F]

The title compound was prepared in a manner analogous to that described in example 125 starting from 500 mg (1.43 mmol) of the compound of intermediate 21 and 392 mg (2.01 mmol) of 5-(2-fluorophenyl)-1,3,4-thiadiazol-2-amine to obtain 340 mg (45%) of the desired compound 127.

$^1$H-NMR (300 MHz, DMSO-d$_6$): δ [ppm]=2.55-2.63 (m, 4H), 3.24 (s, 2H), 3.61-3.71 (m, 4H), 7.40-7.52 (m, 2H), 7.58-7.70 (m, 2H), 8.04 (dd, 1H), 8.28 (d, 1H), 8.95 (d, 1H), 9.94 (s, 1H), 13.47 (m, 1H).

LC-MS (Method 4): R$_t$=1.15 min; MS (ESIpos): m/z=526 [M+H]$^+$.

Example 128

3-{[2-(morpholin-4-yl)propanoyl]amino}-N-(5-phenyl-1,3,4-thiadiazol-2-yl)-4-(trifluoromethyl)benzamide

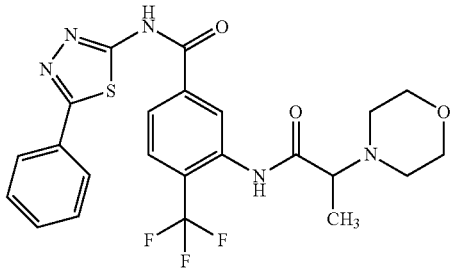 [SMILES: CC(C(=O)Nc1cc(C(=O)Nc2nnc(-c3ccccc3)s2)ccc1C(F)(F)F)N1CCOCC1]

Triethylamine was added to a solution of the compound of intermediate 111 (250 mg, 550 µmol), morpholine (72 µL, 824 µmol) and potassium iodide (14.1 mg, 85.2 µmol). The reaction mixture was stirred for 36 h at 50° C. After cooling to room temperature the same amounts of morpholine and potassium iodide were added again. The mixture was stirred over night at 90° C. After cooling to room temperature the mixture was poured into water. The aqueous phase was extracted three times with a mixture of DCM/isopropanol 8:2. The combined organic layers were washed with brine, dried over MgSO$_4$ and its volume was reduced under reduced pressure. The precipitate was removed by filtration. The filtrate was concentrated and the remaining residue was purified by preparative HPLC (method 5) yielding the desired compound 128 (53.4 mg, 101 µmol, 18%).

$^1$H-NMR (300 MHz, DMSO-d$_6$): δ [ppm]=1.25 (d, 3H), 2.52-2.59 (m, 4H), 3.38 (q, 1H), 3.65-3.68 (m, 4H), 7.52-7.57 (m, 3H), 7.91-8.02 (m, 3H), 8.07 (s, 1H), 8.82 (s, 1H), 10.07 (s, 1H), 13.55 (m, 1H).

LC-MS (Method 3): R$_t$=0.79 min; MS (ESIpos): m/z=506 [M+H]$^+$.

Example 129

3-{[2-(4-methylpiperazin-1-yl)propanoyl]amino}-N-(5-phenyl-1,3,4-thiadiazol-2-yl)-4-(trifluoromethyl)benzamide

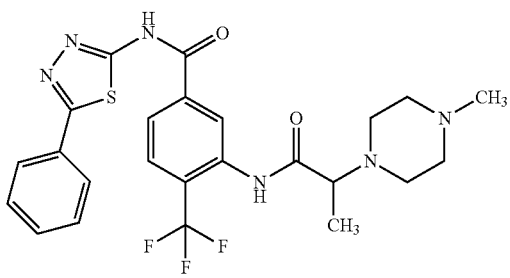 [SMILES: CC(C(=O)Nc1cc(C(=O)Nc2nnc(-c3ccccc3)s2)ccc1C(F)(F)F)N1CCN(C)CC1]

The title compound was prepared in a manner analogous to that described in example 128 starting from 250 mg (550 µmol) of the compound of intermediate 111 and 82.6 mg (824 µmol) of 1-methylpiperazine to obtain 57.1 mg (19%) of the desired compound 129.

$^1$H-NMR (300 MHz, DMSO-d$_6$): δ [ppm]=1.24 (d, 3H), 2.36 (s, 3H), 2.58-2.70 (m, 8H), 3.44 (q, 1H), 7.58-7.48 (m, 3H), 7.90 (d, 1H), 7.93-7.96 (m, 2H), 8.09 (d, 1H), 8.75 (s, 1H), 9.97 (s, 1H), 12.37 (s, br. 1H).

LC-MS (Method 3): R$_t$=0.78 min; MS (ESIpos): m/z=519 [M+H]$^+$.

Example 130

N-{4-methoxy-3-[(morpholin-4-ylacetyl)amino]phenyl}-5-phenyl-1,3,4-thiadiazole-2-carboxamide

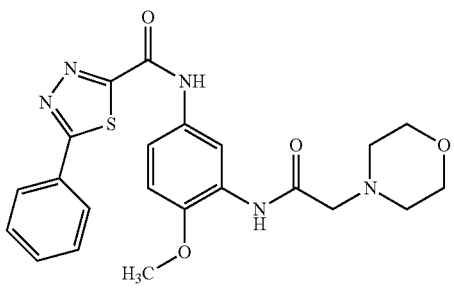 [SMILES: COc1ccc(NC(=O)c2nnc(-c3ccccc3)s2)cc1NC(=O)CN1CCOCC1]

The title compound was prepared in a manner analogous to that described in example 125 starting from 200 mg (154 µmol) of the compound of intermediate 36 and 171 mg (829 µmol) of 5-phenyl-1,3,4-thiadiazole-2-carboxylic acid to obtain 262 mg (520 µmol, 69%) of the desired compound 130.

$^1$H-NMR (300 MHz, DMSO-d$_6$): δ [ppm]=2.53-2.60 (m, 4H), 3.16 (s, 2H), 3.60-3.75 (m, 4H), 3.90 (s, 3H), 7.09 (d, 1H), 7.46-7.66 (m, 4H), 8.08-8.11 (m, 2H), 8.73 (d, 1H), 9.76 (s, 1H), 11.17 (s, 1H).

LC-MS (Method 4): R$_t$=0.92 min; MS (ESIpos): m/z=454 [M+H]$^+$.

Example 131

3-[(morpholin-4-ylacetyl)amino]-N-(5-phenylpyridin-2-yl)-4-(trifluoromethoxy)benzamide

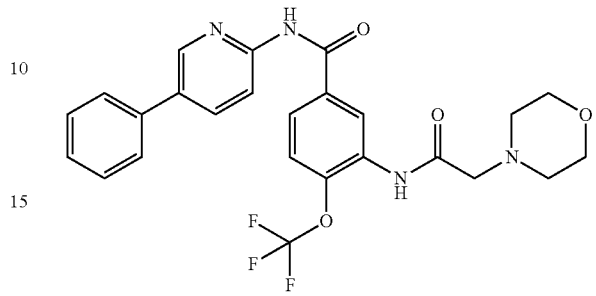

To a solution of intermediate 21 (150 mg, 431 µmol) and 5-phenylpyridin-2-amine (103 mg, 603 µmol) in DMF (1.66 mL) was added (benzotriazol-1-yloxy)tripyrrolidinophosphonium hexafluorophosphate (PYBOP, 336 mg, 646 µmol) and diisopropylethylamine (225 µL, 1.29 mmol). The resulting mixture was stirred at 50° C. over night. After cooling to room temperature the reaction mixture was poured into water. The aqueous phase was extracted three times with a mixture of DCM/isopropanol 8:2. The combined organic layers were dried over MgSO$_4$ and the solvent was removed under reduced pressure. The residue was purified by preparative HPLC (eluent: acetonitrile/water+0.1% HCOOH, gradient) to obtain the desired product 131 (60.3 mg, 28%).

$^1$H-NMR (300 MHz, DMSO-d$_6$): δ [ppm]=2.55-2.62 (m, 4H), 3.23 (s, 2H), 3.61-3.70 (m, 4H), 7.37-7.45 (m, 1H), 7.45-7.55 (m, 2H), 7.56-7.63 (m, 1H), 7.72-7.79 (m, 2H), 7.88-7.95 (m, 1H), 8.20 (s, 1H), 8.26 (s, 1H), 8.73 (d, 1H), 8.83 (d, 1H), 9.90 (s, 1H), 11.09 (s, 1H).

LC-MS (Method 1): R$_t$=1.16 min; MS (ESIneg): m/z=499 [M−H]$^-$.

Example 132

3-{[(4-methylpiperazin-1-yl)acetyl]amino}-N-(5-phenylpyridin-2-yl)-4-(trifluoromethoxy)benzamide formiate

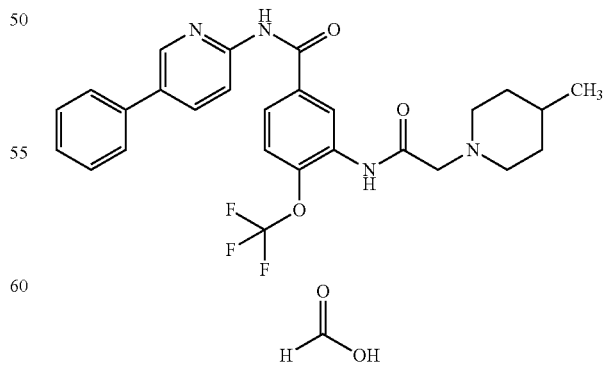

The title compound was prepared in a manner analogous to that described in example 131 starting from 150 mg (415 µmol) of the compound of intermediate 112 and 99.0 mg (581 µmol) of 5-phenylpyridin-2-amine to obtain 8.20 mg (3%) of the desired compound 132.

¹H-NMR (300 MHz, DMSO-$d_6$): δ [ppm]=2.72-2.84 (m, 4H), 3.38 (s, 3H), 7.35-7.60 (m, 5H), 7.73-7.77 (m, 2H), 7.98 (dd, 1H), 8.11-8.31 (m, 2H), 8.59 (s, 1H), 8.73 (d, 1H), 9.38 (br. s, 1H), 9.80 (s, 1H), 11.06 (s, 1H).

LC-MS (Method 4): $R_t$=1.03 min; MS (ESIpos): m/z=514 [M−HCOOH+H]⁺.

Example 133

4-(cyclopropyloxy)-N-[6-(2-fluorophenyl)pyridin-3-yl]-3-[(morpholin-4-ylacetyl)amino]benzamide

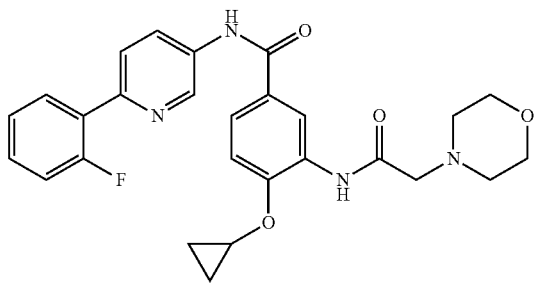 [SMILES: O=C(CN1CCOCC1)Nc1cc(C(=O)Nc2ccc(-c3ccccc3F)nc2)ccc1OC1CC1]

60 mg (0.17 mmol) of 3-amino-4-(cyclopropyloxy)-N-[6-(2-fluorophenyl)pyridin-3-yl]benzamide (intermediate 116) were dissolved in 3 mL of anh DMF. 28.8 mg (0.20 mmol) of morpholin-4-ylacetic acid, 86 µL (0.50 mmol) of N-ethyl-N-isopropylpropan-2-amine and 111.7 mg (0.22 mmol) of PYBOP were added. It was stirred for 3 h at 40° C. It was concentrated and the residue was purified by HPLC (method 5) yielding 47 mg (57%) of the title compound.

¹H-NMR (300 MHz, DMSO-$d_6$): δ [ppm]=0.72-0.82 (m, 2H), 0.88-0.97 (m, 2H), 2.52-2.58 (m, 4H), 3.16 (s, 2H), 3.61-3.71 (m, 4H), 4.07-4.16 (m, 1H), 7.26-7.38 (m, 2H), 7.41-7.51 (m, 2H), 7.75-7.86 (m, 2H), 7.91-8.00 (m, 1H), 8.26-8.33 (m, 1H), 8.80 (d, 1H), 9.05 (d, 1H), 9.70 (s, 1H), 10.49 (s, 1H).

LC-MS (Method 3): $R_t$=1.23 min; MS (ESIpos): m/z=491 [M+H]⁺.

Example 134

4-(cyclopropyloxy)-N-[6-(2-fluorophenyl)pyridin-3-yl]-3-({[1-(morpholin-4-yl)cyclopropyl]carbonyl}amino)benzamide

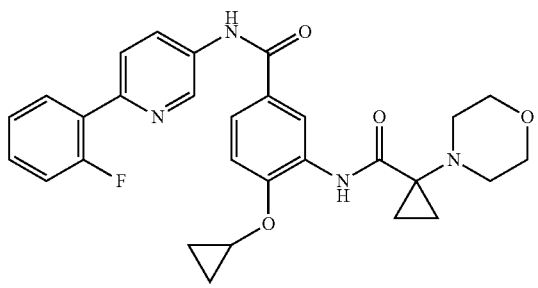 [SMILES: O=C(Nc1ccc(-c2ccccc2F)nc1)c1ccc(OC2CC2)c(NC(=O)C2(N3CCOCC3)CC2)c1]

70 mg (0.19 mmol) of 3-amino-4-(cyclopropyloxy)-N-[6-(2-fluorophenyl)pyridin-3-yl]benzamide (intermediate 116) were dissolved in 3.5 mL of anh DMF. 48.0 mg (0.23 mmol) of 1-(morpholin-4-yl)cyclopropanecarboxylic acid hydrochloride (intermediate 44), 134 µL (0.77 mmol) of N-ethyl-N-isopropylpropan-2-amine and 130.3 mg (0.25 mmol) of PYBOP were added. It was stirred for 3 h at 40° C. and for 5 h at 50° C. It was concentrated and the residue was purified by HPLC (Waters Autopurification system SOD; column: YMC-Triart C18 5µ 100×30 mm; eluent A: water+0.1% vol. formic acid (99%), eluent B: acetonitrile; gradient: 0-0.50 min 30% B, 25 mL/min; 0.51-5.5 min 60-85% B, 70 mL/min; temperature: room temperature) yielding 37.5 mg (37%) of the title compound.

¹H-NMR (300 MHz, DMSO-$d_6$): δ [ppm]=0.76-0.86 (m, 2H), 0.91-1.00 (m, 2H), 1.07-1.16 (m, 2H), 1.16-1.25 (m, 2H), 2.39-2.45 (m, 4H), 3.67-3.76 (m, 4H), 4.10-4.18 (m, 1H), 7.27-7.37 (m, 2H), 7.41-7.51 (m, 2H), 7.74-7.83 (m, 2H), 7.91-7.99 (m, 1H), 8.29 (dd, 1H), 8.89 (d, 1H), 9.05 (d, 1H), 10.45-10.52 (m, 2H).

LC-MS (Method 3): $R_t$=1.34 min; MS (ESIpos): m/z=517 [M+H]⁺.

Example 135

4-(cyclopropyloxy)-N-[6-(2-fluorophenyl)pyridin-3-yl]-3-({[1-(4-methylpiperazin-1-yl)cyclopropyl]carbonyl}amino)benzamide

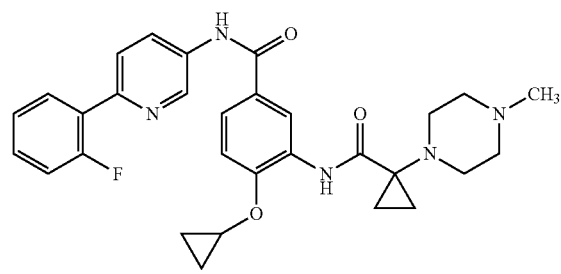 [SMILES: CN1CCN(C2(C(=O)Nc3cc(C(=O)Nc4ccc(-c5ccccc5F)nc4)ccc3OC3CC3)CC2)CC1]

70 mg (0.19 mmol) of 3-amino-4-(cyclopropyloxy)-N-[6-(2-fluorophenyl)pyridin-3-yl]benzamide (intermediate 116) were dissolved in 3.5 mL of anh DMF. 42.6 mg (0.23 mmol) of 1-(4-methylpiperazin-1-yl)cyclopropanecarboxylic acid hydrochloride (intermediate 42), 101 µL (0.58 mmol) of N-ethyl-N-isopropylpropan-2-amine and 130.3 mg (0.25 mmol) of PYBOP were added. It was stirred for 3 h at 40° C. and for 5 h at 50° C. It was concentrated and the residue was purified by HPLC (Waters Autopurification system SOD; column: YMC-Triart C18 5µ 100×30 mm; eluent A: water+0.2% vol. ammonia (32%), eluent B: acetonitrile; gradient: 0-0.50 min 25% B, 25 mL/min; 0.51-5.5 min 50-70% B, 70 mL/min; temperature: room temperature) affording 15.5 mg (14%) of the title compound.

¹H-NMR (300 MHz, DMSO-$d_6$): δ [ppm]=0.76-0.86 (m, 2H), 0.91-1.00 (m, 2H), 1.07-1.16 (m, 2H), 1.16-1.25 (m, 2H), 2.39-2.45 (m, 4H), 3.67-3.76 (m, 4H), 4.10-4.18 (m, 1H), 7.27-7.37 (m, 2H), 7.41-7.51 (m, 2H), 7.74-7.83 (m, 2H), 7.91-7.99 (m, 1H), 8.29 (dd, 1H), 8.89 (d, 1H), 9.05 (d, 1H), 10.45-10.52 (m, 2H).

LC-MS (Method 3): $R_t$=1.32 min; MS (ESIpos): m/z=530 [M+H]⁺.

Example 136

4-(cyclopropyloxy)-3-({[1-(4-cyclopropylpiperazin-1-yl)cyclopropyl]carbonyl}amino)-N-[6-(2-fluorophenyl)pyridin-3-yl]benzamide

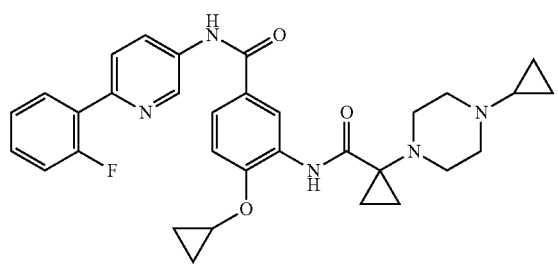 [SMILES: O=C(Nc1ccc(-c2ccccc2F)nc1)c1ccc(OC2CC2)c(NC(=O)C2(N3CCN(C4CC4)CC3)CC2)c1]

70 mg (0.19 mmol) of 3-amino-4-(cyclopropyloxy)-N-[6-(2-fluorophenyl)pyridin-3-yl]benzamide (intermediate 116) were dissolved in 3.5 mL of anh DMF. 48.6 mg (0.23 mmol) of 1-(4-cyclopropylpiperazin-1-yl)cyclopropanecarboxylic acid hydrochloride (intermediate 43), 101 µL (0.58 mmol) of N-ethyl-N-isopropylpropan-2-amine and 130.3 mg (0.25 mmol) of PYBOP were added. It was stirred for 3 h at 40° C. It was concentrated and the residue was purified by HPLC (Waters Autopurification system SOD; column: XBridge C18 5µ 100×30 mm; eluent A: water+0.2% vol. ammonia (32%), eluent B: acetonitrile; gradient: 0-0.50 min 24% B, 25 mL/min; 0.51-5.5 min 48-86% B, 70 mL/min; temperature: room temperature) affording 15.5 mg (14%) of the title compound.

$^1$H-NMR (300 MHz, DMSO-d$_6$): δ [ppm]=0.26-0.34 (m, 2H), 0.41-0.50 (m, 2H), 0.83-1.01 (m, 4H), 1.03-1.21 (m, 4H), 1.62-1.71 (m, 1H), 2.32-2.44 (m, 4H), 2.60-2.77 (m, 4H), 4.10-4.19 (m, 1H), 7.27-7.37 (m, 2H), 7.41-7.51 (m, 2H), 7.72-7.84 (m, 2H), 7.91-8.00 (m, 1H), 8.28 (dd, 1H), 8.92 (d, 1H), 9.05 (d, 1H), 10.43-10.54 (m, 2H).

LC-MS (Method 3): R$_t$=1.47 min; MS (ESIpos): m/z=556 [M+H]$^+$.

Example 137

3-{[(3,4-dimethylpiperazin-1-yl)acetyl]amino}-N-[6-(2-fluorophenyl)pyridin-3-yl]-4-(trifluoromethoxy)benzamide

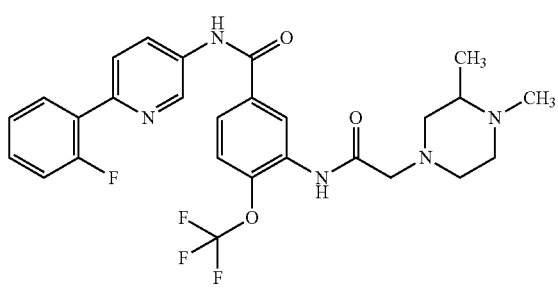 [SMILES: CC1CN(CC(=O)Nc2cc(C(=O)Nc3ccc(-c4ccccc4F)nc3)ccc2OC(F)(F)F)CCN1C]

100 mg (0.19 mmol) of 3-[(chloroacetyl)amino]-N-[6-(2-fluorophenyl)pyridin-3-yl]-4-(trifluoromethoxy)benzamide (intermediate 14) were dissolved in 1 mL of anh DMF. 94 µL (0.67 mmol) of N,N-diethylethanamine, 54 mg (0.29 mmol) of 1,2-dimethylpiperazine dihydrochloride, and 5 mg (0.03 mmol) of potassium iodide were added. It was stirred for 2 h at rt and over night at 50° C. It was concentrated and the residue was purified by HPLC (method 5) giving 19.5 mg (16%) of the title compound.

$^1$H-NMR (300 MHz, DMSO-d$_6$): δ [ppm]=0.96 (d, 3H), 1.99-2.11 (m, 2H), 2.13-2.29 (m, 4H), 2.33-2.43 (m, 1H), 2.67-2.82 (m, 3H), 3.18 (s, 2H), 7.26-7.38 (m, 2H), 7.41-7.52 (m, 1H), 7.61-7.70 (m, 1H), 7.77-7.88 (m, 2H), 7.90-8.00 (m, 1H), 8.24-8.33 (m, 1H), 8.84 (s, 1H), 9.05 (s, 1H), 9.92 (s, 1H), 10.71 (s, 1H).

LC-MS (Method 3): R$_t$=1.38 min; MS (ESIpos): m/z=546 [M+H]$^+$.

Example 138

N-[6-(2-fluorophenyl)pyridin-3-yl]-4-(methylsulfanyl)-3-[(morpholin-4-ylacetyl)amino]benzamide

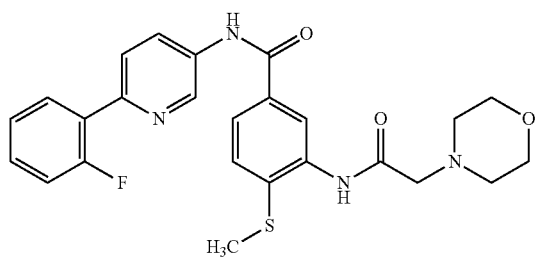 [SMILES: CSc1ccc(C(=O)Nc2ccc(-c3ccccc3F)nc2)cc1NC(=O)CN1CCOCC1]

6.61 g (18.70 mmol) of 3-amino-N-[6-(2-fluorophenyl)pyridin-3-yl]-4-(methylsulfanyl)benzamide (intermediate 118), 3.095 g (21.32 mmol) of morpholin-4-ylacetic acid and 14.794 g (28.43 mmol) of PYBOP were dissolved in 178 mL of anh DMF. 4.64 mL (26.65 mmol) of N-ethyl-N-isopropylpropan-2-amine were added. It was stirred at 55° C. over night. 1 g (1.92 mmol) of PYBOP was added and it was stirred for 2 h at 55° C. The reaction mixture was allowed to reach rt. It was combined with a 1 g batch. It was poured into water. The solid material was filtered off and was triturated with a little EtOAc under heating. The solid material was filtered off. The solid material was crystallized from methanol/EtOAc 8:2 obtaining 5.5 g (53%) of the title compound.

$^1$H-NMR (400 MHz, DMSO-d$_6$): δ [ppm]=2.56 (s, 3H), 2.58-2.62 (m, 4H), 3.20 (s, 2H), 3.67-3.73 (m, 4H), 7.28-7.35 (m, 2H), 7.43-7.49 (m, 1H), 7.56 (d, 1H), 7.79-7.84 (m, 2H), 7.93-7.98 (m, 1H), 8.30 (dd, 1H), 8.55 (d, 1H), 9.06 (d, 1H), 9.87 (s, 1H), 10.57 (s, 1H).

LC-MS (Method 4): R$_t$=1.00 min; MS (ESIpos): m/z=481 [M+H]$^+$.

Example 139

N-[6-(2-fluorophenyl)pyridin-3-yl]-4-(methylsulfonyl)-3-[(morpholin-4-ylacetyl)amino]benzamide

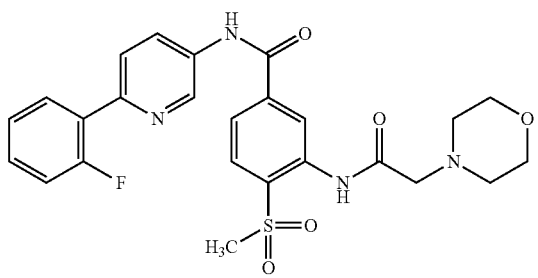 [SMILES: CS(=O)(=O)c1ccc(C(=O)Nc2ccc(-c3ccccc3F)nc2)cc1NC(=O)CN1CCOCC1]

200 mg (0.42 mmol) of N-[6-(2-fluorophenyl)pyridin-3-yl]-4-(methylsulfanyl)-3-[(morpholin-4-ylacetyl)amino]benzamide and 256 mg (0.83 mmol) of Oxone® were suspended in 7 mL of methanol. 2 mL of water were added and it was stirred for 3 h at rt. 256 mg (0.83 mmol) of Oxone® were added and it was stirred over night at rt. The solid material was filtered off and washed with a lot of water. The aqueous filtrate was extracted three times with dichloromethane. The extract and the solid residue were combined and concentrated. The residue was triturated with methanol. The solid residue was filtered off. The filtrate was concentrated, dissolved in dichloromethane and washed with saturated aqueous sodium hydrogen sulfite solution. The organic layer was concentrated and purified by HPLC (method 5) to yield 20.1 mg (9%) of the title compound.

$^1$H-NMR (400 MHz, DMSO-$d_6$): δ [ppm]=2.57-2.62 (m, 4H), 3.23 (s, 2H), 3.35 (s, 3H), 3.67-3.72 (m, 4H), 7.29-7.36 (m, 2H), 7.43-7.50 (m, 1H), 7.82-7.86 (m, 1H), 7.90 (dd, 1H), 7.93-7.99 (m, 1H), 8.06 (d, 1H), 8.31 (dd, 1H), 9.06 (d, 1H), 9.08 (d, 1H), 10.84 (s, 1H), 11.03 (s, 1H).

LC-MS (Method 4): $R_t$=0.85 min; MS (ESIpos): m/z=513 [M+H]$^+$.

Example 140

4-(cyclopropyloxy)-3-({[1-(dimethylamino)cyclopropyl]carbonyl}amino)-N-[6-(2-fluorophenyl)pyridin-3-yl]benzamide

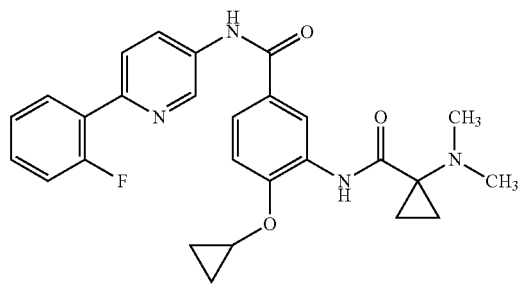 [SMILES: CN(C)C1(C(=O)Nc2cc(C(=O)Nc3ccc(-c4ccccc4F)nc3)ccc2OC2CC2)CC1]

70 mg (0.19 mmol) of 3-amino-4-(cyclopropyloxy)-N-[6-(2-fluorophenyl)pyridin-3-yl]benzamide (intermediate 116), 29.9 mg (0.23 mmol) of 1-(dimethylamino)cyclopropanecarboxylic acid, 130.3 mg (0.25 mmol) of PYBOP and 101 µL (0.58 mmol) of N-ethyl-N-isopropylpropan-2-amine in 3.5 mL of anh DMF were stirred 5 h at 50° C. The reaction mixture was concentrated and purified by HPLC (Waters Autopurification system SQD; column: YMC-Triart C18 5µ 100×30 mm; eluent A: water+0.1% vol. formic acid (99%), eluent B: acetonitrile; gradient: 0-0.50 min 29% B, 25 mL/min; 0.51-5.5 min 58-82% B, 70 mL/min; temperature: room temperature) to obtain 16 mg (17%) of the title compound.

$^1$H-NMR (300 MHz, DMSO-$d_6$): δ [ppm]=0.70-0.78 (m, 2H), 0.85-0.94 (m, 2H), 1.05-1.16 (m, 4H), 2.24 (s, 6H), 4.10-4.19 (m, 1H), 7.27-7.37 (m, 2H), 7.40-7.51 (m, 2H), 7.73-7.84 (m, 2H), 7.90-8.00 (m, 1H), 8.25-8.32 (m, 1H), 8.78 (d, 1H), 9.05 (d, 1H), 10.22 (s, 1H), 10.48 (s, 1H).

LC-MS (Method 3): $R_t$=1.43 min; MS (ESIpos): m/z=475 [M+H]$^+$.

Example 141

4-(cyclopropyloxy)-N-[6-(2-fluorophenyl)pyridin-3-yl]-3-[(1H-pyrazol-1-ylacetyl)amino]benzamide

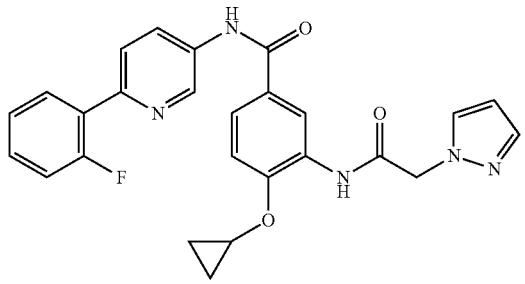 [SMILES: O=C(Cn1cccn1)Nc1cc(C(=O)Nc2ccc(-c3ccccc3F)nc2)ccc1OC1CC1]

70 mg (0.19 mmol) of 3-amino-4-(cyclopropyloxy)-N-[6-(2-fluorophenyl)pyridin-3-yl]benzamide (intermediate 116), 29.2 mg (0.23 mmol) of 1H-pyrazol-1-ylacetic acid, 130.3 mg (0.25 mmol) of PYBOP and 101 µL (0.58 mmol) of N-ethyl-N-isopropylpropan-2-amine in 3.5 mL of anh DMF were stirred for 5 h at 50° C. The reaction mixture was concentrated and purified by HPLC (Waters Autopurification system SOD; column: YMC-Triart C18 5µ 100×30 mm; eluent A: water+0.1% vol. formic acid (99%), eluent B: acetonitrile; gradient: 0-0.50 min 24% B, 25 mL/min; 0.51-5.5 min 48-66% B, 70 mL/min; temperature: room temperature) to yield 33 mg (36%) of the title compound.

$^1$H-NMR (300 MHz, DMSO-$d_6$): δ [ppm]=0.70-0.78 (m, 2H), 0.83-0.91 (m, 2H), 4.01-4.09 (m, 1H), 5.13 (s, 2H), 6.33 (t, 1H), 7.27-7.37 (m, 2H), 7.41-7.50 (m, 2H), 7.55 (d, 1H), 7.76-7.86 (m, 3H), 7.90-7.99 (m, 1H), 8.25-8.31 (m, 1H), 8.62 (d, 1H), 9.03 (d, 1H), 9.26 (s, 1H), 10.48 (s, 1H).

LC-MS (Method 3): $R_t$=1.20 min; MS (ESIpos): m/z=472 [M+H]$^+$.

Example 142

4-tert-butyl-N-[6-(2-fluorophenyl)pyridin-3-yl]-3-{[2-(morpholin-4-yl)propanoyl]amino}benzamide

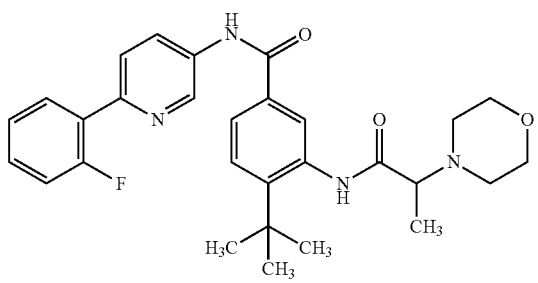 [SMILES: CC(C(=O)Nc1cc(C(=O)Nc2ccc(-c3ccccc3F)nc2)ccc1C(C)(C)C)N1CCOCC1]

To 350 mg (0.77 mmol) of 4-tert-butyl-3-[(2-chloropropanoyl)amino]-N-[6-(2-fluorophenyl)pyridin-3-yl]benzamide (intermediate 122) in 2.5 mL of anh DMF were added 400 µL (4.62 mmol) of morpholine, 322 µL (2.31 mmol) of N,N-diethylethanamine and 64 mg (0.39 mmol) of potassium iodide. It was stirred over night at rt. 100 µL (1.16 mmol) of morpholine and 32 mg (0.19 mmol) of potassium iodide were added. It was stirred for 28 h at 50° C. The reaction was allowed to reach rt and poured into water. It was extracted three times with EtOAc. The combined organic phases were dried over sodium sulfate and concentrated. The residue was purified by HPLC (method 2) and silica gel chromatography (hexane/EtOAc 1:1 to EtOAc) providing 23 mg (6%) of the title compound.

$^1$H-NMR (300 MHz, DMSO-$d_6$): δ [ppm]=1.22 (d, 3H), 1.40 (s, 9H), 2.51-2.65 (m, 4H), 3.28-3.37 (m, 1H, with water signal), 3.58-3.68 (m, 4H), 7.25-7.34 (m, 2H), 7.39-7.48 (m, 1H), 7.53 (d, 1H), 7.74-7.81 (m, 2H), 7.89-7.96 (m, 1H), 8.13 (d, 1H), 8.26 (dd, 1H), 9.03 (d, 1H), 9.50 (s, 1H), 10.51 (s, 1H).

LC-MS (Method 4): $R_t$=1.12 min; MS (ESIpos): m/z=505 [M+H]$^+$.

Example 143

4-tert-butyl-3-{[2-(morpholin-4-yl)propanoyl]amino}-N-(5-phenyl-1,3-thiazol-2-yl)benzamide

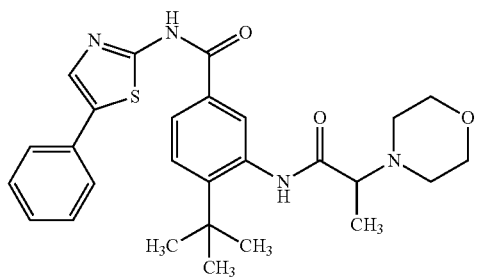 [SMILES: CC(C(=O)Nc1cc(C(=O)Nc2ncc(-c3ccccc3)s2)ccc1C(C)(C)C)N1CCOCC1]

To 663 mg (1.50 mmol) of 4-tert-butyl-3-[(2-chloropropanoyl)amino]-N-(5-phenyl-1,3-thiazol-2-yl)benzamide (intermediate 125) in 4.9 mL of anh DMF were added 523 µL (6.00 mmol) of morpholine, 627 µL (4.50 mmol) of N,N-diethylethanamine and 62 mg (0.38 mmol) of potassium iodide. It was stirred over night at rt. 196 µL (2.25 mmol) of morpholine and 15.5 mg (0.09 mmol) of potassium iodide were added. It was stirred for 28 h at 50° C. The reaction was allowed to reach rt and poured into water. It was extracted three times with EtOAc. The combined organic phases were dried over sodium sulfate and concentrated. The solid residue was triturated with methanol and filtered off. The solid material was purified by HPLC (method 2) providing 20 mg (3%) of the title compound.

$^1$H-NMR (400 MHz, DMSO-$d_6$): δ [ppm]=1.23 (d, 3H), 1.39 (s, 9H), 2.52-2.65 (m, 4H), 3.28-3.34 (m, 1H and water signal), 3.59-3.69 (m, 4H), 7.26-7.31 (m, 1H), 7.37-7.43 (m, 2H), 7.52 (d, 1H), 7.60-7.64 (m, 2H), 7.90 (dd, 1H), 7.93 (s, 1H), 8.25 (d, 1H), 9.48 (s, 1H), 12.68 (br s, 1H).

LC-MS (Method 4): $R_t$=1.18 min; MS (ESIpos): m/z=493 [M+H]$^+$.

Example 144

N-[5-(2-methylphenyl)-1,3,4-thiadiazol-2-yl]-3-{[(4-methylpiperazin-1-yl)acetyl]amino}-4-(trifluoromethoxy)benzamide

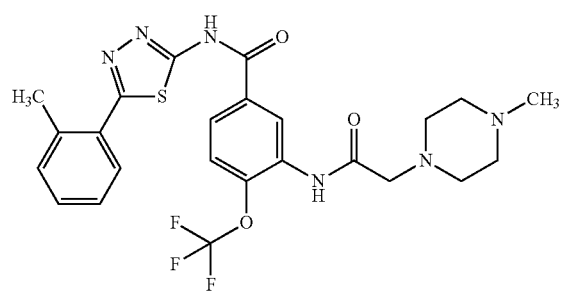 [SMILES: Cc1ccccc1-c1nnc(NC(=O)c2ccc(OC(F)(F)F)c(NC(=O)CN3CCN(C)CC3)c2)s1]

To a solution of the compound of intermediate 126 (150 mg, 0.32 mmol) and 5-(2-methylphenyl)-1,3,4-thiadiazol-2-amine (123 mg, 0.64 mmol, 2 equiv) in DMF (2.0 mL) was added (benzotriazol-1-yloxy)tripyrrolidinophosphonium hexafluorophosphate (PYBOP, 334 mg, 0.64 mmol, 2 equiv) and diisopropylethylamine (0.28 mL, 1.60 mmol, 5 equiv). The resulting mixture was stirred at room temperature over night and was then concentrated. Purification by HPLC (Waters Autopurification system, column: XBrigde C18 5 µm 100×30 mm, solvent: water/methanol+0.2% ammonia (32%) gradient, rate: 70 mL/min, temperature: room temperature) yielded 65.0 mg (34% of theory) of the title compound.

$^1$H-NMR (300 MHz, DMSO-$d_6$): δ [ppm]=2.23 (s, 3H), 2.53 (s, 3H), 2.55-2.67 (m, 5H), 3.23 (s, 2H), 7.31-7.47 (m, 3H), 7.63 (d, 1H), 7.70 (d, 1H), 8.01 (dd, 1H), 8.99 (d, 1H), 9.93 (s, 1H), 13.09 (s, 1H).

LC-MS (Method 3): $R_t$=0.77 min; MS (ESIpos): m/z=535 [M+H]$^+$.

Example 145

N-[5-(3-methylphenyl)-1,3,4-thiadiazol-2-yl]-3-{[(4-methylpiperazin-1-yl)acetyl]amino}-4-(trifluoromethoxy)benzamide

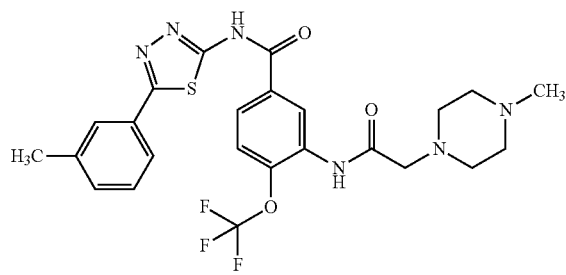

To a solution of the compound of intermediate 126 (150 mg, 0.32 mmol) and 5-(3-methylphenyl)-1,3,4-thiadiazol-2-amine (123 mg, 0.64 mmol, 2 equiv) in DMF (2.0 mL) was added (benzotriazol-1-yloxy)tripyrrolidinophosphonium hexafluorophosphate (PYBOP, 334 mg, 0.64 mmol, 2 equiv) and diisopropylethylamine (0.28 mL, 1.60 mmol, 5 equiv). The resulting mixture was stirred at room temperature over night and was then concentrated. Purification by HPLC (Waters Autopurification system, column: XBrigde C18 5 μm 100×30 mm, solvent: water/methanol+0.2% ammonia (32%) gradient, rate: 70 mL/min, temperature: room temperature) yielded 71.0 mg (41% of theory) of the title compound.

$^1$H-NMR (300 MHz, DMSO-d$_6$): δ [ppm]=2.26 (s, 3H), 2.40 (s, 3H), 2.57-2.69 (m, 5H), 3.24 (s, 2H), 7.33 (d, 1H), 7.42 (t, 1H), 7.63 (d, 1H), 7.71-7.84 (m, 2H), 8.01 (dd, 1H), 8.97 (d, 1H), 9.92 (s, 1H), 12.90 (s, 1H).

LC-MS (Method 3): R$_t$=0.80 min; MS (ESIpos): m/z=535 [M+H]$^+$.

Example 146

N-[5-(3-methoxyphenyl)-1,3,4-thiadiazol-2-yl]-3-{[(4-methylpiperazin-1-yl)acetyl]amino}-4-(trifluoromethoxy)benzamide

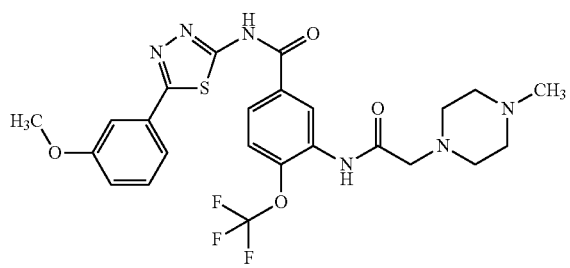

To a solution of the compound of intermediate 126 (150 mg, 0.32 mmol) and 5-(3-methoxyphenyl)-1,3,4-thiadiazol-2-amine (132 mg, 0.64 mmol, 2 equiv) in DMF (2.0 mL) was added (benzotriazol-1-yloxy)tripyrrolidinophosphonium hexafluorophosphate (PYBOP, 334 mg, 0.64 mmol, 2 equiv) and diisopropylethylamine (0.28 mL, 1.60 mmol, 5 equiv). The resulting mixture was stirred at room temperature over night and was then poured into a mixture of water and ethanol (9/1). The precipitate was collected by filtration, washed with water and dried. Purification by HPLC (Waters Autopurification system, column: XBrigde C18 5 μm 100×30 mm, solvent: water/methanol+0.2% ammonia (32%) gradient, rate: 70 mL/min, temperature: room temperature) yielded 13.0 mg (7% of theory) of the title compound.

$^1$H-NMR (300 MHz, DMSO-d$_6$): δ [ppm]=2.27 (s, 3H), 2.57-2.70 (m, 5H), 3.24 (s, 2H), 3.86 (s, 3H), 7.05-7.13 (m, 1H), 7.40-7.55 (m, 3H), 7.62 (d, 1H), 8.01 (dd, 1H), 8.97 (d, 1H), 9.92 (s, 1H), 12.86 (s, 1H).

LC-MS (Method 3): R$_t$=0.76 min; MS (ESIpos): m/z=551 [M+H]$^+$.

Example 147

N-[5-(4-chlorophenyl)-1,3,4-thiadiazol-2-yl]-3-{[(4-methylpiperazin-1-yl)acetyl]amino}-4-(trifluoromethoxy)benzamide

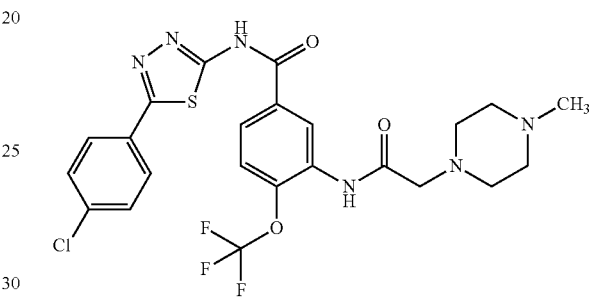

To a solution of the compound of intermediate 126 (150 mg, 0.32 mmol) and 5-(4-chlorophenyl)-1,3,4-thiadiazol-2-amine (136 mg, 0.64 mmol, 2 equiv) in DMF (2.0 mL) was added (benzotriazol-1-yloxy)tripyrrolidinophosphonium hexafluorophosphate (PYBOP, 334 mg, 0.64 mmol, 2 equiv) and diisopropylethylamine (0.28 mL, 1.60 mmol, 5 equiv). The resulting mixture was stirred at room temperature over night. After filtration, purification by HPLC (method 5) yielded 55.5 mg (31% of theory) of the title compound.

$^1$H-NMR (400 MHz, DMSO-d$_6$): δ [ppm]=2.29 (s, 3H), 2.48-2.59 (m, 4H), 2.59-2.71 (m, 4H), 3.25 (s, 2H), 7.57-7.64 (m, 3H), 7.96-8.03 (m, 3H), 8.96 (d, 1H), 9.91 (s, 1H), 12.70 (s, 1H).

LC-MS (Method 3): R$_t$=0.86 min; MS (ESIpos): m/z=555 [M+H]$^+$.

Example 148

N-[5-(2-chlorophenyl)-1,3,4-thiadiazol-2-yl]-3-{[(4-methylpiperazin-1-yl)acetyl]amino}-4-(trifluoromethoxy)benzamide

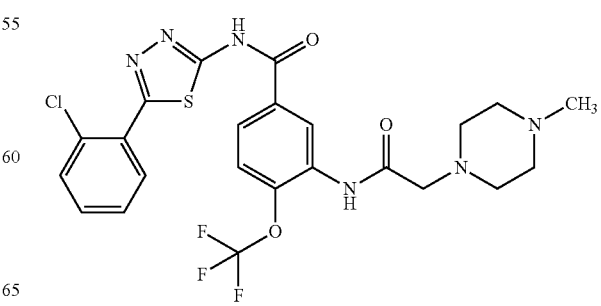

To a solution of the compound of intermediate 126 (150 mg, 0.32 mmol) and 5-(2-chlorophenyl)-1,3,4-thiadiazol-2-amine (136 mg, 0.64 mmol, 2 equiv) in DMF (2.0 mL) was added (benzotriazol-1-yloxy)tripyrrolidinophosphonium hexafluorophosphate (PYBOP, 334 mg, 0.64 mmol, 2 equiv) and diisopropylethylamine (0.28 mL, 1.60 mmol, 5 equiv). The resulting mixture was stirred at room temperature overnight. After filtration, purification by HPLC (1. method 5; 2. Waters Autopurification system, column: XBrigde C18 5 μm 100×30 mm, solvent: water/acetonitrile+0.1% formic acid gradient, rate: 70 mL/min, temperature: room temperature) provided a solid, which was triturated with ethanol, collected by filtration and dried. 31.2 mg (17% of theory) of the title compound were obtained.

$^1$H-NMR (300 MHz, DMSO-$d_6$): δ [ppm]=2.28 (s, 3H), 2.59-2.69 (m, 5H), 3.25 (s, 2H), 7.49-7.71 (m, 4H), 8.02 (dd, 1H), 8.08-8.17 (m, 1H), 8.97 (d, 1H), 9.92 (s, 1H), 12.85 (s, 1H).

LC-MS (Method 4): $R_t$=1.04 min; MS (ESIpos): m/z=555 [M+H]$^+$.

Example 149

N-[5-(4-fluorophenyl)-1,3,4-thiadiazol-2-yl]-3-{[(4-methylpiperazin-1-yl)acetyl]amino}-4-(trifluoromethoxy)benzamide

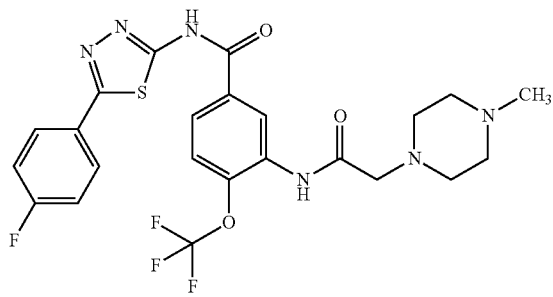 [SMILES: CN1CCN(CC(=O)Nc2cc(C(=O)Nc3nnc(-c4ccc(F)cc4)s3)ccc2OC(F)(F)F)CC1]

To a solution of the compound of intermediate 126 (150 mg, 0.32 mmol) and 5-(4-fluorophenyl)-1,3,4-thiadiazol-2-amine (125 mg, 0.64 mmol, 2 equiv) in DMF (2.0 mL) was added (benzotriazol-1-yloxy)tripyrrolidinophosphonium hexafluorophosphate (PYBOP, 334 mg, 0.64 mmol, 2 equiv) and diisopropylethylamine (0.28 mL, 1.60 mmol, 5 equiv). The resulting mixture was stirred at room temperature overnight and was then poured into a mixture of water and ethanol (9/1). The precipitate was collected by filtration, washed with water and dried. The remaining material was triturated with DMSO, collected by filtration, washed with water and dried. 38.0 mg (22% of theory) of the title compound were obtained.

$^1$H-NMR (300 MHz, DMSO-$d_6$): δ [ppm]=2.27 (s, 3H), 2.58-2.69 (m, 4H), 3.24 (s, 2H), 7.33-7.43 (m, 2H), 7.62 (dd, 1H), 7.98-8.07 (m, 3H), 8.97 (d, 1H), 9.91 (s, 1H), 12.83 (s, 1H).

LC-MS (Method 3): $R_t$=0.77 min; MS (ESIpos): m/z=539 [M+H]$^+$.

Example 150

N-[5-(2-fluorophenyl)-1,3,4-thiadiazol-2-yl]-3-{[(4-methylpiperazin-1-yl)acetyl]amino}-4-(trifluoromethoxy)benzamide

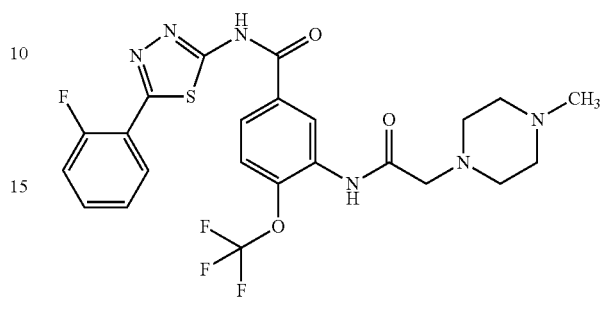

To a solution of the compound of intermediate 126 (150 mg, 0.32 mmol) and 5-(2-fluorophenyl)-1,3,4-thiadiazol-2-amine (125 mg, 0.64 mmol, 2 equiv) in DMF (2.0 mL) was added (benzotriazol-1-yloxy)tripyrrolidinophosphonium hexafluorophosphate (PYBOP, 334 mg, 0.64 mmol, 2 equiv) and diisopropylethylamine (0.28 mL, 1.60 mmol, 5 equiv). The resulting mixture was stirred at room temperature overnight and was then poured into a mixture of water and ethanol (9/1). The precipitate was collected by filtration, washed with water and dried. Purification by HPLC (1. method 5, 2. Waters Autopurification system, column: XBrigde C18 5 μm 100×30 mm, solvent: water/acetonitrile+ 0.1% formic acid (99%) gradient, rate: 70 mL/min, temperature: room temperature) yielded 31.0 mg (18% of theory) of the title compound.

$^1$H-NMR (300 MHz, DMSO-$d_6$): δ [ppm]=2.27 (s, 3H), 2.57-2.69 (m, 5H), 3.24 (s, 2H), 7.35-7.52 (m, 2H), 7.54-7.68 (m, 2H), 8.02 (dd, 1H), 8.26 (td, 1H), 8.98 (d, 1H), 9.92 (s, 1H), 12.85 (s, 1H).

LC-MS (Method 4): $R_t$=0.98 min; MS (ESIpos): m/z=539 [M+H]$^+$.

Example 151

N-[5-(3-chlorophenyl)-1,3,4-thiadiazol-2-yl]-3-{[(4-methylpiperazin-1-yl)acetyl]amino}-4-(trifluoromethoxy)benzamide

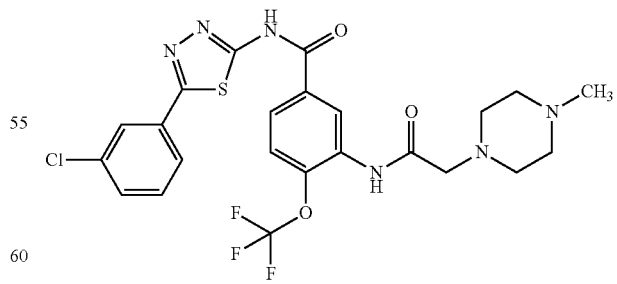

To a solution of the compound of intermediate 126 (150 mg, 0.32 mmol) and 5-(3-chlorophenyl)-1,3,4-thiadiazol-2-amine (136 mg, 0.64 mmol, 2 equiv) in DMF (2.0 mL) was added (benzotriazol-1-yloxy)tripyrrolidinophosphonium hexafluorophosphate (PYBOP, 334 mg, 0.64 mmol, 2 equiv)

and diisopropylethylamine (0.28 mL, 1.60 mmol, 5 equiv). The resulting mixture was stirred at room temperature over night and was then poured into a mixture of water and ethanol (1/1). The precipitate was collected by filtration, washed with water and dried. Purification by HPLC (method 5) yielded 10.0 mg (6% of theory) of the title compound.

$^1$H-NMR (300 MHz, DMSO-d$_6$): δ [ppm]=2.31 (s, 3H), 2.50-2.70 (m, 8H), 3.25 (s, 2H), 7.51-7.66 (m, 3H), 7.88-7.93 (m, 1H), 7.97-8.06 (m, 2H), 8.95 (d, 1H), 9.90 (s, 1H), 12.61 (s, 1H).

LC-MS (Method 3): R$_t$=0.79 min; MS (ESIpos): m/z=555 [M+H]$^+$.

Example 152

N-[5-(3-fluorophenyl)-1,3,4-thiadiazol-2-yl]-3-{[(4-methylpiperazin-1-yl)acetyl]amino}-4-(trifluoromethoxy)benzamide

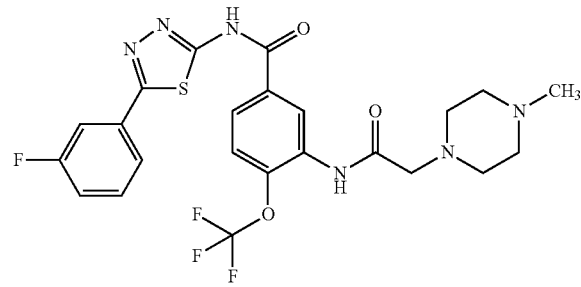 [SMILES: CN1CCN(CC(=O)Nc2cc(C(=O)Nc3nnc(-c4cccc(F)c4)s3)ccc2OC(F)(F)F)CC1]

To a solution of the compound of intermediate 126 (150 mg, 0.32 mmol) and 5-(3-fluorophenyl)-1,3,4-thiadiazol-2-amine (125 mg, 0.64 mmol, 2 equiv) in DMF (2.0 mL) was added (benzotriazol-1-yloxy)tripyrrolidinophosphonium hexafluorophosphate (PYBOP, 334 mg, 0.64 mmol, 2 equiv) and diisopropylethylamine (0.28 mL, 1.60 mmol, 5 equiv). The resulting mixture was stirred at room temperature over night. After filtration, purification by HPLC (method 5) provided a solid, which was triturated with ethanol, collected by filtration and dried. 43.0 mg (25% of theory) of the title compound were obtained.

$^1$H-NMR (400 MHz, DMSO-d$_6$): δ [ppm]=2.31 (s, 3H), 2.50-2.71 (m, 8H), 3.25 (s, 2H), 7.33-7.39 (m, 1H), 7.55-7.64 (m, 2H), 7.77-7.82 (m, 2H), 8.02 (dd, 1H), 8.95 (d, 1H), 9.90 (s, 1H), 12.67 (s, 1H).

LC-MS (Method 3): R$_t$=0.81 min; MS (ESIpos): m/z=539 [M+H]$^+$.

Example 153

N-[5-(3-fluorophenyl)-1,3,4-thiadiazol-2-yl]-3-[(morpholin-4-ylacetyl)amino]-4-(trifluoromethoxy)benzamide

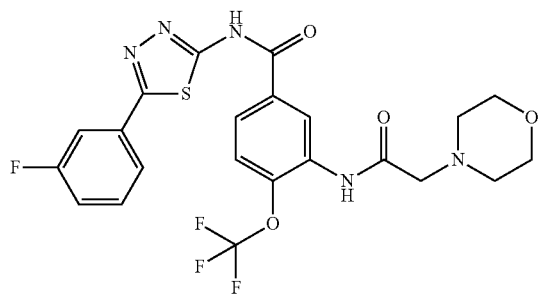 [SMILES: O=C(CN1CCOCC1)Nc1cc(C(=O)Nc2nnc(-c3cccc(F)c3)s2)ccc1OC(F)(F)F]

To a solution of the compound of intermediate 21 (220 mg, 0.57 mmol) and 5-(3-fluorophenyl)-1,3,4-thiadiazol-2-amine (200 mg, 1.02 mmol, 1.8 equiv) in DMF (2.5 mL) was added (benzotriazol-1-yloxy)tripyrrolidinophosphonium hexafluorophosphate (PYBOP, 592 mg, 1.14 mmol, 2 equiv) and diisopropylethylamine (0.5 mL, 2.84 mmol, 5 equiv). The resulting mixture was stirred at room temperature over night and was then poured into a mixture of ethanol and water. The precipitate was collected by filtration and dried. 161 mg (49% of theory) of the title compound were obtained. $^1$H-NMR (400 MHz, DMSO-d$_6$): δ [ppm]=2.55-2.63 (m, 4H), 3.24 (s, 2H), 3.62-3.69 (m, 4H), 7.35-7.44 (m, 1H), 7.56-7.64 (m, 1H), 7.64-7.69 (m, 1H), 7.79-7.86 (m, 2H), 8.03 (dd, 1H), 8.95 (d, 1H), 9.94 (s, 1H), 13.47 (s, 1H).

LC-MS (Method 4): R$_t$=1.16 min; MS (ESIpos): m/z=526 [M+H]$^+$.

Example 154

N-[5-(3-chlorophenyl)-1,3,4-thiadiazol-2-yl]-3-[(morpholin-4-ylacetyl)amino]-4-(trifluoromethoxy)benzamide

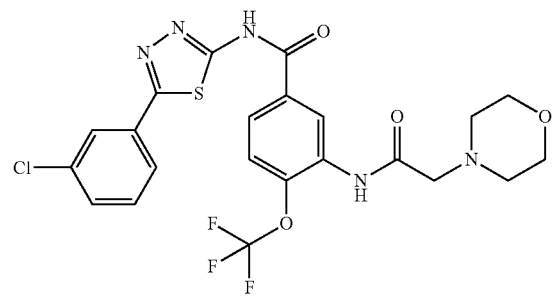 [SMILES: O=C(CN1CCOCC1)Nc1cc(C(=O)Nc2nnc(-c3cccc(Cl)c3)s2)ccc1OC(F)(F)F]

To a solution of the compound of intermediate 21 (220 mg, 0.57 mmol) and 5-(3-chlorophenyl)-1,3,4-thiadiazol-2-amine (217 mg, 1.02 mmol, 1.8 equiv) in DMF (2.5 mL) was added (benzotriazol-1-yloxy)tripyrrolidinophosphonium hexafluorophosphate (PYBOP, 592 mg, 1.14 mmol, 2 equiv) and diisopropylethylamine (0.5 mL, 2.84 mmol, 5 equiv). The resulting mixture was stirred at room temperature over night and was then poured into a mixture of ethanol and water. The precipitate was collected by filtration and dried. The remaining material was purified by HPLC (column: chromatorex C18, mobile phase: acetonitrile/water+0.1% formic acid gradient) to yield 20.6 mg (6% of theory) of the title compound.

$^1$H-NMR (400 MHz, DMSO-d$_6$): δ [ppm]=3.24 (s, 2H), 3.62-3.69 (m, 4H), 7.53-7.66 (m, 3H), 7.87-7.95 (m, 1H), 7.99-8.06 (m, 2H), 8.95 (s, 1H), 9.91 (s, 1H), 13.45 (s, 1H).

LC-MS (Method 4): R$_t$=1.24 min; MS (ESIpos): m/z=542 [M+H]$^+$.

Example 155

N[1]-(2-methoxyethyl)-2-{[(4-methylpiperazin-1-yl)acetyl]amino}-N[4]-(5-phenyl-1,3,4-thiadiazol-2-yl)terephthalamide

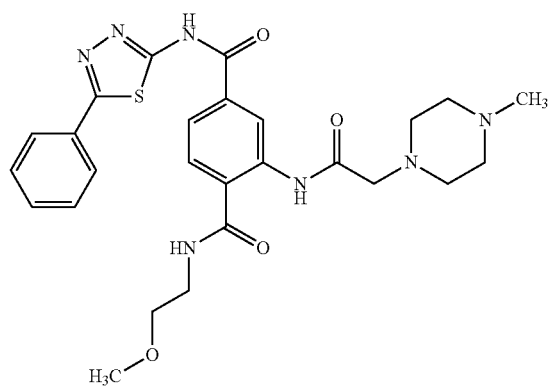 [SMILES: COCCNC(=O)c1ccc(C(=O)Nc2nnc(-c3ccccc3)s2)cc1NC(=O)CN1CCN(C)CC1]

To a solution of the compound of intermediate 127 (150 mg, 0.31 mmol) and 2-methoxyethanamine (54 μL, 0.62 mmol, 2 equiv) in DMF (2.0 mL) was added (benzotriazol-1-yloxy)tripyrrolidinophosphonium hexafluorophosphate (PYBOP, 325 mg, 0.62 mmol, 2 equiv) and diisopropylethylamine (0.27 mL, 1.56 mmol, 5 equiv). The resulting mixture was stirred at room temperature over night. After filtration, purification by HPLC (method 2) yielded 45.5 mg (26% of theory) of the title compound.

$^1$H-NMR (400 MHz, DMSO-d$_6$): δ [ppm]=2.33 (s, 3H), 2.53-2.70 (m, 8H), 3.17 (s, 2H), 3.30 (s, 3H), 3.45-3.54 (m, 4H), 7.50-7.58 (m, 3H), 7.78 (d, 1H), 7.91 (dd, 1H), 7.95-8.00 (m, 2H), 8.87 (t, 1H), 9.17 (d, 1H), 11.66 (s, 1H).

LC-MS (Method 4): R$_t$=0.84 min; MS (ESIpos): m/z=538 [M+H]$^+$.

Example 156

N[1]-(2-methoxyethyl)-2-[(morpholin-4-ylacetyl)amino]-N[4]-(5-phenyl-1,3,4-thiadiazol-2-yl)terephthalamide

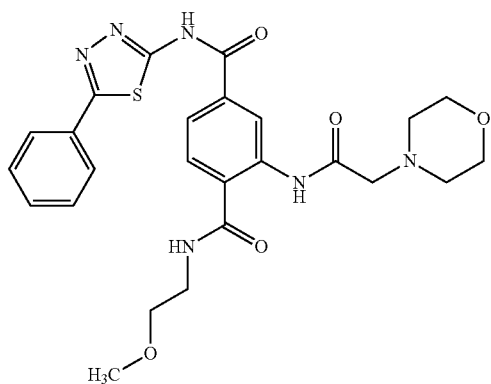 [SMILES: COCCNC(=O)c1ccc(C(=O)Nc2nnc(-c3ccccc3)s2)cc1NC(=O)CN1CCOCC1]

To a solution of the compound of intermediate 128 (150 mg, 0.33 mmol) and 2-methoxyethanamine (56 μL, 0.64 mmol, 2 equiv) in DMF (2.0 mL) was added (benzotriazol-1-yloxy)tripyrrolidinophosphonium hexafluorophosphate (PYBOP, 334 mg, 0.64 mmol, 2 equiv) and diisopropylethylamine (0.28 mL, 1.60 mmol, 5 equiv). The resulting mixture was stirred at room temperature over night. After filtration, purification by HPLC (method 2) provided a solid, which was triturated with ethanol, collected by filtration and dried. 9.2 mg (6% of theory) of the title compound were obtained.

$^1$H-NMR (400 MHz, DMSO-d$_6$): δ [ppm]=2.50-2.56 (m, 4H), 3.17 (s, 2H), 3.29 (s, 3H), 3.44-3.53 (m, 4H), 3.70-3.76 (m, 4H), 7.52-7.59 (m, 3H), 7.80 (d, 1H), 7.92 (dd, 1H), 7.96-8.02 (m, 2H), 8.88-8.93 (m, 1H), 9.18 (d, 1H), 11.77 (s, 1H), 13.35 (s, 1H).

LC-MS (Method 4): R$_t$=0.91 min; MS (ESIpos): m/z=525 [M+H]$^+$.

Example 157

4-methyl-3-({[1-(4-methylpiperazin-1-yl)cyclopropyl]carbonyl}amino)-N-(5-phenyl-1,3,4-thiadiazol-2-yl)benzamide hydrochloride (1:1)

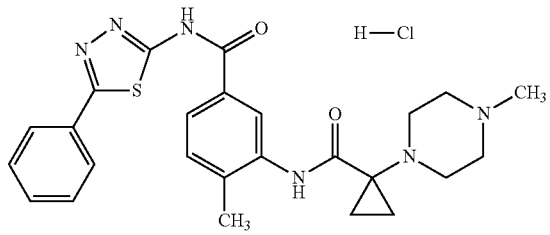 [SMILES: Cc1ccc(C(=O)Nc2nnc(-c3ccccc3)s2)cc1NC(=O)C1(N2CCN(C)CC2)CC1 ; Cl]

To a suspension of 213 mg (0.97 mmol) of the compound from intermediate 42 in 6 mL of dichloromethane were added 0.51 mL of 1-chloro-N,N,2-trimethylprop-1-en-1-amine (3.87 mmol, 4 equiv). The reaction mixture was stirred at room temperature for 2 h. The resulting mixture was concentrated under reduced pressure, was then triturated with dichloromethane and was concentrated under reduced pressure. The remaining material was provided in 6 mL of dichloromethane and 0.24 mL of pyridine (2.90 mmol, 3 equiv) and 300 mg (0.97 mmol) of the compound of intermediate 130 were added. The resulting suspension was stirred at room temperature for 3 days. The resulting mixture was concentrated under reduced pressure, was then triturated with a mixture of 5 mL of water and 5 mL of ethanol, and the resulting mixture was stirred for 30 minutes. After partial concentration, the suspension was allowed to stand at room temperature over night. The precipitate was removed by filtration and dried under reduced pressure to yield 152 mg (30% of theory) of the title compound.

$^1$H-NMR (400 MHz, DMSO-d$_6$): δ [ppm]=1.13-1.23 (m, 4H), 2.36 (s, 3H), 2.64-2.82 (m, 5H), 2.91-3.02 (m, 2H), 3.14-3.28 (m, 2H), 7.47 (d, 1H), 7.53-7.59 (m, 3H), 7.91-8.03 (m, 3H), 8.33 (d, 1H), 9.76 (s, 1H), 10.39 (s, 1H), 13.13 (s, 1H).

LC-MS (Method 4): R$_t$=0.87 min; MS (ESIpos): m/z=477 [M−HCl+H]$^+$.

Example 158

3-{[(4-methylpiperazin-1-yl)acetyl]amino}-N-(5-phenylpyridin-2-yl)-4-(trifluoromethoxy)benzamide

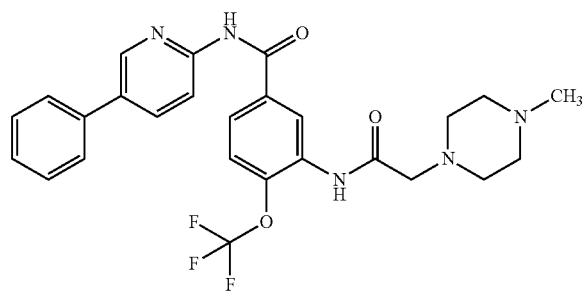 [SMILES: CN1CCN(CC(=O)Nc2cc(C(=O)Nc3ccc(-c4ccccc4)cn3)ccc2OC(F)(F)F)CC1]

To a solution of the compound of intermediate 126 (300 mg, 0.64 mmol) and 5-phenylpyridin-2-amine (218 mg, 1.28 mmol, 2 equiv) in DMF (2.0 mL) was added (benzotriazol-1-yloxy)tripyrrolidinophosphonium hexafluorophosphate (PYBOP, 667 mg, 1.28 mmol, 2 equiv) and diisopropylethylamine (0.56 mL, 3.21 mmol, 5 equiv). The resulting mixture was stirred at room temperature over night. After concentration, the remaining material was triturated with water and extracted with dichloromethane. The combined organic phases were dried over sodium sulfate and concentrated. Purification (1. MPLC: Biotage Isolera; silica gel; hexane/EtOAc gradient; 2. HPLC: column: chromatorex C18, 10 μm, 125×30 mm, mobile phase: acetonitrile/water gradient) yielded 83.0 mg (24% of theory) of the title compound.

$^1$H-NMR (400 MHz, DMSO-$d_6$): δ [ppm]=2.18 (s, 3H), 2.28-2.50 (m, 4H), 2.52-2.64 (m, 4H), 3.21 (s, 2H), 7.38-7.43 (m, 1H), 7.48-7.53 (m, 2H), 7.59 (dd, 1H), 7.73-7.77 (m, 2H), 7.90 (dd, 1H), 8.18 (dd, 1H), 8.28 (d, 1H), 8.72-8.74 (m, 1H), 8.89 (d, 1H), 9.92 (s, 1H), 11.08 (s, 1H).

LC-MS (Method 3): $R_t$=1.33 min; MS (ESIpos): m/z=514 [M+H]$^+$.

Example 159

4-(cyclopropyloxy)-3-({[1-(morpholin-4-yl)cyclopropyl]carbonyl}amino)-N-(5-phenyl-1,3,4-thiadiazol-2-yl)benzamide

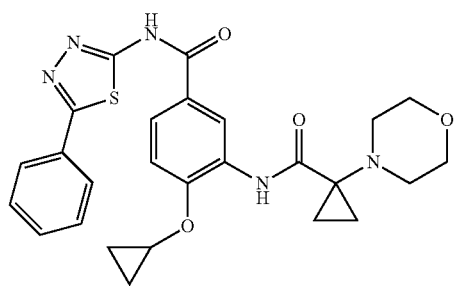 [SMILES: O=C(Nc1nnc(-c2ccccc2)s1)c1ccc(OC2CC2)c(NC(=O)C2(N3CCOCC3)CC2)c1]

100 mg (0.28 mmol) of 3-amino-4-(cyclopropyloxy)-N-(5-phenyl-1,3,4-thiadiazol-2-yl)benzamide (intermediate 132) were dissolved in 1 mL of anh DMF and 0.15 mL (0.86 mmol) of N-ethyl-N-isopropylpropan-2-amine. 71 mg (0.34 mmol) of 1-(morpholin-4-yl)cyclopropanecarboxylic acid hydrochloride and 177 mg (0.34 mmol) of PYBOP were added. It was stirred overnight at rt. The precipitate was filtered off and washed with methanol. It was dried and 65 mg (45%) of the title compound was isolated.

$^1$H-NMR (300 MHz, DMSO-$d_6$): δ [ppm]=0.78-0.86 (m, 2H), 0.91-1.01 (m, 2H), 1.07-1.16 (m, 2H), 1.18-1.26 (m, 2H), 2.43 (br. s, 4H, partly DMSO signal), 3.71 (br. s, 4H), 4.11-4.20 (m, 1H), 7.45-7.59 (m, 4H), 7.92-8.02 (m, 3H), 8.99-9.04 (m, 1H), 10.48 (s, 1H), 13.07 (br. s, 1H).

LC-MS (method 3): $R_t$=0.87 min; MS (ESIpos): m/z=506 [M+H]$^+$.

Example 160

3-{[(3,4-dimethylpiperazin-1-yl)acetyl]amino}-N-(5-phenyl-1,3,4-thiadiazol-2-yl)-4-(trifluoromethoxy)benzamide

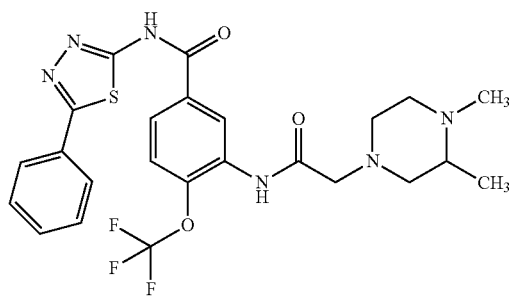 [SMILES: CC1CN(CC(=O)Nc2cc(C(=O)Nc3nnc(-c4ccccc4)s3)ccc2OC(F)(F)F)CCN1C]

100 mg (0.21 mmol) of 3-[(chloroacetyl)amino]-N-(5-phenyl-1,3,4-thiadiazol-2-yl)-4-(trifluoromethoxy)benzamide (intermediate 41) and 116.7 mg (0.62 mmol) of 1,2-dimethylpiperazine dihydrochloride were dissolved in 0.9 mL of anh DMF. 5.4 mg (0.033 mmol) of potassium iodide and 0.054 mL (0.31 mmol) of N-ethyl-N-isopropylpropan-2-amine were added. It was stirred at rt overnight. The reaction mixture was poured into ten volumes of water. The precipitate was filtered off and washed three times with water. The solid material was purified by HPLC (method 5) to give 23.7 mg (20%) of the title compound.

$^1$H-NMR (300 MHz, DMSO-$d_6$): δ [ppm]=1.00 (d, 3H), 2.07-2.17 (m, 1H), 2.18-2.38 (m, 5H), 2.39-2.46 (m, 1H), 2.74-2.88 (m, 3H), 3.19-3.23 (m, 2H), 7.47-7.58 (m, 3H), 7.58-7.64 (m, 1H), 7.91-8.04 (m, 3H), 8.96 (d, 1H), 9.89 (s, 1H), 12.66-13.03 (m, 1H).

LC-MS (method 3): $R_t$=0.79 min; MS (ESIpos): m/z=535 [M+H]$^+$.

Example 161

3-({[(2R)-2,4-dimethylpiperazin-1-yl]acetyl}amino)-N-[6-(2-fluorophenyl)pyridin-3-yl]-4-(trifluoromethoxy)benzamide

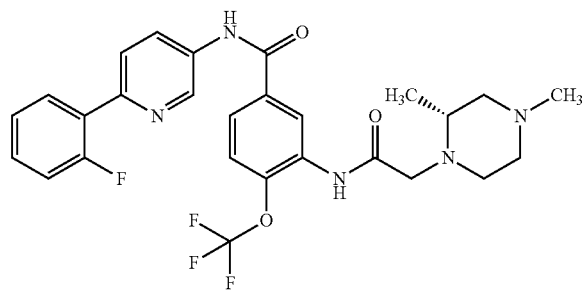 [SMILES: C[C@@H]1CN(C)CCN1CC(=O)Nc1cc(C(=O)Nc2ccc(-c3ccccc3F)nc2)ccc1OC(F)(F)F]

75 mg (0.16 mmol) of 3-[(chloroacetyl)amino]-N-[6-(2-fluorophenyl)pyridin-3-yl]-4-(trifluoromethoxy)benzamide (intermediate 14) were dissolved in 0.69 mL of anh DMF. 4.1 mg (0.025 mmol) of potassium iodide, 0.112 mL (0.64 mmol) of N-ethyl-N-isopropylpropan-2-amine and 45.0 mg (0.24 mmol) of (3R)-1,3-dimethylpiperazine dihydrochloride were added. It was stirred at rt overnight. 0.112 mL (0.64 mmol) of N-ethyl-N-isopropylpropan-2-amine were added. It was stirred for 2 h at rt. The reaction mixture was concentrated to dryness and purified by HPLC (method 2) to afford 20.2 mg (23%) of the title compound.

$^1$H-NMR (400 MHz, DMSO-$d_6$): δ [ppm]=1.01 (d, 3H), 1.82-2.04 (m, 1H), 2.10-2.39 (m, 3H), 2.59-2.93 (m, 4H, partly overlapping with the DMSO signal), 3.09-3.20 (m, 1H), 3.42-3.51 (m, 1H), 7.30-7.39 (m, 2H), 7.44-7.52 (m, 1H), 7.64-7.73 (m, 1H), 7.81-7.89 (m, 2H), 7.94-8.01 (m, 1H), 8.31 (dd, 1H), 8.81-8.92 (m, 1H), 9.04-9.09 (m, 1H), 10.08 (s, 1H), 10.75 (s, 1H).

LC-MS (method 4): $R_t$=1.01 min; MS (ESIpos): m/z=546 [M+H]$^+$.

Example 162

3-({[(2S)-2,4-dimethylpiperazin-1-yl]acetyl}amino)-N-[6-(2-fluorophenyl)pyridin-3-yl]-4-(trifluoromethoxy)benzamide

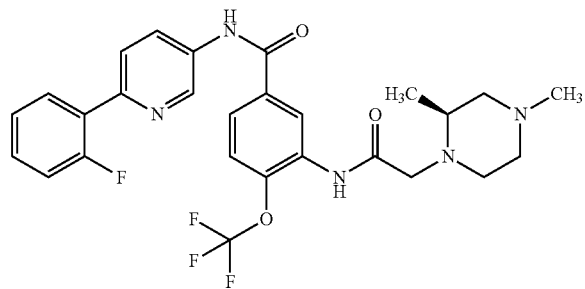 [SMILES: C[C@H]1CN(C)CCN1CC(=O)Nc1cc(C(=O)Nc2ccc(-c3ccccc3F)nc2)ccc1OC(F)(F)F]

75 mg (0.16 mmol) of 3-[(chloroacetyl)amino]-N-[6-(2-fluorophenyl)pyridin-3-yl]-4-(trifluoromethoxy)benzamide (intermediate 14) were dissolved in 0.69 mL of anh DMF. 4.1 mg (0.025 mmol) of potassium iodide, 0.042 mL (0.24 mmol) of N-ethyl-N-isopropylpropan-2-amine and 27.5 mg (0.24 mmol) of (3S)-1,3-dimethylpiperazine were added. It was stirred at rt overnight. The volatiles were removed under vacuum. The residue was purified by HPLC (method 2) to afford 26.3 mg (30%) of the title compound.

$^1$H-NMR (400 MHz, DMSO-$d_6$): δ [ppm]=1.02 (d, 3H), 1.91-2.09 (m, 1H), 2.23-2.38 (m, 3H), 2.58-2.92 (m, 5H, partly overlapping with the DMSO signal), 3.12-3.22 (m, 1H), 3.44-3.51 (m, 1H), 7.31-7.38 (m, 2H), 7.45-7.51 (m, 1H), 7.65-7.70 (m, 1H), 7.82-7.89 (m, 2H), 7.94-8.00 (m, 1H), 8.31 (dd, 1H), 8.83 (br. s, 1H), 9.05-9.08 (m, 1H), 10.06 (s, 1H), 10.75 (s, 1H).

LC-MS (method 4): $R_t$=1.01 min; MS (ESIpos): m/z=546 [M+H]$^+$.

Example 163

3-({[(3S)-3,4-dimethylpiperazin-1-yl]acetyl}amino)-N-[6-(2-fluorophenyl)pyridin-3-yl]-4-(trifluoromethoxy)benzamide

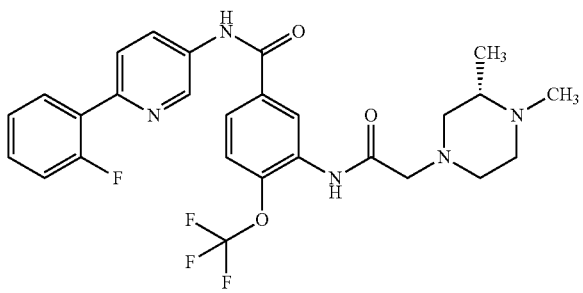 [SMILES: C[C@H]1CN(CC(=O)Nc2cc(C(=O)Nc3ccc(-c4ccccc4F)nc3)ccc2OC(F)(F)F)CCN1C]

75 mg (0.16 mmol) of 3-[(chloroacetyl)amino]-N-[6-(2-fluorophenyl)pyridin-3-yl]-4-(trifluoromethoxy)benzamide (intermediate 14) were dissolved in 0.69 mL of anh DMF. 4.1 mg (0.025 mmol) of potassium iodide, 0.042 mL (0.24 mmol) of N-ethyl-N-isopropylpropan-2-amine and 27.5 mg (0.24 mmol) of (2S)-1,2-dimethylpiperazine were added. It was stirred at rt overnight. The reaction mixture was concentrated to dryness under vacuum. The residue was purified by HPLC (method 2) yielding 34.5 mg (39%) of the title compound.

$^1$H-NMR (400 MHz, DMSO-$d_6$): δ [ppm]=1.01-1.12 (m, 3H), 2.09-2.45 (m, 5H, partly overlapping with the DMSO signal), 2.77-3.02 (m, 3H), 3.25 (br. s, 2H), 7.30-7.39 (m, 2H), 7.44-7.52 (m, 1H), 7.64-7.70 (m, 1H), 7.82-7.91 (m, 2H), 7.94-8.00 (m, 1H), 8.31 (dd, 1H), 8.75-8.81 (m, 1H), 9.07 (d, 1H), 9.91 (s, 1H), 10.75 (s, 1H).

LC-MS (method 4): $R_t$=0.99 min; MS (ESIpos): m/z=546 [M+H]$^+$.

Example 164

3-({[(3R)-3,4-dimethylpiperazin-1-yl]acetyl}amino)-
N-[6-(2-fluorophenyl)pyridin-3-yl]-4-(trifluoromethoxy)benzamide

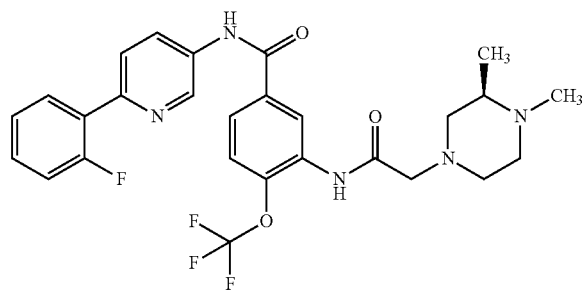 [SMILES: C[C@@H]1CN(CC(=O)Nc2cc(C(=O)Nc3ccc(-c4ccccc4F)nc3)ccc2OC(F)(F)F)CCN1C]

75 mg (0.16 mmol) of 3-[(chloroacetyl)amino]-N-[6-(2-fluorophenyl)pyridin-3-yl]-4-(trifluoromethoxy)benzamide (intermediate 14) were dissolved in 0.69 mL of anh DMF. 4.1 mg (0.025 mmol) of potassium iodide, 0.112 mL (0.64 mmol) of N-ethyl-N-isopropylpropan-2-amine and 45.0 mg (0.24 mmol) of (2R)-1,2-dimethylpiperazine dihydrochloride were added. It was stirred at rt overnight. The reaction mixture was concentrated to dryness under vacuum. The residue was purified by HPLC (method 2) affording 31.2 mg (36%) of the title compound.

$^1$H-NMR (400 MHz, DMSO-d$_6$): δ [ppm]=1.08 (d, 3H), 2.16-2.30 (m, 1H), 2.39 (br. s, 3H), 2.80-2.92 (m, 2H), 2.92-3.06 (m, 1H), 3.26 (br. s, 2H), 7.30-7.38 (m, 2H), 7.44-7.52 (m, 1H), 7.63-7.69 (m, 1H), 7.82-7.91 (m, 2H), 7.97 (dt, 1H), 8.31 (dd, 1H), 8.76 (s, 1H), 9.07 (d, 1H), 9.90 (s, 1H), 10.75 (s, 1H).

LC-MS (method 4): R$_t$=1.01 min; MS (ESIpos): m/z=546 [M+H]$^+$.

Example 165

3-{[(2,4-dimethylpiperazin-1-yl)acetyl]amino}-N-[6-(2-fluorophenyl)pyridin-3-yl]-4-(trifluoromethoxy)benzamide

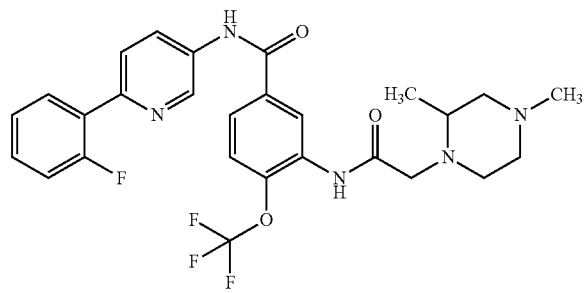

75 mg (0.16 mmol) of 3-[(chloroacetyl)amino]-N-[6-(2-fluorophenyl)pyridin-3-yl]-4-(trifluoromethoxy)benzamide (intermediate 14) were dissolved in 0.69 mL of anh DMF. 4.1 mg (0.025 mmol) of potassium iodide, 0.042 mL (0.24 mmol) of N-ethyl-N-isopropylpropan-2-amine and 27.5 mg (0.24 mmol) of 1,3-dimethylpiperazine were added. It was stirred at rt overnight. The volatiles were removed under vacuum. The residue was purified by HPLC (method 2) to afford 25.7 mg (29%) of the title compound.

$^1$H-NMR (400 MHz, DMSO-d$_6$): δ [ppm]=1.03 (d, 3H), 1.96-2.18 (m, 1H), 2.33 (br. s, 3H), 2.61-2.79 (m, 2H, partly overlapping with the DMSO signal), 2.79-2.95 (m, 2H), 3.14-3.23 (m, 1H), 3.44-3.52 (m, 1H), 7.30-7.38 (m, 2H), 7.45-7.51 (m, 1H), 7.65-7.70 (m, 1H), 7.82-7.90 (m, 2H), 7.97 (dt, 1H), 8.31 (dd, 1H), 8.82 (br. s, 1H), 9.07 (d, 1H), 10.05 (s, 1H), 10.76 (s, 1H).

LC-MS (method 4): R$_t$=1.01 min; MS (ESIpos): m/z=546 [M+H]$^+$.

Example 166

N-[6-(2-fluorophenyl)pyridin-3-yl]-3-{[(8-methyl-3,8-diazabicyclo[3.2.1]oct-3-yl)acetyl]amino}-4-(trifluoromethoxy)benzamide

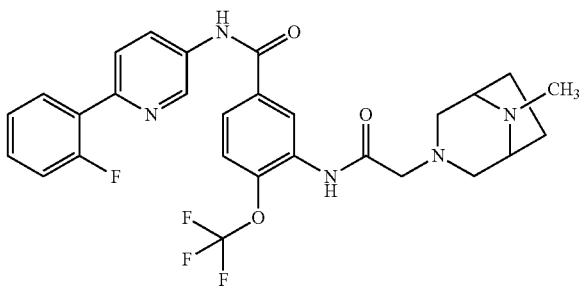 [SMILES: CN1C2CCC1CN(CC(=O)Nc1cc(C(=O)Nc3ccc(-c4ccccc4F)nc3)ccc1OC(F)(F)F)C2]

75 mg (0.16 mmol) of 3-[(chloroacetyl)amino]-N-[6-(2-fluorophenyl)pyridin-3-yl]-4-(trifluoromethoxy)benzamide (intermediate 14) were dissolved in 0.69 mL of anh DMF. 4.1 mg (0.025 mmol) of potassium iodide, 0.112 mL (0.64 mmol) of N-ethyl-N-isopropylpropan-2-amine and 47.9 mg (0.24 mmol) of 8-methyl-3,8-diazabicyclo[3.2.1]octane dihydrochloride were added. It was stirred at rt overnight. The reaction mixture was concentrated to dryness and the residue was purified by HPLC (method 2) to yield 37.5 mg (42%) of the title compound.

$^1$H-NMR (400 MHz, DMSO-d$_6$): d [ppm]=2.46 (s, 3H), 2.66-2.73 (m, 2H), 2.74-2.81 (m, 2H), 3.27 (s, 2H), 3.47-3.55 (m, 2H), 7.31-7.38 (m, 2H), 7.44-7.51 (m, 1H), 7.64-7.69 (m, 1H), 7.82-7.87 (m, 1H), 7.90 (dd, 1H), 7.94-8.00 (m, 1H), 8.32 (dd, 1H), 8.80 (d, 1H), 9.07 (d, 1H), 9.63 (s, 1H), 10.75 (s, 1H).

LC-MS (method 4): R$_t$=1.01 min; MS (ESIpos): m/z=558 [M+H]$^+$.

Example 167

3-{[(2,4-dimethylpiperazin-1-yl)acetyl]amino}-N-(5-phenyl-1,3,4-thiadiazol-2-yl)-4-(trifluoromethoxy)benzamide

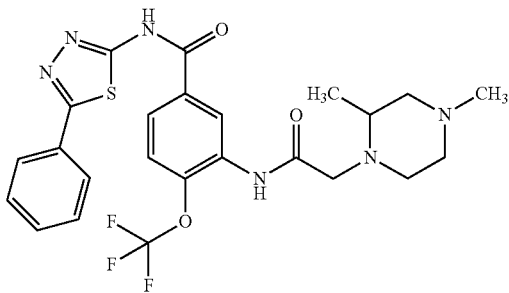 [SMILES: CC1CN(C)CCN1CC(=O)Nc1cc(C(=O)Nc2nnc(-c3ccccc3)s2)ccc1OC(F)(F)F]

75 mg (0.16 mmol) of 3-[(chloroacetyl)amino]-N-(5-phenyl-1,3,4-thiadiazol-2-yl)-4-(trifluoromethoxy)benzamide (intermediate 41) were dissolved in 0.71 mL of anh DMF. 4.2 mg (0.025 mmol) of potassium iodide, 0.043 mL (0.25 mmol) of N-ethyl-N-isopropylpropan-2-amine and 28.1 mg (0.25 mmol) of 1,3-dimethylpiperazine were added. It was stirred at rt overnight. The reaction mixture was concentrated and purified by HPLC (method 2) to obtain 25.2 mg (28%) of the title compound.

$^1$H-NMR (400 MHz, DMSO-$d_6$): δ [ppm]=1.02 (d, 3H), 1.94-2.08 (m, 1H), 2.30 (s, 3H), 2.59-2.75 (m, 3H, partly overlapping with the DMSO signal), 2.76-2.93 (m, 3H), 3.14-3.21 (m, 1H), 3.44-3.51 (m, 1H), 7.52-7.60 (m, 3H), 7.63-7.69 (m, 1H), 7.95-8.05 (m, 3H), 8.97-9.00 (m, 1H), 10.06 (s, 1H), 12.47-13.11 (m, 1H).

LC-MS (method 3): $R_t$=0.77 min; MS (ESIpos): m/z=535 [M+H]$^+$.

Example 168

3-{[(4-methyl-1,4-diazepan-1-yl)acetyl]amino}-N-(5-phenyl-1,3,4-thiadiazol-2-yl)-4-(trifluoromethoxy)benzamide

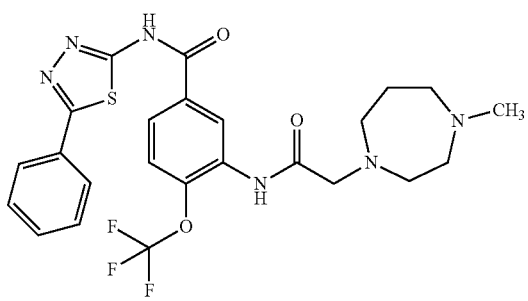 [SMILES: CN1CCCN(CC(=O)Nc2cc(C(=O)Nc3nnc(-c4ccccc4)s3)ccc2OC(F)(F)F)CC1]

100 mg (0.21 mmol) of 3-[(chloroacetyl)amino]-N-(5-phenyl-1,3,4-thiadiazol-2-yl)-4-(trifluoromethoxy)benzamide (intermediate 41), 35.6 mg (0.31 mmol) of 1-methyl-1,4-diazepane and 5.4 mg (0.032 mmol) of potassium iodide were dissolved in 0.9 mL of anh DMF. 0.054 mL (0.31 mmol) of N-ethyl-N-isopropylpropan-2-amine were added. It was stirred at rt overnight. The crude reaction mixture was purified by HPLC (method 5) obtaining 24 mg (21%) of the title compound.

$^1$H-NMR (400 MHz, DMSO-$d_6$): δ [ppm]=1.84-1.92 (m, 2H), 2.53 (br. s, 3H, partly overlapping with the DMSO signal), 2.81-2.87 (m, 2H), 2.88-2.99 (m, 6H), 3.41 (s, 2H), 7.44-7.58 (m, 4H), 7.90-7.95 (m, 2H), 8.03 (dd, 1H), 8.86 (d, 1H), 9.82 (s, 1H).

LC-MS (method 4): $R_t$=0.97 min; MS (ESIpos): m/z=535 [M+H]$^+$.

Example 169

3-[(1,4-oxazepan-4-ylacetyl)amino]-N-(5-phenyl-1,3,4-thiadiazol-2-yl)-4-(trifluoromethoxy)benzamide

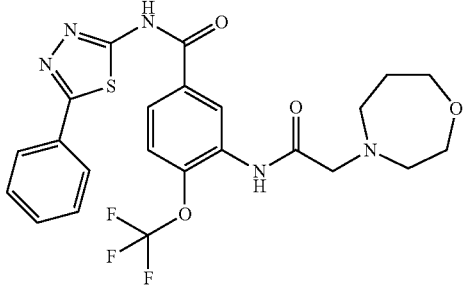 [SMILES: O=C(CN1CCCOCC1)Nc1cc(C(=O)Nc2nnc(-c3ccccc3)s2)ccc1OC(F)(F)F]

100 mg (0.21 mmol) of 3-[(chloroacetyl)amino]-N-(5-phenyl-1,3,4-thiadiazol-2-yl)-4-(trifluoromethoxy)benzamide (intermediate 41), 42.9 mg (0.31 mmol) of 1,4-oxazepane hydrochloride and 5.4 mg (0.032 mmol) of potassium iodide were dissolved in 0.9 mL of anh DMF. 0.116 mL (0.67 mmol) of N-ethyl-N-isopropylpropan-2-amine were added. It was stirred at rt overnight. The crude reaction mixture was purified by HPLC (method 5) giving 45 mg (39%) of the title compound.

$^1$H-NMR (400 MHz, DMSO-$d_6$): δ [ppm]=1.85-1.93 (m, 2H), 2.79-2.86 (m, 4H), 3.40 (s, 2H), 3.65-3.70 (m, 2H), 3.75 (t, 2H), 7.52-7.60 (m, 3H), 7.63-7.68 (m, 1H), 8.03 (dd, 2H), 8.02 (dd, 1H), 8.97 (d, 1H), 9.97 (s, 1H), 13.30-13.57 (m, 1H).

LC-MS (method 3): $R_t$=0.75 min; MS (ESIpos): m/z=522 [M+H]$^+$.

Example 170

4-(cyclopropyloxy)-3-[(morpholin-4-ylacetyl)amino]-N-(5-phenyl-1,3,4-thiadiazol-2-yl)benzamide

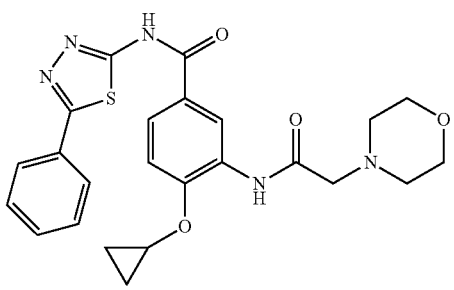 [SMILES: O=C(CN1CCOCC1)Nc1cc(C(=O)Nc2nnc(-c3ccccc3)s2)ccc1OC1CC1]

100 mg (0.28 mmol) of 3-amino-4-(cyclopropyloxy)-N-(5-phenyl-1,3,4-thiadiazol-2-yl)benzamide (intermediate 132) were dissolved in 2 mL of anh DMF. 0.20 mL (1.14 mmol) of N-ethyl-N-isopropylpropan-2-amine, 74 mg (0.41 mmol) of morpholin-4-ylacetic acid hydrochloride and 177 mg (0.34 mmol) of PYBOP were added. It was stirred overnight at rt. The precipitate was filtered off and washed once with methanol. It was dried at 45° C. under vacuum affording 17 mg (12%) of the title compound.

$^1$H-NMR (300 MHz, DMSO-d$_6$): δ [ppm]=0.73-0.98 (m, 4H), 2.52-2.58 (m, 4H), 3.16 (s, 2H), 3.61-3.71 (m, 4H), 4.08-4.17 (m, 1H), 7.44-7.59 (m, 4H), 7.93-8.04 (m, 3H), 8.94 (d, 1H), 9.71 (s, 1H), 12.98-13.23 (m, 1H).

LC-MS (method 3): R$_t$=0.78 min; MS (ESIpos): m/z=480 [M+H]$^+$.

Example 171

4-(cyclopropyloxy)-3-({[1-(4-methylpiperazin-1-yl)cyclopropyl]carbonyl}amino)-N-(5-phenyl-1,3,4-thiadiazol-2-yl)benzamide

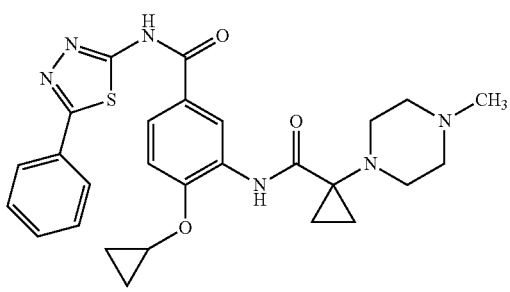 [SMILES: CN1CCN(C2(C(=O)Nc3cc(C(=O)Nc4nnc(-c5ccccc5)s4)ccc3OC3CC3)CC2)CC1]

100 mg (0.28 mmol) of 3-amino-4-(cyclopropyloxy)-N-(5-phenyl-1,3,4-thiadiazol-2-yl)benzamide (intermediate 132) were dissolved in 2 mL of anh DMF. 0.099 mL (0.57 mmol) of N-ethyl-N-isopropylpropan-2-amine, 63 mg (0.28 mmol) of 1-(4-methylpiperazin-1-yl)cyclopropanecarboxylic acid hydrochloride and 177 mg (0.34 mmol) of PYBOP were added. It was stirred overnight at rt. The precipitate was filtered off and washed three times with water. The solid material was purified by HPLC (method 5) giving a solid material, which was triturated in DMF at 45° C. and then filtered off.

The solid was triturated twice with ethyl acetate and dried under vacuum yielding 31.8 mg (22%) of the title compound.

$^1$H-NMR (400 MHz, DMSO-d$_6$): δ [ppm]=0.86-1.01 (m, 4H), 1.09-1.22 (m, 4H), 2.25 (s, 3H), 2.39-2.48 (m, 4H, partly overlapping with the DMSO signal), 4.13-4.19 (m, 1H), 7.47-7.59 (m, 4H), 7.94-8.01 (m, 3H), 9.05 (d, 1H), 10.48 (s, 1H).

LC-MS (method 3): R$_t$=0.87 min; MS (ESIpos): m/z=519 [M+H]$^+$.

Example 172

3-{[(4-ethylpiperazin-1-yl)acetyl]amino}-N-(5-phenyl-1,3,4-thiadiazol-2-yl)-4-(trifluoromethoxy)benzamide

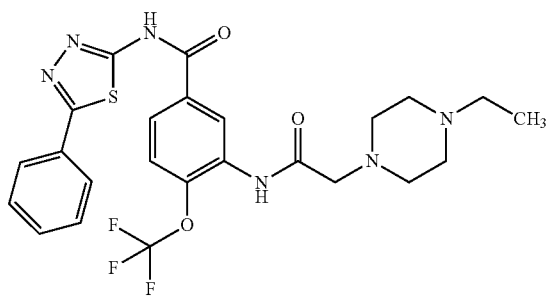 [SMILES: CCN1CCN(CC(=O)Nc2cc(C(=O)Nc3nnc(-c4ccccc4)s3)ccc2OC(F)(F)F)CC1]

To a suspension of 120 mg (0.26 mmol) of the compound from intermediate 41 in 1.5 mL of DMF were added 0.07 mL of triethylamine (0.53 mmol, 2 equiv), 0.07 mL of 1-ethylpiperazine (0.53 mmol, 2 equiv), and 9.0 mg of potassium iodide (0.05 mmol, 0.2 equiv). The reaction mixture was stirred at room temperature over night. After filtration, purification by HPLC (method 2) provided a solid, which was triturated with ethanol, collected by filtration and dried. 49.8 mg (35% of theory) of the title compound were obtained.

$^1$H-NMR (300 MHz, DMSO-d$_6$): δ [ppm]=1.02 (t, 3H), 2.42 (m, 2H), 2.45-2.56 (m, 4H), 2.57-2.70 (m, 4H), 3.23 (s, 2H), 7.44-7.57 (m, 3H), 7.57-7.64 (m, 1H), 7.90-8.05 (m, 3H), 8.98 (d, 1H), 9.92 (s, 1H), 12.90 (s, 1H).

LC-MS (method 4): R$_t$=1.01 min; MS (ESIpos): m/z=535 [M+H]$^+$.

Example 173

4-chloro-3-{[(4-methylpiperazin-1-yl)acetyl]amino}-N-(5-phenyl-1,3,4-thiadiazol-2-yl)benzamide

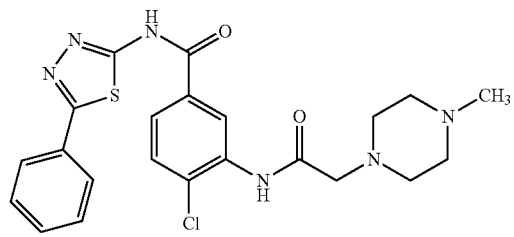 [SMILES: CN1CCN(CC(=O)Nc2cc(C(=O)Nc3nnc(-c4ccccc4)s3)ccc2Cl)CC1]

To a suspension of 310 mg (0.76 mmol) of the compound from intermediate 136 in 6 mL of DMF were added 0.21 mL of triethylamine (1.52 mmol, 2 equiv), 0.17 mL of 1-methylpiperazine (1.52 mmol, 2 equiv), and 25.0 mg of potassium iodide (0.15 mmol, 0.2 equiv). The reaction mixture was stirred at room temperature over night. After concentration, the remaining solid was triturated with a mixture of 15 mL of water and 10 mL of ethanol, stirred for 30 minutes, collected by filtration and dried. 244 mg (64% of theory) of the title compound were obtained.

Example 174

4-cyano-3-{[(4-methylpiperazin-1-yl)acetyl]amino}-N-(5-phenyl-1,3,4-thiadiazol-2-yl)benzamide

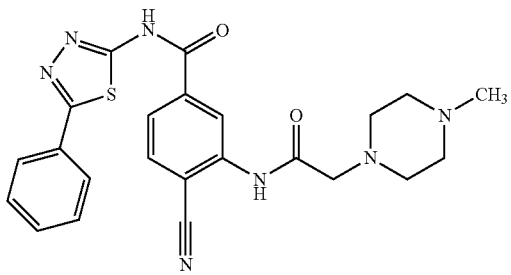 [SMILES: CN1CCN(CC(=O)Nc2cc(C(=O)Nc3nnc(-c4ccccc4)s3)ccc2C#N)CC1]

To a suspension of 120 mg (0.30 mmol) of the compound from intermediate 140 in 3 mL of DMF were added 0.08 mL of triethylamine (0.60 mmol, 2 equiv), 0.07 mL of 1-methylpiperazine (0.60 mmol, 2 equiv), and 10.0 mg of potassium iodide (0.06 mmol, 0.2 equiv). The reaction mixture was stirred at room temperature over night. After concentration, the remaining solid was triturated with a mixture of 15 mL of water and 10 mL of ethanol, stirred for 30 minutes, collected by filtration and dried. 61.0 mg (42% of theory) of the title compound were obtained.

$^1$H-NMR (400 MHz, DMSO-$d_6$): δ [ppm]=2.40 (s, 3H), 2.65-2.80 (m, 8H), 3.29 (s, 2H), 7.48-7.56 (m, 3H), 7.92-7.98 (m, 3H), 8.01-8.05 (m, 1H), 8.67-8.73 (m, 1H), 10.22 (s, 1H).

LC-MS (method 4): $R_t$=0.89 min; MS (ESIpos): m/z=462 [M+H]$^+$.

Example 175

4-(difluoromethoxy)-N-[5-(2-methylphenyl)-1,3,4-thiadiazol-2-yl]-3-{[(4-methylpiperazin-1-yl)acetyl]amino}benzamide

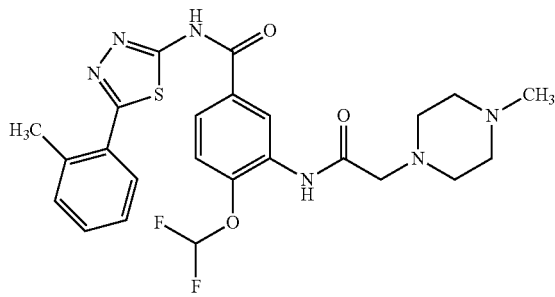

$^1$H-NMR (300 MHz, DMSO-$d_6$): δ [ppm]=2.30 (s, 3H), 2.54-2.70 (m, 8H), 3.25 (s, 2H), 7.48-7.58 (m, 3H), 7.72 (d, 1H), 7.89-8.01 (m, 3H), 8.95 (d, 1H), 9.99 (s, 1H), 12.60 (s, 1H).

LC-MS (method 4): $R_t$=0.85 min; MS (ESIpos): m/z=471 [M+H]$^+$.

To a suspension of 116 mg (0.24 mmol) of the compound of intermediate 143 in 2 mL of DMF were added 0.07 mL of triethylamine (0.49 mmol, 2 equiv), 0.05 mL of 1-methylpiperazine (0.49 mmol, 2 equiv), and 8.1 mg of potassium iodide (0.05 mmol, 0.2 equiv). The reaction mixture was stirred at room temperature for 4 h. 3 mL of water and 3 mL of ethanol were added and the mixture was stirred for 10 minutes. The precipitate was collected by filtration, washed with water and dried. The remaining solid was triturated with 10 mL of ethanol, stirred for 30 minutes at 75° C., collected by filtration at 55° C. and dried. Purification by HPLC (column: chromatorex C18, 10 µm, 195×51 mm, mobile phase: acetonitrile/water gradient) yielded 18.5 mg (14% of theory) of the title compound.

$^1$H-NMR (300 MHz, DMSO-$d_6$): δ [ppm]=2.23 (s, 3H), 2.43-2.54 (m, 4H), 2.53 (s, 3H), 2.55-2.68 (m, 4H), 3.21 (s, 2H), 7.33-7.47 (m, 4H), 7.46 (t, 1H), 7.67-7.74 (m, 1H), 7.99 (dd, 1H), 9.01 (d, 1H), 9.91 (s, 1H), 13.06 (s, 1H).

LC-MS (method 3): $R_t$=0.77 min; MS (ESIpos): m/z=517 [M+H]$^+$.

Example 176

4-(methoxymethyl)-N-[5-(2-methylphenyl)-1,3,4-thiadiazol-2-yl]-3-[(morpholin-4-ylacetyl)amino]benzamide

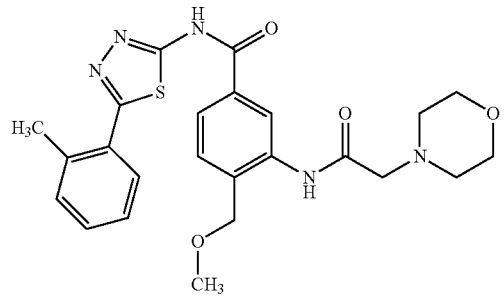 [SMILES: COCc1ccc(C(=O)Nc2nnc(-c3ccccc3C)s2)cc1NC(=O)CN1CCOCC1]

To a suspension of 180 mg (0.42 mmol) of the compound of intermediate 146 in 4 mL of DMF were added 0.12 mL of triethylamine (0.84 mmol, 2 equiv), 0.07 mL of morpholine (0.84 mmol, 2 equiv), and 14.0 mg of potassium iodide (0.08 mmol, 0.2 equiv). The reaction mixture was stirred at room temperature over night. After concentration, the remaining solid was triturated with 15 mL of water and 10 mL of ethanol, stirred for 30 minutes, collected by filtration and dried. The remaining solid was triturated with 10 mL of ethanol and stirred under reflux, collected by filtration and dried. 137 mg (65% of theory) of the title compound were obtained.

$^1$H-NMR (400 MHz, DMSO-$d_6$): δ [ppm]=2.54 (s, 3H), 2.55-2.60 (m, 4H), 3.19 (s, 2H), 3.38 (s, 3H), 3.64-3.72 (m, 4H), 4.58 (s, 2H), 7.33-7.47 (m, 3H), 7.53 (d, 1H), 7.71 (d, 1H), 7.87-7.93 (m, 1H), 8.79 (s, 1H), 10.01 (s, 1H), 13.23 (s, 1H).

LC-MS (method 4): $R_t$=1.03 min; MS (ESIpos): m/z=482 [M+H]$^+$.

Example 177

4-(methoxymethyl)-N-[5-(2-methylphenyl)-1,3,4-thiadiazol-2-yl]-3-{[(4-methylpiperazin-1-yl)acetyl]amino}benzamide hydrochloride (1:1)

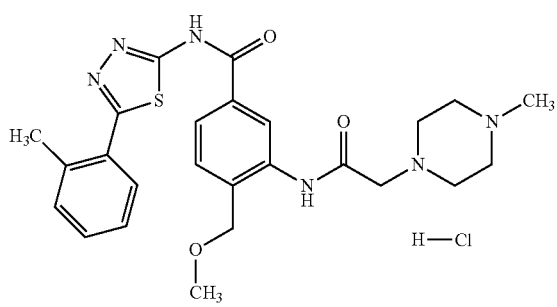

To a suspension of 180 mg (0.42 mmol) of the compound of intermediate 146 in 4 mL of DMF were added 0.12 mL of triethylamine (0.84 mmol, 2 equiv), 0.09 mL of 1-methylpiperazine (0.84 mmol, 2 equiv), and 14.0 mg of potassium iodide (0.08 mmol, 0.2 equiv). The reaction mixture was stirred at room temperature over night. After concentration, the remaining solid was triturated with 15 mL of water and 10 mL of ethanol, stirred for 30 minutes, collected by filtration and dried. The remaining solid was triturated with 10 mL of ethanol and stirred under reflux, collected by filtration and dried. 78 mg (34% of theory) of the title compound were obtained.

$^1$H-NMR (400 MHz, DMSO-d$_6$): δ [ppm]=2.54 (s, 3H), 2.65-2.95 (m, 4H), 2.75 (s, 3H), 3.03-3.27 (m, 4H), 3.36 (s, 3H), 4.59 (s, 2H), 7.33-7.49 (m, 4H), 7.55 (d, 1H), 7.71 (d, 1H), 7.95 (dd, 1H), 8.66 (s, 1H), 9.88 (s, 1H).

LC-MS (method 4): R$_t$=0.95 min; MS (ESIpos): m/z=495 [M+H−HCl]$^+$.

The following examples were prepared in analogy to the described methods, supra.

TABLE 1

| Example No | Structure | IUPAC Name | R$_t$ [min] method |
|---|---|---|---|
| 178 | 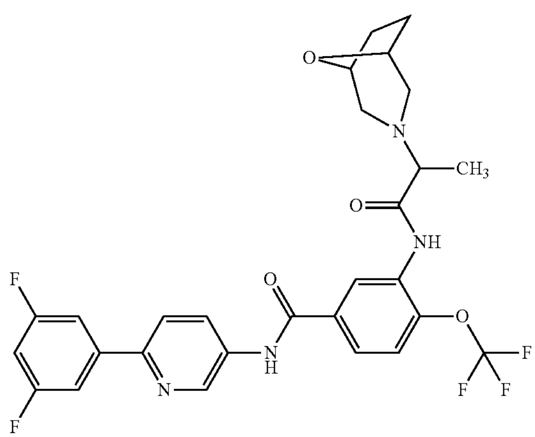 [SMILES: CC(C(=O)Nc1cc(C(=O)Nc2ccc(-c3cc(F)cc(F)c3)nc2)ccc1OC(F)(F)F)N1CC2CCC(C1)O2] | N-[6-(3,5-difluorophenyl)pyridin-3-yl]-3-{[2-(8-oxa-3-azabicyclo[3.2.1]oct-3-yl)propanoyl]amino}-4-(trifluoromethoxy)benzamide | 1.317 |
| 179 | 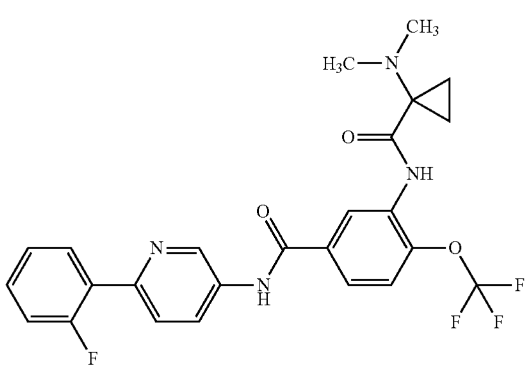 [SMILES: CN(C)C1(C(=O)Nc2cc(C(=O)Nc3ccc(-c4ccccc4F)nc3)ccc2OC(F)(F)F)CC1] | 3-({[1-(dimethylamino)cyclopropyl]carbonyl}amino)-N-[6-(2-fluorophenyl)pyridin-3-yl]-4-(trifluoromethoxy)benzamide | 1.297 |

TABLE 1-continued

| Example No | Structure | IUPAC Name | R$_t$ [min] method |
|---|---|---|---|
| 180 | 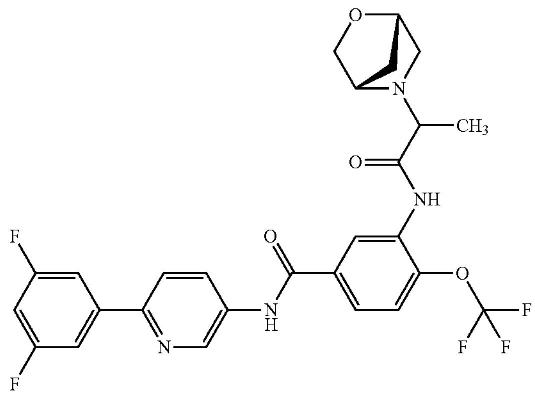 [SMILES: CC(C(=O)Nc1cc(C(=O)Nc2ccc(-c3cc(F)cc(F)c3)nc2)ccc1OC(F)(F)F)N1C[C@@H]2C[C@H]1CO2] | N-[6-(3,5-difluorophenyl)pyridin-3-yl]-3-({(2R*)-2-[(1S,4S)-2-oxa-5-azabicyclo[2.2.1]hept-5-yl]propanoyl}amino)-4-(trifluoromethoxy)benzamide | 0.877 |
| 181 | 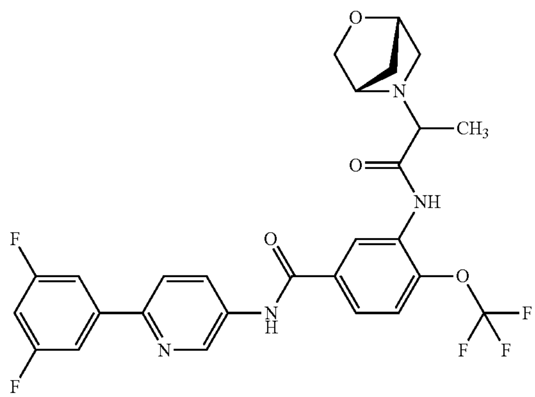 [SMILES: CC(C(=O)Nc1cc(C(=O)Nc2ccc(-c3cc(F)cc(F)c3)nc2)ccc1OC(F)(F)F)N1C[C@@H]2C[C@H]1CO2] | N-[6-(3,5-difluorophenyl)pyridin-3-yl]-3-({(2S*)-2-[(1S,4S)-2-oxa-5-azabicyclo[2.2.1]hept-5-yl]propanoyl}amino)-4-(trifluoromethoxy)benzamide | 0.887 |
| 182 | 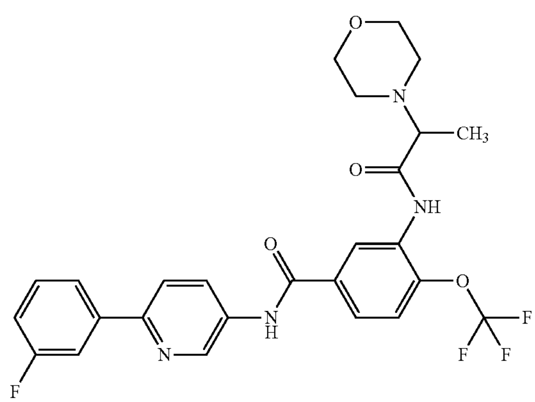 [SMILES: CC(C(=O)Nc1cc(C(=O)Nc2ccc(-c3cccc(F)c3)nc2)ccc1OC(F)(F)F)N1CCOCC1] | N-[6-(3-fluorophenyl)pyridin-3-yl]-3-{[2-(morpholin-4-yl)propanoyl]amino}-4-(trifluoromethoxy)benzamide | 1.007 |
| 183 | 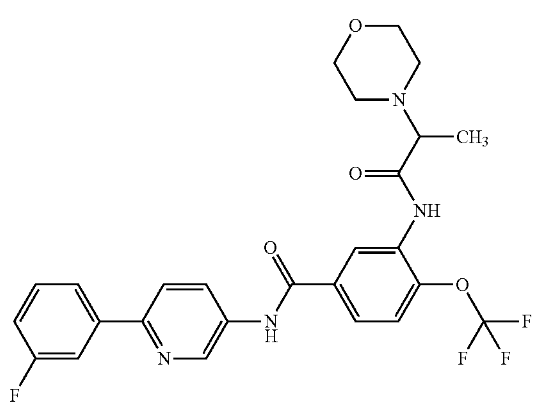 [SMILES: CC(C(=O)Nc1cc(C(=O)Nc2ccc(-c3cccc(F)c3)nc2)ccc1OC(F)(F)F)N1CCOCC1] | N-[6-(3-fluorophenyl)pyridin-3-yl]-3-{[2-(morpholin-4-yl)propanoyl]amino}-4-(trifluoromethoxy)benzamide | 1.007 |

TABLE 1-continued
| Example No | Structure | IUPAC Name | R_t [min] method |
|---|---|---|---|
| 184 | 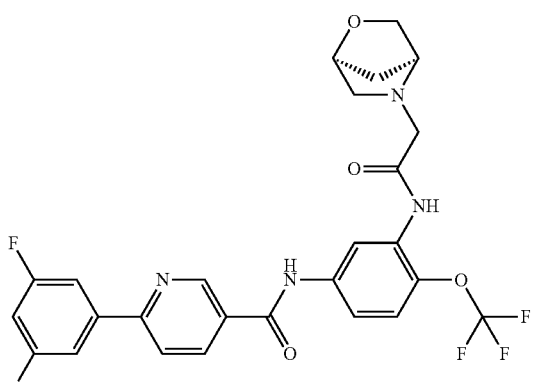 | 6-(3,5-difluorophenyl)-N-[3-{[(1S,4S)-2-oxa-5-azabicyclo[2.2.1]hept-5-ylacetyl]amino}-4-(trifluoromethoxy)phenyl]nicotinamide | 0.887 |
| 185 | 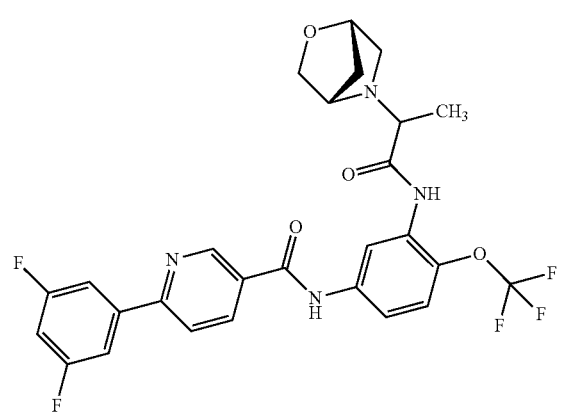 [SMILES: CC(C(=O)Nc1cc(NC(=O)c2ccc(-c3cc(F)cc(F)c3)nc2)ccc1OC(F)(F)F)N1C[C@@H]2C[C@H]1CO2] | 6-(3,5-difluorophenyl)-N-[3-({(2R*)-2-[(1S,4S)-2-oxa-5-azabicyclo[2.2.1]hept-5-yl]propanoyl}amino)-4-(trifluoromethoxy)phenyl]nicotinamide | 0.877 |
| 186 | 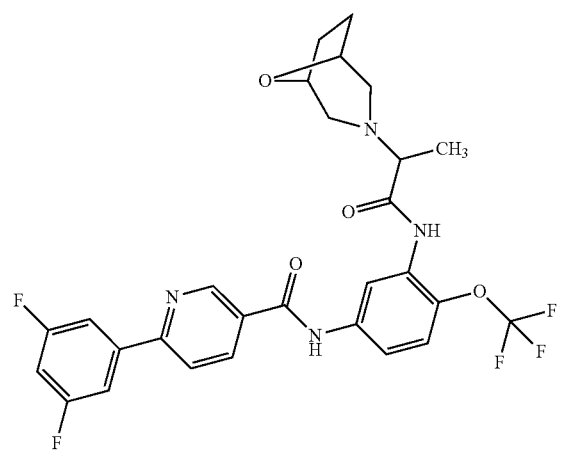 [SMILES: CC(C(=O)Nc1cc(NC(=O)c2ccc(-c3cc(F)cc(F)c3)nc2)ccc1OC(F)(F)F)N1CC2CCC(C1)O2] | 6-(3,5-difluorophenyl)-N-[3-{[2-(8-oxa-3-azabicyclo[3.2.1]oct-3-yl)propanoyl]amino}-4-(trifluoromethoxy)phenyl]nicotinamide | 1.317 |

TABLE 1-continued

| Example No | Structure | IUPAC Name | R_t [min] method |
|---|---|---|---|
| 187 | 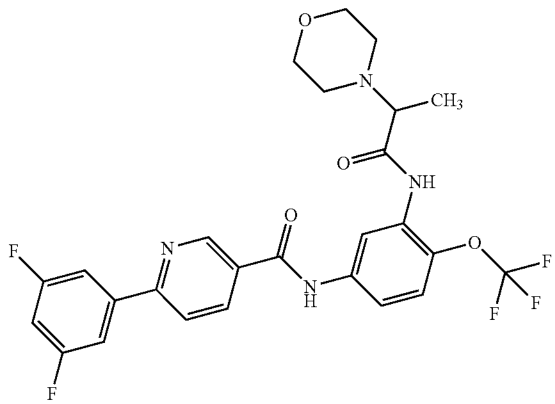 [SMILES: CC(C(=O)Nc1cc(NC(=O)c2ccc(-c3cc(F)cc(F)c3)nc2)ccc1OC(F)(F)F)N1CCOCC1] | 6-(3,5-difluorophenyl)-N-[3-{[2-(morpholin-4-yl)propanoyl]amino}-4-(trifluoromethoxy)phenyl]nicotinamide | 1.077 |
| 188 | 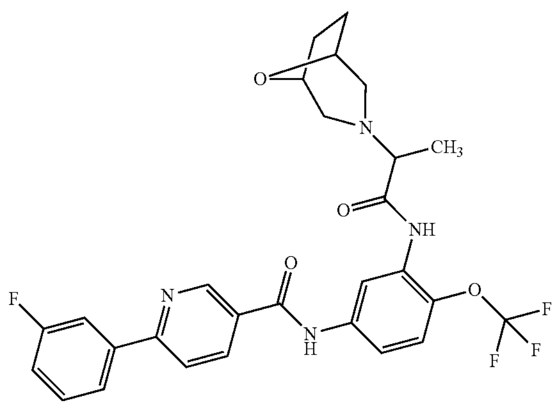 [SMILES: CC(C(=O)Nc1cc(NC(=O)c2ccc(-c3cccc(F)c3)nc2)ccc1OC(F)(F)F)N1CC2CCC(C1)O2] | 6-(3-fluorophenyl)-N-[3-{[2-(8-oxa-3-azabicyclo[3.2.1]oct-3-yl)propanoyl]amino}-4-(trifluoromethoxy)phenyl]nicotinamide | 1.267 |
| 189 | 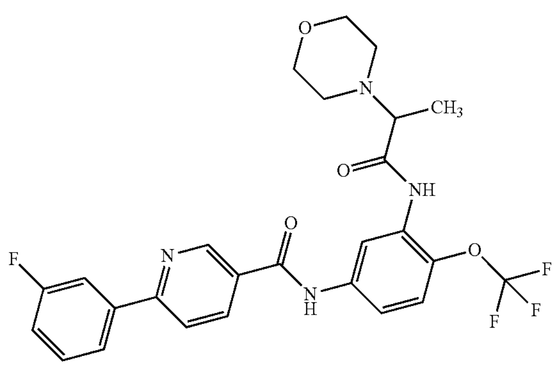 [SMILES: CC(C(=O)Nc1cc(NC(=O)c2ccc(-c3cccc(F)c3)nc2)ccc1OC(F)(F)F)N1CCOCC1] | 6-(3-fluorophenyl)-N-[3-{[2-(morpholin-4-yl)propanoyl]amino}-4-(trifluoromethoxy)phenyl]nicotinamide | 1.017 |
| 190 | 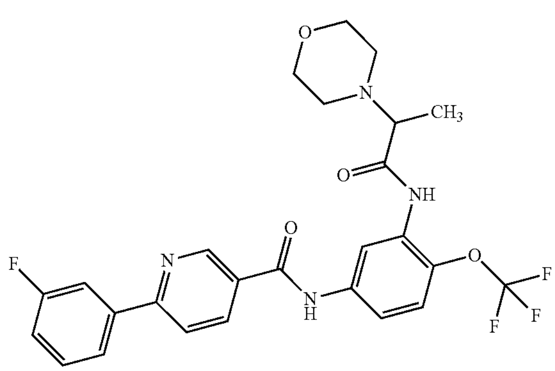 [SMILES: CC(C(=O)Nc1cc(NC(=O)c2ccc(-c3cccc(F)c3)nc2)ccc1OC(F)(F)F)N1CCOCC1] | 6-(3-fluorophenyl)-N-[3-{[2-(morpholin-4-yl)propanoyl]amino}-4-(trifluoromethoxy)phenyl]nicotinamide | 1.017 |

TABLE 1-continued

| Example No | Structure | IUPAC Name | R_t [min] method |
|---|---|---|---|
| 191 | 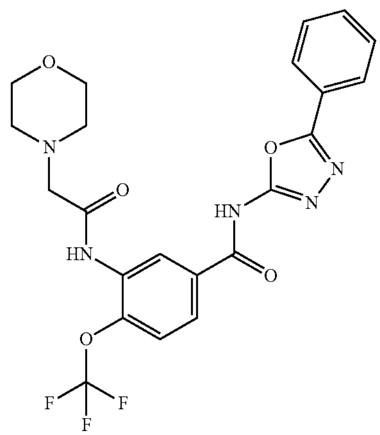 [SMILES: O=C(CN1CCOCC1)Nc1cc(C(=O)Nc2nnc(-c3ccccc3)o2)ccc1OC(F)(F)F] | 3-[(morpholin-4-ylacetyl)amino]-N-(5-phenyl-1,3,4-oxadiazol-2-yl)-4-(trifluoromethoxy)benzamide | 0.807 |
| 192 | 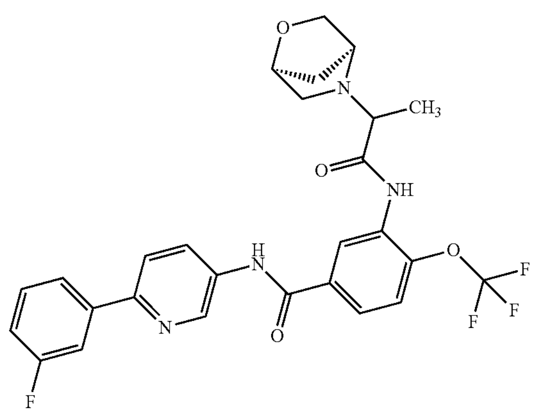 [SMILES: CC(C(=O)Nc1cc(C(=O)Nc2ccc(-c3cccc(F)c3)nc2)ccc1OC(F)(F)F)N1C[C@@H]2C[C@H]1CO2] | N-[6-(3-fluorophenyl)pyridin-3-yl]-3-({2-[(1S,4S)-2-oxa-5-azabicyclo[2.2.1]hept-5-yl]propanoyl}amino)-4-(trifluoromethoxy)benzamide | 0.837 |
| 193 | 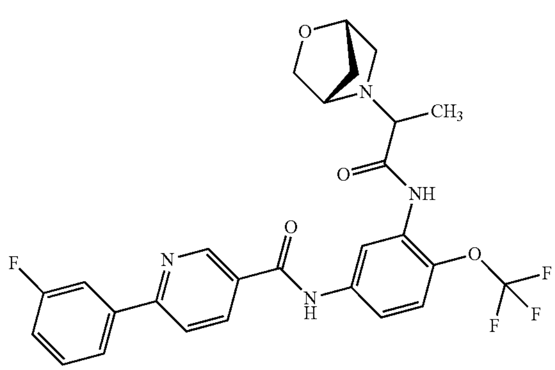 [SMILES: CC(C(=O)Nc1cc(NC(=O)c2ccc(-c3cccc(F)c3)nc2)ccc1OC(F)(F)F)N1C[C@@H]2C[C@H]1CO2] | 6-(3-fluorophenyl)-N-[3-({(2R*)-2-[(1S,4S)-2-oxa-5-azabicyclo[2.2.1]hept-5-yl]propanoyl}amino)-4-(trifluoromethoxy)phenyl]nicotinamide | 0.847 |

TABLE 1-continued

| Example No | Structure | IUPAC Name | $R_t$ [min] method |
|---|---|---|---|
| 194 | 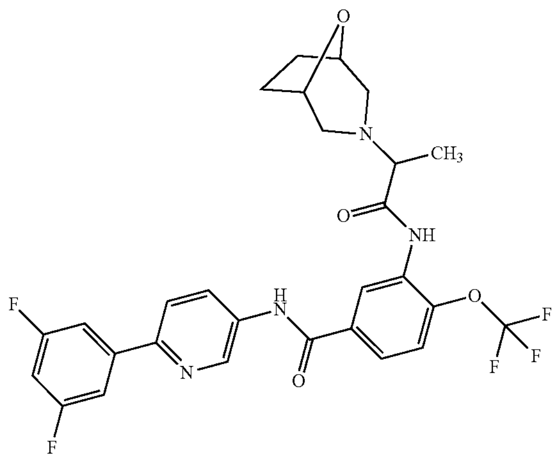 [SMILES: CC(C(=O)Nc1cc(C(=O)Nc2ccc(-c3cc(F)cc(F)c3)nc2)ccc1OC(F)(F)F)N1CC2CCC(C1)O2] | N-[6-(3,5-difluorophenyl)pyridin-3-yl]-3-{[2-(8-oxa-3-azabicyclo[3.2.1]oct-3-yl)propanoyl]amino}-4-(trifluoromethoxy)benzamide | 1.317 |
| 195 | 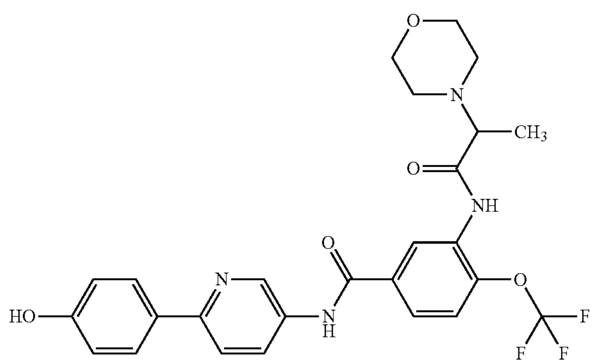 [SMILES: CC(C(=O)Nc1cc(C(=O)Nc2ccc(-c3ccc(O)cc3)nc2)ccc1OC(F)(F)F)N1CCOCC1] | N-[6-(4-hydroxyphenyl)pyridin-3-yl]-3-{[2-(morpholin-4-yl)propanoyl]amino}-4-(trifluoromethoxy)benzamide | 0.737 |
| 196 | 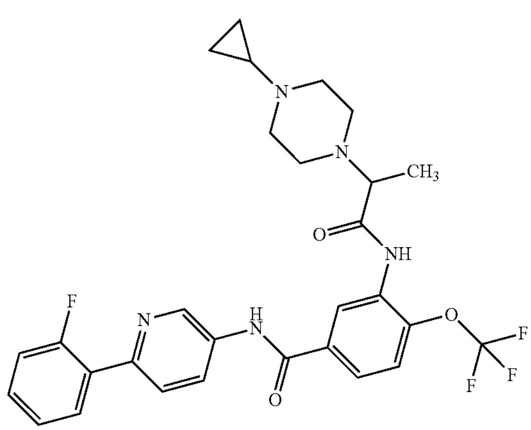 [SMILES: CC(C(=O)Nc1cc(C(=O)Nc2ccc(-c3ccccc3F)nc2)ccc1OC(F)(F)F)N1CCN(C2CC2)CC1] | 3-{[2-(4-cyclopropylpiperazin-1-yl)propanoyl]amino}-N-[6-(2-fluorophenyl)pyridin-3-yl]-4-(trifluoromethoxy)benzamide | 0.867 |

TABLE 1-continued

| Example No | Structure | IUPAC Name | R_t [min] method |
|---|---|---|---|
| 197 | 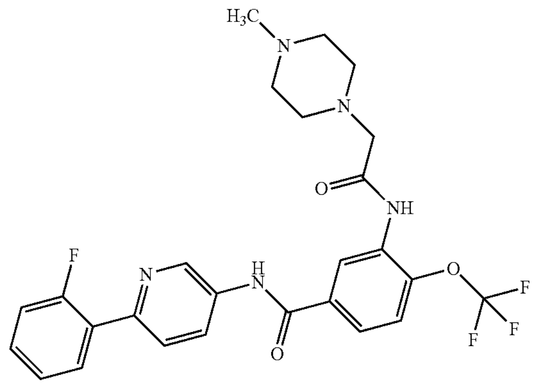 [SMILES: CN1CCN(CC(=O)Nc2cc(C(=O)Nc3ccc(-c4ccccc4F)nc3)ccc2OC(F)(F)F)CC1] | N-[6-(2-fluorophenyl)pyridin-3-yl]-3-{[(4-methylpiperazin-1-yl)acetyl]amino}-4-(trifluoromethoxy)benzamide | 0.787 |
| 198 | 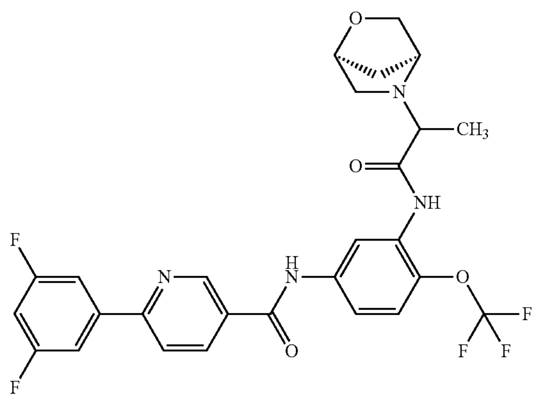 [SMILES: CC(C(=O)Nc1cc(NC(=O)c2ccc(-c3cc(F)cc(F)c3)nc2)ccc1OC(F)(F)F)N1C[C@@H]2C[C@H]1CO2] | 6-(3,5-difluorophenyl)-N-[3-({2-[(1S,4S)-2-oxa-5-azabicyclo[2.2.1]hept-5-yl]propanoyl}amino)-4-(trifluoromethoxy)phenyl]nicotinamide | 0.877 |
| 199 | 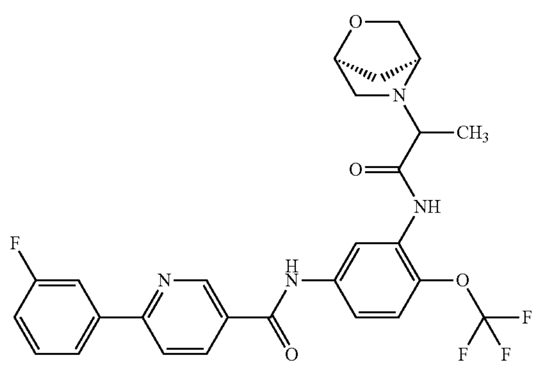 [SMILES: CC(C(=O)Nc1cc(NC(=O)c2ccc(-c3cccc(F)c3)nc2)ccc1OC(F)(F)F)N1C[C@@H]2C[C@H]1CO2] | 6-(3-fluorophenyl)-N-[3-({2-[(1S,4S)-2-oxa-5-azabicyclo[2.2.1]hept-5-yl]propanoyl}amino)-4-(trifluoromethoxy)phenyl]nicotinamide | 0.837 |
| 200 | 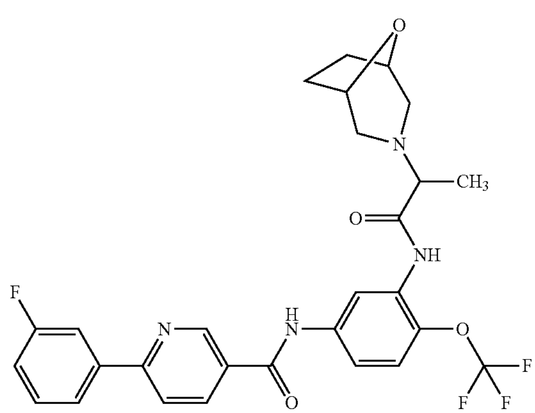 [SMILES: CC(C(=O)Nc1cc(NC(=O)c2ccc(-c3cccc(F)c3)nc2)ccc1OC(F)(F)F)N1CC2CCC(C1)O2] | 6-(3-fluorophenyl)-N-[3-{[2-(8-oxa-3-azabicyclo[3.2.1]oct-3-yl)propanoyl]amino}-4-(trifluoromethoxy)phenyl]nicotinamide | 1.267 |

TABLE 1-continued
| Example No | Structure | IUPAC Name | R_t [min] method |
|---|---|---|---|
| 201 | 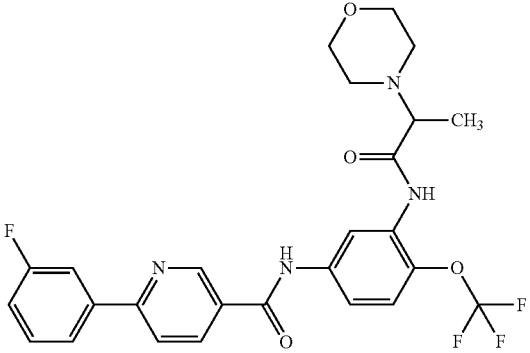 [SMILES: CC(C(=O)Nc1cc(NC(=O)c2ccc(-c3cccc(F)c3)nc2)ccc1OC(F)(F)F)N1CCOCC1] | 6-(3-fluorophenyl)-N-[3-{[2-(morpholin-4-yl)propanoyl]amino}-4-(trifluoromethoxy)phenyl]nicotinamide | 1.017 |
| 202 | 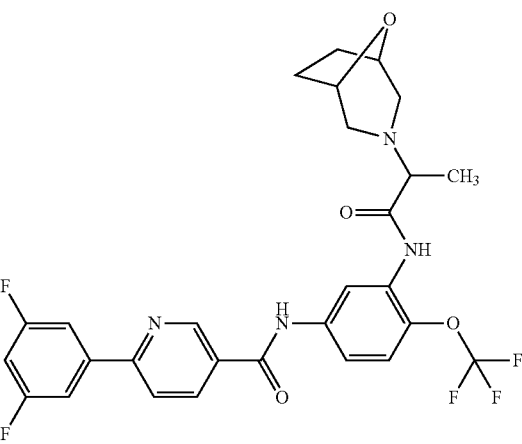 [SMILES: CC(C(=O)Nc1cc(NC(=O)c2ccc(-c3cc(F)cc(F)c3)nc2)ccc1OC(F)(F)F)N1CC2CCC(C1)O2] | 6-(3,5-difluorophenyl)-N-[3-{[2-(8-oxa-3-azabicyclo[3.2.1]oct-3-yl)propanoyl]amino}-4-(trifluoromethoxy)phenyl]nicotinamide | 1.317 |
| 203 | 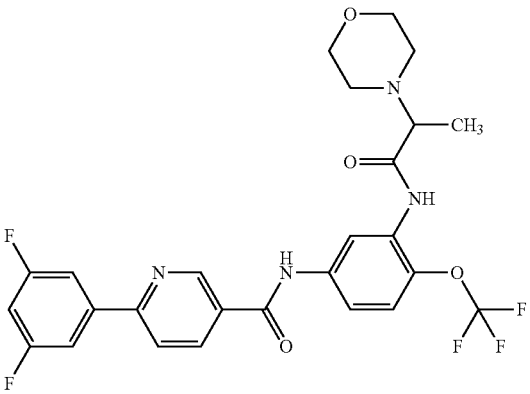 [SMILES: CC(C(=O)Nc1cc(NC(=O)c2ccc(-c3cc(F)cc(F)c3)nc2)ccc1OC(F)(F)F)N1CCOCC1] | 6-(3,5-difluorophenyl)-N-[3-{[2-(morpholin-4-yl)propanoyl]amino}-4-(trifluoromethoxy)phenyl]nicotinamide | 1.077 |

TABLE 1-continued
| Example No | Structure | IUPAC Name | R_t [min] method |
|---|---|---|---|
| 204 | 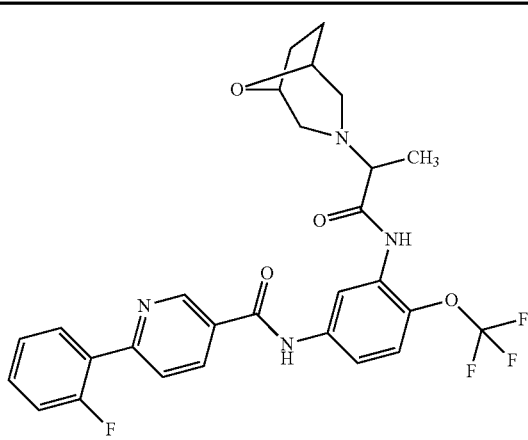 | 6-(2-fluorophenyl)-N-[3-{[2-(8-oxa-3-azabicyclo[3.2.1]oct-3-yl)propanoyl]amino}-4-(trifluoromethoxy)phenyl]nicotinamide | 1.237 |
| 205 | 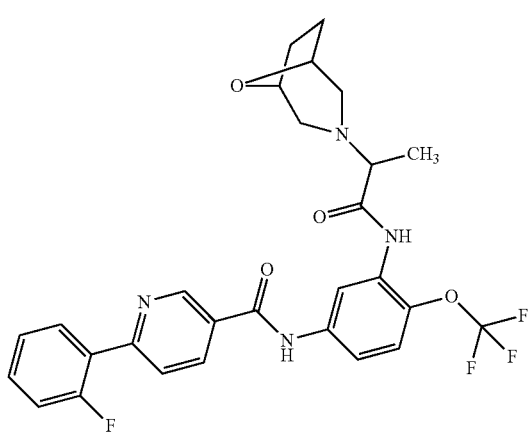 [SMILES: CC(C(=O)Nc1cc(NC(=O)c2ccc(-c3ccccc3F)nc2)ccc1OC(F)(F)F)N1CC2CCC(C1)O2] | 6-(2-fluorophenyl)-N-[3-{[2-(8-oxa-3-azabicyclo[3.2.1]oct-3-yl)propanoyl]amino}-4-(trifluoromethoxy)phenyl]nicotinamide | 1.237 |
| 206 | 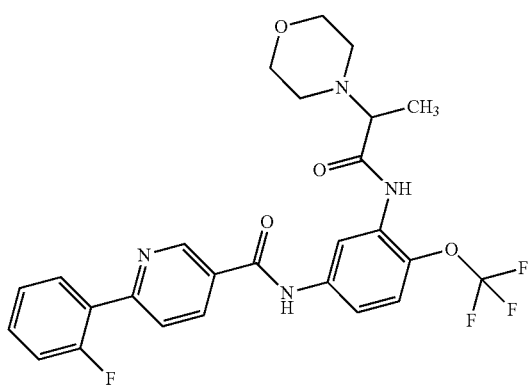 [SMILES: CC(C(=O)Nc1cc(NC(=O)c2ccc(-c3ccccc3F)nc2)ccc1OC(F)(F)F)N1CCOCC1] | 6-(2-fluorophenyl)-N-[3-{[2-(morpholin-4-yl)propanoyl]amino}-4-(trifluoromethoxy)phenyl]nicotinamide | 0.987 |

TABLE 1-continued

| Example No | Structure | IUPAC Name | R_t [min] method |
|---|---|---|---|
| 207 | 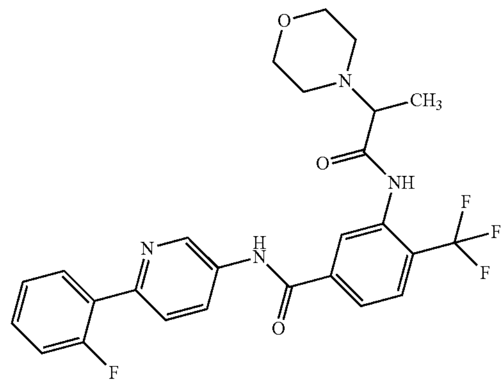 [SMILES: CC(C(=O)Nc1cc(C(=O)Nc2ccc(-c3ccccc3F)nc2)ccc1C(F)(F)F)N1CCOCC1] | N-[6-(2-fluorophenyl)pyridin-3-yl]-3-{[2-(morpholin-4-yl)propanoyl]amino}-4-(trifluoromethyl)benzamide | 0.957 |
| 208 | 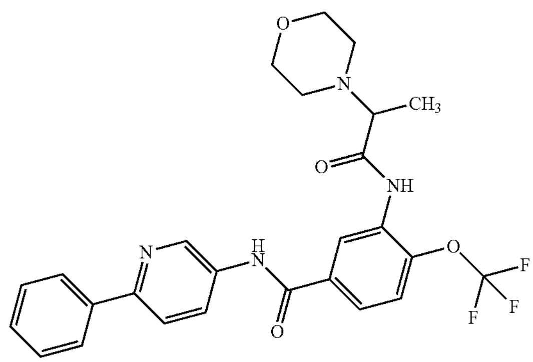 [SMILES: CC(C(=O)Nc1cc(C(=O)Nc2ccc(-c3ccccc3)nc2)ccc1OC(F)(F)F)N1CCOCC1] | 3-{[2-(morpholin-4-yl)propanoyl]amino}-N-(6-phenylpyridin-3-yl)-4-(trifluoromethoxy)benzamide | 0.937 |
| 209 | 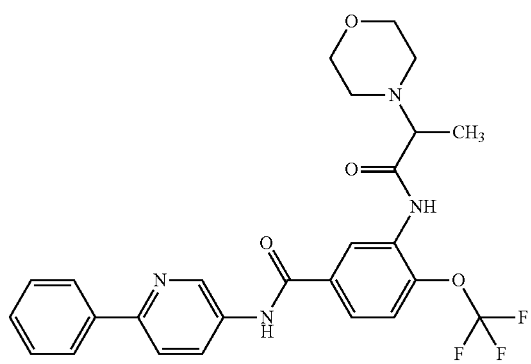 [SMILES: CC(C(=O)Nc1cc(C(=O)Nc2ccc(-c3ccccc3)nc2)ccc1OC(F)(F)F)N1CCOCC1] | 3-{[2-(morpholin-4-yl)propanoyl]amino}-N-(6-phenylpyridin-3-yl)-4-(trifluoromethoxy)benzamide | 0.937 |
| 210 | 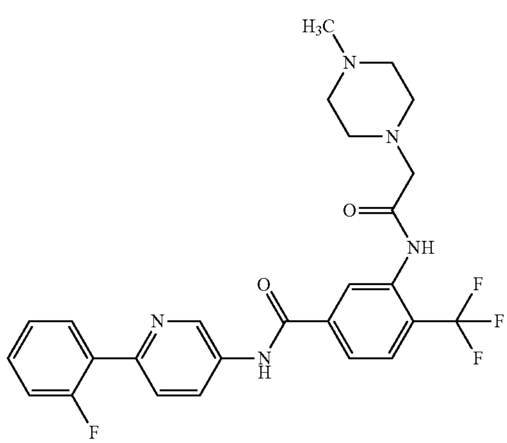 [SMILES: CN1CCN(CC(=O)Nc2cc(C(=O)Nc3ccc(-c4ccccc4F)nc3)ccc2C(F)(F)F)CC1] | N-[6-(2-fluorophenyl)pyridin-3-yl]-3-{[(4-methylpiperazin-1-yl)acetyl]amino}-4-(trifluoromethyl)benzamide | 0.767 |

TABLE 1-continued

| Example No | Structure | IUPAC Name | R_t [min] method |
|---|---|---|---|
| 211 | 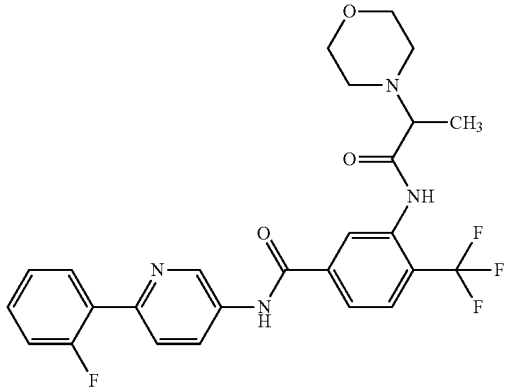 [SMILES: CC(C(=O)Nc1cc(C(=O)Nc2ccc(-c3ccccc3F)nc2)ccc1C(F)(F)F)N1CCOCC1] | N-[6-(2-fluorophenyl)pyridin-3-yl]-3-{[2-(morpholin-4-yl)propanoyl]amino}-4-(trifluoromethyl)benzamide | 0.957 |
| 212 | 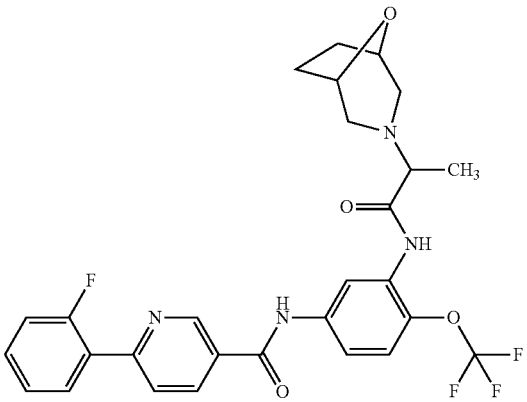 [SMILES: CC(C(=O)Nc1cc(NC(=O)c2ccc(-c3ccccc3F)nc2)ccc1OC(F)(F)F)N1CC2CCC(C1)O2] | 6-(2-fluorophenyl)-N-[3-{[2-(8-oxa-3-azabicyclo[3.2.1]oct-3-yl)propanoyl]amino}-4-(trifluoromethoxy)phenyl]nicotinamide | 1.237 |
| 213 | 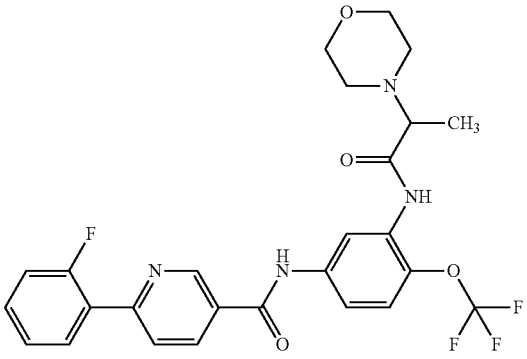 [SMILES: CC(C(=O)Nc1cc(NC(=O)c2ccc(-c3ccccc3F)nc2)ccc1OC(F)(F)F)N1CCOCC1] | 6-(2-fluorophenyl)-N-[3-{[2-(morpholin-4-yl)propanoyl]amino}-4-(trifluoromethoxy)phenyl]nicotinamide | 0.987 |
| 214 | 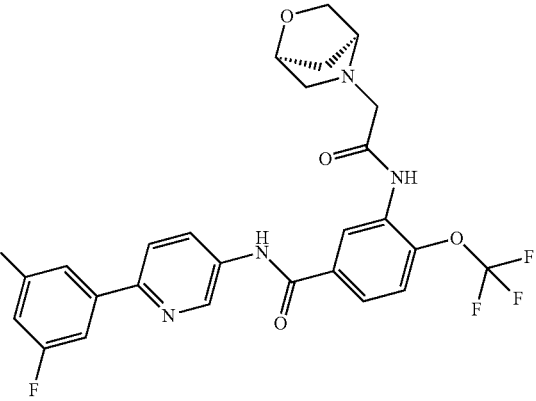 | N-[6-(3,5-difluorophenyl)pyridin-3-yl]-3-{[(1S,4S)-2-oxa-5-azabicyclo[2.2.1]hept-5-ylacetyl]amino}-4-(trifluoromethoxy)benzamide | 0.887 |

TABLE 1-continued

| Example No | Structure | IUPAC Name | R_t [min] method |
|---|---|---|---|
| 215 | 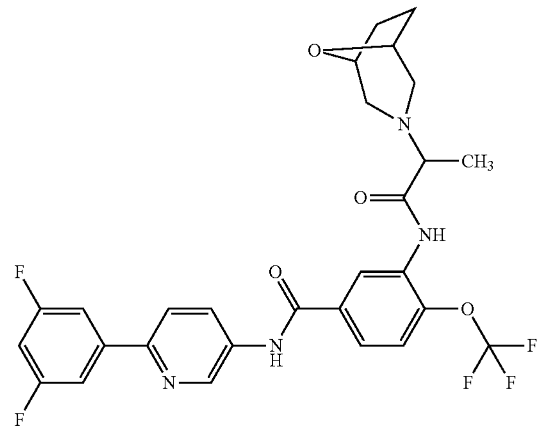 [SMILES: CC(C(=O)Nc1cc(C(=O)Nc2ccc(-c3cc(F)cc(F)c3)nc2)ccc1OC(F)(F)F)N1CC2CCC(C1)O2] | N-[6-(3,5-difluorophenyl)pyridin-3-yl]-3-{[2-(8-oxa-3-azabicyclo[3.2.1]oct-3-yl)propanoyl]amino}-4-(trifluoromethoxy)benzamide | 1.317 |
| 216 | 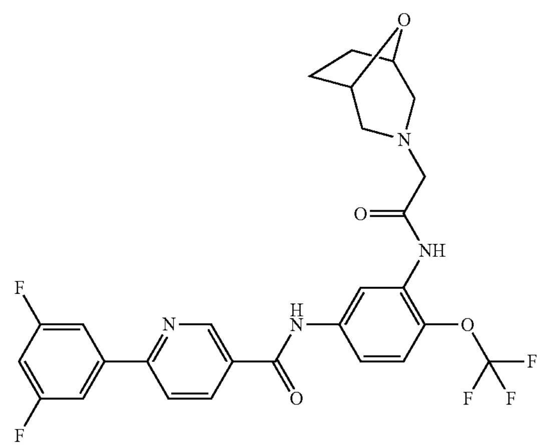 [SMILES: O=C(CN1CC2CCC(C1)O2)Nc1cc(NC(=O)c2ccc(-c3cc(F)cc(F)c3)nc2)ccc1OC(F)(F)F] | 6-(3,5-difluorophenyl)-N-{3-[(8-oxa-3-azabicyclo[3.2.1]oct-3-ylacetyl)amino]-4-(trifluoromethoxy)phenyl}nicotinamide | 1.277 |
| 217 | 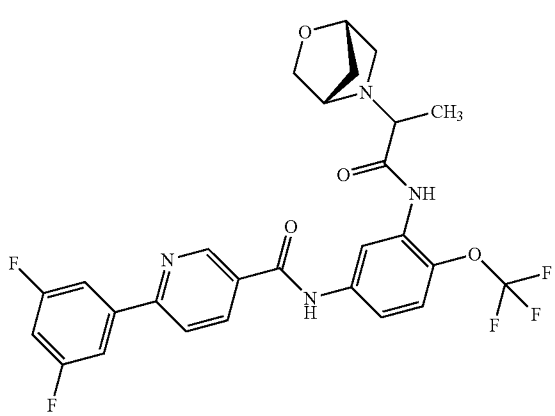 [SMILES: CC(C(=O)Nc1cc(NC(=O)c2ccc(-c3cc(F)cc(F)c3)nc2)ccc1OC(F)(F)F)N1C[C@@H]2C[C@H]1CO2] | 6-(3,5-difluorophenyl)-N-[3-({(2S*)-2-[(1S,4S)-2-oxa-5-azabicyclo[2.2.1]hept-5-yl]propanoyl}amino)-4-(trifluoromethoxy)phenyl]nicotinamide | 0.887 |

TABLE 1-continued

| Example No | Structure | IUPAC Name | R<sub>t</sub> [min] method |
|---|---|---|---|
| 218 | 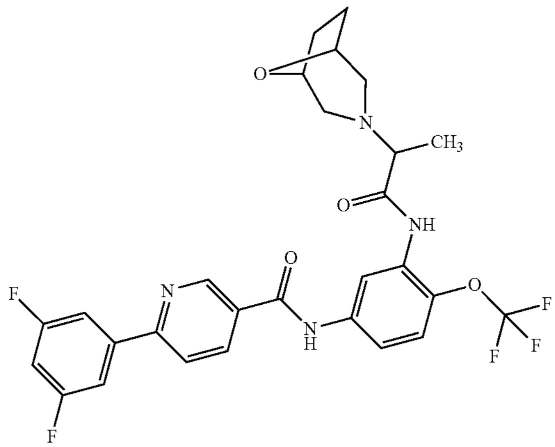 [SMILES: CC(C(=O)Nc1cc(NC(=O)c2ccc(-c3cc(F)cc(F)c3)nc2)ccc1OC(F)(F)F)N1CC2CCC(C1)O2] | 6-(3,5-difluorophenyl)-N-[3-{[2-(8-oxa-3-azabicyclo[3.2.1]oct-3-yl)propanoyl]amino}-4-(trifluoromethoxy)phenyl]nicotinamide | 1.317 |
| 219 | 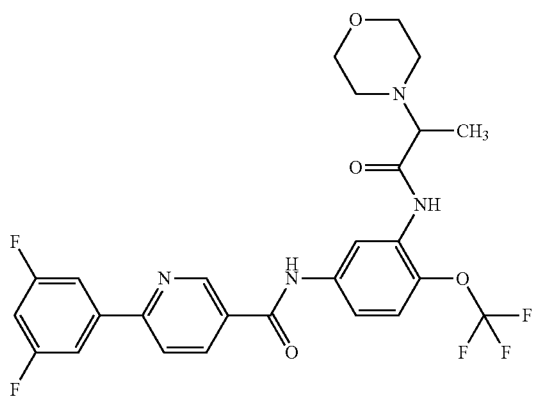 [SMILES: CC(C(=O)Nc1cc(NC(=O)c2ccc(-c3cc(F)cc(F)c3)nc2)ccc1OC(F)(F)F)N1CCOCC1] | 6-(3,5-difluorophenyl)-N-[3-{[2-(morpholin-4-yl)propanoyl]amino}-4-(trifluoromethoxy)phenyl]nicotinamide | 1.077 |
| 220 | 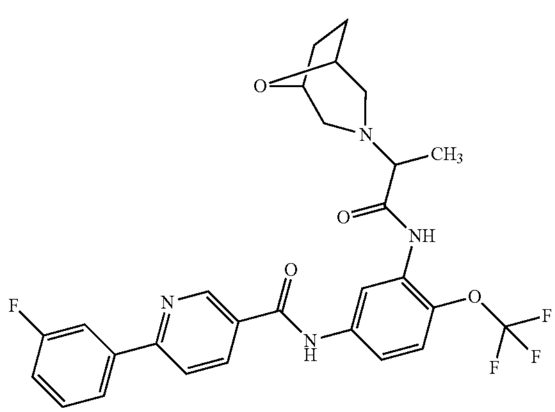 [SMILES: CC(C(=O)Nc1cc(NC(=O)c2ccc(-c3cccc(F)c3)nc2)ccc1OC(F)(F)F)N1CC2CCC(C1)O2] | 6-(3-fluorophenyl)-N-[3-{[2-(8-oxa-3-azabicyclo[3.2.1]oct-3-yl)propanoyl]amino}-4-(trifluoromethoxy)phenyl]nicotinamide | 1.267 |

TABLE 1-continued

| Example No | Structure | IUPAC Name | R_t [min] method |
|---|---|---|---|
| 221 | 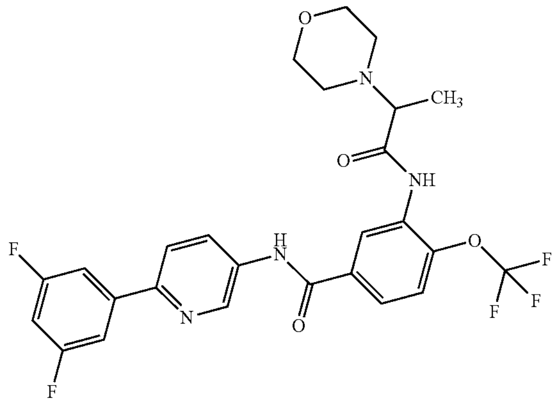 [SMILES: CC(C(=O)Nc1cc(C(=O)Nc2ccc(-c3cc(F)cc(F)c3)nc2)ccc1OC(F)(F)F)N1CCOCC1] | N-[6-(3,5-difluorophenyl)pyridin-3-yl]-3-{[2-(morpholin-4-yl)propanoyl]amino}-4-(trifluoromethoxy)benzamide | 1.087 |
| 222 | 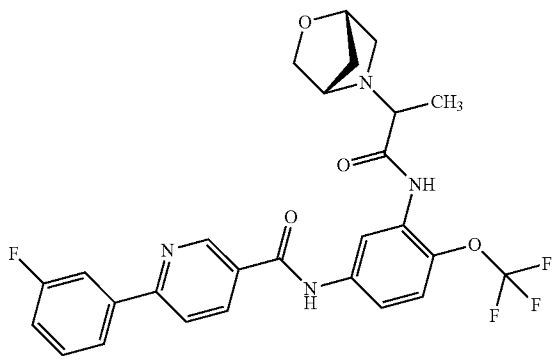 [SMILES: CC(C(=O)Nc1cc(NC(=O)c2ccc(-c3cccc(F)c3)nc2)ccc1OC(F)(F)F)N1C[C@@H]2C[C@H]1CO2] | 6-(3-fluorophenyl)-N-[3-({(2S*)-2-[(1S,4S)-2-oxa-5-azabicyclo[2.2.1]hept-5-yl]propanoyl}amino)-4-(trifluoromethoxy)phenyl]nicotinamide | 0.837 |
| 223 | 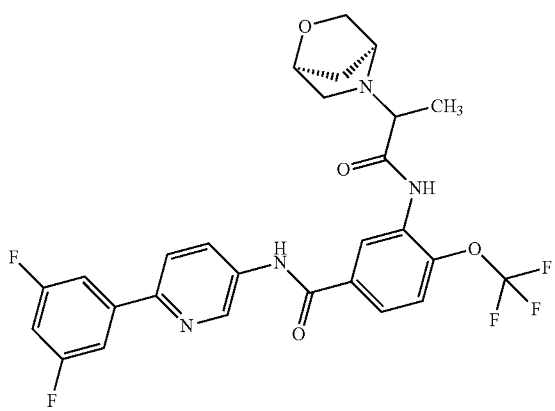 [SMILES: CC(C(=O)Nc1cc(C(=O)Nc2ccc(-c3cc(F)cc(F)c3)nc2)ccc1OC(F)(F)F)N1C[C@@H]2C[C@H]1CO2] | N-[6-(3,5-difluorophenyl)pyridin-3-yl]-3-({2-[(1S,4S)-2-oxa-5-azabicyclo[2.2.1]hept-5-yl]propanoyl}amino)-4-(trifluoromethoxy)benzamide | 0.877 |
| 224 | 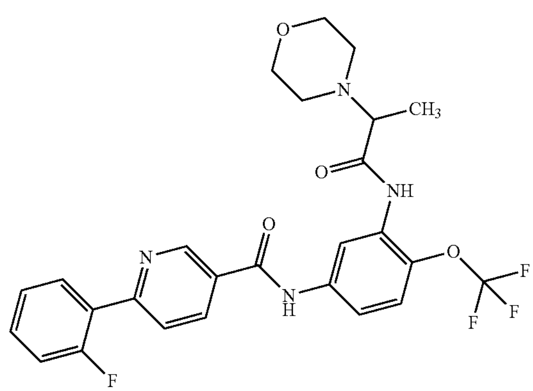 [SMILES: CC(C(=O)Nc1cc(NC(=O)c2ccc(-c3ccccc3F)nc2)ccc1OC(F)(F)F)N1CCOCC1] | 6-(2-fluorophenyl)-N-[3-{[2-(morpholin-4-yl)propanoyl]amino}-4-(trifluoromethoxy)phenyl]nicotinamide | 0.987 |

TABLE 1-continued

| Example No | Structure | IUPAC Name | R_t [min] method |
|---|---|---|---|
| 225 | 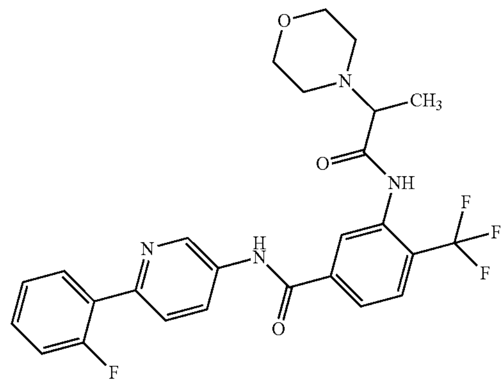 [SMILES: CC(C(=O)Nc1cc(C(=O)Nc2ccc(-c3ccccc3F)nc2)ccc1C(F)(F)F)N1CCOCC1] | N-[6-(2-fluorophenyl)pyridin-3-yl]-3-{[2-(morpholin-4-yl)propanoyl]amino}-4-(trifluoromethyl)benzamide | 0.957 |
| 226 | 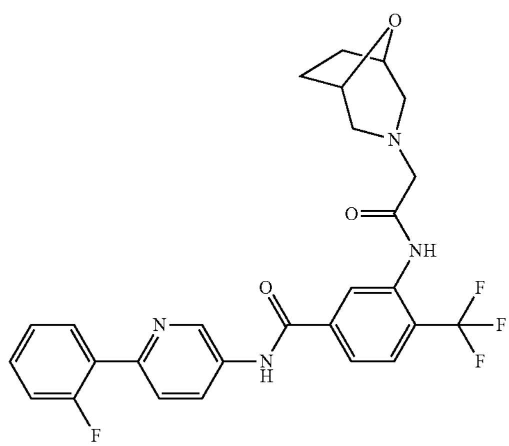 [SMILES: O=C(CN1CC2CCC(C1)O2)Nc1cc(C(=O)Nc2ccc(-c3ccccc3F)nc2)ccc1C(F)(F)F] | N-[6-(2-fluorophenyl)pyridin-3-yl]-3-[(8-oxa-3-azabicyclo[3.2.1]oct-3-ylacetyl)amino]-4-(trifluoromethyl)benzamide | 1.137 |
| 227 | 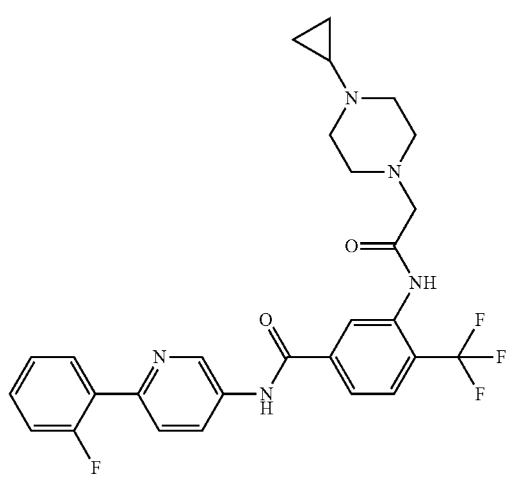 [SMILES: O=C(CN1CCN(C2CC2)CC1)Nc1cc(C(=O)Nc2ccc(-c3ccccc3F)nc2)ccc1C(F)(F)F] | 3-{[(4-cyclopropylpiperazin-1-yl)acetyl]amino}-N-[6-(2-fluorophenyl)pyridin-3-yl]-4-(trifluoromethyl)benzamide | 0.817 |

US 10,130,633 B2
TABLE 1-continued
| Example No | Structure | IUPAC Name | R, [min] method |
|---|---|---|---|
| 228 | 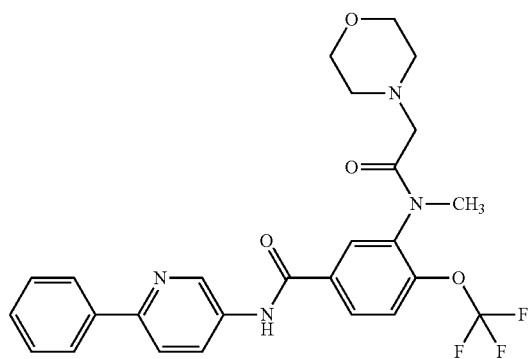 [SMILES: CN(C(=O)CN1CCOCC1)c1cc(C(=O)Nc2ccc(-c3ccccc3)nc2)ccc1OC(F)(F)F] | 3-[methyl(morpholin-4-ylacetyl)amino]-N-(6-phenylpyridin-3-yl)-4-(trifluoromethoxy)benzamide | 0.787 |
| 229 | 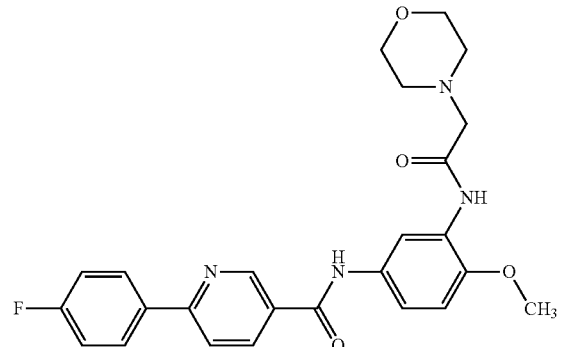 | 6-(4-fluorophenyl)-N-{4-methoxy-3-[(morpholin-4-ylacetyl)amino]phenyl} nicotinamide | 0.777 |
| 230 | 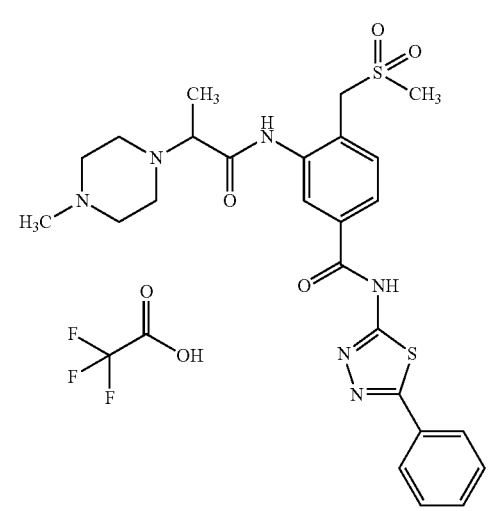 [SMILES: CC(C(=O)Nc1cc(C(=O)Nc2nnc(-c3ccccc3)s2)ccc1CS(C)(=O)=O)N1CCN(C)CC1 ; O=C(O)C(F)(F)F] | 3-{[2-(4-methylpiperazin-1-yl)propanoyl]amino}-4-[(methylsulfonyl)methyl]-N-(5-phenyl-1,3,4-thiadiazol-2-yl)benzamide trifluoroacetate (1:1) | 0.707 |

TABLE 1-continued
| Example No | Structure | IUPAC Name | R_t [min] method |
|---|---|---|---|
| 231 | 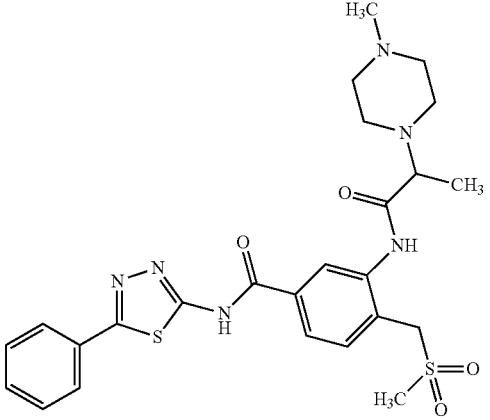 [SMILES: CC(C(=O)Nc1cc(C(=O)Nc2nnc(-c3ccccc3)s2)ccc1CS(C)(=O)=O)N1CCN(C)CC1] | 3-{[2-(4-methylpiperazin-1-yl)propanoyl]amino}-4-[(methylsulfonyl)methyl]-N-(5-phenyl-1,3,4-thiadiazol-2-yl)benzamide | 0.707 |
| 232 | 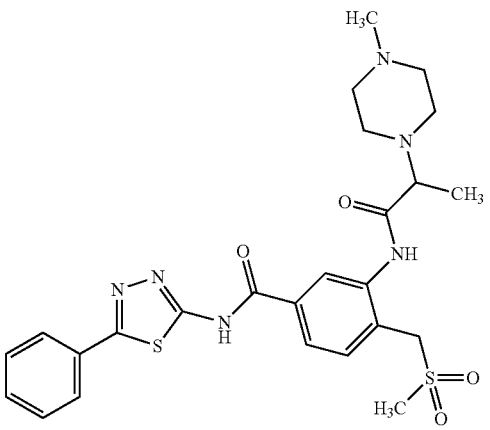 [SMILES: CC(C(=O)Nc1cc(C(=O)Nc2nnc(-c3ccccc3)s2)ccc1CS(C)(=O)=O)N1CCN(C)CC1] | 3-{[2-(4-methylpiperazin-1-yl)propanoyl]amino}-4-[(methylsulfonyl)methyl]-N-(5-phenyl-1,3,4-thiadiazol-2-yl)benzamide | 0.707 |
| 233 | 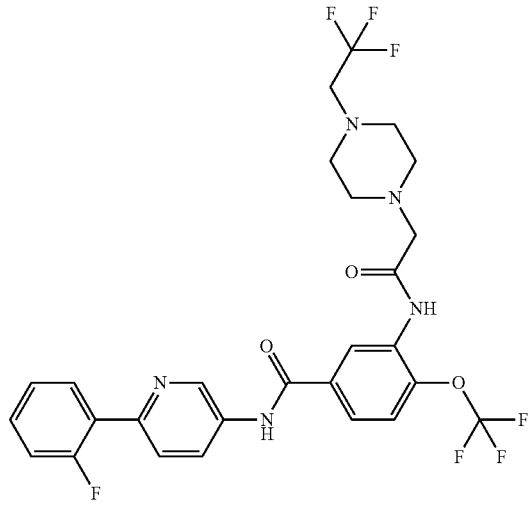 [SMILES: O=C(CN1CCN(CC(F)(F)F)CC1)Nc1cc(C(=O)Nc2ccc(-c3ccccc3F)nc2)ccc1OC(F)(F)F] | N-[6-(2-fluorophenyl)pyridin-3-yl]-3-({[4-(2,2,2-trifluoroethyl)piperazin-1-yl]acetyl}amino)-4-(trifluoromethoxy)benzamide | 1.117 |

TABLE 1-continued

| Example No | Structure | IUPAC Name | R_f [min] method |
|---|---|---|---|
| 234 | 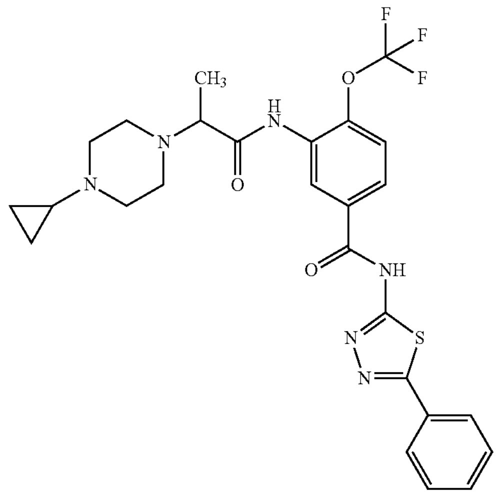 [SMILES: CC(C(=O)Nc1cc(C(=O)Nc2nnc(-c3ccccc3)s2)ccc1OC(F)(F)F)N1CCN(C2CC2)CC1] | 3-{[2-(4-cyclopropylpiperazin-1-yl)propanoyl]amino}-N-(5-phenyl-1,3,4-thiadiazol-2-yl)-4-(trifluoromethoxy)benzamide | 0.877 |
| 235 | 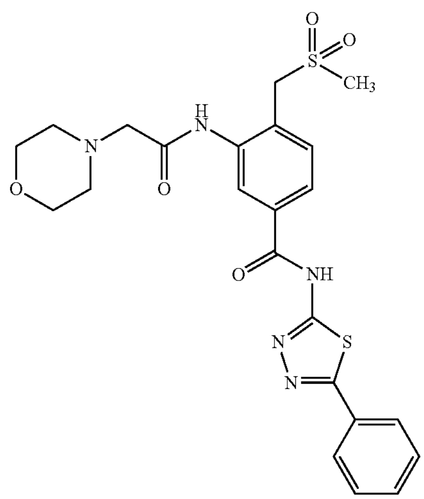 [SMILES: CS(=O)(=O)Cc1ccc(C(=O)Nc2nnc(-c3ccccc3)s2)cc1NC(=O)CN1CCOCC1] | 4-[(methylsulfonyl)methyl]-3-[(morpholin-4-ylacetyl)amino]-N-(5-phenyl-1,3,4-thiadiazol-2-yl)benzamide | 0.717 |
| 236 | 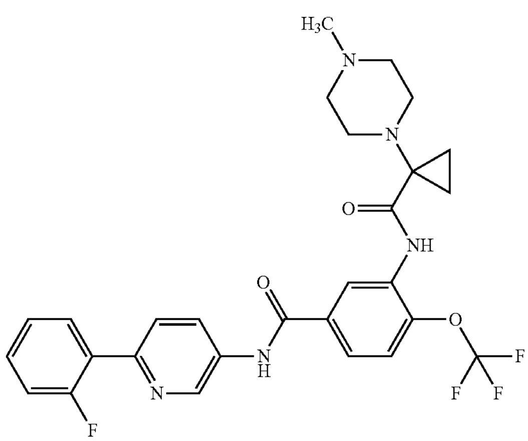 [SMILES: CN1CCN(C2(C(=O)Nc3cc(C(=O)Nc4ccc(-c5ccccc5F)nc4)ccc3OC(F)(F)F)CC2)CC1] | N-[6-(2-fluorophenyl)pyridin-3-yl]-3-({[1-(4-methylpiperazin-1-yl)cyclopropyl]carbonyl}amino)-4-(trifluoromethoxy)benzamide | 0.847 |

TABLE 1-continued

| Example No | Structure | IUPAC Name | R_t [min] method |
|---|---|---|---|
| 237 | 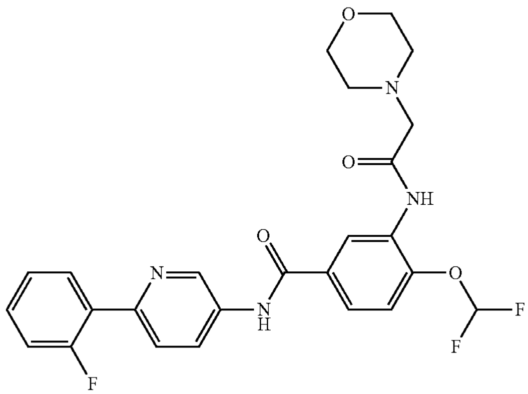 [SMILES: O=C(CN1CCOCC1)Nc1cc(C(=O)Nc2ccc(-c3ccccc3F)nc2)ccc1OC(F)F] | 4-(difluoromethoxy)-N-[6-(2-fluorophenyl)pyridin-3-yl]-3-[(morpholin-4-ylacetyl)amino]benzamide | 0.867 |
| 238 | 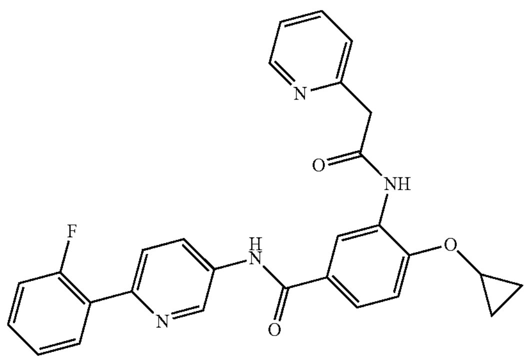 [SMILES: O=C(Cc1ccccn1)Nc1cc(C(=O)Nc2ccc(-c3ccccc3F)nc2)ccc1OC1CC1] | 4-(cyclopropyloxy)-N-[6-(2-fluorophenyl)pyridin-3-yl]-3-[(pyridin-2-ylacetyl)amino]benzamide | 1.017 |
| 239 | 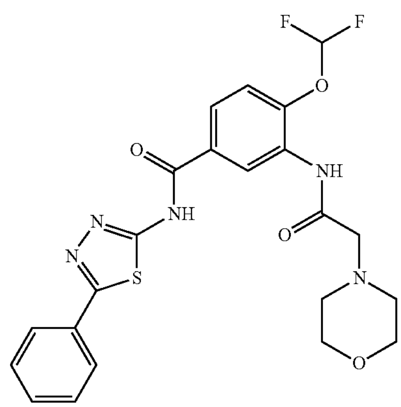 [SMILES: O=C(CN1CCOCC1)Nc1cc(C(=O)Nc2nnc(-c3ccccc3)s2)ccc1OC(F)F] | 4-(difluoromethoxy)-3-[(morpholin-4-ylacetyl)amino]-N-(5-phenyl-1,3,4-thiadiazol-2-yl)benzamide | 0.877 |
| 240 | 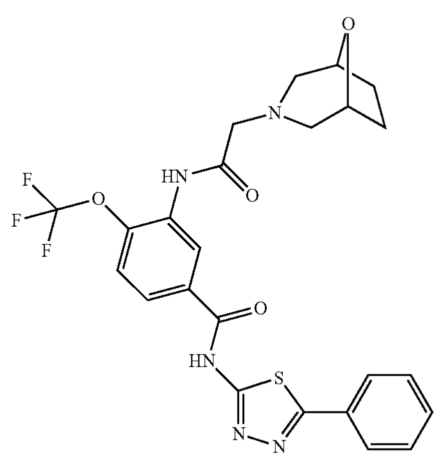 [SMILES: O=C(CN1CC2CCC(C1)O2)Nc1cc(C(=O)Nc2nnc(-c3ccccc3)s2)ccc1OC(F)(F)F] | 3-[(8-oxa-3-azabicyclo[3.2.1]oct-3-ylacetyl)amino]-N-(5-phenyl-1,3,4-thiadiazol-2-yl)-4-(trifluoromethoxy)benzamide | |

TABLE 1-continued

| Example No | Structure | IUPAC Name | R$_t$ [min] method |
|---|---|---|---|
| 241 | 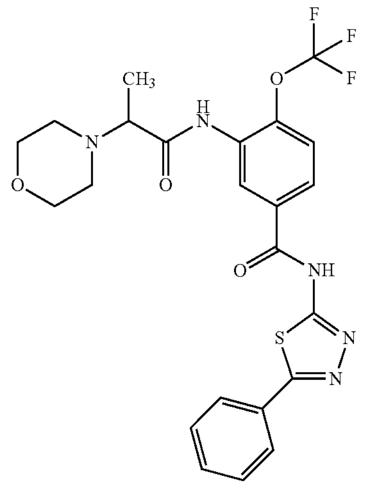 [SMILES: CC(C(=O)Nc1cc(C(=O)Nc2nnc(-c3ccccc3)s2)ccc1OC(F)(F)F)N1CCOCC1] | 3-{[2-(morpholin-4-yl)propanoyl]amino}-N-(5-phenyl-1,3,4-thiadiazol-2-yl)-4-(trifluoromethoxy)benzamide | 0.987 |
| 242 | 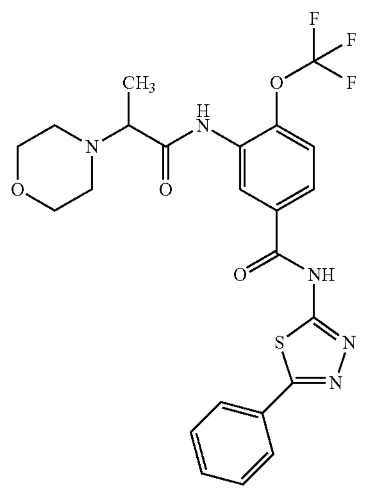 [SMILES: CC(C(=O)Nc1cc(C(=O)Nc2nnc(-c3ccccc3)s2)ccc1OC(F)(F)F)N1CCOCC1] | 3-{[2-(morpholin-4-yl)propanoyl]amino}-N-(5-phenyl-1,3,4-thiadiazol-2-yl)-4-(trifluoromethoxy)benzamide | 0.987 |
| 243 | 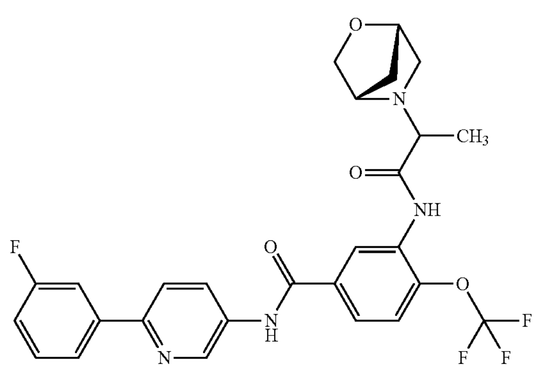 [SMILES: CC(C(=O)Nc1cc(C(=O)Nc2ccc(-c3cccc(F)c3)nc2)ccc1OC(F)(F)F)N1C[C@@H]2C[C@H]1CO2] | N-[6-(3-fluorophenyl)pyridin-3-yl]-3-({(2R*)-2-[(1S,4S)-2-oxa-5-azabicyclo[2.2.1]hept-5-yl]propanoyl}amino)-4-(trifluoromethoxy)benzamide | 0.837 |

TABLE 1-continued

| Example No | Structure | IUPAC Name | R$_t$ [min] method |
|---|---|---|---|
| 244 | 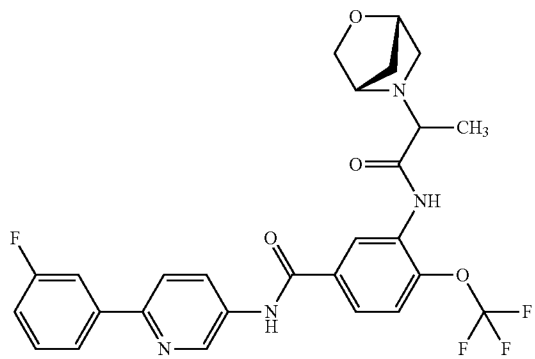 [SMILES: CC(C(=O)Nc1cc(C(=O)Nc2ccc(-c3cccc(F)c3)nc2)ccc1OC(F)(F)F)N1C[C@@H]2C[C@H]1CO2] | N-[6-(3-fluorophenyl)pyridin-3-yl]-3-({(2S*)-2-[(1S,4S)-2-oxa-5-azabicyclo[2.2.1]hept-5-yl]propanoyl}amino)-4-(trifluoromethoxy)benzamide | 0.837 |
| 245 | 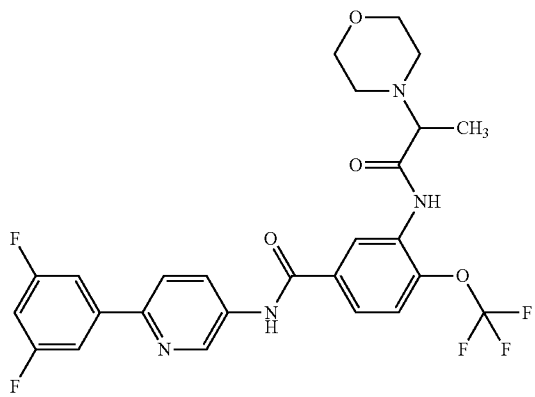 [SMILES: CC(C(=O)Nc1cc(C(=O)Nc2ccc(-c3cc(F)cc(F)c3)nc2)ccc1OC(F)(F)F)N1CCOCC1] | N-[6-(3,5-difluorophenyl)pyridin-3-yl]-3-{[2-(morpholin-4-yl)propanoyl]amino}-4-(trifluoromethoxy)benzamide | 1.087 |
| 246 | 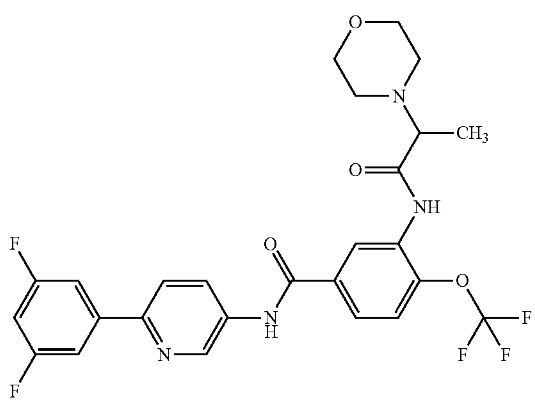 [SMILES: CC(C(=O)Nc1cc(C(=O)Nc2ccc(-c3cc(F)cc(F)c3)nc2)ccc1OC(F)(F)F)N1CCOCC1] | N-[6-(3,5-difluorophenyl)pyridin-3-yl]-3-{[2-(morpholin-4-yl)propanoyl]amino}-4-(trifluoromethoxy)benzamide | 1.087 |
| 247 | 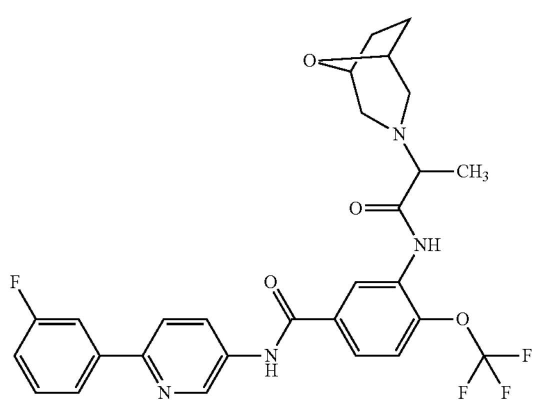 [SMILES: CC(C(=O)Nc1cc(C(=O)Nc2ccc(-c3cccc(F)c3)nc2)ccc1OC(F)(F)F)N1CC2CCC(C1)O2] | N-[6-(3-fluorophenyl)pyridin-3-yl]-3-{[2-(8-oxa-3-azabicyclo[3.2.1]oct-3-yl)propanoyl]amino}-4-(trifluoromethoxy)benzamide | 1.247 |

TABLE 1-continued

| Example No | Structure | IUPAC Name | R_t [min] method |
|---|---|---|---|
| 248 | 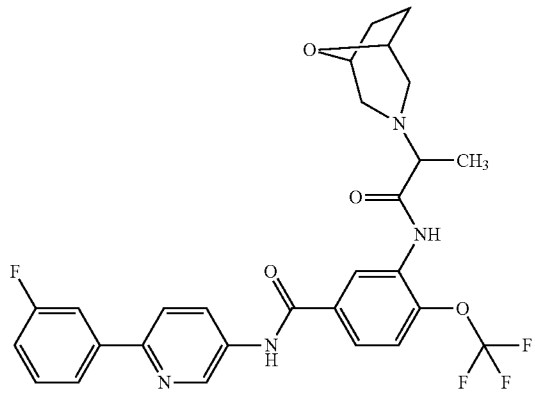 [SMILES: CC(C(=O)Nc1cc(C(=O)Nc2ccc(-c3cccc(F)c3)nc2)ccc1OC(F)(F)F)N1CC2CCC(C1)O2] | N-[6-(3-fluorophenyl)pyridin-3-yl]-3-{[2-(8-oxa-3-azabicyclo[3.2.1]oct-3-yl)propanoyl]amino}-4-(trifluoromethoxy)benzamide | 1.247 |
| 249 | 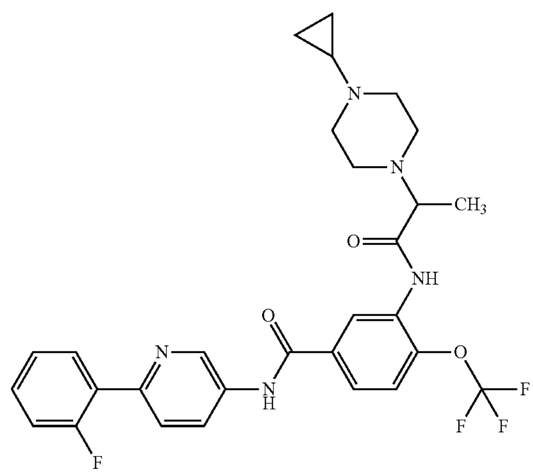 [SMILES: CC(C(=O)Nc1cc(C(=O)Nc2ccc(-c3ccccc3F)nc2)ccc1OC(F)(F)F)N1CCN(C2CC2)CC1] | 3-{[2-(4-cyclopropylpiperazin-1-yl)propanoyl]amino}-N-[6-(2-fluorophenyl)pyridin-3-yl]-4-(trifluoromethoxy)benzamide | 0.867 |
| 250 | 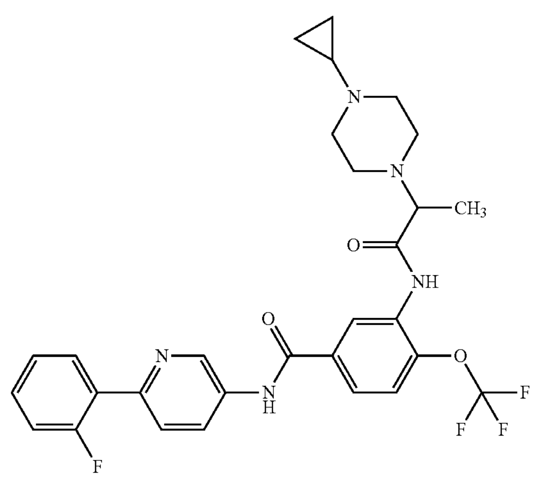 [SMILES: CC(C(=O)Nc1cc(C(=O)Nc2ccc(-c3ccccc3F)nc2)ccc1OC(F)(F)F)N1CCN(C2CC2)CC1] | 3-{[2-(4-cyclopropylpiperazin-1-yl)propanoyl]amino}-N-[6-(2-fluorophenyl)pyridin-3-yl]-4-(trifluoromethoxy)benzamide | |

TABLE 1-continued
| Example No | Structure | IUPAC Name | R_t [min] method |
|---|---|---|---|
| 251 | 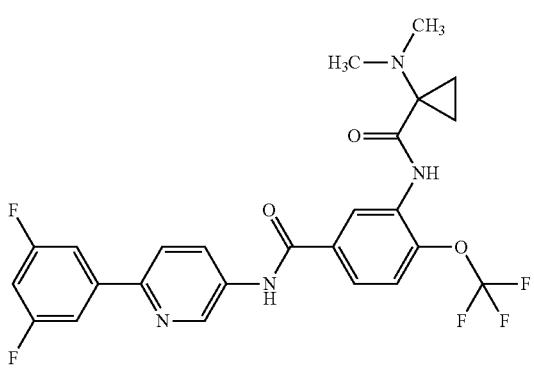 [SMILES: CN(C)C1(C(=O)Nc2cc(C(=O)Nc3ccc(-c4cc(F)cc(F)c4)nc3)ccc2OC(F)(F)F)CC1] | N-[6-(3,5-difluorophenyl) pyridin-3-yl]-3-({[1-(dimethylamino)cyclopropyl] carbonyl}amino)-4-(trifluoromethoxy)benzamide | 1.417 |
| 252 | 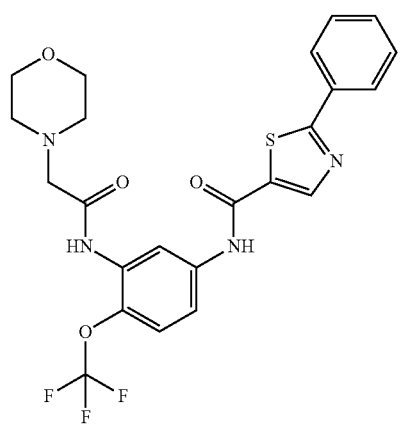 [SMILES: O=C(CN1CCOCC1)Nc1cc(NC(=O)c2cnc(-c3ccccc3)s2)ccc1OC(F)(F)F] | N-{3-[(morpholin-4-ylacetyl)amino]-4-(trifluoromethoxy)phenyl}-2-phenyl-1,3-thiazole-5-carboxamide | 1.017 |
| 253 | 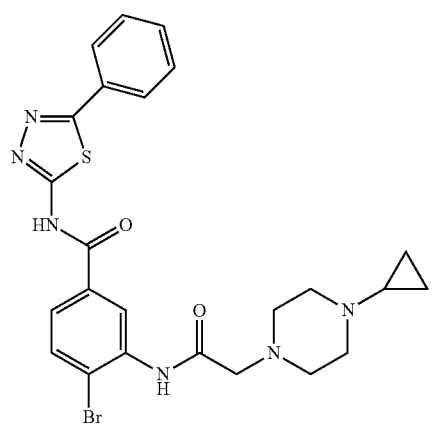 [SMILES: O=C(CN1CCN(C2CC2)CC1)Nc1cc(C(=O)Nc2nnc(-c3ccccc3)s2)ccc1Br] | 4-bromo-3-{[(4-cyclopropylpiperazin-1-yl)acetyl]amino}-N-(5-phenyl-1,3,4-thiadiazol-2-yl)benzamide | 0.807 |

TABLE 1-continued

| Example No | Structure | IUPAC Name | R_t [min] method |
|---|---|---|---|
| 254 | 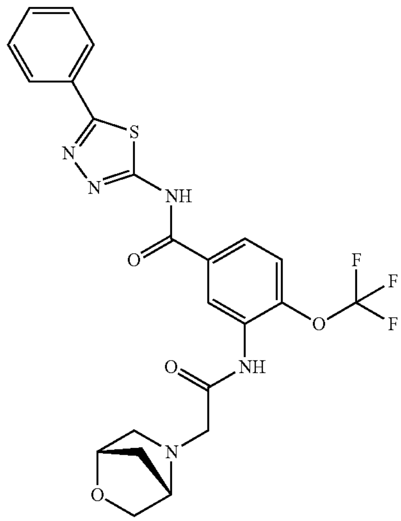 [SMILES: O=C(CN1C[C@@H]2C[C@H]1CO2)Nc1cc(C(=O)Nc2nnc(-c3ccccc3)s2)ccc1OC(F)(F)F] | 3-{[(1S,4S)-2-oxa-5-azabicyclo[2.2.1]hept-5-ylacetyl]amino}-N-(5-phenyl-1,3,4-thiadiazol-2-yl)-4-(trifluoromethoxy)benzamide | 0.817 |
| 255 | 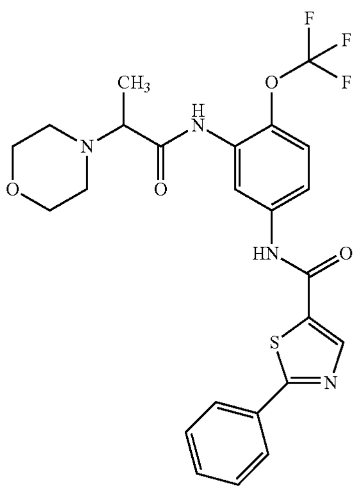 [SMILES: CC(C(=O)Nc1cc(NC(=O)c2cnc(-c3ccccc3)s2)ccc1OC(F)(F)F)N1CCOCC1] | N-[3-{[2-(morpholin-4-yl)propanoyl]amino}-4-(trifluoromethoxy)phenyl]-2-phenyl-1,3-thiazole-5-carboxamide | 1.037 |
| 256 | 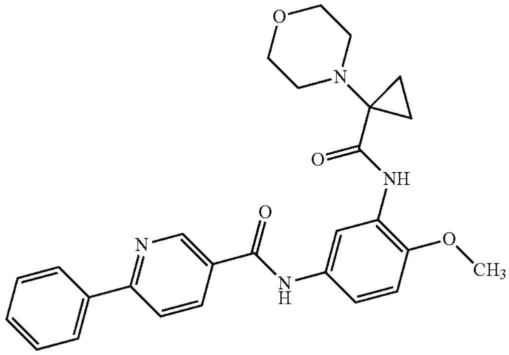 [SMILES: COc1ccc(NC(=O)c2ccc(-c3ccccc3)nc2)cc1NC(=O)C1(N2CCOCC2)CC1] | N-[4-methoxy-3-({[1-(morpholin-4-yl)cyclopropyl]carbonyl}amino)phenyl]-6-phenylnicotinamide | 1.167 |

TABLE 1-continued

| Example No | Structure | IUPAC Name | R$_t$ [min] method |
|---|---|---|---|
| 257 | 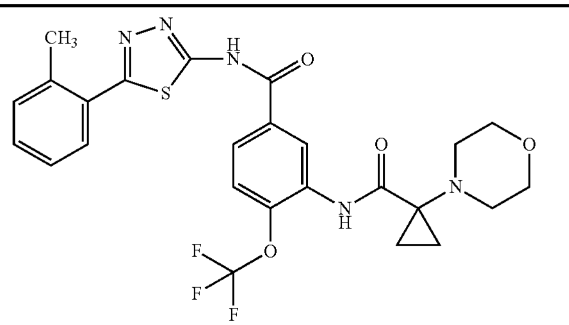 | N-[5-(2-methylphenyl)-1,3,4-thiadiazol-2-yl]-3-({[1-(morpholin-4-yl)cyclopropyl]carbonyl}amino)-4-(trifluoromethoxy)benzamide | 1.381 |
| 258 | 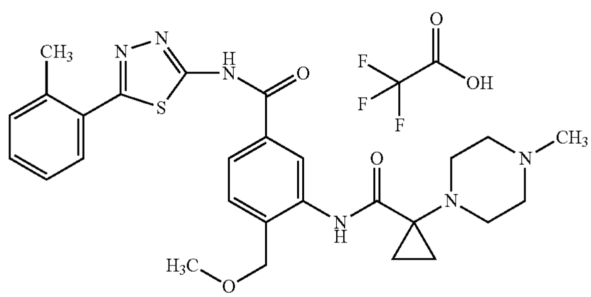 | 4-(methoxymethyl)-N-[5-(2-methylphenyl)-1,3,4-thiadiazol-2-yl]-3-({[1-(4-methylpiperazin-1-yl)cyclopropyl]carbonyl}amino)benzamide trifluoroacetate (1:1) | 0.951 |
| 259 | 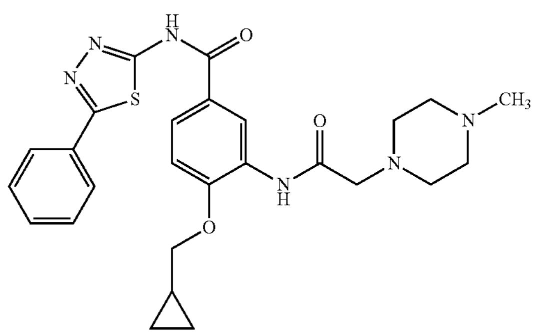 [SMILES: CN1CCN(CC(=O)Nc2cc(C(=O)Nc3nnc(-c4ccccc4)s3)ccc2OCC2CC2)CC1] | 4-(cyclopropylmethoxy)-3-{[(4-methylpiperazin-1-yl)acetyl]amino}-N-(5-phenyl-1,3,4-thiadiazol-2-yl)benzamide | 0.974 |
| 260 | 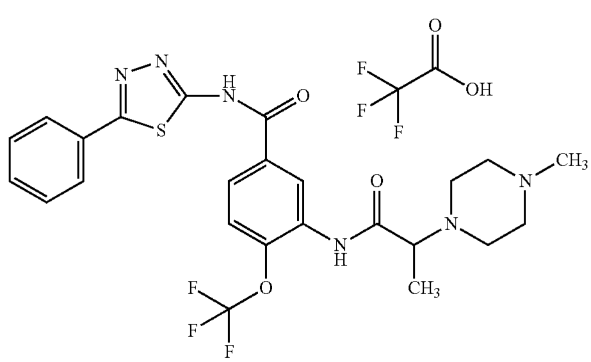 | 3-{[2-(4-methylpiperazin-1-yl)propanoyl]amino}-N-(5-phenyl-1,3,4-thiadiazol-2-yl)-4-(trifluoromethoxy)benzamide trifluoroacetate (1:1) | 0.951 |
| 261 | 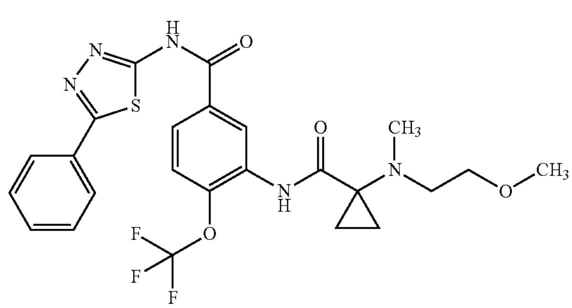 [SMILES: COCCN(C)C1(C(=O)Nc2cc(C(=O)Nc3nnc(-c4ccccc4)s3)ccc2OC(F)(F)F)CC1] | 3-[({1-[(2-methoxyethyl)(methyl)amino]cyclopropyl}carbonyl)amino]-N-(5-phenyl-1,3,4-thiadiazol-2-yl)-4-(trifluoromethoxy)benzamide | 0.843 |

TABLE 1-continued

| Example No | Structure | IUPAC Name | R$_t$ [min] method |
|---|---|---|---|
| 262 | 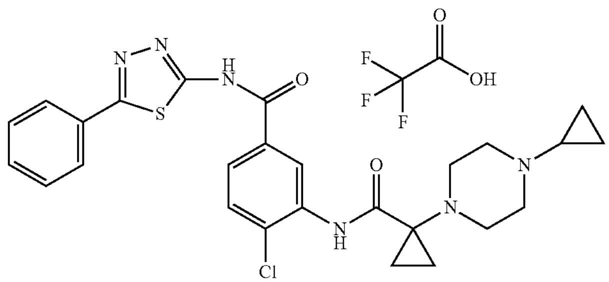 | 4-chloro-3-({[1-(4-cyclopropylpiperazin-1-yl)cyclopropyl]carbonyl}amino)-N-(5-phenyl-1,3,4-thiadiazol-2-yl)benzamide trifluoroacetate (1:1) | 0.971 |
| 263 | 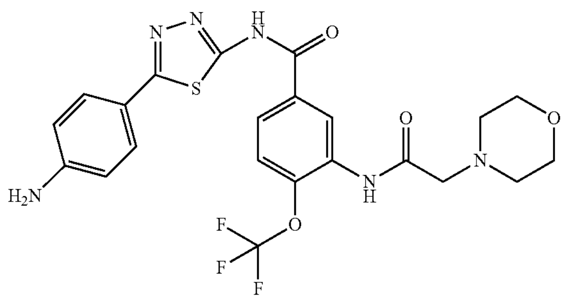 [SMILES: Nc1ccc(-c2nnc(NC(=O)c3ccc(OC(F)(F)F)c(NC(=O)CN4CCOCC4)c3)s2)cc1] | N-[5-(4-aminophenyl)-1,3,4-thiadiazol-2-yl]-3-[(morpholin-4-ylacetyl)amino]-4-(trifluoromethoxy)benzamide | 0.934 |
| 264 | 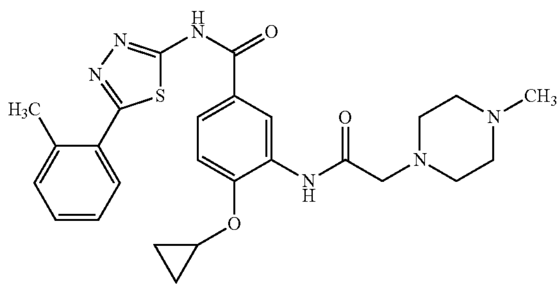 [SMILES: Cc1ccccc1-c1nnc(NC(=O)c2ccc(OC3CC3)c(NC(=O)CN3CCN(C)CC3)c2)s1] | 4-(cyclopropyloxy)-N-[5-(2-methylphenyl)-1,3,4-thiadiazol-2-yl]-3-{[(4-methylpiperazin-1-yl)acetyl]amino}benzamide | 0.843 |
| 265 | 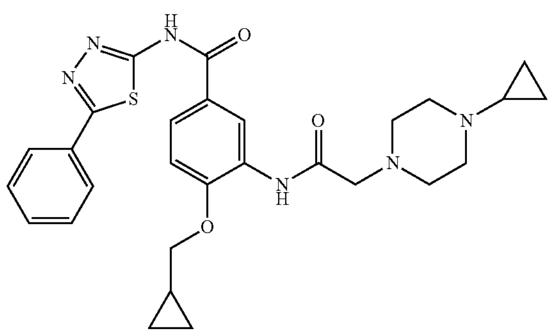 [SMILES: O=C(CN1CCN(C2CC2)CC1)Nc1cc(C(=O)Nc2nnc(-c3ccccc3)s2)ccc1OCC1CC1] | 4-(cyclopropylmethoxy)-3-{[(4-cyclopropylpiperazin-1-yl)acetyl]amino}-N-(5-phenyl-1,3,4-thiadiazol-2-yl)benzamide | 0.984 |
| 266 | 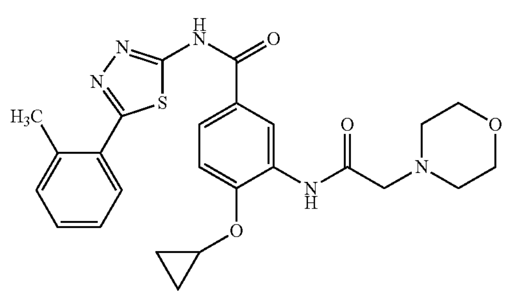 [SMILES: Cc1ccccc1-c1nnc(NC(=O)c2ccc(OC3CC3)c(NC(=O)CN3CCOCC3)c2)s1] | 4-(cyclopropyloxy)-N-[5-(2-methylphenyl)-1,3,4-thiadiazol-2-yl]-3-[(morpholin-4-ylacetyl)amino]benzamide | 0.843 |

US 10,130,633 B2

TABLE 1-continued

| Example No | Structure | IUPAC Name | R$_t$ [min] method |
|---|---|---|---|
| 267 | 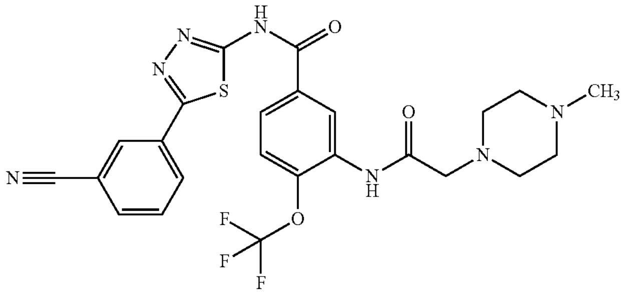 [SMILES: CN1CCN(CC(=O)Nc2cc(C(=O)Nc3nnc(-c4cccc(C#N)c4)s3)ccc2OC(F)(F)F)CC1] | N-[5-(3-cyanophenyl)-1,3,4-thiadiazol-2-yl]-3-{[(4-methylpiperazin-1-yl)acetyl]amino}-4-(trifluoromethoxy)benzamide | 0.763 |
| 268 | 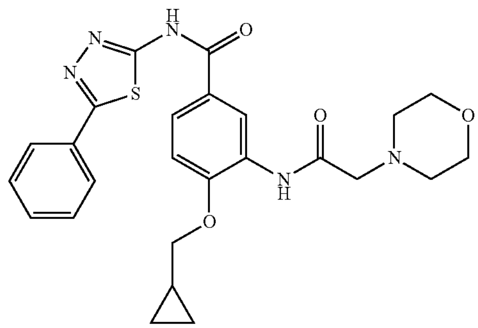 [SMILES: O=C(CN1CCOCC1)Nc1cc(C(=O)Nc2nnc(-c3ccccc3)s2)ccc1OCC1CC1] | 4-(cyclopropylmethoxy)-3-[(morpholin-4-ylacetyl)amino]-N-(5-phenyl-1,3,4-thiadiazol-2-yl)benzamide | 0.803 |
| 269 | 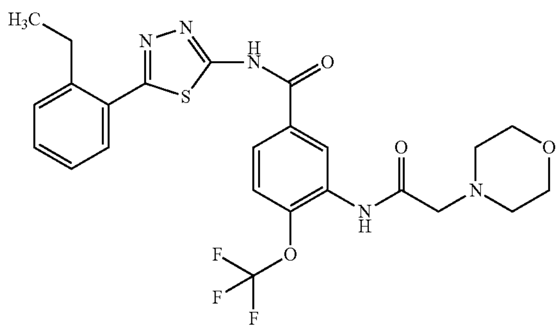 [SMILES: CCc1ccccc1-c1nnc(NC(=O)c2ccc(OC(F)(F)F)c(NC(=O)CN3CCOCC3)c2)s1] | N-[5-(2-ethylphenyl)-1,3,4-thiadiazol-2-yl]-3-[(morpholin-4-ylacetyl)amino]-4-(trifluoromethoxy)benzamide | 1.251 |
| 270 | 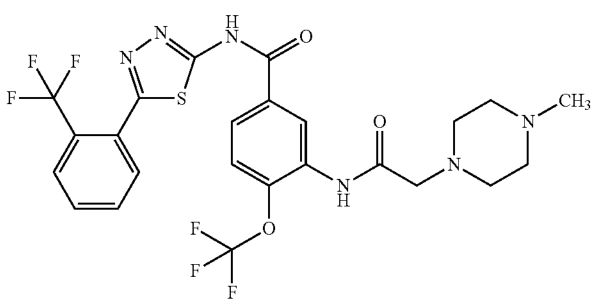 [SMILES: CN1CCN(CC(=O)Nc2cc(C(=O)Nc3nnc(-c4ccccc4C(F)(F)F)s3)ccc2OC(F)(F)F)CC1] | 3-{[(4-methylpiperazin-1-yl)acetyl]amino}-4-(trifluoromethoxy)-N-{5-[2-(trifluoromethyl)phenyl]-1,3,4-thiadiazol-2-yl}benzamide | 0.803 |
| 271 | 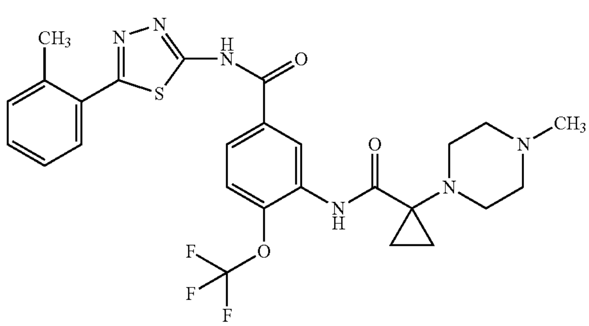 [SMILES: Cc1ccccc1-c1nnc(NC(=O)c2ccc(OC(F)(F)F)c(NC(=O)C3(N4CCN(C)CC4)CC3)c2)s1] | N-[5-(2-methylphenyl)-1,3,4-thiadiazol-2-yl]-3-({[1-(4-methylpiperazin-1-yl)cyclopropyl]carbonyl}amino)-4-(trifluoromethoxy)benzamide | 1.031 |

TABLE 1-continued

| Example No | Structure | IUPAC Name | R_t [min] method |
|---|---|---|---|
| 272 | 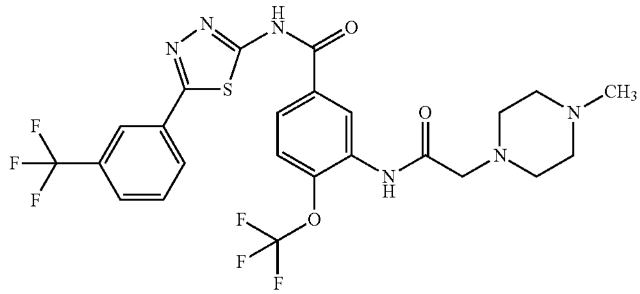 [SMILES: CN1CCN(CC(=O)Nc2cc(C(=O)Nc3nnc(-c4cccc(C(F)(F)F)c4)s3)ccc2OC(F)(F)F)CC1] | 3-{[(4-methylpiperazin-1-yl)acetyl]amino}-4-(trifluoromethoxy)-N-{5-[3-(trifluoromethyl)phenyl]-1,3,4-thiadiazol-2-yl}benzamide | 0.823 |
| 273 | 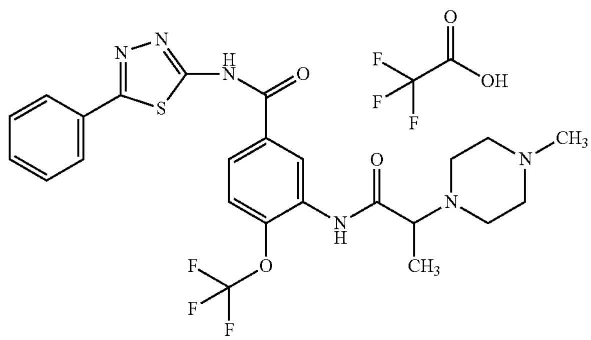 | 3-{[2-(4-methylpiperazin-1-yl)propanoyl]amino}-N-(5-phenyl-1,3,4-thiadiazol-2-yl)-4-(trifluoromethoxy)benzamide trifluoroacetate (1:1) | 0.951 |
| 274 | 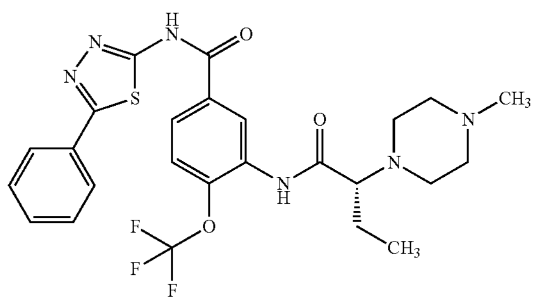 [SMILES: CC[C@H](C(=O)Nc1cc(C(=O)Nc2nnc(-c3ccccc3)s2)ccc1OC(F)(F)F)N1CCN(C)CC1] | 3-{[(2R)-2-(4-methylpiperazin-1-yl)butanoyl]amino}-N-(5-phenyl-1,3,4-thiadiazol-2-yl)-4-(trifluoromethoxy)benzamide | 1.034 |
| 275 | 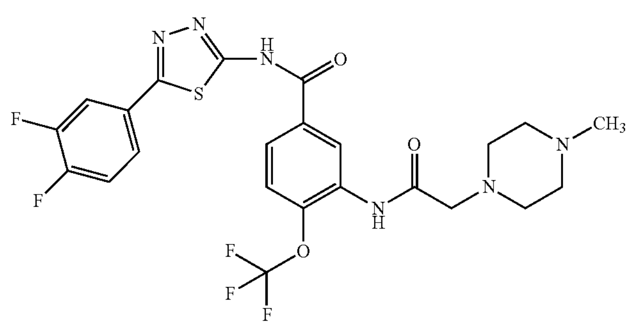 [SMILES: CN1CCN(CC(=O)Nc2cc(C(=O)Nc3nnc(-c4ccc(F)c(F)c4)s3)ccc2OC(F)(F)F)CC1] | N-[5-(3,4-difluorophenyl)-1,3,4-thiadiazol-2-yl]-3-{[(4-methylpiperazin-1-yl)acetyl]amino}-4-(trifluoromethoxy)benzamide | 1.011 |
| 276 | 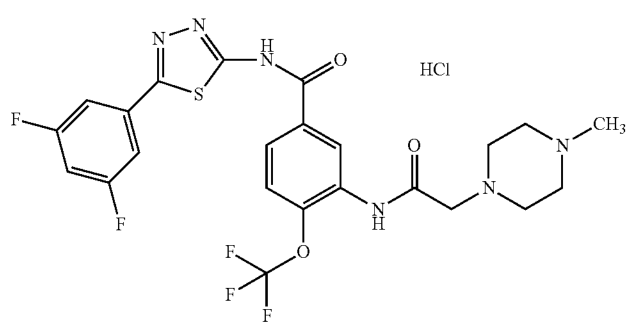 [SMILES: CN1CCN(CC(=O)Nc2cc(C(=O)Nc3nnc(-c4cc(F)cc(F)c4)s3)ccc2OC(F)(F)F)CC1 ; Cl] | N-[5-(3,5-difluorophenyl)-1,3,4-thiadiazol-2-yl]-3-{[(4-methylpiperazin-1-yl)acetyl]amino}-4-(trifluoromethoxy)benzamide hydrochloride (1:1) | 1.011 |

TABLE 1-continued

| Example No | Structure | IUPAC Name | R<sub>f</sub> [min] method |
|---|---|---|---|
| 277 | 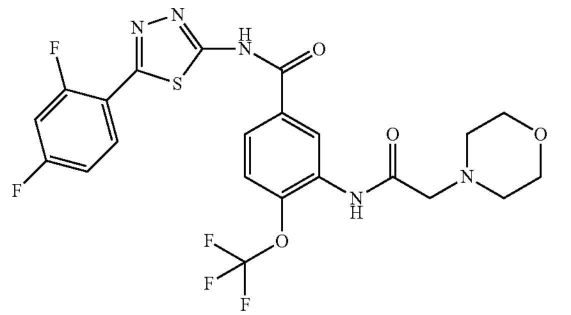 [SMILES: O=C(CN1CCOCC1)Nc1cc(C(=O)Nc2nnc(-c3ccc(F)cc3F)s2)ccc1OC(F)(F)F] | N-[5-(2,4-difluorophenyl)-1,3,4-thiadiazol-2-yl]-3-[(morpholin-4-ylacetyl)amino]-4-(trifluoromethoxy)benzamide | 1.171 |
| 278 | 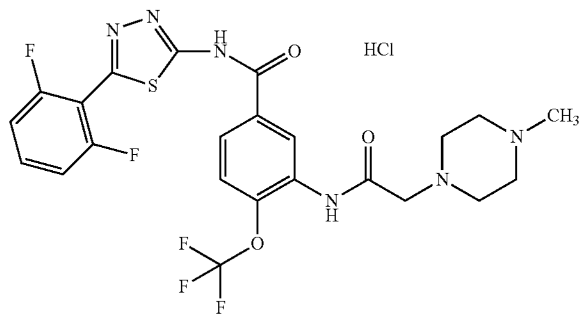 [SMILES: CN1CCN(CC(=O)Nc2cc(C(=O)Nc3nnc(-c4c(F)cccc4F)s3)ccc2OC(F)(F)F)CC1 ; Cl] | N-[5-(2,6-difluorophenyl)-1,3,4-thiadiazol-2-yl]-3-{[(4-methylpiperazin-1-yl)acetyl]amino}-4-(trifluoromethoxy)benzamide hydrochloride (1:1) | 0.931 |
| 279 | 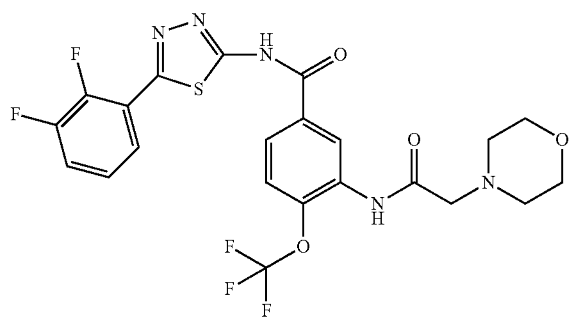 [SMILES: O=C(CN1CCOCC1)Nc1cc(C(=O)Nc2nnc(-c3cccc(F)c3F)s2)ccc1OC(F)(F)F] | N-[5-(2,3-difluorophenyl)-1,3,4-thiadiazol-2-yl]-3-[(morpholin-4-ylacetyl)amino]-4-(trifluoromethoxy)benzamide | 1.154 |
| 280 | 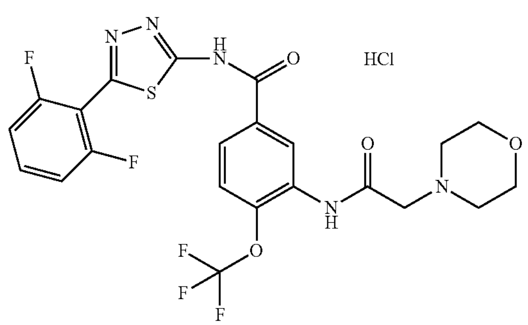 [SMILES: O=C(CN1CCOCC1)Nc1cc(C(=O)Nc2nnc(-c3c(F)cccc3F)s2)ccc1OC(F)(F)F ; Cl] | N-[5-(2,6-difluorophenyl)-1,3,4-thiadiazol-2-yl]-3-[(morpholin-4-ylacetyl)amino]-4-(trifluoromethoxy)benzamide hydrochloride (1:1) | 1.101 |
| 281 | 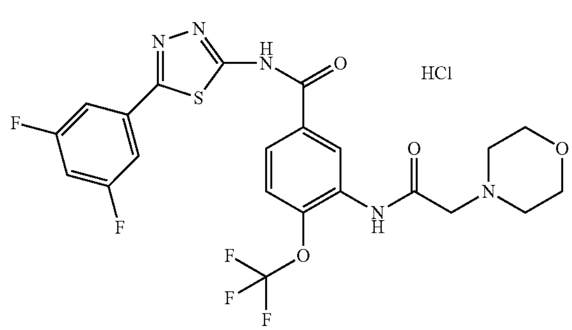 [SMILES: O=C(CN1CCOCC1)Nc1cc(C(=O)Nc2nnc(-c3cc(F)cc(F)c3)s2)ccc1OC(F)(F)F ; Cl] | N-[5-(3,5-difluorophenyl)-1,3,4-thiadiazol-2-yl]-3-[(morpholin-4-ylacetyl)amino]-4-(trifluoromethoxy)benzamide hydrochloride (1:1) | 1.211 |

TABLE 1-continued

| Example No | Structure | IUPAC Name | R_t [min] method |
|---|---|---|---|
| 282 | 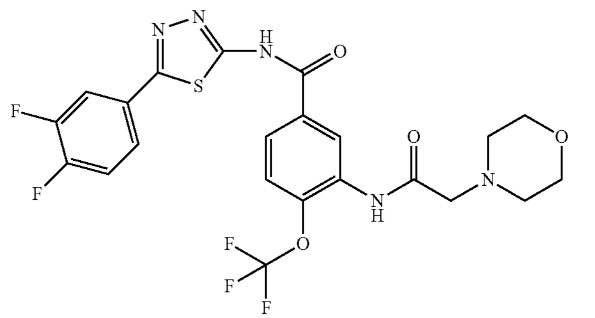 [SMILES: O=C(CN1CCOCC1)Nc1cc(C(=O)Nc2nnc(-c3ccc(F)c(F)c3)s2)ccc1OC(F)(F)F] | N-[5-(3,4-difluorophenyl)-1,3,4-thiadiazol-2-yl]-3-[(morpholin-4-ylacetyl)amino]-4-(trifluoromethoxy)benzamide | 1.191 |
| 283 | 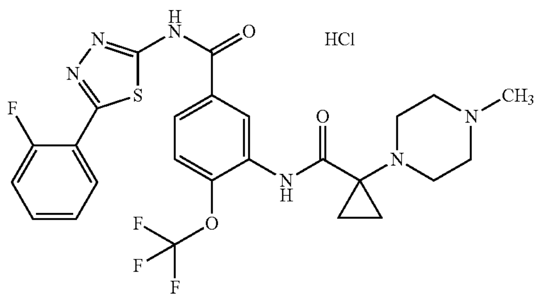 [SMILES: CN1CCN(C2(C(=O)Nc3cc(C(=O)Nc4nnc(-c5ccccc5F)s4)ccc3OC(F)(F)F)CC2)CC1 ; Cl] | N-[5-(2-fluorophenyl)-1,3,4-thiadiazol-2-yl]-3-({[1-(4-methylpiperazin-1-yl)cyclopropyl]carbonyl}amino)-4-(trifluoromethoxy)benzamide hydrochloride (1:1) | 0.984 |
| 284 | 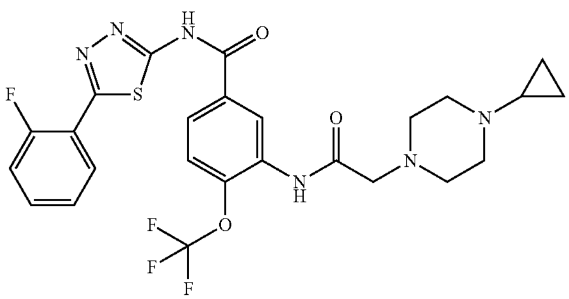 [SMILES: O=C(CN1CCN(C2CC2)CC1)Nc1cc(C(=O)Nc2nnc(-c3ccccc3F)s2)ccc1OC(F)(F)F] | 3-{[(4-cyclopropylpiperazin-1-yl)acetyl]amino}-N-[5-(2-fluorophenyl)-1,3,4-thiadiazol-2-yl]-4-(trifluoromethoxy)benzamide | 1.014 |
| 285 | 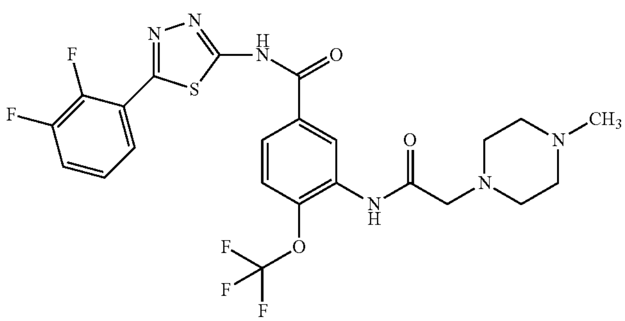 [SMILES: CN1CCN(CC(=O)Nc2cc(C(=O)Nc3nnc(-c4cccc(F)c4F)s3)ccc2OC(F)(F)F)CC1] | N-[5-(2,3-difluorophenyl)-1,3,4-thiadiazol-2-yl]-3-{[(4-methylpiperazin-1-yl)acetyl]amino}-4-(trifluoromethoxy)benzamide | 0.994 |
| 286 | 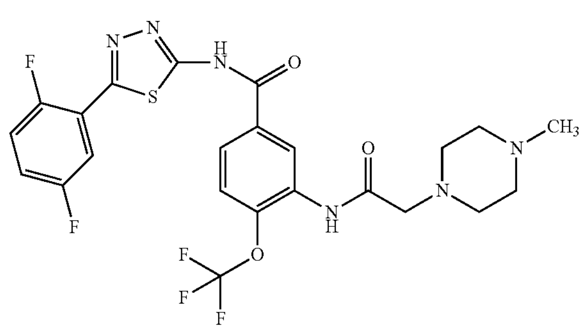 [SMILES: CN1CCN(CC(=O)Nc2cc(C(=O)Nc3nnc(-c4cc(F)ccc4F)s3)ccc2OC(F)(F)F)CC1] | N-[5-(2,5-difluorophenyl)-1,3,4-thiadiazol-2-yl]-3-{[(4-methylpiperazin-1-yl)acetyl]amino}-4-(trifluoromethoxy)benzamide | 0.994 |

TABLE 1-continued

| Example No | Structure | IUPAC Name | R_t [min] method |
|---|---|---|---|
| 287 | 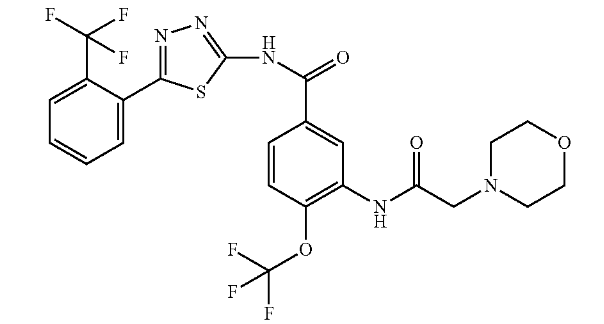 [SMILES: O=C(CN1CCOCC1)Nc1cc(C(=O)Nc2nnc(-c3ccccc3C(F)(F)F)s2)ccc1OC(F)(F)F] | 3-[(morpholin-4-ylacetyl)amino]-4-(trifluoromethoxy)-N-{5-[2-(trifluoromethyl)phenyl]-1,3,4-thiadiazol-2-yl}benzamide | 1.161 |
| 288 | 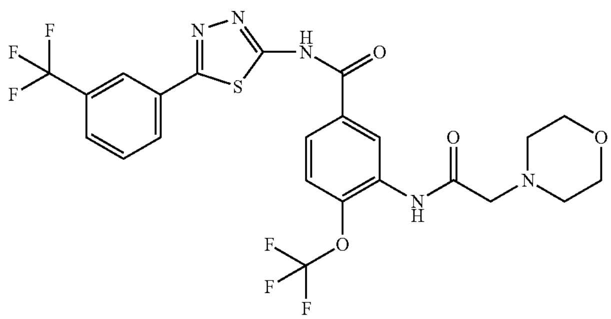 [SMILES: O=C(CN1CCOCC1)Nc1cc(C(=O)Nc2nnc(-c3cccc(C(F)(F)F)c3)s2)ccc1OC(F)(F)F] | 3-[(morpholin-4-ylacetyl)amino]-4-(trifluoromethoxy)-N-{5-[3-(trifluoromethyl)phenyl]-1,3,4-thiadiazol-2-yl}benzamide | 1.281 |
| 289 | 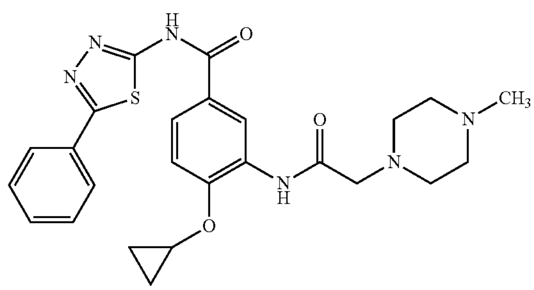 [SMILES: CN1CCN(CC(=O)Nc2cc(C(=O)Nc3nnc(-c4ccccc4)s3)ccc2OC2CC2)CC1] | 4-(cyclopropyloxy)-3-{[(4-methylpiperazin-1-yl)acetyl]amino}-N-(5-phenyl-1,3,4-thiadiazol-2-yl)benzamide | 0.874 |
| 290 | 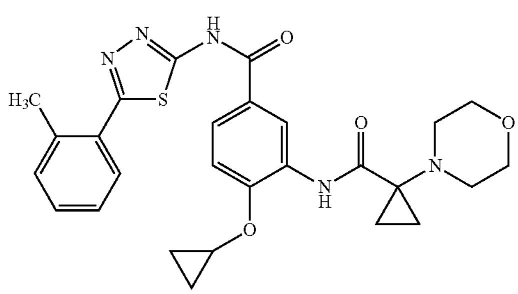 [SMILES: Cc1ccccc1-c1nnc(NC(=O)c2ccc(OC3CC3)c(NC(=O)C3(N4CCOCC4)CC3)c2)s1] | 4-(cyclopropyloxy)-N-[5-(2-methylphenyl)-1,3,4-thiadiazol-2-yl]-3-({[1-(morpholin-4-yl)cyclopropyl]carbonyl}amino)benzamide | 0.923 |
| 291 | 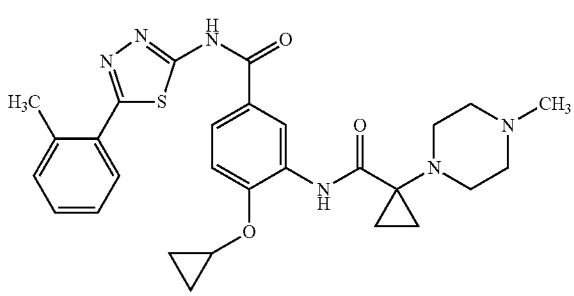 [SMILES: Cc1ccccc1-c1nnc(NC(=O)c2ccc(OC3CC3)c(NC(=O)C3(N4CCN(C)CC4)CC3)c2)s1] | 4-(cyclopropyloxy)-N-[5-(2-methylphenyl)-1,3,4-thiadiazol-2-yl]-3-({[1-(4-methylpiperazin-1-yl)cyclopropyl]carbonyl}amino)benzamide | 0.953 |

Example 292

4-(difluoromethoxy)-N-[5-(2-fluorophenyl)-1,3,4-thiadiazol-2-yl]-3-{[(4-methylpiperazin-1-yl)acetyl]amino}benzamide

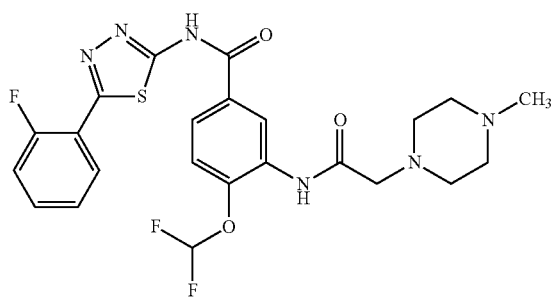 [SMILES: CN1CCN(CC(=O)Nc2cc(C(=O)Nc3nnc(-c4ccccc4F)s3)ccc2OC(F)F)CC1]

To a suspension of 300 mg (0.66 mmol) of the compound of intermediate 148 in 6 mL of DMF were added 0.18 mL of triethylamine (1.31 mmol, 2 equiv), 0.15 mL of 1-methylpiperazine (1.31 mmol, 2 equiv), and 22.0 mg of potassium iodide (0.13 mmol, 0.2 equiv). The reaction mixture was stirred at room temperature over night. After concentration, the remaining solid was triturated with 10 mL of water and 5 mL of ethanol, stirred for 30 minutes, collected by filtration and dried. The remaining solid was triturated with 8 mL of ethanol and stirred under reflux, collected by filtration and dried. 217 mg (62% of theory) of the title compound were obtained.

$^1$H-NMR (400 MHz, DMSO-$d_6$): δ [ppm]=2.24 (s, 3H), 2.56-2.69 (m, 4H), 3.21 (s, 2H), 7.37-7.51 (m, 3H), 7.45 (t, 1H), 7.56-7.65 (m, 1H), 8.00 (dd, 1H), 8.27 (dt, 1H), 9.01 (d, 1H), 9.89 (s, 1H).

LC-MS (Method 4): $R_t$=0.92 min; MS (ESIpos): m/z=521 [M+H]$^+$.

Example 293

3-{[(4-cyclopropylpiperazin-1-yl)acetyl]amino}-4-(difluoromethoxy)-N-[5-(2-fluorophenyl)-1,3,4-thiadiazol-2-yl]benzamide

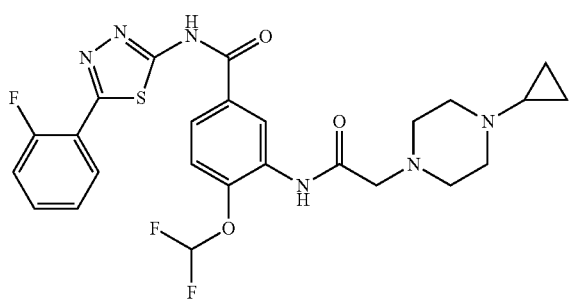 [SMILES: O=C(CN1CCN(C2CC2)CC1)Nc1cc(C(=O)Nc2nnc(-c3ccccc3F)s2)ccc1OC(F)F]

To a suspension of 150 mg (0.33 mmol) of the compound of intermediate 148 in 3 mL of DMF were added 0.28 mL of triethylamine (1.97 mmol, 6 equiv), 131 mg of 1-cyclopropylpiperazine dihydrochloride (0.66 mmol, 2 equiv), and 11.0 mg of potassium iodide (0.07 mmol, 0.2 equiv). The reaction mixture was stirred at room temperature over night. After concentration, the remaining solid was triturated with 8 mL of water and 4 mL of ethanol, stirred for 30 minutes, collected by filtration and dried. The remaining solid was triturated with 5 mL of ethanol and stirred under reflux, collected by filtration and dried. 89 mg (50% of theory) of the title compound were obtained.

$^1$H-NMR (400 MHz, DMSO-$d_6$): δ [ppm]=0.14-0.95 (m, 4H), 1.50-2.00 (m, 1H), 2.55-3.03 (m, 6H), 3.18-3.30 (m, 2H), 7.38-7.54 (m, 3H), 7.46 (t, 1H), 7.58-7.67 (m, 1H), 8.04 (d, 1H), 8.28 (td, 1H), 8.92 (s, 1H), 9.86 (s, 1H), 13.34 (s, 1H).

LC-MS (Method 4): $R_t$=0.95 min; MS (ESIpos): m/z=547 [M+H]$^+$.

Example 294

4-(difluoromethoxy)-N-[5-(2-fluorophenyl)-1,3,4-thiadiazol-2-yl]-3-[(morpholin-4-ylacetyl)amino]benzamide

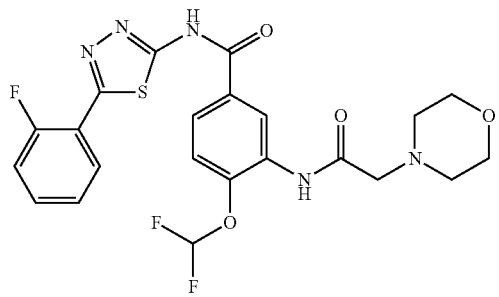 [SMILES: O=C(CN1CCOCC1)Nc1cc(C(=O)Nc2nnc(-c3ccccc3F)s2)ccc1OC(F)F]

To a suspension of 150 mg (0.33 mmol) of the compound of intermediate 148 in 3 mL of DMF were added 0.09 mL of triethylamine (0.66 mmol, 2 equiv), 0.06 mL of morpholine (0.66 mmol, 2 equiv), and 11.0 mg of potassium iodide (0.07 mmol, 0.2 equiv). The reaction mixture was stirred at room temperature over night. After concentration, the remaining solid was triturated with 8 mL of water and 4 mL of ethanol, stirred for 30 minutes, collected by filtration and dried. The remaining solid was triturated with 5 mL of ethanol and stirred under reflux, collected by filtration and dried. 117 mg (70% of theory) of the title compound were obtained.

$^1$H-NMR (400 MHz, DMSO-$d_6$): δ [ppm]=2.55-2.63 (m, 4H), 3.22 (s, 2H), 3.61-3.72 (m, 4H), 7.38-7.54 (m, 3H), 7.46 (t, 1H), 7.57-7.67 (m, 1H), 8.01 (dd, 1H), 8.28 (t, 1H), 8.99 (d, 1H), 9.91 (s, 1H), 13.35 (s, 1H).

LC-MS (Method 4): $R_t$=1.01 min; MS (ESIpos): m/z=508 [M+H]$^+$.

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, *arachis* oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media.

For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired.

Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to *arachis* oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution:

A 5 mg/ml solution of the desired compound of this invention can be made using sterile, injectable water, and the pH is adjusted if necessary. The solution is diluted for administration to 1-2 mg/ml with sterile 5% dextrose and is administered as an IV infusion over about 60 minutes.

Lyophilised Powder for IV Administration:

A sterile preparation can be prepared with (i) 100-1000 mg of the desired compound of this invention as a lyophilised powder, (ii) 32-327 mg/ml sodium citrate, and (iii) 300-3000 mg Dextran 40. The formulation is reconstituted with sterile, injectable saline or dextrose 5% to a concentration of 10 to 20 mg/ml, which is further diluted with saline or dextrose 5% to 0.2-0.4 mg/ml, and is administered either IV bolus or by IV infusion over 15-60 minutes.

Intramuscular suspension:

The following solution or suspension can be prepared, for intramuscular injection:

50 mg/ml of the desired, water-insoluble compound of this invention 5 mg/ml sodium carboxymethylcellulose 4 mg/ml TWEEN 80

9 mg/ml sodium chloride 9 mg/ml benzyl alcohol

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Methods of Treatment

The compounds and compositions provided herein can be used as inhibitors of one or more members of the Wnt pathway, including one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation and correct a genetic disorder due to mutations in Wnt signaling components. Non-limiting examples of diseases which can be treated with the compounds and compositions provided herein include a variety of cancers, diabetic retinopathy, neovascular glaucoma, rheumatoid arthritis, psoriasis, mycotic and viral infections, osteochondrodysplasia, Alzheimer's disease, osteoarthritis, polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemarm Syndrome and Rett syndrome.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day.

The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg.

The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Combination Therapies

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known chemotherapeutic agents or anti-cancer agents, e.g. anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The term "(chemotherapeutic) anti-cancer agents", includes but is not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, 1-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Biological Assays

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Measurement of the Inhibitory Activity of Selected Compounds on the Wnt Signaling Cascade In order to discover and characterize small molecules which inhibit the constitutive active colorectal cancer cell (CRC) Wnt pathway, a cellular reporter assay was employed. The corresponding assay cell was generated by transfection of the colorectal cancer cell line HCT116 (ATCC, #CCL-247) with the Super TopFlash vector (Morin, Science 275, 1997, 1787-1790; Molenaar et al., Cell 86 (3), 1996, 391-399). The HCT116 cell line is cultivated at 37° C. and 5% $CO_2$ in DMEM/F-12 (Life Technologies, #11320-074), supplemented with 2 mM glutamine, 20 mM HEPES, 1.4 mM pyruvate, 0.15% Na-bicarbonate and 10% foetal bovine serum (GIBCO, #10270), this cancer cell line is pathophysiological relevant since it carries a deletion of position S45 in the β-catenin gene, leading to constitutive active Wnt signaling. Stable transfectants were generated by cotransfection with pcDNA3 and selection of stable transfected cells with 1 mg/ml G418.

In a parallel approach, HCT116 cells were cotransfected with the FOP control vector and pcDNA3. The FOP vector is identical to the TOP construct, but it contains instead of functional TCF elements a randomized, non-functional sequence. For this transfection a stable transfected cell line was generated as well.

In preparation of the assay, the two cell lines were plated 24 hours before at 10000 cells per well of a 384 micro titre plate (MTP) in 30 μL growth medium. Selective inhibitory activity for small molecules on the mutated Wnt pathway was determined after parallel incubation of both (TOP and FOP) HCT116 reporter cell lines with a compound dilution series from 50 μM to 15 nM in steps of 3.16-fold dilutions in CAFTY buffer (130 mM NaCl, 5 mM KCl, 20 mM HEPES, 1 mM $MgCl_2$, 5 mM $NaHCO_3$, pH 7.4) containing 2 mM $Ca^{2+}$ and 0.01% BSA. The compounds were thereby serially predituted in 100% DMSO and thereafter in addition 50 fold into the CAFTY compound dilution buffer (described above). From this dilution 10 μL were added to the cells in 30 μL growth medium and incubated for 36 hours at 37° C. and 5% $CO_2$. Thereafter luciferase assay buffer (1:1 mixture of luciferase substrate buffer (20 mM Tricine, 2.67 mM $MgSO_4$, 0.1 mM EDTA, 4 mM DTT, 270 μM Coenzyme A, 470 μM Luciferin, 530 μM ATP, ph adjusted to pH 7.8 with a sufficient volume of 5M NaOH) and Triton buffer (30 mL Triton X-100, 115 mL glycerol, 308 mg Dithiothreitol, 4.45 g $Na2HPO_4.2H_2O$, 3.03 g TRIS HCl, ad 1l $H_2O$, pH 7.8) was added as equal volume to the compound solution on the cells to determine luciferase expression as a measure of Wnt signaling activity in a luminometer.

In order to determine the inhibitory activity of compounds for the WT Wnt signaling pathway, the Super TopFlash vector respectively FOP vector were cotransfected with pcDNA3 into HEK293 and stable transfected HEK293 cells were isolated by antibiotic selection. In preparation of compound testing, a dose response curve for the Wnt dependent luciferase expression was recorded by stimulating the assay cells with human recombinant Wnt-3a (R&D, #5036-WN-010) at different concentrations for 16 hours at 37° C. and 5% $CO_2$ followed by subsequent luciferase measurement as described above to determine the Wnt-3a EC50 for the HEK293 TOP cell line on the day of testing. The recombinant human Wnt-3a was thereby used between 2500 and 5 ng/ml in two-fold dilution steps. To determine the inhibitory activity of compounds on the WT Wnt pathway they were prepared and diluted as described above for the constitutive active Wnt pathway and coincubated with the $EC_{50}$ concentration of Wnt-3a for 16 hours at 37° C. and 5% $CO_2$ on the HEK293 TOP respectively control HEK293 FOP cells. Measurement of luciferase expression was done as described for the constitutive active Wnt assay.

TABLE 2

| Example No | HCT116 TOPFlash $IC_{50}$ [mol/L] | HCT116 FOPFlash $IC_{50}$ [mol/L] |
|---|---|---|
| 1 | 1.14E−6 | ≥5.00E−5 |
| 2 | 1.33E−7 | ≥5.00E−5 |
| 3 | 1.80E−6 | ≥5.00E−5 |
| 4 | 3.00E−7 | ≥5.00E−5 |
| 5 | 4.03E−8 | ≥5.00E−5 |
| 6 | 6.00E−8 | 8.90E−6 |
| 7 | 2.37E−8 | ≥5.00E−5 |
| 8 | 5.10E−8 | 8.35E−6 |
| 9 | 1.42E−8 | 2.02E−5 |
| 10 | 1.12E−8 | 1.50E−5 |
| 11 | 7.27E−7 | ≥5.00E−5 |
| 12 | 5.30E−7 | ≥5.00E−5 |
| 13 | 3.62E−7 | ≥5.00E−5 |
| 14 | 1.90E−7 | ≥5.00E−5 |
| 15 | 1.37E−7 | ≥5.00E−5 |
| 16 | 1.78E−8 | ≥5.00E−5 |
| 17 | 4.30E−8 | ≥5.00E−5 |
| 18 | 4.44E−7 | 9.90E−6 |
| 19 | 2.62E−8 | 1.10E−5 |
| 20 | 2.46E−6 | ≥5.00E−5 |
| 21 | 2.85E−7 | 9.20E−6 |
| 22 | 6.95E−7 | ≥5.00E−5 |
| 23 | 9.80E−8 | ≥5.00E−5 |
| 24 | 1.11E−6 | ≥5.00E−5 |
| 25 | 3.26E−7 | ≥5.00E−5 |
| 26 | 1.18E−7 | ≥5.00E−5 |
| 27 | 6.57E−8 | ≥5.00E−5 |
| 28 | 5.23E−8 | ≥5.00E−5 |
| 29 | 1.56E−7 | ≥5.00E−5 |
| 30 | 9.01E−8 | ≥5.00E−5 |
| 31 | 8.05E−7 | 3.60E−5 |
| 32 | 9.25E−7 | ≥5.00E−5 |
| 33 | 1.11E−7 | ≥5.00E−5 |
| 34 | 1.22E−6 | ≥5.00E−5 |
| 35 | 1.25E−6 | ≥5.00E−5 |
| 36 | 1.20E−6 | 2.20E−5 |
| 37 | 2.08E−8 | ≥5.00E−5 |
| 38 | 2.75E−8 | ≥5.00E−5 |
| 39 | 3.38E−8 | 3.20E−5 |
| 40 | 5.24E−8 | ≥5.00E−5 |
| 41 | 1.49E−7 | ≥5.00E−5 |
| 42 | 2.42E−7 | ≥5.00E−5 |
| 43 | 4.91E−8 | ≥5.00E−5 |
| 44 | 3.66E−7 | ≥5.00E−5 |
| 45 | 1.98E−7 | 2.65E−5 |
| 46 | 1.64E−7 | ≥5.00E−5 |
| 47 | 3.98E−8 | ≥5.00E−5 |
| 48 | 7.37E−8 | ≥5.00E−5 |
| 49 | 4.66E−8 | ≥5.00E−5 |
| 50 | 4.60E−8 | ≥5.00E−5 |
| 51 | 1.19E−7 | ≥5.00E−5 |
| 52 | 2.65E−8 | ≥5.00E−5 |
| 53 | 1.81E−7 | ≥5.00E−5 |
| 54 | 1.04E−7 | 2.80E−5 |

TABLE 2-continued

| Example No | HCT116 TOPFlash IC$_{50}$ [mol/L] | HCT116 FOPFlash IC$_{50}$ [mol/L] |
|---|---|---|
| 55 | 1.50E−7 | ≥5.00E−5 |
| 56 | 1.04E−7 | ≥5.00E−5 |
| 57 | 1.24E−7 | ≥5.00E−5 |
| 58 | 8.30E−8 | 2.00E−5 |
| 59 | 3.85E−7 | ≥5.00E−5 |
| 60 | 2.02E−8 | ≥5.00E−5 |
| 61 | 2.65E−8 | ≥5.00E−5 |
| 62 | 6.73E−8 | ≥5.00E−5 |
| 63 | 5.08E−8 | ≥5.00E−5 |
| 64 | 2.30E−8 | ≥5.00E−5 |
| 65 | 5.20E−9 | ≥5.00E−5 |
| 66 | 1.10E−8 | ≥5.00E−5 |
| 67 | 2.96E−8 | ≥5.00E−5 |
| 68 | 7.72E−9 | ≥5.00E−5 |
| 69 | 1.48E−8 | ≥5.00E−5 |
| 70 | 2.40E−8 | 4.60E−6 |
| 71 | 2.92E−8 | 4.50E−5 |
| 72 | 1.06E−7 | 8.00E−6 |
| 73 | 9.85E−8 | ≥5.00E−5 |
| 74 | 8.58E−8 | 4.22E−5 |
| 75 | 1.85E−8 | ≥5.00E−5 |
| 76 | 3.14E−8 | ≥5.00E−5 |
| 77 | 3.70E−7 | 1.40E−5 |
| 78 | 5.08E−7 | ≥5.00E−5 |
| 79 | 2.04E−8 | ≥5.00E−5 |
| 80 | 2.70E−8 | ≥5.00E−5 |
| 81 | 2.31E−8 | ≥5.00E−5 |
| 82 | 2.55E−6 | ≥5.00E−5 |
| 83 | 5.15E−7 | ≥5.00E−5 |
| 84 | 4.53E−7 | ≥5.00E−5 |
| 85 | 1.50E−7 | ≥5.00E−5 |
| 86 | 8.90E−7 | ≥5.00E−5 |
| 87 | 8.58E−7 | 4.80E−5 |
| 88 | 4.17E−7 | ≥5.00E−5 |
| 89 | 2.16E−7 | 4.40E−5 |
| 90 | 1.73E−7 | ≥5.00E−5 |
| 91 | 6.50E−7 | 4.40E−5 |
| 92 | 3.60E−7 | ≥5.00E−5 |
| 93 | 2.40E−7 | ≥5.00E−5 |
| 94 | 4.33E−7 | ≥5.00E−5 |
| 95 | 5.81E−8 | ≥5.00E−5 |
| 96 | 8.55E−7 | ≥5.00E−5 |
| 97 | 1.93E−6 | ≥5.00E−5 |
| 98 | 8.70E−8 | 2.64E−5 |
| 99 | 9.35E−7 | 9.30E−6 |
| 100 | 8.58E−7 | ≥5.00E−5 |
| 101 | 3.20E−6 | ≥5.00E−5 |
| 102 | 4.58E−7 | 1.95E−5 |
| 103 | 7.52E−7 | 2.10E−5 |
| 104 | 2.03E−6 | ≥5.00E−5 |
| 105 | 6.40E−8 | ≥5.00E−5 |
| 106 | 2.85E−7 | ≥5.00E−5 |
| 107 | 2.09E−7 | ≥5.00E−5 |
| 108 | 4.63E−7 | ≥5.00E−5 |
| 109 | 2.08E−7 | 2.99E−5 |
| 110 | 4.50E−7 | 4.20E−5 |
| 111 | 3.22E−8 | ≥5.00E−5 |
| 112 | 2.70E−7 | ≥5.00E−5 |
| 113 | 2.30E−8 | ≥5.00E−5 |
| 114 | 4.60E−8 | ≥5.00E−5 |
| 115 | 8.80E−9 | 2.20E−6 |
| 116 | 8.40E−8 | 8.10E−6 |
| 117 | 1.80E−8 | 4.45E−5 |
| 118 | 1.26E−8 | ≥5.00E−5 |
| 119 | 6.50E−7 | ≥5.00E−5 |
| 120 | 1.05E−7 | ≥5.00E−5 |
| 121 | 8.25E−7 | ≥5.00E−5 |
| 122 | 2.02E−7 | ≥5.00E−5 |
| 123 | 5.60E−7 | ≥5.00E−5 |
| 124 | 7.25E−8 | ≥5.00E−5 |
| 125 | 1.70E−6 | ≥5.00E−5 |
| 126 | 5.25E−7 | ≥5.00E−5 |
| 127 | 8.85E−7 | ≥5.00E−5 |
| 128 | 7.10E−7 | ≥5.00E−5 |
| 129 | 9.00E−7 | ≥5.00E−5 |
| 130 | 3.18E−7 | ≥5.00E−5 |
| 131 | 5.10E−8 | ≥5.00E−5 |
| 132 | 3.55E−8 | 2.00E−5 |
| 133 | 5.46E−8 | ≥5.00E−5 |
| 134 | 1.66E−8 | 5.20E−6 |
| 135 | 8.48E−8 | ≥5.00E−5 |
| 136 | 2.14E−8 | ≥5.00E−5 |
| 137 | 2.72E−7 | 2.00E−5 |
| 138 | 1.50E−7 | ≥5.00E−5 |
| 139 | 5.00E−7 | 2.50E−5 |
| 140 | 2.93E−7 | 1.00E−5 |
| 141 | 6.80E−7 | ≥5.00E−5 |
| 142 | 1.18E−7 | 7.15E−6 |
| 143 | 2.04E−7 | ≥5.00E−5 |
| 144 | 1.95E−7 | ≥5.00E−5 |
| 145 | 1.52E−7 | ≥5.00E−5 |
| 146 | 3.65E−7 | ≥5.00E−5 |
| 147 | 2.20E−6 | ≥5.00E−5 |
| 148 | 2.05E−7 | 3.65E−5 |
| 149 | 7.04E−7 | 4.75E−5 |
| 150 | 7.60E−8 | ≥5.00E−5 |
| 151 | 7.10E−8 | ≥5.00E−5 |
| 152 | 2.00E−7 | ≥5.00E−5 |
| 153 | 1.32E−7 | 3.00E−5 |
| 154 | 4.20E−7 | ≥5.00E−5 |
| 155 | 5.92E−7 | 3.25E−5 |
| 156 | 5.42E−7 | ≥5.00E−5 |
| 157 | 9.66E−8 | ≥5.00E−5 |
| 158 | 7.36E−8 | 2.18E−5 |
| 159 | 4.14E−8 | ≥5.00E−5 |
| 160 | 9.48E−7 | 2.80E−5 |
| 161 | 3.25E−7 | 1.00E−5 |
| 162 | 8.55E−8 | ≥5.00E−5 |
| 163 | 5.70E−8 | ≥5.00E−5 |
| 164 | 2.20E−7 | ≥5.00E−5 |
| 165 | 5.10E−8 | 7.20E−6 |
| 166 | 1.48E−7 | 3.90E−5 |
| 167 | 6.85E−7 | ≥5.00E−5 |
| 168 | 1.08E−6 | 1.20E−5 |
| 169 | 6.60E−8 | ≥5.00E−5 |
| 170 | 1.18E−7 | ≥5.00E−5 |
| 171 | 1.02E−7 | ≥5.00E−5 |
| 172 | 8.55E−7 | ≥5.00E−5 |
| 173 | 5.20E−7 | ≥5.00E−5 |
| 174 | 3.80E−6 | ≥5.00E−5 |
| 175 | 2.15E−7 | 7.10E−6 |
| 176 | 3.15E−7 | ≥5.00E−5 |
| 177 | 4.60E−7 | 3.50E−5 |
| 178 | 4.24E−8 | 3.80E−6 |
| 179 | 3.62E−7 | ≥5.00E−5 |
| 180 | 1.48E−7 | 9.80E−6 |
| 181 | 5.30E−8 | ≥5.00E−5 |
| 182 | 2.88E−7 | 4.40E−5 |
| 183 | 2.90E−8 | ≥5.00E−5 |
| 184 | 1.96E−7 | 1.10E−5 |
| 185 | 1.60E−7 | 1.00E−5 |
| 186 | 9.55E−8 | 5.40E−6 |
| 187 | 1.75E−7 | 4.20E−5 |
| 188 | 1.20E−7 | 5.50E−6 |
| 189 | 1.38E−7 | 1.00E−5 |
| 190 | 8.70E−8 | 9.50E−6 |
| 191 | 4.10E−6 | ≥5.00E−5 |
| 192 | 1.35E−7 | 1.24E−5 |
| 193 | 1.48E−7 | 8.80E−6 |
| 194 | 3.99E−8 | 3.50E−5 |
| 195 | 2.22E−7 | ≥5.00E−5 |
| 196 | 1.43E−7 | ≥5.00E−5 |
| 197 | 1.20E−6 | 3.40E−5 |
| 198 | 1.44E−7 | 1.50E−5 |
| 199 | 7.17E−8 | 8.80E−6 |
| 200 | 1.90E−7 | 6.40E−6 |
| 201 | 1.06E−7 | 2.86E−5 |
| 202 | 2.00E−7 | 5.80E−6 |
| 203 | 1.24E−7 | 1.52E−5 |
| 204 | 7.65E−8 | 3.28E−5 |
| 205 | 2.02E−8 | 1.82E−5 |
| 206 | 8.76E−8 | 3.65E−5 |
| 207 | 1.53E−7 | 8.55E−6 |
| 208 | 1.04E−8 | 9.70E−6 |

TABLE 2-continued

| Example No | HCT116 TOPFlash $IC_{50}$ [mol/L] | HCT116 FOPFlash $IC_{50}$ [mol/L] |
|---|---|---|
| 209 | 1.12E−7 | 1.10E−5 |
| 210 | 1.52E−7 | 2.95E−5 |
| 211 | 4.02E−8 | 2.46E−5 |
| 212 | 1.80E−7 | ≥5.00E−5 |
| 213 | 1.40E−7 | ≥5.00E−5 |
| 214 | 3.75E−7 | 6.30E−6 |
| 215 | 2.45E−7 | 3.30E−6 |
| 216 | 2.60E−7 | 3.60E−6 |
| 217 | 4.38E−7 | ≥5.00E−5 |
| 218 | 3.30E−7 | 1.50E−5 |
| 219 | 2.45E−7 | ≥5.00E−5 |
| 220 | 3.75E−7 | 1.30E−5 |
| 221 | 2.35E−7 | 1.22E−5 |
| 222 | 2.63E−7 | 1.52E−5 |
| 223 | 2.38E−7 | 1.71E−5 |
| 224 | 3.82E−7 | ≥5.00E−5 |
| 225 | 2.37E−7 | 1.12E−5 |
| 226 | 2.45E−7 | 6.50E−6 |
| 227 | 2.45E−7 | 1.02E−5 |
| 228 | 2.87E−6 | 2.90E−5 |
| 229 | 2.30E−6 | ≥5.00E−5 |
| 230 | 7.20E−7 | ≥5.00E−5 |
| 231 | 1.02E−6 | ≥5.00E−5 |
| 232 | 2.20E−6 | ≥5.00E−5 |
| 233 | 9.85E−7 | ≥5.00E−5 |
| 234 | 6.35E−7 | 4.05E−5 |
| 235 | 1.31E−6 | ≥5.00E−5 |
| 236 | 2.76E−7 | ≥5.00E−5 |
| 237 | 1.39E−7 | 1.30E−5 |
| 238 | 1.75E−6 | ≥5.00E−5 |
| 239 | 2.89E−6 | ≥5.00E−5 |
| 240 | 1.18E−6 | ≥5.00E−5 |
| 241 | 1.82E−6 | ≥5.00E−5 |
| 242 | 7.53E−7 | ≥5.00E−5 |
| 243 | 2.80E−8 | 7.70E−6 |
| 244 | 1.20E−7 | ≥5.00E−5 |
| 245 | 7.85E−9 | 5.20E−6 |
| 246 | 4.75E−8 | 2.78E−5 |
| 247 | 1.10E−8 | 7.20E−6 |
| 248 | 3.40E−7 | ≥5.00E−5 |
| 249 | 1.98E−7 | 3.80E−5 |
| 250 | 1.92E−7 | 3.10E−5 |
| 251 | 2.20E−7 | 1.60E−5 |
| 252 | 2.30E−6 | ≥5.00E−5 |
| 253 | 4.04E−6 | ≥5.00E−5 |
| 254 | 4.34E−6 | ≥5.00E−5 |
| 255 | 2.10E−6 | ≥5.00E−5 |
| 256 | 2.40E−7 | ≥5.00E−5 |
| 257 | 1.70E−8 | ≥5.00E−5 |
| 258 | 4.55E−8 | 2.40E−5 |
| 259 | 1.19E−7 | ≥5.00E−5 |
| 260 | 1.23E−7 | 9.80E−6 |
| 261 | 1.50E−7 | ≥5.00E−5 |
| 262 | 1.95E−7 | ≥5.00E−5 |
| 263 | 2.50E−7 | ≥5.00E−5 |
| 264 | 2.55E−7 | ≥5.00E−5 |
| 265 | 3.20E−7 | ≥5.00E−5 |
| 266 | 3.45E−7 | ≥5.00E−5 |
| 267 | 3.65E−7 | ≥5.00E−5 |
| 268 | 3.65E−7 | ≥5.00E−5 |
| 269 | 3.75E−7 | ≥5.00E−5 |
| 270 | 3.90E−7 | ≥5.00E−5 |
| 271 | 4.80E−7 | ≥5.00E−5 |
| 272 | 5.45E−7 | ≥5.00E−5 |
| 273 | 9.30E−7 | 2.70E−5 |
| 274 | 3.02E−6 | ≥5.00E−5 |
| Ref. | 1.38E−6 | 3.10E−6 |

"Ref." in Table 2 means the compound niclosamide disclosed in prior art (compound 1-8 on page 36 of WO2011/035321A1) which is less selective than the compounds of the present invention.

Some of the compounds of general formula (I) show low solubility in aqueous media and organic solvents. This can affect the possibility to assess the activity of such compounds with the described assays. For example, the $IC_{50}$ value we determined for 4-methoxy-3-[(morpholin-4-ylacetyl)amino]-N-(5-phenyl-1,3,4-thiadiazol-2-yl)benzamide in the HCT116 TOPFlash assay was higher than expected. But it turned out that the solubility of this compound was determined to be lower than 0.1 mg/L or 0.22 μmol/L, respectively in a buffer at pH6.5. Therefore, the high $IC_{50}$ value of the compound might be a result of the low solubility.

Measurement of the Inhibitory Activity of Selected Compounds on the Wildtype Wnt Signaling Cascade In order to discover and characterize small molecules which inhibit the wildtype Wnt pathway, a cellular reporter assay was employed. The corresponding assay cell was generated by transfection of the mammalian cell line HEK293 (ATCC, #CRL-1573) with the Super TopFlash vector (Morin, Science 275, 1997, 1787-1790; Molenaar et al., Cell 86 (3), 1996, 391-399). The HEK293 cell line is cultivated at 37° C. and 5% $CO_2$ in DMEM (Life Technologies, #41965-039), supplemented with 2 mM glutamine, 20 mM HEPES, 1.4 mM pyruvate, 0.15% Na-bicarbonate and 10% foetal bovine serum (GIBCO, #10270). Stable transfectants were generated by selection with 300 μg/ml Hygromycin.

In a parallel approach, HEK293 cells were cotransfected with the FOP control vector and pcDNA3. The FOP vector is identical to the TOP construct, but it contains instead of functional TCF elements a randomized, non-functional sequence. For this transfection a stable transfected cell line was generated as well, based on selection with Geneticin (1 mg/ml).

In preparation of the assay, the two cell lines were plated 24 hours before beginning the test at 10000 cells per well in a 384 micro titre plate (MTP) in 30 μl growth medium. Before compound testing a dose response curve for the Wnt dependent luciferase expression was recorded by stimulating the assay cell line with human recombinant Wnt-3a (R&D, #5036-WN-010) at different concentrations for 16 hours at 37° C. and 5% $CO_2$ followed by subsequent luciferase measurement, to determine the Wnt-3a $EC_{50}$ for the HEK293 TOP cell line on the day of testing. The recombinant human Wnt-3a was thereby applied between 2500 and 5 ng/ml in two-fold dilution steps. Selective inhibitory activity for small molecules on the wildtype Wnt pathway was determined after parallel incubation of both (TOP and FOP) HEK293 reporter cell lines with a compound dilution series from 50 μM to 15 nM in steps of 3.16-fold dilutions in CAFTY buffer (130 mM NaCl, 5 mM KCl, 20 mM HEPES, 1 mM $MgCl_2$, 5 mM $NaHCO_3$, pH 7.4) containing 2 mM $Ca^{2+}$ and 0.01% BSA.

The compounds were thereby serially prediluted in 100% DMSO and thereafter 50 fold into the CAFTY compound dilution buffer (described above). From this dilution 10 μl were added in combination with the $EC_{50}$ concentration of recombinant Wnt3a to the cells in 30 μl growth medium and incubated for 16 hours at 37° C. and 5% $CO_2$. Thereafter luciferase assay buffer (1:1 mixture of luciferase substrate buffer (20 mM Tricine, 2.67 mM $MgSO_4$, 0.1 mM EDTA, 4 mM DTT, 270 μM Coenzyme A, 470 μM Luciferin, 530 μM ATP, ph adjusted to pH 7.8 with a sufficient volume of 5M NaOH) and Triton buffer (30 ml Triton X-100, 115 ml glycerol, 308 mg Dithiothreitol, 4.45 g $Na_2HPO_4 \cdot 2H_2O$, 3.03 g TRIS HCl (CAS Number 1185-53-1), ad 1l $H_2O$, pH 7.8) was added in an equal volume to determine luciferase expression as a measure of Wnt signaling activity in a luminometer. The Wnt inhibitory activity was determined as $IC_{50}$ of resulting dose response curves.

TABLE 3

| Example No | HEK TOP OncoFlash IC$_{50}$ [mol/L] | HEK FOP IC$_{50}$ [mol/L] |
|---|---|---|
| 1 | 3.30E−6 | ≥5.00E−5 |
| 2 | 1.20E−7 | 6.90E−6 |
| 6 | 1.30E−8 | 2.80E−6 |
| 7 | 3.80E−8 | 7.40E−6 |
| 8 | 1.30E−7 | 8.10E−6 |
| 9 | 9.00E−9 | 8.20E−6 |
| 10 | 9.20E−8 | 1.90E−5 |
| 11 | 7.00E−7 | 8.10E−6 |
| 14 | 5.50E−7 | ≥5.00E−5 |
| 15 | 4.80E−8 | ≥5.00E−5 |
| 16 | 9.20E−8 | ≥5.00E−5 |
| 17 | 3.30E−8 | ≥5.00E−5 |
| 19 | 9.90E−7 | ≥5.00E−5 |
| 20 | 2.20E−6 | ≥5.00E−5 |
| 21 | 1.40E−7 | 5.80E−6 |
| 22 | 1.10E−6 | 2.40E−5 |
| 24 | 6.50E−7 | 1.70E−5 |
| 25 | 9.00E−8 | 1.00E−5 |
| 26 | 3.50E−7 | ≥5.00E−5 |
| 27 | 1.00E−6 | ≥5.00E−5 |
| 28 | 8.00E−7 | 2.00E−5 |
| 30 | 1.40E−6 | ≥5.00E−5 |
| 32 | 2.60E−7 | 4.00E−6 |
| 33 | 3.70E−7 | 7.40E−6 |
| 35 | 9.10E−7 | ≥5.00E−5 |
| 37 | 2.80E−7 | ≥5.00E−5 |
| 38 | 2.00E−7 | ≥5.00E−5 |
| 40 | 5.30E−7 | ≥5.00E−5 |
| 41 | 7.20E−7 | ≥5.00E−5 |
| 42 | 1.06E−7 | ≥5.00E−5 |
| 43 | 1.10E−7 | ≥5.00E−5 |
| 44 | 1.96E−007 | ≥5.00E−5 |
| 45 | 1.90E−7 | ≥5.00E−5 |
| 46 | 6.90E−7 | ≥5.00E−5 |
| 47 | 9.00E−8 | ≥5.00E−5 |
| 48 | 1.30E−7 | ≥5.00E−5 |
| 49 | 4.50E−8 | ≥5.00E−5 |
| 50 | 9.70E−8 | ≥5.00E−5 |
| 51 | 3.73E−7 | ≥5.00E−5 |
| 53 | 8.20E−7 | ≥5.00E−5 |
| 54 | 1.30E−7 | ≥5.00E−5 |
| 56 | 1.90E−7 | ≥5.00E−5 |
| 57 | 5.00E−7 | ≥5.00E−5 |
| 58 | 2.70E−7 | ≥5.00E−5 |
| 60 | 2.90E−7 | 4.10E−5 |
| 61 | 1.20E−7 | ≥5.00E−5 |
| 62 | 1.80E−7 | ≥5.00E−5 |
| 63 | 1.40E−7 | ≥5.00E−5 |
| 64 | 3.70E−8 | ≥5.00E−5 |
| 65 | 1.50E−7 | ≥5.00E−5 |
| 66 | 1.30E−7 | ≥5.00E−5 |
| 67 | 1.30E−8 | ≥5.00E−5 |
| 68 | 5.17E−9 | ≥5.00E−5 |
| 70 | 8.50E−8 | 6.30E−6 |
| 71 | 1.60E−7 | ≥5.00E−5 |
| 75 | 2.70E−8 | ≥5.00E−5 |
| 76 | 5.40E−8 | ≥5.00E−5 |
| 79 | 6.40E−8 | 1.50E−5 |
| 80 | 1.50E−7 | 1.00E−5 |
| 81 | 1.50E−8 | ≥5.00E−5 |
| 95 | 5.00E−8 | ≥5.00E−5 |
| 105 | 3.00E−7 | ≥5.00E−5 |
| 111 | 5.80E−008 | ≥5.00E−5 |
| 113 | 8.90E−7 | ≥5.00E−5 |
| 115 | 5.20E−8 | 4.70E−6 |
| 117 | 1.40E−8 | 1.00E−5 |
| 118 | 5.70E−8 | 1.60E−5 |
| 124 | 8.40E−8 | 1.30E−5 |
| 126 | 3.60E−8 | ≥5.00E−5 |
| 131 | 1.00E−7 | 1.30E−5 |
| 132 | 7.00E−8 | 1.10E−5 |
| 133 | 1.30E−7 | ≥5.00E−5 |
| 134 | 3.10E−8 | 1.20E−5 |
| 136 | 7.50E−8 | ≥5.00E−5 |
| 151 | 2.50E−7 | ≥5.00E−5 |
| 159 | 5.40E−8 | ≥5.00E−5 |

QPCR Protocol

Real-time RT-PCR using a TaqMan fluorogenic detection system is a simple and sensitive assay for quantitative analysis of gene transcription. The TaqMan fluorogenic detection system can monitor PCR in real time using a dual-labeled fluorogenic hybridization probe (TaqMan probe) and a polymerase with 5'-3' exonuclease activity.

Cells from different cancer cell lines (as HCT116, but not limited to) were grown at 500-1000 cells/well in 384 well cell culture plates. For cell lysis the cell medium was carefully removed. The cells were washed carefully once with 50 µL/well PBS. Then 9.75 µL/well cell lysis buffer (50 mM TRIS HCl pH 8.0, 40 mM NaCl, 1.5 mM MgCl$_2$, 0.5% IGEPAL CA 630, 50 mM Guanidium thiocyanate) and 0.25 µL RNASeOUT (40 U/µl, Invitrogen, 10777-019)) per well were added. The plate was incubated for 5 min at room temperature. Then 30 µL DNAse/RNAse-free water per well added and the lysates were mixed. For the One-Step RT-PCR 2 µL lysate (each) was transferred to a 384 well PCR plate. The PCR reaction was composed by 5 µL 2× One Step RT qPCR MasterMix Plus, 0.05 µL Euroscript RT/RNAse Inhibitor (50 U/µl, 20 U/µl) and 200 nM of the appropriate Primer/Hydrolysis Probe mix (primer sequences of forward, reverse and probe are given below for each analysed gene of interest or house keeping gene). 10 µL water were added per well. Seal the plate with an adhesive optical film. The RT-PCR protocol was setup with 30 min 48° C., then 10 min 95° C. followed by 50 cycles of 15 sec 95° C./1 min 60° C. and a cooling step of 40° C. for 30 sec using a Lightcycler L5440 from Roche.

Relative expression was calculated using CP values from the gene of interest (e.g. AXIN2, but not limited to) and a house keeping gene (L32).

Used Primers

```
L32
(forward primer: AAGTTCATCCGGCACCAGTC;

reverse primer: TGGCCCTTGAATCTTCTACGA;

probe: CCCAGAGGCATTGACAACAGGG)

AXIN2
(forward primer: AGGCCAGTGAGTTGGTTGTC;

reverse primer: AGCTCTGAGCCTTCAGCATC;

probe: TCTGTGGGGAAGAAATTCCATACCG)
```

Sequence Listings

| SEQ ID NO | |
|---|---|
| 1 | AAGTTCATCCGGCACCAGTC |
| 2 | TGGCCCTTGAATCTTCTACGA |
| 3 | CCCAGAGGCATTGACAACAGGG |
| 4 | AGGCCAGTGAGTTGGTTGTC |
| 5 | AGCTCTGAGCCTTCAGCATC |
| 6 | TCTGTGGGGAAGAAATTCCATACCG |

The invention claimed is:

1. A compound of formula (I):

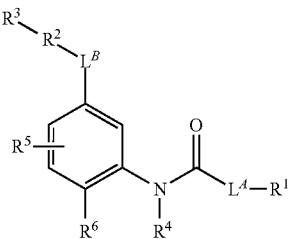

(I)

wherein:

$L^A$ is
—$CH_2$—, —$CH(CH_3)$— or

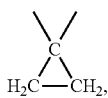

$L^B$ is —N(H)—C(=O)— or —C(=O)—N(H)—;
$R^1$ is a
  5- to 8-membered heterocycloalkyl-, optionally substituted, one or more times, identically or differently, with a substituent selected from the group consisting of:
  halo-, hydroxy-, cyano-, $C_1$-$C_3$-alkyl-, $C_1$-$C_3$-alkoxy-, halo-$C_1$-$C_3$-alkyl-, hydroxy-$C_1$-$C_3$-alkyl-, halo-$C_1$-$C_3$-alkoxy-, and $C_3$-$C_7$-cycloalkyl-;
$R^2$ is a group selected from the group consisting of:

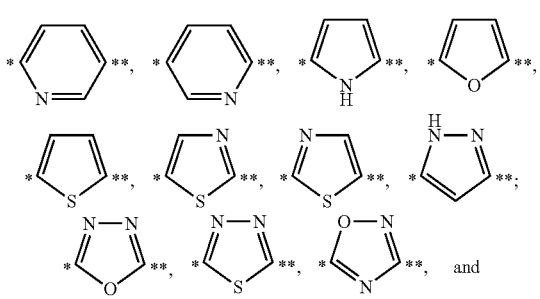

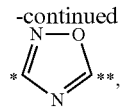

wherein "*" indicates the point of attachment to $R^3$, and "**" indicates the point of attachment to $L^B$, and wherein said group is optionally substituted, one or more times, identically or differently, with a $C_1$-$C_3$-alkyl- group;

$R^3$ is a phenyl- group,
  wherein said phenyl- group is optionally substituted, one or more times, identically or differently, with a substituent selected from the group consisting of:
  halo-, hydroxy-, —N($R^9$)($R^{10}$), —N(H)C(=O)$R^9$, cyano-, nitro-, $C_1$-$C_3$-alkyl-, $C_1$-$C_3$-alkoxy-, halo-$C_1$-$C_3$-alkyl-, hydroxy-$C_1$-$C_3$-alkyl-, amino-$C_1$-$C_3$-alkyl-, and halo-$C_1$-$C_3$-alkoxy-;

$R^4$ is a hydrogen atom or a $C_1$-$C_3$-alkyl- group;

$R^5$ is a hydrogen atom, a halogen atom, or a group selected from the group consisting of:
  cyano-, $C_1$-$C_3$-alkyl-, and $C_1$-$C_3$-alkoxy-;

$R^6$ is a group selected from the group consisting of:
  $C_1$-$C_6$-alkyl-, $C_2$-$C_6$-alkenyl-, $C_2$-$C_6$-alkynyl-, $C_1$-$C_6$-alkoxy-, $C_3$-$C_6$-cycloalkoxy-, halo-, hydroxy-, cyano-, aryl-, heteroaryl-, —N($R^9$)($R^{10}$), —C(=O)—O—$C_1$-$C_4$-alkyl, —C(=O)—N($R^9$)($R^{10}$), $R^9$—S—, $R^9$—S(=O)—, and $R^9$—S(=O)$_2$—, wherein said $C_1$-$C_6$-alkyl-, $C_2$-$C_6$-alkenyl-, $C_2$-$C_6$-alkynyl-, aryl-, heteroaryl-, and $C_1$-$C_6$-alkoxy- group is optionally substituted, one or more times, identically or differently, with a substituent selected from the group consisting of:
halo-, cyano-, nitro-, hydroxy-, $C_1$-$C_3$-alkyl-, $C_1$-$C_3$-alkoxy-, halo-$C_1$-$C_3$-alkoxy-, hydroxy-$C_1$-$C_3$-alkoxy-, $C_1$-$C_3$-alkoxy-$C_2$-$C_3$-alkoxy-, $C_3$-$C_7$-cycloalkyl-, $C_4$-$C_7$-cycloalkenyl-, 3- to 10-membered heterocycloalkyl-, 4- to 10-membered heterocycloalkenyl-, aryl-, heteroaryl-, —C(=O)$R^9$, —C(=O)O—($C_1$-$C_4$-alkyl), —OC(=O)—$R^9$, —N(H)C(=O)$R^9$, —N($R^{10}$)C(=O)$R^9$, —N(H)C(=O)NR$^{10}$R$^9$, —N($R^{11}$)C(=O)NR$^{10}$R$^9$, —N(H)R$^9$, —NR$^{10}$R$^9$, —C(=O)N(H)R$^9$, —C(=O)NR$^{10}$R$^9$, $R^9$—S—, $R^9$—S(=O)—, $R^9$—S(=O)$_2$—, —N(H)S(=O)$R^9$, —N($R^{10}$)S(=O)$R^9$, —S(=O)N(H)$R^9$, —S(=O)NR$^{10}$R$^9$, —N(H)S(=O)$_2$R$^9$, —N(R$^9$)S(=O)$_2$R$^{10}$, —S(=O)$_2$N(H)R$^9$, —S(=O)$_2$NR$^{10}$R$^9$, —S(=O)(=NR$^{10}$)R$^9$, and —N=S(=O)(R$^{10}$)R$^9$; and R$^9$, R$^{10}$, and R$^{11}$ are independently a hydrogen atom, a C$_1$-C$_3$-alkyl- group, or a C$_1$-C$_3$-alkoxy-C$_1$-C$_3$-alkyl- group;

or

R$^9$ and R$^{10}$ are taken together with the atom or the group of atoms to which they are attached to form a 3- to 10-membered heterocycloalkyl- or 4- to 10-membered heterocycloalkenyl- group, or a tautomer, an N-oxide, or a salt thereof, or a mixture of any of the foregoing.

2. The compound according to claim 1, wherein:

R$^1$ is a group selected from the group consisting of:

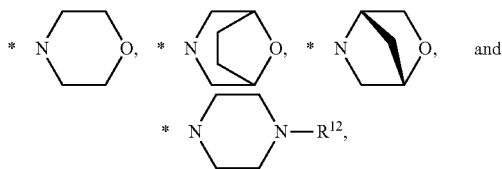

wherein * indicates the point of attachment to L$^A$, and wherein R$^{12}$ is a methyl-, ethyl- or cyclopropyl- group, or a tautomer, an N-oxide, or a salt thereof, or a mixture of any of the foregoing.

3. The compound according to claim 1, wherein:

R$^2$ is a group selected from the group consisting of:

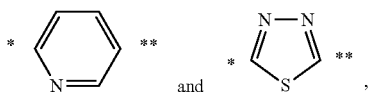

wherein "*" indicates the point of attachment to R$^3$, and "**" indicates the point of attachment to L$^B$, or a tautomer, an N-oxide, or a salt thereof, or a mixture of any of the foregoing.

4. The compound according to claim 1, wherein:

R$^3$ is

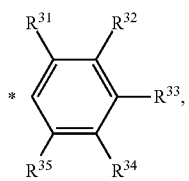

wherein "*" indicates the point of attachment to R$^2$;

R$^{31}$, R$^{32}$, R$^{34}$ and R$^{35}$ are independently a hydrogen atom or a group selected from the group consisting of:

halo-, hydroxy-, —NH$_2$, cyano-, nitro-, C$_1$-C$_3$-alkyl-, C$_1$-C$_3$-alkoxy-, halo-C$_1$-C$_3$-alkyl-, hydroxy-C$_1$-C$_3$-alkyl-, and halo-C$_1$-C$_3$-alkoxy-; and R$^{33}$ is a hydrogen atom or a substituent selected from the group consisting of:

hydroxy-, —CHF$_2$, —NH$_2$, —NR$^{10}$R$^9$, —CH$_2$NH$_2$, and —N(H)C(=O)CH$_3$, or a tautomer, an N-oxide, or a salt thereof, or a mixture of any of the foregoing.

5. The compound according to claim 1, wherein:

R$^4$ is a hydrogen atom; and

R$^5$ is a hydrogen atom, or a tautomer, an N-oxide, or a salt thereof, or a mixture of any of the foregoing.

6. The compound according to claim 1, wherein:

R$^6$ is a group selected from the group consisting of:

C$_1$-C$_6$-alkyl-, C$_1$-C$_6$-alkoxy-, C$_3$-C$_6$-cycloalkoxy-, halo-, hydroxy-, cyano-, —C(=O)—O—C$_1$-C$_4$-alkyl, —C(=O)—N(R$^9$)(R$^1$), R$^9$—S—, R$^9$—S(=O)—, and R$^9$—S(=O)$_2$—, wherein said C$_1$-C$_6$-alkyl- and C$_1$-C$_6$-alkoxy- groups are optionally substituted, one or more times, identically or differently, with a substituent selected from the group consisting of:

halo-, C$_1$-C$_3$-alkoxy-, C$_1$-C$_3$-alkoxy-C$_2$-C$_3$-alkoxy-, and C$_3$-C$_7$-cycloalkyl-, or a tautomer, an N-oxide, or a salt thereof, or a mixture of any of the foregoing.

7. The compound according to claim 1, which is selected from the group consisting of:

N-[6-(2-fluorophenyl)pyridin-3-yl]-4-methoxy-3-[(morpholin-4-ylacetyl)amino]benzamide;

N-[6-(2-fluorophenyl)pyridin-3-yl]-4-methoxy-3-[(8-oxa-3-azabicyclo[3.2.1]oct-3-ylacetyl)amino]benzamide;

N-[6-(2-fluorophenyl)pyridin-3-yl]-4-methoxy-3-{[(1S,4S)-2-oxa-5-azabicyclo[2.2.1]hept-5-ylacetyl]amino}benzamide;

4-methoxy-3-[(morpholin-4-ylacetyl)amino]-N-(6-phenylpyridin-3-yl)benzamide;

N-[6-(2-fluorophenyl)pyridin-3-yl]-3-[(morpholin-4-ylacetyl)amino]-4-(trifluoromethoxy)benzamide;

N-[6-(2-fluorophenyl)pyridin-3-yl]-3-[(8-oxa-3-azabicyclo[3.2.1]oct-3-ylacetyl)amino]-4-(trifluoromethoxy)benzamide;

N-[6-(2-fluorophenyl)pyridin-3-yl]-3-{[2-(morpholin-4-yl)propanoyl]amino}-4-(trifluoromethoxy)benzamide;

N-[6-(2-fluorophenyl)pyridin-3-yl]-3-{[(2S)-2-(morpholin-4-yl)propanoyl]amino}-4-(trifluoromethoxy)benzamide;

N-[6-(2-fluorophenyl)pyridin-3-yl]-3-{[(2R)-2-(morpholin-4-yl)propanoyl]amino}-4-(trifluoromethoxy)benzamide;

3-{[2-(morpholin-4-yl)propanoyl]amino}-N-(6-phenylpyridin-3-yl)-4-(trifluoromethoxy)benzamide;

3-[(morpholin-4-ylacetyl)amino]-N-(5-phenyl-1,3-thiazol-2-yl)-4-(trifluoromethyl)benzamide;

3-[(morpholin-4-ylacetyl)amino]-N-(6-phenylpyridin-3-yl)-4-(trifluoromethyl)benzamide;

3-[(morpholin-4-ylacetyl)amino]-N-(5-phenyl-1,3-thiazol-2-yl)-4-(trifluoromethoxy)benzamide;

3-[(morpholin-4-ylacetyl)amino]-N-(6-phenylpyridin-3-yl)-4-(trifluoromethoxy)benzamide;

N-{3-[(morpholin-4-ylacetyl)amino]-4-(trifluoromethoxy)phenyl}-5-phenyl-1,3-thiazole-2-carboxamide;

N-{3-[(morpholin-4-ylacetyl)amino]-4-(trifluoromethoxy)phenyl}-5-phenylthiophene-2-carboxamide;

N-{4-tert-butyl-3-[(morpholin-4-ylacetyl)amino]phenyl}-6-phenylnicotinamide;

N-{4-tert-butyl-3-[(morpholin-4-ylacetyl)amino]phenyl}-5-phenylthiophene-2-carboxamide;

N-{4-chloro-3-[(morpholin-4-ylacetyl)amino]phenyl}-5-phenylthiophene-2-carboxamide;

N-{4-methyl-3-[(morpholin-4-ylacetyl)amino]phenyl}-5-phenylthiophene-2-carboxamide;

N-{4-methoxy-3-[(morphpholin-4-ylacetyl)amino]phenyl}-5-phenyl-1,3-thiazole-2-carboxamide;
N-{4-methoxy-3-[(morphpholin-4-ylacetyl)amino]phenyl}-5-phenyl-1H-pyrrole-2-carboxamide;
N-{4-methoxy-3-[(morpholin-4-ylacetyl)amino]phenyl}-5-phenylthiophene-2-carboxamide;
6-(2,3-difluorophenyl)-N-{3-[(morpholin-4-ylacetyl)amino]-4-(trifluoromethoxy)phenyl}nicotinamide;
6-(3,5-difluorophenyl)-N-{3-[(morpholin-4-ylacetyl)amino]-4-(trifluoromethoxy)phenyl}nicotinamide;
6-(3-fluorophenyl)-N-{3-[(morpholin-4-ylacetyl)amino]-4-(trifluoromethoxy)phenyl}nicotinamide;
6-(2,6-difluorophenyl)-N-{3-[(morpholin-4-ylacetyl)amino]-4-(trifluoromethoxy)phenyl}nicotinamide;
6-(2-fluorophenyl)-N-{3-[(morpholin-4-ylacetyl)amino]-4-(trifluoromethoxy)phenyl}nicotinamide;
6-(2-fluorophenyl)-N-{4-methoxy-3-[(morpholin-4-ylacetyl)amino]phenyl}nicotinamide;
6-(3-fluorophenyl)-N-{4-methoxy-3-[(morpholin-4-ylacetyl)amino]phenyl}nicotinamide;
N-{3-[(morpholin-4-ylacetyl)amino]-4-(trifluoromethoxy)phenyl}-6-phenylnicotinamide;
N-{4-methoxy-3-[(morpholin-4-ylacetyl)amino]phenyl}-6-phenylnicotinamide;
N-{4-methoxy-3-[(morpholin-4-ylacetyl)amino]phenyl}-5-(4-methoxyphenyl)thiophene-2-carboxamide;
5-(4-fluorophenyl)-N-{4-methoxy-3-[(morpholin-4-ylacetyl)amino]phenyl}thiophene-2-carboxamide;
4-(difluoromethoxy)-3-({[1-(morpholin-4-yl)cyclopropyl]carbonyl}amino)-N-(5-phenyl-1,3,4-thiadiazol-2-yl)benzamide;
3-({[1-(4-cyclopropylpiperazin-1-yl)cyclopropyl]carbonyl}amino)-4-(difluoromethoxy)-N-(5-phenyl-1,3,4-thiadiazol-2-yl)benzamide;
4-(difluoromethoxy)-3-({[1-(4-methylpiperazin-1-yl)cyclopropyl]carbonyl}amino)-N-(5-phenyl-1,3,4-thiadiazol-2-yl)benzamide;
4-(difluoromethoxy)-3-{[(4-methylpiperazin-1-yl)acetyl]amino}-N-(5-phenyl-1,3,4-thiadiazol-2-yl)benzamide;
3-{[(4-cyclopropylpiperazin-1-yl)acetyl]amino}-4-(difluoromethoxy)-N-(5-phenyl-1,3,4-thiadiazol-2-yl)benzamide;
4-(methoxymethyl)-3-({[1-(morpholin-4-yl)cyclopropyl]carbonyl}amino)-N-(5-phenyl-1,3,4-thiadiazol-2-yl)benzamide;
3-({[1-(4-cyclopropylpiperazin-1-yl)cyclopropyl]carbonyl}amino)-4-(methoxymethyl)-N-(5-phenyl-1,3,4-thiadiazol-2-yl)benzamide;
4-(methoxymethyl)-3-{[(4-methylpiperazin-1-yl)acetyl]amino}-N-(5-phenyl-1,3,4-thiadiazol-2-yl)benzamide;
4-[(methylsulfonyl)methyl]-3-({[1-(morpholin-4-yl)cyclopropyl]carbonyl}amino)-N-(5-phenyl-1,3,4-thiadiazol-2-yl)benzamide;
3-({[1-(4-cyclopropylpiperazin-1-yl)cyclopropyl]carbonyl}amino)-4-[(methylsulfonyl)methyl]-N-(5-phenyl-1,3,4-thiadiazol-2-yl)benzamide;
3-({[1-(4-methylpiperazin-1-yl)cyclopropyl]carbonyl}amino)-4-[(methylsulfonyl)methyl]-N-(5-phenyl-1,3,4-thiadiazol-2-yl)benzamide;
3-({[1-(morpholin-4-yl)cyclopropyl]carbonyl}amino)-N-(5-phenyl-1,3,4-thiadiazol-2-yl)-4-(trifluoromethoxy)benzamide;
3-({[1-(4-cyclopropylpiperazin-1-yl)cyclopropyl]carbonyl}amino)-N-(5-phenyl-1,3,4-thiadiazol-2-yl)-4-(trifluoromethoxy)benzamide;
3-({[1-(4-methylpiperazin-1-yl)cyclopropyl]carbonyl}amino)-N-(5-phenyl-1,3,4-thiadiazol-2-yl)-4-(trifluoromethoxy)benzamide;
3-{[(4-cyclopropylpiperazin-1-yl)acetyl]amino}-N-(5-phenyl-1,3,4-thiadiazol-2-yl)-4-(trifluoromethoxy)benzamide;
3-{[(4-methylpiperazin-1-yl)acetyl]amino}-N-(5-phenyl-1,3,4-thiadiazol-2-yl)-4-(trifluoromethoxy)benzamide;
3-[(morpholin-4-ylacetyl)amino]-N-(5-phenyl-1,3,4-thiadiazol-2-yl)-4-(trifluoromethoxy)benzamide;
2-({[1-(morpholin-4-yl)cyclopropyl]carbonyl}amino)-N4-(5-phenyl-1,3,4-thiadiazol-2-yl)terephthalamide;
3-{[2-(morpholin-4-yl)propanoyl]amino}-N-(5-phenyl-1,3,4-thiadiazol-2-yl)-4-(trifluoromethoxy)benzamide;
3-{[2-(4-methylpiperazin-1-yl)propanoyl]amino}-N-(5-phenyl-1,3,4-thiadiazol-2-yl)-4-(trifluoromethoxy)benzamide;
3-{[(4-methylpiperazin-1-yl)acetyl]amino}-N-(5-phenyl-1,3,4-thiadiazol-2-yl)-4-(trifluoromethyl)benzamide;
6-(3,5-difluorophenyl)-N-[3-({[1-(morpholin-4-yl)cyclopropyl]carbonyl}amino)-4-(trifluoromethoxy)phenyl]nicotinamide;
N-[3-({[1-(morpholin-4-yl)cyclopropyl]carbonyl}amino)-4-(trifluoromethoxy)phenyl]-6-phenylnicotinamide;
6-(2-fluorophenyl)-N-[4-methoxy-3-({[1-(morpholin-4-yl)cyclopropyl]carbonyl}amino)phenyl]nicotinamide;
3-{[(4-cyclopropylpiperazin-1-yl)acetyl]amino}-N-[6-(2-fluorophenyl)pyridin-3-yl]-4-(trifluoromethoxy)benzamide;
N-[6-(2-fluorophenyl)pyridin-3-yl]-3-{[2-(4-methylpiperazin-1-yl)propanoyl]amino}-4-(trifluoromethoxy)benzamide;
N-[6-(2-fluorophenyl)pyridin-3-yl]-3-{[(2S)-2-(4-methylpiperazin-1-yl)propanoyl]amino}-4-(trifluoromethoxy)benzamide;
N-[6-(2-fluorophenyl)pyridin-3-yl]-3-{[(2R)-2-(4-methylpiperazin-1-yl)propanoyl]amino}-4-(trifluoromethoxy)benzamide;
3-({[1-(4-cyclopropylpiperazin-1-yl)cyclopropyl]carbonyl}amino)-N-[6-(2-fluorophenyl)pyridin-3-yl]-4-(trifluoromethoxy)benzamide;
N-[6-(2-fluorophenyl)pyridin-3-yl]-3-({[1-(morpholin-4-yl)cyclopropyl]carbonyl}amino)-4-(trifluoromethoxy)benzamide;
N-[6-(3-fluorophenyl)pyridin-3-yl]-3-{[2-(morpholin-4-yl)propanoyl]amino}-4-(trifluoromethoxy)benzamide;
N-[6-(3-fluorophenyl)pyridin-3-yl]-3-{[2-(8-oxa-3-azabicyclo[3.2.1]oct-3-yl)propanoyl]amino}-4-(trifluoromethoxy)benzamide;
N-[6-(3,5-difluorophenyl)pyridin-3-yl]-3-({[1-(morpholin-4-yl)cyclopropyl]carbonyl}amino)-4-(trifluoromethoxy)benzamide;
N-[6-(3,5-difluorophenyl)pyridin-3-yl]-3-[(morpholin-4-ylacetyl)amino]-4-(trifluoromethoxy)benzamide;
N-[6-(3,5-difluorophenyl)pyridin-3-yl]-3-[(8-oxa-3-azabicyclo[3.2.1]oct-3-ylacetyl)amino]-4-(trifluoromethoxy)benzamide;
N-[6-(2-fluorophenyl)pyridin-3-yl]-3-[(morpholin-4-ylacetyl)amino]-4-(trifluoromethyl)benzamide;
$N^4$-[6-(2-fluorophenyl)pyridin-3-yl]-2-({[1-(morpholin-4-yl)cyclopropyl]carbonyl}amino)terephthalamide;
N-[6-(2-fluorophenyl)pyridin-3-yl]-4-methyl-3-({[1-(morpholin-4-yl)cyclopropyl]carbonyl}amino)benzamide;

4-fluoro-N-[6-(2-fluorophenyl)pyridin-3-yl]-3-({[1-(morpholin-4-yl)cyclopropyl]carbonyl}amino)benzamide;
4-fluoro-3-({[1-(morpholin-4-yl)cyclopropyl]carbonyl}amino)-N-(5-phenyl-1,3,4-thiadiazol-2-yl)benzamide;
4-chloro-N-[6-(2-fluorophenyl)pyridin-3-yl]-3-({[1-(morpholin-4-yl)cyclopropyl]carbonyl}amino)benzamide;
N-[6-(2-fluorophenyl)pyridin-3-yl]-4-methoxy-3-({[1-(morpholin-4-yl)cyclopropyl]carbonyl}amino)benzamide;
4-methoxy-3-({[1-(morpholin-4-yl)cyclopropyl]carbonyl}amino)-N-(6-phenylpyridin-3-yl)benzamide;
4-(methoxymethyl)-3-[(morpholin-4-ylacetyl)amino]-N-(5-phenyl-1,3,4-thiadiazol-2-yl)benzamide;
3-{[(4-cyclopropylpiperazin-1-yl)acetyl]amino}-4-(methoxymethyl)-N-(5-phenyl-1,3,4-thiadiazol-2-yl)benzamide;
4-(difluoromethoxy)-3-[(8-oxa-3-azabicyclo[3.2.1]oct-3-ylacetyl)amino]-N-(5-phenyl-1,3,4-thiadiazol-2-yl)benzamide;
4-[(methylsulfonyl)methyl]-3-{[2-(morpholin-4-yl)propanoyl]amino}-N-(5-phenyl-1,3,4-thiadiazol-2-yl)benzamide;
3-{[2-(4-methylpiperazin-1-yl)propanoyl]amino}-4-[(methylsulfonyl)methyl]-N-(5-phenyl-1,3,4-thiadiazol-2-yl)benzamide;
N-[5-(2-fluorophenyl)-1,3,4-thiadiazol-2-yl]-3-({[1-(morpholin-4-yl)cyclopropyl]carbonyl}amino)-4-(trifluoromethoxy)benzamide;
N-[5-(4-fluorophenyl)-1,3,4-thiadiazol-2-yl]-3-({[1-(morpholin-4-yl)cyclopropyl]carbonyl}amino)-4-(trifluoromethoxy)benzamide;
4-methoxy-3-{[(4-methylpiperazin-1-yl)acetyl]amino}-N-(5-phenyl-1,3,4-thiadiazol-2-yl)benzamide;
4-(benzyloxy)-3-({[1-(morpholin-4-yl)cyclopropyl]carbonyl}amino)-N-(5-phenyl-1,3,4-thiadiazol-2-yl)benzamide;
4-hydroxy-3-({[1-(morpholin-4-yl)cyclopropyl]carbonyl}amino)-N-(5-phenyl-1,3,4-thiadiazol-2-yl)benzamide;
4-bromo-3-{[(4-methylpiperazin-1-yl)acetyl]amino}-N-(5-phenyl-1,3,4-thiadiazol-2-yl)benzamide;
3-({[1-(morpholin-4-yl)cyclopropyl]carbonyl}amino)-N-(5-phenylpyridin-2-yl)-4-(trifluoromethoxy)benzamide;
N-[5-(3-methylphenyl)-1,3,4-thiadiazol-2-yl]-3-[(morpholin-4-ylacetyl)amino]-4-(trifluoromethoxy)benzamide;
3-[(morpholin-4-ylacetyl)amino]-N-[5-(4-nitrophenyl)-1,3,4-thiadiazol-2-yl]-4-(trifluoromethoxy)benzamide;
N-[5-(2-methylphenyl)-1,3,4-thiadiazol-2-yl]-3-[(morpholin-4-ylacetyl)amino]-4-(trifluoromethoxy)benzamide;
N-[5-(4-fluorophenyl)-1,3,4-thiadiazol-2-yl]-3-[(morpholin-4-ylacetyl)amino]-4-(trifluoromethoxy)benzamide;
3-({[4-(2,2-difluoroethyl)piperazin-1-yl]acetyl}amino)-N-[6-(2-fluorophenyl)pyridin-3-yl]-4-(trifluoromethoxy)benzamide;
N-[5-(2-methoxyphenyl)-1,3,4-thiadiazol-2-yl]-3-{[(4-methylpiperazin-1-yl)acetyl]amino}-4-(trifluoromethoxy)benzamide;
N-[5-(4-methylphenyl)-1,3,4-thiadiazol-2-yl]-3-{[(4-methylpiperazin-1-yl)acetyl]amino}-4-(trifluoromethoxy)benzamide;
4-methyl-3-({[1-(morpholin-4-yl)cyclopropyl]carbonyl}amino)-N-(5-phenyl-1,3,4-thiadiazol-2-yl)benzamide;
3-{[(4-methylpiperazin-1-yl)acetyl]amino}-4-[(methylsulfonyl)methyl]-N-(5-phenyl-1,3,4-thiadiazol-2-yl)benzamide;
methyl 2-{[(4-methylpiperazin-1-yl)acetyl]amino}-4-[(5-phenyl-1,3,4-thiadiazol-2-yl)carbamoyl]benzoate;
methyl 2-[(morpholin-4-ylacetyl)amino]-4-[(5-phenyl-1,3,4-thiadiazol-2-yl)carbamoyl]benzoate;
N-(4-methoxy-3-{[2-(morpholin-4-yl)propanoyl]amino}phenyl)-2-phenyl-1,3-thiazole-5-carboxamide;
N-[3-({[1-(morpholin-4-yl)cyclopropyl]carbonyl}amino)-4-(trifluoromethoxy)phenyl]-2-phenyl-1,3-thiazole-5-carboxamide;
N-[6-(2-fluoro-4-hydroxyphenyl)pyridin-3-yl]-3-{[2-(morpholin-4-yl)propanoyl]amino}-4-(trifluoromethoxy)benzamide;
N-[6-(3-fluoro-4-hydroxyphenyl)pyridin-3-yl]-3-{[2-(morpholin-4-yl)propanoyl]amino}-4-(trifluoromethoxy)benzamide;
N-[6-(4-aminophenyl)pyridin-3-yl]-3-{[2-(morpholin-4-yl)propanoyl]amino}-4-(trifluoromethoxy)benzamide;
N-{6-[4-(difluoromethyl)phenyl]pyridin-3-yl}-3-{[2-(morpholin-4-yl)propanoyl]amino}-4-(trifluoromethoxy)benzamide;
N-[6-(4-acetamidophenyl)pyridin-3-yl]-3-{[2-(morpholin-4-yl)propanoyl]amino}-4-(trifluoromethoxy)benzamide;
N-{6-[4-(dimethylamino)phenyl]pyridin-3-yl}-3-{[2-(morpholin-4-yl)propanoyl]amino}-4-(trifluoromethoxy)benzamide;
N-{6-[4-(dimethylamino)phenyl]pyridin-3-yl}-3-{[(2S)-2-(morpholin-4-yl)propanoyl]amino}-4-(trifluoromethoxy)benzamide;
N-{6-[4-(dimethylamino)phenyl]pyridin-3-yl}-3-{[(2R)-2-(morpholin-4-yl)propanoyl]amino}-4-(trifluoromethoxy)benzamide;
N-[6-(4-aminophenyl)pyridin-3-yl]-3-{[(2R)-2-(morpholin-4-yl)propanoyl]amino}-4-(trifluoromethoxy)benzamide;
N-[6-(4-aminophenyl)pyridin-3-yl]-3-{[(2S)-2-(morpholin-4-yl)propanoyl]amino}-4-(trifluoromethoxy)benzamide;
N-{6-[4-(hydroxymethyl)phenyl]pyridin-3-yl}-3-{[(2S)-2-(morpholin-4-yl)propanoyl]amino}-4-(trifluoromethoxy)benzamide;
N-{6-[4-(hydroxymethyl)phenyl]pyridin-3-yl}-3-{[(2R)-2-(morpholin-4-yl)propanoyl]amino}-4-(trifluoromethoxy)benzamide;
N-{3-[(morpholin-4-ylacetyl)amino]-4-(trifluoromethoxy)phenyl}-5-phenyl-1,2,4-oxadiazole-3-carboxamide;
3-[(morpholin-4-ylacetyl)amino]-N-(2-phenyl-1,3-thiazol-5-yl)-4-(trifluoromethoxy)benzamide;
1-methyl-N-{3-[(morpholin-4-ylacetyl)amino]-4-(trifluoromethoxy)phenyl}-5-phenyl-1H-pyrazole-3-carboxamide;
N-{3-[(morpholin-4-ylacetyl)amino]-4-(trifluoromethoxy)phenyl}-5-phenyl-1H-pyrazole-3-carboxamide;
3-[(morpholin-4-ylacetyl)amino]-N-(3-phenyl-1,2,4-oxadiazol-5-yl)-4-(trifluoromethoxy)benzamide;
N-[6-(4-aminophenyl)pyridin-3-yl]-3-[(morpholin-4-ylacetyl)amino]-4-(trifluoromethoxy)benzamide;

N-[5-(2-fluorophenyl)-1,3,4-thiadiazol-2-yl]-3-[(morpholin-4-ylacetyl)amino]-4-(trifluoromethoxy)benzamide;

3-{[2-(morpholin-4-yl)propanoyl]amino}-N-(5-phenyl-1,3,4-thiadiazol-2-yl)-4-(trifluoromethyl)benzamide;

3-{[2-(4-methylpiperazin-1-yl)propanoyl]amino}-N-(5-phenyl-1,3,4-thiadiazol-2-yl)-4-(trifluoromethyl)benzamide;

N-{4-methoxy-3-[(morpholin-4-ylacetyl)amino]phenyl}-5-phenyl-1,3,4-thiadiazole-2-carboxamide;

3-[(morpholin-4-ylacetyl)amino]-N-(5-phenylpyridin-2-yl)-4-(trifluoromethoxy)benzamide;

4-(cyclopropyloxy)-N-[6-(2-fluorophenyl)pyridin-3-yl]-3-[(morpholin-4-ylacetyl)amino]benzamide;

4-(cyclopropyloxy)-N-[6-(2-fluorophenyl)pyridin-3-yl]-3-({[1-(morpholin-4-yl)cyclopropyl]carbonyl}amino)benzamide;

4-(cyclopropyloxy)-N-[6-(2-fluorophenyl)pyridin-3-yl]-3-({[1-(4-methylpiperazin-1-yl)cyclopropyl]carbonyl}amino)benzamide;

4-(cyclopropyloxy)-3-({[1-(4-cyclopropylpiperazin-1-yl)cyclopropyl]carbonyl}amino)-N-[6-(2-fluorophenyl)pyridin-3-yl]benzamide;

3-{[(3,4-dimethylpiperazin-1-yl)acetyl]amino}-N-[6-(2-fluorophenyl)pyridin-3-yl]-4-(trifluoromethoxy)benzamide;

N-[6-(2-fluorophenyl)pyridin-3-yl]-4-(methylsulfanyl)-3-[(morpholin-4-ylacetyl)amino]benzamide;

N-[6-(2-fluorophenyl)pyridin-3-yl]-4-(methylsulfonyl)-3-[(morpholin-4-ylacetyl)amino]benzamide;

4-tert-butyl-N-[6-(2-fluorophenyl)pyridin-3-yl]-3-{[2-(morpholin-4-yl)propanoyl]amino}benzamide;

4-tert-butyl-3-{[2-(morpholin-4-yl)propanoyl]amino}-N-(5-phenyl-1,3-thiazol-2-yl)benzamide;

N-[5-(2-methylphenyl)-1,3,4-thiadiazol-2-yl]-3-{[(4-methylpiperazin-1-yl)acetyl]amino}-4-(trifluoromethoxy)benzamide;

N-[5-(3-methylphenyl)-1,3,4-thiadiazol-2-yl]-3-{[(4-methylpiperazin-1-yl)acetyl]amino}-4-(trifluoromethoxy)benzamide;

N-[5-(3-methoxyphenyl)-1,3,4-thiadiazol-2-yl]-3-{[(4-methylpiperazin-1-yl)acetyl]amino}-4-(trifluoromethoxy)benzamide;

N-[5-(4-chlorophenyl)-1,3,4-thiadiazol-2-yl]-3-{[(4-methylpiperazin-1-yl)acetyl]amino}-4-(trifluoromethoxy)benzamide;

N-[5-(2-chlorophenyl)-1,3,4-thiadiazol-2-yl]-3-{[(4-methylpiperazin-1-yl)acetyl]amino}-4-(trifluoromethoxy)benzamide;

N-[5-(4-fluorophenyl)-1,3,4-thiadiazol-2-yl]-3-{[(4-methylpiperazin-1-yl)acetyl]amino}-4-(trifluoromethoxy)benzamide;

N-[5-(2-fluorophenyl)-1,3,4-thiadiazol-2-yl]-3-{[(4-methylpiperazin-1-yl)acetyl]amino}-4-(trifluoromethoxy)benzamide;

N-[5-(3-chlorophenyl)-1,3,4-thiadiazol-2-yl]-3-{[(4-methylpiperazin-1-yl)acetyl]amino}-4-(trifluoromethoxy)benzamide;

N-[5-(3-fluorophenyl)-1,3,4-thiadiazol-2-yl]-3-{[(4-methylpiperazin-1-yl)acetyl]amino}-4-(trifluoromethoxy)benzamide;

N-[5-(3-fluorophenyl)-1,3,4-thiadiazol-2-yl]-3-[(morpholin-4-ylacetyl)amino]-4-(trifluoromethoxy)benzamide;

N-[5-(3-chlorophenyl)-1,3,4-thiadiazol-2-yl]-3-[(morpholin-4-ylacetyl)amino]-4-(trifluoromethoxy)benzamide;

$N^1$-(2-methoxyethyl)-2-{[(4-methylpiperazin-1-yl)acetyl]amino}-$N^4$-(5-phenyl-1,3,4-thiadiazol-2-yl)terephthalamide;

$N^1$-(2-methoxyethyl)-2-[(morpholin-4-ylacetyl)amino]-$N^4$-(5-phenyl-1,3,4-thiadiazol-2-yl)terephthalamide;

3-{[(4-methylpiperazin-1-yl)acetyl]amino}-N-(5-phenylpyridin-2-yl)-4-(trifluoromethoxy)benzamide;

4-(cyclopropyloxy)-3-({[1-(morpholin-4-yl)cyclopropyl]carbonyl}amino)-N-(5-phenyl-1,3,4-thiadiazol-2-yl)benzamide;

3-{[(3,4-dimethylpiperazin-1-yl)acetyl]amino}-N-(5-phenyl-1,3,4-thiadiazol-2-yl)-4-(trifluoromethoxy)benzamide;

3-({[(2R)-2,4-dimethylpiperazin-1-yl]acetyl}amino)-N-[6-(2-fluorophenyl)pyridin-3-yl]-4-(trifluoromethoxy)benzamide;

3-({[(2S)-2,4-dimethylpiperazin-1-yl]acetyl}amino)-N-[6-(2-fluorophenyl)pyridin-3-yl]-4-(trifluoromethoxy)benzamide;

3-({[(3 S)-3,4-dimethylpiperazin-1-yl]acetyl}amino)-N-[6-(2-fluorophenyl)pyridin-3-yl]-4-(trifluoromethoxy)benzamide;

3-({[(3R)-3,4-dimethylpiperazin-1-yl]acetyl}amino)-N-[6-(2-fluorophenyl)pyridin-3-yl]-4-(trifluoromethoxy)benzamide;

3-{[(2,4-dimethylpiperazin-1-yl)acetyl]amino}-N-[6-(2-fluorophenyl)pyridin-3-yl]-4-(trifluoromethoxy)benzamide;

N-[6-(2-fluorophenyl)pyridin-3-yl]-3-{[(8-methyl-3,8-diazabicyclo[3.2.1]oct-3-yl)acetyl]amino}-4-(trifluoromethoxy)benzamide;

3-{[(2,4-dimethylpiperazin-1-yl)acetyl]amino}-N-(5-phenyl-1,3,4-thiadiazol-2-yl)-4-(trifluoromethoxy)benzamide;

3-{[(4-methyl-1,4-diazepan-1-yl)acetyl]amino}-N-(5-phenyl-1,3,4-thiadiazol-2-yl)-4-(trifluoromethoxy)benzamide;

3-[(1,4-oxazepan-4-ylacetyl)amino]-N-(5-phenyl-1,3,4-thiadiazol-2-yl)-4-(trifluoromethoxy)benzamide;

4-(cyclopropyloxy)-3-[(morpholin-4-ylacetyl)amino]-N-(5-phenyl-1,3,4-thiadiazol-2-yl)benzamide;

4-(cyclopropyloxy)-3-({[1-(4-methylpiperazin-1-yl)cyclopropyl]carbonyl}amino)-N-(5-phenyl-1,3,4-thiadiazol-2-yl)benzamide;

3-{[(4-ethylpiperazin-1-yl)acetyl]amino}-N-(5-phenyl-1,3,4-thiadiazol-2-yl)-4-(trifluoromethoxy)benzamide;

4-chloro-3-{[(4-methylpiperazin-1-yl)acetyl]amino}-N-(5-phenyl-1,3,4-thiadiazol-2-yl)benzamide;

4-cyano-3-{[(4-methylpiperazin-1-yl)acetyl]amino}-N-(5-phenyl-1,3,4-thiadiazol-2-yl)benzamide;

4-(difluoromethoxy)-N-[5-(2-methylphenyl)-1,3,4-thiadiazol-2-yl]-3-{[(4-methylpiperazin-1-yl)acetyl]amino}benzamide;

4-(methoxymethyl)-N-[5-(2-methylphenyl)-1,3,4-thiadiazol-2-yl]-3-[(morpholin-4-ylacetyl)amino]benzamide;

N-[6-(3,5-difluorophenyl)pyridin-3-yl]-3-{[2-(8-oxa-3-azabicyclo[3.2.1]oct-3-yl)propanoyl]amino}-4-(trifluoromethoxy)benzamide;

N-[6-(3,5-difluorophenyl)pyridin-3-yl]-3-({(2R*)-2-[(1S,4S)-2-oxa-5-azabicyclo[2.2.1]hept-5-yl]propanoyl}amino)-4-(trifluoromethoxy)benzamide;

N-[6-(3,5-difluorophenyl)pyridin-3-yl]-3-({(2S*)-2-[(1S,4S)-2-oxa-5-azabicyclo[2.2.1]hept-5-yl]propanoyl}amino)-4-(trifluoromethoxy)benzamide;

6-(3,5-difluorophenyl)-N-[3-{[(1S,4S)-2-oxa-5-azabicyclo[2.2.1]hept-5-ylacetyl]amino}-4-(trifluoromethoxy)phenyl]nicotinamide;

6-(3,5-difluorophenyl)-N-[3-{[2-(8-oxa-3-azabicyclo[3.2.1]oct-3-yl)propanoyl]amino}-4-(trifluoromethoxy)phenyl]nicotinamide;

6-(3,5-difluorophenyl)-N-[3-{[2-(morpholin-4-yl)propanoyl]amino}-4-(trifluoromethoxy)phenyl]nicotinamide;

6-(3-fluorophenyl)-N-[3-{[2-(8-oxa-3-azabicyclo[3.2.1]oct-3-yl)propanoyl]amino}-4-(trifluoromethoxy)phenyl]nicotinamide;

6-(3-fluorophenyl)-N-[3-{[2-(morpholin-4-yl)propanoyl]amino}-4-(trifluoromethoxy)phenyl]nicotinamide;

3-[(morpholin-4-ylacetyl)amino]-N-(5-phenyl-1,3,4-oxadiazol-2-yl)-4-(trifluoromethoxy)benzamide;

6-(3-fluorophenyl)-N-[3-({(2R*)-2-[(1S,4S)-2-oxa-5-azabicyclo[2.2.1]hept-5-yl]propanoyl}amino)-4-(trifluoromethoxy)phenyl]nicotinamide;

N-[6-(4-hydroxyphenyl)pyridin-3-yl]-3-{[2-(morpholin-4-yl)propanoyl]amino}-4-(trifluoromethoxy)benzamide;

3-{[2-(4-cyclopropylpiperazin-1-yl)propanoyl]amino}-N-[6-(2-fluorophenyl)pyridin-3-yl]-4-(trifluoromethoxy)benzamide;

N-[6-(2-fluorophenyl)pyridin-3-yl]-3-{[(4-methylpiperazin-1-yl)acetyl]amino}-4-(trifluoromethoxy)benzamide;

6-(3,5-difluorophenyl)-N-[3-({(2R*)-2-[(1S,4S)-2-oxa-5-azabicyclo[2.2.1]hept-5-yl]propanoyl}amino)-4-(trifluoromethoxy)phenyl]nicotinamide;

6-(3,5-difluorophenyl)-N-[3-({2-[(1S,4S)-2-oxa-5-azabicyclo[2.2.1]hept-5-yl]propanoyl}amino)-4-(trifluoromethoxy)phenyl]nicotinamide;

6-(3-fluorophenyl)-N-[3-({2-[(1S,4S)-2-oxa-5-azabicyclo[2.2.1]hept-5-yl]propanoyl}amino)-4-(trifluoromethoxy)phenyl]nicotinamide;

6-(2-fluorophenyl)-N-[3-{[2-(8-oxa-3-azabicyclo[3.2.1]oct-3-yl)propanoyl]amino}-4-(trifluoromethoxy)phenyl]nicotinamide;

6-(2-fluorophenyl)-N-[3-{[2-(morpholin-4-yl)propanoyl]amino}-4-(trifluoromethoxy)phenyl]nicotinamide;

N-[6-(2-fluorophenyl)pyridin-3-yl]-3-{[2-(morpholin-4-yl)propanoyl]amino}-4-(trifluoromethyl)benzamide;

N-[6-(2-fluorophenyl)pyridin-3-yl]-3-{[(4-methylpiperazin-1-yl)acetyl]amino}-4-(trifluoromethyl)benzamide;

N-[6-(3,5-difluorophenyl)pyridin-3-yl]-3-{[(1S,4S)-2-oxa-5-azabicyclo[2.2.1]hept-5-ylacetyl]amino}-4-(trifluoromethoxy)benzamide;

6-(3,5-difluorophenyl)-N-{3-[(8-oxa-3-azabicyclo[3.2.1]oct-3-ylacetyl)amino]-4-(trifluoromethoxy)phenyl}nicotinamide;

6-(3,5-difluorophenyl)-N-[3-({(2S*)-2-[(1S,4S)-2-oxa-5-azabicyclo[2.2.1]hept-5-yl]propanoyl}amino)-4-(trifluoromethoxy)phenyl]nicotinamide;

N-[6-(3,5-difluorophenyl)pyridin-3-yl]-3-{[2-(morpholin-4-yl)propanoyl]amino}-4-(trifluoromethoxy)benzamide;

6-(3-fluorophenyl)-N-[3-({(2S*)-2-[(1S,4S)-2-oxa-5-azabicyclo[2.2.1]hept-5-yl]propanoyl}amino)-4-(trifluoromethoxy)phenyl]nicotinamide;

N-[6-(3,5-difluorophenyl)pyridin-3-yl]-3-({2-[(1S,4S)-2-oxa-5-azabicyclo[2.2.1]hept-5-yl]propanoyl}amino)-4-(trifluoromethoxy)benzamide;

N-[6-(2-fluorophenyl)pyridin-3-yl]-3-[(8-oxa-3-azabicyclo[3.2.1]oct-3-ylacetyl)amino]-4-(trifluoromethyl)benzamide;

3-{[(4-cyclopropylpiperazin-1-yl)acetyl]amino}-N-[6-(2-fluorophenyl)pyridin-3-yl]-4-(trifluoromethyl)benzamide;

3-[methyl(morpholin-4-ylacetyl)amino]-N-(6-phenylpyridin-3-yl)-4-(trifluoromethoxy)benzamide;

6-(4-fluorophenyl)-N-{4-methoxy-3-[(morpholin-4-ylacetyl)amino]phenyl}nicotinamide;

N-[6-(2-fluorophenyl)pyridin-3-yl]-3-({[4-(2,2,2-trifluoroethyl)piperazin-1-yl]acetyl}amino)-4-(trifluoromethoxy)benzamide;

3-{[2-(4-cyclopropylpiperazin-1-yl)propanoyl]amino}-N-(5-phenyl-1,3,4-thiadiazol-2-yl)-4-(trifluoromethoxy)benzamide;

4-[(methylsulfonyl)methyl]-3-[(morpholin-4-ylacetyl)amino]-N-(5-phenyl-1,3,4-thiadiazol-2-yl)benzamide;

N-[6-(2-fluorophenyl)pyridin-3-yl]-3-({[1-(4-methylpiperazin-1-yl)cyclopropyl]carbonyl}amino)-4-(trifluoromethoxy)benzamide;

4-(difluoromethoxy)-N-[6-(2-fluorophenyl)pyridin-3-yl]-3-[(morpholin-4-ylacetyl)amino]benzamide;

4-(difluoromethoxy)-3-[(morpholin-4-ylacetyl)amino]-N-(5-phenyl-1,3,4-thiadiazol-2-yl)benzamide;

3-[(8-oxa-3-azabicyclo[3.2.1]oct-3-ylacetyl)amino]-N-(5-phenyl-1,3,4-thiadiazol-2-yl)-4-(trifluoromethoxy)benzamide;

N-[6-(3-fluorophenyl)pyridin-3-yl]-3-({2-[(1S,4S)-2-oxa-5-azabicyclo[2.2.1]hept-5-yl]propanoyl}amino)-4-(trifluoromethoxy)benzamide;

N-[6-(3-fluorophenyl)pyridin-3-yl]-3-({(2R*)-2-[(1S,4S)-2-oxa-5-azabicyclo[2.2.1]hept-5-yl]propanoyl}amino)-4-(trifluoromethoxy)benzamide;

N-[6-(3-fluorophenyl)pyridin-3-yl]-3-({(2S*)-2-[(1S,4S)-2-oxa-5-azabicyclo[2.2.1]hept-5-yl]propanoyl}amino)-4-(trifluoromethoxy)benzamide;

N-{3-[(morpholin-4-ylacetyl)amino]-4-(trifluoromethoxy)phenyl}-2-phenyl-1,3-thiazole-5-carboxamide;

4-bromo-3-{[(4-cyclopropylpiperazin-1-yl)acetyl]amino}-N-(5-phenyl-1,3,4-thiadiazol-2-yl)benzamide;

3-{[(1S,4S)-2-oxa-5-azabicyclo[2.2.1]hept-5-ylacetyl]amino}-N-(5-phenyl-1,3,4-thiadiazol-2-yl)-4-(trifluoromethoxy)benzamide;

N-[3-{[2-(morpholin-4-yl)propanoyl]amino}-4-(trifluoromethoxy)phenyl]-2-phenyl-1,3-thiazole-5-carboxamide;

N-[4-methoxy-3-({[1-(morpholin-4-yl)cyclopropyl]carbonyl}amino)phenyl]-6-phenylnicotinamide;

N-[5-(2-methylphenyl)-1,3,4-thiadiazol-2-yl]-3-({[1-(morpholin-4-yl)cyclopropyl]carbonyl}amino)-4-(trifluoromethoxy)benzamide;

4-(cyclopropylmethoxy)-3-{[(4-methylpiperazin-1-yl)acetyl]amino}-N-(5-phenyl-1,3,4-thiadiazol-2-yl)benzamide;

N-[5-(4-aminophenyl)-1,3,4-thiadiazol-2-yl]-3-[(morpholin-4-ylacetyl)amino]-4-(trifluoromethoxy)benzamide;

4-(cyclopropyloxy)-N-[5-(2-methylphenyl)-1,3,4-thiadiazol-2-yl]-3-{[(4-methylpiperazin-1-yl)acetyl]amino}benzamide;

4-(cyclopropylmethoxy)-3-{[(4-cyclopropylpiperazin-1-yl)acetyl]amino}-N-(5-phenyl-1,3,4-thiadiazol-2-yl)benzamide;

4-(cyclopropyloxy)-N-[5-(2-methylphenyl)-1,3,4-thiadiazol-2-yl]-3-[(morpholin-4-ylacetyl)amino]benzamide;

N-[5-(3-cyanophenyl)-1,3,4-thiadiazol-2-yl]-3-{[(4-methylpiperazin-1-yl)acetyl]amino}-4-(trifluoromethoxy)benzamide;

4-(cyclopropylmethoxy)-3-[(morpholin-4-ylacetyl)amino]-N-(5-phenyl-1,3,4-thiadiazol-2-yl)benzamide;

N-[5-(2-ethylphenyl)-1,3,4-thiadiazol-2-yl]-3-[(morpholin-4-ylacetyl)amino]-4-(trifluoromethoxy)benzamide;

3-{[(4-methylpiperazin-1-yl)acetyl]amino}-4-(trifluoromethoxy)-N-{5-[2-(trifluoromethyl)phenyl]-1,3,4-thiadiazol-2-yl}benzamide;

N-[5-(2-methylphenyl)-1,3,4-thiadiazol-2-yl]-3-({[1-(4-methylpiperazin-1-yl)cyclopropyl]carbonyl}amino)-4-(trifluoromethoxy)benzamide;

3-{[(4-methylpiperazin-1-yl)acetyl]amino}-4-(trifluoromethoxy)-N-{5-[3-(trifluoromethyl)phenyl]-1,3,4-thiadiazol-2-yl}benzamide;

N-[5-(3,4-difluorophenyl)-1,3,4-thiadiazol-2-yl]-3-{[(4-methylpiperazin-1-yl)acetyl]amino}-4-(trifluoromethoxy)benzamide;

N-[5-(2,4-difluorophenyl)-1,3,4-thiadiazol-2-yl]-3-[(morpholin-4-ylacetyl)amino]-4-(trifluoromethoxy)benzamide;

N-[5-(2,3-difluorophenyl)-1,3,4-thiadiazol-2-yl]-3-[(morpholin-4-ylacetyl)amino]-4-(trifluoromethoxy)benzamide;

N-[5-(3,4-difluorophenyl)-1,3,4-thiadiazol-2-yl]-3-[(morpholin-4-ylacetyl)amino]-4-(trifluoromethoxy)benzamide;

3-{[(4-cyclopropylpiperazin-1-yl)acetyl]amino}-N-[5-(2-fluorophenyl)-1,3,4-thiadiazol-2-yl]-4-(trifluoromethoxy)benzamide;

N-[5-(2,3-difluorophenyl)-1,3,4-thiadiazol-2-yl]-3-{[(4-methylpiperazin-1-yl)acetyl]amino}-4-(trifluoromethoxy)benzamide;

N-[5-(2,5-difluorophenyl)-1,3,4-thiadiazol-2-yl]-3-{[(4-methylpiperazin-1-yl)acetyl]amino}-4-(trifluoromethoxy)benzamide;

3-[(morpholin-4-ylacetyl)amino]-4-(trifluoromethoxy)-N-{5-[2-(trifluoromethyl)phenyl]-1,3,4-thiadiazol-2-yl}benzamide;

3-[(morpholin-4-ylacetyl)amino]-4-(trifluoromethoxy)-N-{5-[3-(trifluoromethyl)phenyl]-1,3,4-thiadiazol-2-yl}benzamide;

4-(cyclopropyloxy)-3-{[(4-methylpiperazin-1-yl)acetyl]amino}-N-(5-phenyl-1,3,4-thiadiazol-2-yl)benzamide;

4-(cyclopropyloxy)-N-[5-(2-methylphenyl)-1,3,4-thiadiazol-2-yl]-3-({[1-(morpholin-4-yl)cyclopropyl]carbonyl}amino)benzamide;

4-(cyclopropyloxy)-N-[5-(2-methylphenyl)-1,3,4-thiadiazol-2-yl]-3-({[1-(4-methylpiperazin-1-yl)cyclopropyl]carbonyl}amino)benzamide;

4-(difluoromethoxy)-N-[5-(2-fluorophenyl)-1,3,4-thiadiazol-2-yl]-3-{[(4-methylpiperazin-1-yl)acetyl]amino}benzamide;

3-{[(4-cyclopropylpiperazin-1-yl)acetyl]amino}-4-(difluoromethoxy)-N-[5-(2-fluorophenyl)-1,3,4-thiadiazol-2-yl]benzamide; and 4-(difluoromethoxy)-N-[5-(2-fluorophenyl)-1,3,4-thiadiazol-2-yl]-3-[(morpholin-4-ylacetyl)amino]benzamide, or a tautomer, an N-oxide, or a salt thereof, or a mixture of any of the foregoing.

8. The compound according to claim 1, which is selected from the group consisting of:

4-(difluoromethoxy)-3-{[2-(4-methylpiperazin-1-yl)propanoyl]amino}-N-(5-phenyl-1,3,4-thiadiazol-2-yl)benzamide trifluoroacetate (1:1);

4-(methoxymethyl)-3-({[1-(4-methylpiperazin-1-yl)cyclopropyl]carbonyl}amino)-N-(5-phenyl-1,3,4-thiadiazol-2-yl)benzamide hydrochloride (1:1);

3-{[(4-methylpiperazin-1-yl)acetyl]amino}-N-(5-phenylpyridin-2-yl)-4-(trifluoromethoxy)benzamide formiate;

4-methyl-3-({[1-(4-methylpiperazin-1-yl)cyclopropyl]carbonyl}amino)-N-(5-phenyl-1,3,4-thiadiazol-2-yl)benzamide hydrochloride;

N-[5-(2,6-difluorophenyl)-1,3,4-thiadiazol-2-yl]-3-[(morpholin-4-ylacetyl)amino]-4-(trifluoromethoxy)benzamide hydrochloride;

4-(methoxymethyl)-N-[5-(2-methylphenyl)-1,3,4-thiadiazol-2-yl]-3-{[(4-methylpiperazin-1-yl)acetyl]amino}benzamide hydrochloride;

3-{[2-(4-methylpiperazin-1-yl)propanoyl]amino}-4-[(methylsulfonyl)methyl]-N-(5-phenyl-1,3,4-thiadiazol-2-yl)benzamide trifluoroacetate;

4-(methoxymethyl)-N-[5-(2-methylphenyl)-1,3,4-thiadiazol-2-yl]-3-({[1-(4-methylpiperazin-1-yl)cyclopropyl]carbonyl}amino)benzamide trifluoroacetate;

3-{[2-(4-methylpiperazin-1-yl)propanoyl]amino}-N-(5-phenyl-1,3,4-thiadiazol-2-yl)-4-(trifluoromethoxy)benzamide trifluoroacetate;

4-chloro-3-({[1-(4-cyclopropylpiperazin-1-yl)cyclopropyl]carbonyl}amino)-N-(5-phenyl-1,3,4-thiadiazol-2-yl)benzamide trifluoroacetate;

N-[5-(3,5-difluorophenyl)-1,3,4-thiadiazol-2-yl]-3-{[(4-methylpiperazin-1-yl)acetyl]amino}-4-(trifluoromethoxy)benzamide hydrochloride;

N-[5-(2,6-difluorophenyl)-1,3,4-thiadiazol-2-yl]-3-{[(4-methylpiperazin-1-yl)acetyl]amino}-4-(trifluoromethoxy)benzamide hydrochloride;

N-[5-(3,5-difluorophenyl)-1,3,4-thiadiazol-2-yl]-3-[(morpholin-4-ylacetyl)amino]-4-(trifluoromethoxy)benzamide hydrochloride; and N-[5-(2-fluorophenyl)-1,3,4-thiadiazol-2-yl]-3-({[1-(4-methylpiperazin-1-yl)cyclopropyl]carbonyl}amino)-4-(trifluoromethoxy)benzamide hydrochloride, or a tautomer or an N-oxide thereof, or a mixture of any of the foregoing.

9. A pharmaceutical composition comprising the compound of formula (I) according to claim 1, or a tautomer, an N-oxide, or a pharmaceutically acceptable salt thereof, or a mixture of any of the foregoing, and a pharmaceutically acceptable diluent or carrier.

10. A method for treatment of colorectal cancer, comprising administering to a patient in need thereof a therapeutically effective amount of the compound of formula (I) according to claim 1, or a tautomer, an N-oxide, or a pharmaceutically acceptable salt thereof, or a mixture of any of the foregoing.

11. A method of preparing a compound of formula (I) according to claim 1, comprising reacting an intermediate compound of formula (VI):

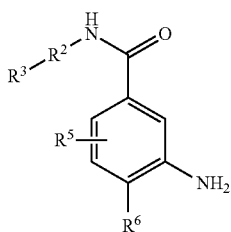

(VI)

wherein $R^2$, $R^3$, $R^5$, and $R^6$ are as defined in claim 1, with a carboxylic acid $HO_2C$-$L^A$-$R^1$ or the corresponding acyl chloride $Cl$—$C(=O)$-$L^A$-$R^1$, wherein $L^A$ and $R^1$ are as defined in claim 1, or with $Cl$—$C(=O)$-$L^A$-$LG$, wherein $L^A$ is as defined in claim 1, and LG is a leaving group, and subsequently with agents suitable for the introduction of $R^1$, to give, following optional deprotection, a compound of formula (Ia):

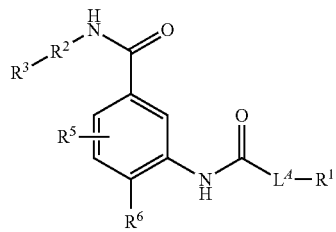

(Ia)

wherein $L^A$, $R^1$, $R^2$, $R^3$, $R^5$, and $R^6$ are as defined in claim 1.

12. A method of preparing a compound of formula (I) according to claim 1, comprising reacting an intermediate compound of formula (XI):

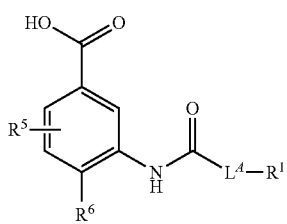

(XI)

wherein $L^A$, $R^1$, $R^5$, and $R^6$ are as defined in claim 1, with a compound of formula $R^3R^2NH_2$, wherein $R^2$ and $R^3$ are as defined in claim 1, to give, following optional deprotection, a compound of formula (Ia):

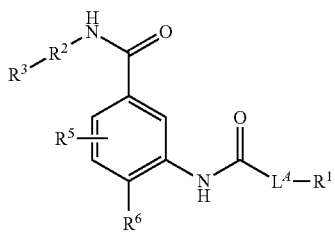

(Ia)

wherein $L^A$, $R^1$, $R^2$, $R^3$, $R^5$, and $R^6$ are as defined in claim 1.

13. A method of preparing a compound of formula (I) according to claim 1, comprising reacting an intermediate compound of formula (XIa):

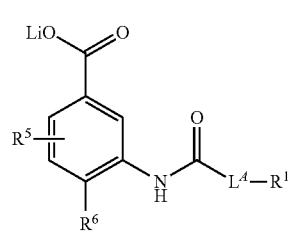

(XIa)

wherein $L^A$, $R^1$, $R^5$, and $R^6$ are as defined in claim 1, with a compound of formula $R^3R^2NH_2$, wherein $R^2$ and $R^3$ are as defined in claim 1, to give, following optional deprotection, a compound of formula (Ia):

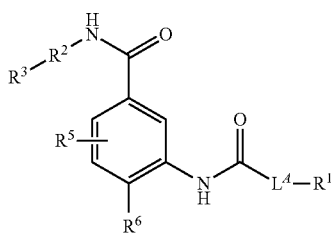

(Ia)

wherein $L^A$, $R^1$, $R^2$, $R^3$, $R^5$, and $R^6$ are as defined in claim 1.

14. A method of preparing a compound of formula (I) according to claim 1, comprising reacting an intermediate compound of formula (XVII):

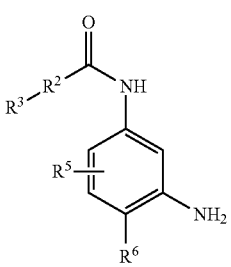

(XVII)

wherein $R^2$, $R^3$, $R^5$, and $R^6$ are as defined in claim 1, with a carboxylic acid $HO_2C$-$L^A$-$R^1$ or the corresponding acyl chloride Cl—C(=O)-$L^A$-$R^1$, wherein $L^A$ and $R^1$ are as defined in claim 1, or with Cl—C(=O)-$L^A$-LG, wherein $L^A$ is as defined in claim 1, and LG is a leaving group, and subsequently with agents suitable for the introduction of $R^1$, to give, following optional deprotection, a compound of formula (Ib):

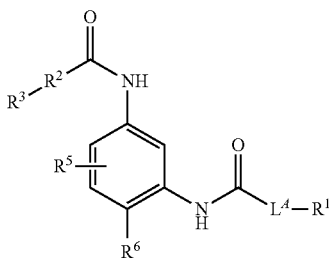

(Ib)

wherein $L^A$, $R^1$, $R^2$, $R^3$, $R^5$, and $R^6$ are as defined in claim 1.

15. A method of preparing a compound of formula (I) according to claim 1, comprising reacting an intermediate compound of formula (XXII):

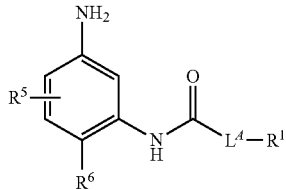

(XXII)

wherein $L^A$, $R^1$, $R^5$ and $R^6$ are as defined in claim 1, with a carboxylic acid $HO_2C$—$R^2$—$R^3$, wherein $R^2$ and $R^3$ are as defined in claim 1, or with a carboxylic acid X—$R^2$—$CO_2H$, wherein $R^2$ is as defined in claim 1, and subsequently coupling with $R^3$—X' in a palladium catalysed coupling reaction, wherein $R^3$ is as defined in claim 1, and both X and X' are groups enabling palladium catalysed coupling reactions, with the proviso that if X is a boronic ester or an ester thereof, X' is bromo, iodo, trifluoromethylsulfonyloxy or nonaflyl, to give, following optional deprotection, a compound of formula (Ib):

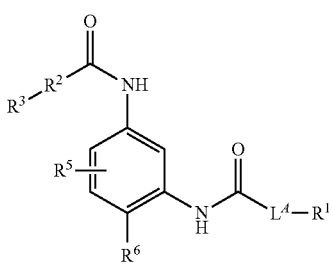

(Ib)

wherein $L^A$, $R^1$, $R^2$, $R^3$, $R^5$, and $R^6$ are as defined in claim 1.

16. A method of preparing a compound of formula (I) according to claim 1, comprising reacting an intermediate compound of formula (XXIV):

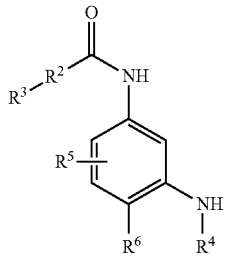

(XXIV)

wherein $R^2$, $R^3$, $R^4$, $R^5$ and $R^6$ are as defined in claim 1, with a carboxylic acid $HO_2C$-$L^A$-$R^1$ or the corresponding acyl chloride Cl—C(=O)-$L^A$-$R^1$, wherein $L^A$ and $R^1$ are as defined in claim 1, to give, following optional deprotection, a compound of formula (Ic):

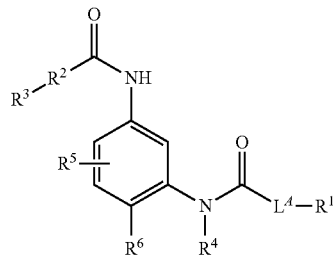

(Ic)

wherein $L^A$, $R^1$, $R^2$, $R^3$, $R^4$, $R^5$ and $R^6$ are as defined in claim 1.

17. A method of preparing a compound of formula (I) according to claim 1, comprising reacting an intermediate compound of formula (XXV):

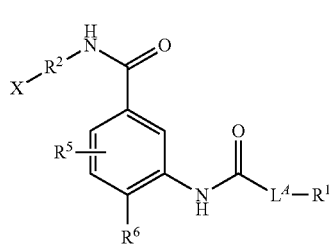

(XXV)

wherein $L^A$, $R^1$, $R^2$, $R^5$ and $R^6$ are as defined in claim 1, with a compound of formula $R^3$—X', wherein $R^3$ is as defined in claim 1, wherein both X and X' are groups enabling palladium catalysed coupling reactions, with the proviso that if X is a boronic ester or an ester thereof, X' is chloro, bromo, iodo, trifluoromethylsulfonyloxy or nonaflyl, to give, following optional deprotection, a compound of formula (Ia):

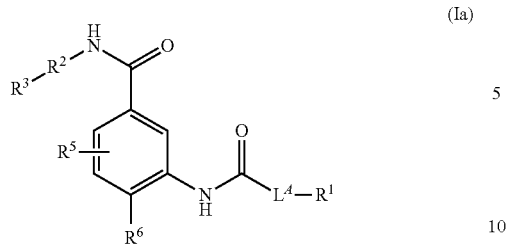
wherein $L^A$, $R^1$, $R^2$, $R^3$, $R^4$, $R^5$ and $R^6$ are as defined in claim 1.
* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Unknown
<220> FEATURE:
<221> NAME/KEY: source
<222> LOCATION: 1..20
<223> OTHER INFORMATION: /mol_type="unassigned DNA"
      /note="L32 forward primer"
      /organism="Unknown"

<400> SEQUENCE: 1
aagttcatcc ggcaccagtc                                          20

<210> SEQ ID NO 2
<211> LENGTH: 21
<212> TYPE: DNA
<213> ORGANISM: Unknown
<220> FEATURE:
<221> NAME/KEY: source
<222> LOCATION: 1..21
<223> OTHER INFORMATION: /mol_type="unassigned DNA"
      /note="L32 revers primer"
      /organism="Unknown"

<400> SEQUENCE: 2
tggcccttga atcttctacg a                                        21

<210> SEQ ID NO 3
<211> LENGTH: 22
<212> TYPE: DNA
<213> ORGANISM: Unknown
<220> FEATURE:
<221> NAME/KEY: source
<222> LOCATION: 1..22
<223> OTHER INFORMATION: /mol_type="unassigned DNA"
      /note="L32 probe"
      /organism="Unknown"

<400> SEQUENCE: 3
cccagaggca ttgacaacag gg                                       22

<210> SEQ ID NO 4
<211> LENGTH: 20
<212> TYPE: DNA
<213> ORGANISM: Unknown
<220> FEATURE:
<221> NAME/KEY: source
<222> LOCATION: 1..20
<223> OTHER INFORMATION: /mol_type="unassigned DNA"
      /note="AXIN2 forward primer"
      /organism="Unknown"

<400> SEQUENCE: 4
aggccagtga gttggttgtc                                          20

<210> SEQ ID NO 5
<211> LENGTH: 20
<212> TYPE: DNA
<213> ORGANISM: Unknown
<220> FEATURE:
<221> NAME/KEY: source
<222> LOCATION: 1..20
<223> OTHER INFORMATION: /mol_type="unassigned DNA"
      /note="AXIN2 revers primer"
      /organism="Unknown"

<400> SEQUENCE: 5

```
agctctgagc cttcagcatc                                        20

<210> SEQ ID NO 6
<211> LENGTH: 25
<212> TYPE: DNA
<213> ORGANISM: Unknown
<220> FEATURE:
<221> NAME/KEY: source
<222> LOCATION: 1..25
<223> OTHER INFORMATION: /mol_type="unassigned DNA"
      /note="AXIN2 probe"
      /organism="Unknown"

<400> SEQUENCE: 6
tctgtgggga agaaattcca taccg                                  25
```